US012612460B2

(12) United States Patent
Lu et al.

(10) Patent No.: US 12,612,460 B2
(45) Date of Patent: Apr. 28, 2026

(54) ANTI-PD-1 ANTIBODIES AND FUSION PROTEINS

(71) Applicant: Kadmon Corporation, LLC, Bridgewater, NJ (US)

(72) Inventors: Dan Lu, Montvale, NJ (US); Zhanna Polonskaya, Mountainside, NJ (US); Tzu-Pei Chang, New York, NY (US); Stella Aviaty Martomo, Edgewater, NJ (US); Jeegar P. Patel, Hillsborough, NJ (US); Faical Miyara, Bronxville, NY (US)

(73) Assignee: Kadmon Corporation, LLC, Morristown, NJ (US)

( * ) Notice: Subject to any disclaimer, the term of this patent is extended or adjusted under 35 U.S.C. 154(b) by 0 days.

(21) Appl. No.: 18/989,801

(22) Filed: Dec. 20, 2024

(65) Prior Publication Data

US 2025/0136693 A1 May 1, 2025

Related U.S. Application Data

(63) Continuation of application No. 18/011,878, filed as application No. PCT/US2021/038740 on Jun. 23, 2021, now abandoned.

(60) Provisional application No. 63/111,459, filed on Nov. 9, 2020, provisional application No. 63/043,114, filed on Jun. 23, 2020.

(51) Int. Cl.
| | |
|---|---|
| *C07K 16/28* | (2006.01) |
| *A61P 35/00* | (2006.01) |
| *C07K 14/715* | (2006.01) |
| *C12N 15/63* | (2006.01) |

(52) U.S. Cl.
CPC .......... *C07K 16/2818* (2013.01); *A61P 35/00* (2018.01); *C07K 14/7155* (2013.01); *C12N 15/63* (2013.01); *C07K 2317/31* (2013.01); *C07K 2317/526* (2013.01); *C07K 2317/565* (2013.01)

(58) Field of Classification Search
CPC ............................ C07K 14/5443; A61K 40/36
See application file for complete search history.

(56) References Cited

U.S. PATENT DOCUMENTS

| | | | |
|---|---|---|---|
| 5,739,277 | A | 4/1998 | Presta et al. |
| 7,087,411 | B2 | 8/2006 | Daly et al. |
| 8,945,560 | B1 | 2/2015 | Clube |
| 9,517,264 | B2 | 12/2016 | Fachini et al. |
| 9,650,442 | B2 | 5/2017 | Hosse et al. |
| 10,329,346 | B2 | 6/2019 | Auer et al. |
| 2013/0078249 | A1 | 3/2013 | Ast et al. |
| 2016/0340399 | A1 | 11/2016 | Amann et al. |
| 2016/0340429 | A1 | 11/2016 | Waksal et al. |
| 2017/0088597 | A1 | 3/2017 | Wong et al. |
| 2018/0118828 | A1 | 5/2018 | Bernett et al. |
| 2018/0118829 | A1 | 5/2018 | Mabry, III et al. |

FOREIGN PATENT DOCUMENTS

| | | | |
|---|---|---|---|
| EP | 3495390 A1 | 6/2019 | |
| JP | 2019533444 A | 11/2019 | |
| JP | 2023531920 A | 7/2023 | |
| WO | 9316185 A2 | 8/1993 | |
| WO | 0026667 A1 | 5/2000 | |
| WO | 2010029357 A2 | 3/2010 | |
| WO | 2012146628 A1 | 11/2012 | |
| WO | 2014023709 A1 | 2/2014 | |
| WO | 2017194442 A1 | 11/2017 | |
| WO | 2019006472 A1 | 1/2019 | |
| WO | 2019170885 A1 | 9/2019 | |
| WO | WO-2019204665 A1 * | 10/2019 | ........ C07K 14/7155 |
| WO | 2020077276 A2 | 4/2020 | |

OTHER PUBLICATIONS

Ha, Ji-Hee, Jung-Eun Kim, and Yong-Sung Kim. "Immunoglobulin Fc heterodimer platform technology: from design to applications in therapeutic antibodies and proteins." Frontiers in Immunology 7 (2016): 394. (Year: 2016).*

Von Kreudenstein, Thomas Spreter, et al. "Improving biophysical properties of a bispecific antibody scaffold to aid developability: quality by molecular design." MAbs. vol. 5. No. 5. Taylor & Francis, 2013. (Year: 2013).*

Altschul, Stephen F. et al., "Basic Local Alignment Search Tool", J. Mol. Biol. (1990)215, 403-410.

Austin, JW et al., "Immunoglobulin heavy chain junction region, partial [*Homo sapiens*]", Genbank entry, National Center for Biotechnology Information, Jan. 17, 2019, retrieved on Dec. 6, 2022, from https://www.ncbi.nlm.nih. gov/protein/MOP35868.1.

Chothia, Cyrus et al., "Canonical Structures for the Hypervariable Regions of Immunoglobulins", J. Mol. Biol. (1987) 196, 901-917.

Devereux et al., Nucleic Acids Research 12:1 387-395, 1984.

Ghetie, Victor et al., "Multiple Roles for the Major Histocompatibility Complex Class I-Related Receptor FcRn", Annu. Rev. Immunol. 2000, 18:739-766.

(Continued)

*Primary Examiner* — Julie Wu

*Assistant Examiner* — Bryan William Heck

(74) *Attorney, Agent, or Firm* — McNeill PLLC

(57) ABSTRACT

Provided herein are recombinant antibodies, antigen-binding fragments, and fusion proteins thereof useful for binding to and inhibiting programmed death 1 (PD-1), nucleic acid molecules encoding the same and therapeutic compositions thereof, as well as methods of using such antibodies, including the methods for enhancing T cell and NK cell function to increase cell and cytokine mediated immunity and methods of treatment of various immune dysfunction related disorders including cancer and infectious diseases.

19 Claims, 75 Drawing Sheets

Specification includes a Sequence Listing.

(56) References Cited

OTHER PUBLICATIONS

Kabat et al., Sequences of Proteins of Immunological Interest, 5th Ed. Public Health Service, National Institutes of Health, Bethesda, Md, 1991.

Lefranc, Marie-Paule et al., "IMGT unique numbering for immunoglobulin and T cell receptor variable domains and Ig superfamily V-like domains", Developmental and Comparative Immunology 27 (2003) 55-77.

PCT International Search Report from PCT/US2021/038740, mailed Jan. 5, 2022, 8 pages.

PCT Written Opinion of the International Searching Authority from PCT/US2021/038740, mailed Jan. 5, 2022, 16 pages.

Brinkmann, Ulrich et al., "The making of bispecific antibodies", MABS, 2017, 9(2):182-212.

\* cited by examiner

| ID | FR1 | CDR1 | FR2 | CDR2 | FR3 | CDR3 | FR4 | SEQ |
|---|---|---|---|---|---|---|---|---|
| 38B1LC | DIQMTQSPSSLSASVGDRVTITC | RASQSISTWLA (80) | WYQQKPGKAPKLLIY | EASKLER (92) | GVPSRFSGSGSGTDFTLTISSLQPEDFATYYC | QQAYSFPFT (75) | FGPGTKVDIK | 93 |
| 38B1QLC | DIQMTQSPSSLSASVGDRVTITC | RASQSISTWLA (80) | WYQQKPGKAPKLLIY | DASTLQT (94) | GVPSRFSGSGSGTDFTLTISSLQPEDFATYYC | QQGYSFPFT (71) | FGPGTKVDIK | 95 |
| 38B2LC | DIQMTQSPSSLSASVGDRVTITC | RASQSISNWLA (96) | WYQQKPGKAPKLLIY | DASSLES (97) | GVPSRFSGSGSGTDFTLTISSLQPEDFATYYC | QQGDSFPFT (82) | FGQGTKLEIK | 98 |
| 38C11LC | DIQMTQSPSSLSASVGDRVTITC | RASQSISRWLA (99) | WYQQKPGKAPKLLIY | DASTVQS (100) | GVPSRFSGSGSGTDFTLTISSLQPEDFATYYC | QQAYSFPFT (47) | FGPGTKVDIK | 101 |
| 38C2LC | DIQMTQSPSSLSASVGDRVTITC | RASGDINKWVA (102) | WYQQKPGKAPKLLIY | DASSLQS (103) | GVPSRFSGSGSGTDFTLTISSLQPEDFATYYC | QQANSPFA (104) | FGGGTKVEIK | 105 |
| 38G11LC | DIQMTQSPSSLSASVGDRVTITC | RASNISRWLA (106) | WYQQKPGKAPKLLIY | DASSLQS (103) | GVPSRFSGSGSGTDFTLTISSLQPEDFATYYC | QQANSFPFT (47) | FGPGTKVDIK | 107 |
| 38G6LC | DIQMTQSPSSLSASVGDRVTITC | RVSQSISWLA (108) | WYQQKPGKAPKLLIY | DASSLQS (103) | GVPSRFSGSGSGTDFTLTISSLQPEDFATYYC | QQANSFPFT (47) | FGPGTKVDIK | 109 |
| 38H3LC | DIQMTQSPSSLSASVGDRVTITC | RASQSISTWLA (110) | WYQQKPGKAPKLLIY | EASRLQS (111) | GVPSRFSGSGSGTDFTLTISSLQPEDFATYYC | QQAYSFPFT (47) | FGPGTKVDIK | 112 |
| 39A3LC | DIQMTQSPSSLSASVGDRVTITC | RASQSISNWLA (77) | WYQQKPGKAPKLLIY | DASSLQS (103) | GVPSRFSGSGSGTDFTLTISSLQPEDFATYYC | QQGDSFPLT (75) | FGGGTKVEIK | 114 |
| 39B11LC | DIQMTQSPSSLSASVGDRVTITC | RASQSISNWLA (77) | WYQQKPGKAPKLLIY | EASRLQS (111) | GVPSRFSGSGSGTDFTLTISSLQPEDFATYYC | QQANSFPFT (47) | FGPGTKVDIK | 115 |
| 39B3LC | DIQMTQSPSSLSASVGDRVTITC | RASQSIGPWLA (116) | WYQQKPGKAPKLLIY | DASNLET (87) | GVPSRFSGSGSGTDFTLTISSLQPEDFATYYC | QQANSFPFT (113) | FGPGTKVDIK | 117 |
| 39B6LC | DIQMTQSPSSLSASVGDRVTITC | RASEDISHWLA (118) | WYQQKPGKAPKLLIY | DAKQLHP (119) | GVPSRFSGSGSGTDFTLTISSLQPEDFATYYC | QQANSFPFT (47) | FGGGTRLEIK | 120 |
| 39F6LC | DIQMTQSPSSLSASVGDRVTITC | RASQSISTWLA (80) | WYQQKPGKAPKLLIY | DASTLQS (78) | GVPSRFSGSGSGTDFTLTISSLQPEDFATYYC | QQANSFPFT (47) | FGPGTKVDIK | 121 |
| 39G6LC | DIQMTQSPSSLSASVGDRVTITC | RASQINVWLA (122) | WYQQKPGKAPKLLIY | DASSLQS (103) | GVPSRFSGSGSGTDFTLTISSLQPEDFATYYC | QQANSFPFT (47) | FGPGTKVDIK | 123 |
| 39G8LC | DIQMTQSPSSLSASVGDRVTITC | RASQSISPWLA (124) | WYQQKPGKAPKLLIY | DASKLET (125) | GVPSRFSGSGSGTDFTLTISSLQPEDFATYYC | QQANSFPFT (47) | FGGGTKVEIK | 126 |
| 39H11LC | DIQMTQSPSSLSASVGDRVTITC | RASQSIGIWWA (127) | WYQQKPGKAPKLLIY | DASNLQS (38) | GVPSRFSGSGSGTDFTLTISSLQPEDFATYYC | QQADSFPFT (75) | FGGGTKVEIK | 128 |
| 39H2LC | DIQMTQSPSSLSASVGDRVTITC | RASNIGPWLA (129) | WYQQKPGKAPKLLIY | DASTLHS (130) | GVPSRFSGSGSGTDFTLTISSLQPEDFATYYC | QQANSPFT (68) | FGGGTRLEIK | 131 |
| 39H7LC | DIQMTQSPSSLSASVGDRVTITC | RASQSISNWLA (132) | WYQQKPGKAPKLLIY | DASNLQA (133) | GVPSRFSGSGSGTDFTLTISSLQPEDFATYYC | QQAYSFPFT (47) | FGPGTKVDIK | 134 |
| Motif | DIQMTQSPSSLSASVGDRVTITC | $RX_{13}X_{14}X_{15}X_{16}JX_{17}X_{18}WX_{19}X_{20}$ (135) | WYQQKPGKAPKLLIY | $X_{21}AX_{22}X_{23}X_{24}X_{25}X_{26}$ (136) | GVPSRFSGSGSGTDFTLTISSLQPEDFATYYC | $QQX_{27}X_{28}SFPX_{29}X_{30}$ (137) | FGQGTKVDIK | 138 |

FIG. 1C (Cont.)

| | HCDR1 (SEQ ID NO:) | HCDR2 (SEQ ID NO:) | HCDR3 (SEQ ID NO:) | SEQ ID NO: |
|---|---|---|---|---|
| R3A9HC | QVQLVQSGAEVKKPGASVKVSCKAS GHTFTSYYIH (139) | WVRQAPGQGLEWM GIINPSGGSTSYAQKFQG (140) | RVTMTRDTSTSTVVMELSSLRSEDTAVYYCAR DRAYGGAGDY (141) | WGQGTLVTVSS 142 |

| | LCDR1 (SEQ ID NO:) | LCDR2 (SEQ ID NO:) | LCDR3 (SEQ ID NO.) | SEQ ID NO: |
|---|---|---|---|---|
| R3A9LC | DIQMTQSPSSLSASVGDRVTITC RASQSVGTWLA (143) | WYQQKPGKAPKLLIY SASTLQS (144) | GVPSRFSGSGSGTDFTLTISSLQPEDFATYYC QQSYSAPLT (145) | FGGGTKVEIK 146 |
| m3A7LC | DIQMTQSPSSLSASVGDRVTITC RASRSISWWLA (147) | WYQQKPGKAPKLLIY AASSLQS (148) | GVPSRFSGSGSGTDFTLTISSLQPEDFATYYC QQSYSAPVT (149) | FGGGTKVEIK 150 |
| m2C1LC | DIQMTQSPSSLSASVGDRVTITC RASRSISSWLA (151) | WYQQKPGKAPKLLIY AASSLQS (148) | GVPSRFSGSGSGTDFTLTISSLQPEDFATYYC QQSYSIPAT (152) | FGGGTKVEIK 153 |
| m2A1LC | DIQMTQSPSSLSASVGDRVTITC RASRGISSWLA (154) | WYQQKPGKAPKLLIY AASSLQS (148) | GVPSRFSGSGSGTDFTLTISSLQPEDFATYYC QQSYSPPWT (155) | FGGGTKVEIK 156 |
| m4A5LC | DIQMTQSPSSLSASVGDRVTITC RASQSIDTWLA (157) | WYQQKPGKAPKLLIY AASTLES (158) | GVPSRFSGSGSGTDFTLTISSLQPEDFATYYC QQSYRAPLT (159) | FGGGTKVEIK 160 |
| m4D1LC | DIQMTQSPSSLSASVGDRVTITC RASQSISAWLA (161) | WYQQKPGKAPKLLIY KASSLES (162) | GVPSRFSGSGSGTDFTLTISSLQPEDFATYYC QQSYSPPAT (163) | FGGGTKVEIK 164 |
| m3C6LC | DIQMTQSPSSLSASVGDRVTITC RASQSIDTWLA (157) | WYQQKPGKAPKLLIY EASSLQG (165) | GVPSRFSGSGSGTDFTLTISSLQPEDFATYYC QQSYSTWT (166) | FGGGTKVEIK 167 |

FIG. 1D

| | |
|---|---|
| ◆ | ZP01-19B6 |
| ■ | ZP01-19B10 |
| ▽ | ZP01-23A8 |
| ✳ | ZP01-23H9 |
| ◇ | ZP01-24H9 |
| ● | ZP01-23A11 |

1C-antibody/IL-15

2C-antibody/IL-15

1N-antibody/IL-15

2N-antibody/IL-15

1C-antibody/IL-15

1N-antibody/IL-15

1N or 2N: Cis presentation

1C or 2C: Trans presentation

PD1-PDL1

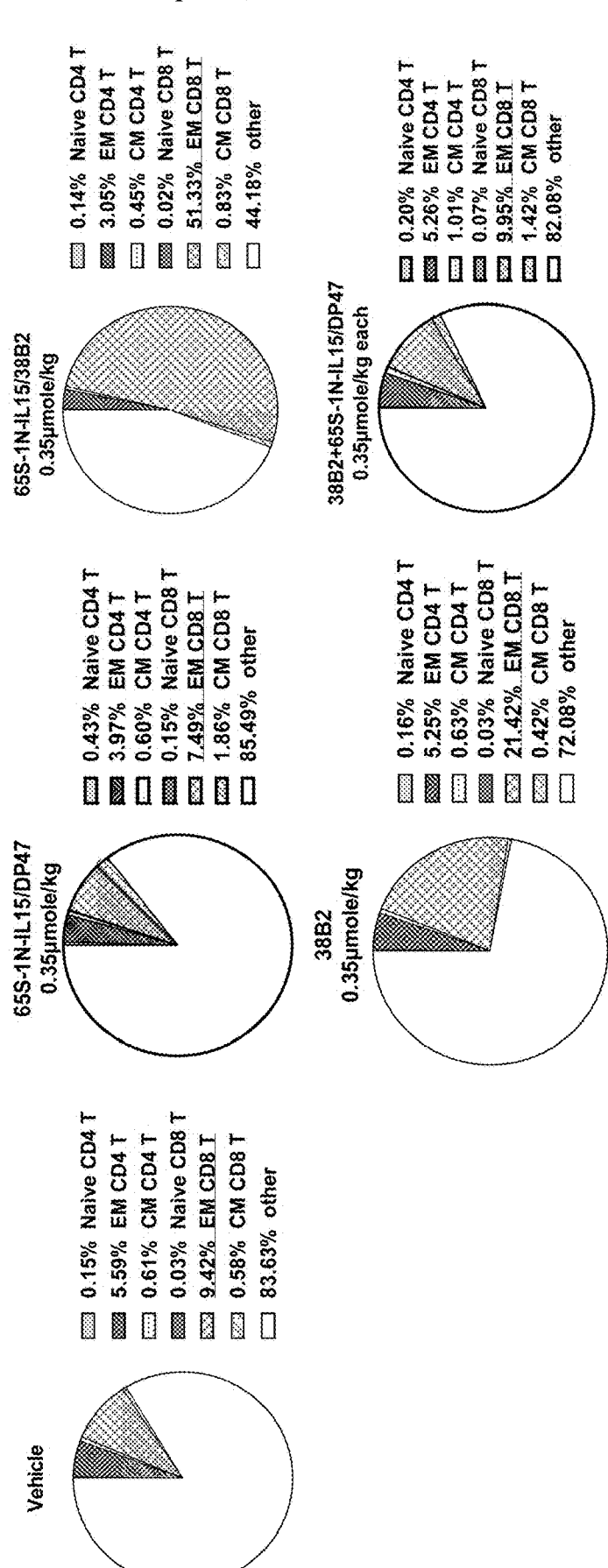

65S-1N-iL15/38B2
0.35µmole/kg

| | |
|---|---|
| 0.14% | Naive CD4 T |
| 3.05% | EM CD4 T |
| 0.45% | CM CD4 T |
| 0.02% | Naive CD8 T |
| 51.33% | EM CD8 T |
| 0.83% | CM CD8 T |
| 44.18% | other |

38B2+65S-1N-iL15/DP47
0.35µmole/kg each

| | |
|---|---|
| 0.20% | Naive CD4 T |
| 5.26% | EM CD4 T |
| 1.01% | CM CD4 T |
| 0.07% | Naive CD8 T |
| 9.95% | EM CD8 T |
| 1.42% | CM CD8 T |
| 82.08% | other |

65S-1N-iL15/DP47
0.35µmole/kg

| | |
|---|---|
| 0.43% | Naive CD4 T |
| 3.97% | EM CD4 T |
| 0.60% | CM CD4 T |
| 0.15% | Naive CD8 T |
| 7.49% | EM CD8 T |
| 1.86% | CM CD8 T |
| 85.49% | other |

38B2
0.35µmole/kg

| | |
|---|---|
| 0.16% | Naive CD4 T |
| 5.25% | EM CD4 T |
| 0.63% | CM CD4 T |
| 0.03% | Naive CD8 T |
| 21.42% | EM CD8 T |
| 0.42% | CM CD8 T |
| 72.08% | other |

Vehicle

| | |
|---|---|
| 0.15% | Naive CD4 T |
| 5.59% | EM CD4 T |
| 0.61% | CM CD4 T |
| 0.03% | Naive CD8 T |
| 9.42% | EM CD8 T |
| 0.58% | CM CD8 T |
| 83.63% | other |

Fig. 37D

SEQUENCE LISTING

Sequence total quantity: 244
SEQ ID NO: 1　　　　moltype = AA　length = 10
FEATURE　　　　　　Location/Qualifiers
REGION　　　　　　　1..10
　　　　　　　　　　note = 19B6 HCDR1
source　　　　　　　1..10
　　　　　　　　　　mol_type = protein -continued

```
                          organism = synthetic construct
SEQUENCE: 1
GYTFTGYYMH                                                    10

SEQ ID NO: 2              moltype = AA   length = 17
FEATURE                   Location/Qualifiers
REGION                    1..17
                          note = 19B6 HCDR2
source                    1..17
                          mol_type = protein
                          organism = synthetic construct
SEQUENCE: 2
IINPSGGSTS YAQKFQG                                            17

SEQ ID NO: 3              moltype = AA   length = 15
FEATURE                   Location/Qualifiers
REGION                    1..15
                          note = 19B6 HCDR3
source                    1..15
                          mol_type = protein
                          organism = synthetic construct
SEQUENCE: 3
TAGYDWLPSG LGMDV                                              15

SEQ ID NO: 4              moltype = AA   length = 124
FEATURE                   Location/Qualifiers
REGION                    1..124
                          note = 19B6 VH
source                    1..124
                          mol_type = protein
                          organism = synthetic construct
SEQUENCE: 4
QVQLVQSGAE VKKPGASVKV SCKASGYTFT GYYMHWVRQA PGQGLEWMGI INPSGGSTSY  60
AQKFQGRVTM TRDTSTSTVY MELSSLRSED TAVYYCAKTA GYDWLPSGLG MDVWGQGTTV  120
TVSS                                                          124

SEQ ID NO: 5              moltype = AA   length = 10
FEATURE                   Location/Qualifiers
REGION                    1..10
                          note = 19B10 HCDR1
source                    1..10
                          mol_type = protein
                          organism = synthetic construct
SEQUENCE: 5
GFTFSSYAMH                                                    10

SEQ ID NO: 6              moltype = AA   length = 17
FEATURE                   Location/Qualifiers
REGION                    1..17
                          note = 19B10 HCDR2
source                    1..17
                          mol_type = protein
                          organism = synthetic construct
SEQUENCE: 6
GISNSGGNTY YADSVKG                                            17

SEQ ID NO: 7              moltype = AA   length = 9
FEATURE                   Location/Qualifiers
REGION                    1..9
                          note = 19B10 HCDR3
source                    1..9
                          mol_type = protein
                          organism = synthetic construct
SEQUENCE: 7
DNYYYYMDV                                                     9

SEQ ID NO: 8              moltype = AA   length = 118
FEATURE                   Location/Qualifiers
REGION                    1..118
                          note = 19B10 VH
source                    1..118
                          mol_type = protein
                          organism = synthetic construct
SEQUENCE: 8
EVQLLESGGG LVQPGGSLRL SCAASGFTFS SYAMHWVRQA PGKGLEWVSG ISNSGGNTYY  60
ADSVKGRFTI SRDNSKNTLY LQMNSLRAED TAVYYCARDN YYYYMDVWGK GTTVTVSS   118

SEQ ID NO: 9              moltype = AA   length = 10
FEATURE                   Location/Qualifiers
```

-continued

---

```
REGION                    1..10
                          note = 23A8 HCDR1
source                    1..10
                          mol_type = protein
                          organism = synthetic construct
SEQUENCE: 9
GFTFSSSAMH                                                    10

SEQ ID NO: 10             moltype = AA  length = 17
FEATURE                   Location/Qualifiers
REGION                    1..17
                          note = 23A8 HCDR2
source                    1..17
                          mol_type = protein
                          organism = synthetic construct
SEQUENCE: 10
GISGSGSSTY YADSVKG                                            17

SEQ ID NO: 11             moltype = AA  length = 10
FEATURE                   Location/Qualifiers
REGION                    1..10
                          note = 23A8 HCDR3
source                    1..10
                          mol_type = protein
                          organism = synthetic construct
SEQUENCE: 11
DNNYYYYMDV                                                    10

SEQ ID NO: 12             moltype = AA  length = 119
FEATURE                   Location/Qualifiers
REGION                    1..119
                          note = 23A8 VH
source                    1..119
                          mol_type = protein
                          organism = synthetic construct
SEQUENCE: 12
EVQLLESGGG LVQPGGSLRL SCAASGFTFS SSAMHWVRQA PGKGLEWVSG ISGSGSSTYY  60
ADSVKGRFTI SRDNSKNTLY LQMNSLRAED TAVYYCARDN NYYYYMDVWG KGTTVTVSS   119

SEQ ID NO: 13             moltype = AA  length = 10
FEATURE                   Location/Qualifiers
REGION                    1..10
                          note = 23A11 HCDR1
source                    1..10
                          mol_type = protein
                          organism = synthetic construct
SEQUENCE: 13
GYTFTDYSLH                                                    10

SEQ ID NO: 14             moltype = AA  length = 17
FEATURE                   Location/Qualifiers
REGION                    1..17
                          note = 23A11 HCDR2
source                    1..17
                          mol_type = protein
                          organism = synthetic construct
SEQUENCE: 14
EVIPMFDTAY YAQTFQG                                            17

SEQ ID NO: 15             moltype = AA  length = 18
FEATURE                   Location/Qualifiers
REGION                    1..18
                          note = 23A11 HCDR3
source                    1..18
                          mol_type = protein
                          organism = synthetic construct
SEQUENCE: 15
EPFTMVRGGR YYYYGMDV                                           18

SEQ ID NO: 16             moltype = AA  length = 127
FEATURE                   Location/Qualifiers
REGION                    1..127
                          note = 23A11 VH
source                    1..127
                          mol_type = protein
                          organism = synthetic construct
SEQUENCE: 16
QVQLVQSGAE VKKPGSSVKV SCKASGYTFT DYSLHWVRQA PGQGLEWMGE VIPMFDTAYY  60
AQTFQGRVTI TADESTSTAY MELSSLRSED TAVYYCAREP FTMVRGGRYY YYGMDVWGQG  120
```

-continued

```
TTVTVSS                                                                  127

SEQ ID NO: 17          moltype = AA  length = 10
FEATURE                Location/Qualifiers
REGION                 1..10
                       note = 23H9 HCDR1
source                 1..10
                       mol_type = protein
                       organism = synthetic construct
SEQUENCE: 17
GGTFSSSVIS                                                               10

SEQ ID NO: 18          moltype = AA  length = 17
FEATURE                Location/Qualifiers
REGION                 1..17
                       note = 23H9 HCDR2
source                 1..17
                       mol_type = protein
                       organism = synthetic construct
SEQUENCE: 18
GIIPIFGTAN YAQKFQG                                                       17

SEQ ID NO: 19          moltype = AA  length = 20
FEATURE                Location/Qualifiers
REGION                 1..20
                       note = 23H9 HCDR3
source                 1..20
                       mol_type = protein
                       organism = synthetic construct
SEQUENCE: 19
EGLGCSGGSC YSGYYYGMDV                                                    20

SEQ ID NO: 20          moltype = AA  length = 129
FEATURE                Location/Qualifiers
REGION                 1..129
                       note = 23H9 VH
source                 1..129
                       mol_type = protein
                       organism = synthetic construct
SEQUENCE: 20
QVQLVQSGAE VKKPGSSVKV SCKASGGTFS SSVISWVRQA PGQGLEWMGG IIPIFGTANY  60
AQKFQGRVTI TADESTSTAY MELSSLRSED TAVYYCAREG LGCSGGSCYS GYYYGMDVWG  120
QGTTVTVSS                                                               129

SEQ ID NO: 21          moltype = AA  length = 10
FEATURE                Location/Qualifiers
REGION                 1..10
                       note = 24H9 HCDR1
source                 1..10
                       mol_type = protein
                       organism = synthetic construct
SEQUENCE: 21
GFTFSSYWMS                                                               10

SEQ ID NO: 22          moltype = AA  length = 17
FEATURE                Location/Qualifiers
REGION                 1..17
                       note = 24H9 HCDR2
source                 1..17
                       mol_type = protein
                       organism = synthetic construct
SEQUENCE: 22
AISGSGGSTY YADSVKG                                                       17

SEQ ID NO: 23          moltype = AA  length = 8
FEATURE                Location/Qualifiers
REGION                 1..8
                       note = 24H9 HCDR3
source                 1..8
                       mol_type = protein
                       organism = synthetic construct
SEQUENCE: 23
SPLQWVDV                                                                 8

SEQ ID NO: 24          moltype = AA  length = 117
FEATURE                Location/Qualifiers
REGION                 1..117
                       note = 24H9 VH
source                 1..117
```

-continued

```
                              mol_type = protein
                              organism = synthetic construct
SEQUENCE: 24
EVQLLESGGG LVQPGGSLRL SCAASGFTFS SYWMSWVRQA PGKGLEWVSA ISGSGGSTYY   60
ADSVKGRFTI SRDNSKNTLY LQMNSLRAED TAVYYCASSP LQWVDVWGQG TTVTVSS      117

SEQ ID NO: 25        moltype = AA  length = 11
FEATURE              Location/Qualifiers
REGION               1..11
                     note = 19B6 LCDR1
source               1..11
                     mol_type = protein
                     organism = synthetic construct
SEQUENCE: 25
RASQSINSWL A                                                       11

SEQ ID NO: 26        moltype = AA  length = 7
FEATURE              Location/Qualifiers
REGION               1..7
                     note = 19B6 LCDR2
source               1..7
                     mol_type = protein
                     organism = synthetic construct
SEQUENCE: 26
YASSLQS                                                            7

SEQ ID NO: 27        moltype = AA  length = 9
FEATURE              Location/Qualifiers
REGION               1..9
                     note = 19B6 LCDR3
source               1..9
                     mol_type = protein
                     organism = synthetic construct
SEQUENCE: 27
QQGYSVPLS                                                          9

SEQ ID NO: 28        moltype = AA  length = 107
FEATURE              Location/Qualifiers
REGION               1..107
                     note = 19B6 VL
source               1..107
                     mol_type = protein
                     organism = synthetic construct
SEQUENCE: 28
DIQMTQSPSS LSASVGDRVT ITCRASQSIN SWLAWYQQKP GKAPKLLIYY ASSLQSGVPS   60
RFSGSGSGTD FTLTISSLQP EDFATYYCQQ GYSVPLSFGQ GTKLEIK               107

SEQ ID NO: 29        moltype = AA  length = 11
FEATURE              Location/Qualifiers
REGION               1..11
                     note = 19B10 LCDR1
source               1..11
                     mol_type = protein
                     organism = synthetic construct
SEQUENCE: 29
RASQSVSTWL A                                                       11

SEQ ID NO: 30        moltype = AA  length = 7
FEATURE              Location/Qualifiers
REGION               1..7
                     note = 19B10 LCDR2
source               1..7
                     mol_type = protein
                     organism = synthetic construct
SEQUENCE: 30
AASNLET                                                            7

SEQ ID NO: 31        moltype = AA  length = 9
FEATURE              Location/Qualifiers
REGION               1..9
                     note = 19B10 LCDR3
source               1..9
                     mol_type = protein
                     organism = synthetic construct
SEQUENCE: 31
QQTYSTPYT                                                          9

SEQ ID NO: 32        moltype = AA  length = 107
FEATURE              Location/Qualifiers
```

-continued

```
REGION                    1..107
                          note = 19B10 VL
source                    1..107
                          mol_type = protein
                          organism = synthetic construct
SEQUENCE: 32
DIQMTQSPSS LSASVGDRVT ITCRASQSVS TWLAWYQQKP GKAPKLLIYA ASNLETGVPS   60
RFSGSGSGTD FTLTISSLQP EDFATYYCQQ TYSTPYTFGQ GTKLEIK                 107

SEQ ID NO: 33             moltype = AA  length = 11
FEATURE                   Location/Qualifiers
REGION                    1..11
                          note = 23A8 LCDR1
source                    1..11
                          mol_type = protein
                          organism = synthetic construct
SEQUENCE: 33
RASQSIGTWL A                                                        11

SEQ ID NO: 34             moltype = AA  length = 7
FEATURE                   Location/Qualifiers
REGION                    1..7
                          note = 23A8 LCDR2
source                    1..7
                          mol_type = protein
                          organism = synthetic construct
SEQUENCE: 34
AASTLRS                                                             7

SEQ ID NO: 35             moltype = AA  length = 9
FEATURE                   Location/Qualifiers
REGION                    1..9
                          note = 23A8 LCDR3
source                    1..9
                          mol_type = protein
                          organism = synthetic construct
SEQUENCE: 35
QQSYSTPYT                                                           9

SEQ ID NO: 36             moltype = AA  length = 107
FEATURE                   Location/Qualifiers
REGION                    1..107
                          note = 23A8 VL
source                    1..107
                          mol_type = protein
                          organism = synthetic construct
SEQUENCE: 36
DIQMTQSPSS LSASVGDRVT ITCRASQSIG TWLAWYQQKP GKAPKLLIYA ASTLRSGVPS   60
RFSGSGSGTD FTLTISSLQP EDFATYYCQQ SYSTPYTFGQ GTKLEIK                 107

SEQ ID NO: 37             moltype = AA  length = 11
FEATURE                   Location/Qualifiers
REGION                    1..11
                          note = 23A11 LCDR1
source                    1..11
                          mol_type = protein
                          organism = synthetic construct
SEQUENCE: 37
RASQNINKNL N                                                        11

SEQ ID NO: 38             moltype = AA  length = 7
FEATURE                   Location/Qualifiers
REGION                    1..7
                          note = 23A11 LCDR2 / 39H11 LCDR2
source                    1..7
                          mol_type = protein
                          organism = synthetic construct
SEQUENCE: 38
DASNLQS                                                             7

SEQ ID NO: 39             moltype = AA  length = 5
FEATURE                   Location/Qualifiers
REGION                    1..5
                          note = 23A11 LCDR3
source                    1..5
                          mol_type = protein
                          organism = synthetic construct
SEQUENCE: 39
QHSET                                                               5
```

-continued

```
SEQ ID NO: 40         moltype = AA   length = 103
FEATURE               Location/Qualifiers
REGION                1..103
                      note = 23A11 VL
source                1..103
                      mol_type = protein
                      organism = synthetic construct
SEQUENCE: 40
DIQMTQSPSS LSASVGDRVT ITCRASQNIN KNLNWYQQKP GKAPKLLIYD ASNLQSGVPS  60
RFSGSGSGTD FTLTISSLQP EDFATYYCQH SETFGQGTKV EIK                    103

SEQ ID NO: 41         moltype = AA   length = 16
FEATURE               Location/Qualifiers
REGION                1..16
                      note = 23H9 LCDR1 / 31B1 LCDR1 / 33C4 LCDR1 / 33G8 LCDR1
source                1..16
                      mol_type = protein
                      organism = synthetic construct
SEQUENCE: 41
RSSQSLLHSN GYNYLD                                                  16

SEQ ID NO: 42         moltype = AA   length = 7
FEATURE               Location/Qualifiers
REGION                1..7
                      note = 23H9 LCDR2
source                1..7
                      mol_type = protein
                      organism = synthetic construct
SEQUENCE: 42
LSSHRAS                                                            7

SEQ ID NO: 43         moltype = AA   length = 9
FEATURE               Location/Qualifiers
REGION                1..9
                      note = 23H9 LCDR3
source                1..9
                      mol_type = protein
                      organism = synthetic construct
SEQUENCE: 43
MQGAHWPYT                                                          9

SEQ ID NO: 44         moltype = AA   length = 112
FEATURE               Location/Qualifiers
REGION                1..112
                      note = 23H9 VL
source                1..112
                      mol_type = protein
                      organism = synthetic construct
SEQUENCE: 44
DIVMTQSPLS LPVTPGEPAS ISCRSSQSLL HSNGYNYLDW YLQKPGQSPQ LLIYLSSHRA  60
SGVPDRFSGS GSGTDFTLKI SRVEAEDVGV YYCMQGAHWP YTFGQGTKVE IK          112

SEQ ID NO: 45         moltype = AA   length = 11
FEATURE               Location/Qualifiers
REGION                1..11
                      note = 24H9 LCDR1
source                1..11
                      mol_type = protein
                      organism = synthetic construct
SEQUENCE: 45
RASQGISSWL A                                                       11

SEQ ID NO: 46         moltype = AA   length = 7
FEATURE               Location/Qualifiers
REGION                1..7
                      note = 24H9 LCDR2
source                1..7
                      mol_type = protein
                      organism = synthetic construct
SEQUENCE: 46
SASSLQS                                                            7

SEQ ID NO: 47         moltype = AA   length = 9
FEATURE               Location/Qualifiers
REGION                1..9
                      note = 24H9 LCDR3 / 32G6 LCDR3 / 38A4 LCDR3 / 38A6 LCDR3 /
                      38A8 LCDR3 / 38C11 LCDR3 / 38G11 LCDR3 / 38G9 LCDR3 /
                      39B11 LCDR3 / 39B3 LCDR3 / 39B6 LCDR3 / 39F11 LCDR3 / 39G5
```

-continued

```
                         LCDR3 / 39H2 LCDR3
source                   1..9
                         mol_type = protein
                         organism = synthetic construct
SEQUENCE: 47
QQANSFPFT                                                               9

SEQ ID NO: 48            moltype = AA  length = 107
FEATURE                  Location/Qualifiers
REGION                   1..107
                         note = 24H9 VL
source                   1..107
                         mol_type = protein
                         organism = synthetic construct
SEQUENCE: 48
DIQMTQSPSS LSASVGDRVT ITCRASQGIS SWLAWYQQKP GKAPKLLIYS ASSLQSGVPS  60
RFSGSGSGTD FTLTISSLQP EDFATYYCQQ ANSFPFTFGP GTKVDIK               107

SEQ ID NO: 49            moltype = AA  length = 7
FEATURE                  Location/Qualifiers
REGION                   1..7
                         note = 31B1 LCDR2
source                   1..7
                         mol_type = protein
                         organism = synthetic construct
SEQUENCE: 49
EASSLHS                                                                 7

SEQ ID NO: 50            moltype = AA  length = 9
FEATURE                  Location/Qualifiers
REGION                   1..9
                         note = 31B1 LCDR3
source                   1..9
                         mol_type = protein
                         organism = synthetic construct
SEQUENCE: 50
MQGTHWPYT                                                               9

SEQ ID NO: 51            moltype = AA  length = 112
FEATURE                  Location/Qualifiers
REGION                   1..112
                         note = 31B1 VL
source                   1..112
                         mol_type = protein
                         organism = synthetic construct
SEQUENCE: 51
DIVMTQSPLS LPVTPGEPAS ISCRSSQSLL HSNGYNYLDW YLQKPGQSPQ LLIYEASSLH  60
SGVPDRFSGS GSGTDFTLKI SRVEAEDVGV YYCMQGTHWP YTFGQGTKVE IK          112

SEQ ID NO: 52            moltype = AA  length = 7
FEATURE                  Location/Qualifiers
REGION                   1..7
                         note = 33C4 LCDR2
source                   1..7
                         mol_type = protein
                         organism = synthetic construct
SEQUENCE: 52
EASSLHT                                                                 7

SEQ ID NO: 53            moltype = AA  length = 9
FEATURE                  Location/Qualifiers
REGION                   1..9
                         note = 33C4 LCDR3
source                   1..9
                         mol_type = protein
                         organism = synthetic construct
SEQUENCE: 53
MQGSHWPYT                                                               9

SEQ ID NO: 54            moltype = AA  length = 112
FEATURE                  Location/Qualifiers
REGION                   1..112
                         note = 33C4 VL
source                   1..112
                         mol_type = protein
                         organism = synthetic construct
SEQUENCE: 54
DIVMTQSPLS LPVTPGEPAS ISCRSSQSLL HSNGYNYLDW YLQKPGQSPQ LLIYEASSLH  60
TGVPDRFSGS GSGTDFTLKI SRVEAEDVGV YYCMQGSHWP YTFGQGTKLE IK          112
```

-continued

```
SEQ ID NO: 55              moltype = AA   length = 7
FEATURE                    Location/Qualifiers
REGION                     1..7
                           note = 33G8 LCDR2
source                     1..7
                           mol_type = protein
                           organism = synthetic construct
SEQUENCE: 55
QASTLGS                                                                 7

SEQ ID NO: 56              moltype = AA   length = 9
FEATURE                    Location/Qualifiers
REGION                     1..9
                           note = 33G8 LCDR3
source                     1..9
                           mol_type = protein
                           organism = synthetic construct
SEQUENCE: 56
MQGTHWPYT                                                               9

SEQ ID NO: 57              moltype = AA   length = 112
FEATURE                    Location/Qualifiers
REGION                     1..112
                           note = 33G8 VL
source                     1..112
                           mol_type = protein
                           organism = synthetic construct
SEQUENCE: 57
DIVMTQSPLS LPVTPGEPAS ISCRSSQSLL HSNGYNYLDW YLQKPGQSPQ LLIYQASTLG   60
SGVPDRFSGS GSGTDFTLKI SRVEAEDVGV YYCMQGTHWP YTFGQGTKLE IK          112

SEQ ID NO: 58              moltype = AA   length = 16
FEATURE                    Location/Qualifiers
REGION                     1..16
                           note = 34C1 LCDR1
source                     1..16
                           mol_type = protein
                           organism = synthetic construct
SEQUENCE: 58
RSSESLLYSN GNTYLD                                                      16

SEQ ID NO: 59              moltype = AA   length = 7
FEATURE                    Location/Qualifiers
REGION                     1..7
                           note = 34C1 LCDR2
source                     1..7
                           mol_type = protein
                           organism = synthetic construct
SEQUENCE: 59
EVSNRAS                                                                 7

SEQ ID NO: 60              moltype = AA   length = 9
FEATURE                    Location/Qualifiers
REGION                     1..9
                           note = 34C1 LCDR3
source                     1..9
                           mol_type = protein
                           organism = synthetic construct
SEQUENCE: 60
MQGTRWPYT                                                               9

SEQ ID NO: 61              moltype = AA   length = 112
FEATURE                    Location/Qualifiers
REGION                     1..112
                           note = 34C1 VL
source                     1..112
                           mol_type = protein
                           organism = synthetic construct
SEQUENCE: 61
DIVMTQSPLS LPVTPGEPAS ISCRSSESLL YSNGNTYLDW YLQKPGQSPQ LLIYEVSNRA   60
SGVPDRFSGS GSGTDFTLKI SRVEAEDVGV YYCMQGTRWP YTFGQGTKVE IK          112

SEQ ID NO: 62              moltype = AA   length = 16
FEATURE                    Location/Qualifiers
REGION                     1..16
                           note = 23H9 derivatives motif LCDR1
VARIANT                    4
                           note = X can be Q or E
```

```
VARIANT               8
                      note = X can be H or Y
VARIANT               12
                      note = X can be Y or N
VARIANT               13
                      note = X can be T or N
source                1..16
                      mol_type = protein
                      organism = synthetic construct
SEQUENCE: 62
RSSXSLLXSN GXXYLD                                                         16

SEQ ID NO: 63         moltype =   length =
SEQUENCE: 63
000

SEQ ID NO: 64         moltype = AA  length = 9
FEATURE               Location/Qualifiers
REGION                1..9
                      note = 23H9 derivatives motif LCDR3
VARIANT               4
                      note = X can be A, T, or S
VARIANT               5
                      note = X can be H or R
source                1..9
                      mol_type = protein
                      organism = synthetic construct
SEQUENCE: 64
MQGXXWPYT                                                                 9

SEQ ID NO: 65         moltype = AA  length = 112
FEATURE               Location/Qualifiers
REGION                1..112
                      note = 23H9 derivatives motif VL
VARIANT               27
                      note = X can be Q or E
VARIANT               31
                      note = X can be H or Y
VARIANT               35
                      note = X can be Y or N
VARIANT               36
                      note = X can be T or N
VARIANT               55
                      note = X can be L, Q or E
VARIANT               56
                      note = X can be S, A, or V
VARIANT               58
                      note = X can be H, N, T, or S
VARIANT               59
                      note = X can be R or L
VARIANT               60
                      note = X can be G, A, or H
VARIANT               61
                      note = X can be S or T
VARIANT               97
                      note = X can be A, T, or S
VARIANT               98
                      note = X can be H or R
source                1..112
                      mol_type = protein
                      organism = synthetic construct
SEQUENCE: 65
DIVMTQSPLS LPVTPGEPAS ISCRSSXSLL XSNGXXYLDW YLQKPGQSPQ LLIYXXSXXX  60
XGVPDRFSGS GSGTDFTLKI SRVEAEDVGV YYCMQGXXWP YTFGQGTKVE IK        112

SEQ ID NO: 66         moltype = AA  length = 11
FEATURE               Location/Qualifiers
REGION                1..11
                      note = 32A11 LCDR1 / 38A8 LCDR1
source                1..11
                      mol_type = protein
                      organism = synthetic construct
SEQUENCE: 66
RASESISIWL A                                                              11

SEQ ID NO: 67         moltype = AA  length = 7
FEATURE               Location/Qualifiers
REGION                1..7
                      note = 32A11 LCDR2 / 32D11 LCDR2 / 38A8 LCDR2 / 39B3 LCDR2
```

-continued

```
source                        1..7
                              mol_type = protein
                              organism = synthetic construct
SEQUENCE: 67
DASNLET                                                                      7

SEQ ID NO: 68                 moltype = AA   length = 9
FEATURE                       Location/Qualifiers
REGION                        1..9
                              note = 32A11 LCDR3 / 39H11 LCDR3
source                        1..9
                              mol_type = protein
                              organism = synthetic construct
SEQUENCE: 68
QQADSFPFT                                                                    9

SEQ ID NO: 69                 moltype = AA   length = 107
FEATURE                       Location/Qualifiers
REGION                        1..107
                              note = 32A11 VL
source                        1..107
                              mol_type = protein
                              organism = synthetic construct
SEQUENCE: 69
DIQMTQSPSS LSASVGDRVT ITCRASESIS IWLAWYQQKP GKAPKLLIYD ASNLETGVPS 60
RFSGSGSGTN FTLTISSLQP EDFATYYCQQ ADSFPFTFGP GTKVDIK            107

SEQ ID NO: 70                 moltype = AA   length = 11
FEATURE                       Location/Qualifiers
REGION                        1..11
                              note = 32D11 LCDR1
source                        1..11
                              mol_type = protein
                              organism = synthetic construct
SEQUENCE: 70
RASQSINIWL A                                                                 11

SEQ ID NO: 71                 moltype = AA   length = 9
FEATURE                       Location/Qualifiers
REGION                        1..9
                              note = 32D11 LCDR3 / 38B10 LCDR3
source                        1..9
                              mol_type = protein
                              organism = synthetic construct
SEQUENCE: 71
QQGYSFPFT                                                                    9

SEQ ID NO: 72                 moltype = AA   length = 107
FEATURE                       Location/Qualifiers
REGION                        1..107
                              note = 32D11 VL
source                        1..107
                              mol_type = protein
                              organism = synthetic construct
SEQUENCE: 72
DIQMTQSPSS LSASVGDRVT ITCRASQSIN IWLAWYQQKP GKAPKLLIYD ASNLETGVPS 60
RFSGSGSGTD FTLTISSLQP EDFATYYCQQ GYSFPFTFGP GTKVDIK            107

SEQ ID NO: 73                 moltype = AA   length = 11
FEATURE                       Location/Qualifiers
REGION                        1..11
                              note = 32D2 LCDR1
source                        1..11
                              mol_type = protein
                              organism = synthetic construct
SEQUENCE: 73
RASQGISRWL A                                                                 11

SEQ ID NO: 74                 moltype = AA   length = 7
FEATURE                       Location/Qualifiers
REGION                        1..7
                              note = 32D2 LCDR2
source                        1..7
                              mol_type = protein
                              organism = synthetic construct
SEQUENCE: 74
EASTLQS                                                                      7

SEQ ID NO: 75                 moltype = AA   length = 9
```

-continued

```
FEATURE             Location/Qualifiers
REGION              1..9
                    note = 32D2 LCDR3 / 38B1 LCDR3 / 38H3 LCDR3 / 39G8 LCDR3 /
                     39H7 LCDR3
source              1..9
                    mol_type = protein
                    organism = synthetic construct
SEQUENCE: 75
QQAYSFPFT                                                                    9

SEQ ID NO: 76       moltype = AA  length = 107
FEATURE             Location/Qualifiers
REGION              1..107
                    note = 32D2 VL
source              1..107
                    mol_type = protein
                    organism = synthetic construct
SEQUENCE: 76
DIQMTQSPSS LSASVGDRVT ITCRASQGIS RWLAWYQQKP GKAPKLLIYE ASTLQSGVPS  60
RFSGSGSGTD FTLTISSLQP EDFATYYCQQ AYSFPFTFGQ GTKVDIK              107

SEQ ID NO: 77       moltype = AA  length = 11
FEATURE             Location/Qualifiers
REGION              1..11
                    note = 32G6 LCDR1 / 38A11 LCDR1 / 38A4 LCDR1 / 39A3 LCDR1 /
                     39B11 LCDR1
source              1..11
                    mol_type = protein
                    organism = synthetic construct
SEQUENCE: 77
RASQSISSWL A                                                                11

SEQ ID NO: 78       moltype = AA  length = 7
FEATURE             Location/Qualifiers
REGION              1..7
                    note = 32G6 LCDR2 / 38A11 LCDR2 / 39F11 LCDR2
source              1..7
                    mol_type = protein
                    organism = synthetic construct
SEQUENCE: 78
DASTLQS                                                                      7

SEQ ID NO: 79       moltype = AA  length = 107
FEATURE             Location/Qualifiers
REGION              1..107
                    note = 32G6 VL
source              1..107
                    mol_type = protein
                    organism = synthetic construct
SEQUENCE: 79
DIQMTQSPSS LSASVGDRVT ITCRASQSIS SWLAWYQQKP GKAPKLLIYD ASTLQSGVPS  60
RFSGSGSGTD FTLTISSLQP EDFATYYCQQ ANSFPFTFGP GTKVDIK              107

SEQ ID NO: 80       moltype = AA  length = 11
FEATURE             Location/Qualifiers
REGION              1..11
                    note = 38A10 LCDR1 / 38B1 LCDR1 / 38B10 LCDR1 /39F11 LCDR1
source              1..11
                    mol_type = protein
                    organism = synthetic construct
SEQUENCE: 80
RASQSISTWL A                                                                11

SEQ ID NO: 81       moltype = AA  length = 7
FEATURE             Location/Qualifiers
REGION              1..7
                    note = 38A10 LCDR2
source              1..7
                    mol_type = protein
                    organism = synthetic construct
SEQUENCE: 81
DASRLQN                                                                      7

SEQ ID NO: 82       moltype = AA  length = 9
FEATURE             Location/Qualifiers
REGION              1..9
                    note = 38A10 LCDR3 / 38B2 LCDR3
source              1..9
                    mol_type = protein
```

-continued

```
                                organism = synthetic construct
SEQUENCE: 82
QQGDSFPFT                                                        9

SEQ ID NO: 83          moltype = AA   length = 107
FEATURE                Location/Qualifiers
REGION                 1..107
                       note = 38A10 VL
source                 1..107
                       mol_type = protein
                       organism = synthetic construct
SEQUENCE: 83
DIQMTQSPSS LSASVGDRVT ITCRASQSIS TWLAWYQQKP GKAPKLLIYD ASRLQNGVPS  60
RFSGSGSGTD FTLTISSLQP EDFATYYCQQ GDSFPFTFGP GTKVDIK               107

SEQ ID NO: 84          moltype = AA   length = 9
FEATURE                Location/Qualifiers
REGION                 1..9
                       note = 38A11 LCDR3
source                 1..9
                       mol_type = protein
                       organism = synthetic construct
SEQUENCE: 84
QQGNSFPFT                                                        9

SEQ ID NO: 85          moltype = AA   length = 107
FEATURE                Location/Qualifiers
REGION                 1..107
                       note = 38A11 VL
source                 1..107
                       mol_type = protein
                       organism = synthetic construct
SEQUENCE: 85
DIQMTQSPSS LSASVGDRVT ITCRASQSIS SWLAWYQQKP GKAPKLLIYD ASTLQSGVPS  60
RFSGSGSGTD FTLTISSLQP EDFATYYCQQ GNSFPFTFGP GTKVDIK               107

SEQ ID NO: 86          moltype = AA   length = 7
FEATURE                Location/Qualifiers
REGION                 1..7
                       note = 38A4 LCDR2
source                 1..7
                       mol_type = protein
                       organism = synthetic construct
SEQUENCE: 86
DASNLQT                                                          7

SEQ ID NO: 87          moltype = AA   length = 107
FEATURE                Location/Qualifiers
REGION                 1..107
                       note = 38A4 VL
source                 1..107
                       mol_type = protein
                       organism = synthetic construct
SEQUENCE: 87
DIQMTQSPSS LSASVGDRVT ITCRASQSIS SWLAWYQQKP GKAPKLLIYD ASNLQTGVPS  60
RFSGSGSGTD FTLTISSLQP EDFATYYCQQ ANSFPFTFGQ GTRLEIK               107

SEQ ID NO: 88          moltype = AA   length = 11
FEATURE                Location/Qualifiers
REGION                 1..11
                       note = 38A6 LCDR1
source                 1..11
                       mol_type = protein
                       organism = synthetic construct
SEQUENCE: 88
RASQDISRWL G                                                     11

SEQ ID NO: 89          moltype = AA   length = 7
FEATURE                Location/Qualifiers
REGION                 1..7
                       note = 38A6 LCDR2
source                 1..7
                       mol_type = protein
                       organism = synthetic construct
SEQUENCE: 89
AASTLQS                                                          7

SEQ ID NO: 90          moltype = AA   length = 107
FEATURE                Location/Qualifiers
```

-continued

```
REGION                   1..107
                         note = 38A6 VL
source                   1..107
                         mol_type = protein
                         organism = synthetic construct
SEQUENCE: 90
DIQMTQSPSS LSASVGDRVT ITCRASQDIS RWLGWYQQKP GKAPKLLIYA ASTLQSGVPS    60
RFSGSGSGTD FTLTISSLQP EDFATYYCQQ ANSFPFTFGP GTKLEIK                 107

SEQ ID NO: 91            moltype = AA   length = 107
FEATURE                  Location/Qualifiers
REGION                   1..107
                         note = 38A8 VL
source                   1..107
                         mol_type = protein
                         organism = synthetic construct
SEQUENCE: 91
DIQMTQSPSS LSASVGDRVT ITCRASESIS IWLAWYQQKP GKAPKLLIYD ASNLETGVPS    60
RFSGSGSGTD FTLTISSLQP EDFATYYCQQ ANSFPFTFGP GTKVDIK                 107

SEQ ID NO: 92            moltype = AA   length = 7
FEATURE                  Location/Qualifiers
REGION                   1..7
                         note = 38B1 LCDR2
source                   1..7
                         mol_type = protein
                         organism = synthetic construct
SEQUENCE: 92
EASKLER                                                               7

SEQ ID NO: 93            moltype = AA   length = 107
FEATURE                  Location/Qualifiers
REGION                   1..107
                         note = 38B1 VL
source                   1..107
                         mol_type = protein
                         organism = synthetic construct
SEQUENCE: 93
DIQMTQSPSS LSASVGDRVT ITCRASQSIS TWLAWYQQKP GKAPKLLIYE ASKLERGVPS    60
RFSGSGSGTD FTLTISSLQP EDFATYYCQQ AYSFPFTFGP GTKVDIK                 107

SEQ ID NO: 94            moltype = AA   length = 7
FEATURE                  Location/Qualifiers
REGION                   1..7
                         note = 38B10 LCDR2
source                   1..7
                         mol_type = protein
                         organism = synthetic construct
SEQUENCE: 94
DASTLQT                                                               7

SEQ ID NO: 95            moltype = AA   length = 107
FEATURE                  Location/Qualifiers
REGION                   1..107
                         note = 38B10 VL
source                   1..107
                         mol_type = protein
                         organism = synthetic construct
SEQUENCE: 95
DIQMTQSPSS LSASVGDRVT ITCRASQSIS TWLAWYQQKP GKAPKLLISD ASTLQTGVPS    60
RFSGSGSGTD FTLTISSLQP EDFATYYCQQ GYSFPFTFGP GTKVDIK                 107

SEQ ID NO: 96            moltype = AA   length = 11
FEATURE                  Location/Qualifiers
REGION                   1..11
                         note = 38B2 LCDR1
source                   1..11
                         mol_type = protein
                         organism = synthetic construct
SEQUENCE: 96
RASESISSWL A                                                         11

SEQ ID NO: 97            moltype = AA   length = 7
FEATURE                  Location/Qualifiers
REGION                   1..7
                         note = 38B2 LCDR2
source                   1..7
                         mol_type = protein
                         organism = synthetic construct
```

-continued

```
SEQUENCE: 97
DASSLES                                                                 7

SEQ ID NO: 98              moltype = AA   length = 107
FEATURE                    Location/Qualifiers
REGION                     1..107
                           note = 38B2 VL
source                     1..107
                           mol_type = protein
                           organism = synthetic construct
SEQUENCE: 98
DIQMTQSPSS LSASVGDRVT ITCRASESIS SWLAWYQQKP GKAPKLLIYD ASSLESGVPS    60
RFSGSGSGTD FTLTISSLQP EDFATYYCQQ GDSFPFTFGQ GTKLEIK                  107

SEQ ID NO: 99              moltype = AA   length = 11
FEATURE                    Location/Qualifiers
REGION                     1..11
                           note = 38C11 LCDR1
source                     1..11
                           mol_type = protein
                           organism = synthetic construct
SEQUENCE: 99
RASQSISRWL A                                                           11

SEQ ID NO: 100             moltype = AA   length = 7
FEATURE                    Location/Qualifiers
REGION                     1..7
                           note = 38C11 LCDR2
source                     1..7
                           mol_type = protein
                           organism = synthetic construct
SEQUENCE: 100
DASTVQS                                                                 7

SEQ ID NO: 101             moltype = AA   length = 107
FEATURE                    Location/Qualifiers
REGION                     1..107
                           note = 38C11 VL
source                     1..107
                           mol_type = protein
                           organism = synthetic construct
SEQUENCE: 101
DIQMTQSPSS LSASVGDRVT ITCRASQSIS RWLAWYQQKP GKAPKLLISD ASTVQSGVPS    60
RFSGSGSGTD FTLTISSLQP EDFATYYCQQ ANSFPFTFGP GTKVDIK                  107

SEQ ID NO: 102             moltype = AA   length = 11
FEATURE                    Location/Qualifiers
REGION                     1..11
                           note = 38C6 LCDR1
source                     1..11
                           mol_type = protein
                           organism = synthetic construct
SEQUENCE: 102
RAGRDINKWV A                                                           11

SEQ ID NO: 103             moltype = AA   length = 7
FEATURE                    Location/Qualifiers
REGION                     1..7
                           note = 38C6 LCDR2 / 38G11 LCDR2 / 38G9 LCDR2 / 39A3 LCDR2 /
                            39G5 LCDR2
source                     1..7
                           mol_type = protein
                           organism = synthetic construct
SEQUENCE: 103
DASSLQS                                                                 7

SEQ ID NO: 104             moltype = AA   length = 9
FEATURE                    Location/Qualifiers
REGION                     1..9
                           note = 38C6 LCDR3
source                     1..9
                           mol_type = protein
                           organism = synthetic construct
SEQUENCE: 104
QQANSFPFA                                                               9

SEQ ID NO: 105             moltype = AA   length = 107
FEATURE                    Location/Qualifiers
REGION                     1..107
```

-continued

```
                        note = 38C6 VL
source                  1..107
                        mol_type = protein
                        organism = synthetic construct
SEQUENCE: 105
DIQMTQSPSS LSASVGDRVT ITCRAGRDIN KWVAWYQQKP GKAPKLLIYD ASSLQSGVPS   60
RFSGSGSGTD FTLTISSLQP EDFATYYCQQ ANSFPFAFGQ GTKVEIK               107

SEQ ID NO: 106          moltype = AA  length = 11
FEATURE                 Location/Qualifiers
REGION                  1..11
                        note = 38G11 LCDR1
source                  1..11
                        mol_type = protein
                        organism = synthetic construct
SEQUENCE: 106
RASENISRWL A                                                        11

SEQ ID NO: 107          moltype = AA  length = 107
FEATURE                 Location/Qualifiers
REGION                  1..107
                        note = 38G11 VL
source                  1..107
                        mol_type = protein
                        organism = synthetic construct
SEQUENCE: 107
DIQMTQSPSS LSASVGDRVT ITCRASENIS RWLAWYQQKP GKAPKLLIYD ASSLQSGVPS   60
RFSGSGSGTD FTLTISSLQP EDFATYYCQQ ANSFPFTFGP GTKVDIK               107

SEQ ID NO: 108          moltype = AA  length = 11
FEATURE                 Location/Qualifiers
REGION                  1..11
                        note = 38G9 LCDR1
source                  1..11
                        mol_type = protein
                        organism = synthetic construct
SEQUENCE: 108
RVSQSISNWL A                                                        11

SEQ ID NO: 109          moltype = AA  length = 97
FEATURE                 Location/Qualifiers
REGION                  1..97
                        note = 38G9 VL
source                  1..97
                        mol_type = protein
                        organism = synthetic construct
SEQUENCE: 109
DIQMTQSPSS LSASVGDRVT ITCRVSQSIS NWLAWYQQKP GKAPKLLIYD ASSLQSGVPS   60
RFSGSGSGTD FTLTISSLQP EDFATYYCQQ ANSFPFT                           97

SEQ ID NO: 110          moltype = AA  length = 11
FEATURE                 Location/Qualifiers
REGION                  1..11
                        note = 38H3 LCDR1
source                  1..11
                        mol_type = protein
                        organism = synthetic construct
SEQUENCE: 110
RASQGISTWL A                                                        11

SEQ ID NO: 111          moltype = AA  length = 7
FEATURE                 Location/Qualifiers
REGION                  1..7
                        note = 38H3 LCDR2 / 39B11 LCDR2
source                  1..7
                        mol_type = protein
                        organism = synthetic construct
SEQUENCE: 111
EASRLQS                                                              7

SEQ ID NO: 112          moltype = AA  length = 107
FEATURE                 Location/Qualifiers
REGION                  1..107
                        note = 38H3 VL
source                  1..107
                        mol_type = protein
                        organism = synthetic construct
SEQUENCE: 112
DIQMTQSPSS LSASVGDRVT ITCRASQGIS TWLAWYQQKP GKAPKLLIYE ASRLQSGVPS   60
```

-continued

```
RFSGSGSGTD FTLTISSLQP EDFATYYCQQ AYSFPFTFGP GTKVDIK                    107

SEQ ID NO: 113          moltype = AA  length = 9
FEATURE                 Location/Qualifiers
REGION                  1..9
                        note = 39A3 LCDR3
source                  1..9
                        mol_type = protein
                        organism = synthetic construct
SEQUENCE: 113
QQGDSFPLT                                                              9

SEQ ID NO: 114          moltype = AA  length = 107
FEATURE                 Location/Qualifiers
REGION                  1..107
                        note = 39A3 VL
source                  1..107
                        mol_type = protein
                        organism = synthetic construct
SEQUENCE: 114
DIQMTQSPSS LSASVGDRVT ITCRASQSIS SWLAWYQQKP GKAPKLLIYD ASSLQSGVPS     60
RFSGSGSGTD FTLTISSLQP EDFATYYCQQ GDSFPLTFGQ GTKVEIK                   107

SEQ ID NO: 115          moltype = AA  length = 107
FEATURE                 Location/Qualifiers
REGION                  1..107
                        note = 39B11 VL
source                  1..107
                        mol_type = protein
                        organism = synthetic construct
SEQUENCE: 115
DIQMTQSPSS LSASVGDRVT ITCRASQSIS SWLAWYQQKP GKAPKLLIYE ASRLQSGVPS     60
RFSGSGSGTD FTLTISSLQP EDFATYYCQQ ANSFPFTFGP GTKVDIK                   107

SEQ ID NO: 116          moltype = AA  length = 11
FEATURE                 Location/Qualifiers
REGION                  1..11
                        note = 39B3 LCDR1
source                  1..11
                        mol_type = protein
                        organism = synthetic construct
SEQUENCE: 116
RASQSIGPWL A                                                          11

SEQ ID NO: 117          moltype = AA  length = 107
FEATURE                 Location/Qualifiers
REGION                  1..107
                        note = 39B3 VL
source                  1..107
                        mol_type = protein
                        organism = synthetic construct
SEQUENCE: 117
DIQMTQSPSS LSASVGDRVT ITCRASQSIG PWLAWYQQKP GKAPKLLIYD ASNLETGVPS     60
RFSGSGSGTD FTLTISSLQP EDFATYYCQQ ANSFPFTFGP GTKVDIK                   107

SEQ ID NO: 118          moltype = AA  length = 11
FEATURE                 Location/Qualifiers
REGION                  1..11
                        note = 39B6 LCDR1
source                  1..11
                        mol_type = protein
                        organism = synthetic construct
SEQUENCE: 118
RASEDISHWL A                                                          11

SEQ ID NO: 119          moltype = AA  length = 7
FEATURE                 Location/Qualifiers
REGION                  1..7
                        note = 39B6 LCDR2
source                  1..7
                        mol_type = protein
                        organism = synthetic construct
SEQUENCE: 119
DAKDLHP                                                               7

SEQ ID NO: 120          moltype = AA  length = 107
FEATURE                 Location/Qualifiers
REGION                  1..107
                        note = 39B6 VL
```

-continued

```
source                  1..107
                        mol_type = protein
                        organism = synthetic construct
SEQUENCE: 120
DIQMTQSPSS LSASVGDRVT ITCRASEDIS HWLAWYQQKP GKAPKLLIYD AKDLHPGVPS    60
RFSGSGSGTD FTLTISSLQP EDFATYYCQQ ANSFPFTFGQ GTRLEIK                 107

SEQ ID NO: 121          moltype = AA  length = 107
FEATURE                 Location/Qualifiers
REGION                  1..107
                        note = 39F11 VL
source                  1..107
                        mol_type = protein
                        organism = synthetic construct
SEQUENCE: 121
DIQMTQSPSS LSASVGDRVT ITCRASQSIS TWLAWYQQKP GKAPKLLIYD ASTLQSGVPS    60
RFSGSGSGTD FTLTISSLQP EDFATYYCQQ ANSFPFTFGP GTKVDIK                 107

SEQ ID NO: 122          moltype = AA  length = 11
FEATURE                 Location/Qualifiers
REGION                  1..11
                        note = 39G5 LCDR1
source                  1..11
                        mol_type = protein
                        organism = synthetic construct
SEQUENCE: 122
RASQNINVWL A                                                         11

SEQ ID NO: 123          moltype = AA  length = 107
FEATURE                 Location/Qualifiers
REGION                  1..107
                        note = 39G5 VL
source                  1..107
                        mol_type = protein
                        organism = synthetic construct
SEQUENCE: 123
DIQMTQSPSS LSASVGDRVT ITCRASQNIN VWLAWYQQKP GKAPKLLIYD ASSLQSGVPS    60
RFSGSGSGTD FTLTISSLQP EDFATYYCQQ ANSFPFTFGP GTKVDIK                 107

SEQ ID NO: 124          moltype = AA  length = 11
FEATURE                 Location/Qualifiers
REGION                  1..11
                        note = 39G8 LCDR1
source                  1..11
                        mol_type = protein
                        organism = synthetic construct
SEQUENCE: 124
RASQGISPWL A                                                         11

SEQ ID NO: 125          moltype = AA  length = 7
FEATURE                 Location/Qualifiers
REGION                  1..7
                        note = 39G8 LCDR2
source                  1..7
                        mol_type = protein
                        organism = synthetic construct
SEQUENCE: 125
DASKLET                                                               7

SEQ ID NO: 126          moltype = AA  length = 107
FEATURE                 Location/Qualifiers
REGION                  1..107
                        note = 39G8 VL
source                  1..107
                        mol_type = protein
                        organism = synthetic construct
SEQUENCE: 126
DIQMTQSPSS LSASVGDRVT ITCRASQGIS PWLAWYQQKP GKAPKLLIYD ASKLETGVPS    60
RFSGSGSGTD FTLTISSLQP EDFATYYCQQ AYSFPFTFGG GTKVEIK                 107

SEQ ID NO: 127          moltype = AA  length = 11
FEATURE                 Location/Qualifiers
REGION                  1..11
                        note = 39H11 LCDR1
source                  1..11
                        mol_type = protein
                        organism = synthetic construct
SEQUENCE: 127
RASQSIGIWV A                                                         11
```

```
SEQ ID NO: 128          moltype = AA   length = 107
FEATURE                 Location/Qualifiers
REGION                  1..107
                        note = 39H11 VL
source                  1..107
                        mol_type = protein
                        organism = synthetic construct
SEQUENCE: 128
DIQMTQSPSS LSASVGDRVT ITCRASQSIG IWVAWYQQKP GKAPKLLIYD ASNLQSGVPS     60
RFSGSGSGTD FTLTISSLQP EDFATYYCQQ ADSFPFTFGQ GTKVEIK                  107

SEQ ID NO: 129          moltype = AA   length = 11
FEATURE                 Location/Qualifiers
REGION                  1..11
                        note = 39H2 LCDR1
source                  1..11
                        mol_type = protein
                        organism = synthetic construct
SEQUENCE: 129
RASQNIGPWL A                                                          11

SEQ ID NO: 130          moltype = AA   length = 7
FEATURE                 Location/Qualifiers
REGION                  1..7
                        note = 39H2 LCDR2
source                  1..7
                        mol_type = protein
                        organism = synthetic construct
SEQUENCE: 130
DASTLHS                                                                7

SEQ ID NO: 131          moltype = AA   length = 107
FEATURE                 Location/Qualifiers
REGION                  1..107
                        note = 39H2 VL
source                  1..107
                        mol_type = protein
                        organism = synthetic construct
SEQUENCE: 131
DIQMTQSPSS LSASVGDRVT ITCRASQNIG PWLAWYQQKP GKAPKLLIYD ASTLHSGVPS     60
RFSGSGSGTD FTLTISSLQP EDFATYYCQQ ANSFPFTFGQ GTRLEIK                  107

SEQ ID NO: 132          moltype = AA   length = 11
FEATURE                 Location/Qualifiers
REGION                  1..11
                        note = 39H7 LCDR1
source                  1..11
                        mol_type = protein
                        organism = synthetic construct
SEQUENCE: 132
RASQSISNWL A                                                          11

SEQ ID NO: 133          moltype = AA   length = 7
FEATURE                 Location/Qualifiers
REGION                  1..7
                        note = 39H7 LCDR2
source                  1..7
                        mol_type = protein
                        organism = synthetic construct
SEQUENCE: 133
DASNLQA                                                                7

SEQ ID NO: 134          moltype = AA   length = 107
FEATURE                 Location/Qualifiers
REGION                  1..107
                        note = 39H7 VL
source                  1..107
                        mol_type = protein
                        organism = synthetic construct
SEQUENCE: 134
DIQMTQSPSS LSASVGDRVT ITCRASQSIS NWLAWYQQKP GKAPKLLIYD ASNLQAGVPS     60
RFSGSGSGTD FTLTISSLQP EDFATYYCQQ AYSFPFTFGP GTKVDIK                  107

SEQ ID NO: 135          moltype =    length =
SEQUENCE: 135
000

SEQ ID NO: 136          moltype =    length =
```

```
SEQUENCE: 136
000

SEQ ID NO: 137        moltype = AA  length = 9
FEATURE               Location/Qualifiers
REGION                1..9
                      note = 24H9 derivatives motif LCR3
VARIANT               3
                      note = X can be A, or G
VARIANT               4
                      note = X can be N, D, or Y
VARIANT               8
                      note = X can be F or L
VARIANT               9
                      note = X can be A, or T
source                1..9
                      mol_type = protein
                      organism = synthetic construct
SEQUENCE: 137
QQXXSFPXX                                                          9

SEQ ID NO: 138        moltype = AA  length = 107
FEATURE               Location/Qualifiers
REGION                1..107
                      note = 24H9 derivatives motif VL
VARIANT               25
                      note = X can be A or V
VARIANT               26
                      note = X can be S or G
VARIANT               27
                      note = X can be Q, E, or R
VARIANT               28
                      note = X can be G, S, D or N
VARIANT               30
                      note = X can be G, S, or N
VARIANT               31
                      note = X can be S, I, R, T, K, P, N,H, or V
VARIANT               33
                      note = X can be L or V
VARIANT               34
                      note = X can be G or A
VARIANT               50
                      note = X can be S, D, E, or A
VARIANT               52
                      note = X can be S, or K
VARIANT               53
                      note = X can be S, N, T, R, or D
VARIANT               54
                      note = X can be L or V
VARIANT               55
                      note = X can be Q, E, or H
VARIANT               56
                      note = X can be S, N, A, R, P, or T
VARIANT               91
                      note = X can be A, or G
VARIANT               92
                      note = X can be N, D, or Y
VARIANT               96
                      note = X can be F or L
VARIANT               97
                      note = X can be A, or T
source                1..107
                      mol_type = protein
                      organism = synthetic construct
SEQUENCE: 138
DIQMTQSPSS LSASVGDRVT ITCRXXXXIX XWXXWYQQKP GKAPKLLIYX AXXXXXGVPS   60
RFSGSGSGTD FTLTISSLQP EDFATYYCQQ XXSFPXXFGP GTKVDIK                107

SEQ ID NO: 139        moltype = AA  length = 10
FEATURE               Location/Qualifiers
REGION                1..10
                      note = R3A9 HCDR1
source                1..10
                      mol_type = protein
                      organism = synthetic construct
SEQUENCE: 139
GHTFTSYYIH                                                         10

SEQ ID NO: 140        moltype = AA  length = 18
```

-continued

```
FEATURE              Location/Qualifiers
REGION               1..18
                     note = R3A9 HCDR2
source               1..18
                     mol_type = protein
                     organism = synthetic construct
SEQUENCE: 140
GIINPSGGST SYAQKFQG                                              18

SEQ ID NO: 141       moltype = AA   length = 10
FEATURE              Location/Qualifiers
REGION               1..10
                     note = R3A9 HCDR3
source               1..10
                     mol_type = protein
                     organism = synthetic construct
SEQUENCE: 141
DRAYGGAGDY                                                      10

SEQ ID NO: 142       moltype = AA   length = 119
FEATURE              Location/Qualifiers
REGION               1..119
                     note = R3A9 VH
source               1..119
                     mol_type = protein
                     organism = synthetic construct
SEQUENCE: 142
QVQLVQSGAE VKKPGASVKV SCKASGHTFT SYYIHWVRQA PGQGLEWMGI INPSGGSTSY  60
AQKFQGRVTM TRDTSTSTVY MELSSLRSED TAVYYCARDR AYGGAGDYWG QGTLVTVSS  119

SEQ ID NO: 143       moltype = AA   length = 11
FEATURE              Location/Qualifiers
REGION               1..11
                     note = R3A9 LCDR1
source               1..11
                     mol_type = protein
                     organism = synthetic construct
SEQUENCE: 143
RASQSVGTWL A                                                    11

SEQ ID NO: 144       moltype = AA   length = 7
FEATURE              Location/Qualifiers
REGION               1..7
                     note = R3A9 LCDR2
source               1..7
                     mol_type = protein
                     organism = synthetic construct
SEQUENCE: 144
SASTLQS                                                          7

SEQ ID NO: 145       moltype = AA   length = 9
FEATURE              Location/Qualifiers
REGION               1..9
                     note = R3A9 LCDR3
source               1..9
                     mol_type = protein
                     organism = synthetic construct
SEQUENCE: 145
QQSYSAPLT                                                        9

SEQ ID NO: 146       moltype = AA   length = 107
FEATURE              Location/Qualifiers
REGION               1..107
                     note = R3A9 VL
source               1..107
                     mol_type = protein
                     organism = synthetic construct
SEQUENCE: 146
DIQMTQSPSS LSASVGDRVT ITCRASQSVG TWLAWYQQKP GKAPKLLIYS ASTLQSGVPS  60
RFSGSGSGTD FTLTISSLQP EDFATYYCQQ SYSAPLTFGG GTKVEIK             107

SEQ ID NO: 147       moltype = AA   length = 11
FEATURE              Location/Qualifiers
REGION               1..11
                     note = m3A7 LCDR1
source               1..11
                     mol_type = protein
                     organism = synthetic construct
SEQUENCE: 147
```

-continued

```
RASRSISNWL A                                                     11

SEQ ID NO: 148          moltype = AA   length = 7
FEATURE                 Location/Qualifiers
REGION                  1..7
                        note = m3A7 LCDR2 / m2C1 LCDR2
source                  1..7
                        mol_type = protein
                        organism = synthetic construct
SEQUENCE: 148
AASSLQS                                                          7

SEQ ID NO: 149          moltype = AA   length = 9
FEATURE                 Location/Qualifiers
REGION                  1..9
                        note = m3A7 LCDR3
source                  1..9
                        mol_type = protein
                        organism = synthetic construct
SEQUENCE: 149
QQSYSAPVT                                                        9

SEQ ID NO: 150          moltype = AA   length = 107
FEATURE                 Location/Qualifiers
REGION                  1..107
                        note = m3A7 VL
source                  1..107
                        mol_type = protein
                        organism = synthetic construct
SEQUENCE: 150
DIQMTQSPSS LSASVGDRVT ITCRASRSIS NWLAWYQQKP GKAPKLLIYA ASSLQSGVPS  60
RFSGSGSGTD FTLTISSLQP EDFATYYCQQ SYSAPVTFGQ GTKVEIK             107

SEQ ID NO: 151          moltype = AA   length = 11
FEATURE                 Location/Qualifiers
REGION                  1..11
                        note = m2C1 LCDR1
source                  1..11
                        mol_type = protein
                        organism = synthetic construct
SEQUENCE: 151
RASRSISSWL A                                                     11

SEQ ID NO: 152          moltype = AA   length = 9
FEATURE                 Location/Qualifiers
REGION                  1..9
                        note = m2C1 LCDR3
source                  1..9
                        mol_type = protein
                        organism = synthetic construct
SEQUENCE: 152
QQSYSIPAT                                                        9

SEQ ID NO: 153          moltype = AA   length = 107
FEATURE                 Location/Qualifiers
REGION                  1..107
                        note = m2C1 VL
source                  1..107
                        mol_type = protein
                        organism = synthetic construct
SEQUENCE: 153
DIQMTQSPSS LSASVGDRVT ITCRASRSIS SWLAWYQQKP GKAPKLLIYA ASSLQSGVPS  60
RFSGSGSGTD FTLTISSLQP EDFATYYCQQ SYSIPATFGQ GTKVEIK             107

SEQ ID NO: 154          moltype = AA   length = 11
FEATURE                 Location/Qualifiers
REGION                  1..11
                        note = m2A1 LCDR1
source                  1..11
                        mol_type = protein
                        organism = synthetic construct
SEQUENCE: 154
RASRGISSWL A                                                     11

SEQ ID NO: 155          moltype = AA   length = 9
FEATURE                 Location/Qualifiers
REGION                  1..9
                        note = m2A1 LCDR3
source                  1..9
```

```
                          mol_type = protein
                          organism = synthetic construct
SEQUENCE: 155
QQSYSPPWT                                                         9

SEQ ID NO: 156           moltype = AA  length = 107
FEATURE                  Location/Qualifiers
REGION                   1..107
                         note = m2A1 VL
source                   1..107
                         mol_type = protein
                         organism = synthetic construct
SEQUENCE: 156
DIQMTQSPSS LSASVGDRVT ITCRASRGIS SWLAWYQQKP GKAPKLLIYA ASSLQSGVPS  60
RFSGSGSGTD FTLTISSLQP EDFATYYCQQ SYSPPWTFGQ GTKVEIK               107

SEQ ID NO: 157           moltype = AA  length = 11
FEATURE                  Location/Qualifiers
REGION                   1..11
                         note = m4A5 LCDR1 / m3C6 LCDR1
source                   1..11
                         mol_type = protein
                         organism = synthetic construct
SEQUENCE: 157
RASQSIDTWL A                                                      11

SEQ ID NO: 158           moltype = AA  length = 7
FEATURE                  Location/Qualifiers
REGION                   1..7
                         note = m4A5 LCDR2
source                   1..7
                         mol_type = protein
                         organism = synthetic construct
SEQUENCE: 158
AASTLES                                                           7

SEQ ID NO: 159           moltype = AA  length = 9
FEATURE                  Location/Qualifiers
REGION                   1..9
                         note = m4A5 LCDR3
source                   1..9
                         mol_type = protein
                         organism = synthetic construct
SEQUENCE: 159
QQSYRAPLT                                                         9

SEQ ID NO: 160           moltype = AA  length = 107
FEATURE                  Location/Qualifiers
REGION                   1..107
                         note = m4A5 VL
source                   1..107
                         mol_type = protein
                         organism = synthetic construct
SEQUENCE: 160
DIQMTQSPSS LSASVGDRVT ITCRASQSID TWLAWYQQKP GKAPKLLIYA ASTLESGVPS  60
RFSGSGSGTD FTLTISSLQP EDFATYYCQQ SYRAPLTFGQ GTKVEIK               107

SEQ ID NO: 161           moltype = AA  length = 11
FEATURE                  Location/Qualifiers
REGION                   1..11
                         note = m4D1 LCDR1
source                   1..11
                         mol_type = protein
                         organism = synthetic construct
SEQUENCE: 161
RASQSISAWL A                                                      11

SEQ ID NO: 162           moltype = AA  length = 7
FEATURE                  Location/Qualifiers
REGION                   1..7
                         note = m4D1 LCDR2
source                   1..7
                         mol_type = protein
                         organism = synthetic construct
SEQUENCE: 162
KASSLES                                                           7

SEQ ID NO: 163           moltype = AA  length = 9
FEATURE                  Location/Qualifiers
```

-continued

```
REGION                  1..9
                        note = m4D1 LCDR3
source                  1..9
                        mol_type = protein
                        organism = synthetic construct
SEQUENCE: 163
QQSYSPPAT                                                               9

SEQ ID NO: 164          moltype = AA   length = 107
FEATURE                 Location/Qualifiers
REGION                  1..107
                        note = m4D1 VL
source                  1..107
                        mol_type = protein
                        organism = synthetic construct
SEQUENCE: 164
DIQMTQSPSS LSASVGDRVT ITCRASQSIS AWLAWYQQKP GKAPKLLIYK ASSLESGVPS  60
RFSGSGSGTD FTLTISSLQP EDFATYYCQQ SYSPPATFGG GTKVEIK              107

SEQ ID NO: 165          moltype = AA   length = 7
FEATURE                 Location/Qualifiers
REGION                  1..7
                        note = m3C6 LCDR2
source                  1..7
                        mol_type = protein
                        organism = synthetic construct
SEQUENCE: 165
EASSLQG                                                                 7

SEQ ID NO: 166          moltype = AA   length = 8
FEATURE                 Location/Qualifiers
REGION                  1..8
                        note = m3C6 LCDR3
source                  1..8
                        mol_type = protein
                        organism = synthetic construct
SEQUENCE: 166
QQSYSTWT                                                                8

SEQ ID NO: 167          moltype = AA   length = 106
FEATURE                 Location/Qualifiers
REGION                  1..106
                        note = m3C6 VL
source                  1..106
                        mol_type = protein
                        organism = synthetic construct
SEQUENCE: 167
DIQMTQSPSS LSASVGDRVT ITCRASQSID TWLAWYQQKP GKAPKLLIYE ASSLQGGVPS  60
RFSGSGSGTD FTLTISSLQP EDFATYYCQQ SYSTWTFGQG TKVEIK              106

SEQ ID NO: 168          moltype = AA   length = 447
FEATURE                 Location/Qualifiers
REGION                  1..447
                        note = 38B2 full length HC
source                  1..447
                        mol_type = protein
                        organism = synthetic construct
SEQUENCE: 168
EVQLLESGGG LVQPGGSLRL SCAASGFTFS SYWMSWVRQA PGKGLEWVSA ISGSGGSTYY  60
ADSVKGRFTI SRDNSKNTLY LQMNSLRAED TAVYYCASSP LQWVDVWGQG TTVTVSSAST 120
KGPSVFPLAP SSKSTSGGTA ALGCLVKDYF PEPVTVSWNS GALTSGVHTF PAVLQSSGLY 180
SLSSVVTVPS SSLGTQTYIC NVNHKPSNTK VDKRVEPKSC DKTHTCPPCP APELLGGPSV 240
FLFPPKPKDT LMISRTPEVT CVVVDVSHED PEVKFNWYVD GVEVHNAKTK PREEQYNSTY 300
RVVSVLTVLH QDWLNGKEYK CKVSNKALPA PIEKTISKAK GQPREPQVYT LPPSREEMTK 360
NQVSLTCLVK GFYPSDIAVE WESNGQPENN YKTTPPVLDS DGSFFLYSKL TVDKSRWQQG 420
NVFSCSVMHE ALHNHYTQKS LSLSPGK                                  447

SEQ ID NO: 169          moltype = AA   length = 447
FEATURE                 Location/Qualifiers
REGION                  1..447
                        note = 38B2 HC (T350V/T366L/ K392L/ T394W) LALAPG
source                  1..447
                        mol_type = protein
                        organism = synthetic construct
SEQUENCE: 169
EVQLLESGGG LVQPGGSLRL SCAASGFTFS SYWMSWVRQA PGKGLEWVSA ISGSGGSTYY  60
ADSVKGRFTI SRDNSKNTLY LQMNSLRAED TAVYYCASSP LQWVDVWGQG TTVTVSSAST 120
KGPSVFPLAP SSKSTSGGTA ALGCLVKDYF PEPVTVSWNS GALTSGVHTF PAVLQSSGLY 180
SLSSVVTVPS SSLGTQTYIC NVNHKPSNTK VDKRVEPKSC DKTHTCPPCP APEAAGGPSV 240
```

-continued

```
FLFPPKPKDT LMISRTPEVT CVVVDVSHED PEVKFNWYVD GVEVHNAKTK PREEQYNSTY    300
RVVSVLTVLH QDWLNGKEYK CKVSNKALGA PIEKTISKAK GQPREPQVYV LPPSREEMTK    360
NQVSLLCLVK GFYPSDIAVE WESNGQPENN YLTWPPVLDS DGSFFLYSKL TVDKSRWQQG    420
NVFSCSVMHE ALHNHYTQKS LSLSPGK                                        447

SEQ ID NO: 170            moltype = AA  length = 214
FEATURE                   Location/Qualifiers
REGION                    1..214
                          note = 38B2 full length LC
source                    1..214
                          mol_type = protein
                          organism = synthetic construct
SEQUENCE: 170
DIQMTQSPSS LSASVGDRVT ITCRASESIS SWLAWYQQKP GKAPKLLIYD ASSLESGVPS    60
RFSGSGSGTD FTLTISSLQP EDFATYYCQQ GDSFPFTFGQ GTKLEIKRTV AAPSVFIFPP    120
SDEQLKSGTA SVVCLLNNFY PREAKVQWKV DNALQSGNSQ ESVTEQDSKD STYSLSSTLT    180
LSKADYEKHK VYACEVTHQG LSSPVTKSFN RGEC                                214

SEQ ID NO: 171            moltype = AA  length = 449
FEATURE                   Location/Qualifiers
REGION                    1..449
                          note = m3A7 full length mHC LALAPG
source                    1..449
                          mol_type = protein
                          organism = synthetic construct
SEQUENCE: 171
QVQLVQSGAE VKKPGASVKV SCKASGHTFT SYYIHWVRQA PGQGLEWMGI INPSGGSTSY    60
AQKFQGRVTM TRDTSTSTVY MELSSLRSED TAVYYCARDR AYGGAGDYWG QGTLVTVSSA    120
KTTAPSVYPL APVCGDTTGS SVTLGCLVKG YFPEPVTLTW NSGSLSSGVH TFPAVLQSDL    180
YTLSSSVTVT SSTWPSQSIT CNVAHPASST KVDKKIEPRG PTIKPCPPCK CPAPNAAGGP    240
SVFIFPPKIK DVLMISLSPI VTCVVVDVSE DDPDVQISWF VNNVEVHTAQ TQTHREDYNS    300
TLRVVSALPI QHQDWMSGKE FKCKVNNKDL GAPIERTISK PKGSVRAPQV YVLPPPEEEM    360
TKKQVTLTCM VTDFMPEDIY VEWTNNGKTE LNYKNTEPVL DSDGSYFMYS KLRVEKKNWV    420
ERNSYSCSVV HEGLHNHHTT KSFSRTPGK                                      449

SEQ ID NO: 172            moltype = AA  length = 449
FEATURE                   Location/Qualifiers
REGION                    1..449
                          note = m3A7 mHC (L351Y/F405A/Y407V) LALAPG
source                    1..449
                          mol_type = protein
                          organism = synthetic construct
SEQUENCE: 172
QVQLVQSGAE VKKPGASVKV SCKASGHTFT SYYIHWVRQA PGQGLEWMGI INPSGGSTSY    60
AQKFQGRVTM TRDTSTSTVY MELSSLRSED TAVYYCARDR AYGGAGDYWG QGTLVTVSSA    120
KTTAPSVYPL APVCGDTTGS SVTLGCLVKG YFPEPVTLTW NSGSLSSGVH TFPAVLQSDL    180
YTLSSSVTVT SSTWPSQSIT CNVAHPASST KVDKKIEPRG PTIKPCPPCK CPAPNAAGGP    240
SVFIFPPKIK DVLMISLSPI VTCVVVDVSE DDPDVQISWF VNNVEVHTAQ TQTHREDYNS    300
TLRVVSALPI QHQDWMSGKE FKCKVNNKDL GAPIERTISK PKGSVRAPQV YVYPPPEEEM    360
TKKQVTLTCM VTDFMPEDIY VEWTNNGKTE LNYKNTEPVL DSDGSYAMVS KLRVEKKNWV    420
ERNSYSCSVV HEGLHNHHTT KSFSRTPGK                                      449

SEQ ID NO: 173            moltype = AA  length = 214
FEATURE                   Location/Qualifiers
REGION                    1..214
                          note = m3A7 full length mLC
source                    1..214
                          mol_type = protein
                          organism = synthetic construct
SEQUENCE: 173
DIQMTQSPSS LSASVGDRVT ITCRASRSIS NWLAWYQQKP GKAPKLLIYA ASSLQSGVPS    60
RFSGSGSGTD FTLTISSLQP EDFATYYCQQ SYSAPVTFGQ GTKVEIKRAD AAPTVSIFPP    120
SSEQLTSGGA SVVCFLNNFY PKDINVKWKI DGSERQNGVL NSWTDQDSKD STYSMSSTLT    180
LTKDEYERHN SYTCEATHKT STSPIVKSFN RNEC                                214

SEQ ID NO: 174            moltype = AA  length = 688
FEATURE                   Location/Qualifiers
REGION                    1..688
                          note = hSD15 + 38B2 HC LALAPG
source                    1..688
                          mol_type = protein
                          organism = synthetic construct
SEQUENCE: 174
ITCPPPMSVE HADIWVKSYS LYSRERYICN SGFKRKAGTS SLTECVLNKA TNVAHWTTPS    60
LKCIRDPALV HQRPAPPSGG SGGGGSGGGS GGGGSLQNWV NVISDLKKIE DLIQSMHIDA    120
TLYTESDVHP SCKVTAMKCF LLELQVISLE SGDASIHDTV ENLIILANNS LSSNGNVTES    180
GCKECEELEE KNIKEFLQSF VHIVQMFINT SGGGSGGGG SGGGGSGGGG SGGGGSGGGG    240
SEVQLLESGG GLVQPGGSLR LSCAASGFTF SSYWMSWVRQ APGKGLEWVS AISGSGGSTY    300
YADSVKGRFT ISRDNSKNTL YLQMNSLRAE DTAVYYCASS PLQWVDVWGQ GTTVTVSSAS    360
```

```
TKGPSVFPLA PSSKSTSGGT AALGCLVKDY FPEPVTVSWN SGALTSGVHT FPAVLQSSGL  420
YSLSSVVTVP SSSLGTQTYI CNVNHKPSNT KVDKRVEPKS CDKTHTCPPC PAPEAAGGPS  480
VPLFPPKPKD TLMISRTPEV TCVVVDVSHE DPEVKFNWYV DGVEVHNAKT KPREEQYNST  540
YRVVSVLTVL HQDWLNGKEY KCKVSNKALG APIEKTISKA KGQPREPQVY TLPPSREEMT  600
KNQVSLTCLV KGFYPSDIAV EWESNGQPEN NYKTTPPVLD SDGSFFLYSK LTVDKSRWQQ  660
GNVFSCSVMH EALHNHYTQK SLSLSPGK                                     688

SEQ ID NO: 175              moltype = AA  length = 688
FEATURE                     Location/Qualifiers
REGION                      1..688
                            note = hSD15 + 38B2HC (T350V/L351Y/F405A/Y407V) LALAPG
source                      1..688
                            mol_type = protein
                            organism = synthetic construct
SEQUENCE: 175
ITCPPPMSVE HADIWVKSYS LYSRERYICN SGFKRKAGTS SLTECVLNKA TNVAHWTTPS  60
LKCIRDPALV HQRPAPPSGG SGGGGSGGGS GGGGSLQNWV NVISDLKKIE DLIQSMHIDA  120
TLYTESDVHP SCKVTAMKCF LLELQVISLE SGDASIHDTV ENLIILANNS LSSNGNVTES  180
GCKECEELEE KNIKEFLQSF VHIVQMFINT SGGGGSGGGG SGGGGSGGGG SGGGGSGGGG  240
SEVQLLESGG GLVQPGGSLR LSCAASGFTF SSYWMSWVRQ APGKGLEWVS AISGSGGSTY  300
YADSVKGRFT ISRDNSKNTL YLQMNSLRAE DTAVYYCASS PLQWVDVWGQ GTTVTVSSAS  360
TKGPSVFPLA PSSKSTSGGT AALGCLVKDY FPEPVTVSWN SGALTSGVHT FPAVLQSSGL  420
YSLSSVVTVP SSSLGTQTYI CNVNHKPSNT KVDKRVEPKS CDKTHTCPPC PAPEAAGGPS  480
VPLFPPKPKD TLMISRTPEV TCVVVDVSHE DPEVKFNWYV DGVEVHNAKT KPREEQYNST  540
YRVVSVLTVL HQDWLNGKEY KCKVSNKALG APIEKTISKA KGQPREPQVY VYPPSREEMT  600
KNQVSLTCLV KGFYPSDIAV EWESNGQPEN NYKTTPPVLD SDGSFALVSK LTVDKSRWQQ  660
GNVFSCSVMH EALHNHYTQK SLSLSPGK                                     688

SEQ ID NO: 176              moltype = AA  length = 656
FEATURE                     Location/Qualifiers
REGION                      1..656
                            note = 38B2HC LALAPG + hSD15
source                      1..656
                            mol_type = protein
                            organism = synthetic construct
SEQUENCE: 176
EVQLLESGGG LVQPGGSLRL SCAASGFTFS SYWMSWVRQA PGKGLEWVSA ISGSGGSTYY  60
ADSVKGRFTI SRDNSKNTLY LQMNSLRAED TAVYYCASSP LQWVDVWGQG TTVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKRVEPKSC DKTHTCPPCP APEAAGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALGA PIEKTISKAK GQPREPQVYT LPPSREEMTK  360
NQVSLTCLVK GFYPSDIAVE WESNGQPENN YKTTPPVLDS DGSFFLYSKL TVDKSRWQQG  420
NVFSCSVMHE ALHNHYTQKS LSLSPGSCPP PMSVEHADIW VKSYSLYSRE RYICNSGFKR  480
KAGTSSLTEC VLNKATNVAH WTTPSLKCIR DPALVHQRPA PPSGGSGGGG SGGGGSGGGS  540
LQNWVNVISD LKKIEDLIQS MHIDATLYTE SDVHPSCKVT AMKCFLLELQ VISLESGDAS  600
IHDTVENLII LANNSLSSNG NVTESGCKEC EELEEKNIKE FLQSFVHIVQ MFINTS      656

SEQ ID NO: 177              moltype = AA  length = 656
FEATURE                     Location/Qualifiers
REGION                      1..656
                            note = 38B2 HC (T350V/L351Y/F405A/Y407V) LALAPG + hSD15
source                      1..656
                            mol_type = protein
                            organism = synthetic construct
SEQUENCE: 177
EVQLLESGGG LVQPGGSLRL SCAASGFTFS SYWMSWVRQA PGKGLEWVSA ISGSGGSTYY  60
ADSVKGRFTI SRDNSKNTLY LQMNSLRAED TAVYYCASSP LQWVDVWGQG TTVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKRVEPKSC DKTHTCPPCP APEAAGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALGA PIEKTISKAK GQPREPQVYV YPPSREEMTK  360
NQVSLTCLVK GFYPSDIAVE WESNGQPENN YKTTPPVLDS DGSFALVSKL TVDKSRWQQG  420
NVFSCSVMHE ALHNHYTQKS LSLSPGSCPP PMSVEHADIW VKSYSLYSRE RYICNSGFKR  480
KAGTSSLTEC VLNKATNVAH WTTPSLKCIR DPALVHQRPA PPSGGSGGGG SGGGGSGGGS  540
LQNWVNVISD LKKIEDLIQS MHIDATLYTE SDVHPSCKVT AMKCFLLELQ VISLESGDAS  600
IHDTVENLII LANNSLSSNG NVTESGCKEC EELEEKNIKE FLQSFVHIVQ MFINTS      656

SEQ ID NO: 178              moltype = AA  length = 688
FEATURE                     Location/Qualifiers
REGION                      1..688
                            note = N65A_hSD15+38B2 HC (T350V/L351Y/F405A/Y407V) LALAPG
source                      1..688
                            mol_type = protein
                            organism = synthetic construct
SEQUENCE: 178
ITCPPPMSVE HADIWVKSYS LYSRERYICN SGFKRKAGTS SLTECVLNKA TNVAHWTTPS  60
LKCIRDPALV HQRPAPPSGG SGGGGSGGGS GGGGSLQNWV NVISDLKKIE DLIQSMHIDA  120
TLYTESDVHP SCKVTAMKCF LLELQVISLE SGDASIHDTV EALIILANNS LSSNGNVTES  180
```

-continued

```
GCKECEELEE KNIKEFLQSF VHIVQMFINT SGGGGSGGGG SGGGGSGGGG SGGGGSGGGG   240
SEVQLLESGG GLVQPGGSLR LSCAASGFTF SSYWMSWVRQ APGKGLEWVS AISGSGGSTY   300
YADSVKGRFT ISRDNSKNTL YLQMNSLRAE DTAVYYCASS PLQWVDVWGQ GTTVTVSSAS   360
TKGPSVFPLA PSSKSTSGGT AALGCLVKDY FPEPVTVSWN SGALTSGVHT FPAVLQSSGL   420
YSLSSVVTVP SSSLGTQTYI CNVNHKPSNT KVDKRVEPKS CDKTHTCPPC PAPEAAGGPS   480
VFLFPPKPKD TLMISRTPEV TCVVVDVSHE DPEVKFNWYV DGVEVHNAKT KPREEQYNST   540
YRVVSVLTVL HQDWLNGKEY KCKVSNKALG APIEKTISKA KGQPREPQVY VYPPSREEMT   600
KNQVSLTCLV KGFYPSDIAV EWESNGQPEN NYKTTPPVLD SDGSFALVSK LTVDKSRWQQ   660
GNVFSCSVMH EALHNHYTQK SLSLSPGK                                     688

SEQ ID NO: 179          moltype = AA  length = 688
FEATURE                 Location/Qualifiers
REGION                  1..688
                        note = N65D_hSD15 + 38B2 HC (T350V/L351Y/F405A/Y407V) LALAPG
source                  1..688
                        mol_type = protein
                        organism = synthetic construct
SEQUENCE: 179
ITCPPPMSVE HADIWVKSYS LYSRERYICN SGFKRKAGTS SLTECVLNKA TNVAHWTTPS   60
LKCIRDPALV HQRPAPPSGG SGGGGSGGGS GGGGSLQNWV NVISDLKKIE DLIQSMHIDA   120
TLYTESDVHP SCKVTAMKCF LLELQVISLE SGDASIHDTV EDLIILANNS LSSNGNVTES   180
GCKECEELEE KNIKEFLQSF VHIVQMFINT SGGGGSGGGG SGGGGSGGGG SGGGGSGGGG   240
SEVQLLESGG GLVQPGGSLR LSCAASGFTF SSYWMSWVRQ APGKGLEWVS AISGSGGSTY   300
YADSVKGRFT ISRDNSKNTL YLQMNSLRAE DTAVYYCASS PLQWVDVWGQ GTTVTVSSAS   360
TKGPSVFPLA PSSKSTSGGT AALGCLVKDY FPEPVTVSWN SGALTSGVHT FPAVLQSSGL   420
YSLSSVVTVP SSSLGTQTYI CNVNHKPSNT KVDKRVEPKS CDKTHTCPPC PAPEAAGGPS   480
VFLFPPKPKD TLMISRTPEV TCVVVDVSHE DPEVKFNWYV DGVEVHNAKT KPREEQYNST   540
YRVVSVLTVL HQDWLNGKEY KCKVSNKALG APIEKTISKA KGQPREPQVY VYPPSREEMT   600
KNQVSLTCLV KGFYPSDIAV EWESNGQPEN NYKTTPPVLD SDGSFALVSK LTVDKSRWQQ   660
GNVFSCSVMH EALHNHYTQK SLSLSPGK                                     688

SEQ ID NO: 180          moltype = AA  length = 688
FEATURE                 Location/Qualifiers
REGION                  1..688
                        note = N65S_hSD15+38B2 HC (T350V/L351Y/F405A/Y407V)
source                  1..688
                        mol_type = protein
                        organism = synthetic construct
SEQUENCE: 180
ITCPPPMSVE HADIWVKSYS LYSRERYICN SGFKRKAGTS SLTECVLNKA TNVAHWTTPS   60
LKCIRDPALV HQRPAPPSGG SGGGGSGGGS GGGGSLQNWV NVISDLKKIE DLIQSMHIDA   120
TLYTESDVHP SCKVTAMKCF LLELQVISLE SGDASIHDTV ESLIILANNS LSSNGNVTES   180
GCKECEELEE KNIKEFLQSF VHIVQMFINT SGGGGSGGGG SGGGGSGGGG SGGGGSGGGG   240
SEVQLLESGG GLVQPGGSLR LSCAASGFTF SSYWMSWVRQ APGKGLEWVS AISGSGGSTY   300
YADSVKGRFT ISRDNSKNTL YLQMNSLRAE DTAVYYCASS PLQWVDVWGQ GTTVTVSSAS   360
TKGPSVFPLA PSSKSTSGGT AALGCLVKDY FPEPVTVSWN SGALTSGVHT FPAVLQSSGL   420
YSLSSVVTVP SSSLGTQTYI CNVNHKPSNT KVDKRVEPKS CDKTHTCPPC PAPEAAGGPS   480
VFLFPPKPKD TLMISRTPEV TCVVVDVSHE DPEVKFNWYV DGVEVHNAKT KPREEQYNST   540
YRVVSVLTVL HQDWLNGKEY KCKVSNKALG APIEKTISKA KGQPREPQVY VYPPSREEMT   600
KNQVSLTCLV KGFYPSDIAV EWESNGQPEN NYKTTPPVLD SDGSFALVSK LTVDKSRWQQ   660
GNVFSCSVMH EALHNHYTQK SLSLSPGK                                     688

SEQ ID NO: 181          moltype = AA  length = 690
FEATURE                 Location/Qualifiers
REGION                  1..690
                        note = mSD15 + m3A7 mHc LALAPG
source                  1..690
                        mol_type = protein
                        organism = synthetic construct
SEQUENCE: 181
ITCPPPVSIE HADIRVKNYS VNSRERYVCN SGFKRKAGTS TLIECVINKN TNVAHWTTPS   60
LKCIRDPALV HQRPAPPSGG SGGGGSGGGS GGGGSLQNWI DVRYDLEKIE SLIQSIHIDT   120
TLYTDSDFHP SCKVTAMNCF LLELQVILHE YSNMTLNETV RNVLYLANST LSSNKNVAES   180
GCKECEELEE KTFTEFLQSF IRIVQMFINT SGGGGSGGGG SGGGGSGGGG SGGGGSGGGG   240
SQVQLVQSGA EVKKPGASVK VSCKASGHTF TSYYIHWVRQ APGQGLEWMG IINPSGGSTS   300
YAQKFQGRVT MTRDTSTSTV YMELSSLRSE DTAVYYCARD RAYGGAGDYW GQGTLVTVSS   360
AKTTAPSVYP LAPVCGDTTG SSVTLGCLVK GYFPEPVTLT WNSGSLSSGV HTFPAVLQSD   420
LYTLSSSVTV TSSTWPSQSI TCNVAHPASS TKVDKKIEPR GPTIKPCPPC KCPAPNAAGG   480
PSVFIFPPKI KDVLMISLSP IVTCVVVDVS EDDPDVQISW FVNNVEVHTA QTQTHREDYN   540
STLRVVSALP IQHQDWMSGK EFKCKVNNKD LGAPIERTIS KPKGSVRAPQ VYVLPPPEEE   600
MTKKQVTLTC MVTDFMPEDI YVEWTNNGKT ELNYKNTEPV LDSDGSYFMY SKLRVEKKNW   660
VERNSYSCSV VHEGLHNHHT TKSFSRTPGK                                   690

SEQ ID NO: 182          moltype = AA  length = 690
FEATURE                 Location/Qualifiers
REGION                  1..690
                        note = mSD15 + m3A7 mHc(T366L/ K392L/T394W) LALAPG
source                  1..690
                        mol_type = protein
```

-continued

```
                         organism = synthetic construct
SEQUENCE: 182
ITCPPPVSIE HADIRVKNYS VNSRERYVCN SGFKRKAGTS TLIECVINKN TNVAHWTTPS  60
LKCIRDPALV HQRPAPPSGG SGGGGSGGGS GGGGSLQNWI DVRYDLEKIE SLIQSIHIDT  120
TLYTDSDFHP SCKVTAMNCF LLELQVILHE YSNMTLNETV RNVLYLANST LSSNKNVAES  180
GCKECEELEE KTFTEFLQSF IRIVQMFINT SGGGGSGGGG SGGGGSGGGG SGGGGSGGGG  240
SQVQLVQSGA EVKKPGASVK VSCKASGHTF TSYYIHWVRQ APGQGLEWMG IINPSGGSTS  300
YAQKFQGRVT MTRDTSTSTV YMELSSLRSE DTAVYYCARD RAYGGAGDYW GQGTLVTVSS  360
AKTTAPSVYP LAPVCGDTTG SSVTLGCLVK GYFPEPVTLT WNSGSLSSGV HTFPAVLQSD  420
LYTLSSSVTV TSSTWPSQSI TCNVAHPASS TKVDKKIEPR GPTIKPCPPC KCPAPNAAGG  480
PSVFIFPPKI KDVLMISLSP IVTCVVVDVS EDDPDVQISW FVNNVEVHTA QTQTHREDYN  540
STLRVVSALP IQHQDWMSGK EFKCKVNNKD LGAPIERTIS KPKGSVRAPQ VYVLPPPEEE  600
MTKKQVTLLC MVTDFMPEDI YVEWTNNGKT ELNYLNWEPV LDSDGSYFMY SKLRVEKKNW  660
VERNSYSCSV VHEGLHNHHT TKSFSRTPGK                                   690

SEQ ID NO: 183        moltype = AA  length = 658
FEATURE               Location/Qualifiers
REGION                1..658
                      note = m3A7 mHc LALPG + mSD15
source                1..658
                      mol_type = protein
                      organism = synthetic construct
SEQUENCE: 183
QVQLVQSGAE VKKPGASVKV SCKASGHTFT SYYIHWVRQA PGQGLEWMGI INPSGGSTSY  60
AQKFQGRVTM TRDTSTSTVY MELSSLRSED TAVYYCARDR AYGGAGDYWG QGTLVTVSSA  120
KTTAPSVYPL APVCGDTTGS SVTLGCLVKG YFPEPVTLTW NSGSLSSGVH TFPAVLQSDL  180
YTLSSSVTVT SSTWPSQSIT CNVAHPASST KVDKKIEPRG PTIKPCPPCK CPAPNAAGGP  240
SVFIFPPKIK DVLMISLSPI VTCVVVDVSE DDPDVQISWF VNNVEVHTAQ TQTHREDYNS  300
TLRVVSALPI QHQDWMSGKE FKCKVNNKDL GAPIERTISK PKGSVRAPQV YVLPPPEEEM  360
TKKQVTLLCM VTDFMPEDIY VEWTNNGKTE LNYKNTEPVL DSDGSYFMYS KLRVEKKNWV  420
ERNSYSCSVV HEGLHNHHTT KSFSRTPGSC PPPVSIEHAD IRVKNYSVNS RERYVCNSGF  480
KRKAGTSTLI ECVINKNTNV AHWTTPSLKC IRDPALVHQR PAPPSGGSGG GGSGGGGSGG  540
GSLQNWIDVR YDLEKIESLI QSIHIDTTLY TDSDFHPSCK VTAMNCFLLE LQVILHEYSN  600
MTLNETVRNV LYLANSTLSS NKNVAESGCK ECEELEEKTF TEFLQSFIRI VQMFINTS    658

SEQ ID NO: 184        moltype = AA  length = 658
FEATURE               Location/Qualifiers
REGION                1..658
                      note = m3A7 mHC(T366L/K392L/T394W) + mSD15 LALAPG
source                1..658
                      mol_type = protein
                      organism = synthetic construct
SEQUENCE: 184
QVQLVQSGAE VKKPGASVKV SCKASGHTFT SYYIHWVRQA PGQGLEWMGI INPSGGSTSY  60
AQKFQGRVTM TRDTSTSTVY MELSSLRSED TAVYYCARDR AYGGAGDYWG QGTLVTVSSA  120
KTTAPSVYPL APVCGDTTGS SVTLGCLVKG YFPEPVTLTW NSGSLSSGVH TFPAVLQSDL  180
YTLSSSVTVT SSTWPSQSIT CNVAHPASST KVDKKIEPRG PTIKPCPPCK CPAPNAAGGP  240
SVFIFPPKIK DVLMISLSPI VTCVVVDVSE DDPDVQISWF VNNVEVHTAQ TQTHREDYNS  300
TLRVVSALPI QHQDWMSGKE FKCKVNNKDL GAPIERTISK PKGSVRAPQV YVLPPPEEEM  360
TKKQVTLLCM VTDFMPEDIY VEWTNNGKTE LNYLNWEPVL DSDGSYFMYS KLRVEKKNWV  420
ERNSYSCSVV HEGLHNHHTT KSFSRTPGSC PPPVSIEHAD IRVKNYSVNS RERYVCNSGF  480
KRKAGTSTLI ECVINKNTNV AHWTTPSLKC IRDPALVHQR PAPPSGGSGG GGSGGGGSGG  540
GSLQNWIDVR YDLEKIESLI QSIHIDTTLY TDSDFHPSCK VTAMNCFLLE LQVILHEYSN  600
MTLNETVRNV LYLANSTLSS NKNVAESGCK ECEELEEKTF TEFLQSFIRI VQMFINTS    658

SEQ ID NO: 185        moltype = AA  length = 445
FEATURE               Location/Qualifiers
REGION                1..445
                      note = DP47 mHC (L351Y/F405A/Y407V) LALAPG
source                1..445
                      mol_type = protein
                      organism = synthetic construct
SEQUENCE: 185
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCAKGS GFDYWGQGTL VTVSSAKTTA  120
PSVYPLAPVC GDTTGSSVTL GCLVKGYFPE PVTLTWNSGS LSSGVHTFPA VLQSDLYTLS  180
SSVTVTSSTW PSQSITCNVA HPASSTKVDK KIEPRGPTIK PCPPCKCPAP NAAGPSVFI  240
FPPKIKDVLM ISLSPIVTCV VVDVSEDDPD VQISWFVNNV EVHTAQTQTH REDYNSTLRV  300
VSALPIQHQD WMSGKEFKCK VNNKDLGAPI ERTISKPKGS VRAPQVYVYP PPEEEMTKKQ  360
VTLLCMVTDF MPEDIYVEWT NNGKTELNYK NTEPVLDSDG SYAMVSKLRV EKKNWVERNS  420
YSCSVVHEGL HNHHTTKSFS RTPGK                                       445

SEQ ID NO: 186        moltype = AA  length = 215
FEATURE               Location/Qualifiers
REGION                1..215
                      note = DP47 mLC
source                1..215
                      mol_type = protein
                      organism = synthetic construct
```

```
SEQUENCE: 186
EIVLTQSPGT LSLSPGERAT LSCRASQSVS SSYLAWYQQK PGQAPRLLIY GASSRATGIP  60
DRFSGSGSGT DFTLTISRLE PEDFAVYYCQ QYGSSPLTFG QGTKVEIKRA DAAPTVSIFP  120
PSSEQLTSGG ASVVCFLNNF YPKDINVKWK IDGSERQNGV LNSWTDQDSK DSTYSMSSTL  180
TLTKDEYERH NSYTCEATHK TSTSPIVKSF NRNEC                            215

SEQ ID NO: 187           moltype = AA  length = 686
FEATURE                  Location/Qualifiers
REGION                   1..686
                         note = mSD15 + DP47 mHC LALAPG
source                   1..686
                         mol_type = protein
                         organism = synthetic construct
SEQUENCE: 187
ITCPPPVSIE HADIRVKNYS VNSRERYVCN SGFKRKAGTS TLIECVINKN TNVAHWTTPS  60
LKCIRDPALV HQRPAPPSGG SGGGGSGGGS GGGGSLQNWI DVRYDLEKIE SLIQSIHIDT  120
TLYTDSDFHP SCKVTAMNCF LLELQVILHE YSNMTLNETV RNVLYLANST LSSNKNVAES  180
GCKECEELEE KTFTEFLQSF IRIVQMFINT SGGGGSGGGG SGGGGSGGGG SGGGGSGGGG  240
SEVQLLESGG GLVQPGGSLR LSCAASGFTF SSYAMSWVRQ APGKGLEWVS AISGSGGSTY  300
YADSVKGRFT ISRDNSKNTL YLQMNSLRAE DTAVYYCAKG SGFDYWGQGT LVTVSSAKTT  360
APSVYPLAPV CGDTTGSSVT LGCLVKGYFP EPVTLTWNSG SLSSGVHTFP AVLQSDLYTL  420
SSSVTVTSST WPSQSITCNV AHPASSTKVD KKIEPRGPTI KPCPPCKCPA PNAAGGPSVF  480
IFPPKIKDVL MISLSPIVTC VVVDVSEDDP DVQISWFVNN VEVHTAQTQT HREDYNSTLR  540
VVSALPIQHQ DWMSGKEFKC KVNNKDLGAP IERTISKPKG SVRAPQVYVL PPPEEEMTKK  600
QVTLTCMVTD FMPEDIYVEW TNNGKTELNY KNTEPVLDSD GSYFMYSKLR VEKKNWVERN  660
SYSCSVVHEG LHNHHTTKSF SRTPGK                                     686

SEQ ID NO: 188           moltype = AA  length = 686
FEATURE                  Location/Qualifiers
REGION                   1..686
                         note = mSD15 + DP47 mHC (T366L/K392L/T394W) LALAPG
source                   1..686
                         mol_type = protein
                         organism = synthetic construct
SEQUENCE: 188
ITCPPPVSIE HADIRVKNYS VNSRERYVCN SGFKRKAGTS TLIECVINKN TNVAHWTTPS  60
LKCIRDPALV HQRPAPPSGG SGGGGSGGGS GGGGSLQNWI DVRYDLEKIE SLIQSIHIDT  120
TLYTDSDFHP SCKVTAMNCF LLELQVILHE YSNMTLNETV RNVLYLANST LSSNKNVAES  180
GCKECEELEE KTFTEFLQSF IRIVQMFINT SGGGGSGGGG SGGGGSGGGG SGGGGSGGGG  240
SEVQLLESGG GLVQPGGSLR LSCAASGFTF SSYAMSWVRQ APGKGLEWVS AISGSGGSTY  300
YADSVKGRFT ISRDNSKNTL YLQMNSLRAE DTAVYYCAKG SGFDYWGQGT LVTVSSAKTT  360
APSVYPLAPV CGDTTGSSVT LGCLVKGYFP EPVTLTWNSG SLSSGVHTFP AVLQSDLYTL  420
SSSVTVTSST WPSQSITCNV AHPASSTKVD KKIEPRGPTI KPCPPCKCPA PNAAGGPSVF  480
IFPPKIKDVL MISLSPIVTC VVVDVSEDDP DVQISWFVNN VEVHTAQTQT HREDYNSTLR  540
VVSALPIQHQ DWMSGKEFKC KVNNKDLGAP IERTISKPKG SVRAPQVYVL PPPEEEMTKK  600
QVTLLCMVTD FMPEDIYVEW TNNGKTELNY LNWEPVLDSD GSYFMYSKLR VEKKNWVERN  660
SYSCSVVHEG LHNHHTTKSF SRTPGK                                     686

SEQ ID NO: 189           moltype = AA  length = 654
FEATURE                  Location/Qualifiers
REGION                   1..654
                         note = DP47 mHc LALAPG + mSD15
source                   1..654
                         mol_type = protein
                         organism = synthetic construct
SEQUENCE: 189
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCAKGS GFDYWGQGTL VTVSSAKTTA  120
PSVYPLAPVC GDTTGSSVTL GCLVKGYFPE PVTLTWNSGS LSSGVHTFPA VLQSDLYTLS  180
SSVTVTSSTW PSQSITCNVA HPASSTKVDK KIEPRGPTIK PCPPCKPAP NAAGGPSVFI  240
FPPKIKDVLM ISLSPIVTCV VVDVSEDDPD VQISWFVNNV EVHTAQTQTH REDYNSTLRV  300
VSALPIQHQD WMSGKEFKCK VNNKDLGAPI ERTISKPKGS VRAPQVYVLP PPEEEMTKKQ  360
VTLTCMVTDF MPEDIYVEWT NNGKTELNYK NTEPVLDSDG SYFMYSKLRV EKKNWVERNS  420
YSCSVVHEGL HNHHTTKSFS RTPGSCPPPV SIEHADIRVK NYSVNSRERY VCNSGFKRKA  480
GTSTLIECVI NKNTNVAHWT TPSLKCIRDP ALVHQRPAPP SGGSGGGGSG GGSGGGGSLQ  540
NWIDVRYDLE KIESLIQSIH IDTTLYTDSD FHPSCKVTAM NCFLLELQVI LHEYSNMTLN  600
ETVRNVLYLA NSTLSSNKNV AESGCKECEE LEEKTFTEFL QSFIRIVQMF INTS        654

SEQ ID NO: 190           moltype = AA  length = 654
FEATURE                  Location/Qualifiers
REGION                   1..654
                         note = DP47 mHC (T366L/K392L/T394W) LALAPG + mSD15
source                   1..654
                         mol_type = protein
                         organism = synthetic construct
SEQUENCE: 190
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCAKGS GFDYWGQGTL VTVSSAKTTA  120
PSVYPLAPVC GDTTGSSVTL GCLVKGYFPE PVTLTWNSGS LSSGVHTFPA VLQSDLYTLS  180
```

-continued

```
SSVTVTSSTW PSQSITCNVA HPASSTKVDK KIEPRGPTIK PCPPCKCPAP NAAGGPSVFI    240
FPPKIKDVLM ISLSPIVTCV VVDVSEDDPD VQISWFVNNV EVHTAQTQTH REDYNSTLRV    300
VSALPIQHQD WMSGKEFKCK VNNKDLGAPI ERTISKPKGS VRAPQVYVLP PPEEEMTKKQ    360
VTLLCMVTDF MPEDIYVEWT NNGKTELNYL NWEPVLDSDG SYFMYSKLRV EKKNWVERNS    420
YSCSVVHEGL HNHHTTKSFS RTPGSCPPPV SIEHADIRVK NYSVNSRERY VCNSGFKRKA    480
GTSTLIECVI NKNTNVAHWT TPSLKCIRDP ALVHQRPAPP SGGSGGGGSG GGSGGGGSLQ    540
NWIDVRYDLE KIESLIQSIH IDTTLYTDSD FHPSCKVTAM NCFLLELQVI LHEYSNMTLN    600
ETVRNVLYLA NSTLSSNKNV AESGCKECEE LEEKTFTEFL QSFIRIVQMF INTS          654
```

```
SEQ ID NO: 191          moltype = AA   length = 445
FEATURE                 Location/Qualifiers
REGION                  1..445
                        note = DP47 HC (T350V/T366L/K392L/T394W) LALAPG
source                  1..445
                        mol_type = protein
                        organism = synthetic construct
SEQUENCE: 191
EVQLLESGGG LVQPGGSLRL SCAASGFTFS SYAMSWVRQA PGKGLEWVSA ISGSGGSTYY    60
ADSVKGRFTI SRDNSKNTLY LQMNSLRAED TAVYYCAKGS GFDYWGQGTL VTVSSASTKG    120
PSVFPLAPSS KSTSGGTAAL GCLVKDYFPE PVTVSWNSGA LTSGVHTFPA VLQSSGLYSL    180
SSVVTVPSSS LGTQTYICNV NHKPSNTKVD KRVEPKSCDK THTCPPCPAP EAAGGPSVFL    240
FPPKPKDTLM ISRTPEVTCV VVDVSHEDPE VKFNWYVDGV EVHNAKTKPR EEQYNSTYRV    300
VSVLTVLHQD WLNGKEYKCK VSNKALGAPI EKTISKAKGQ PREPQVYVLP PSREEMTKNQ    360
VSLLCLVKGF YPSDIAVEWE SNGQPENNYL TWPPVLDSDG SFFLYSKLTV DKSRWQQGNV    420
FSCSVMHEAL HNHYTQKSLS LSPGK                                         445
```

```
SEQ ID NO: 192          moltype = AA   length = 215
FEATURE                 Location/Qualifiers
REGION                  1..215
                        note = DP47 LC
source                  1..215
                        mol_type = protein
                        organism = synthetic construct
SEQUENCE: 192
EIVLTQSPGT LSLSPGERAT LSCRASQSVS SSYLAWYQQK PGQAPRLLIY GASSRATGIP    60
DRFSGSGSGT DFTLTISRLE PEDFAVYYCQ QYGSSPLTFG QGTKVEIKRT VAAPSVFIFP    120
PSDEQLKSGT ASVVCLLNNF YPREAKVQWK VDNALQSGNS QESVTEQDSK DSTYSLSSTL    180
TLSKADYEKH KVYACEVTHQ GLSSPVTKSF NRGEC                              215
```

```
SEQ ID NO: 193          moltype = AA   length = 686
FEATURE                 Location/Qualifiers
REGION                  1..686
                        note = hSD15 + DP47 HC LALPG
source                  1..686
                        mol_type = protein
                        organism = synthetic construct
SEQUENCE: 193
ITCPPPMSVE HADIWVKSYS LYSRERYICN SGFKRKAGTS SLTECVLNKA TNVAHWTTPS    60
LKCIRDPALV HQRPAPPSGG SGGGGSGGGS GGGGSLQNWV NVISDLKKIE DLIQSMHIDA    120
TLYTESDVHP SCKVTAMKCF LLELQVISLE SGDASIHDTV ENLIILANNS LSSNGNVTES    180
GCKECEELEE KNIKEFLQSF VHIVQMFINT SGGGGSGGGG SGGGGSGGGG SGGGGSGGGG    240
SEVQLLESGG GLVQPGGSLR LSCAASGFTF SSYAMSWVRQ APGKGLEWVS AISGSGGSTY    300
YADSVKGRFT ISRDNSKNTL YLQMNSLRAE DTAVYYCAKG SGFDYWGQGT LVTVSSASTK    360
GPSVFPLAPS SKSTSGGTAA LGCLVKDYFP EPVTVSWNSG ALTSGVHTFP AVLQSSGLYS    420
LSSVVTVPSS SLGTQTYICN VNHKPSNTKV DKRVEPKSCD KTHTCPPCPA PEAAGGPSVF    480
LFPPKPKDTL MISRTPEVTC VVVDVSHEDP EVKFNWYVDG VEVHNAKTKP REEQYNSTYR    540
VVSVLTVLHQ DWLNGKEYKC KVSNKALGAP IEKTISKAKG QPREPQVYTL PPSREEMTKN    600
QVSLTCLVKG FYPSDIAVEW ESNGQPENNY KTTPPVLDSD GSFFLYSKLT VDKSRWQQGN    660
VFSCSVMHEA LHNHYTQKSL SLSPGK                                        686
```

```
SEQ ID NO: 194          moltype = AA   length = 686
FEATURE                 Location/Qualifiers
REGION                  1..686
                        note = hSD15 + DP47 HC (T350V/L351Y/F405A/Y407V) LALAPG
source                  1..686
                        mol_type = protein
                        organism = synthetic construct
SEQUENCE: 194
ITCPPPMSVE HADIWVKSYS LYSRERYICN SGFKRKAGTS SLTECVLNKA TNVAHWTTPS    60
LKCIRDPALV HQRPAPPSGG SGGGGSGGGS GGGGSLQNWV NVISDLKKIE DLIQSMHIDA    120
TLYTESDVHP SCKVTAMKCF LLELQVISLE SGDASIHDTV ENLIILANNS LSSNGNVTES    180
GCKECEELEE KNIKEFLQSF VHIVQMFINT SGGGGSGGGG SGGGGSGGGG SGGGGSGGGG    240
SEVQLLESGG GLVQPGGSLR LSCAASGFTF SSYAMSWVRQ APGKGLEWVS AISGSGGSTY    300
YADSVKGRFT ISRDNSKNTL YLQMNSLRAE DTAVYYCAKG SGFDYWGQGT LVTVSSASTK    360
GPSVFPLAPS SKSTSGGTAA LGCLVKDYFP EPVTVSWNSG ALTSGVHTFP AVLQSSGLYS    420
LSSVVTVPSS SLGTQTYICN VNHKPSNTKV DKRVEPKSCD KTHTCPPCPA PEAAGGPSVF    480
LFPPKPKDTL MISRTPEVTC VVVDVSHEDP EVKFNWYVDG VEVHNAKTKP REEQYNSTYR    540
VVSVLTVLHQ DWLNGKEYKC KVSNKALGAP IEKTISKAKG QPREPQVYVY PPSREEMTKN    600
QVSLTCLVKG FYPSDIAVEW ESNGQPENNY KTTPPVLDSD GSFALVSKLT VDKSRWQQGN    660
```

```
VFSCSVMHEA LHNHYTQKSL SLSPGK                                    686

SEQ ID NO: 195          moltype = AA   length = 654
FEATURE                 Location/Qualifiers
REGION                  1..654
                        note = DP47 HC +LALAPG hSD15
source                  1..654
                        mol_type = protein
                        organism = synthetic construct
SEQUENCE: 195
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCAKGS GFDYWGQGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCDK THTCPPCPAP EAAGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALGAPI EKTISKAKGQ PREPQVYTLP PSREEMTKNQ  360
VSLTCLVKGF YPSDIAVEWE SNGQPENNYK TTPPVLDSDG SFFLYSKLTV DKSRWQQGNV  420
FSCSVMHEAL HNHYTQKSLS LSPGSCPPPM SVEHADIWVK SYSLYSRERY ICNSGFKRKA  480
GTSSLTECVL NKATNVAHWT TPSLKCIRDP ALVHQRPAPP SGGSGGGGSG GGSGGGGSLQ  540
NWVNVISDLK KIEDLIQSMH IDATLYTESD VHPSCKVTAM KCFLLELQVI SLESGDASIH  600
DTVENLIILA NNSLSSNGNV TESGCKECEE LEEKNIKEFL QSFVHIVQMF INTS         654

SEQ ID NO: 196          moltype = AA   length = 654
FEATURE                 Location/Qualifiers
REGION                  1..654
                        note = DP47 HC (T350V/L351Y/F405A/Y407V) LALAPG + hSD15
source                  1..654
                        mol_type = protein
                        organism = synthetic construct
SEQUENCE: 196
EVQLLESGGG LVQPGGSLRL SCAASGFTFS SYAMSWVRQA PGKGLEWVSA ISGSGGSTYY  60
ADSVKGRFTI SRDNSKNTLY LQMNSLRAED TAVYYCAKGS GFDYWGQGTL VTVSSASTKG  120
PSVFPLAPSS KSTSGGTAAL GCLVKDYFPE PVTVSWNSGA LTSGVHTFPA VLQSSGLYSL  180
SSVVTVPSSS LGTQTYICNV NHKPSNTKVD KRVEPKSCDK THTCPPCPAP EAAGGPSVFL  240
FPPKPKDTLM ISRTPEVTCV VVDVSHEDPE VKFNWYVDGV EVHNAKTKPR EEQYNSTYRV  300
VSVLTVLHQD WLNGKEYKCK VSNKALGAPI EKTISKAKGQ PREPQVYVYP PSREEMTKNQ  360
VSLTCLVKGF YPSDIAVEWE SNGQPENNYK TTPPVLDSDG SFALVSKLTV DKSRWQQGNV  420
FSCSVMHEAL HNHYTQKSLS LSPGSCPPPM SVEHADIWVK SYSLYSRERY ICNSGFKRKA  480
GTSSLTECVL NKATNVAHWT TPSLKCIRDP ALVHQRPAPP SGGSGGGGSG GGSGGGGSLQ  540
NWVNVISDLK KIEDLIQSMH IDATLYTESD VHPSCKVTAM KCFLLELQVI SLESGDASIH  600
DTVENLIILA NNSLSSNGNV TESGCKECEE LEEKNIKEFL QSFVHIVQMF INTS         654

SEQ ID NO: 197          moltype = AA   length = 686
FEATURE                 Location/Qualifiers
REGION                  1..686
                        note = N65A-hSD15 + DP47 HC (T350V/L351Y/F405A/Y407V) LALAPG
source                  1..686
                        mol_type = protein
                        organism = synthetic construct
SEQUENCE: 197
ITCPPPMSVE HADIWVKSYS LYSRERYICN SGFKRKAGTS SLTECVLNKA TNVAHWTTPS  60
LKCIRDPALV HQRPAPPSGG SGGGGSGGGG GGGGSLQNWV NVISDLKKIE DLIQSMHIDA  120
TLYTESDVHP SCKVTAMKCF LLELQVISLE SGDASIHDTV EALIILANNS LSSNGNVTES  180
GCKECEELEE KNIKEFLQSF VHIVQMFINT SGGGGSGGGG SGGGGSGGGG SGGGGSGGGG  240
SEVQLLESGG GLVQPGGSLR LSCAASGFTF SSYAMSWVRQ APGKGLEWVS AISGSGGSTY  300
YADSVKGRFT ISRDNSKNTL YLQMNSLRAE DTAVYYCAKG SGFDYWGQGT LVTVSSASTK  360
GPSVFPLAPS SKSTSGGTAA LGCLVKDYFP EPVTVSWNSG ALTSGVHTFP AVLQSSGLYS  420
LSSVVTVPSS SLGTQTYICN VNHKPSNTKV DKRVEPKSCD KTHTCPPCPA PEAAGGPSVF  480
LFPPKPKDTL MISRTPEVTC VVVDVSHEDP EVKFNWYVDG VEVHNAKTKP REEQYNSTYR  540
VVSVLTVLHQ DWLNGKEYKC KVSNKALGAP IEKTISKAKG QPREPQVYVY PPSREEMTKN  600
QVSLTCLVKG FYPSDIAVEW ESNGQPENNY KTTPPVLDSD GSFALVSKLT VDKSRWQQGN  660
VFSCSVMHEA LHNHYTQKSL SLSPGK                                       686

SEQ ID NO: 198          moltype = AA   length = 686
FEATURE                 Location/Qualifiers
REGION                  1..686
                        note = N65D-hSD15 + DP47 HC (T350V/L351Y/F405A/Y407V) LALAPG
source                  1..686
                        mol_type = protein
                        organism = synthetic construct
SEQUENCE: 198
ITCPPPMSVE HADIWVKSYS LYSRERYICN SGFKRKAGTS SLTECVLNKA TNVAHWTTPS  60
LKCIRDPALV HQRPAPPSGG SGGGGSGGGG GGGGSLQNWV NVISDLKKIE DLIQSMHIDA  120
TLYTESDVHP SCKVTAMKCF LLELQVISLE SGDASIHDTV EDLIILANNS LSSNGNVTES  180
GCKECEELEE KNIKEFLQSF VHIVQMFINT SGGGGSGGGG SGGGGSGGGG SGGGGSGGGG  240
SEVQLLESGG GLVQPGGSLR LSCAASGFTF SSYAMSWVRQ APGKGLEWVS AISGSGGSTY  300
YADSVKGRFT ISRDNSKNTL YLQMNSLRAE DTAVYYCAKG SGFDYWGQGT LVTVSSASTK  360
GPSVFPLAPS SKSTSGGTAA LGCLVKDYFP EPVTVSWNSG ALTSGVHTFP AVLQSSGLYS  420
LSSVVTVPSS SLGTQTYICN VNHKPSNTKV DKRVEPKSCD KTHTCPPCPA PEAAGGPSVF  480
```

-continued

```
LFPPKPKDTL MISRTPEVTC VVVDVSHEDP EVKFNWYVDG VEVHNAKTKP REEQYNSTYR  540
VVSVLTVLHQ DWLNGKEYKC KVSNKALGAP IEKTISKAKG QPREPQVYVY PPSREEMTKN  600
QVSLTCLVKG FYPSDIAVEW ESNGQPENNY KTTPPVLDSD GSFALVSKLT VDKSRWQQGN  660
VFSCSVMHEA LHNHYTQKSL SLSPGK                                       686

SEQ ID NO: 199          moltype = AA  length = 686
FEATURE                 Location/Qualifiers
REGION                  1..686
                        note = N65S-hSD15 + DP47 HC (T350V/L351Y/F405A/Y407V) LALAPG
source                  1..686
                        mol_type = protein
                        organism = synthetic construct
SEQUENCE: 199
ITCPPPMSVE HADIWVKSYS LYSRERYICN SGFKRKAGTS SLTECVLNKA TNVAHWTTPS  60
LKCIRDPALV HQRPAPPSGG SGGGGSGGGS GGGGSLQNWV NVISDLKKIE DLIQSMHIDA  120
TLYTESDVHP SCKVTAMKCF LLELQVISLE SGDASIHDTV ESLIILANNS LSSNGNVTES  180
GCKECEELEE KNIKEFLQSF VHIVQMFINT SGGGGSGGGG SGGGGSGGGG SGGGGSGGGG  240
SEVQLLESGG GLVQPGGSLR LSCAASGFTF SSYAMSWVRQ APGKGLEWVS AISGSGGSTY  300
YADSVKGRFT ISRDNSKNTL YLQMNSLRAE DTAVYYCAKG SGFDYWGQGT LVTVSSASTK  360
GPSVFPLAPS SKSTSGGTAA LGCLVKDYFP EPVTVSWNSG ALTSGVHTFP AVLQSSGLYS  420
LSSVVTVPSS SLGTQTYICN VNHKPSNTKV DKRVEPKSCD KTHTCPPCPA PEAAGGPSVF  480
LFPPKPKDTL MISRTPEVTC VVVDVSHEDP EVKFNWYVDG VEVHNAKTKP REEQYNSTYR  540
VVSVLTVLHQ DWLNGKEYKC KVSNKALGAP IEKTISKAKG QPREPQVYVY PPSREEMTKN  600
QVSLTCLVKG FYPSDIAVEW ESNGQPENNY KTTPPVLDSD GSFALVSKLT VDKSRWQQGN  660
VFSCSVMHEA LHNHYTQKSL SLSPGK                                       686

SEQ ID NO: 200          moltype = AA  length = 120
FEATURE                 Location/Qualifiers
REGION                  1..120
                        note = D7A8 VH
source                  1..120
                        mol_type = protein
                        organism = synthetic construct
SEQUENCE: 200
EVQLLESGGG LVQPGGSLRL SCAASGFTFS AYRMFWVRQA PGKGLEWVSS IYPSGGITFY  60
ADSVKGRFTI SRDNSKNTLY LQMNSLRAED TAIYYCARIK LGTVTTVDYW GQGTLVTVSS  120

SEQ ID NO: 201          moltype = AA  length = 450
FEATURE                 Location/Qualifiers
REGION                  1..450
                        note = D7A8 full length HC
source                  1..450
                        mol_type = protein
                        organism = synthetic construct
SEQUENCE: 201
EVQLLESGGG LVQPGGSLRL SCAASGFTFS AYRMFWVRQA PGKGLEWVSS IYPSGGITFY  60
ADSVKGRFTI SRDNSKNTLY LQMNSLRAED TAIYYCARIK LGTVTTVDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKRVEP KSCDKTHTCP PCPAPELLGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 202          moltype = AA  length = 450
FEATURE                 Location/Qualifiers
REGION                  1..450
                        note = D7A8 HC (S354C/T366W) LALA
source                  1..450
                        mol_type = protein
                        organism = synthetic construct
SEQUENCE: 202
EVQLLESGGG LVQPGGSLRL SCAASGFTFS AYRMFWVRQA PGKGLEWVSS IYPSGGITFY  60
ADSVKGRFTI SRDNSKNTLY LQMNSLRAED TAIYYCARIK LGTVTTVDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKRVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPCREE  360
MTKNQVSLWC LVKGFYPSDI AVEWESNGQP ENNYKTTPPV LDSDGSFFLY SKLTVDKSRW  420
QQGNVFSCSV MHEALHNHYT QKSLSLSPGK                                   450

SEQ ID NO: 203          moltype = AA  length = 450
FEATURE                 Location/Qualifiers
REGION                  1..450
                        note = D7A8 HC (T350V/ T366L/ K392L/ T394W) LALA
source                  1..450
                        mol_type = protein
                        organism = synthetic construct
SEQUENCE: 203
```

```
EVQLLESGGG LVQPGGSLRL SCAASGFTFS AYRMFWVRQA PGKGLEWVSS IYPSGGITFY    60
ADSVKGRFTI SRDNSKNTLY LQMNSLRAED TAIYYCARIK LGTVTTVDYW GQGTLVTVSS   120
ASTKGPSVFP LAPSSKSTSG GTAALGCLVK DYFPEPVTVS WNSGALTSGV HTFPAVLQSS   180
GLYSLSSVVT VPSSSLGTQT YICNVNHKPS NTKVDKRVEP KSCDKTHTCP PCPAPEAAGG   240
PSVFLFPPKP KDTLMISRTP EVTCVVVDVS HEDPEVKFNW YVDGVEVHNA KTKPREEQYN   300
STYRVVSVLT VLHQDWLNGK EYKCKVSNKA LPAPIEKTIS KAKGQPREPQ VYVLPPSREE   360
MTKNQVSLLC LVKGFYPSDI AVEWESNGQP ENNYLTWPPV LDSDGSFFLY SKLTVDKSRW   420
QQGNVFSCSV MHEALHNHYT QKSLSLSPGK                                    450

SEQ ID NO: 204          moltype = AA  length = 113
FEATURE                 Location/Qualifiers
REGION                  1..113
                        note = D7A8 VL
source                  1..113
                        mol_type = protein
                        organism = synthetic construct
SEQUENCE: 204
QSALTQPASV SGSPGQSITI SCTGTSSDVG AYNYVSWYQQ HPGKAPKLMI YDVSNRPSGV    60
SNRFSGSKSG NTASLTISGL QAEDEADYYC SSYTSSSTRV FGTGTKVTVL GQP          113

SEQ ID NO: 205          moltype = AA  length = 216
FEATURE                 Location/Qualifiers
REGION                  1..216
                        note = D7A8 full length LC
source                  1..216
                        mol_type = protein
                        organism = synthetic construct
SEQUENCE: 205
QSALTQPASV SGSPGQSITI SCTGTSSDVG AYNYVSWYQQ HPGKAPKLMI YDVSNRPSGV    60
SNRFSGSKSG NTASLTISGL QAEDEADYYC SSYTSSSTRV FGTGTKVTVL GQPKANPTVT   120
LFPPSSEELQ ANKATLVCLI SDFYPGAVTV AWKADGSPVK AGVETTKPSK QSNNKYAASS   180
YLSLTPEQWK SHRSYSCQVT HEGSTVEKTV APTECS                            216

SEQ ID NO: 206          moltype = AA  length = 681
FEATURE                 Location/Qualifiers
REGION                  1..681
                        note = hSD15 + D7A8 HC LALA
source                  1..681
                        mol_type = protein
                        organism = synthetic construct
SEQUENCE: 206
ITCPPPMSVE HADIWVKSYS LYSRERYICN SGFKRKAGTS SLTECVLNKA TNVAHWTTPS    60
LKCIRDPALV HQRPAPPSGG SGGGGSGGGS GGGGSLQNWV NVISDLKKIE DLIQSMHIDA   120
TLYTESDVHP SCKVTAMKCF LLELQVISLE SGDASIHDTV ENLIILANNS LSSNGNVTES   180
GCKECEELEE KNIKEFLQSF VHIVQMFINT SGGGGSGGGG SGGGGSGGGG SEVQLLESGG   240
GLVQPGGSLR LSCAASGFTF SAYRMFWVRQ APGKGLEWVS SIYPSGGITF YADSVKGRFT   300
ISRDNSKNTL YLQMNSLRAE DTAIYYCARI KLGTVTTVDY WGQGTLVTVS SASTKGPSVF   360
PLAPSSKSTS GGTAALGCLV KDYFPEPVTV SWNSGALTSG VHTFPAVLQS SGLYSLSSVV   420
TVPSSSLGTQ TYICNVNHKP SNTKVDKRVE PKSCDKTHTC PPCPAPEAAG GPSVFLFPPK   480
PKDTLMISRT PEVTCVVVDV SHEDPEVKFN WYVDGVEVHN AKTKPREEQY NSTYRVVSVL   540
TVLHQDWLNG KEYKCKVSNK ALPAPIEKTI SKAKGQPREP QVYTLPPSRE EMTKNQVSLT   600
CLVKGFYPSD IAVEWESNGQ PENNYKTTPP VLDSDGSFFL YSKLTVDKSR WQQGNVFSCS   660
VMHEALHNHY TQKSLSLSPG K                                            681

SEQ ID NO: 207          moltype = AA  length = 681
FEATURE                 Location/Qualifiers
REGION                  1..681
                        note = hSD15 + D7A8HC (Y349C/T366S/L368A/Y407V) LALA
source                  1..681
                        mol_type = protein
                        organism = synthetic construct
SEQUENCE: 207
ITCPPPMSVE HADIWVKSYS LYSRERYICN SGFKRKAGTS SLTECVLNKA TNVAHWTTPS    60
LKCIRDPALV HQRPAPPSGG SGGGGSGGGS GGGGSLQNWV NVISDLKKIE DLIQSMHIDA   120
TLYTESDVHP SCKVTAMKCF LLELQVISLE SGDASIHDTV ENLIILANNS LSSNGNVTES   180
GCKECEELEE KNIKEFLQSF VHIVQMFINT SGGGGSGGGG SGGGGSGGGG SEVQLLESGG   240
GLVQPGGSLR LSCAASGFTF SAYRMFWVRQ APGKGLEWVS SIYPSGGITF YADSVKGRFT   300
ISRDNSKNTL YLQMNSLRAE DTAIYYCARI KLGTVTTVDY WGQGTLVTVS SASTKGPSVF   360
PLAPSSKSTS GGTAALGCLV KDYFPEPVTV SWNSGALTSG VHTFPAVLQS SGLYSLSSVV   420
TVPSSSLGTQ TYICNVNHKP SNTKVDKRVE PKSCDKTHTC PPCPAPEAAG GPSVFLFPPK   480
PKDTLMISRT PEVTCVVVDV SHEDPEVKFN WYVDGVEVHN AKTKPREEQY NSTYRVVSVL   540
TVLHQDWLNG KEYKCKVSNK ALPAPIEKTI SKAKGQPREP QVCTLPPSRE EMTKNQVSLS   600
CAVKGFYPSD IAVEWESNGQ PENNYKTTPP VLDSDGSFFL VSKLTVDKSR WQQGNVFSCS   660
VMHEALHNHY TQKSLSLSPG K                                            681

SEQ ID NO: 208          moltype = AA  length = 681
FEATURE                 Location/Qualifiers
REGION                  1..681
                        note = hSD15 + D7A8HC (T350V/L351Y/F405A/Y407V) LALA
```

```
source                   1..681
                         mol_type = protein
                         organism = synthetic construct
SEQUENCE: 208
ITCPPPMSVE HADIWVKSYS LYSRERYICN SGFKRKAGTS SLTECVLNKA TNVAHWTTPS  60
LKCIRDPALV HQRPAPPSGG SGGGGSGGGS GGGGSLQNWV NVISDLKKIE DLIQSMHIDA  120
TLYTESDVHP SCKVTAMKCF LLELQVISLE SGDASIHDTV ENLIILANNS LSSNGNVTES  180
GCKECEELEE KNIKEFLQSF VHIVQMFINT SGGGGSGGGG SGGGGSGGGG SEVQLLESGG  240
GLVQPGGSLR LSCAASGFTF SAYRMFWVRQ APGKGLEWVS SIYPSGGITF YADSVKGRFT  300
ISRDNSKNTL YLQMNSLRAE DTAIYYCARI KLGTVTTVDY WGQGTLVTVS SASTKGPSVF  360
PLAPSSKSTS GGTAALGCLV KDYFPEPVTV SWNSGALTSG VHTFPAVLQS SGLYSLSSVV  420
TVPSSSLGTQ TYICNVNHKP SNTKVDKRVE PKSCDKTHTC PPCPAPEAAG GPSVFLFPPK  480
PKDTLMISRT PEVTCVVVDV SHEDPEVKFN WYVDGVEVHN AKTKPREEQY NSTYRVVSVL  540
TVLHQDWLNG KEYKCKVSNK ALPAPIEKTI SKAKGQPREP QVYVYPPSRE EMTKNQVSLT  600
CLVKGFYPSD IAVEWESNGQ PENNYKTTPP VLDSDGSFAL VSKLTVDKSR WQQGNVFSCS  660
VMHEALHNHY TQKSLSLSPG K                                            681

SEQ ID NO: 209          moltype = AA  length = 659
FEATURE                 Location/Qualifiers
REGION                  1..659
                        note = D7A8 HC LALA + hSD15
source                  1..659
                        mol_type = protein
                        organism = synthetic construct
SEQUENCE: 209
EVQLLESGGG LVQPGGSLRL SCAASGFTFS AYRMFWVRQA PGKGLEWVSS IYPSGGITFY  60
ADSVKGRFTI SRDNSKNTLY LQMNSLRAED TAIYYCARIK LGTVTTVDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKRVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYTLPPSREE  360
MTKNQVSLTC LVKGFYPSDI AVEWESNGQP ENNYKTTPPV LDSDGSFFLY SKLTVDKSRW  420
QQGNVFSCSV MHEALHNHYT QKSLSLSPGS CPPPMSVEHA DIWVKSYSLY SRERYICNSG  480
FKRKAGTSSL TECVLNKATN VAHWTTPSLK CIRDPALVHQ RPAPPSGGSG GGGSGGGGSG  540
GGGSLQNWVNV ISDLKKIEDL IQSMHIDATL YTESDVHPSC KVTAMKCFLL ELQVISLESG  600
DASIHDTVEN LIILANNSLS SNGNVTESGC KECEELEEKN IKEFLQSFVH IVQMFINTS   659

SEQ ID NO: 210          moltype = AA  length = 658
FEATURE                 Location/Qualifiers
REGION                  1..658
                        note = D7A8 HC (Y349C/T366S/L368A/Y407V) LALA+ hSD15
source                  1..658
                        mol_type = protein
                        organism = synthetic construct
SEQUENCE: 210
EVQLLESGGG LVQPGGSLRL SCAASGFTFS AYRMFWVRQA PGKGLEWVSS IYPSGGITFY  60
ADSVKGRFTI SRDNSKNTLY LQMNSLRAED TAIYYCARIK LGTVTTVDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKRVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VCTLPPSREE  360
MTKNQVSLSC AVKGFYPSDI AVEWESNGQP ENNYKTTPPV LDSDGSFFLV SKLTVDKSRW  420
QQGNVFSCSV MHEALHNHYT QKSLSLSPGC PPPMSVEHAD IWVKSYSLYS RERYICNSGF  480
KRKAGTSSL ECVLNKATNV AHWTTPSLKC IRDPALVHQR PAPPSGGSGG GGSGGGGSGGG  540
GSLQNWVNVI SDLKKIEDLI QSMHIDATLY TESDVHPSCK VTAMKCFLLE LQVISLESGD  600
ASIHDTVENL IILANNSLSS NGNVTESGCK ECEELEEKNI KEFLQSFVHI VQMFINTS    658

SEQ ID NO: 211          moltype = AA  length = 658
FEATURE                 Location/Qualifiers
REGION                  1..658
                        note = D7A8 HC (T350V/L351Y/F405A/Y407V) LALA+ hSD15
source                  1..658
                        mol_type = protein
                        organism = synthetic construct
SEQUENCE: 211
EVQLLESGGG LVQPGGSLRL SCAASGFTFS AYRMFWVRQA PGKGLEWVSS IYPSGGITFY  60
ADSVKGRFTI SRDNSKNTLY LQMNSLRAED TAIYYCARIK LGTVTTVDYW GQGTLVTVSS  120
ASTKGPSVFP LAPSSKSTSG GTAALGCLVK DYFPEPVTVS WNSGALTSGV HTFPAVLQSS  180
GLYSLSSVVT VPSSSLGTQT YICNVNHKPS NTKVDKRVEP KSCDKTHTCP PCPAPEAAGG  240
PSVFLFPPKP KDTLMISRTP EVTCVVVDVS HEDPEVKFNW YVDGVEVHNA KTKPREEQYN  300
STYRVVSVLT VLHQDWLNGK EYKCKVSNKA LPAPIEKTIS KAKGQPREPQ VYVYPPSREE  360
MTKNQVSLTC LVKGFYPSDI AVEWESNGQP ENNYKTTPPV LDSDGSFALV SKLTVDKSRW  420
QQGNVFSCSV MHEALHNHYT QKSLSLSPGC PPPMSVEHAD IWVKSYSLYS RERYICNSGF  480
KRKAGTSSLT ECVLNKATNV AHWTTPSLKC IRDPALVHQR PAPPSGGSGG GGSGGGGSGG  540
GSLQNWVNVI SDLKKIEDLI QSMHIDATLY TESDVHPSCK VTAMKCFLLE LQVISLESGD  600
ASIHDTVENL IILANNSLSS NGNVTESGCK ECEELEEKNI KEFLQSFVHI VQMFINTS    658

SEQ ID NO: 212          moltype = AA  length = 114
FEATURE                 Location/Qualifiers
```

-continued

```
REGION                    1..114
                          note = Human IL-15 (mature protein, residue N65 is in bold)
source                    1..114
                          mol_type = protein
                          organism = synthetic construct
SEQUENCE: 212
NWVNVISDLK KIEDLIQSMH IDATLYTESD VHPSCKVTAM KCFLLELQVI SLESGDASIH   60
DTVENLIILA NNSLSSNGNV TESGCKECEE LEEKNIKEFL QSFVHIVQMF INTS         114

SEQ ID NO: 213            moltype = AA  length = 266
FEATURE                   Location/Qualifiers
REGION                    1..266
                          note = Human IL-15 R? subunit (signal peptide is
                           underlined, residue N60 is in bold)
source                    1..266
                          mol_type = protein
                          organism = synthetic construct
SEQUENCE: 213
MAPRRARGCR TLGLPALLLL LLLRPPATRG ITCPPPMSVE HADIWVKSYS LYSRERYICN   60
SGFKRKAGTS SLTECVLNKA TNVAHWTTPS LKCIRDPALV HQRPAPPSTV TTAGVTPQPE  120
SLSPSGKEPA ASSPSSNNTA ATTAAIVPGS QLMPSKSPST GTTEISSHES SHGTPSQTTA  180
KNWELTASAS HQPPGVYPQH SDTTVAISTS TVLLCGLSAV SLLACYLKSR QTPPLASVEM  240
EAMEALPVTW GTSSRDEDLE NCSHHL                                       266

SEQ ID NO: 214            moltype = AA  length = 61
FEATURE                   Location/Qualifiers
REGION                    1..61
                          note = IL-15R? sushi domain
source                    1..61
                          mol_type = protein
                          organism = synthetic construct
SEQUENCE: 214
CPPPMSVEHA DIWVKSYSLY SRERYICNSG FKRKAGTSSL TECVLNKATN VAHWTTPSLK   60
C                                                                  61

SEQ ID NO: 215            moltype = AA  length = 34
FEATURE                   Location/Qualifiers
REGION                    1..34
                          note = Linker 1
source                    1..34
                          mol_type = protein
                          organism = synthetic construct
SEQUENCE: 215
IRDPALVHQR PAPPSGGSGG GGSGGGSGGG GSLQ                               34

SEQ ID NO: 216            moltype = AA  length = 30
FEATURE                   Location/Qualifiers
REGION                    1..30
                          note = Linker 2
source                    1..30
                          mol_type = protein
                          organism = synthetic construct
SEQUENCE: 216
GGGGSGGGGS GGGGSGGGGS GGGGSGGGGS                                    30

SEQ ID NO: 217            moltype = AA  length = 34
FEATURE                   Location/Qualifiers
REGION                    1..34
                          note = Exemplary linker
source                    1..34
                          mol_type = protein
                          organism = synthetic construct
SEQUENCE: 217
IRDPSGGGGS GGGGSGGGGS GGGGSGGGGS GGGG                               34

SEQ ID NO: 218            moltype = AA  length = 34
FEATURE                   Location/Qualifiers
REGION                    1..34
                          note = Exemplary linker
source                    1..34
                          mol_type = protein
                          organism = synthetic construct
SEQUENCE: 218
IRDPGGGGSG GGGSGGGGSG GGGSGGGGSG GGGS                               34

SEQ ID NO: 219            moltype = AA  length = 214
FEATURE                   Location/Qualifiers
REGION                    1..214
                          note = 38B2 LC
```

```
source                  1..214
                        mol_type = protein
                        organism = synthetic construct
SEQUENCE: 219
DIQMTQSPSS LSASVGDRVT ITCRASESIS SWLAWYQQKP GKAPKLLIYD ASSLESGVPS  60
RFSGSGSGTD FTLTISSLQP EDFATYYCQQ GDSFPFTFGQ GTKLEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                               214

SEQ ID NO: 220          moltype = AA   length = 447
FEATURE                 Location/Qualifiers
REGION                  1..447
                        note = 38B2 HC1-1 (T350V/T366L/K392L/T394W) LALAPG
source                  1..447
                        mol_type = protein
                        organism = synthetic construct
SEQUENCE: 220
EVQLLESGGG LVQPGGSLRL SCAASGFTFS SYWMSWVRQA PGKGLEWVSA ISGSGGSTYY  60
ADSVKGRFTI SRDNSKNTLY LQMNSLRAED TAVYYCASSP LQWVDVWGQG TTVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APEAAGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALGA PIEKTISKAK GQPREPQVYV LPPSRDELTK  360
NQVSLLCLVK GFYPSDIAVE WESNGQPENN YLTWPPVLDS DGSFFLYSKL TVDKSRWQQG  420
NVFSCSVMHE ALHNHYTQKS LSLSPGK                                       447

SEQ ID NO: 221          moltype = AA   length = 447
FEATURE                 Location/Qualifiers
REGION                  1..447
                        note = 38B2 HC1-2 (T350V/L351Y/F405A/Y407V) LALAPG
source                  1..447
                        mol_type = protein
                        organism = synthetic construct
SEQUENCE: 221
EVQLLESGGG LVQPGGSLRL SCAASGFTFS SYWMSWVRQA PGKGLEWVSA ISGSGGSTYY  60
ADSVKGRFTI SRDNSKNTLY LQMNSLRAED TAVYYCASSP LQWVDVWGQG TTVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APEAAGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALGA PIEKTISKAK GQPREPQVYV YPPSRDELTK  360
NQVSLTCLVK GFYPSDIAVE WESNGQPENN YKTTPPVLDS DGSFALVSKL TVDKSRWQQG  420
NVFSCSVMHE ALHNHYTQKS LSLSPGK                                       447

SEQ ID NO: 222          moltype = AA   length = 447
FEATURE                 Location/Qualifiers
REGION                  1..447
                        note = 38B2 HC1-3 (CW-CSAV) S354C/T366W LALAPG
source                  1..447
                        mol_type = protein
                        organism = synthetic construct
SEQUENCE: 222
EVQLLESGGG LVQPGGSLRL SCAASGFTFS SYWMSWVRQA PGKGLEWVSA ISGSGGSTYY  60
ADSVKGRFTI SRDNSKNTLY LQMNSLRAED TAVYYCASSP LQWVDVWGQG TTVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APEAAGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALGA PIEKTISKAK GQPREPQVYT LPPCRDELTK  360
NQVSLWCLVK GFYPSDIAVE WESNGQPENN YKTTPPVLDS DGSFFLYSKL TVDKSRWQQG  420
NVFSCSVMHE ALHNHYTQKS LSLSPGK                                       447

SEQ ID NO: 223          moltype = AA   length = 447
FEATURE                 Location/Qualifiers
REGION                  1..447
                        note = 38B2 HC1-4 (CW-CSAV) Y349C/T366S/L368A/Y407V LALAPG
source                  1..447
                        mol_type = protein
                        organism = synthetic construct
SEQUENCE: 223
EVQLLESGGG LVQPGGSLRL SCAASGFTFS SYWMSWVRQA PGKGLEWVSA ISGSGGSTYY  60
ADSVKGRFTI SRDNSKNTLY LQMNSLRAED TAVYYCASSP LQWVDVWGQG TTVTVSSAST  120
KGPSVFPLAP SSKSTSGGTA ALGCLVKDYF PEPVTVSWNS GALTSGVHTF PAVLQSSGLY  180
SLSSVVTVPS SSLGTQTYIC NVNHKPSNTK VDKKVEPKSC DKTHTCPPCP APEAAGGPSV  240
FLFPPKPKDT LMISRTPEVT CVVVDVSHED PEVKFNWYVD GVEVHNAKTK PREEQYNSTY  300
RVVSVLTVLH QDWLNGKEYK CKVSNKALGA PIEKTISKAK GQPREPQVCT LPPSRDELTK  360
NQVSLSCAVK GFYPSDIAVE WESNGQPENN YKTTPPVLDS DGSFFLVSKL TVDKSRWQQG  420
NVFSCSVMHE ALHNHYTQKS LSLSPGK                                       447

SEQ ID NO: 224          moltype = AA   length = 688
FEATURE                 Location/Qualifiers
```

-continued

```
REGION                 1..688
                       note = 65N-38B2 HC2-1 (T350V/L351Y/F405A/Y407V) LALAPG
source                 1..688
                       mol_type = protein
                       organism = synthetic construct
SEQUENCE: 224
ITCPPPMSVE HADIWVKSYS LYSRERYICN SGFKRKAGTS SLTECVLNKA TNVAHWTTPS    60
LKCIRDPALV HQRPAPPSGG SGGGGSGGGS GGGGSLQNWV NVISDLKKIE DLIQSMHIDA   120
TLYTESDVHP SCKVTAMKCF LLELQVISLE SGDASIHDTV ENLIILANNS LSSNGNVTES   180
GCKECEELEE KNIKEFLQSF VHIVQMFINT SGGGGSGGGG SGGGGSGGGG SGGGGSGGGG   240
SEVQLLESGG GLVQPGGSLR LSCAASGFTF SSYWMSWVRQ APGKGLEWVS AISGSGGSTY   300
YADSVKGRFT ISRDNSKNTL YLQMNSLRAE DTAVYYCASS PLQWVDVWGQ GTTVTVSSAS   360
TKGPSVFPLA PSSKSTSGGT AALGCLVKDY FPEPVTVSWN SGALTSGVHT FPAVLQSSGL   420
YSLSSVVTVP SSSLGTQTYI CNVNHKPSNT KVDKKVEPKS CDKTHTCPPC PAPEAAGGPS   480
VFLFPPKPKD TLMISRTPEV TCVVVDVSHE DPEVKFNWYV DGVEVHNAKT KPREEQYNST   540
YRVVSVLTVL HQDWLNGKEY KCKVSNKALG APIEKTISKA KGQPREPQVY VYPPSRDELT   600
KNQVSLTCLV KGFYPSDIAV EWESNGQPEN NYKTTPPVLD SDGSFALVSK LTVDKSRWQQ   660
GNVFSCSVMH EALHNHYTQK SLSLSPGK                                      688

SEQ ID NO: 225         moltype = AA  length = 688
FEATURE                Location/Qualifiers
REGION                 1..688
                       note = 65N-38B2 HC2-2 (T350V/ T366L/K392L/T394W) LALAPG
source                 1..688
                       mol_type = protein
                       organism = synthetic construct
SEQUENCE: 225
ITCPPPMSVE HADIWVKSYS LYSRERYICN SGFKRKAGTS SLTECVLNKA TNVAHWTTPS    60
LKCIRDPALV HQRPAPPSGG SGGGGSGGGS GGGGSLQNWV NVISDLKKIE DLIQSMHIDA   120
TLYTESDVHP SCKVTAMKCF LLELQVISLE SGDASIHDTV ENLIILANNS LSSNGNVTES   180
GCKECEELEE KNIKEFLQSF VHIVQMFINT SGGGGSGGGG SGGGGSGGGG SGGGGSGGGG   240
SEVQLLESGG GLVQPGGSLR LSCAASGFTF SSYWMSWVRQ APGKGLEWVS AISGSGGSTY   300
YADSVKGRFT ISRDNSKNTL YLQMNSLRAE DTAVYYCASS PLQWVDVWGQ GTTVTVSSAS   360
TKGPSVFPLA PSSKSTSGGT AALGCLVKDY FPEPVTVSWN SGALTSGVHT FPAVLQSSGL   420
YSLSSVVTVP SSSLGTQTYI CNVNHKPSNT KVDKKVEPKS CDKTHTCPPC PAPEAAGGPS   480
VFLFPPKPKD TLMISRTPEV TCVVVDVSHE DPEVKFNWYV DGVEVHNAKT KPREEQYNST   540
YRVVSVLTVL HQDWLNGKEY KCKVSNKALG APIEKTISKA KGQPREPQVY VLPPSRDELT   600
KNQVSLLCLV KGFYPSDIAV EWESNGQPEN NYLTWPPVLD SDGSFFLYSK LTVDKSRWQQ   660
GNVFSCSVMH EALHNHYTQK SLSLSPGK                                      688

SEQ ID NO: 226         moltype = AA  length = 688
FEATURE                Location/Qualifiers
REGION                 1..688
                       note = 65N-38B2 HC2-3 (CW-CSAV) Y349C/T366S/L368A/ Y407V
                       LALAPG
source                 1..688
                       mol_type = protein
                       organism = synthetic construct
SEQUENCE: 226
ITCPPPMSVE HADIWVKSYS LYSRERYICN SGFKRKAGTS SLTECVLNKA TNVAHWTTPS    60
LKCIRDPALV HQRPAPPSGG SGGGGSGGGS GGGGSLQNWV NVISDLKKIE DLIQSMHIDA   120
TLYTESDVHP SCKVTAMKCF LLELQVISLE SGDASIHDTV ENLIILANNS LSSNGNVTES   180
GCKECEELEE KNIKEFLQSF VHIVQMFINT SGGGGSGGGG SGGGGSGGGG SGGGGSGGGG   240
SEVQLLESGG GLVQPGGSLR LSCAASGFTF SSYWMSWVRQ APGKGLEWVS AISGSGGSTY   300
YADSVKGRFT ISRDNSKNTL YLQMNSLRAE DTAVYYCASS PLQWVDVWGQ GTTVTVSSAS   360
TKGPSVFPLA PSSKSTSGGT AALGCLVKDY FPEPVTVSWN SGALTSGVHT FPAVLQSSGL   420
YSLSSVVTVP SSSLGTQTYI CNVNHKPSNT KVDKKVEPKS CDKTHTCPPC PAPEAAGGPS   480
VFLFPPKPKD TLMISRTPEV TCVVVDVSHE DPEVKFNWYV DGVEVHNAKT KPREEQYNST   540
YRVVSVLTVL HQDWLNGKEY KCKVSNKALG APIEKTISKA KGQPREPQVC TLPPSRDELT   600
KNQVSLSCAV KGFYPSDIAV EWESNGQPEN NYKTTPPVLD SDGSFFLVSK LTVDKSRWQQ   660
GNVFSCSVMH EALHNHYTQK SLSLSPGK                                      688

SEQ ID NO: 227         moltype = AA  length = 688
FEATURE                Location/Qualifiers
REGION                 1..688
                       note = 65N-38B2 HC2-4 S354C/T366W LALAPG
source                 1..688
                       mol_type = protein
                       organism = synthetic construct
SEQUENCE: 227
ITCPPPMSVE HADIWVKSYS LYSRERYICN SGFKRKAGTS SLTECVLNKA TNVAHWTTPS    60
LKCIRDPALV HQRPAPPSGG SGGGGSGGGS GGGGSLQNWV NVISDLKKIE DLIQSMHIDA   120
TLYTESDVHP SCKVTAMKCF LLELQVISLE SGDASIHDTV ENLIILANNS LSSNGNVTES   180
GCKECEELEE KNIKEFLQSF VHIVQMFINT SGGGGSGGGG SGGGGSGGGG SGGGGSGGGG   240
SEVQLLESGG GLVQPGGSLR LSCAASGFTF SSYWMSWVRQ APGKGLEWVS AISGSGGSTY   300
YADSVKGRFT ISRDNSKNTL YLQMNSLRAE DTAVYYCASS PLQWVDVWGQ GTTVTVSSAS   360
TKGPSVFPLA PSSKSTSGGT AALGCLVKDY FPEPVTVSWN SGALTSGVHT FPAVLQSSGL   420
YSLSSVVTVP SSSLGTQTYI CNVNHKPSNT KVDKKVEPKS CDKTHTCPPC PAPEAAGGPS   480
VFLFPPKPKD TLMISRTPEV TCVVVDVSHE DPEVKFNWYV DGVEVHNAKT KPREEQYNST   540
```

```
YRVVSVLTVL HQDWLNGKEY KCKVSNKALG APIEKTISKA KGQPREPQVY TLPPCRDELT  600
KNQVSLWCLV KGFYPSDIAV EWESNGQPEN NYKTTPPVLD SDGSFFLYSK LTVDKSRWQQ  660
GNVFSCSVMH EALHNHYTQK SLSLSPGK                                     688

SEQ ID NO: 228          moltype = AA   length = 688
FEATURE                 Location/Qualifiers
REGION                  1..688
                        note = 65S-38B2 HC2-1 (T350V/L351Y/F405A/Y407V) LALAPG
source                  1..688
                        mol_type = protein
                        organism = synthetic construct
SEQUENCE: 228
ITCPPPMSVE HADIWVKSYS LYSRERYICN SGFKRKAGTS SLTECVLNKA TNVAHWTTPS  60
LKCIRDPALV HQRPAPPSGG SGGGGSGGGS GGGGSLQNWV NVISDLKKIE DLIQSMHIDA  120
TLYTESDVHP SCKVTAMKCF LLELQVISLE SGDASIHDTV ESLIILANNS LSSNGNVTES  180
GCKECEELEE KNIKEFLQSF VHIVQMFINT SGGGGSGGGG SGGGGSGGGG SGGGGSGGGG  240
SEVQLLESGG GLVQPGGSLR LSCAASGFTF SSYWMSWVRQ APGKGLEWVS AISGSGGSTY  300
YADSVKGRFT ISRDNSKNTL YLQMNSLRAE DTAVYYCASS PLQWVDVWGQ GTTVTVSSAS  360
TKGPSVFPLA PSSKSTSGGT AALGCLVKDY FPEPVTVSWN SGALTSGVHT FPAVLQSSGL  420
YSLSSVVTVP SSSLGTQTYI CNVNHKPSNT KVDKKVEPKS CDKTHTCPPC PAPEAAGGPS  480
VFLFPPKPKD TLMISRTPEV TCVVVDVSHE DPEVKFNWYV DGVEVHNAKT KPREEQYNST  540
YRVVSVLTVL HQDWLNGKEY KCKVSNKALG APIEKTISKA KGQPREPQVY VYPPSRDELT  600
KNQVSLTCLV KGFYPSDIAV EWESNGQPEN NYKTTPPVLD SDGSFALVSK LTVDKSRWQQ  660
GNVFSCSVMH EALHNHYTQK SLSLSPGK                                     688

SEQ ID NO: 229          moltype = AA   length = 688
FEATURE                 Location/Qualifiers
REGION                  1..688
                        note = 65S-38B2 HC2-2 (T350V/T366L/K392L/T394W) LALAPG
source                  1..688
                        mol_type = protein
                        organism = synthetic construct
SEQUENCE: 229
ITCPPPMSVE HADIWVKSYS LYSRERYICN SGFKRKAGTS SLTECVLNKA TNVAHWTTPS  60
LKCIRDPALV HQRPAPPSGG SGGGGSGGGS GGGGSLQNWV NVISDLKKIE DLIQSMHIDA  120
TLYTESDVHP SCKVTAMKCF LLELQVISLE SGDASIHDTV ESLIILANNS LSSNGNVTES  180
GCKECEELEE KNIKEFLQSF VHIVQMFINT SGGGGSGGGG SGGGGSGGGG SGGGGSGGGG  240
SEVQLLESGG GLVQPGGSLR LSCAASGFTF SSYWMSWVRQ APGKGLEWVS AISGSGGSTY  300
YADSVKGRFT ISRDNSKNTL YLQMNSLRAE DTAVYYCASS PLQWVDVWGQ GTTVTVSSAS  360
TKGPSVFPLA PSSKSTSGGT AALGCLVKDY FPEPVTVSWN SGALTSGVHT FPAVLQSSGL  420
YSLSSVVTVP SSSLGTQTYI CNVNHKPSNT KVDKKVEPKS CDKTHTCPPC PAPEAAGGPS  480
VFLFPPKPKD TLMISRTPEV TCVVVDVSHE DPEVKFNWYV DGVEVHNAKT KPREEQYNST  540
YRVVSVLTVL HQDWLNGKEY KCKVSNKALG APIEKTISKA KGQPREPQVY VLPPSRDELT  600
KNQVSLLCLV KGFYPSDIAV EWESNGQPEN NYLTWPPVLD SDGSFFLYSK LTVDKSRWQQ  660
GNVFSCSVMH EALHNHYTQK SLSLSPGK                                     688

SEQ ID NO: 230          moltype = AA   length = 688
FEATURE                 Location/Qualifiers
REGION                  1..688
                        note = 65S-38B2 HC2-3 (CW-CSAV) Y349C/T366S/L368A/Y407V
                         LALAP
source                  1..688
                        mol_type = protein
                        organism = synthetic construct
SEQUENCE: 230
ITCPPPMSVE HADIWVKSYS LYSRERYICN SGFKRKAGTS SLTECVLNKA TNVAHWTTPS  60
LKCIRDPALV HQRPAPPSGG SGGGGSGGGS GGGGSLQNWV NVISDLKKIE DLIQSMHIDA  120
TLYTESDVHP SCKVTAMKCF LLELQVISLE SGDASIHDTV ESLIILANNS LSSNGNVTES  180
GCKECEELEE KNIKEFLQSF VHIVQMFINT SGGGGSGGGG SGGGGSGGGG SGGGGSGGGG  240
SEVQLLESGG GLVQPGGSLR LSCAASGFTF SSYWMSWVRQ APGKGLEWVS AISGSGGSTY  300
YADSVKGRFT ISRDNSKNTL YLQMNSLRAE DTAVYYCASS PLQWVDVWGQ GTTVTVSSAS  360
TKGPSVFPLA PSSKSTSGGT AALGCLVKDY FPEPVTVSWN SGALTSGVHT FPAVLQSSGL  420
YSLSSVVTVP SSSLGTQTYI CNVNHKPSNT KVDKKVEPKS CDKTHTCPPC PAPEAAGGPS  480
VFLFPPKPKD TLMISRTPEV TCVVVDVSHE DPEVKFNWYV DGVEVHNAKT KPREEQYNST  540
YRVVSVLTVL HQDWLNGKEY KCKVSNKALG APIEKTISKA KGQPREPQVC TLPPSRDELT  600
KNQVSLSCAV KGFYPSDIAV EWESNGQPEN NYKTTPPVLD SDGSFFLVSK LTVDKSRWQQ  660
GNVFSCSVMH EALHNHYTQK SLSLSPGK                                     688

SEQ ID NO: 231          moltype = AA   length = 688
FEATURE                 Location/Qualifiers
REGION                  1..688
                        note = 65S-38B2 HC2-4 S354C/T366W LALAPG
source                  1..688
                        mol_type = protein
                        organism = synthetic construct
SEQUENCE: 231
ITCPPPMSVE HADIWVKSYS LYSRERYICN SGFKRKAGTS SLTECVLNKA TNVAHWTTPS  60
LKCIRDPALV HQRPAPPSGG SGGGGSGGGS GGGGSLQNWV NVISDLKKIE DLIQSMHIDA  120
TLYTESDVHP SCKVTAMKCF LLELQVISLE SGDASIHDTV ESLIILANNS LSSNGNVTES  180
```

-continued

```
GCKECEELEE KNIKEFLQSF VHIVQMFINT SGGGGSGGGG SGGGGSGGGG SGGGGSGGGG   240
SEVQLLESGG GLVQPGGSLR LSCAASGFTF SSYWMSWVRQ APGKGLEWVS AISGSGGSTY   300
YADSVKGRFT ISRDNSKNTL YLQMNSLRAE DTAVYYCASS PLQWVDVWGQ GTTVTVSSAS   360
TKGPSVFPLA PSSKSTSGGT AALGCLVKDY FPEPVTVSWN SGALTSGVHT FPAVLQSSGL   420
YSLSSVVTVP SSSLGTQTYI CNVNHKPSNT KVDKKVEPKS CDKTHTCPPC PAPEAAGGPS   480
VFLFPPKPKD TLMISRTPEV TCVVVDVSHE DPEVKFNWYV DGVEVHNAKT KPREEQYNST   540
YRVVSVLTVL HQDWLNGKEY KCKVSNKALG APIEKTISKA KGQPREPQVY TLPPCRDELT   600
KNQVSLWCLV KGFYPSDIAV EWESNGQPEN NYKTTPPVLD SDGSFFLYSK LTVDKSRWQQ   660
GNVFSCSVMH EALHNHYTQK SLSLSPGK                                      688

SEQ ID NO: 232             moltype = AA   length = 688
FEATURE                    Location/Qualifiers
REGION                     1..688
                           note = 65D-38B2 HC2-1 (T350V/L351Y/F405A/Y407V) LALAPG
source                     1..688
                           mol_type = protein
                           organism = synthetic construct
SEQUENCE: 232
ITCPPPMSVE HADIWVKSYS LYSRERYICN SGFKRKAGTS SLTECVLNKA TNVAHWTTPS   60
LKCIRDPALV HQRPAPPSGG SGGGGSGGGS GGGGSLQNWV NVISDLKKIE DLIQSMHIDA   120
TLYTESDVHP SCKVTAMKCF LLELQVISLE SGDASIHDTV EDLIILANNS LSSNGNVTES   180
GCKECEELEE KNIKEFLQSF VHIVQMFINT SGGGGSGGGG SGGGGSGGGG SGGGGSGGGG   240
SEVQLLESGG GLVQPGGSLR LSCAASGFTF SSYWMSWVRQ APGKGLEWVS AISGSGGSTY   300
YADSVKGRFT ISRDNSKNTL YLQMNSLRAE DTAVYYCASS PLQWVDVWGQ GTTVTVSSAS   360
TKGPSVFPLA PSSKSTSGGT AALGCLVKDY FPEPVTVSWN SGALTSGVHT FPAVLQSSGL   420
YSLSSVVTVP SSSLGTQTYI CNVNHKPSNT KVDKKVEPKS CDKTHTCPPC PAPEAAGGPS   480
VFLFPPKPKD TLMISRTPEV TCVVVDVSHE DPEVKFNWYV DGVEVHNAKT KPREEQYNST   540
YRVVSVLTVL HQDWLNGKEY KCKVSNKALG APIEKTISKA KGQPREPQVY VYPPSRDELT   600
KNQVSLTCLV KGFYPSDIAV EWESNGQPEN NYKTTPPVLD SDGSFALVSK LTVDKSRWQQ   660
GNVFSCSVMH EALHNHYTQK SLSLSPGK                                      688

SEQ ID NO: 233             moltype = AA   length = 688
FEATURE                    Location/Qualifiers
REGION                     1..688
                           note = 65D-38B2 HC2-2 (T350V/T366L/K392L/T394W) LALAPG
source                     1..688
                           mol_type = protein
                           organism = synthetic construct
SEQUENCE: 233
ITCPPPMSVE HADIWVKSYS LYSRERYICN SGFKRKAGTS SLTECVLNKA TNVAHWTTPS   60
LKCIRDPALV HQRPAPPSGG SGGGGSGGGS GGGGSLQNWV NVISDLKKIE DLIQSMHIDA   120
TLYTESDVHP SCKVTAMKCF LLELQVISLE SGDASIHDTV EDLIILANNS LSSNGNVTES   180
GCKECEELEE KNIKEFLQSF VHIVQMFINT SGGGGSGGGG SGGGGSGGGG SGGGGSGGGG   240
SEVQLLESGG GLVQPGGSLR LSCAASGFTF SSYWMSWVRQ APGKGLEWVS AISGSGGSTY   300
YADSVKGRFT ISRDNSKNTL YLQMNSLRAE DTAVYYCASS PLQWVDVWGQ GTTVTVSSAS   360
TKGPSVFPLA PSSKSTSGGT AALGCLVKDY FPEPVTVSWN SGALTSGVHT FPAVLQSSGL   420
YSLSSVVTVP SSSLGTQTYI CNVNHKPSNT KVDKKVEPKS CDKTHTCPPC PAPEAAGGPS   480
VFLFPPKPKD TLMISRTPEV TCVVVDVSHE DPEVKFNWYV DGVEVHNAKT KPREEQYNST   540
YRVVSVLTVL HQDWLNGKEY KCKVSNKALG APIEKTISKA KGQPREPQVY VLPPSRDELT   600
KNQVSLLCLV KGFYPSDIAV EWESNGQPEN NYLTWPPVLD SDGSFFLYSK LTVDKSRWQQ   660
GNVFSCSVMH EALHNHYTQK SLSLSPGK                                      688

SEQ ID NO: 234             moltype = AA   length = 688
FEATURE                    Location/Qualifiers
REGION                     1..688
                           note = 65D-38B2 HC2-3 (CW-CSAV) Y349C/T366S/L368A/Y407V
                            LALAPG
source                     1..688
                           mol_type = protein
                           organism = synthetic construct
SEQUENCE: 234
ITCPPPMSVE HADIWVKSYS LYSRERYICN SGFKRKAGTS SLTECVLNKA TNVAHWTTPS   60
LKCIRDPALV HQRPAPPSGG SGGGGSGGGS GGGGSLQNWV NVISDLKKIE DLIQSMHIDA   120
TLYTESDVHP SCKVTAMKCF LLELQVISLE SGDASIHDTV EDLIILANNS LSSNGNVTES   180
GCKECEELEE KNIKEFLQSF VHIVQMFINT SGGGGSGGGG SGGGGSGGGG SGGGGSGGGG   240
SEVQLLESGG GLVQPGGSLR LSCAASGFTF SSYWMSWVRQ APGKGLEWVS AISGSGGSTY   300
YADSVKGRFT ISRDNSKNTL YLQMNSLRAE DTAVYYCASS PLQWVDVWGQ GTTVTVSSAS   360
TKGPSVFPLA PSSKSTSGGT AALGCLVKDY FPEPVTVSWN SGALTSGVHT FPAVLQSSGL   420
YSLSSVVTVP SSSLGTQTYI CNVNHKPSNT KVDKKVEPKS CDKTHTCPPC PAPEAAGGPS   480
VFLFPPKPKD TLMISRTPEV TCVVVDVSHE DPEVKFNWYV DGVEVHNAKT KPREEQYNST   540
YRVVSVLTVL HQDWLNGKEY KCKVSNKALG APIEKTISKA KGQPREPQVC TLPPSRDELT   600
KNQVSLSCAV KGFYPSDIAV EWESNGQPEN NYKTTPPVLD SDGSFFLVSK LTVDKSRWQQ   660
GNVFSCSVMH EALHNHYTQK SLSLSPGK                                      688

SEQ ID NO: 235             moltype = AA   length = 688
FEATURE                    Location/Qualifiers
REGION                     1..688
                           note = 65D-38B2 HC2-4 S354C/ T366W LALAPG
source                     1..688
```

```
                        mol_type = protein
                        organism = synthetic construct
SEQUENCE: 235
ITCPPPMSVE HADIWVKSYS LYSRERYICN SGFKRKAGTS SLTECVLNKA TNVAHWTTPS   60
LKCIRDPALV HQRPAPPSGG SGGGGSGGGS GGGGSLQNWV NVISDLKKIE DLIQSMHIDA  120
TLYTESDVHP SCKVTAMKCF LLELQVISLE SGDASIHDTV EDLIILANNS LSSNGNVTES  180
GCKECEELEE KNIKEFLQSF VHIVQMFINT SGGGGSGGGG SGGGGSGGGG SGGGGSGGGG  240
SEVQLLESGG GLVQPGGSLR LSCAASGFTF SSYWMSWVRQ APGKGLEWVS AISGSGGSTY  300
YADSVKGRFT ISRDNSKNTL YLQMNSLRAE DTAVYYCASS PLQWVDVWGQ GTTVTVSSAS  360
TKGPSVFPLA PSSKSTSGGT AALGCLVKDY FPEPVTVSWN SGALTSGVHT FPAVLQSSGL  420
YSLSSVVTVP SSSLGTQTYI CNVNHKPSNT KVDKKVEPKS CDKTHTCPPC PAPEAAGGPS  480
VFLFPPKPKD TLMISRTPEV TCVVVDVSHE DPEVKFNWYV DGVEVHNAKT KPREEQYNST  540
YRVVSVLTVL HQDWLNGKEY KCKVSNKALG APIEKTISKA KGQPREPQVY TLPPCRDELT  600
KNQVSLWCLV KGFYPSDIAV EWESNGQPEN NYKTTPPVLD SDGSFFLYSK LTVDKSRWQQ  660
GNVFSCSVMH EALHNHYTQK SLSLSPGK                                     688

SEQ ID NO: 236       moltype = AA  length = 688
FEATURE              Location/Qualifiers
REGION               1..688
                     note = 65S-38B2 HC2-5 (T350V/L351Y/F405A/Y407V) LALAPG
source               1..688
                        mol_type = protein
                        organism = synthetic construct
SEQUENCE: 236
ITCPPPMSVE HADIWVKSYS LYSRERYICN SGFKRKAGTS SLTECVLNKA TNVAHWTTPS   60
LKCIRDPALV HQRPAPPSGG GGSGGGGSGG GSGGGGSNWV NVISDLKKIE DLIQSMHIDA  120
TLYTESDVHP SCKVTAMKCF LLELQVISLE SGDASIHDTV ESLIILANNS LSSNGNVTES  180
GCKECEELEE KNIKEFLQSF VHIVQMFINT SGGGGSGGGG SGGGGSGGGG SGGGGSGGGG  240
SEVQLLESGG GLVQPGGSLR LSCAASGFTF SSYWMSWVRQ APGKGLEWVS AISGSGGSTY  300
YADSVKGRFT ISRDNSKNTL YLQMNSLRAE DTAVYYCASS PLQWVDVWGQ GTTVTVSSAS  360
TKGPSVFPLA PSSKSTSGGT AALGCLVKDY FPEPVTVSWN SGALTSGVHT FPAVLQSSGL  420
YSLSSVVTVP SSSLGTQTYI CNVNHKPSNT KVDKKVEPKS CDKTHTCPPC PAPEAAGGPS  480
VFLFPPKPKD TLMISRTPEV TCVVVDVSHE DPEVKFNWYV DGVEVHNAKT KPREEQYNST  540
YRVVSVLTVL HQDWLNGKEY KCKVSNKALG APIEKTISKA KGQPREPQVY VYPPSRDELT  600
KNQVSLTCLV KGFYPSDIAV EWESNGQPEN NYKTTPPVLD SDGSFALVSK LTVDKSRWQQ  660
GNVFSCSVMH EALHNHYTQK SLSLSPGK                                     688

SEQ ID NO: 237       moltype = AA  length = 688
FEATURE              Location/Qualifiers
REGION               1..688
                     note = 65S-38B2 HC2-6 (T350V/T366L/K392L/T394W) LALAPG
source               1..688
                        mol_type = protein
                        organism = synthetic construct
SEQUENCE: 237
ITCPPPMSVE HADIWVKSYS LYSRERYICN SGFKRKAGTS SLTECVLNKA TNVAHWTTPS   60
LKCIRDPALV HQRPAPPSGG GGSGGGGSGG GSGGGGSNWV NVISDLKKIE DLIQSMHIDA  120
TLYTESDVHP SCKVTAMKCF LLELQVISLE SGDASIHDTV ESLIILANNS LSSNGNVTES  180
GCKECEELEE KNIKEFLQSF VHIVQMFINT SGGGGSGGGG SGGGGSGGGG SGGGGSGGGG  240
SEVQLLESGG GLVQPGGSLR LSCAASGFTF SSYWMSWVRQ APGKGLEWVS AISGSGGSTY  300
YADSVKGRFT ISRDNSKNTL YLQMNSLRAE DTAVYYCASS PLQWVDVWGQ GTTVTVSSAS  360
TKGPSVFPLA PSSKSTSGGT AALGCLVKDY FPEPVTVSWN SGALTSGVHT FPAVLQSSGL  420
YSLSSVVTVP SSSLGTQTYI CNVNHKPSNT KVDKKVEPKS CDKTHTCPPC PAPEAAGGPS  480
VFLFPPKPKD TLMISRTPEV TCVVVDVSHE DPEVKFNWYV DGVEVHNAKT KPREEQYNST  540
YRVVSVLTVL HQDWLNGKEY KCKVSNKALG APIEKTISKA KGQPREPQVY VLPPSRDELT  600
KNQVSLLCLV KGFYPSDIAV EWESNGQPEN NYLTWPPVLD SDGSFFLYSK LTVDKSRWQQ  660
GNVFSCSVMH EALHNHYTQK SLSLSPGK                                     688

SEQ ID NO: 238       moltype = AA  length = 688
FEATURE              Location/Qualifiers
REGION               1..688
                     note = 65S-38B2 HC2-7 (CW-CSAV) Y349C/T366S/L368A/Y407V
                       LALAPG
source               1..688
                        mol_type = protein
                        organism = synthetic construct
SEQUENCE: 238
ITCPPPMSVE HADIWVKSYS LYSRERYICN SGFKRKAGTS SLTECVLNKA TNVAHWTTPS   60
LKCIRDPALV HQRPAPPSGG GGSGGGGSGG GSGGGGSNWV NVISDLKKIE DLIQSMHIDA  120
TLYTESDVHP SCKVTAMKCF LLELQVISLE SGDASIHDTV ESLIILANNS LSSNGNVTES  180
GCKECEELEE KNIKEFLQSF VHIVQMFINT SGGGGSGGGG SGGGGSGGGG SGGGGSGGGG  240
SEVQLLESGG GLVQPGGSLR LSCAASGFTF SSYWMSWVRQ APGKGLEWVS AISGSGGSTY  300
YADSVKGRFT ISRDNSKNTL YLQMNSLRAE DTAVYYCASS PLQWVDVWGQ GTTVTVSSAS  360
TKGPSVFPLA PSSKSTSGGT AALGCLVKDY FPEPVTVSWN SGALTSGVHT FPAVLQSSGL  420
YSLSSVVTVP SSSLGTQTYI CNVNHKPSNT KVDKKVEPKS CDKTHTCPPC PAPEAAGGPS  480
VFLFPPKPKD TLMISRTPEV TCVVVDVSHE DPEVKFNWYV DGVEVHNAKT KPREEQYNST  540
YRVVSVLTVL HQDWLNGKEY KCKVSNKALG APIEKTISKA KGQPREPQVC TLPPSRDELT  600
KNQVSLSCAV KGFYPSDIAV EWESNGQPEN NYKTTPPVLD SDGSFFLVSK LTVDKSRWQQ  660
GNVFSCSVMH EALHNHYTQK SLSLSPGK                                     688
```

-continued

```
SEQ ID NO: 239            moltype = AA  length = 688
FEATURE                   Location/Qualifiers
REGION                    1..688
                          note = 65S-38B2 HC2-8 S354C/T366W LALAPG
source                    1..688
                          mol_type = protein
                          organism = synthetic construct
SEQUENCE: 239
ITCPPPMSVE HADIWVKSYS LYSRERYICN SGFKRKAGTS SLTECVLNKA TNVAHWTTPS   60
LKCIRDPALV HQRPAPPSGG GGSGGGGSGG GSGGGGSNWV NVISDLKKIE DLIQSMHIDA   120
TLYTESDVHP SCKVTAMKCF LLELQVISLE SGDASIHDTV ESLIILANNS LSSNGNVTES   180
GCKECEELEE KNIKEFLQSF VHIVQMFINT SGGGGSGGGG SGGGGSGGGG SGGGGSGGGG   240
SEVQLLESGG GLVQPGGSLR LSCAASGFTF SSYWMSWVRQ APGKGLEWVS AISGSGGSTY   300
YADSVKGRFT ISRDNSKNTL YLQMNSLRAE DTAVYYCASS PLQWVDVWGQ GTTVTVSSAS   360
TKGPSVFPLA PSSKSTSGGT AALGCLVKDY FPEPVTVSWN SGALTSGVHT FPAVLQSSGL   420
YSLSSVVTVP SSSLGTQTYI CNVNHKPSNT KVDKKVEPKS CDKTHTCPPC PAPEAAGGPS   480
VFLFPPKPKD TLMISRTPEV TCVVVDVSHE DPEVKFNWYV DGVEVHNAKT KPREEQYNST   540
YRVVSVLTVL HQDWLNGKEY KCKVSNKALG APIEKTISKA KGQPREPQVY TLPPCRDELT   600
KNQVSLWCLV KGFYPSDIAV EWESNGQPEN NYKTTPPVLD SDGSFFLYSK LTVDKSRWQQ   660
GNVFSCSVMH EALHNHYTQK SLSLSPGK                                     688

SEQ ID NO: 240            moltype = AA  length = 447
FEATURE                   Location/Qualifiers
REGION                    1..447
                          note = 38B2 HC1-3B (CW-CSAV) S354C/T366W LALA
source                    1..447
                          mol_type = protein
                          organism = synthetic construct
SEQUENCE: 240
EVQLLESGGG LVQPGGSLRL SCAASGFTFS SYWMSWVRQA PGKGLEWVSA ISGSGGSTYY   60
ADSVKGRFTI SRDNSKNTLY LQMNSLRAED TAVYYCASSP LQWVDVWGQG TTVTVSSAST   120
KGPSVFPLAP SSKSTSGGTA ALGCLVKDYF PEPVTVSWNS GALTSGVHTF PAVLQSSGLY   180
SLSSVVTVPS SSLGTQTYIC NVNHKPSNTK VDKKVEPKSC DKTHTCPPCP APEAAGGPSV   240
FLFPPKPKDT LMISRTPEVT CVVVDVSHED PEVKFNWYVD GVEVHNAKTK PREEQYNSTY   300
RVVSVLTVLH QDWLNGKEYK CKVSNKALPA PIEKTISKAK GQPREPQVYT LPPCRDELTK   360
NQVSLWCLVK GFYPSDIAVE WESNGQPENN YKTTPPVLDS DGSFFLYSKL TVDKSRWQQG   420
NVFSCSVMHE ALHNHYTQKS LSLSPGK                                      447

SEQ ID NO: 241            moltype = AA  length = 688
FEATURE                   Location/Qualifiers
REGION                    1..688
                          note = 65S-38B2 HC2-3B (CW-CSAV) Y349C/T366S/L368A/Y407V
                           LALA
source                    1..688
                          mol_type = protein
                          organism = synthetic construct
SEQUENCE: 241
ITCPPPMSVE HADIWVKSYS LYSRERYICN SGFKRKAGTS SLTECVLNKA TNVAHWTTPS   60
LKCIRDPALV HQRPAPPSGG SGGGGSGGGS GGGGSLQNWV NVISDLKKIE DLIQSMHIDA   120
TLYTESDVHP SCKVTAMKCF LLELQVISLE SGDASIHDTV ESLIILANNS LSSNGNVTES   180
GCKECEELEE KNIKEFLQSF VHIVQMFINT SGGGGSGGGG SGGGGSGGGG SGGGGSGGGG   240
SEVQLLESGG GLVQPGGSLR LSCAASGFTF SSYWMSWVRQ APGKGLEWVS AISGSGGSTY   300
YADSVKGRFT ISRDNSKNTL YLQMNSLRAE DTAVYYCASS PLQWVDVWGQ GTTVTVSSAS   360
TKGPSVFPLA PSSKSTSGGT AALGCLVKDY FPEPVTVSWN SGALTSGVHT FPAVLQSSGL   420
YSLSSVVTVP SSSLGTQTYI CNVNHKPSNT KVDKKVEPKS CDKTHTCPPC PAPEAAGGPS   480
VFLFPPKPKD TLMISRTPEV TCVVVDVSHE DPEVKFNWYV DGVEVHNAKT KPREEQYNST   540
YRVVSVLTVL HQDWLNGKEY KCKVSNKALP APIEKTISKA KGQPREPQVC TLPPSRDELT   600
KNQVSLSCAV KGFYPSDIAV EWESNGQPEN NYKTTPPVLD SDGSFFLVSK LTVDKSRWQQ   660
GNVFSCSVMH EALHNHYTQK SLSLSPGK                                     688

SEQ ID NO: 242            moltype = AA  length = 688
FEATURE                   Location/Qualifiers
REGION                    1..688
                          note = 65S-38B2 HC2-7B (CW-CSAV) Y349C/T366S/L368A/Y407V
                           LALA
source                    1..688
                          mol_type = protein
                          organism = synthetic construct
SEQUENCE: 242
ITCPPPMSVE HADIWVKSYS LYSRERYICN SGFKRKAGTS SLTECVLNKA TNVAHWTTPS   60
LKCIRDPALV HQRPAPPSGG GGSGGGGSGG GSGGGGSNWV NVISDLKKIE DLIQSMHIDA   120
TLYTESDVHP SCKVTAMKCF LLELQVISLE SGDASIHDTV ESLIILANNS LSSNGNVTES   180
GCKECEELEE KNIKEFLQSF VHIVQMFINT SGGGGSGGGG SGGGGSGGGG SGGGGSGGGG   240
SEVQLLESGG GLVQPGGSLR LSCAASGFTF SSYWMSWVRQ APGKGLEWVS AISGSGGSTY   300
YADSVKGRFT ISRDNSKNTL YLQMNSLRAE DTAVYYCASS PLQWVDVWGQ GTTVTVSSAS   360
TKGPSVFPLA PSSKSTSGGT AALGCLVKDY FPEPVTVSWN SGALTSGVHT FPAVLQSSGL   420
YSLSSVVTVP SSSLGTQTYI CNVNHKPSNT KVDKKVEPKS CDKTHTCPPC PAPEAAGGPS   480
VFLFPPKPKD TLMISRTPEV TCVVVDVSHE DPEVKFNWYV DGVEVHNAKT KPREEQYNST   540
```

-continued

```
YRVVSVLTVL HQDWLNGKEY KCKVSNKALP APIEKTISKA KGQPREPQVC TLPPSRDELT   600
KNQVSLSCAV KGFYPSDIAV EWESNGQPEN NYKTTPPVLD SDGSFFLVSK LTVDKSRWQQ   660
GNVFSCSVMH EALHNHYTQK SLSLSPGK                                     688

SEQ ID NO: 243          moltype = AA  length = 688
FEATURE                 Location/Qualifiers
REGION                  1..688
                        note = 65D-38B2 HC2-3B (CW-CSAV) Y349C/T366S/L368A/Y407V
                         LALA
source                  1..688
                        mol_type = protein
                        organism = synthetic construct
SEQUENCE: 243
ITCPPPMSVE HADIWVKSYS LYSRERYICN SGFKRKAGTS SLTECVLNKA TNVAHWTTPS   60
LKCIRDPALV HQRPAPPSGG SGGGGSGGGS GGGGSLQNWV NVISDLKKIE DLIQSMHIDA   120
TLYTESDVHP SCKVTAMKCF LLELQVISLE SGDASIHDTV EDLIILANNS LSSNGNVTES   180
GCKECEELEE KNIKEFLQSF VHIVQMFINT SGGGGSGGGG SGGGGSGGGG SGGGGSGGGG   240
SEVQLLESGG GLVQPGGSLR LSCAASGFTF SSYWMSWVRQ APGKGLEWVS AISGSGGSTY   300
YADSVKGRFT ISRDNSKNTL YLQMNSLRAE DTAVYYCASS PLQWVDVWGQ GTTVTVSSAS   360
TKGPSVFPLA PSSKSTSGGT AALGCLVKDY FPEPVTVSWN SGALTSGVHT FPAVLQSSGL   420
YSLSSVVTVP SSSLGTQTYI CNVNHKPSNT KVDKKVEPKS CDKTHTCPPC PAPEAAGGPS   480
VFLFPPKPKD TLMISRTPEV TCVVVDVSHE DPEVKFNWYV DGVEVHNAKT KPREEQYNST   540
YRVVSVLTVL HQDWLNGKEY KCKVSNKALP APIEKTISKA KGQPREPQVC TLPPSRDELT   600
KNQVSLSCAV KGFYPSDIAV EWESNGQPEN NYKTTPPVLD SDGSFFLVSK LTVDKSRWQQ   660
GNVFSCSVMH EALHNHYTQK SLSLSPGK                                     688

SEQ ID NO: 244          moltype = AA  length = 20
FEATURE                 Location/Qualifiers
REGION                  1..20
                        note = Exemplary linker
source                  1..20
                        mol_type = protein
                        organism = synthetic construct
SEQUENCE: 244
GGGGSGGGGS GGGGSGGGGS                                              20
```

ANTI-PD-1 ANTIBODIES AND FUSION PROTEINS

CROSS-REFERENCE TO RELATED APPLICATION

This application is a continuation of U.S. application Ser. No. 18/011,878, filed Dec. 21, 2022, which is a national phase entry pursuant to 35 U.S.C. § 371 of International Application No. PCT/US2021/038740, filed Jun. 23, 2021, which claims the benefit of priority to U.S. Provisional Patent Application No. 63/043,114, filed Jun. 23, 2020, and to U.S. Provisional Patent Application No. 63/111,459, filed Nov. 9, 2020, the entire contents of which are incorporated by reference herein in their entireties.

SEQUENCE LISTING

The present application contains a Sequence Listing which has been submitted electronically in XML format. Said XML copy, created on Dec. 13, 2024, is named "01183-0208-01US-KAD.xml" and is 362,391 bytes in size. The information in the electronic format of the sequence listing is incorporated herein by reference in its entirety.

FIELD

The present disclosure relates generally to the field of molecular biology and medicine. More particularly, the disclosure provides fusion proteins comprising an anti-PD-1 antibody or antigen-binding fragment thereof linked to an IL-15 polypeptide, which in turn is linked to an IL-15 receptor alpha (IL-15Rα) polypeptide comprising the IL-15Rα sushi domain. In addition, the disclosure provides antibodies, and antigen-binding fragments thereof, that specifically bind to PD-1 as well as fusion proteins comprising such anti-PD-1 antibodies and PD-1 binding fragments thereof. Also disclosed are therapeutic compositions comprising the antibody fusions or antibodies for treating disease.

BACKGROUND

PD-1 is a 55 KD type I transmembrane protein of 286 amino acids, which contains a membrane proximal immunoreceptor tyrosine inhibitory motif (ITIM) and a membrane distal tyrosine-based switch motif (ITSM). The PD-1 cytosolic domain contains two tyrosines, with the closest tyrosine (VAYEEL in mouse PD-1) located within the ITIM. The human PD-1 protein and the murine PD-1 protein share about 60% amino acid identity, with four potential N-glycosylation sites and residues that define the Ig-V domain are conserved. ITIM-like motifs surrounding the ITIM and C-terminal tyrosine in the cytoplasmic region are also conserved between human orthologue and murine orthologue. PD-1 is a member of CD-28 family of receptors, which is primarily expressed on mature T cells in peripheral tissues and the tumor microenvironment. PD-1 is also expressed on other non-T cell subsets including B cells, professional antigen presenting cells (APCs), and natural killer (NK) cells.

The ligands for PD-1 are the B7 family members PD-L1 (also known as B7-H1 and CD274) and PD-L2 (also known as B7-DC and CD273). PD-L1 is expressed primarily on both lymphoid and non-lymphoid tissues such as CD4 and CD8 T cells, macrophage lineage cells, peripheral tissues as well as on tumor cells, virally infected cells and autoimmune tissue cells. However, PD-L2 has a more restricted expression than PD-L1, being expressed only on macrophages and activated dendritic cells. PD-1 ligands are expressed in many human cancers, including melanoma, glioma, non-small cell lung cancer, squamous cell carcinoma of head and neck, leukemia, pancreatic cancer, renal cell carcinoma, and hepatocellular carcinoma, and may be inducible in nearly all cancer. Interaction between PD-1 and its ligands results in dephosphorylation and inactivation of the T cell kinase ZAP70, and the recruitment of SHP2. SHP2 directly dephosphorylates PI3K, which inhibits downstream activation of Aktin causing a decrease in tumor infiltrating lymphocytes, and a decrease in T cell receptor mediated proliferation, leading to immune evasion. Inhibiting interaction between PD-1 and PD-L1 reverses immune suppression and the effect may be additive when the interaction of PD-1 with PD-L2 is blocked as well.

Several commercial anti-PD-1 antibodies are currently used to treat diseases that involve PD-1-mediated immune suppression. However, only a subset of patients responds well to these therapies. Depending on the indication and other factors, the typical response rate of patients for each monotherapy ranges from 10% to 30%. One possible reason for this lack of response could be the absence of an inflammatory tumor microenvironment (TME), including activated anti-tumor CD8+ and CD4+ T cells as well as other effectors such as NK cells.

Combination therapies involving PD-1 antibodies with various cytokines such as IL-2, IL-15, IL-21, tumor necrosis factor (TNF), and granulocyte-macrophage colony-stimulating factor (GM-CSF) may have some efficacy in treating cancer and infection. However, these therapies are limited by the systemic toxicity that is associated both with the high blood concentrations of cytokines that is required to obtain efficacy and with the lack of specificity of the administered cytokine for affected cells and tissues.

IL-15 is a 12.5 KD glycoprotein with 114 amino acids and belongs to the four α-helix bundle family of cytokines that also includes IL-2, IL-4, IL-7, IL-9, granulocyte colony-stimulating factor (G-CSF), and GM-CSF. IL-15 is secreted by macrophages, dendritic cells, and monocytes. IL-15 can stimulate central memory CD8 cells to exert immunity without modulating effects on other T cells. Additionally, IL-15 can activate NK cells and effector and memory CD8 T cells and can rescue T cells from apoptosis induced by regulatory T cells (Tregs). Administration of IL-15 is also associated with a lower risk of inducing systemic toxicity at a higher dose compared to other cytokines. Human IL-15 can be soluble or membrane-bound. The membrane-bound IL-15, which is the major form of IL-15, is either formed by binding of IL-15 to cellular membrane directly or by presentation of IL-15 by the membrane-bound IL-15R receptor.

The IL-15 receptor is composed of three subunits: IL-15Rα, IL-15Rβ, and IL-15Rγ. IL-15 typically forms a complex with IL-15 receptor α expressed on APCs prior to binding to functional IL-15Rβ and γ units on T cells and NK cells. IL-15 can bind to IL-15Rα receptor alone with affinity (Ka=1.1011 M-1). It can also bind to IL-15Rβγc signaling complex with lower affinity (Ka=1.109 M-1). The sushi domain (29.5 KD) of the IL-15Rα plays a critical role in complex formation of IL-15 and IL-15Rα.

One of the limitations with systemic IL-15 treatment is its very short half-life in vivo. Therefore, there is a need to generate a suitable immune-stimulatory form of IL-15/IL-15Rα that has a longer half-life in vivo while retaining its ability to modulate the immune response. Additionally, there is a need for effective IL-15 antagonists that can be selectively targeted to the disease site to avoid unwanted systemic toxicities and provide a more effective therapeutic benefit.

Compounds that modulate PD-1 activity have potential as therapeutic agents for the treatment of various diseases and disorders, including cancer, inflammation, and autoimmune diseases. There is a significant unmet need to develop new strategies to target various effector molecules to a disease site to provide therapeutic benefit without the side effects associated with non-specific immune activity.

SUMMARY

Provided herein are fusion proteins, antibodies, and antigen-binding fragments thereof that bind to PD-1. In embodiments, the fusion proteins comprise an anti-PD-1 antibody, or antigen-binding fragment thereof. Also disclosed are anti-PD-1 antibodies and the antigen-binding fragments thereof that bind PD-1. Also provided are therapeutic compositions of such fusion proteins, antibodies, and antigen-binding fragments thereof, as well as methods of using these fusion proteins, antibodies and antigen-binding fragments thereof.

In one aspect, the disclosure provides a fusion protein comprising a PD-1 binding protein, an IL-15 receptor (IL-15R) binding protein (e.g., IL-15 or an IL-15R binding portion thereof), and an IL-15 binding protein (e.g., IL-15Rα or an IL-15 binding portion thereof comprising the IL-15Rα sushi domain). In one aspect, the PD-1 binding protein is an antibody or PD-1 binding fragment thereof. In one embodiment, the IL-15 receptor-binding portion is IL-15. In embodiments, IL-15 is joined, directly or indirectly, to the sushi domain of IL-15Rα.

In one embodiment, the fusion protein comprises an anti-PD-1 antibody and an IL-15 polypeptide, wherein the C-terminus of the IL-15 polypeptide is covalently linked, directly or via a polypeptide linker, to the N-terminus of the heavy chain variable region of one of the antibody heavy chains (i.e., the antibody heavy chains form a heterodimer wherein one of the heavy chains is linked to an IL-15 polypeptide. In one embodiment, the N-terminus of the IL-15 polypeptide is linked to the C-terminus of an IL-15Rα sushi domain polypeptide.

In one embodiment, the fusion protein comprises an anti PD-1 antibody and two IL-15 polypeptides, wherein each IL-15 polypeptide is covalently linked to the N-terminus of an antibody heavy chain.

In embodiments in which only one heavy chain is linked to IL-15/IL-15Rα sushi domain, the Fc domains of the antibody may comprise one or more amino acid substitutions promoting heterodimer formation (i.e., the association of a heavy chain fusion with a heavy chain lacking the fusion). In embodiments, an amino acid residue in the CH3 domain of one heavy chain (CH3-1) comprises an amino acid substitution replacing an amino acid with an amino acid residue having a larger side chain volume, thereby generating a "knob" within the CH3 domain, which is positionable in a "hole" present within the CH3 domain of the other heavy chain (CH3-2), generated by replacing an amino acid residue with an amino acid residue having a smaller side chain volume. In embodiments, the amino acid substitutions are selected from the following groups:

(1) CH3 domain of first heavy chain: S354C, T366W; CH3 domain of second heavy chain: Y349C, T366S, L368A, Y407V (2) CH3 domain of first heavy chain: T350V, L351Y, F405A, Y407V; CH3 domain of second heavy chain: T350V, T366L, K392L, T394W (3) CH3 domain of first heavy chain: L351Y, F405A, Y407V; CH3 domain of second heavy chain: T366L, K392L, T394W.

Either the first or second heavy chain may be linked to the IL-15/IL-15Rα sushi domain.

In embodiments, the IL-15Rα polypeptide and the IL-15 polypeptide are joined by a first linker. In embodiments, the IL-15 polypeptide and the anti-PD-1 antibody, or antigen-binding portion thereof, are joined by a second linker. In embodiments, the length of the linker may independently be between 10 to 40 amino acids. In embodiments, the length of the linker is 25 to 35 amino acids. In embodiments, the linker sequences comprises near neutral amino acids selected from the group comprising Gly (G), Asn (N), Ser (S), Thr (T), Ala (A), Leu (L), and Gln (Q), most preferably in the group comprising Gly (G), Asn (N), and Ser (S). In certain embodiments, the linker sequences are glycine and serine rich, and in some embodiments, the linker contains only serine and glycine residues.

In certain embodiments, the IL-15 and/or the IL-15Rα sushi domain comprise one or more amino acid substitutions. In embodiments, the amino acid substitutions are located at position 1, 4, 8, 30, 45, 61, 64, 65, and/or 108 of IL-15. In some embodiments, the amino acid substitutions are located at positions 45, 65, and/or 108 of IL-15. In some embodiments the amino acid substitutions are one or more of N1D, N4D, D8N, D30N, D61N, E64Q, L45A, N65S/A/D/K, and/or Q108S/E substitutions in IL-15. In some embodiments, the amino acid substitutions are L45A, N65S/A/D/K, and/or Q108S substitutions in IL-15. In one embodiment, the amino acid substitution is an N65S substitution in IL-15.

In one embodiment, the amino acid substitution is an N60 substitution in the IL-15Rα sushi domain. In one embodiment, the amino acid substitution is an N60A substitution in the IL-15Rα sushi domain.

In embodiments, the fusion protein comprises an IL-15 polypeptide comprising one of the following amino acid substitutions: N65S, N65A, or N65D. In embodiments, the fusion protein comprises an IL-15 polypeptide comprising one or more of the following amino acid substitutions: (1) L45A, (2) N65S, N65A, or N65D, and (3) Q108S. In one embodiment, the fusion protein comprises an IL-15Rα sushi domain polypeptide comprisings an N60A amino acid substitution.

In one aspect, the disclosure relates to a fusion protein comprising:

(i) an anti-PD-1 antibody, or an antigen-binding fragment thereof, wherein the antibody or antigen-binding fragment thereof comprises a heavy chain variable region and a light chain variable region, wherein each of the heavy chain and the light chain variable regions comprise a CDR1, CDR2, and CDR3;

(ii) an IL-15 polypeptide or derivative thereof;

(iii) an IL-15Rα sushi domain polypeptide or derivative thereof; and (iv) a linker polypeptide joining the IL-15Rα sushi domain polypeptide and the IL-15 polypeptide or derivative thereof.

In one aspect, the disclosure relates to a fusion protein comprising:

(i) an anti-PD-1 antibody, or an antigen-binding fragment thereof, wherein the antibody or antigen-binding fragment thereof comprises a heavy chain variable region and a light chain variable region, wherein each of the heavy chain and the light chain variable regions comprise a CDR1, CDR2, and CDR3;

(ii) an IL-15 polypeptide comprising the amino acid sequence of SEQ ID NO: 212, or an amino acid sequence that is at least 90% or at least 95% identical to SEQ ID NO: 212;

(iii) an IL-15Rα sushi domain polypeptide comprising the amino acid sequence of SEQ ID NO: 214, or an amino acid sequence that is at least 95% identical to SEQ ID NO: 214; and (iv) a first linker polypeptide joining the IL-15Rα sushi domain polypeptide and the IL-15 polypeptide.

The anti-PD-1 antibody, or antigen-binding fragment thereof, portion of the fusion protein can be any antibody, or antigen-binding fragment thereof, that specifically binds PD-1, including those comprising the corresponding heavy and light chain variable regions and/or CDRs provided in FIG. 1, or otherwise discribed herein. In embodiments, the fusion protein comprises an anti-PD-1 antibody, or antigen-binding fragment thereof, wherein the CDRs of the heavy and light chain variable regions comprise the following sequences:

the sequence of CDR1 of the heavy chain variable region (CDR1H) comprises the sequence of SEQ ID NO: 21;

the sequence of CDR2 of the heavy chain variable region (CDR2H) comprises the sequence of SEQ ID NO: 22;

the sequence of CDR2 of the heavy chain variable region (CDR3H) comprises the sequence of SEQ ID NO: 23;

the sequence of CDR1 of the light chain variable region (CDR1L) comprises the sequence $RX_{13}X_{14}X_{15}X_{16}IX_{17}X_{18}WX_{19}X_{20}$ (SEQ ID NO:135);

wherein $X_{13}$ is A or V;

wherein $X_{14}$ is S or G;

wherein $X_{15}$ is Q, E, or R;

wherein $X_{16}$ is G, S, D or N;

wherein $X_{17}$ is G, S, or N;

wherein $X_{18}$ is S, I, R, T, K, P, N, H, or V;

wherein $X_{19}$ is L or V; and wherein $X_{20}$ is G or A; and the sequence of CDR2 of the light chain variable region (CDR2L) comprises the sequence $X_{21}AX_{22}X_{23}X_{24}X_{25}X_{26}$ (SEQ ID NO: 136); and wherein $X_{21}$ is S, D, E, or A;

wherein $X_{22}$ is S or K;

wherein $X_{23}$ is S, N, T, R, or D;

wherein $X_{24}$ is L or V;

wherein $X_{25}$ is Q, E, or H; and wherein $X_{26}$ is S, N, A, R, P, or T; and the sequence of CDR3 of the light chain variable region (CDR3L) comprises the sequence $QQX_{27}X_{28}SFPX_{29}X_{30}$ (SEQ ID NO: 137);

wherein $X_{27}$ is A or G;

wherein $X_{28}$ is N, D, or Y;

wherein $X_{29}$ is F or L; and wherein $X_{30}$ is A or T.

In embodiments, the fusion protein comprises an anti-PD-1 antibody, or antigen-binding fragment thereof, wherein the CDRs of the heavy and light chain variable regions comprise the following sequences:

the sequence of CDR1H comprises the sequence of SEQ ID NO: 21;

the sequence of CDR2H comprises the sequence of SEQ ID NO: 22;

the sequence of CDR2H comprises the sequence of SEQ ID NO: 23;

the sequence of CDR1L comprises the sequence of SEQ ID NO: 96;

the sequence of CDR2L comprises the sequence of SEQ ID NO: 97; and the sequence of CDR3L comprises the sequence of SEQ ID NO: 82.

In embodiments, the fusion protein comprises an anti-PD-1 antibody, or antigen-binding fragment thereof, wherein:

the heavy chain variable region comprises SEQ ID NO: 24, or a sequence that is at least 90%, at least 95%, at least 96%, at least 97%, at least 98%, or at least 99% identical to SEQ ID NO: 24; and the light chain variable region comprises SEQ ID NO: 98, or a sequence that is at least 90%, at least 95%, at least 96%, at least 97%, at least 98%, or at least 99% identical to SEQ ID NO: 98.

In embodiments, the fusion protein comprises an anti-PD-1 antibody, or antigen-binding fragment thereof, wherein the CDRs of the heavy chain and light chain variable regions comprise the following sequences:

the sequences of CDR1H, CDR2H and CDR3H comprise respectively SEQ ID NOS: 21, 22, and 23; and the sequences of CDR1L, CDR2L and CDR3L comprise respectively, SEQ ID NOS: 45, 46, and 47; SEQ ID NOS: 66, 67, and 68; SEQ ID NOS: 70, 67, and 71; SEQ ID NOS: 73, 74, and 75; SEQ ID NOS: 77, 78, and 47; SEQ ID NOS: 80, 81, and 82; SEQ ID NOS: 77, 78, and 84; SEQ ID NOS: 77, 86, and 47; SEQ ID NOS: 88, 89, and 47; SEQ ID NOS: 66, 67, and 47; SEQ ID NOS: 80, 92, and 75; SEQ ID NOS: 80, 94, and 71; SEQ ID NOS: 99, 100, and 47; SEQ ID NOS: 102, 103, and 104; SEQ ID NOS: 106, 103, and 47; SEQ ID NOS: 108, 103, and 47; SEQ ID NOS: 110, 111, and 75; SEQ ID NOS: 77, 103, and 113; SEQ ID NOS: 77, 111, and 47; SEQ ID NOS: 116, 67, and 47; SEQ ID NOS: 118, 119, and 47; SEQ ID NOS: 80, 78, and 47; SEQ ID NOS: 122, 103 and 47; SEQ ID NOS: 124, 125, and 75; SEQ ID NOS: 127, 38, and 68; SEQ ID NOS: 129, 130, and 47; or SEQ ID NOS: 132, 133, and 75.

In embodiments, the fusion protein comprises an anti-PD-1 antibody, or antigen-binding fragment thereof, wherein:

the heavy chain variable region comprises SEQ ID NO: 24, or a sequence that is at least 90%, at least 95%, at least 96%, at least 97%, at least 98%, or at least 99% identical to SEQ ID NO: 24; and the light chain variable region comprises SEQ ID NO: 48, 69, 72, 76, 79, 83, 85, 87, 90, 91, 93, 95, 101, 105, 107, 109, 112, 114, 115, 117, 120, 121, 123, 126, 128, 131, or 134, or a sequence that is at least 90%, at least 95%, at least 96%, at least 97%, at least 98%, or at least 99% identical to any of SEQ ID NO: 48, 69, 72, 76, 79, 83, 85, 87, 90, 91, 93, 95, 101, 105, 107, 109, 112, 114, 115, 117, 120, 121, 123, 126, 128, 131, or 134.

In embodiments, the fusion protein comprises an anti-PD-1 antibody, or antigen-binding fragment thereof, wherein the CDRs of the heavy and light chain variable regions comprise the following sequences:

the sequence of CDR1H comprises the sequence of SEQ ID NO: 17;

the sequence of CDR2H comprises the sequence of SEQ ID NO: 18;

the sequence of CDR3H comprises the sequence of SEQ ID NO: 19;

the sequence of CDR1L comprises the sequence $RSSX_{1}SLLX_{2}SNGX_{3}X_{4}YLD$ (SEQ ID NO: 62), wherein $X_{1}$ is Q or E;

wherein $X_{2}$ is H or Y;

wherein $X_{3}$ is Y or N; and wherein $X_{4}$ is T or N;

the sequence of CDR2L comprises the sequence $X_5X_6SX_7X_8X_9X_{10}$ (SEQ ID NO: 63), wherein $X_5$ is L, Q or E;

wherein $X_6$ is S, A, or V;

wherein $X_7$ is H, N, T, or S;

wherein $X_8$ is R or L;

wherein $X_9$ is G, A, or H; and wherein $X_{10}$ is S or T; and the sequence of CDR3L comprises the sequence $MQGX_{11}X_{12}WPYT$ (SEQ ID NO: 64), wherein $X_{11}$ is A, T, or S; and wherein $X_{12}$ is H or R.

In embodiments, the fusion protein comprises an anti-PD-1 antibody, or antigen-binding fragment thereof, wherein the CDRs of the heavy chain and light chain variable regions comprise the following sequences:

the sequence of CDR1H comprise the sequence of SEQ ID NO: 17;

the sequence of CDR2H comprises the sequence of SEQ ID NO: 18;

the sequence of CDR3H comprises the sequence of SEQ ID NO: 19;

the sequence of CDR1L comprises the sequence of SEQ ID NO: 41;

the sequence of CDR2L comprises the sequence of SEQ ID NO: 49; and the sequence of CDR3 of the light chain variable region (CDR3L) comprises the sequence of SEQ ID NO: 50.

In embodiments, the fusion protein comprises an anti-PD-1 antibody, or antigen-binding fragment thereof, wherein:

the heavy chain variable region comprises SEQ ID NO: 20, or a sequence that is at least 90%, at least 95%, at least 96%, at least 97%, at least 98%, or at least 99% identical to SEQ ID NO: 20; and the light chain variable region comprises SEQ ID NO: 51, or a sequence that is at least 90%, at least 95%, at least 96%, at least 97%, at least 98%, or at least 99% identical to SEQ ID NO: 51.

In embodiments, the fusion protein comprises an anti-PD-1 antibody, or antigen-binding fragment thereof, wherein the CDRs of the heavy chain and light chain variable regions comprise the following sequences:

the sequence of CDR1H, CDR2H and CDR3H comprise SEQ ID NOS: 17, 18, and 19, respectively; and the sequence of CDR1L, CDR2L and CDR3L comprise respectively, SEQ ID NOS: 41, 42, and 43; SEQ ID NOS: 41, 52, and 53; SEQ ID NOS: 41, 55, and 56; or SEQ ID NOS: 58, 59, and 60.

In further embodiments the fusion protein comprises an anti-PD-1 antibody, or antigen-binding fragment thereof, wherein:

the heavy chain variable region comprises SEQ ID NO: 20, or a sequence that is at least 90%, at least 95%, at least 96%, at least 97%, at least 98%, or at least 99% identical to SEQ ID NO: 20; and the light chain variable region comprises SEQ ID NO: 44, 54, 57, or 61, or a sequence that is at least 90%, at least 95%, at least 96%, at least 97%, at least 98%, or at least 99% identical to any one of SEQ ID NO: 44, 54, 57, or 61.

In another aspect the disclosure provides an anti-PD-1 antibody, or an antigen-binding fragment thereof, wherein the antibody or antigen-binding fragment thereof binds to PD-1, and wherein the antibody or antigen-binding fragment thereof comprises a heavy chain variable region and a light chain variable region wherein each of the heavy chain and the light chain variable regions comprise a CDR1, CDR2, and CDR3 and wherein the antibody heavy chains comprise a constant region comprising three constant domains CH1, CH2, and CH3.

In embodiments, the CDRs of the anti-PD-1 antibody, or antigen-binding fragment thereof, comprise the following sequences:

the sequence of CDR1H comprises the sequence of SEQ ID NO: 21;

the sequence of CDR2H comprises the sequence of SEQ ID NO: 22;

the sequence of CDR3H comprises the sequence of SEQ ID NO: 23;

the sequence of CDR1L comprises the sequence $RX_{13}X_{14}X_{15}X_{16}IX_{17}X_{18}WX_{19}X_{20}$ (SEQ ID NO:135);

wherein $X_{13}$ is A or V;

wherein $X_{14}$ is S or G;

wherein $X_{15}$ is Q, E, or R;

wherein $X_{16}$ is G, S, D or N;

wherein $X_{17}$ is G, S, or N;

wherein $X_{18}$ is S, I, R, T, K, P, N, H, or V;

wherein $X_{19}$ is L or V;

wherein $X_{20}$ is G or A; and the sequence of CDR2L comprises the sequence $X_{21}AX_{22}X_{23}X_{24}X_{25}X_{26}$ (SEQ ID NO: 136); and wherein $X_{21}$ is S, D, E, or A;

wherein $X_{22}$ is S or K;

wherein $X_{23}$ is S, N, T, R, or D;

wherein $X_{24}$ is L or V;

wherein $X_{25}$ is Q, E, or H; and wherein $X_{26}$ is S, N, A, R, P, or T; and the sequence of CDR3L comprises the sequence $QQX_{27}X_{28}SFPX_{29}X_{30}$ (SEQ ID NO: 137);

wherein $X_{27}$ is A or G;

wherein $X_{28}$ is N, D, or Y;

wherein $X_{29}$ is F or L; and wherein $X_{30}$ is A or T.

In embodiments, the CDRs of the anti-PD-1 antibody, or antigen-binding fragment thereof, comprise the following sequences:

the sequence of CDR1H comprises the sequence of SEQ ID NO: 21;

the sequence of CDR2H comprises the sequence of SEQ ID NO: 22;

the sequence of CDR2H comprises the sequence of SEQ ID NO: 23;

the sequence of CDR1L comprises the sequence of SEQ ID NO: 96;

the sequence of CDR2L comprises the sequence of SEQ ID NO: 97; and the sequence of CDR3L comprises the sequence of SEQ ID NO: 82.

In embodiments, the anti-PD-1 antibody, or antigen-binding fragment thereof, comprises:

a heavy chain variable region comprising SEQ ID NO: 24, or a sequence that is at least 90%, at least 95%, at least 96%, at least 97%, at least 98%, or at least 99% identical to SEQ ID NO: 24; and a light chain variable region comprising SEQ ID NO: 98, or a sequence that is at least 90%, at least 95%, at least 96%, at least 97%, at least 98%, or at least 99% identical to SEQ ID NO: 98.

In embodiments, the CDRs of the anti-PD-1 antibody, or antigen-binding fragment thereof, comprise the following sequences:

the sequences of CDR1H, CDR2H and CDR3H comprise respectively SEQ ID NOS: 21, 22, and 23; and the sequences of CDR1L, CDR2L and CDR3L comprise respectively, SEQ ID NOS: 45, 46, and 47; SEQ ID NOS: 66, 67, and 68; SEQ ID NOS: 70, 67, and 71; SEQ ID NOS: 73, 74, and 75; SEQ ID NOS: 77, 78, and 47; SEQ ID NOS: 80, 81, and 82; SEQ ID NOS: 77, 78, and 84; SEQ ID NOS: 77, 86, and 47; SEQ ID NOS: 88, 89, and 47; SEQ ID NOS: 66, 67, and 47; SEQ ID NOS: 80, 92, and 75; SEQ ID NOS: 80, 94, and 71; SEQ ID NOS: 99, 100, and 47; SEQ ID NOS: 102, 103, and 104; SEQ ID NOS: 106, 103, and 47; SEQ ID NOS: 108, 103, and 47; SEQ ID NOS: 110, 111, and 75; SEQ ID NOS: 77, 103, and 113; SEQ ID NOS: 77, 111, and 47; SEQ ID NOS: 116, 67, and 47; SEQ ID NOS: 118, 119, and 47; SEQ ID NOS: 80, 78, and 47; SEQ ID NOS: 122, 103 and 47; SEQ ID NOS: 124, 125, and 75; SEQ ID NOS: 127, 38, and 68; SEQ ID NOS: 129, 130, and 47; or SEQ ID NOS: 132, 133, and 75.

In embodiments, the anti-PD-1 antibody, or antigen-binding fragment thereof, comprises:

a heavy chain variable region comprising SEQ ID NO: 24, or a sequence that is at least 90%, at least 95%, at least 96%, at least 97%, at least 98%, or at least 99% identical to SEQ ID NO: 24; and a light chain variable region comprising SEQ ID NO: 48, 69, 72, 76, 79, 83, 85, 90, 91, 93, 101, 105, 107, 109, 112, 114, 115, 117, 120, 121, 123, 126, 128, 131, or 134, or a sequence that is at least 90%, at least 95%, at least 96%, at least 97%, at least 98%, or at least 99% identical to any one of SEQ ID NO: 48, 69, 72, 76, 79, 83, 85, 90, 91, 93, 101, 105, 107, 109, 112, 114, 115, 117, 120, 121, 123, 126, 128, 131, or 134.

In embodiments, the CDRs of the anti-PD-1 antibody, or antigen-binding fragment thereof, comprise the following sequences:

the sequence of CDR1H comprises the sequence of SEQ ID NO: 17;

the sequence of CDR2H comprises the sequence of SEQ ID NO: 18;

the sequence of CDR3H comprises the sequence of SEQ ID NO: 19;

the sequence of CDR1L comprises the sequence RSSX$_1$SLLX$_2$SNGX$_3$X$_4$YLD (SEQ ID NO: 62),
wherein X$_1$ is Q or E;
wherein X$_2$ is H or Y;
wherein X$_3$ is Y or N; and
wherein X$_4$ is T or N;

the sequence of CDR2L comprises the sequence X$_5$X$_6$SX$_7$X$_8$X$_9$X$_{10}$ (SEQ ID NO: 63),
wherein X$_5$ is L, Q or E;
wherein X$_6$ is S, A, or V;
wherein X$_7$ is H, N, T, or S;
wherein X$_8$ is R or L;
wherein X$_9$ is G, A, or H; and
wherein X$_{10}$ is S or T; and the sequence of CDR3L comprises the sequence MQGX$_{11}$X$_{12}$WPYT (SEQ ID NO: 64),
wherein X$_{11}$ is A, T, or S; and
wherein X$_{12}$ is H or R.

In embodiments, the CDRs of the anti-PD-1 antibody, or antigen-binding fragment thereof, comprise the following sequences:

the sequence of CDR1H comprises the sequence of SEQ ID NO: 17;

the sequence of CDR2H comprises the sequence of SEQ ID NO: 18;

the sequence of CDR3H comprises the sequence of SEQ ID NO: 19;

the sequence of CDR1L comprises the sequence of SEQ ID NO: 41;

the sequence of CDR2L comprises the sequence of SEQ ID NO: 49; and the sequence of CDR3L comprises the sequence of SEQ ID NO: 50.

In embodiments, the anti-PD-1 antibody, or antigen-binding fragment thereof, comprises:

a heavy chain variable region comprising SEQ ID NO: 20, or a sequence that is at least 90%, at least 95%, at least 96%, at least 97%, at least 98%, or at least 99% identical to SEQ ID NO: 20; and a light chain variable region comprising SEQ ID NO: 51, or a sequence that is at least 90%, at least 95%, at least 96%, at least 97%, at least 98%, or at least 99% identical to SEQ ID NO: 51.

In embodiments, the CDRs of the anti-PD-1 antibody, or antigen-binding fragment thereof, comprise the following sequences:

the sequence of CDR1H, CDR2H and CDR3H comprise SEQ ID NOS: 17, 18, and 19, respectively; and the sequence of CDR1L, CDR2L and CDR3L comprise respectively, SEQ ID NOS: 41, 42, and 43; SEQ ID NOS: 41, 52, and 53; SEQ ID NOS: 41, 55, and 56; or SEQ ID NOS: 58, 59, and 60.

In embodiments, the anti-PD-1 antibody, or antigen-binding fragment thereof, comprises:

a heavy chain variable region comprising SEQ ID NO: 20, or a sequence that is at least 90%, at least 95%, at least 96%, at least 97%, at least 98%, or at least 99% identical to SEQ ID NO: 20; and a light chain variable region comprising SEQ ID NO: 44, 54, 57, or 61, or a sequence that is at least 90%, at least 95%, at least 96%, at least 97%, at least 98%, or at least 99% identical to any one of SEQ ID NO: 44, 54, 57, or 61.

In one aspect, the disclosure relates to a fusion protein comprising:

(i) an anti-PD-1 antibody, or an antigen-binding fragment thereof, wherein the antibody or antigen-binding fragment thereof comprises a heavy chain variable region and a light chain variable region, wherein each of the heavy chain and the light chain variable regions comprise a CDR1, CDR2, and CDR3; and wherein:

the sequence of CDR1H comprises the sequence of SEQ ID NO: 21;

the sequence of CDR2H comprises the sequence of SEQ ID NO: 22;

the sequence of CDR3H comprises the sequence of SEQ ID NO: 23;

the sequence of CDR1L comprises the sequence of SEQ ID NO: 96;

the sequence of CDR2L comprises the sequence of SEQ ID NO: 97; and the sequence of CDR3L comprises the sequence of SEQ ID NO: 82;

(ii) an IL-15 polypeptide comprising the amino acid sequence of SEQ ID NO: 212, or an amino acid sequence that is at least 90% or at least 95% identical to SEQ ID NO: 212;

(iii) an IL-15Rα sushi domain polypeptide comprising the amino acid sequence of SEQ ID NO: 214, or an amino acid sequence that is at least 95% identical to SEQ ID NO: 214;

(iv) a first linker polypeptide joining the IL-15Rα sushi domain polypeptide and the IL-15 polypeptide; and optionally wherein the anti-PD-1 antibody, or an antigen-binding fragment thereof, comprises two heavy chains, wherein:

(a) the CH3 domain of first heavy chain comprises the amino acid substitutions S354C and T366W (Kabat EU index numbering); and (b) the CH3 domain of second heavy chain comprises the amino acid substitutions Y349C, T366S, L368A, and Y407V (Kabat EU index numbering).

In one aspect, the disclosure relates to a fusion protein comprising:

(i) an anti-PD-1 antibody, or an antigen-binding fragment thereof, wherein the antibody or antigen-binding fragment thereof comprises a heavy chain variable region and a light chain variable region, wherein each of the heavy chain and the light chain variable regions comprise a CDR1, CDR2, and CDR3; and wherein:

the sequence of CDR1H comprises the sequence of SEQ ID NO: 21;

the sequence of CDR2H comprises the sequence of SEQ ID NO: 22;

the sequence of CDR3H comprises the sequence of SEQ ID NO: 23;

the sequence of CDR1L comprises the sequence of SEQ ID NO: 96;

the sequence of CDR2L comprises the sequence of SEQ ID NO: 97; and the sequence of CDR3L comprises the sequence of SEQ ID NO: 82;

(ii) an IL-15 polypeptide comprising the amino acid sequence of SEQ ID NO: 212, or an amino acid sequence that is at least 90% or at least 95% identical to SEQ ID NO: 212;

(iii) an IL-15Rα sushi domain polypeptide comprising the amino acid sequence of SEQ ID NO: 214, or an amino acid sequence that is at least 95% identical to SEQ ID NO: 214;

(iv) a first linker polypeptide joining the IL-15Rα sushi domain polypeptide and the IL-15 polypeptide; and optionally wherein the anti-PD-1 antibody, or an antigen-binding fragment thereof, comprises two heavy chains, wherein:

(a) the CH3 domain of first heavy chain comprises the amino acid substitutions T350V, L351Y, F405A, and Y407V (Kabat EU index numbering); and (b) the CH3 domain of second heavy chain comprises the amino acid substitutions T350V, T366L, K392L, and T394W (Kabat EU index numbering).

In one aspect, the disclosure relates to a fusion protein comprising:

(i) an anti-PD-1 antibody, or an antigen-binding fragment thereof, wherein the antibody or antigen-binding fragment thereof comprises a heavy chain variable region and a light chain variable region, wherein each of the heavy chain and the light chain variable regions comprise a CDR1, CDR2, and CDR3; and wherein:

the sequence of CDR1H comprises the sequence of SEQ ID NO: 21;

the sequence of CDR2H comprises the sequence of SEQ ID NO: 22;

the sequence of CDR3H comprises the sequence of SEQ ID NO: 23;

the sequence of CDR1L comprises the sequence of SEQ ID NO: 96;

the sequence of CDR2L comprises the sequence of SEQ ID NO: 97; and the sequence of CDR3L comprises the sequence of SEQ ID NO: 82;

(ii) an IL-15 polypeptide comprising the amino acid sequence of SEQ ID NO: 212, or an amino acid sequence that is at least 90% or at least 95% identical to SEQ ID NO: 212;

(iii) an IL-15Rα sushi domain polypeptide comprising the amino acid sequence of SEQ ID NO: 214, or an amino acid sequence that is at least 95% identical to SEQ ID NO: 214;

(iv) a first linker polypeptide joining the IL-15Rα sushi domain polypeptide and the IL-15 polypeptide; and optionally wherein the anti-PD-1 antibody, or an antigen-binding fragment thereof, comprises two heavy chains, wherein:

(a) the CH3 domain of first heavy chain comprises the amino acid substitutions L351Y, F405A, and Y407V (Kabat EU index numbering); and (b) the CH3 domain of second heavy chain comprises the amino acid substitutions T366L, K392L, and T394W (Kabat EU index numbering).

In one aspect, the disclosure relates to a fusion protein comprising:

(i) an anti-PD-1 antibody, or an antigen-binding fragment thereof, wherein the antibody or antigen-binding fragment thereof comprises a heavy chain variable region and a light chain variable region, wherein each of the heavy chain and the light chain variable regions comprise a CDR1, CDR2, and CDR3; and wherein:

the sequence of CDR1H comprises the sequence of SEQ ID NO: 21;

the sequence of CDR2H comprises the sequence of SEQ ID NO: 22;

the sequence of CDR3H comprises the sequence of SEQ ID NO: 23;

the sequence of CDR1L comprises the sequence of SEQ ID NO: 96;

the sequence of CDR2L comprises the sequence of SEQ ID NO: 97; and the sequence of CDR3L comprises the sequence of SEQ ID NO: 82;

(ii) an IL-15 polypeptide comprising the amino acid sequence of SEQ ID NO: 212, optionally wherein amino acid N65 of SEQ ID NO: 212 is substituted with an S, D, or A;

(iii) an IL-15Rα sushi domain polypeptide comprising the amino acid sequence of SEQ ID NO: 214, optionally wherein amino acid N28 of SEQ ID NO: 214 is substituted with an A;

(iv) a first linker polypeptide joining the IL-15Rα sushi domain polypeptide and the IL-15 polypeptide; and optionally wherein the anti-PD-1 antibody, or an antigen-binding fragment thereof, comprises two heavy chains, wherein:

(a) the CH3 domain of first heavy chain comprises the amino acid substitutions S354C and T366W (Kabat EU index numbering); and (b) the CH3 domain of second heavy chain comprises the amino acid substitutions Y349C, T366S, L368A, and Y407V (Kabat EU index numbering).

In one aspect, the disclosure relates to a fusion protein comprising:

(i) an anti-PD-1 antibody, or an antigen-binding fragment thereof, wherein the antibody or antigen-binding fragment thereof comprises a heavy chain variable region and a light chain variable region, wherein each of the heavy chain and the light chain variable regions comprise a CDR1, CDR2, and CDR3; and wherein:

the sequence of CDR1H comprises the sequence of SEQ ID NO: 21;

the sequence of CDR2H comprises the sequence of SEQ ID NO: 22;

the sequence of CDR3H comprises the sequence of SEQ ID NO: 23;

the sequence of CDR1L comprises the sequence of SEQ ID NO: 96;

the sequence of CDR2L comprises the sequence of SEQ ID NO: 97; and the sequence of CDR3L comprises the sequence of SEQ ID NO: 82;

(ii) an IL-15 polypeptide comprising the amino acid sequence of SEQ ID NO: 212, optionally wherein amino acid N65 of SEQ ID NO: 212 is substituted with an S, D, or A;

(iii) an IL-15Rα sushi domain polypeptide comprising the amino acid sequence of SEQ ID NO: 214, optionally wherein amino acid N28 of SEQ ID NO: 214 is substituted with an A;

(iv) a first linker polypeptide joining the IL-15Rα sushi domain polypeptide and the IL-15 polypeptide; and optionally wherein the anti-PD-1 antibody, or an antigen-binding fragment thereof, comprises two heavy chains, wherein:

(a) the CH3 domain of first heavy chain comprises the amino acid substitutions T350V, L351Y, F405A, and Y407V (Kabat EU index numbering); and (b) the CH3 domain of second heavy chain comprises the amino acid substitutions T350V, T366L, K392L, and T394W (Kabat EU index numbering).

In one aspect, the disclosure relates to a fusion protein comprising:

(i) an anti-PD-1 antibody, or an antigen-binding fragment thereof, wherein the antibody or antigen-binding fragment thereof comprises a heavy chain variable region and a light chain variable region, wherein each of the heavy chain and the light chain variable regions comprise a CDR1, CDR2, and CDR3; and wherein:

the sequence of CDR1H comprises the sequence of SEQ ID NO: 21;

the sequence of CDR2H comprises the sequence of SEQ ID NO: 22;

the sequence of CDR3H comprises the sequence of SEQ ID NO: 23;

the sequence of CDR1L comprises the sequence of SEQ ID NO: 96;

the sequence of CDR2L comprises the sequence of SEQ ID NO: 97; and the sequence of CDR3L comprises the sequence of SEQ ID NO: 82;

(ii) an IL-15 polypeptide comprising the amino acid sequence of SEQ ID NO: 212, optionally wherein amino acid N65 of SEQ ID NO: 212 is substituted with an S, D, or A;

(iii) an IL-15Rα sushi domain polypeptide comprising the amino acid sequence of SEQ ID NO: 214, optionally wherein amino acid N28 of SEQ ID NO: 214 is substituted with an A;

(iv) a first linker polypeptide joining the IL-15Rα sushi domain polypeptide and the IL-15 polypeptide; and optionally wherein the anti-PD-1 antibody, or an antigen-binding fragment thereof, comprises two heavy chains, wherein:

(a) the CH3 domain of first heavy chain comprises the amino acid substitutions L351Y, F405A, and Y407V (Kabat EU index numbering); and (b) the CH3 domain of second heavy chain comprises the amino acid substitutions T366L, K392L, and T394W (Kabat EU index numbering).

In one aspect, the disclosure relates to a fusion protein comprising:

(i) an anti-PD-1 antibody, or an antigen-binding fragment thereof, wherein the antibody or antigen-binding fragment thereof comprises a heavy chain variable region and a light chain variable region, wherein each of the heavy chain and the light chain variable regions comprise a CDR1, CDR2, and CDR3; and wherein:

the sequence of CDR1H comprise the sequence of SEQ ID NO: 17;

the sequence of CDR2H comprises the sequence of SEQ ID NO: 18;

the sequence of CDR3H comprises the sequence of SEQ ID NO: 19;

the sequence of CDR1L comprises the sequence of SEQ ID NO: 41;

the sequence of CDR2L comprises the sequence of SEQ ID NO: 49; and the sequence of CDR3L comprises the sequence of SEQ ID NO: 50;

(ii) an IL-15 polypeptide comprising the amino acid sequence of SEQ ID NO: 212, or an amino acid sequence that is at least 90% or at least 95% identical to SEQ ID NO: 212;

(iii) an IL-15Rα sushi domain polypeptide comprising the amino acid sequence of SEQ ID NO: 214, or an amino acid sequence that is at least 95% identical to SEQ ID NO: 214;

(iv) a first linker polypeptide joining the IL-15Rα sushi domain polypeptide and the IL-15 polypeptide; and optionally wherein the anti-PD-1 antibody, or an antigen-binding fragment thereof, comprises two heavy chains, wherein:

(a) the CH3 domain of first heavy chain comprises the amino acid substitutions S354C and T366W (Kabat EU index numbering); and (b) the CH3 domain of second heavy chain comprises the amino acid substitutions Y349C, T366S, L368A, and Y407V (Kabat EU index numbering).

In one aspect, the disclosure relates to a fusion protein comprising:

(i) an anti-PD-1 antibody, or an antigen-binding fragment thereof, wherein the antibody or antigen-binding fragment thereof comprises a heavy chain variable region and a light chain variable region, wherein each of the heavy chain and the light chain variable regions comprise a CDR1, CDR2, and CDR3; and wherein:

the sequence of CDR1H comprise the sequence of SEQ ID NO: 17;

the sequence of CDR2H comprises the sequence of SEQ ID NO: 18;

the sequence of CDR3H comprises the sequence of SEQ ID NO: 19;

the sequence of CDR1L comprises the sequence of SEQ ID NO: 41;

the sequence of CDR2L comprises the sequence of SEQ ID NO: 49; and the sequence of CDR3L comprises the sequence of SEQ ID NO: 50;

(ii) an IL-15 polypeptide comprising the amino acid sequence of SEQ ID NO: 212, or an amino acid sequence that is at least 90% or at least 95% identical to SEQ ID NO: 212;

(iii) an IL-15Rα sushi domain polypeptide comprising the amino acid sequence of SEQ ID NO: 214, or an amino acid sequence that is at least 95% identical to SEQ ID NO: 214;

(iv) a first linker polypeptide joining the IL-15Rα sushi domain polypeptide and the IL-15 polypeptide; and optionally wherein the anti-PD-1 antibody, or an antigen-binding fragment thereof, comprises two heavy chains, wherein:

(a) the CH3 domain of first heavy chain comprises the amino acid substitutions T350V, L351Y, F405A, and Y407V (Kabat EU index numbering); and (b) the CH3 domain of second heavy chain comprises the amino acid substitutions T350V, T366L, K392L, and T394W (Kabat EU index numbering).

In one aspect, the disclosure relates to a fusion protein comprising:

(i) an anti-PD-1 antibody, or an antigen-binding fragment thereof, wherein the antibody or antigen-binding fragment thereof comprises a heavy chain variable region and a light chain variable region, wherein each of the heavy chain and the light chain variable regions comprise a CDR1, CDR2, and CDR3; and wherein:

the sequence of CDR1H comprise the sequence of SEQ ID NO: 17;

the sequence of CDR2H comprises the sequence of SEQ ID NO: 18;

the sequence of CDR3H comprises the sequence of SEQ ID NO: 19;

the sequence of CDR1L comprises the sequence of SEQ ID NO: 41;

the sequence of CDR2L comprises the sequence of SEQ ID NO: 49; and the sequence of CDR3L comprises the sequence of SEQ ID NO: 50;

(ii) an IL-15 polypeptide comprising the amino acid sequence of SEQ ID NO: 212, or an amino acid sequence that is at least 90% or at least 95% identical to SEQ ID NO: 212;

(iii) an IL-15Rα sushi domain polypeptide comprising the amino acid sequence of SEQ ID NO: 214, or an amino acid sequence that is at least 95% identical to SEQ ID NO: 214;

(iv) a first linker polypeptide joining the IL-15Rα sushi domain polypeptide and the IL-15 polypeptide; and optionally wherein the anti-PD-1 antibody, or an antigen-binding fragment thereof, (a) the CH3 domain of first heavy chain comprises the amino acid substitutions L351Y, F405A, and Y407V (Kabat EU index numbering); and (b) the CH3 domain of second heavy chain comprises the amino acid substitutions T366L, K392L, and T394W (Kabat EU index numbering).

In one aspect, the disclosure relates to a fusion protein comprising:

(i) an anti-PD-1 antibody, or an antigen-binding fragment thereof, wherein the antibody or antigen-binding fragment thereof comprises a heavy chain variable region and a light chain variable region, wherein each of the heavy chain and the light chain variable regions comprise a CDR1, CDR2, and CDR3; and wherein:

the sequence of CDR1H comprise the sequence of SEQ ID NO: 17;

the sequence of CDR2H comprises the sequence of SEQ ID NO: 18;

the sequence of CDR3H comprises the sequence of SEQ ID NO: 19;

the sequence of CDR1L comprises the sequence of SEQ ID NO: 41;

the sequence of CDR2L comprises the sequence of SEQ ID NO: 49; and the sequence of CDR3L comprises the sequence of SEQ ID NO: 50;

(ii) an IL-15 polypeptide comprising the amino acid sequence of SEQ ID NO: 212, optionally wherein amino acid N65 of SEQ ID NO: 212 is substituted with an S, D, or A;

(iii) an IL-15Rα sushi domain polypeptide comprising the amino acid sequence of SEQ ID NO: 214, optionally wherein amino acid N28 of SEQ ID NO: 214 is substituted with an A;

(iv) a first linker polypeptide joining the IL-15Rα sushi domain polypeptide and the IL-15 polypeptide; and optionally wherein the anti-PD-1 antibody, or an antigen-binding fragment thereof, comprises two heavy chains, wherein:

(a) the CH3 domain of first heavy chain comprises the amino acid substitutions S354C and T366W (Kabat EU index numbering); and (b) the CH3 domain of second heavy chain comprises the amino acid substitutions Y349C, T366S, L368A, and Y407V (Kabat EU index numbering).

In one aspect, the disclosure relates to a fusion protein comprising:

(i) an anti-PD-1 antibody, or an antigen-binding fragment thereof, wherein the antibody or antigen-binding fragment thereof comprises a heavy chain variable region and a light chain variable region, wherein each of the heavy chain and the light chain variable regions comprise a CDR1, CDR2, and CDR3; and wherein:

the sequence of CDR1H comprise the sequence of SEQ ID NO: 17;

the sequence of CDR2H comprises the sequence of SEQ ID NO: 18;

the sequence of CDR3H comprises the sequence of SEQ ID NO: 19;

the sequence of CDR1L comprises the sequence of SEQ ID NO: 41;

the sequence of CDR2L comprises the sequence of SEQ ID NO: 49; and the sequence of CDR3L comprises the sequence of SEQ ID NO: 50;

(ii) an IL-15 polypeptide comprising the amino acid sequence of SEQ ID NO: 212, optionally wherein amino acid N65 of SEQ ID NO: 212 is substituted with an S, D, or A;

(iii) an IL-15Rα sushi domain polypeptide comprising the amino acid sequence of SEQ ID NO: 214, optionally wherein amino acid N28 of SEQ ID NO: 214 is substituted with an A;

(iv) a first linker polypeptide joining the IL-15Rα sushi domain polypeptide and the IL-15 polypeptide; and optionally wherein the anti-PD-1 antibody, or an antigen-binding fragment thereof, comprises two heavy chains, wherein:

(a) the CH3 domain of first heavy chain comprises the amino acid substitutions T350V, L351Y, F405A, and Y407V (Kabat EU index numbering); and (b) the CH3 domain of second heavy chain comprises the amino acid substitutions T350V, T366L, K392L, and T394W (Kabat EU index numbering).

In one aspect, the disclosure relates to a fusion protein comprising:

(i) an anti-PD-1 antibody, or an antigen-binding fragment thereof, wherein the antibody or antigen-binding fragment thereof comprises a heavy chain variable region and a light chain variable region, wherein each of the heavy chain and the light chain variable regions comprise a CDR1, CDR2, and CDR3; and wherein:

the sequence of CDR1H comprise the sequence of SEQ ID NO: 17;

the sequence of CDR2H comprises the sequence of SEQ ID NO: 18;

the sequence of CDR3H comprises the sequence of SEQ ID NO: 19;

the sequence of CDR1L comprises the sequence of SEQ ID NO: 41;

the sequence of CDR2L comprises the sequence of SEQ ID NO: 49; and the sequence of CDR3L comprises the sequence of SEQ ID NO: 50;

(ii) an IL-15 polypeptide comprising the amino acid sequence of SEQ ID NO: 212, optionally wherein amino acid N65 of SEQ ID NO: 212 is substituted with an S, D, or A;

(iii) an IL-15Rα sushi domain polypeptide comprising the amino acid sequence of SEQ ID NO: 214, optionally wherein amino acid N28 of SEQ ID NO: 214 is substituted with an A;

(iv) a first linker polypeptide joining the IL-15Rα sushi domain polypeptide and the IL-15 polypeptide; and optionally wherein the anti-PD-1 antibody, or an antigen-binding fragment thereof, comprises two heavy chains, wherein:

(a) the CH3 domain of first heavy chain comprises the amino acid substitutions L351Y, F405A, and Y407V (Kabat EU index numbering); and (b) the CH3 domain of second heavy chain comprises the amino acid substitutions T366L, K392L, and T394W (Kabat EU index numbering).

In one embodiment, the anti-PD-1 antibody or antigen-binding fragment thereof provided by the disclosure is a multispecific or a bispecific antibody or antigen-binding fragment thereof. In one embodiment, the antibody or antigen-binding fragment is a bispecific antibody comprising a complementary region that binds to PD-L1 or PD-L2. The disclosure also provides conjugates of the antibodies or the fusion molecules, for example, and without limitation, to fluorescent labels, imaging agents, therapeutic agents, or cytotoxic agents.

The disclosure further provides pharmaceutical compositions comprising one or more of an anti-PD-1 antibody or antigen-binding fragment thereof, or fusion protein comprising an anti-PD-1 antibody or antigen-binding fragment thereof, and a pharmaceutically acceptable carrier.

In embodiments, the disclosure provides nucleic acid molecules encoding the anti-PD-1 antibodies or antigen-binding fragments thereof disclosed herein and nucleic acid molecules encoding the fusion proteins disclosed herein, as well as vectors comprising such nucleic acid molecules. Also provided are cells comprising a vector encoding the anti-PD-1 antibodies or antigen-binding fragments thereof disclosed herein, or the fusion proteins disclosed herein.

In embodiments, the disclosure provides a method of inhibiting binding of PD-1 to a ligand of PD-1, the method comprising administering to a subject in need thereof an effective amount of an anti-PD-1 antibody, or antigen-binding fragment thereof, or a fusion protein disclosed herein.

In embodiments, the disclosure provides a method of treating a disease in a subject in need thereof, the method comprising administering to said subject a therapeutically effective amount of a composition comprising an anti-PD-1 antibody, or antigen-binding fragment thereof, or a fusion protein disclosed herein in a pharmaceutically acceptable form.

In embodiments, the disclosure provides a method for increasing T cell activation in a subject in need thereof, the method comprising administering an effective amount of an anti-PD-1 antibody, or antigen-binding fragment thereof, or a fusion protein disclosed herein. In one embodiment, the disclosure provides a method of stimulating the immune system in a subject in need thereof, the method comprising administering to said subject an effective amount of a composition comprising an anti-PD-1 antibody, or antigen-binding fragment thereof, or a fusion protein disclosed herein in a pharmaceutically acceptable form. In one embodiment, the disclosure provides a method of reducing replication of a virus in a subject in need thereof, the method comprising administering to the subject an effective amount of a composition comprising an anti-PD-1 antibody, or antigen-binding fragment thereof, or a fusion protein disclosed herein.

The disclosure also provides a method of inhibiting the interaction of PD-1 with PD-L1 and/or PD-L2 in a subject, the method comprising administering to a subject in need thereof an effective amount of an anti-PD-1 antibody, or antigen-binding fragment thereof, or a fusion protein disclosed herein. The disclosure further provides a method of inhibiting immunosuppression mediated by PD-1 in a subject in need thereof, the method comprising administering to the subject an effective amount of an anti-PD-1 antibody, or antigen-binding fragment thereof, or a fusion protein disclosed herein.

The disclosure further provides a method of stimulating an immune response against a cell or tissue that expresses PD-1 in a subject in need thereof, the method comprising administering to the subject an effective amount of an anti-PD-1 antibody, or antigen-binding fragment thereof, or a fusion protein disclosed herein. In certain embodiments, the cell or tissue expressing PD-1 is a cancerous cell or a cell infected with a pathogen, including, but not limited to, a virus or a bacterium.

In one aspect, the present disclosure provides a method of treating cancer, an immune disorder, or an infection in a patient in need thereof, the method comprising (a) treating a cell, in vitro, with an anti-PD-1 antibody, or antigen-binding fragment thereof, or a fusion protein disclosed herein; and (b) administering the treated cell to the patient. In some embodiments, the cell is a T cell.

In another aspect, the disclosure provides a method of increasing T cell activation in response to an antigen in a subject, the method comprising administering to the subject an effective amount of an anti-PD-1 antibody, or antigen-binding fragment thereof, or a fusion protein disclosed herein, or a pharmaceutical composition disclosed herein.

In another aspect, the disclosure provides a method of treating a condition in a subject that would benefit from an upregulation of the subject's immune response, the method comprising administering to the subject an effective amount of an anti-PD-1 antibody, or antigen-binding fragment thereof, or a fusion protein disclosed herein. In certain embodiments, the subject has upregulated expression of PD-L1, or the subject has been identified as positive for expression of PD-L1.

In one embodiment, the disclosure provides methods of using the anti-PD-1 antibodies, or antigen-binding fragments thereof, or fusion proteins disclosed herein for treating a subject that does not respond to therapy with a checkpoint inhibitor (primary resistance), and/or for treating a subject that initially responds to checkpoint inhibitor treatment, but later becomes resistant to checkpoint inhibitor blockade (secondary or acquired resistance). Such methods for treating comprise administering to said subject an anti-PD-1 antibody, or antigen-binding fragment thereof, or a fusion protein disclosed herein. In some embodiments, the subject has acquired resistance to therapy with one or more of a PD-1 inhibitor, a PD-L1 inhibitor, and a CTLA-4 inhibitor.

In one embodiment, the disclosure provides a method of administering an anti-PD-1 antibody, or antigen-binding fragment thereof, or a fusion protein disclosed herein to a subject in need thereof, the method further comprising administering an additional therapeutic agent or therapy to the subject, wherein the additional therapeutic agent or therapy is selected from the group consisting of a cancer vaccine, a checkpoint inhibitor, an antibody to a tumor-specific antigen, a *Bacillus* Calmette-Guerin (BCG) vaccine, a cytotoxin, an interleukin 6 receptor (IL-6R) inhibitor, an interleukin 4 receptor (IL-4R) inhibitor, an IL-10 inhibitor, IL-2, IL-7, IL-21, IL-15, an antibody-drug conjugate, an anti-inflammatory drug, and a dietary supplement. In embodiments, the disclosure provides a method of administering an anti-PD-1 antibody, or antigen-binding fragment thereof, or a fusion protein disclosed herein to a subject in need thereof, the method further comprising administering to the subject a checkpoint inhibitor selected from a CTLA-4, a PD-1, a PD-L1, and a PD-L2 inhibitor. In embodiments, the disclosure provides a method of administering an anti-PD-1 antibody, or antigen-binding fragment thereof, or a fusion protein disclosed herein to a subject in need thereof, the method further comprising administering to the subject one or more of an inhibitor of LAG3, TIGIT, LAP, Podoplanin, Protein C receptor, ICOS, GITR, CD226, and/or CD160. In embodiments, the disclosure provides a method of administering an anti-PD-1 antibody, or antigen-binding fragment thereof, or a fusion protein disclosed herein to a subject in need thereof, the method further comprising administering an additional therapeutic agent or therapy, wherein the additional therapeutic agent or therapy is administered concurrently or consecutively with the anti-PD-1 antibody, or antigen-binding fragment thereof, or fusion protein disclosed herein. In embodiments, the disclosure provides a method of administering an anti-PD-1 antibody, or antigen-binding fragment thereof, or a fusion protein disclosed herein to a subject in need thereof, the method further comprising administering to the subject an additional therapeutic agent or therapy, wherein the additional therapeutic agent or therapy is administered separately, or as a mixture with the anti-PD-1 antibody, or antigen-binding fragment thereof, or fusion protein disclosed herein. In one embodiment, the disclosure provides a method of administering an anti-PD-1 antibody, or antigen-binding fragment thereof, or a fusion protein disclosed herein in combination with chemotherapy, radiotherapy, or surgery.

BRIEF DESCRIPTION OF THE FIGURES

FIG. 1A, FIG. 1B, FIG. 1C, and FIG. 1D show the heavy and light chain variable domain sequences and CDR sequences of anti-PD-1 antibodies disclosed herein. CDR sequences are according to Kabat (CDR sequences according to AbM/Chothia exclude the underlined amino acids). FIG. 1A provides the heavy and light chain variable regions of six anti-human PD-1 (hPD-1) antibodies that were identified by library screening. FIG. 1B provides the light chain and CDR sequences of 23H9 as well as of 23H9 variants that were identified by light chain shuffling, wherein a library of light chains was paired with the 23H9 heavy chain sequence. $X_1$ is Q or E; $X_2$ is H or Y; $X_3$ is Y or N; $X_4$ is T or N; $X_5$ is L, Q or E; $X_6$ is S, A, or V; $X_7$ is H, N, T, or S; $X_8$ is R or L; $X_9$ is G, A, or H; $X_{10}$ is S or T; $X_{11}$ is A, T, or S; and $X_{12}$ is H or R. FIG. 1C provides the light chain and CDR sequences of 24H9 as well as of 24H9 variants that were identified by light chain shuffling, wherein a library of light chains was paired with the 24H9 heavy chain sequence. $X_{13}$ is A or V; $X_{14}$ is S or G; $X_{15}$ is Q, E, or R; $X_{16}$ is G, S, D or N; $X_{17}$ is G, S, or N; $X_{18}$ is S, I, R, T, K, P, N, H, or V; $X_{19}$ is L or V; $X_{20}$ is G or A; $X_{21}$ is S, D, E, or A; $X_{22}$ is S or K; $X_{23}$ is S, N, T, R, or D; $X_{24}$ is L or V; $X_{25}$ is Q, E, or H; $X_{26}$ is S, N, A, R, P, or T; $X_{27}$ is A or G; $X_{28}$ is N, D, or Y; $X_{29}$ is F or L; and $X_{30}$ is A or T. FIG. 1D provides sequences for hPD-1/mPD-1 cross-reacting antibody R3A9 as well as R3A9 derivatives that were identified by light chain shuffling, wherein a library of light chains was paired with the R3A9 heavy chain sequence.

FIG. 4A: EC50 23A8>23H9>19B10. MFI 23A8>23H9>19B10. FIG. 4B: 23H9>24H9 and 23A8. FIG. 4C: 23H9>24H9 and 23A8.

FIG. 8A. MFI to hPD1-HEK293: 24H9 derivatives (38B2 and 38A6>24H9) >23H9 derivative (31B1 and 33C4>23H9). FIG. 8B. MFI to hP01-Jurkat: 23H9 derivatives (33C4>31B1>23H9)>24H9 derivatives (38B2>38A6>24H9). FIG. 8C and FIG. 8D. EC50 value for binding to SEB-activated human PBMCs from two donors: 23H9 derivatives (31B1 same as 33C4) <24H9 derivatives (38A6 same as 31B1). MFI for binding to SEB-activated human PBMCs: 23H9 derivatives (31B1 same as 33C4)>24H9 derivatives (38A6 same as 31B1).

FIG. 9A. EC50 of 23H9 and its derivatives 31B1 and 33C4: 31B1 (0.139 µg/ml)>33C4 (0.165 µg/ml)>23H9 (0.511 µg/ml). Maximum fold induction (luminescence): 31B1 (6.48) >33C4 (6.24)>23H9 (5.56). FIG. 9B. EC50 of 24H9 and its derivatives 38A6 and 38B2: 38B2 (0.855 µg/ml)>38A6 (0.164 µg/ml)>24H9 (0.855 µg/ml). Maximum fold induction (luminescence): 38B2 (6.54)>38A6 (5.66)>24H9 (4.97).

FIG. 10A. IL-2 accumulation in PBMCs from donor FA: IL-2 concentration increased in the presence of the indicated antibodies in a dose-dependent manner. FIG. 10B. 23H9 and 31B1: EC50 was 0.344 and 0.107 nM, respectively; IL-2 concentration at 10 nM antibody concentration was 3.9 and 5.81 µg/ml, respectively. FIG. 10C. 24H9 and 38B2: EC50 was >10 nM and 0.019 nM, respectively; IL-2 concentration at in 10 nM antibody concentration was 4.5 and 5.0 µg/ml, respectively.

FIG. 12A, FIG. 12B, FIG. 12C, FIG. 12D, and FIG. 12E depict binding of antibodies 31B1, 33C4, 38B2, and 38A6 to hPD-1FC (FIG. 12A), streptavidin-captured biotin-labeled hPD-1his (FIG. 12B, labels as in FIG. 12A), and anti-his antibody captured hPD-1his (FIG. 12C, labels as in FIG. 12A) as well as blocking of hPD-1-hPD-L1 (FIG. 12D) and hPD-1-hPD-L2 interactions (FIG. 12E).

FIG. 13A. All antibody derivatives shown have similar EC50 values, but 24H9 derivatives 38A6 and 38B2 exhibit higher maximum binding signals. Same labels as in FIG. 13B. FIG. 13B. 23H9 derivatives 31B1 and 33C4 have lower EC50 values and higher maximum binding signals as compared to 24H9 derivatives 38A6 and 38B2. FIG. 13C. Same labels as in FIG. 13D. FIG. 13C and FIG. 13D. 23H9 derivatives 31B1 and 33C4 exhibit higher maximum binding signals and lower EC50 values as compared to 24H9 derivatives 38A6 and 38B2 as determined using PBMCs from two different donors.

FIG. 15A. Experiment 1. FIG. 15B. Experiment 2.

FIG. 19C (labels as in FIG. 19D) and FIG. 19D.

FIG. 20A. Blockade: m4D1 was as potent as m3A7 in blocking mPD1-mPDL 1 interactions. IC50 m4D1=0.5724 nM. IC50 m3A7=0.5615 nM. IC50 m2C1=1.127 nM. FIG. 20B. m4D1 blocks hPD1/hPDL 1 interactions but was not as potent as 38B2. IC50 38B2=0.7248 nM. IC50 m4D1=2.125 nM. IC50 m2C1=31.25 nM.

FIG. 23C. CD8+/CD4+ T cell populations in total spleen cells. Fusion proteins 1N-DP47/IL-15, 2N-DP47/IL-15, 1C-DP47/IL-15, and 2C-DP47/IL-15 were used as controls.

FIG. 29A. Binding of 1N-fusion proteins to a soluble hPD-1-Fc. FIG. 29B. ELISA competition assay for measuring PD-L1 binding to PD-1. FIG. 29C. ELISA competition assay for measuring PD-L2 binding to PD-1.

FIG. 29D. Binding of 1N-fusion proteins to hPD-1 transfected HEK293 cells. FIG. 29E. Promega blockade assay to determine binding of PD-L2 to PD-1. FIG. 29F. Promega blockade assay to determine binding of PD-L2 to PD-1. Fusion proteins comprising antibody DP47 (a non-targeting control antibody) served as controls. mut=N65S.

FIGS. 30A, 30B, and 30C show stimulation of proliferation of M07e cells by anti-PD-1 (38B2)/N65D/S/A-mutated IL-15 fusions. Fusion proteins comprising a non-targeting control antibody served as controls (FIG. 30B). FIG. 30D shows proliferation of hPBMCs upon stimulation with the indicated fusion proteins. FIG. 30E shows binding of the indicated fusion proteins to hIL2RB transfected HEK30 cells.

FIGS. 31A and 31B show proliferation of murine CTLL2 cells (FIG. 31A) and murine BALB/c spleen cells (FIG. 31B) upon stimulation with the indicated fusion proteins. FIGS. 31C and 31D show CD8+ and CD4+ T cell populations in murine BALB/c spleen cells (FIG. 31C) and hPBMCs (FIG. 31D) upon stimulation with the indicated fusion proteins.

FIGS. 32A, FIG. 32B, FIG. 32F, FIG. 32G, FIG. 32I, and FIG. 32K. Tumor volume after treatment with Keytruda or the indicated 1N-fusion proteins. mut=N65S mutation. ct=DP47=non-targeting control antibody. Ketruda=pembrolizumab (formerly lambrolizumab, brand name Keytruda). FIG. 32C. Tumor growth for each mouse (N65S-38B2/IL-15, 12 mg/kg treatment). FIG. 32D, FIG. 32H, and FIG. 32J. % change in body weight. FIG. 32E. Mouse survival at different dose levels. FIGS. 32A, FIG. 32B, FIG. 32C, FIG. 32D, FIG. 32E, FIG. 32F, FIG. 32G, FIG. 32H, FIG. 32I: Dosing was QW=once per week intraperitoneally for three weeks for 1N-fusion proteins, BIW=twice per week intraperitoneally for three weeks for controls. FIG. 32J, and FIG. 32K: Dosing was BIW=twice per week intraperitoneally for three weeks.

FIG. 34A. Tumor volume after treatment with the indicated proteins. FIG. 34B. Mouse survival after treatment with the indicated proteins. FIG. 34C. % change in body weight after treatment with the indicated proteins.

FIG. 35A. Tumor volume after treatment with the indicated proteins. FIG. 35B. Mouse survival after treatment with the indicated proteins. FIG. 35C. % change in body weight after treatment with the indicated proteins.

FIG. 37A, FIG. 37B, FIG. 37C, and FIG. 37D illustrate the results of a mechanism of action study in hPDL1/PD1 transgenic BALB/c mice bearing hPDL1-CT26 tumors. FIG. 37A. $0.5 \times 10^6$ of hPDL 1/CT26 cells were subcutaneously inoculated to the right lower flank of the hPD1/PDL1 transgenic BALB/c mice. When the tumor size reached about 175 mm³, the mice were intravenously injected with of (1) N65S-1N-38B2/IL-15 (0.06 μmol/kg and 0.035 μmol/kg, respectively), (2) N65S-1N-DP47/IL-15 (non-targeted control, 0.035 μmol/kg), (3) antibody 38B2 (0.035 μmol/kg) and (4) the combination of antibody 38B2 (0.035 μmol/kg) and N65S-1N-38B2/IL-15 (0.035 μmol/kg). FIG. 37B. Blood and draining lymph node (DLN) from all groups were collected to perform flow cytometry. Tumors were collected to perform TILs analysis. FIG. 37C. CD8/CD4 ratio in tumors, the blood, and draining lymph nodes (treated with antibody (1) 38B2, (2) PD1 targeted fusion protein N65S-1N-38B2/IL-15, (3) non-targeted fusion protein N65S-1N-DP47/IL-15, or (4) a combination of 38B2 and N65S-1N-38B2/IL-15). FIG. 37D. Analysis of CD8 and CD4 subtypes in tumors (treated with antibody (1) 38B2, (2) PD1 targeted fusion protein N65S-1N-38B2/IL-15, (3) non-targeted fusion protein N65S-1N-DP47/IL-15, or (4) a combination of 38B2 and N65S-1N-38B2/IL-15).

DETAILED DESCRIPTION

Figure 1A:
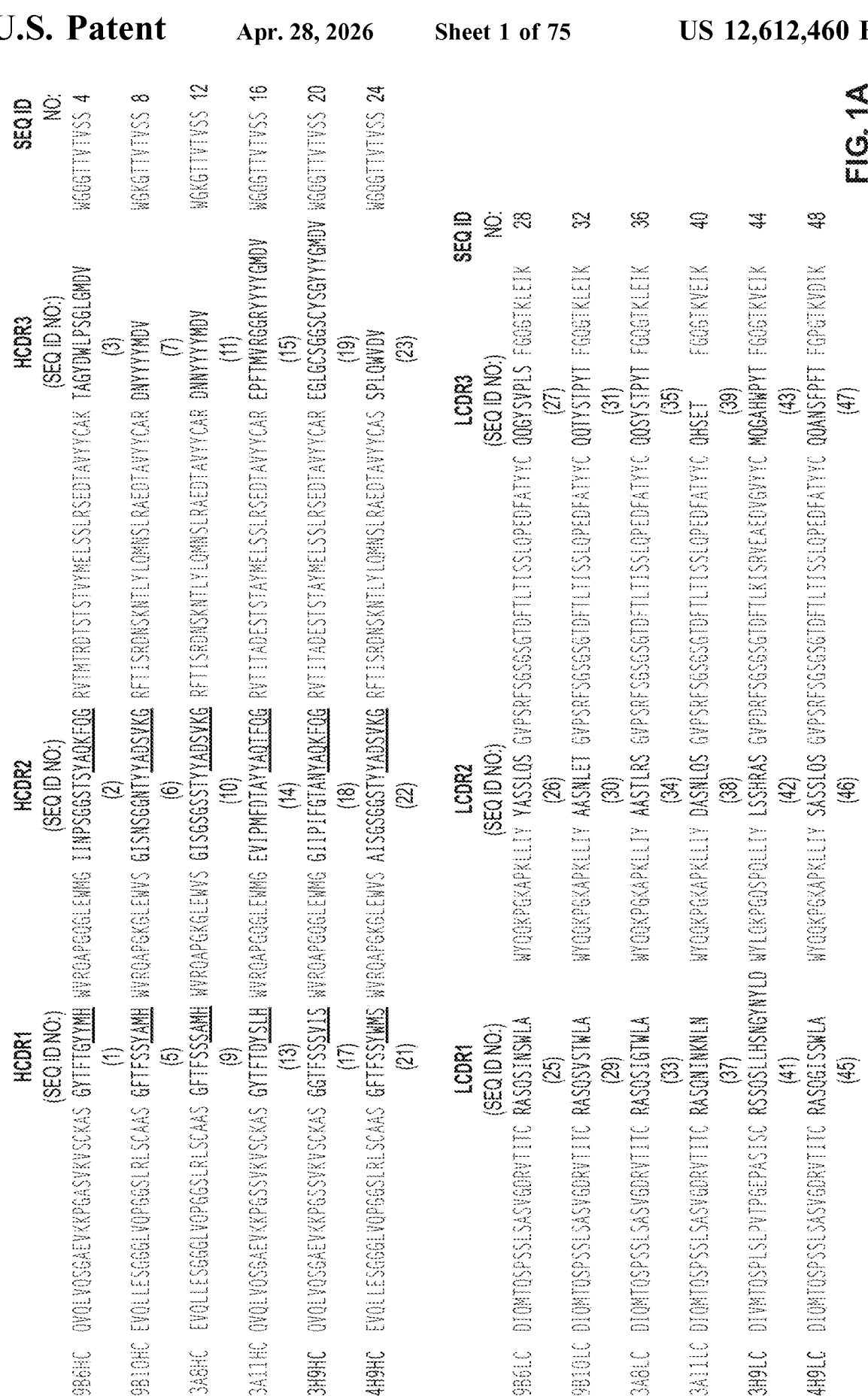

The present disclosure provides fusion proteins comprising an anti-PD-1 antibody or antigen-binding fragment thereof linked to an IL-15 polypeptide, which in turn is linked to an IL-15 receptor alpha (IL-15Rα) polypeptide comprising the IL-15Rα sushi domain. In addition, provided herein are antibodies, and antigen-binding fragments thereof, that specifically bind to PD-1 and fusion proteins comprising such anti-PD-1 antibodies and PD-1 binding fragments thereof.

Fusion Proteins Comprising Anti-PD-1 Antibodies or Antigen-Fragments Thereof

In one aspect, the disclosure provides fusion proteins comprising an antibody, or antigen-binding fragment thereof that binds to PD-1. This portion of the fusion protein can be any antibody or antibody fragment that specifically binds PD-1, including those comprising the corresponding heavy and light chain variable regions or CDRs provided in FIG. 1, or otherwise discribed herein.

Disclosed herein are fusion proteins comprising a stimulatory domain. As used herein, a "stimulatory domain" is a domain that promotes an immune response. The stimulatory domain may stimulate an immune response mediated by, for example, inducing T cell or NK cell activity and/or proliferation. In embodiments, the stimulatory domain stimulates cells that respond to an interleukin or an interferon, such as, without limitation, IL-2, IL-7, IL-15, and IL-21. In one embodiment, the stimulatory domain binds to and stimulates a receptor that is responsive to an interleukin or an interferon, such as, without limitation, IL-2, IL-7, IL-13, IL-15, and IL-21. The stimulatory domain can also be a hybrid domain that is a hetero-complex of two or more ligands covalently linked to each other.

In embodiments, the stimulatory domain includes a sequence or domain that promotes IL-15 stimulation of the IL-15 receptor (IL-15R).

In one embodiment, the stimulatory domain that promotes IL-15R stimulation comprises IL-15 or an IL-15 derivative.

In one embodiment, the stimulatory domain that promotes IL-15R stimulation comprises an IL-15Rα polypeptide comprising the IL-15Rα sushi domain or a derivative thereof. In an embodiment, the stimulatory domain comprises the sushi domain of the IL-15Rα chain.

In an embodiment, the stimulatory domain comprises IL-15 or a derivative thereof, whose binding may be enhanced by the presence of an IL-15Rα polypeptide comprising the IL-15Rα sushi domain or a derivative thereof. In one embodiment, the stimulatory domain comprises a complex of IL-15 or a derivative thereof and an IL-15Rα polypeptide comprising the IL-15Rα sushi domain or a derivative thereof. In some embodiment, the stimulatory domain comprises an IL-15 or a derivative thereof and an IL-15Rα polypeptide comprising the IL-15Rα sushi domain or a derivative thereof, wherein the two polypeptides are covalently linked by a linker (including, but not limited to, a linker comprising SEQ ID NO: 215).

In one embodiment, the IL-15 or a derivative thereof is located N-terminally of the IL-15Rα polypeptide comprising the IL-15Rα sushi domain or derivative thereof. In one embodiment, the IL-15 or a derivative thereof is located C-terminally of the IL-15Rα polypeptide comprising the IL-15Rα sushi domain or derivative thereof. In one embodiment, the stimulatory domain comprises the sequence of the SD15 domain highlighted in any one of SEQ ID NOS: 177-180.

As demonstrated herein, provided herein is a fusion protein which comprises (1) a PD-1 binding domain that blocks binding of PD-1 to PD-L1 and inhibits immunosuppression, and (2) a stimulatory domain that promotes an immune response, wherein the fusion proteins provides for increased immune cell activity, compared to two distinct molecules that provide the beforementioned functions separately. Specifically, the experiments disclosed herein demonstrate that fusion proteins containing both a PD-1 binding domain that blocks binding of PD-1 to PD-L1, and an stimulatory domain IL-15 or a derivative thereof and an IL-15Rα polypeptide comprising the IL-15Rα sushi domain or a derivative thereof, promoted increased proliferation, Th1 cytokine release, and killing activity-related molecules of NK and T cells, compared to providing the domains in separate molecules.

In certain embodiments, the fusion protein comprises a stimulatory domain disclosed herein that is covalently linked to an anti-PD-1 antibody or antigen-binding fragment thereof disclosed herein via a flexible linker. In some embodiments, provided herein is a fusion protein wherein the stimulatory domain disclosed herein is fused directly to an anti-PD-1 antibody or antigen-binding fragment disclosed herein.

As used herein, "covalently linked" or "fused" refers to the association of two or more polypeptides through a covalent bond. In some embodiments, two polypeptides that are covalently linked are fused to each other directly, i.e., without any additional polypeptide sequence between the first and the second peptide. Accordingly, in some embodiments, the N-terminus of the first polypeptide is fused directly to the C-terminus of the second polypeptide or vice versa. In other embodiments, the two polypeptides that are covalently linked are part of a continuous polypeptide chain, but are not directly fused to each other (i.e., the two polypeptides may be separated by one or more amino acids, a linker or another polypeptide). The term "covalently linked" does not imply a specific orientation of the two or more polypeptides that are fused to each other.

IL-15 is a 14-15 KD cytokine with structural similarity to IL-2. IL-15 is also known as MGC9721. A variety of cell types constitutively produce IL-15 mRNA, and these include monocytes, macrophages, DCs, keratinocytes, epidermal skin cells, fibroblasts, various epithelial cells, bone marrow stromal cells, and nerve cells. In addition, IL-15 mRNA is also produced in kidney, placenta, lung, heart, skeletal muscle, and brain tissues. However, only monocytes, DCs, epithelial cells, bone marrow stromal cells, fibroblasts, and very few other cells and tissues secrete detectable levels of IL-15. IL-15 and IL-2 are found to bind the same hematopoietin subunits and share many biological activities. IL-15 regulates T and NK cell activation and proliferation, and the number of CD8 memory cells is affected by a balance between IL-15 and IL-2. In embodiments, the IL-15 or IL-15 derivative disclosed herein has at least 10%, at least 20%, at least 30%, at least 40%, at least 50%, at least 60%, at least 70%, at least 80%, or at least 90% of the activity of human IL-15. IL-15 may be a mammalian IL-15, preferably a primate IL-15, and more preferably a human IL-15. The human IL-15 (Accession number NP_000576) amino acids sequence is provided as SEQ ID NO: 212.

The term "IL-15 derivative" refers to a polypeptide having at least 80%, at least 85%, at least 90%, at least 95%, at least 96%, at least 97%, at least 98%, or at least 99% sequence identity with SEQ ID NO:212, the mature form of human IL-15. Techniques for making such derivatives are known in the art. In some embodiments, the IL-15 or IL-15 derivative sequence may comprise one or more amino acid substitutions. In some embodiments, the amino acid substitutions are located at positions 1, 4, 8, 30, 45, 61, 64, 65, and/or 108 of IL-15 (residue numbers are referring to the mature form of the IL-15 protein). In some embodiments, the amino acid substitutions are located at position 45, 65, and/or 108 of IL-15. In some embodiments the amino acid substitutions in IL-15 are N1D, N4D, D8N, D30N, D61N, E64Q, L45A, N65S/A/D/K, and/or Q108S/E. In some embodiments, the amino acid substitutions in IL-15 are L45A, N65S/A/D/K, and/or Q108S. In embodiments, a fusion protein disclosed herein comprises an IL-15 polypeptide comprising one of the following amino acid substitutions: N65S, N65A, or N65D. In embodiments, a fusion protein disclosed herein comprises an IL-15 polypeptide comprising one or more of the following amino acid substitutions: L45A, N65S, N65A, or N65D, and Q108S.

The amino acid sequence of human IL-15Rα isoform 1 precursor (Accession number NP_002180) is provided in SEQ ID NO:213. The IL-15 receptor, i.e., IL-15 receptor complex, specifically binds IL-15 with high affinity and consists of a unique interleukin 15 receptor αsubunit, IL-2/IL-15Rβ, and the common γ-chain/IL-2Rγ subunit. IL-15Rα is expressed by mitogen-activated macrophages, NK cells, and CD4 and CD8 T cells. The human IL-15Rα consists of seven exons, and alternative mRNA splicing may result in eight molecular IL-15Rα isoforms with different extra or intracellular domains. Full-length isoforms consist of an extracellular portion containing a conserved protein binding motif (sushi domain), a trans-membrane domain, and an intracellular tail.

As used herein, the term "sushi domain" of IL-15Rα refers to a domain beginning at the first cysteine residue (C1) after the signal peptide of IL-15Rα and ending at the fourth cysteine residue (C4) after said signal peptide. The sushi domain corresponding to a portion of the extracellular region of IL-15Rα is involved in binding to IL-15. The sushi domain in the present disclosure has at at least 10%, at least 20%, at least 30%, at least 40%, at least 50%, at least 60%, at least 70%, at least 80%, or at least 90% of the activity of the sushi domain of the human IL-15Rα chain.

The amino acid sequence of human IL-15Rα isoform 1 precursor is provided in SEQ ID NO:213 (this sequence includes the signal sequence). The sushi domain amino acid sequence of human IL-15Rα is provided in SEQ ID NO: 214.

The term "IL-15Rα sushi domain derivative" or "IL-15Rα sushi domain variant" refers to a polypeptide having at least 80%, at least 85%, at least 90%, at least 95%, at least 96%, at least 97%, at least 98%, or at least 99% sequence identity with the sequence of the human IL-15Rα sushi domain (SEQ ID NO:214). Techniques for making such derivatives or variants are known in the art. All such derivatives comprise the four cysteine residues of the sushi domain of IL-15Rα. In some such derivatives, naturally occurring amino acids may be replaced by chemically modified amino acids to alter the polypeptide half-life. In some embodiments, the IL-15Rα sushi domain or IL-15Rα sushi domain derivative sequence may comprise one or more amino acid substitutions. In some embodiments, the amino acid substitution is located at position 60 of IL-15Rα

(numbering of the IL-15Rα residues include the signal peptide, see, e.g., SEQ ID NO:213). In some embodiments, the amino acid substitution in the IL-15Rα sushi domain is N60A (i.e., the asparagine (N) at amino acid 60 is substituted with alanine (A)).

IL-15 binds with high affinity to IL-15Rα, which then associates with an IL-15Rβ/γc complex expressed by the same target cell (cis-presentation). IL-15Rα is also known to trans-present IL-15 with high affinity to a different target cell expressing the IL-15Rβ/γ(c) complex (trans-presentation). IL-15 cis- and trans-presentation mechanisms lead to different dynamics of receptor activation and signal transduction, with cis-presentation inducing fast and transient responses, and trans-presentation inducing slower, more persistent ones.

In some embodiments, the fusion proteins disclosed herein comprise a stimulatory domain, which comprises a hybrid domain comprising the sushi domain of the IL-15Rα chain attached to IL-15 by a linker (including, but not limited to, the linker of SEQ ID NO: 215). In certain embodiments, the stimulatory domain disclosed herein is covalently linked to an anti-PD-1 antibody or antigen-binding fragment thereof disclosed herein via a second linker (including, but not limited to, the linker of SEQ ID NO: 216). In other embodiments, the stimulatory domain exemplified herein is directly fused to an anti PD-1 antibody or antigen-binding fragment disclosed herein.

In one embodiment, provided is an "N-terminal fusion protein," wherein a stimulatory domain is linked directly or via a linker (e.g., via one or more peptides) to the N-terminus of an anti-PD1 binding portion of the fusion protein (e.g., the N-terminus of a heavy chain of an anti-PD-1 antibody disclosed herein).

N-terminal fusion proteins include but are not limited to the following (exemplary) fusion proteins (components recited from N- to C-terminus, "-" indicated direct covalent linkage or linkage via a linker (e.g., via one or more peptides):

(1) (IL-15 or derivative thereof)-(heavy chain of anti-PD-1 antibody or antigen binding fragment thereof)

(2) (IL-15 or derivative thereof)-(light chain of anti-PD-1 antibody or antigen binding fragment thereof)

(3) (IL-15Rα polypeptide comprising the IL-15Rα sushi domain or a derivative thereof)-(IL-15 or derivative thereof)-(heavy chain of anti-PD-1 antibody or antigen binding fragment thereof)

(4) (IL-15Rα polypeptide comprising the IL-15Rα sushi domain or a derivative thereof)-(IL-15 or derivative thereof)-(light chain of anti-PD-1 antibody or antigen binding fragment thereof)

(5) (IL-15 or derivative thereof)-(IL-15Rα polypeptide comprising the IL-15Rα sushi domain or a derivative thereof)-(heavy chain of anti-PD-1 antibody or antigen binding fragment thereof)

(6) (IL-15 or derivative thereof)-(IL-15Rα polypeptide comprising the IL-15Rα sushi domain or a derivative thereof)-(light chain of anti-PD-1 antibody or antigen binding fragment thereof)

N-terminal fusion proteins may comprise more than one stimulatory domain.

In one embodiment, provided is a fusion protein, wherein the stimulatory domain is covalently linked to the N-terminus of one (and only one) of the heavy chains of the anti-PD-1 antibody or antigen binding fragment thereof. An N-terminal fusion protein comprising a single stimulatory domain is referred to as a "1-N-terminal fusion protein."

Provided herein is a fusion protein comprising (1) a stimulatory domain (2) a first heavy chain of an anti-PD-1 antibody or antigen binding fragment thereof, wherein the stimulatory domain is covalently linked to the N-terminus of the first heavy chain, and (3) a second heavy chain of an anti-PD-1 antibody or antigen binding fragment thereof, wherein the second heavy chain is not linked to a stimulatory domain. In some embodiments, the stimulatory domain comprises (i) IL-15 or a derivative thereof, or (ii) an IL-15Rα polypeptide comprising the IL-15Rα sushi domain or a derivative thereof, or (iii) both.

In one embodiment, provided is a fusion protein, wherein a stimulatory domain is covalently linked to the N-termini of both of the heavy chains of the anti-PD-1 antibody or antigen binding fragment thereof. An N-terminal fusion protein comprising two stimulatory domains, both linked to different antibody chains, is referred to as a "2-N-terminal fusion protein."

In one embodiment, provided is an "C-terminal fusion protein," wherein a stimulatory domain is linked directly or via a linker (e.g., via one or more peptides) to the C-terminus of an anti-PD1 binding portion of the fusion protein (e.g., the C-terminus of a heavy chain of an anti-PD-1 antibody disclosed herein).

C-terminal fusion proteins include but are not limited to the following (exemplary) fusion proteins (components recited from N- to C-terminus, "-" indicated direct covalent linkage or linkage via a linker (e.g., via one or more peptides):

(1) (heavy chain of anti-PD-1 antibody or antigen binding fragment thereof)-(IL-15 or derivative thereof)

(2) (light chain of anti-PD-1 antibody or antigen binding fragment thereof)-(IL-15 or derivative thereof)

(3) (heavy chain of anti-PD-1 antibody or antigen binding fragment thereof)-(IL-15Rα polypeptide comprising the IL-15Rα sushi domain or a derivative thereof)-(IL-15 or derivative thereof)

(4) (light chain of anti-PD-1 antibody or antigen binding fragment thereof)-(IL-15Rα polypeptide comprising the IL-15Rα sushi domain or a derivative thereof)-(IL-15 or derivative thereof)

(5) (heavy chain of anti-PD-1 antibody or antigen binding fragment thereof)-(IL-15 or derivative thereof)-(an IL-15Rα polypeptide comprising the IL-15Rα sushi domain or a derivative thereof)

(6) (light chain of anti-PD-1 antibody or antigen binding fragment thereof)-(IL-15 or derivative thereof)-(an IL-15Rα polypeptide comprising the IL-15Rα sushi domain or a derivative thereof)

C-terminal fusion proteins may comprise more than one stimulatory domain.

In one embodiment, provided is a fusion protein, wherein the stimulatory domain is covalently linked to the C-terminus one (and only one) of the heavy chains of the anti-PD-1 antibody or antigen binding fragment thereof. A C-terminal fusion protein comprising a single stimulatory domain is referred to as a "1-C-terminal fusion protein."

Provided herein is a fusion protein comprising (1) a stimulatory domain, (2) a first heavy chain of an anti-PD-1 antibody or antigen binding fragment thereof, wherein the stimulatory domain is covalently linked to the C-terminus of the first heavy chain, and (3) a second heavy chain of an anti-PD-1 antibody or antigen binding fragment thereof, wherein the second heavy chain is not linked to a stimulatory domain. In some embodiments, the stimulatory domain comprises (i) IL-15 or a derivative thereof, or (ii) an IL-15Rα polypeptide comprising the IL-15Rα sushi domain or a derivative thereof, or (iii) both.

In one embodiment, provided is a fusion protein, wherein a stimulatory domain is covalently linked to the C-termini of both of the heavy chains of the anti-PD-1 antibody or antigen binding fragment thereof. A C-terminal fusion protein comprising two stimulatory domains, both linked to different antibody chains, is referred to as a "2-C-terminal fusion protein."

FIG. 21 depicts schematic diagrams of exemplary fusion proteins as described herein.

Figure 25A:
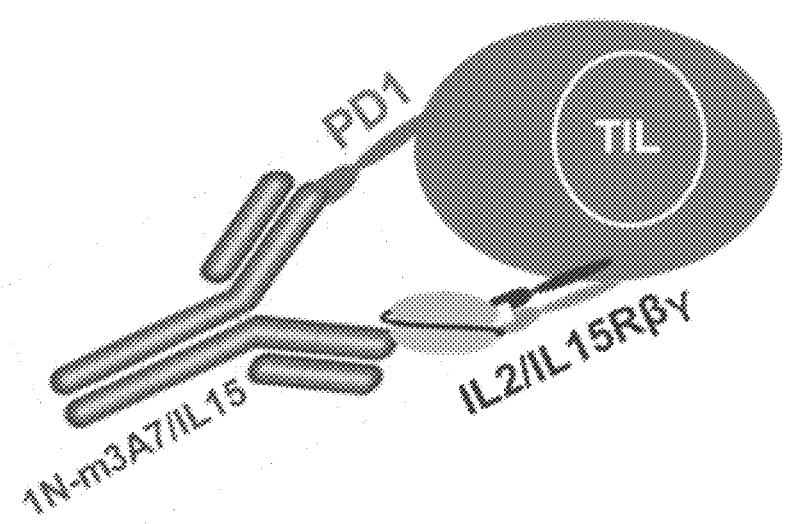
FIG. 25A and FIG. 25B illustrate that, as compared to C-terminal fusions, N-terminal fusion proteins are particularly useful to act on tumor infiltrating lymphocytes (TILs) compared to peripheral T cells. This is due to the cis-presentation enabled by the N-terminal fusion constructs.
Figure 25A:
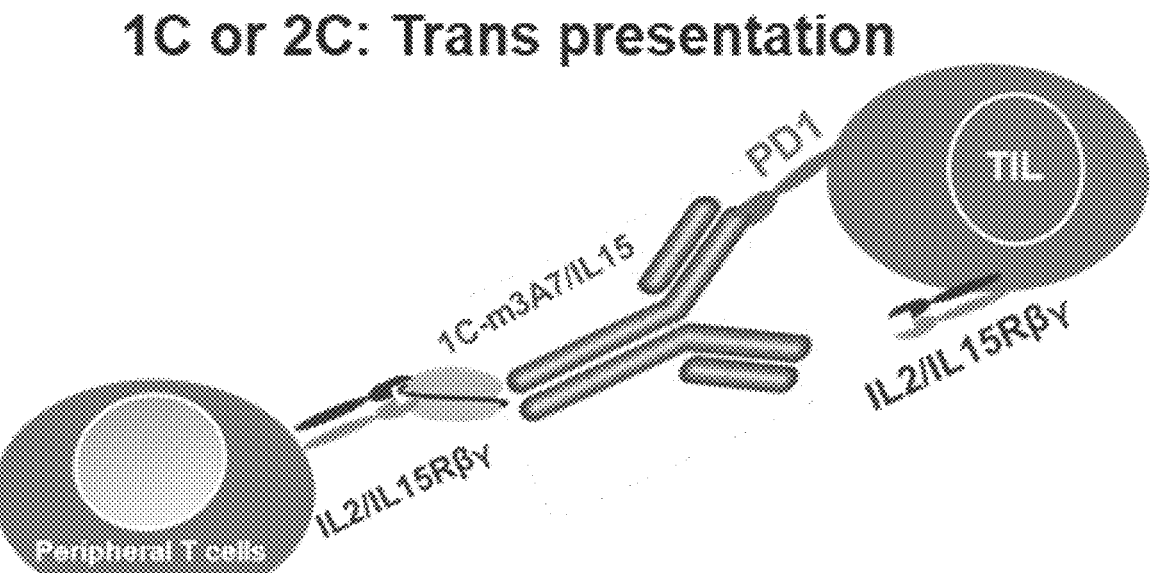
Figure 25B:
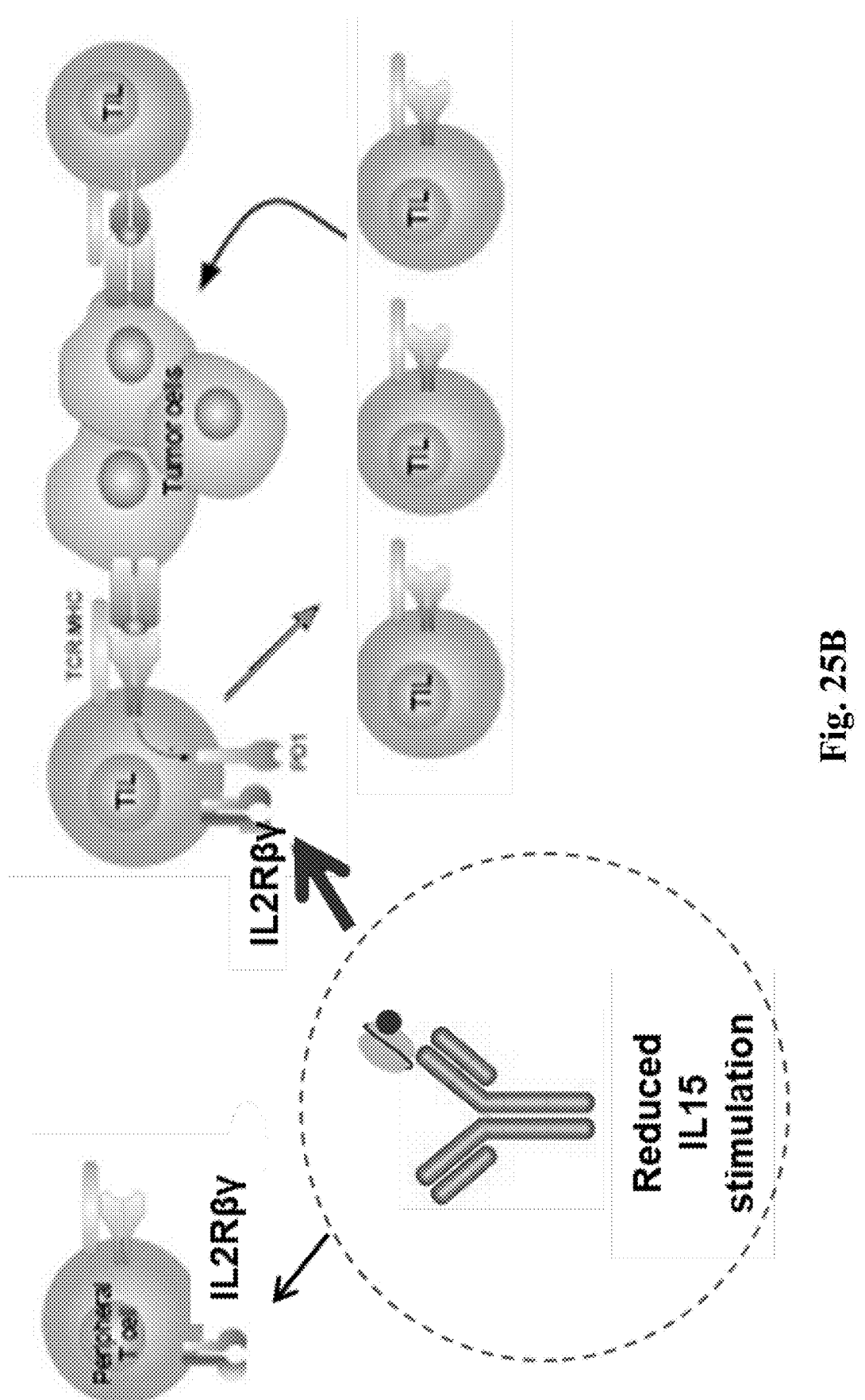

Therapeutic levels of IL-2 are associated with high level of toxicity upon binding to the IL-2 receptor. Similarly, using therapeutic levels of IL-15 can also cause toxicity since IL-15 shares two receptor subunits with IL-2. The N-terminal fusion proteins, however, demonstrate reduced toxity compared to the C-terminal fusion proteins because when presented in cis position, the N-terminal IL-15 fusion proteins can selectively bind to tumor infiltrating lymphocyte (TIL) while showing a lower binding to peripheral T cells. When presented in cis position, N-terminal fusion proteins may bind to IL-15Rβγ and PD-1 simultaneously while reducing the IL-15Rβ/γ binding, allowing the N-terminal fusion proteins to selectively bind to TILs and promoting TIL proliferation. In contrast, C-terminal fusion proteins may bind to both peripheral T cells and TIL equally and may show higher toxicity than the N-terminal fusion proteins. (FIG. 25). 1N-terminal fusion proteins show reduced toxicity compared to an N-terminal fusion protein comprising two stimulatory domains covalently linked to an anti-PD-1 antibody disclosed herein (2N-terminal fusion protein). Mutated N-terminal fusion proteins show a further reduction in toxicity due to even lower binding to peripheral T cells.

In one aspect, the disclosure relates to a fusion protein comprising:

(i) an anti-PD-1 antibody, or an antigen-binding fragment thereof, wherein the anti-PD-1 antibody or antigen-binding fragment thereof comprises a heavy chain variable region and a light chain variable region, wherein each of the heavy chain and the light chain variable regions comprise a CDR1, CDR2, and CDR3, and wherein the antibody heavy chain comprises a constant region comprising three constant domains CH1, CH2, and CH3;

(ii) an interleukin 15 (IL-15) polypeptide comprising an amino acid sequence of SEQ ID NO: 212, or an amino acid sequence that is at least 90% or at least 95% identical to SEQ ID NO: 212;

(iii) an IL-15Rα sushi domain polypeptide comprising an amino acid sequence of SEQ ID NO: 214, or an amino acid sequence that is at least 90% or at least 95% identical to SEQ ID NO: 214; and (iv) a first linker polypeptide joining the IL-15Rα sushi domain polypeptide and the IL-15 polypeptide.

Figures 1B, 1C:
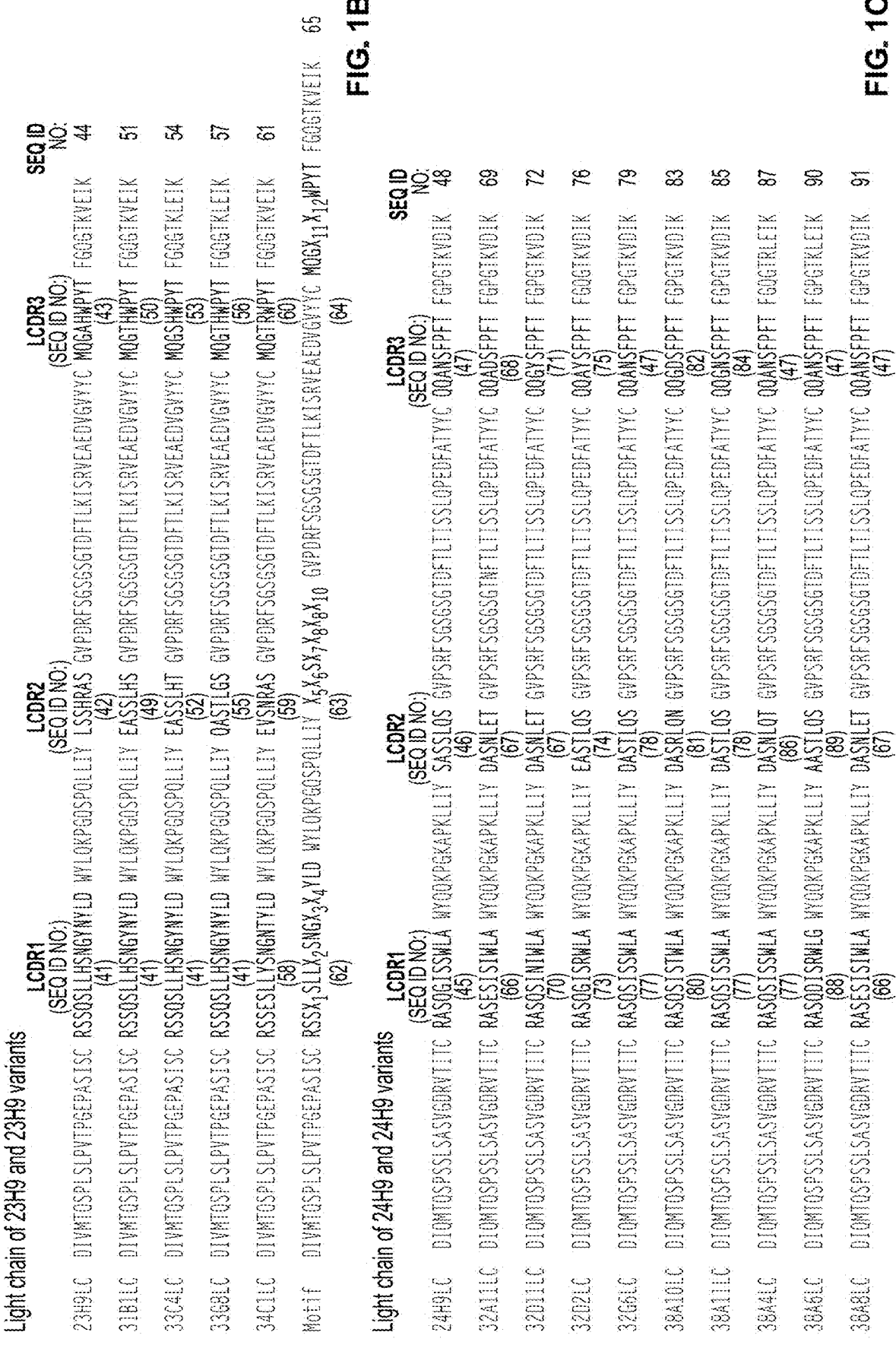

The anti-PD-1 antibody, or antigen-binding fragment thereof, portion of the fusion protein can be any that specifically bind PD-1, including those comprising the corresponding variable regions or CDRs provided in FIG. 1, or otherwise discribed herein. In embodiments, the fusion protein comprises an antibody, or antigen-binding fragment thereof, wherein the CDRs of the heavy and light chain variable regions comprise the following sequences:

the sequence CDR1H comprises the sequence of SEQ ID NO: 21;

the sequence of CDR2H comprises the sequence of SEQ ID NO: 22;

the sequence of CDR3H comprises the sequence of SEQ ID NO: 23;

the sequence of CDR1L comprises the sequence $RX_{13}X_{14}X_{15}X_{16}IX_{17}X_{18}WX_{19}X_{20}$ (SEQ ID NO:135);

wherein $X_{13}$ is A or V;

wherein $X_{14}$ is S or G;

wherein $X_{15}$ is Q, E, or R;

wherein $X_{16}$ is G, S, D or N;

wherein $X_{17}$ is G, S, or N;

wherein $X_{18}$ is S, I, R, T, K, P, N, H, or V;

wherein $X_{19}$ is L or V; and wherein $X_{20}$ is G or A; and the sequence of CDR2L comprises the sequence $X_{21}AX_{22}X_{23}X_{24}X_{25}X_{26}$ (SEQ ID NO: 136); and wherein $X_{21}$ is S, D, E, or A;

wherein $X_{22}$ is S or K;

wherein $X_{23}$ is S, N, T, R, or D;

wherein $X_{24}$ is L or V;

wherein $X_{25}$ is Q, E, or H; and wherein $X_{26}$ is S, N, A, R, P, or T; and the sequence of CDR3L comprises the sequence $QQX_{27}X_{28}SFPX_{29}X_{30}$ (SEQ ID NO: 137);

wherein $X_{27}$ is A or G;

wherein $X_{28}$ is N, D, or Y;

wherein $X_{29}$ is F or L; and wherein $X_{30}$ is A or T.

In embodiments, the fusion protein comprises an anti-PD-1 antibody, or antigen-binding fragment thereof, wherein the CDRs of the heavy and light chain variable regions comprise the following sequences:

the sequence of CDR1H comprises the sequence of SEQ ID NO: 21;

the sequence of CDR2H comprises the sequence of SEQ ID NO: 22;

the sequence of CDR3H comprises the sequence of SEQ ID NO: 23 the sequence of CDR1L comprises the sequence of SEQ ID NO: 96;

the sequence of CDR2L comprises the sequence of SEQ ID NO: 97; and the sequence of CDR3L comprises the sequence of SEQ ID NO: 82.

In further embodiments, the fusion protein comprises an anti-PD-1 antibody, or antigen-binding fragment thereof, wherein:

the heavy chain variable region comprises SEQ ID NO: 24, or a sequence that is at least 90%, at least 95%, at least 96%, at least 97%, at least 98%, or at least 99% identical to SEQ ID NO: 24; and the light chain variable region comprises SEQ ID NO: 98, or a sequence that is at least 90%, at least 95%, at least 96%, at least 97%, at least 98%, or at least 99% identical to SEQ ID NO: 98.

In embodiments, the fusion protein comprises an anti-PD-1 antibody, or antigen-binding fragment thereof, wherein the CDRs of the heavy chain and light chain variable regions comprise the following sequences:

the sequences of CDR1H, CDR2H and CDR3H comprise respectively SEQ ID NOS: 21, 22, and 23; and the sequences of CDR1L, CDR2L and CDR3L comprise respectively, SEQ ID NOS: 45, 46, and 47; SEQ ID NOS: 66, 67, and 68; SEQ ID NOS: 70, 67, and 71; SEQ ID NOS: 73, 74, and 75; SEQ ID NOS: 77, 78, and 47; SEQ ID NOS: 80, 81, and 82; SEQ ID NOS: 77, 78, and 84; SEQ ID NOS: 77, 86, and 47; SEQ ID NOS: 88, 89, and 47; SEQ ID NOS: 66, 67, and 47; SEQ ID NOS: 80, 92, and 75; SEQ ID NOS: 80, 94, and 71; SEQ ID NOS: 99, 100, and 47; SEQ ID NOS: 102, 103, and 104; SEQ ID NOS: 106, 103, and 47; SEQ ID NOS: 108, 103, and 47; SEQ ID NOS: 110, 111, and 75; SEQ ID NOS: 77, 103, and 113; SEQ ID NOS: 77, 111, and 47; SEQ ID NOS: 116, 67, and 47; SEQ ID NOS: 118, 119, and 47; SEQ ID NOS: 80, 78, and 47; SEQ ID NOS: 122, 103 and 47; SEQ ID NOS: 124, 125, and 75; SEQ ID NOS: 127, 38, and 68; SEQ ID NOS: 129, 130, and 47; or SEQ ID NOS: 132, 133, and 75.

In further embodiments, the fusion protein comprises an anti-PD-1 antibody, or antigen-binding fragment thereof, wherein:

the heavy chain variable region comprises SEQ ID NO: 24, or a sequence that is at least 90%, at least 95%, at least 96%, at least 97%, at least 98%, or at least 99% identical to SEQ ID NO: 24; and the light chain variable region comprises SEQ ID NO: 48, 69, 72, 76, 79, 83, 85, 90, 91, 93, 101, 105, 107, 109, 112, 114, 115, 117, 120, 121, 123, 126, 128, 131, or 134, or a sequence that is at least 90%, at least 95%, at least 96%, at least 97%, at least 98%, or at least 99% identical to any one of SEQ ID NO: 48, 69, 72, 76, 79, 83, 85, 90, 91, 93, 101, 105, 107, 109, 112, 114, 115, 117, 120, 121, 123, 126, 128, 131, or 134.

In embodiments, the fusion protein comprises an anti-PD-1 antibody, or antigen-binding fragment thereof, wherein the CDRs of the heavy and light chain variable regions comprise the following sequences:

the sequence of CDR1H comprises the sequence of SEQ ID NO: 17;

the sequence of CDR2H comprises the sequence of SEQ ID NO: 18;

the sequence of CDR3H comprises the sequence of SEQ ID NO: 19;

the sequence of CDR1L comprises the sequence $RSSX_1SLLX_2SNGX_3X_4YLD$ (SEQ ID NO: 62), wherein $X_1$ is Q or E;

wherein $X_2$ is H or Y;

wherein $X_3$ is Y or N; and wherein $X_4$ is T or N;

the sequence of CDR2L comprises the sequence $X_5X_6SX_7X_8X_9X_{10}$ (SEQ ID NO: 63), wherein $X_5$ is L, Q or E;

wherein $X_6$ is S, A, or V;

wherein $X_7$ is H, N, T, or S;

wherein $X_8$ is R or L;

wherein $X_9$ is G, A, or H; and wherein $X_{10}$ is S or T; and the sequence of CDR3L comprises the sequence $MQGX_{11}X_{12}WPYT$ (SEQ ID NO: 64), wherein $X_{11}$ is A, T, or S; and wherein $X_{12}$ is H or R.

In embodiments, the fusion protein comprises an anti-PD-1 antibody, or antigen-binding fragment thereof, wherein the CDRs of the heavy chain and light chain variable regions comprise the following sequences:

the sequence of CDR1H comprises the sequence of SEQ ID NO: 17;

the sequence of CDR2H comprises the sequence of SEQ ID NO: 18;

the sequence of CDR3H comprises the sequence of SEQ ID NO: 19;

the sequence of CDR1L comprises the sequence of SEQ ID NO: 41;

the sequence of CDR2L comprises the sequence of SEQ ID NO: 49; and the sequence of CDR3L comprises the sequence of SEQ ID NO: 50.

In further embodiments, the fusion protein comprises an anti-PD-1 antibody, or antigen-binding fragment thereof, wherein:

the heavy chain variable region comprises SEQ ID NO: 20, or a sequence that is at least 90%, at least 95%, at least 96%, at least 97%, at least 98%, or at least 99% identical to SEQ ID NO: 20; and the light chain variable region comprises SEQ ID NO: 51, or a sequence that is at least 90%, at least 95%, at least 96%, at least 97%, at least 98%, or at least 99% identical to SEQ ID NO: 51.

In embodiments, the fusion protein comprises an anti-PD-1 antibody, or antigen-binding fragment thereof, wherein the CDRs of the heavy chain and light chain variable regions comprise the following sequences:

the sequence of CDR1H, CDR2H and CDR3H comprise SEQ ID NOS: 17, 18, and 19, respectively; and the sequence of CDR1L, CDR2L and CDR3L comprise respectively, SEQ ID NOS: 41, 42, and 43; SEQ ID NOS: 41, 52, and 53; SEQ ID NOS: 41, 55, and 56; or SEQ ID NOS: 58, 59, and 60.

In further embodiments the fusion protein comprises an anti-PD-1 antibody, or antigen-binding fragment thereof, wherein:

the heavy chain variable region comprises SEQ ID NO: 20, or a sequence that is at least 90%, at least 95%, at least 96%, at least 97%, at least 98%, or at least 99% identical to SEQ ID NO: 20; and the light chain variable region comprises SEQ ID NO: 44, 54, 57, or 61, or a sequence that is at least 90%, at least 95%, at least 96%, at least 97%, at least 98%, or at least 99% identical to any one of SEQ ID NO: 44, 54, 57, or 61.

Provided herein is a fusion protein that comprises a sequence described in Tables 24-27.

Provided herein is a fusion protein that comprises a heavy chain comprising a sequence selected from the group consisting of SEQ ID NOS: 174-184, 187-190, 193-199, 206-211, 224-243. Provided herein is a fusion protein that comprises a light chain comprising a sequence selected from the group consisting of SEQ ID NOS: 170, 173, 186, 192, and 205.

Provided herein is a fusion protein that comprises a light chain and a heavy/heavy chain combination recited in Table 26.

Provided herein is a fusion protein that comprises a light chain and one or more heavy chains recited in Table 27.

In embodiments, provided is a fusion protein comprising a light chain sequence comprising SEQ ID NO:219 and/or SEQ ID NO:98 and:

(1) a first heavy chain sequence comprising SEQ ID NO:220 and a second heavy chain sequence comprising SEQ ID NO:224;

(2) a first heavy chain sequence comprising SEQ ID NO:221 and a second heavy chain sequence comprising SEQ ID NO:225;

(3) a first heavy chain sequence comprising SEQ ID NO:222 and a second heavy chain sequence comprising SEQ ID NO:226;

(4) a first heavy chain sequence comprising SEQ ID NO:223 and a second heavy chain sequence comprising SEQ ID NO:227.

In embodiments, provided is a fusion protein comprising a light chain sequence comprising SEQ ID NO:219 and/or SEQ ID NO:98 and:

(1) a first heavy chain sequence comprising SEQ ID NO:220 and a second heavy chain sequence comprising SEQ ID NO:228;

(2) a first heavy chain sequence comprising SEQ ID NO:221 and a second heavy chain sequence comprising SEQ ID NO:229;

(3) a first heavy chain sequence comprising SEQ ID NO:222 and a second heavy chain sequence comprising SEQ ID NO:230;

(4) a first heavy chain sequence comprising SEQ ID NO:223 and a second heavy chain sequence comprising SEQ ID NO:231;

(5) a first heavy chain sequence comprising SEQ ID NO:220 and a second heavy chain sequence comprising SEQ ID NO:236;

(6) a first heavy chain sequence comprising SEQ ID NO:221 and a second heavy chain sequence comprising SEQ ID NO:237;

(7) a first heavy chain sequence comprising SEQ ID NO:222 and a second heavy chain sequence comprising SEQ ID NO:238;

(8) a first heavy chain sequence comprising SEQ ID NO:223 and a second heavy chain sequence comprising SEQ ID NO:239;

(9) a first heavy chain sequence comprising SEQ ID NO:240 and a second heavy chain sequence comprising SEQ ID NO:241; or

(10) a first heavy chain sequence comprising SEQ ID NO:240 and a second heavy chain sequence comprising SEQ ID NO:242.

In embodiments, provided is a fusion protein comprising a light chain sequence comprising SEQ ID NO:219 and/or SEQ ID NO:98 and:

(1) a first heavy chain sequence comprising SEQ ID NO:220 and a second heavy chain sequence comprising SEQ ID NO:232;

(2) a first heavy chain sequence comprising SEQ ID NO:221 and a second heavy chain sequence comprising SEQ ID NO:233;

(3) a first heavy chain sequence comprising SEQ ID NO:222 and a second heavy chain sequence comprising SEQ ID NO:234;

(4) a first heavy chain sequence comprising SEQ ID NO:223 and a second heavy chain sequence comprising SEQ ID NO:235; or (5) a first heavy chain sequence comprising SEQ ID NO:240 and a second heavy chain sequence comprising SEQ ID NO:243.

In embodiments, provided is a fusion protein comprising a light chain sequence comprising SEQ ID NO:219 and/or SEQ ID NO:98 and:

(1) a first heavy chain sequence comprising SEQ ID NO:220 and a second heavy chain sequence comprising SEQ ID NO:224; or a first heavy chain sequence comprising SEQ ID NO:221 and a second heavy chain sequence comprising SEQ ID NO: 225; or (2) a first heavy chain sequence comprising SEQ ID NO:222 and a second heavy chain sequence comprising SEQ ID NO:226; or a first heavy chain sequence comprising SEQ ID NO:223 and a second heavy chain sequence comprising SEQ ID NO: 227.

In embodiments, provided is a fusion protein comprising a light chain sequence comprising SEQ ID NO:219 and/or SEQ ID NO:98 and:

(1) a first heavy chain sequence comprising SEQ ID NO:220 and a second heavy chain sequence comprising SEQ ID NO:228; or a first heavy chain sequence comprising SEQ ID NO:221 and a second heavy chain sequence comprising SEQ ID NO: 229;

(2) a first heavy chain sequence comprising SEQ ID NO:222 and a second heavy chain sequence comprising SEQ ID NO:230; or a first heavy chain sequence comprising SEQ ID NO:223 and a second heavy chain sequence comprising SEQ ID NO: 231;

(3) a first heavy chain sequence comprising SEQ ID NO:220 and a second heavy chain sequence comprising SEQ ID NO:236; or a first heavy chain sequence comprising SEQ ID NO:221 and a second heavy chain sequence comprising SEQ ID NO: 237;

(4) a first heavy chain sequence comprising SEQ ID NO:222 and a second heavy chain sequence comprising SEQ ID NO:238; or a first heavy chain sequence comprising SEQ ID NO:223 and a second heavy chain sequence comprising SEQ ID NO: 239;

(5) a first heavy chain sequence comprising SEQ ID NO:240 and a second heavy chain sequence comprising SEQ ID NO:241; or (6) a first heavy chain sequence comprising SEQ ID NO:240 and a second heavy chain sequence comprising SEQ ID NO:242.

In embodiments, provided is a fusion protein comprising a light chain sequence comprising SEQ ID NO:219 and/or SEQ ID NO:98 and:

(1) a first heavy chain sequence comprising SEQ ID NO:220 and a second heavy chain sequence comprising SEQ ID NO:232; or a first heavy chain sequence comprising SEQ ID NO:221 and a second heavy chain sequence comprising SEQ ID NO: 233;

(2) a first heavy chain sequence comprising SEQ ID NO:222 and a second heavy chain sequence comprising SEQ ID NO:234; or a first heavy chain sequence comprising SEQ ID NO:223 and a second heavy chain sequence comprising SEQ ID NO: 235; or (3) a first heavy chain sequence comprising SEQ ID NO:240 and a second heavy chain sequence comprising SEQ ID NO:243.

Antibodies and Antigen-Binding Fragments Thereof

The term antibody is used here in the broadest sense and includes monoclonal antibodies (including full length or intact monoclonal antibodies), polyclonal antibodies, bispecific antibodies, humanized antibodies, single chain antibodies, chimeric antibodies, synthetic antibodies, recombinant antibodies, hybrid antibodies, mutagenized antibodies and grafted antibodies (grafted antibodies), bispecific antibodies, a specific antibody portion (e.g., a domain antibody), as well as any antigen-binding portion thereof that competes with an intact antibody for specific binding, an antigen-binding portion thereof (e.g., paratopes, CDRs), and any other modified conformations of the immunoglobulin molecule comprising the antigen recognition site so long as they exhibit the desired biological activity and specificity. Accordingly, an antibody is an immunoglobulin molecule or fragment or derivative thereof including any polypeptide comprising an antigen-binding site, capable of specifically binding to a target through at least one antigen recognition site located in the variable region of the immunoglobulin molecule. The disclosed antibody can be murine, rat, human, or any other origin (including chimeric or humanized antibodies).

In certain embodiments, the framework regions of the antibody (or antigen-binding fragment thereof) may be identical to human germline sequences or may be naturally or artificially modified.

In one preferred embodiment, the disclosed antibody structures belong to the IgG class of immunoglobulin molecules. A standard IgG immunoglobulin molecule comprises two identical light chain polypeptides, and two identical heavy chain polypeptides. The molecular weight of the light chain polypeptide is around 23,000 Daltons and the molecular weight of the heavy chain polypeptide varies between 53,000-70,000 Daltons. The four chains are typically joined by disulfide bonds in a "Y" configuration.

Two heavy chains (HC) and two light chains (LC) of an immunoglobulin molecule are covalently bonded to each other, and the end portions of the two heavy chains are bonded to each other by covalent disulfide linkages or non-covalent linkages when the immunoglobulins are generated by either hybridomas, B cells, or genetically engineered host cells. The light and heavy chains both contain regions of structural and functional homology. The term "variable" and "constant" are used functionally. Each heavy chain is comprised of a heavy chain variable region ("HCVR" or "VH") and a heavy chain constant region (comprised of domains CH1, CH2, and CH3). Each light chain is comprised of a light chain variable region ("LCVR or "VL") and a light chain constant region (CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4.

The variable region allows the antibody to recognize and specifically bind epitopes located on antigens. The variable domains of both the light (VL) and heavy (VH) chain portions determine antigen recognition and specificity. The antigen-binding site of an antibody is comprised of the VL domain and VH domain, or a subset of the CDRs. More specifically, the antigen-binding site is defined by one, two, or three CDRs on each of the VH and VL chains (i.e. CDR-H1, CDR-H2, CDR-H3, CDR-L1, CDR-L2, and CDR-L3). Conversely, the constant domains of the light chain (CL) and the heavy chain (CH1, CH2, or CH3) confer biological properties such as secretion, transplacental mobility, Fc receptor binding, complement binding, and the like. By convention, the numbering of the constant region domains increases as they become more distal from the antigen-binding site or amino-terminus of the antibody.

As used herein, the term "Complementarity Determining Regions" (CDRs) refers to portions of an antibody variable domain that are (typically) involved in antigen binding. Each variable region has three non-consecutive CDRs, known as CDR1, CDR2, and CDR3. The CDRs are separated by structurally conserved regions called framework regions (FR-1, -2, -3, and -4) that form a "core" β-sheet structure displaying these loops on the surface of the variable domain. The six CDRs present in each antigen-binding domain are short, non-contiguous sequences of amino acids that are specifically positioned to form the antigen-binding domain as the antibody assumes its three dimensional configuration in an aqueous environment. The length and composition of the CDR sequences are highly variable, especially in the CDR3. The remainder of the amino acids located in the antigen-binding domains or the "framework" regions, show less inter-molecular variability. The antigen-binding domain formed by the positioned CDRs defines a surface complementary to the epitope on the immunoreactive antigen. This complementary surface promotes the non-covalent binding of the antibody to its cognate epitope. Each CDR can comprise amino acid residues from a CDR as defined by e.g. Kabat (i.e., about residues 24-34 (L1), 50-56

(L2) and 89-97 (L3) in the light chain variable domain and 31-35 (H1), 50-65 (H2) and 95-102 (H3) in the heavy chain variable domain (Kabat et al., Sequences of Proteins of Immunological Interest, 5th Ed. Public Health Service, National Institutes of Health, Bethesda, Md. (1987, 1991)). Each CDR can also comprise amino acid residues from a "hypervariable loop" (i.e., about residues 26-32 (LI), 50-52 (L2) and 91-96 (L3) in the light chain variable domain and 26-32 (H1), 53-55 (H2) and 96-101 (H3) in the heavy chain variable domain (Chothia & Lesk 196 J. Mol. Biol. 901 (1987)). In some instances, a CDR can include amino acids from both a CDR region defined according to Kabat and a hypervariable loop. The Kabat numbering may not always correspond to the linear numbering on the amino acid residues due to a shortening of, or insertion into, a structural component, whether framework or CDR, of the basic variable domain structure. The correct Kabat numbering of residues may be determined for a given antibody or antigen-binding fragment thereof by alignment of residues of homology in the sequence of the antibody or antigen-binding fragment thereof with a "standard" Kabat numbered sequence or be defined according to ImMunoGeneTics (IMGT) system (Lefranc, M.-P. et al., Dev. Comp. Immunol., 27, 55-77 (2003)).

As used herein, the term "antigen-binding portion" or "antigen-binding fragment" may be a fragment comprising a Fab, Fab', F(ab')2, Fd, Fv, domain antibodies (dAbs such as shark and camel antibodies), ScFv, a maxibody, a minibody, a nanobody, an intrabody, a diabody, a triabody, a tetrabody, a v-NAR and a bis-scFv, or a polypeptide that contain at least certain portions of an immunoglobulin sufficient to confer specific antigen-binding to the polypeptide.

The antibody may be any class of antibody, such as IgG, IgA, or IgM (or a subclass thereof), and the antibody need not be of any particular class, and any of the immunoglobulin molecules comprising the antigen recognition site of the required specificity, other modified configurations (including glycosylation variants of antibodies, amino acid sequence variants of antibodies, and covalently modified antibodies) can be encompassed. Modified versions of each of these classes and isotypes are known to a person skilled in the art, accordingly, are within the scope of the instant disclosure.

In some embodiments of the aspects described herein, the anti-PD-1 antibody fragment is a Fab fragment, which comprises or consist essentially of a variable (VL) and constant (CL) domain of the light chain and a variable domain (VH) and the first constant domain (CH1) of the heavy chain.

In some embodiments of the aspects described herein, the anti-PD-1 antibody fragment is a Fab' fragment, which refers to a Fab fragment having one or more cysteine residues at the C-terminus of the CH1 domain.

In some embodiments of the aspects described herein, the anti-PD-1 antibody fragment is an Fd fragment comprising or consisting essentially of VH and CH1 domains.

In some embodiments of the aspects described herein, the anti-PD-1 antibody fragment is an Fd' fragment comprising VH and CH1 domains and one or more cysteine residues at the C-terminus of the CH1 domain.

Single-chain Fv or scFv antibody fragments comprise or consist essentially of the VH and VL domains of an antibody, such that these domains are present in a single polypeptide chain. Generally, an Fv polypeptide further comprises a polypeptide linker between the VH and VL domains, which allows the scFv to form the desired structure for antigen-binding. Accordingly, in some embodiments of the aspects described herein, the anti-PD-1 antibody fragment is a Fv fragment comprising or consisting essentially of the VL and VH domains of a single arm of an antibody.

In some embodiments of the aspects described herein, the anti-PD-1 antibody fragment is a diabody comprising two antigen-binding sites, comprising a heavy chain variable domain (VH) connected to a light chain variable domain (VL) in the same polypeptide chain.

In some embodiments of the aspects described herein, the anti-PD-1 antibody fragment is a dAb fragment comprising or consisting essentially of a VH domain.

In some embodiments of the aspects described herein, the anti-PD-1 antibody fragment is a F(ab')2 fragment, which comprises a bivalent fragment comprising two Fab' fragments linked by a disulfide bridge at the hinge region.

In some embodiments of the aspects described herein, the anti-PD-1 antibody fragment is a linear antibody comprising a pair of tandem Fd segments (VH-CH1-VH-CH1) which, together with complementary light chain polypeptides, form a pair of antigen-binding regions.

A person skilled in the arts can use various techniques that have been developed and are available for the production of antibody fragments. Traditionally, these fragments were derived via proteolytic digestion of intact antibodies. However, F(ab')2 fragments can be isolated directly from recombinant host cell culture. Other techniques for the production of antibody fragments will be apparent to the skilled practitioner. In other embodiments, the antibody fragment of choice is a single chain Fv fragment (scFv). See, for example, WO 93/16185. Alternatively, these fragments can also be produced directly by recombinant host cells. For example, antibody fragments can be isolated from the antibody phage libraries discussed herein. In another approach, Fab'-SH fragments can be directly recovered from E. coli and chemically coupled to form F(ab')2 fragments (Carter et al., 1992).

In one embodiment, the antibody is a bispecific antibody comprising a complementary region that binds PD-1.

Contemplated antibodies or antigen-binding fragments may have all types of constant regions, including IgM, IgG, IgD, and IgE, and any isotype, including IgG1, IgG2, IgG3, and IgG4. In one embodiment, the isotype is human IgG1. In another embodiment, the human isotype IgG4 is used. Light chain constant regions can be λ or κ. The antibody or antigen-binding fragment thereof may comprise sequences from more than one class or isotype.

Anti-PD-1 Antibodies and PD-1 Binding Fragments Thereof

The disclosure describes antibodies that bind to PD-1, and antigen-binding fragments thereof that bind to PD-1, as well as fusion proteins comprising such anti-PD-1 antibodies or antigen-binding fragments thereof. The term "PD-1" refers to programmed death-1 protein (also known as CD279), a T cell co-inhibitor. The term PD-1 encompasses recombinant PD-1 and/or a fragment thereof. The term also includes PD-1 or a fragment thereof coupled to, for example, mouse or human Fc, histidine tag, and/or a signal sequence. The term may further encompass a fusion protein comprising PD-1. The amino acid sequence of full-length PD-1 is provided in GenBank as accession number NP_005009.2. The ligands for PD-1 include PD-L1 and PD-L2. The amino acid sequence of full-length PD-L1 is provided in GenBank as accession number NP_054862.1. The amino acid sequence of full-length PD-L2 is provided in GenBank as accession number NP_079515.2.

In embodiments, the anti-PD-1 antibody or antigen binding fragment thereof specifically binds to PD-1 and antagonizes PD-1 mediated immune suppression. The anti-PD-1 antibodies and antigen-binding fragments thereof disclosed herein may interrupt, inhibit, or reduce PD-1 biological activity including downstream events mediated by PD-1. The anti-PD-1 antibodies and antigen-binding fragments thereof disclosed herein may exhibit any one or more of the following features: (a) binding to PD-1 and blocking of downstream signaling events; (b) blocking PD-L1-binding to PD-1; (c) increasing T cell proliferation; (d) upregulating the T cell-mediated immune response; (e) stimulating TNF secretion; (f) reducing inhibitory signal transduction through PD-1; and/or (g) stimulating IFNγ secretion. The anti-PD-1 antibodies and antigen-binding fragments thereof disclosed herein exhibit potent binding and inhibitory activities and are useful for therapeutic and diagnostics uses.

In one aspect, the disclosure provides antibodies and antigen-binding fragments thereof that bind to PD-1. In certain embodiments, the disclosure provides bispecific antibodies and binding proteins that bind specifically to PD-1 and at least one other molecule.

In another aspect the disclosure provides an antibody, or an antigen-binding fragment thereof, wherein the antibody or antigen-binding fragment thereof binds to PD-1, and wherein the antibody or antigen-binding fragment thereof comprises a heavy chain variable region and a light chain variable region wherein each of the heavy chain and the light chain variable regions comprise a CDR1, CDR2, and CDR3 and wherein the antibody heavy chain comprises a constant region comprising three constant domains CH1, CH2, and CH3.

In embodiments, the CDRs of the anti-PD-1 antibody, or antigen-binding fragment thereof, comprise the following sequences:

the sequence of CDR1H comprises the sequence of SEQ ID NO: 21;

the sequence of CDR2H comprises the sequence of SEQ ID NO: 22;

the sequence of CDR3H comprises the sequence of SEQ ID NO: 23;

the sequence of CDR1L comprises the sequence $RX_{13}X_{14}X_{15}X_{16}IX_{17}X_{18}WX_{19}X_{20}$ (SEQ ID NO:135);

wherein $X_{13}$ is A or V;

wherein $X_{14}$ is S or G;

wherein $X_{15}$ is Q, E, or R;

wherein $X_{16}$ is G, S, D or N;

wherein $X_{17}$ is G, S, or N;

wherein $X_{18}$ is S, I, R, T, K, P, N, H, or V;

wherein $X_{19}$ is L or V; and wherein $X_{20}$ is G or A; and the sequence of CDR2L comprises the sequence $X_{21}AX_{22}X_{23}X_{24}X_{25}X_{26}$ (SEQ ID NO: 136); and wherein $X_{21}$ is S, D, E, or A;

wherein $X_{22}$ is S or K;

wherein $X_{23}$ is S, N, T, R, or D;

wherein $X_{24}$ is L or V;

wherein $X_{25}$ is Q, E, or H; and wherein $X_{26}$ is S, N, A, R, P, or T; and the sequence of CDR3L comprises the sequence $QQX_{27}X_{28}SFPX_{29}X_{30}$ (SEQ ID NO: 137);

wherein $X_{27}$ is A or G;

wherein $X_{28}$ is N, D, or Y;

wherein $X_{29}$ is F or L; and wherein $X_{30}$ is A or T.

In embodiments, the CDRs of the anti-PD-1 antibody, or antigen-binding fragment thereof, comprise the following sequences:

the sequence of CDR1H comprises the sequence of SEQ ID NO: 21;

the sequence of CDR2H comprises the sequence of SEQ ID NO: 22;

the sequence of CDR3H comprises the sequence of SEQ ID NO: 23;

the sequence of CDR1L comprises the sequence of SEQ ID NO: 96;

the sequence of CDR2L comprises the sequence of SEQ ID NO: 97; and the sequence of CDR3L comprises the sequence of SEQ ID NO: 82.

In embodiments, the antibody, or antigen-binding fragment thereof, comprises:

a heavy chain variable region comprising SEQ ID NO: 24, or a sequence that is at least 90%, at least 95%, at least 96%, at least 97%, at least 98%, or at least 99% identical to SEQ ID NO: 24; and a light chain variable region comprising SEQ ID NO: 98, or a sequence that is at least 90%, at least 95%, at least 96%, at least 97%, at least 98%, or at least 99% identical to SEQ ID NO: 98.

In embodiments, the CDRs of the anti-PD-1 antibody, or antigen-binding fragment thereof, comprise the following sequences:

the sequences of CDR1H, CDR2H and CDR3H comprise respectively SEQ ID NOS: 21, 22, and 23; and the sequences of CDR1L, CDR2L and CDR3L comprise respectively, SEQ ID NOS: 45, 46, and 47; SEQ ID NOS: 66, 67, and 68; SEQ ID NOS: 70, 67, and 71; SEQ ID NOS: 73, 74, and 75; SEQ ID NOS: 77, 78, and 47; SEQ ID NOS: 80, 81, and 82; SEQ ID NOS: 77, 78, and 84; SEQ ID NOS: 77, 86, and 47; SEQ ID NOS: 88, 89, and 47; SEQ ID NOS: 66, 67, and 47; SEQ ID NOS: 80, 92, and 75; SEQ ID NOS: 80, 94, and 71; SEQ ID NOS: 99, 100, and 47; SEQ ID NOS: 102, 103, and 104; SEQ ID NOS: 106, 103, and 47; SEQ ID NOS: 108, 103, and 47; SEQ ID NOS: 110, 111, and 75; SEQ ID NOS: 77, 103, and 113; SEQ ID NOS: 77, 111, and 47; SEQ ID NOS: 116, 67, and 47; SEQ ID NOS: 118, 119, and 47; SEQ ID NOS: 80, 78, and 47; SEQ ID NOS: 122, 103 and 47; SEQ ID NOS: 124, 125, and 75; SEQ ID NOS: 127, 38, and 68; SEQ ID NOS: 129, 130, and 47; or SEQ ID NOS: 132, 133, and 75.

In embodiments, the anti-PD-1 antibody, or antigen-binding fragment thereof, comprises:

a heavy chain variable region comprising SEQ ID NO: 24, or a sequence that is at least 90%, at least 95%, at least 96%, at least 97%, at least 98%, or at least 99% identical to SEQ ID NO: 24; and a light chain variable region comprising SEQ ID NO: 48, 69, 72, 76, 79, 83, 85, 90, 91, 93, 101, 105, 107, 109, 112, 114, 115, 117, 120, 121, 123, 126, 128, 131, or 134, or a sequence that is at least 90%, at least 95%, at least 96%, at least 97%, at least 98%, or at least 99% identical to any one of SEQ ID NO: 48, 69, 72, 76, 79, 83, 85, 90, 91, 93, 101, 105, 107, 109, 112, 114, 115, 117, 120, 121, 123, 126, 128, 131, or 134.

In embodiments, the CDRs of the anti-PD-1 antibody, or antigen-binding fragment thereof, comprise the following sequences:

the sequence of CDR1H comprises the sequence of SEQ ID NO: 17;

the sequence of CDR2H comprises the sequence of SEQ ID NO: 18;

the sequence of CDR3H comprises the sequence of SEQ ID NO: 19;

the sequence of CDR1L comprises the sequence RSSX$_1$SLLX$_2$SNGX$_3$X$_4$YLD (SEQ ID NO: 62), wherein X$_1$ is Q or E;

wherein X$_2$ is H or Y;

wherein X$_3$ is Y or N; and wherein X$_4$ is T or N;

the sequence of CDR2L comprises the sequence X$_5$X$_6$SX$_7$X$_8$X$_9$X$_{10}$ (SEQ ID NO: 63), wherein X$_5$ is L, Q or E;

wherein X$_6$ is S, A, or V;

wherein X$_7$ is H, N, T, or S;

wherein X$_8$ is R or L;

wherein X$_9$ is G, A, or H; and wherein X$_{10}$ is S or T; and the sequence of CDR3L comprises the sequence MQGX$_{11}$X$_{12}$WPYT (SEQ ID NO: 64), wherein X$_{11}$ is A, T, or S; and wherein X$_{12}$ is H or R.

In embodiments, the CDRs of the anti-PD-1 antibody, or antigen-binding fragment thereof, comprise the following sequences:

the sequence of CDR1H comprises the sequence of SEQ ID NO: 17;

the sequence of CDR2H comprises the sequence of SEQ ID NO: 18;

the sequence of CDR3H comprises the sequence of SEQ ID NO: 19;

the sequence of CDR1L comprises the sequence of SEQ ID NO: 41;

the sequence of CDR2L comprises the sequence of SEQ ID NO: 49; and the sequence of CDR3L comprises the sequence of SEQ ID NO: 50.

In embodiments, the anti-PD-1 antibody, or antigen-binding fragment thereof, comprises:

a heavy chain variable region comprising SEQ ID NO: 20, or a sequence that is at least 90%, at least 95%, at least 96%, at least 97%, at least 98%, or at least 99% identical to SEQ ID NO: 20; and a light chain variable region comprising SEQ ID NO: 51, or a sequence that is at least 90%, at least 95%, at least 96%, at least 97%, at least 98%, or at least 99% identical to SEQ ID NO: 51.

In embodiments, the CDRs of the anti-PD-1 antibody, or antigen-binding fragment thereof, comprise the following sequences:

the sequence of CDR1H, CDR2H and CDR3H comprise SEQ ID NOS: 17, 18, and 19, respectively; and the sequence of CDR1L, CDR2L and CDR3L comprise respectively, SEQ ID NOS: 41, 42, and 43; SEQ ID NOS: 41, 52, and 53; SEQ ID NOS: 41, 55, and 56; or SEQ ID NOS: 58, 59, and 60.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence selected from the group consisting of SEQ ID NOs: 4, 8, 12, 16, 20, and 24, and wherein the sequence of the light chain variable region comprises a sequence that is at least 90%, at least 95%, at least 96%, at least 97%, at least 98%, or at least 99% identical to a light chain variable region amino acid sequence selected from the group consisting of SEQ ID NOs: 28, 32, 36, 40, 44, 48, 51, 54, 57, 61, 65, 69, 72, 76, 79, 83, 85, 88, 90, 91, 93, 95, 98, 101, 105, 107, 109, 112, 114, 115, 117, 120, 121, 123, 126, 128, 131, 134, and 138.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO: 20, and wherein the sequence of the light chain variable region comprises the sequence that is at least 90%, at least 95%, at least 96%, at least 97%, at least 98%, or at least 99% identical to the heavy chain variable region amino acid sequence of SEQ ID NO: 65.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence SEQ ID NO: 20; and wherein the sequence of the light chain variable region comprises a sequence that is at least 90%, at least 95%, at least 96%, at least 97%, at least 98%, or at least 99% identical to a light chain variable region amino acid sequence selected from the group consisting of SEQ ID NOs: 44, 51, 54, 57, and 61.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO: 20, and wherein the sequence of the light chain variable region comprises the sequence that is at least 90%, at least 95%, at least 96%, at least 97%, at least 98%, or at least 99% identical to the light chain variable region amino acid sequence of SEQ ID NO: 51.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO: 20, and wherein the sequence of the light chain variable region comprises the sequence that is at least 90%, at least 95%, at least 96%, at least 97%, at least 98%, or at least 99% identical to the light chain variable region amino acid sequence of SEQ ID NO: 54.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO: 20, and wherein the sequence of the light chain variable region comprises the sequence that is at least 90%, at least 95%, at least 96%, at least 97%, at least 98%, or at least 99% identical to the light chain variable region amino acid sequence of SEQ ID NO: 57.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO: 20, and wherein the sequence of the light chain variable region comprises the sequence that is at least 90%, at least 95%, at least 96%, at least 97%, at least 98%, or at least 99% identical to the light chain variable region amino acid sequence of SEQ ID NO: 61.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO: 24, and wherein the sequence of the light chain variable region comprises the sequence that is at least 90%, at least 95%, at least 96%, at least 97%, at least 98%, or at least 99% identical to the light chain variable region amino acid sequence of SEQ ID NO: 138.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence SEQ ID NO: 20; and wherein the sequence of the light chain variable region comprises a sequence that is at least 90%, at least 95%, at least 96%, at least 97%, at least 98%, or at least 99% identical to a light chain variable region amino acid sequence selected from the group consisting of SEQ ID NOs: 69, 72, 76, 79, 83, 85, 87, 90, 91, 93, 95, 98, 101, 105, 107, 109, 112, 114, 115, 117, 120, 121, 123, 126, 128, 131, 134, and 138.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO: 24, and wherein the sequence of the light chain variable region comprises the sequence that is at least 90%, at least 95%, at least 96%, at least 97%, at least 98%, or at least 99% identical to the light chain variable region amino acid sequence of SEQ ID NO: 98.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO: 24, and wherein the sequence of the light chain variable region comprises the sequence that is at least 90%, at least 95%, at least 96%, at least 97%, at least 98%, or at least 99% identical to the light chain variable region amino acid sequence of SEQ ID NO: 69.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO: 24, and wherein the sequence of the light chain variable region comprises the sequence that is at least 90%, at least 95%, at least 96%, at least 97%, at least 98%, or at least 99% identical to the light chain variable region amino acid sequence of SEQ ID NO: 72.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO: 24, and wherein the sequence of the light chain variable region comprises the sequence that is at least 90%, at least 95%, at least 96%, at least 97%, at least 98%, or at least 99% identical to the light chain variable region amino acid sequence of SEQ ID NO: 76.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO: 24, and wherein the sequence of the light chain variable region comprises the sequence that is at least 90%, at least 95%, at least 96%, at least 97%, at least 98%, or at least 99% identical to the light chain variable region amino acid sequence of SEQ ID NO: 79.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO: 24, and wherein the sequence of the light chain variable region comprises the sequence that is at least 90%, at least 95%, at least 96%, at least 97%, at least 98%, or at least 99% identical to the light chain variable region amino acid sequence of SEQ ID NO: 83.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO: 24, and wherein the sequence of the light chain variable region comprises the sequence that is at least 90%, at least 95%, at least 96%, at least 97%, at least 98%, or at least 99% identical to the light chain variable region amino acid sequence of SEQ ID NO: 85.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO: 24, and wherein the sequence of the light chain variable region comprises the sequence that is at least 90%, at least 95%, at least 96%, at least 97%, at least 98%, or at least 99% identical to the light chain variable region amino acid sequence of SEQ ID NO: 87.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO: 24, and wherein the sequence of the light chain variable region comprises the sequence that is at least 90%, at least 95%, at least 96%, at least 97%, at least 98%, or at least 99% identical to the light chain variable region amino acid sequence of SEQ ID NO: 90.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO: 24, and wherein the sequence of the light chain variable region comprises the sequence that is at least 90%, at least 95%, at least 96%, at least 97%, at least 98%, or at least 99% identical to the light chain variable region amino acid sequence of SEQ ID NO: 91.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO: 24, and wherein the sequence of the light chain variable region comprises the sequence that is at least 90%, at least 95%, at least 96%, at least 97%, at least 98%, or at least 99% identical to the light chain variable region amino acid sequence of SEQ ID NO: 93.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO: 24, and wherein the sequence of the light chain variable region comprises the sequence that is at least 90%, at least 95%, at least 96%, at least 97%, at least 98%, or at least 99% identical to the light chain variable region amino acid sequence of SEQ ID NO: 95.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO: 24, and wherein the sequence of the light chain variable region comprises the sequence that is at least 90%, at least 95%, at least 96%, at least 97%, at least 98%, or at least 99% identical to the light chain variable region amino acid sequence of SEQ ID NO: 101.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO: 24, and wherein the sequence of the light chain variable region comprises the sequence that is at least 90%, at least 95%, at least 96%, at least 97%, at least 98%, or at least 99% identical to the light chain variable region amino acid sequence of SEQ ID NO: 105.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO: 24, and wherein the sequence of the light chain variable region comprises the sequence that is at least 90%, at least 95%, at least 96%, at least 97%, at least 98%, or at least 99% identical to the light chain variable region amino acid sequence of SEQ ID NO: 107.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO: 24, and wherein the sequence of the light chain variable region comprises the sequence that is at least 90%, at least 95%, at least 96%, at least 97%, at least 98%, or at least 99% identical to the light chain variable region amino acid sequence of SEQ ID NO: 109.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO: 24, and wherein the sequence of the light chain variable region comprises the sequence that is at least 90%, at least 95%, at least 96%, at least 97%, at least 98%, or at least 99% identical to the light chain variable region amino acid sequence of SEQ ID NO: 112.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO: 24, and wherein the sequence of the light chain variable region comprises the sequence that is at least 90%, at least 95%, at least 96%, at least 97%, at least 98%, or at least 99% identical to the light chain variable region amino acid sequence of SEQ ID NO: 114.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO: 24, and wherein the sequence of the light chain variable region comprises the sequence that is at least 90%, at least 95%, at least 96%, at least 97%, at least 98%, or at least 99% identical to the light chain variable region amino acid sequence of SEQ ID NO: 115.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO: 24, and wherein the sequence of the light chain variable region comprises the sequence that is at least 90%, at least 95%, at least 96%, at least 97%, at least 98%, or at least 99% identical to the light chain variable region amino acid sequence of SEQ ID NO: 117.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO: 24, and wherein the sequence of the light chain variable region comprises the sequence that is at least 90%, at least 95%, at least 96%, at least 97%, at least 98%, or at least 99% identical to the light chain variable region amino acid sequence of SEQ ID NO: 120.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO: 24, and wherein the sequence of the light chain variable region comprises the sequence that is at least 90%, at least 95%, at least 96%, at least 97%, at least 98%, or at least 99% identical to the light chain variable region amino acid sequence of SEQ ID NO: 121.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO: 24, and wherein the sequence of the light chain variable region comprises the sequence that is at least 90%, at least 95%, at least 96%, at least 97%, at least 98%, or at least 99% identical to the light chain variable region amino acid sequence of SEQ ID NO: 123.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO: 24, and wherein the sequence of the light chain variable region comprises the sequence that is at least 90%, at least 95%, at least 96%, at least 97%, at least 98%, or at least 99% identical to the light chain variable region amino acid sequence of SEQ ID NO: 126.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO: 24, and wherein the sequence of the light chain variable region comprises the sequence that is at least 90%, at least 95%, at least 96%, at least 97%, at least 98%, or at least 99% identical to the light chain variable region amino acid sequence of SEQ ID NO: 128.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO: 24, and wherein the sequence of the light chain variable region comprises the sequence that is at least 90%, at least 95%, at least 96%, at least 97%, at least 98%, or at least 99% identical to the light chain variable region amino acid sequence of SEQ ID NO: 131.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO: 24, and wherein the sequence of the light chain variable region comprises the sequence that is at least 90%, at least 95%, at least 96%, at least 97%, at least 98%, or at least 99% identical to the light chain variable region amino acid sequence of SEQ ID NO: 134.

In one embodiment, the disclosure provides an antibody or antigen-binding fragment thereof, which binds to PD-1, wherein the antibody or antigen-binding fragment comprises a heavy chain variable region and a light chain variable region, wherein the sequence of the heavy chain variable region comprises a sequence that is at least 90%, at least 95%, at least 96%, at least 97%, at least 98%, or at least 99% identical to the heavy chain variable region amino acid sequence of SEQ ID NO: 142, and wherein the sequence of the light chain variable region comprises a sequence that is at least 90%, at least 95%, at least 96%, at least 97%, at least 98%, or at least 99% identical to a light chain variable region amino acid sequence selected from the group consisting of SEQ ID NOs: 146, 150, 153, 156, 160, 164, and 167.

In one embodiment, the disclosure provides an antibody or antigen-binding fragment thereof, which binds to PD-1, wherein the antibody or antigen-binding fragment comprises a heavy chain variable region and a light chain variable region, wherein each of the heavy chain and the light chain variable regions comprises a CDR1, CDR2, and CDR3, and wherein:

the sequence of CDR1H comprises the sequence, SEQ ID NO: 139;

the sequence of CDR2H comprises the sequence, SEQ ID NO: 140;

the sequence of CDR3H comprises the sequence, SEQ ID NO: 141;

the sequence of CDR1L comprises the sequence, SEQ ID NO: 143;

the sequence of CDR2L comprises the sequence, SEQ ID NO: 144; and the sequence of CDR3L comprises the sequence, SEQ ID NO: 145.

In one embodiment, the disclosure provides an antibody or antigen-binding fragment thereof, which binds to PD-1, wherein the antibody or antigen-binding fragment comprises a heavy chain variable region and a light chain variable region, wherein each of the heavy chain and the light chain variable regions comprises a CDR1, CDR2, and CDR3, and wherein:

the sequence of CDR1H comprises the sequence, SEQ ID NO: 139;

the sequence of CDR2H comprises the sequence, SEQ ID NO: 140;

the sequence of CDR3H comprises the sequence, SEQ ID NO: 141;

the sequence of CDR1L comprises the sequence, SEQ ID NO: 147;

the sequence of CDR2L comprises the sequence, SEQ ID NO: 148; and the sequence of CDR3L comprises the sequence, SEQ ID NO: 149.

In one embodiment, the disclosure provides an antibody or antigen-binding fragment thereof, which binds to PD-1, wherein the antibody or antigen-binding fragment comprises a heavy chain variable region and a light chain variable region, wherein each of the heavy chain and the light chain variable regions comprises a CDR1, CDR2, and CDR3, and wherein:

the sequence of CDR1H comprises the sequence, SEQ ID NO: 139;

the sequence of CDR2H comprises the sequence, SEQ ID NO: 140;

the sequence of CDR3H comprises the sequence, SEQ ID NO: 141;

the sequence of CDR1L comprises the sequence, SEQ ID NO: 151;

the sequence of CDR2L comprises the sequence, SEQ ID NO: 148; and the sequence of CDR3L comprises the sequence, SEQ ID NO: 152.

In one embodiment, the disclosure provides an antibody or antigen-binding fragment thereof, which binds to PD-1, wherein the antibody or antigen-binding fragment comprises a heavy chain variable region and a light chain variable region, wherein each of the heavy chain and the light chain variable regions comprises a CDR1, CDR2, and CDR3, and wherein:

the sequence of CDR1H comprises the sequence, SEQ ID NO: 139;

the sequence of CDR2H comprises the sequence, SEQ ID NO: 140;

the sequence of CDR3H comprises the sequence, SEQ ID NO: 141;

the sequence of CDR1L comprises the sequence, SEQ ID NO: 154;

the sequence of CDR2L comprises the sequence, SEQ ID NO: 148; and the sequence of CDR3L comprises the sequence, SEQ ID NO: 155.

In one embodiment, the disclosure provides an antibody or antigen-binding fragment thereof, which binds to PD-1, wherein the antibody or antigen-binding fragment comprises a heavy chain variable region and a light chain variable region, wherein each of the heavy chain and the light chain variable regions comprises a CDR1, CDR2, and CDR3, and wherein:

the sequence of CDR1H comprises the sequence, SEQ ID NO: 139;

the sequence of CDR2H comprises the sequence, SEQ ID NO: 140;

the sequence of CDR3H comprises the sequence, SEQ ID NO: 141;

the sequence of CDR1L comprises the sequence, SEQ ID NO: 157;

the sequence of CDR2L comprises the sequence, SEQ ID NO: 158; and the sequence of CDR3L comprises the sequence, SEQ ID NO: 159.

In one embodiment, the disclosure provides an antibody or antigen-binding fragment thereof, which binds to PD-1, wherein the antibody or antigen-binding fragment comprises a heavy chain variable region and a light chain variable region, wherein each of the heavy chain and the light chain variable regions comprises a CDR1, CDR2, and CDR3, and wherein:

the sequence of CDR1H comprises the sequence, SEQ ID NO: 139;

the sequence of CDR2H comprises the sequence, SEQ ID NO: 140;

the sequence of CDR3H comprises the sequence, SEQ ID NO: 141;

the sequence of CDR1L comprises the sequence, SEQ ID NO: 161;

the sequence of CDR2L comprises the sequence, SEQ ID NO: 162; and the sequence of CDR3L comprises the sequence, SEQ ID NO: 163.

In one embodiment, the disclosure provides an antibody or antigen-binding fragment thereof, which binds to PD-1, wherein the antibody or antigen-binding fragment comprises a heavy chain variable region and a light chain variable region, wherein each of the heavy chain and the light chain variable regions comprises a CDR1, CDR2, and CDR3, and wherein:

the sequence of CDR1H comprises the sequence, SEQ ID NO: 139;

the sequence of CDR2H comprises the sequence, SEQ ID NO: 140;

the sequence of CDR3H comprises the sequence, SEQ ID NO: 141;

the sequence of CDR1L comprises the sequence, SEQ ID NO: 157;

the sequence of CDR2L comprises the sequence, SEQ ID NO: 165; and the sequence of CDR3L comprises the sequence, SEQ ID NO: 166.

In addition to the above description, FIG. 1 shows the heavy and light chain variable regions and associated CDR of antibodies disclosed herein as does the accompanying sequence listing, which is incorporated by reference in its entirety. As shown in the Examples below, light chain shuffling of an anti-PD-1 antibody led to the identification of antibody variants that conferred substantial improvements in PD-1 binding affinity. Analysis of the variants revealed certain CDR positions at which amino acids remained relatively unchanged among the light chain shuffled antibodies and other CDR positions at which variation could be introduced without abolishing PD-1 binding.

The anti-PD-1 antibodies and antigen-binding fragments thereof disclosed herein and the fusion proteins disclosed herein can have one or more amino acid substitutions, deletions, insertions, and/or additions. In some embodiments, one or more CDR residues of the anti-PD-1 antibodies or antigen-binding fragments (or the fusion proteins comprising the anti-PD-1 antibodies or antigen-binding fragments) disclosed herein have been changed by amino acid substitution, deletion, insertion, and/or addition. Amino acid substitutions can be conservative or non-conservative substitutions. The present disclosure also includes anti-PD-1 antibodies, and antigen-binding fragments thereof (and the fusion proteins comprising the anti-PD-1 antibodies or antigen-binding fragments), which are derived from the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). In certain embodiments, the anti-PD-1 antibodies or binding fragments thereof (or the fusion proteins comprising the anti-PD-1 antibodies or antigen-binding fragments) comprise one or more CDRs, or one or more variable domains with an amino acid sequence at least 85% at least 90%, at least 95%, at least 97%, at least 98%, or at least 99%, identical to the CDR and/or variable domain sequences set forth in FIG. 1.

Also provided herein variable heavy chain and variable light chain sequences as well as pairing thereof that are similar, but not identical to the variable heavy chain and variable light chains disclosed in Table 25 and pairings thereof. It will be evident that any of the frameworks described herein can be utilized in combination with any of the CDRs and CDR motifs described herein. In some embodiments, the anti-PD-1 antibody or antigen-binding fragment thereof utilizes a framework described in Table 25.

Also provided herein is a chimeric antigen receptor (CAR) comprising one, two, three, four, five, or six CDRs of the anti-PD1 antibodies and antigen binding fragments disclosed herein. Also provided herein is CAR comprising the six CDRs of any one of the anti-PD1 antibodies and antigen binding fragments disclosed herein.

Disclosed is an immune cell expressing a CAR comprising one, two, three, four, five, or six CDRs of the anti-PD1 antibodies and antigen binding fragments disclosed herein. Disclosed is an immune cell expressing a CAR comprising the six CDRs of any one of the anti-PD1 antibodies and antigen binding fragments disclosed herein. In some embodiments, the immune cell is a T cell.

"Identity" refers to the number or percentage of identical positions shared by two amino acid or nucleic acid sequences in optimally aligned sequences after considering number of gaps and the length of each gap that were needed for the optimal alignment. "Substantially identical" means an amino acid sequence, which differs from the original sequence only by conservative amino acid substitutions, which do not destroy the function of the protein.

Also disclosed herein are anti-PD-1 antibodies or antigen-binding fragments thereof or fusion proteins comprising an amino acid sequence that is at least 80%, or at least 85%, or at least 90%, or at least 95%, or at least 98%, or at least 99% identical to an amino acid sequence disclosed herein. Methods and computer programs for determining sequence similarity are publically available, including, but not limited to, the GCG program package (Devereux et al., Nucleic Acids Research 12:387, 1984), BLASTP, BLASTN, FASTA (Altschul et al., J. Mol. Biol. 215:403 (1990), and the ALIGN program (version 2.0). The Smith Waterman algorithm may also be used to determine similarity. The BLAST program is publicly available from NCBI and other sources (BLAST Manual, Altschul, et al., NCBI NLM NIH, Bethesda, Md. 20894; BLAST 2.0 at www.ncbi.nlm.nih.gov/blast/). In comparing sequences, these methods account for various substitutions, deletions, and other modifications.

In some embodiments of the aspects described herein, amino acid sequence modification(s) of the antibodies or antigen-binding fragments thereof that bind to PD-1 or the fusion proteins that bind to PD-1 described herein are contemplated. Amino acid sequence variants of the anti-PD-1 antibody or antigen-binding fragment thereof or the fusion proteins are prepared by introducing appropriate nucleotide changes into the nucleic acid encoding the anti-PD-1 antibody or antigen-binding fragment thereof or the fusion protein, or by peptide synthesis. Such modifications include, for example, deletions from, and/or insertions into and/or substitutions of, residues within the amino acid sequences of the antibody or antigen-binding fragment thereof. Any combination of deletion, insertion, and substitution is made to arrive at the final construct, if the final construct possesses the desired characteristics, e.g., binding specificity, inhibition of biological activity.

Amino acid substitutions can be made, in some cases, by selecting substitutions that do not differ significantly in their effect on maintaining (a) the structure of the peptide backbone in the area of the substitution, (b) the charge or hydrophobicity of the molecule at the target sit; or (c) the bulk of the side chain (conservative amino acid substitution variant. These variants have at least one amino acid residue in the antibody or antigen-binding fragment thereof or fusion protein replaced by a different residue that has similar side chain properties. Amino acids can be grouped according to similarities in the properties of their side chains (see Lehninger, BIOCHEMISTRY (2nd ed., Worth Publishers, New York, 1975):

(1) non-polar: Ala (A), Val (V), Leu (L), Ile (I), Pro (P), Phe (F), Trp (W), Met (M);

(2) uncharged polar: Gly (G), Ser (S), Thr (T), Cys (C), Tyr (Y), Asn (N), Gln (Q);

(3) acidic: Asp (D), Glu (E);

(4) basic: Lys (K), Arg (R), His (H).

As such, a non-limiting example for a conservative amino acid substitution is one that replaces a non-polar amino acid with another non-polar amino acid.

Alternatively, naturally occurring residues can be divided into groups based on common side-chain properties:

(1) hydrophobic: Ala (A), Val (V), Leu (L), Ile (I), Met (M);

(2) neutral hydrophilic: Ser (S), Thr (T), Cys (C), Asn (N), Gln (Q);

(3) acidic: Asp (D), Glu (E);

(4) basic: Lys (K), Arg (R), His (H);

(5) residues that influence chain orientation: Gly (G), Pro (P);

(6) aromatic: Phe (F), Trp (W), Tyr (Y).

Substitutions made within these groups can be considered conservative substitutions. Examples of non-limiting substitutions include, substitution of valine for alanine, lysine for arginine, glutamine for asparagine, glutamic acid for aspartic acid, serine for cysteine, asparagine for glutamine, aspartic acid for glutamic acid, proline for glycine, arginine for histidine, leucine for isoleucine, isoleucine for leucine, arginine for lysine, leucine for methionine, leucine for phenylalanine, glycine for proline, threonine for serine, serine for threonine, tyrosine for tryptophan, phenylalanine for tyrosine, and/or leucine for valine.

Further contemplated are amino acid sequence insertions, which can include amino- and/or carboxyl-terminal fusions ranging in length from one residue to polypeptides containing a hundred or more residues, as well as intrasequence insertions of single or multiple amino acid residues. Examples of terminal fusions include an antibody or antigen-binding fragment thereof with an N-terminal methionyl residue or an antibody or antigen-binding fragment thereof fused to a cytotoxic polypeptide (or fusion proteins comprising such antibody or antigen-binding fragment thereof). Other examples of terminal fusions of the antibody or antigen-binding fragment thereof include the fusion to the N- or C-terminus of the antibody or antigen-binding fragment thereof to an enzyme or a polypeptide which increases the serum half-life of the antibody or antigen-binding fragment thereof, such as, for example, biotin (or fusion proteins comprising such antibody or antigen-binding fragment thereof).

Any cysteine residue not involved in maintaining the proper conformation of the antibodies or antigen-binding fragments thereof that bind to PD-1 also can be substituted, for example with a serine or an alanine, to improve the oxidative stability of the molecule and prevent aberrant crosslinking.

Conversely, cysteine bond(s) can be added to the anti-PD-1 antibody or antigen-binding fragment thereof to improve its stability (particularly where the anti-PD-1 antibody or antigen-binding fragment thereof is an antibody fragment such as an Fv fragment).

In some embodiments, the anti-PD-1 antibodies or antigen-binding fragments thereof or the fusion protein comprising antibodies or antigen-binding fragments thereof describes have amino acid alterations that alter the original glycosylation pattern of the anti-PD-1 antibody or antigen-binding fragment thereof. By "altering the original glycosylation pattern" is meant deleting one or more carbohydrate moieties found in the antibody or antigen-binding fragment thereof, and/or adding one or more glycosylation sites that are not present in the antibody or antigen-binding fragment thereof. Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, wherein X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine can also be used. The alteration can also be made by the addition of, or substitution by, one or more serine or threonine residues to the sequence of the original antibody or antigen-binding fragment thereof (for O-linked glycosylation sites).

In some embodiments, the anti-PD-1 antibody or antigen-binding fragment thereof may include a modification, including, but not limited to glycosylation, acetylation, pegylation, phosphorylation, phosphorylation, amidation, derivatization by known protecting/blocking groups, proteolytic cleavage, linkage to a cellular ligand or other protein, etc. The process of chemical modifications are known in the art, which may include, but are not limited to, specific chemical cleavage, acetylation, formylation, metabolic synthesis of tunicamycin, etc. Additionally, the molecules may contain one or more non-classical amino acids.

The anti-PD-1 antibodies and antigen-binding fragments thereof disclosed herein may include anti-PD-1 antibodies and antigen-binding fragments thereof whose binding characteristics have been altered by direct mutation, affinity maturation, phage display, or chain shuffling. The affinity and specificity may be altered by mutating CDRs and screening for CDRs with desired characteristics. Methods of mutagenesis are known to one of skill in the art.

Antibody Binding

Also provided herein are anti-PD-1 antibodies and antigen-binding fragments thereof, and fusion proteins comprising anti-PD-1 antibodies or antigen-binding fragments thereof, that bind to the same epitope on PD-1 as one of the anti-PD-1 antibodies or antigen-binding fragments thereof disclosed herein.

In some embodiments, the anti-PD-1 antibodies and antigen-binding fragments thereof provided herein bind selectively to PD-1 over one or more PD family members. In one embodiment, the anti-PD-1 antibody or antigen-binding fragment thereof does not exhibit significant binding to other PD family members, including to CTLA-4 and/or CD28. The human PD-1 gene produces four alternatively spliced PD-1 mRNA transcripts. One of these variants produces a soluble form of PD-1. In one aspect, the disclosure provides anti-PD-1 antibodies or antigen-binding fragments thereof that bind to all isoforms of PD-1. In some embodiments, the provided anti-PD-1 antibodies and antigen-binding fragments thereof bind to mammalian PD-1.

As used herein, "binding" of an antibody or antigen-binding fragment thereof, or fusion protein comprising an antibody or antigen-binding fragment thereof, to PD-1, an epitope on PD-1, or, in certain embodiments described below, particular residues on PD-1, includes the selective interaction of the antibody or antigen-binding fragment thereof with PD-1. Binding therefore includes, e.g., primary and secondary interactions including hydrogen bonds, ionic interactions, salt bridges, as well as hydrophilic and hydrophobic interactions.

In certain embodiments, the anti-PD-1 antibodies or antigen-binding fragments thereof described herein bind to PD-1 with an equilibrium constant for the dissociation ($K_D$))

of $10^{-2}$ to $10^{-10}$ mol/l, $10^{-3}$ to $10^{-10}$ mol/l, $10^{-4}$ to $10^{-10}$ mol/l, $10^{-5}$ to $10^{-10}$ mol/l, $10^{-6}$ to $10^{-10}$ mol/l, $10^{-7}$ to $10^{-10}$ mol/l, $10^{-8}$ to $10^{-10}$ mol/l or $10^{-9}$ to $10^{-10}$ mol/l. In other embodiments, the anti-PD-1 antibodies or antigen-binding fragments thereof described herein bind to PD-1 with a $K_D$ of $10^{-2}$ to $10^{-9}$ mol/l, $10^{-3}$ to $10^{-9}$ mol/l, $10^{-4}$ to $10^{-9}$ mol/l, $10^{-5}$ to $10^{-9}$ mol/l, $10^{-6}$ to $10^{-9}$ mol/l, $10^{-7}$ to $10^{-9}$ mol/l, $10^{-8}$ to $10^{-9}$ mol/l, or $10^{-9}$ $10^{-10}$ mol/l.

As used herein, "affinity," represented by the $K_D$ of an antigen with an antigen-binding protein, is a measure of the binding strength between an antigenic determinant and an antigen-binding site on the antigen-binding protein, such as an antibody or antibody fragment thereof. The value of $K_D$ is inversely proportional to the binding strength between an antigenic determinant and the antigen-binding molecule. Alternatively, the affinity can also be expressed as the association constant ($K_A$), which is $1/K_D$). Affinity can be determined in a manner known per se, depending on the specific antigen of interest by a person skilled in the art.

The term "specificity" herein refers to the ability of an antibody or antigen-binding fragment thereof, such as an anti-PD-1 antibody or antigen-binding fragment thereof, to recognize an epitope within PD-1, while only having little or no detectable reactivity with other portions of PD-1. Specificity can be relatively determined by competition assays or by epitope identification/characterization techniques described herein or their equivalents known in the art.

The term "epitope" herein refers to the specific target to which an antibody binds. Epitopes can be formed both by a contiguous stretch of amino acids (continuous epitopes) and by three-dimensional arrangement of amino acid residues that exists only when the target protein is folded in a particular conformation (discontinuous epitopes.) In general, an epitope comprises at least 3 amino acids, at least 4, at least 5, or about 7-10 amino acids.

Disclosed herein are anti-PD-1 antibodies and antigen-binding fragments thereof as well as fusion proteins comprising an anti-PD1 antibody or antigen-binding fragment thereof that specifically bind to the same epitope as anti-PD-1 antibody 38B2. Also disclosed herein are anti-PD-1 antibodies and antigen-binding fragments thereof as well as fusion proteins comprising an anti-PD1 antibody or antigen-binding fragment thereof that bind to the same epitope as anti-PD-1 antibody 31B1.

As used herein, a "blocking" antibody or an antibody "antagonist" is one that inhibits or reduces the biological activity of the antigen to which it binds. For example, in some embodiments, an anti-PD-1 antagonist antibody or antigen-binding fragment thereof binds PD-1 and inhibits activity of PD-1 and/or binding of PD-1 to binding partners such as PD-L1 or PD-L2. Inhibition of activity and inhibition of binding includes partial inhibition. Methods for the identification of PD-1 antibodies that block PD-1 interactions are described herein and are known to the ones skilled in the art. For instance, competing, cross-blocking, and cross-blocked antibodies can be identified using any suitable method known in the art, including competition ELISAs or BIACORE® assays where binding of the competing or cross-blocking antibody to human PD-1 prevents the binding of an antibody disclosed herein or vice versa.

In certain embodiments, not all CDRs are directly involved in binding to the antigen. In one embodiment, four out of six CDRs of the anti-PD-1 antibody or antigen-binding fragment thereof make contact with the antigen. In one embodiment, five out of six CDRs of the anti-PD-1 antibody or antigen-binding fragment thereof make contact with the antigen. In one embodiment, six out of six CDRs of the anti-PD-1 antibody or antigen-binding fragment thereof make contact with the antigen.

The terms "selective" and "selectivity" herein refer to the preferential binding of an antibody or antigen-binding fragment thereof (i.e., a PD-1 antibody or antigen-binding fragment thereof), for a particular region, target, or peptide; typically a region or epitope in PD-1, as opposed to one or more other biological molecules, including other PD-1 family members.

In one aspect, provided are anti-PD-1 antibodies and antigen-binding fragments thereof that specifically bind to at least part of the binding site on PD-1, thereby blocking PD-1 interactions with the one or more PD-1 ligands. These PD-1 ligands include, but are not limited to, PD-L1 and PD-L2.

In certain embodiments, the anti-PD-1 antibody or antigen-binding fragments according to the disclosure comprises an Fc domain, composed of a first and a second subunit. The Fc domain of an antibody consists of a pair of polypeptide chains comprising heavy chain domains of an immunoglobulin molecule. The two subunits of the Fc domain form a stable association. In embodiments, the two subunits of the Fc domain are identical. In alternative embodiments, the two subunits of the Fc domain are non-identical. In embodiments, one subunit of the Fc domain may be fused with an immunoconjugate molecule. In embodiments, the Fc domain of the antibody may be an IgG Fc domain, an $IgG_1$ Fc domain, an $IgG_2$ Fc domain, an $IgG_3$ Fc domain, an $IgG_4$ Fc domain. In a further particular embodiment, the Fc domain is a human Fc domain.

Fc Domain Modifications Promoting Heterodimerization

Further contemplated are modifications in the Fc domain of the disclosed anti-PD-1 antibodies or antigen-binding fragments thereof promoting dimerization. In embodiments, the Fc domain of the anti-PD-1 antibody or antigen-binding fragment thereof comprises a modification promoting the association of the first and the second subunit of the Fc domain. In one embodiment, said modification is in the CH3 domain of the Fc domain. In a specific embodiment, said modification promoting the association of the first and the second subunit of the Fc domain is a so-called "knob-into-hole" modification, comprising a "knob" modification in one of the two subunits of the Fc domain and a "hole" modification in the other one of the two subunits of the Fc domain.

Knob-into-hole modifications are a "protuberance-into-cavity" strategy, which serves to engineer an interface between a first and second polypeptide for hetero-oligomerization. "Protuberances" (i.e., the knobs) are constructed by replacing small amino acid side chains from the interface of the first polypeptide with larger side chains. Compensatory "cavities" (i.e., holes) of identical or similar size to the protuberances are optionally created on the interface of the second polypeptide by replacing large amino acid side chains with smaller ones. In particular embodiment, an amino acid residue in the CH3 domain of the first Fc subunit is replaced with an amino acid residue having a larger side chain volume, thereby generating a knob within the CH3 domain of the first Fc subunit which is positionable in a hole present within the CH3 domain of the second Fc subunit, generated by replacing one amino acid residue with an amino acid residue having a smaller side chain volume in the CH3 domain of the second Fc subunit. Preferably said amino acid residue having a larger side chain volume is selected from the group consisting of cysteine (C), valine (V), alanine (A), phenylalanine (F), tyrosine (Y), leucine (L), lysine (K), Proline (P), glutamic acid (E), and tryptophan (W). Preferably said amino acid residue having a smaller side chain volume is selected from the group consisting of alanine (A), serine(S), threonine (T), arginine (R), trypto-phan (W), cysteine (C), lysine (L), glutamic acid (E), aspartic acid (D), and valine (V).

The mutations corresponding to the knob and the hole can be made by altering the nucleic acid encoding the polypep-tides, e.g. by site-specific mutagenesis, or by peptide syn-thesis.

In fusion protein embodiments, which only one heavy chain is linked to IL-15/IL-15Rα sushi, the Fc domains of the anti-PD-1 antibody or antigen-binding fragment thereof may comprise one or more amino acid substitutions pro-moting heterodimer formation (i.e., the association the heavy chain fusion with a heavy chain lacking the fusion). In embodiments, an amino acid residue in the CH3 domain of one heavy chain (CH3-1) comprises an amino acid substitution replacing an amino acid with an amino acid residue having a larger side chain volume, thereby generat-ing a "knob" within the CH3 domain, which is positionable in a "hole" present within the CH3 domain of the other heavy chain (CH3-2), generated by replacing an amino acid residue with an amino acid residue having a smaller side chain volume. In embodiments, the CH3 domain of the first subunit of the Fc domain (the "knobs" subunit) may com-prise one or more substitution from the following; T350V, L351Y, S354C, S364H, T366Y, T366W, F405A, Y407V. In specific embodiments, the CH3 domain of the second sub-unit of the Fc domain (the "holes" subunit) may comprise one or more substitutions from the following; Y349C, T350V, T366L, T366S, L368A, K392L, T394W, Y407V, Y407T.

In some embodiments, the amino acid substitutions are selected from:

(1) CH3 domain of first heavy chain: S354C, T366W; CH3 domain of second heavy chain: Y349C, T366S, L368A, Y407V;

(2) CH3 domain of first heavy chain: T350V, L351Y, F405A, Y407V; CH3 domain of second heavy chain: T350V, T366L, K392L, T394W;

(3) CH3 domain of first heavy chain: L351Y, F405A, Y407V; CH3 domain of second heavy chain: T366L, K392L, T394W;

(4) CH3 domain of first heavy chain: T366W; CH3 domain of second heavy chain: Y407T;

(5) CH3 domain of first heavy chain: T366Y; CH3 domain of second heavy chain: Y407T;

(6) CH3 domain of first heavy chain: T366W; CH3 domain of second heavy chain: Y407A;

(7) CH3 domain of first heavy chain: F405A; CH3 domain of second heavy chain: T394W;

(8) CH3 domain of first heavy chain: F405W; CH3 domain of second heavy chain: T394S;

(9) CH3 domain of first heavy chain: T366Y and F405A; CH3 domain of second heavy chain: T394W and Y407T;

(10) CH3 domain of first heavy chain: T366W and F405W; CH3 domain of second heavy chain: T394S; and 407A;

(11) CH3 domain of first heavy chain: F405W and Y407A; CH3 domain of second heavy chain: T366W and T394S.

(12)

Provided herein is an antibody or antigen-binding frag-ment thereof, which binds to PD-1 (or a fusion protein comprising such an antibody or antigen-binding fragment thereof), wherein the antibody comprises a heavy chain comprising a sequence selected from the group consisting of SEQ ID NOS: 168-169, 171-172, 185, 191, and 201-203.

Provided herein is an antibody or antigen-binding frag-ment thereof (or a fusion protein comprising such an anti-body or antigen-binding fragment thereof), which binds to PD-1, wherein the antibody comprises a light chain com-prising a sequence selected from the group consisting of SEQ ID NOS: 170, 173, 186, 192, and 205.

In specific embodiments, the Fc domain according to the disclosure exhibits reduced binding affinity to an Fc receptor and/or reduced effector function, as compared to a native IgG1 Fc domain. In certain embodiments, the Fc domain is engineered to have reduced binding affinity to an Fc receptor and/or reduced effector function, as compared to a non-engineered Fc domain.

Linkers

In embodiments, the fusion proteins provided herein may comprise one or more linkers joining components of the fusion proteins disclosed herein. A linker may be located (i) between the IL-15 polypeptide and the IL15Rα polypeptide comprising the sushi domain; (ii) between a heavy chain of the anti-PD-1 antibody or antigen-binding fragment thereof and the IL-15 polypeptide or the IL15Rα polypeptide com-prising the sushi domain; or (iii) both. In embodiments of the disclosure, the IL-15 polypeptide and the IL15Rα polypep-tide comprising the sushi domain are joined or linked by a first linker amino acid sequence. In embodiments, the IL-15 polypeptide (or the IL15Rα polypeptide) is linked to an antibody, or antigen binding fragment thereof, described herein by a second linker amino acid sequence. In embodi-ments, the second linker joins the N terminus of the heavy chain variable region to the C terminus of the IL-15 poly-peptide. The first and second linkers may have the same or different amino acid sequences.

The linker amino acids sequences described herein may be of a length sufficient to ensure that the fusion protein forms proper secondary and tertiary structures. The length of the linker amino may be between 5 to 40 amino acids, preferably 10 to 40 amino acids, more preferably 15 to 40 amino acids, still more preferably 20 to 40 amino acids, most preferably 25 to 35 amino acids.

Preferably, the linker sequences comprise near neutral amino acids selected in the group comprising Gly (G), Asn (N), Ser (S), Thr (T), Ala (A), Leu (L), and Gln (Q), most preferably in amino acids selected from the group compris-ing Gly (G), Asn (N), and Ser (S). Preferably, the linker sequences are glycine- and serine-rich, and in some embodi-ments, the linker contains only serine and glycine residues.

In some embodiments, the linker comprises a portion of the IL15Rα polypeptide outside of the sushi domain, includ-ing, but not limited to the sequence bolded in the linker of SEQ ID NO:215 (below).

Some non-limiting linker examples of amino acid sequences include

```
                                        (SEQ ID NO: 215)
IRDPALVHQRPAPPSGGSGGGGSGGGSGGGGSLQ, (SEQ ID NO: 216)
GGGGSGGGGSGGGGSGGGGSGGGGSGGGGS;

(SEQ ID NO: 217)
IRDPSGGGGSGGGGSGGGGSGGGGSGGGGSGGGG, (SEQ ID NO: 218)
IRDPGGGGSGGGGSGGGGSGGGGSGGGGSGGGGS,
and (SEQ ID NO: 244)
GGGGSGGGGSGGGGSGGGGS.
```

In embodiments, the linker joining the IL-15 polypeptide and the IL-15Rα sushi comprises IRDPALVHQR-PAPPSGGSGGGGSGGGSGGGGSLQ (SEQ ID NO: 215), IRDPSGGGGSGGGGSGGGGSGGGGSGGGGSGG GG (SEQ ID NO: 217), or IRDPGGGGSGGGGSGGGGSGGGGSGGGGSGGG GS (SEQ ID NO:218).

In embodiments, the linker joining the IL-15 polypeptide to the anti-PD-1 antibody heavy chain comprises GGGGSGGGGSGGGGSGGGGSGGGGSGGGGS (SEQ ID NO: 216) or GGGGSGGGGSGGGGSGGGGS (SEQ ID NO:244).

In embodiments, the heavy and light chains of the anti-PD-1 antibody or antigen-binding fragment thereof disclosed herein may be connected into a single polypeptide chain (a "single-chain Fv" or "scFv") using a third linker that allows the VR and VL domains to associate to form an antigen-binding site. The amino acid sequence of the linkers may be the same or different.

In one embodiment, an IL-15 polypeptide or an IL-15 derivative is covalently linked to an IL-15Rα sushi polypeptide or an IL-15Rα sushi derivative by a linker.

In one embodiment, the IL-15 polypeptide or IL-15 derivative is covalently linked to an anti-PD-1 antibody or antigen-binding fragment thereof by a linker. In one embodiment, the C-terminus of the IL-15 polypeptide or IL-15 derivative is covalently linked to the N-terminus of the anti-PD-1 antibody or antigen-binding fragment thereof by a linker. In one embodiment, the N-terminus of the IL-15 polypeptide or IL-15 derivative is covalently linked to the C-terminus of the anti-PD-1 antibody or antigen-binding fragment thereof by a linker. In one embodiment, the N-terminus of the IL-15 polypeptide or IL-15 derivative is covalently linked to the CH3 region of the anti-PD-1 antibody or antigen-binding fragment thereof by a linker.

In one embodiment, the IL-15Rα sushi or an IL-15Rα sushi derivative is covalently linked to an anti-PD-1 antibody or antigen-binding fragment thereof by a linker. In one embodiment, the C-terminus of the IL-15Rα sushi polypeptide or IL-15Rα sushi derivative is covalently linked to the N-terminus of the anti-PD-1 antibody or antigen-binding fragment thereof by a linker. In one embodiment, the N-terminus of the IL-15Rα sushi polypeptide or IL-15Rα sushi derivative is covalently linked to the C-terminus of the anti-PD-1 antibody or antigen-binding fragment thereof by a linker. In one embodiment, the N-terminus of the IL-15Rα sushi polypeptide or IL-15Rα sushi derivative is covalently linked to the CH3 region of the anti-PD-1 antibody or antigen-binding fragment thereof by a linker.

In some embodiments, an IL-15 polypeptide or an IL-15 derivative is covalently linked to an IL-15Rα sushi polypeptide or a IL-15Rα sushi derivative by a first linker and either the IL-15 polypeptide or IL-15 derivative or the IL-15Rα sushi polypeptide or IL-15Rα sushi derivative is covalently linked to an anti-PD-1 antibody or antigen-binding fragment thereof by a second linker. In some embodiments, the amino acid sequences of the first and the second linker are identical. In other embodiments, the amino acid sequences of the first and the second linker are different.

Conjugates

The anti-PD-1 antibodies, antigen-binding fragments thereof, and the fusion proteins disclosed herein may further comprise one or more functional moieties. Examples of useful functional moieties include, but are not limited to, a blocking moiety, a detectable moiety, a diagnostic moiety, a targeting, and a therapeutic moiety.

A blocking moiety may include moieties of sufficient steric bulk and/or charge such that reduced glycosylation occurs, for example, by blocking the ability of a glycosidase to glycosylate the antibody or antigen-binding fragment thereof. Preferred blocking moieties include cysteine adducts such as cysteine, mixed disulfide adducts, or disulfide linkages and PEG moieties such as polyethylene glycol ("PEG"), polypropylene glycol ("PPG"), polyoxyethylated glycerol ("POG") and other polyoxyethylated polyols, polyvinyl alcohol ("PVA") and other polyalkylene oxides, polyoxyethylated sorbitol, or polyoxyethylated glucose. PEG is a preferred moiety in biological applications for several reasons. PEGylating can improve pharmacokinetic performance of a molecule by increasing the molecule's apparent molecular weight. The increased apparent molecular weight reduces the rate of clearance from the body following subcutaneous or systemic administration. In many cases, pegylation can decrease antigenicity and immunogenicity. PEGylating can also increase the solubility of a biologically active molecule. Additionally, PEG typically is clear, colorless, odorless, soluble in water, stable to heat, inert to many chemical agents, does not hydrolyze, and is nontoxic, making it a preferable choice for biological applications.

The examples of detectable moieties that can be conjugated with the anti-PD-1 antibody or the antigen-binding fragments or fusions disclosed herein may include fluorescent moieties or labels, imaging agents, radioisotopic moieties, radiopaque moieties, and the like, e.g. detectable labels such as biotin, fluorophores, chromophores, spin resonance probes, or radiolabels. Examples of fluorophores include fluorescent dyes (e.g. fluorescein, rhodamine, and the like) and other luminescent molecules (e.g. luminal). A fluorophore may be environmentally-sensitive such that its fluorescence changes if it is located close to one or more residues in the modified protein that undergo structural changes upon binding a substrate (e.g. dansyl probes). Exemplary radiolabels include small molecules containing atoms with one or more low sensitivity nuclei (13C, 15N, 2H, 125I, 123I, 99Tc, 43K, 52Fe, 67Ga, 68Ga, 111 In and the like).

Diagnostic moieties include detectable moieties suitable for revealing the presence of a disease or disorder. Typically, a diagnostic moiety allows for determining the presence, absence, or levels of a molecule, for example, a target peptide, protein, or proteins, that are associated with a disease or disorder. Such diagnostics are also suitable for prognosing and/or diagnosing a disease or disorder and its progression.

Examples of therapeutic moieties include anti-inflammatory agents, anti-cancer agents, anti-neurodegenerative agents, anti-infective agents, or generally a therapeutic. The functional moiety may also have one or more of the above-mentioned functions. Exemplary therapeutic moieties may include an antibiotic, a second anti-PD-1 antibody, or an antibody to another antigen such a tumor-specific antigen, an autoimmune tissue antigen, a virally-infected cell antigen, a Fc receptor, a T cell receptor, or a T cell co-inhibitor, or an immunotoxin, or any other therapeutic moiety useful for treating a disease or condition including cancer, autoimmune disease or chronic viral infection. Exemplary therapeutic moieties may also cytotoxin, radioactive agent, cytokine, interferon, target or reporter moiety, enzyme, toxin, peptide or therapeutic agent at any location along the molecule so long as it is able to bind its target. Examples of immunoconjugates include antibody drug conjugates and antibody-toxin fusion proteins. In certain embodiments, the antibody may be conjugated to an agent specific for a tumor cell or a virally infected cell.

A salvage receptor binding epitope as described, e.g., in U.S. Pat. No. 5,739,277 may also be attached to the antibody or antigen-binding fragment thereof (especially an antibody fragment) to increase the half-life of the antibodies or the antigen-binding fragments described herein. The term "salvage receptor binding epitope" may refer to an epitope of the Fc region of an IgG molecule (e.g., IgG1, IgG2, IgG3, or IgG4) that is responsible for increasing the in vivo serum half-life of the IgG molecule (e.g., Ghetie et al., 18 Ann. Rev. Immunol. 739 (2000).

Nucleic Acids

Also provided herein are nucleic acids encoding anti-PD-1 antibodies, antigen-binding fragments thereof and fusion proteins disclosed herein, as well as vectors, host cells, and expression systems. The term "nucleic acid" as used herein refers to a polymeric form of nucleotides of any length, either ribonucleotides or desoxyribonucleotides and includes but is not limited to, single-, double- or multi-stranded DNA or RNA, genomic DNA, cDNA, DNA-RNA hybrids, or a polymer comprising purine and pyrimidine bases, or other natural, chemically or biochemically modified, non-natural, or derivatized nucleotide bases. The nucleic acids encoding anti-PD-1 antibodies and antigen-binding fragments thereof and fusion proteins disclosed herein may be, e.g., DNA, cDNA, RNA, synthetically produced DNA or RNA, or a recombinantly produced chimeric nucleic acid molecule comprising any of those polynucleotides either alone or in combination.

The term "vector" refers to vehicle comprising a nucleic acid molecule that is capable of transporting the nucleic acid molecule into a cell. A "vector" includes, but is not limited to, a viral vector, a plasmid, a RNA vector or a linear or circular DNA or RNA molecule, which may consists of a chromosomal, non-chromosomal, semi-synthetic or synthetic nucleic acids. In some embodiments, the employed vectors are those capable of autonomous replication (episomal vector) and/or expression of nucleic acids to which they are linked (expression vectors). A number of suitable vectors are known to those of skill in the art and are commercially available.

Antibody and Fusion Protein Preparation and Expression Systems

The anti-PD-1 antibodies, antigen-binding fragments or the fusion proteins disclosed herein are typically produced by recombinant expression. Nucleic acids encoding light and heavy chain variable regions, optionally linked to constant regions, may be inserted into the same expression vectors. Alternatively, the nucleic acids encoding light and heavy chain variable regions, optionally linked to constant regions, are inserted into different expression vectors. The expression vector may further comprise one or more expression control sequences, which include, but are not limited to, promoters (e.g., homologous or heterologous promoters), signal sequences, enhancer elements, and transcription termination sequences. Preferably, the expression control sequences are eukaryotic promoter systems in vectors capable of transforming or transfecting eukaryotic host cells. Typically, the host is maintained under conditions suitable for high-level expression of the nucleotide sequences, and the collection and purification of the cross-reacting antibodies after the vector is incorporated into the appropriate host.

Commonly, expression vectors contain selection markers (e.g., ampicillin-resistance, hygromycin-resistance, tetracycline resistance or neomycin resistance) to permit detection of those cells transformed with the desired DNA sequences.

The host used to express the anti-PD-1 antibodies, antigen-binding fragments thereof or the fusion proteins disclosed herein can be a prokaryotic or eukaryotic host. Examples of suitable hosts include bacterial or eukaryotic hosts, including yeast, insects, fungi, bird and mammalian cells either in vivo, or in situ, or host cells of mammalian, insect, bird, or yeast origin. The mammalian cell or tissue can be of human, primate, hamster, rabbit, rodent, cow, pig, sheep, horse, goat, dog, or cat origin, but any other mammalian cell may be used.

Examples of bacterial hosts that can be used to express the antibodies, antigen-binding fragments or the fusion protein disclosed herein can be E. coli, bacilli, such as Bacillus subtilus, and other enterobacteriaceae, such as Salmonella, Serratia, and various Pseudomonas species.

Yeasts may also be used as hosts for expressing the express the antibodies, antigen-binding fragments or the fusion protein disclosed herein. Saccharomyces and Pichia are exemplary yeast hosts, with suitable vectors having expression control sequences (e.g., promoters), an origin of replication, termination sequences, and the like as desired. Typical promoters include 3-phosphoglycerate kinase and other glycolytic enzymes. Inducible yeast promoters include, among others, promoters from alcohol dehydrogenase, isocytochrome C, and enzymes responsible for methanol, maltose, and galactose utilization.

Mammalian cells in culture may also be used as host cells for expressing the antibodies, antigen-binding fragments or the fusion proteins disclosed herein. Examples of suitable host cell lines capable of secreting heterologous proteins (e.g., intact immunoglobulins) which are well known in the art, include CHO cell lines, various COS cell lines, HeLa cells, 293 cells, myeloma cell lines, transformed B-cells, and hybridomas. Expression vectors for these cells can include expression control sequences, such as an origin of replication, a promoter, an enhancer and necessary processing information sites such as ribosome binding site, RNA splice site and/or transcriptional terminator sequences. Examples of expression control sequences include SV40, adenovirus, bovine papilloma virus, cytomegalovirus and the like.

The anti-PD-1 antibodies, antigen-binding fragments thereof, and the fusion proteins disclosed herein can be expressed using a single expression construct or vector or multiple expression constructs or vectors (e.g., two or three expression constructs). When the antibody heavy and light chains are cloned on separate expression vectors, the vectors are co-transfected to obtain expression and assembly of intact immunoglobulins. Once expressed, the whole antibodies, their dimers, individual light and heavy chains, or other immunoglobulin forms disclosed herein can be purified according to standard procedures of the art, including ammonium sulfate precipitation, affinity columns, column chromatography, HPLC purification, gel electrophoresis, and the like (see generally Scopes, Protein Purification (Springer-Verlag, N.Y., (1982)). Substantially pure immunoglobulins of at least about 90 to 95% homogeneity are preferred, and 98 to 99% or more homogeneity most preferred, for pharmaceutical uses.

The disclosed anti-PD-1 antibodies, antigen-binding fragments, and the fusion proteins can be made by any method known in the art. General techniques for generating human or mouse antibodies or fusion molecules are known in the art.

Methods for Modulating PD-1 Activity

In one aspect, the disclosure provides methods of using the anti-PD-1 antibodies, antigen-binding fragments thereof, and fusion proteins described herein for decreasing the interaction between PD-1 and PD-ligands, including, but not limited to, PD-L1 and PD-L2. In some embodiments, the anti-PD-1 antibody, antigen-binding fragment thereof, or fusion protein disrupts the interaction between PD-1 monomers.

The anti-PD-1 antibodies, antigen-binding fragments thereof, and fusion proteins disclosed herein are useful for reducing immunosuppression, e.g., T cell tolerance. By "reducing" is meant the ability to cause an overall decrease of about 20% or greater, 30% or greater, 40% or greater, 45% or greater, 50% or greater, of 55% or greater, of 60% or greater, of 65% or greater, of 70% or greater, or 75% or greater, 80% or greater, 85% or greater, 90% or greater, or 95% or greater, as compared to a control that is not treated. Immunosuppression can be mediated by immune inhibitory receptors expressed on the surface of an immune cell, and their interactions with their ligands. Methods of measuring T cell activity are known in the art. By way of non-limiting example, T cell tolerance can be induced by contacting T cells with recall antigen, anti-CD3 in the absence of co-stimulation, and/or ionomycin. Levels of, e.g., IL-27, LDH-A, RAB10, and/or ZAP70 (both intracellular or secreted) can be monitored, for example, to determine the extent of T cell tolerogenesis (with levels of IL-2, interferon-γ and TNF correlating with increased T cell tolerance).

The anti-PD-1 antibodies, antigen-binding fragments thereof, and fusion proteins disclosed herein are further useful for enhancing T cell expansion, activation, and proliferation.

Methods of Treatment

PD-1 plays an important role in the immune system in regulating autoimmunity, tumor immunity, and infectious immunity. PD-1-mediated T cell inhibition is an important mechanism to prevent autoimmunity. In addition, cancer and chronic infectious diseases may usurp this regulation mechanism to drive immune suppression. Blocking PD-1 with antagonists, including monoclonal antibodies, has been studied in treatments of cancer and chronic viral infections. The ability of PD-1 to inhibit T cell activation is exploited by chronic viral infections and tumors to evade immune response. In chronic viral infections, PD-1 is highly expressed on virus-specific T cells and these T cells become "exhausted" with loss of effector functions and proliferative capacity.

PD-1 deficient animal models develop various autoimmune phenotypes including autoimmune cardiomayopathy, rheumatoid arthritis, and graft versus host disease. Specifically, they have elevated levels of IgG2b and IgA and develop mild lupus-like autoimmunity and dilated cardiomyopathy. Considering the role of PD-1 in modulating immune responses, the therapeutic agents disclosed herein that antagonize PD-1 signaling can be administered to treat diseases that involve PD-1-mediated immune suppression.

Immunomodulation is a useful therapeutic approach for treating various diseases and disorders. One approach to immunomodulation is to intervene at one or more immune checkpoints by regulators of immune activation that play a key role in maintaining immune homeostasis and preventing autoimmunity. Depending on the disease or disorder, it may be desirable to upregulate or downregulate the immune response. Tumor cells that display non-self-antigens, can evade immune attack by secreting cytokines or ligands that activate immune checkpoints. In cancer therapy, thus it is generally desirable to upregulate the immune response against tumor cells. In contrast, in treatment of autoimmune diseases, it is generally desirable to downregulate the immune response in certain tissues.

In one aspect, the disclosure provides anti-PD-1 antibodies, antigen-binding fragments thereof, and fusion proteins that are useful for treatments of subjects in need thereof.

In the methods described herein, a therapeutically effective amount of an anti-PD-1 antibody, antigen-binding fragment thereof or fusion protein disclosed herein is administered to a mammal in need thereof. The term "mammal" as used herein includes, but is not limited to, humans, laboratory animals, domestic pets, and farm animals. Preferably, the mammal is a human. "Therapeutically effective amount" as described herein refers to an amount of an anti-PD-1 antibody, antigen-binding fragment thereof or fusion protein which, when administered to a mammal, is effective in producing the desired therapeutic effect.

By "subject" is meant a mammal, including, but not limited to, a human or non-human mammal, such as a bovine, equine, canine, ovine, or feline, etc. Individuals and patients are also subjects herein.

The terms "treat," "treated," "treating," or "treatment" as used herein refer to therapeutic treatment, wherein the object is to slow down (lessen) an undesired physiological condition, disorder, or disease, or to obtain beneficial or desired clinical results. For the purposes of this disclosure, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of one or more symptoms of the condition, disorder or disease state; and remission (whether partial or total). Treatment includes eliciting a clinically significant response without excessive levels of side effects. Treatment also includes prolonging survival as compared to expected survival if not receiving treatment. The terms "prevent," "prevention," and the like refer to acting prior to overt disease or disorder onset, to prevent the disease or disorder from developing or to minimize the extent of the disease or disorder or slow its course of development.

In one aspect, the anti-PD-1 antibodies, antigen-binding fragments thereof and fusion proteins disclosed herein may be used to treat subjects suffering from an autoimmune disease, including but not limited to, alopecia areata, autoimmune hepatitis, celiac disease, Graves' disease, Guillain-Barre syndrome, Hashimoto's disease, hemolytic anemia, inflammatory bowel disease, inflammatory myopathies, multiple sclerosis, primary biliary cirrhosis, psoriasis, rheumatoid arthritis, scleroderma, Sjogren's syndrome, systemic lupus, erthyematosus, vitiligo, autoimmune pancreatitis, autoimmune urticaria, autoimmune thrombocytopenia purpura, Crohn's disease, diabetes type I, eosinophilic fasciitis, eosinophilic enterogastritis, Goodpasture's syndrome, myasthenia gravis, psoriatic arthritis, rheumatic fever, ulcerative colitis, vasculitis and Wegener's granulomatosis. In certain embodiments, an activating antibody disclosed herein may be used to treat a subject suffering from autoimmune disease.

In one aspect, the anti-PD-1 antibodies, antigen-binding fragments thereof and fusion proteins disclosed herein may be used to treat subjects suffering from a chronic viral infection. In a specific embodiment, the anti-PD-1 antibodies, antigen-binding fragments thereof and fusion proteins disclosed herein can be used to rescue exhausted T cells and/or decrease viral titers in a subject in need thereof. In certain embodiments, the anti-PD-1 antibodies, antigen-binding fragments thereof and fusion proteins disclosed herein may be used to treat chronic viral infection by administering a therapeutically effective dose to a subject in need thereof. In some embodiments, the subject is suffering from a viral infection caused by lymphocytic choriomeningitis virus (LCMV), human immunodeficiency virus (HIV) or human papilloma virus (HPV) or hepatitis B/C virus (HBV/HCV) or simian immunodeficiency virus (SIV).

In another aspect, the anti-PD-1 antibodies, antigen-binding fragments thereof and fusion proteins disclosed herein can be used to treat subjects suffering from primary or recurrent cancer, including, but not limited to, renal cell carcinoma, colorectal cancer, non-small-cell lung cancer, brain cancer (e.g., glioblastoma multiforme), squamous cell carcinoma of head and neck, gastric cancer, prostate cancer, ovarian cancer, kidney cancer, breast cancer, multiple myeloma, and melanoma.

In certain embodiments, anti-PD-1 antibodies, antigen-binding fragments thereof and fusion proteins disclosed herein may be administered in a therapeutically effective amount to a subject suffering from a cancer or a viral infection.

One or more anti-PD-1 antibodies, antigen-binding fragments thereof or fusion proteins disclosed herein may be administered to relieve or prevent or decrease the severity of one or more of the symptoms or conditions of the disease or disorder. In a certain embodiment, the anti-PD-1 antibodies, antigen-binding fragments thereof and fusion proteins disclosed herein may be administered prophylactically to a subject in need therefore to reduce the risk of developing a chronic viral infection or an autoimmune disease. The anti-PD-1 antibodies, antigen-binding fragments thereof and fusion proteins disclosed herein may be used as an adjunct therapy with any other agent or any other therapy known to those skilled in the art useful for treating cancer, autoimmune disease, or viral infection.

Combination Therapy

The anti-PD-1 antibodies, antigen-binding fragments thereof and fusion proteins disclosed herein may be advantageously combined with an additional therapeutic agent. Such additional agents include, but are not limited to, cytotoxic agents, chemotherapeutic agents, growth inhibitory agents, anti-inflammatory agents, anti-cancer agents, anti-neurodegenerative agents, immunosuppressive agents, and anti-infective agents. The administration of the anti-PD-1 antibody or antigen-binding fragment thereof or the fusion protein and the additional therapeutic agent may be concurrently, consecutively or intermittently. The administration of the anti-PD-1 antibody or antigen-binding fragment thereof or the fusion protein and the additional therapeutic agent may be separately or as a mixture. Further, the methods of treatment provided herein can relate to a treatment in combination with one or more therapies including but not limited to the group of antibody therapy, chemotherapy, cytokine therapy, dendritic cell therapy, gene therapy, hormone therapy, laser light therapy, and radiation therapy.

The anti-PD-1 antibodies, antigen-binding fragments thereof, and the fusion proteins of the present disclosure may be combined synergistically with one or more anti-cancer drugs or therapy used to treat cancer, including, but not limited to, renal cell carcinoma, colorectal cancer, glioblastoma multiforme, squamous cell carcinoma of head and neck, non-small-cell lung cancer, colon cancer, ovarian cancer, adenocarcinoma, prostate cancer, glioma, and melanoma. Examples of such agents include but are not limited to with an antibody to PD-L1, a second antibody to PD-1 (e.g., nivolumab), a LAG-3 inhibitor, a CTLA-4 inhibitor (e.g., ipilimumab), a TIM3 inhibitor, a BTLA inhibitor, a T IGIT inhibitor, a CD47 inhibitor, an antagonist of another T cell co-inhibitor or ligand (e.g., an antibody to CD-28, 2B4, LY108, LAI R 1, ICOS, CD1 60 or VISTA), an indoleamine-2,3-dioxygenase (IDO) inhibitor, a vascular endothelial growth factor (VEGF) antagonist [e.g., a "VEGF-Trap" such as aflibercept or other VEGF-inhibiting fusion protein as set forth in U.S. Pat. No. 7,087,411, or an anti-VEGF antibody or antigen-binding fragment thereof (e.g., bevacizumab, or ranibizumab) or a small molecule kinase inhibitor of VEGF receptor (e.g., sunitinib, sorafenib, or pazopanib)], an Ang2 inhibitor (e.g., nesvacumab), a transforming growth factor β (TGF3) inhibitor, an epidermal growth factor receptor (EGFR) inhibitor (e.g., erlotinib, cetuximab), an agonist to a costimulatory receptor (e.g., an agonist to glucocorticoid-induced TNFR-related protein), an antibody to a tumor-specific antigen (e.g., CA9, CA1 25, melanoma-associated antigen 3 (MAGE3), carcinoembryonic antigen (CEA), anti-viral drugs (e.g., zidovudine, lamivudine, abacavir, ribavirin, lopinavir, efavirenz, cobicistat, tenofovir, rilpivirine and corticosteroids), vimentin, tumor-M2-PK, prostate-specific antigen (PSA), mucin-1, MART-1, and CA1 9-9), a vaccine (e.g., *Bacillus* Calmette-Guerin, a cancer vaccine), an adjuvant to increase antigen presentation (e.g., granulocyte-macrophage colony stimulating factor), a bispecific antibody (e.g., CD3xCD20 bispecific antibody, PSMAxCD3 bispecific antibody), cancer vaccines (e.g., MAGE3, MUC1, EGFRv3, ALVAC-CEA), a cytotoxin, a chemotherapeutic agent (e.g., dacarbazine, temozolomide, cyclophosphamide, docetaxel, doxorubicin, daunorubicin, cisplatin, carboplatin, gemcitabine, methotrexate, mitoxantrone, oxaliplatin, paclitaxel, and vincristine), cyclophosphamide, radiotherapy, an IL-6R inhibitor (e.g., sarilumab), an IL-4R inhibitor (e.g., dupilumab), an IL-1 0 inhibitor, a cytokine such as IL-2, IL-7, IL-21, and IL-15, an antibody-drug conjugate (ADC) (e.g., anti-CD1 9-DM4 ADC, and anti-DS6-DM4 ADC), an anti-inflammatory drug (e.g., corticosteroids, and non-steroidal anti-inflammatory drugs), a dietary supplement such as anti-oxidants or any palliative care to treat cancer, radiation therapy, and/or an antibody to a Fc receptor on immune cells for the treatment of an autoimmune disease.

Methods of Administration

The therapeutic compositions comprising any of the anti-PD-1 antibodies, antigen-binding fragments thereof or fusion proteins described herein may be administered to a subject in need thereof in any convenient manner including but not limited to by injection, transfusion, implantation or transplantation. The compositions described herein may be administered to a subject in need thereof subcutaneously, intradermally, intratumorally, intranodally, intramedullary, intramuscularly, intracranially, by intravenous or intralymphatic injection, or intraperitoneally. In one embodiment, the cell compositions of the present disclosure are preferably administered by intravenous injection.

In certain embodiments, the anti-PD-1 antibody, antigen-binding fragment thereof or the fusion protein is administered to the mammal by intravenous infusion, i.e., introduction of the anti-PD-1 antibody, antigen-binding fragment thereof or the fusion protein into the vein of a mammal over a certain period. In certain embodiments, the period is about 5 min, about 10 min, about 30 min, about 1 h, about 2 h, about 4 h, or about 8 h.

Administrative Regimens

The methods according to this aspect of the disclosure comprise sequentially administering to a subject multiple doses of an anti-PD-1 antibody, antigen-binding fragment thereof, or a fusion protein of the disclosure. As used herein, "sequentially administering," means that each dose of an anti-PD-1 antibody, antigen-binding fragment thereof, or a fusion protein of the disclosure is administered to the subject at a different point in time, e.g., on different days separated by a predetermined interval (e.g., hours, days, weeks or months). The present disclosure includes methods, which comprise sequentially administering to the patient a single initial dose of an anti-PD-1 antibody, antigen-binding fragment thereof, or a fusion protein of the disclosure, followed by one or more secondary doses of an anti-PD-1 antibody, antigen-binding fragment thereof, or a fusion protein of the disclosure, and optionally followed by one or more tertiary doses of an anti-PD-1 antibody, antigen-binding fragment thereof, or a fusion protein of the disclosure. An anti-PD-1 antibody, antigen-binding fragment thereof, or a fusion protein of the disclosure may be administered at a dose between 0.01 mg/kg to 100 mg/kg.

In certain embodiments, a dose of a compound or a composition is administered to a subject every day, every other day, every couple of days, every third day, once a week, twice a week, three times a week, once every two weeks, or once a month. In other embodiments, two, three or four doses of a compound or a composition is administered to a subject every day, every couple of days, every third day, once a week, once every two weeks or once a month. In some embodiments, a dose(s) of a compound or a composition is administered for 2 days, 3 days, 5 days, 7 days, 14 days, 21 days, or 28 days. In certain embodiments, a dose of a compound or a composition is administered for 1 month, 1.5 months, 2 months, 2.5 months, 3 months, 4 months, 5 months, 6 months or more.

Pharmaceutical Compositions

In another aspect, provided are pharmaceutically acceptable compositions that comprise a therapeutically effective amount of an anti-PD-1 antibody, antigen-binding fragment thereof, or a fusion protein of the disclosure formulated together with one or more pharmaceutically acceptable excipients.

The dosage of active agent(s) may vary, depending on the reason for use, the individual subject, and the mode of administration. The dosage may be adjusted based on the subject's weight, the age, and health of the subject, and tolerance for the compound(s) or composition.

The active agent and excipient(s) may be formulated into compositions and dosage forms according to methods known in the art. The pharmaceutical compositions provided herein may be specially formulated in solid or liquid form, including those adapted for parenteral administration, for example, by subcutaneous, intratumoral, intramuscular or intravenous injection as, for example, a sterile solution, or suspension.

Therapeutic compositions comprising anti-PD-1 antibodies or antigen-binding fragments thereof, or fusion proteins thereof may formulated with one or more pharmaceutically-acceptable excipients, which can be a pharmaceutically-acceptable material, composition or vehicle, such as a liquid or solid filler, diluent, carrier, manufacturing aid (e.g., lubricant, talc magnesium, calcium or zinc stearate, or steric acid), solvent or encapsulating material, involved in carrying or transporting the therapeutic compound for administration to the subject, bulking agent, salt, surfactant and/or a preservative. Some examples of materials which can serve as pharmaceutically-acceptable excipients include: sugars, such as lactose, glucose and sucrose; starches, such as corn starch and potato starch; cellulose and its derivatives, such as sodium carboxymethyl cellulose, ethyl cellulose and cellulose acetate; gelatin; talc; waxes; oils, such as peanut oil, cottonseed oil, safflower oil, sesame oil, olive oil, corn oil and soybean oil; glycols, such as ethylene glycol and propylene glycol; polyols, such as glycerin, sorbitol, mannitol and polyethylene glycol; esters, such as ethyl oleate and ethyl laurate; agar; buffering agents; water; isotonic saline; pH buffered solutions; and other non-toxic compatible substances employed in pharmaceutical formulations.

A bulking agent as referred herein may be described as a compound added to increase the mass of a pharmaceutical composition and to contribute to the physical structure of the formulation in the lyophilized form. Examples of bulking agent may include but is not limited to Suitable mannitol, glycine, polyethylene glycol, and sorbitol.

The therapeutic composition may optionally include a surfactant. The use of a surfactant can reduce aggregation of the reconstituted protein and/or reduce the formation of particulates in the reconstituted formulation. Examples of suitable surfactants that might be used according to the present disclosure includes but is not limited to polysorbates (e.g. polysorbates 20 or 80); poloxamers (e.g. poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g. lauroamidopropyl); myristamidopropyl-, palmidopropyl-, or isostearamidopropyl-dimethylamine; sodium methyl cocoyl-, or disodium methyl oleyl-taurate; and polyethyl glycol, polypropyl glycol, and copolymers of ethylene and propylene glycol (e.g. Pluronics, PF68, etc.).

A preservative may optionally be used in the therapeutic composition described herein. Suitable preservatives for use in the formulation provided herein include octadecyldimethylbenzyl ammonium chloride, hexamethonium chloride, benzalkonium chloride (a mixture of alkylbenzyl-dimethyl-ammonium chlorides in which the alkyl groups are long-chain compounds), and benzethonium chloride. Other types of preservatives include aromatic alcohols such as phenol, butyl, and benzyl alcohol, alkyl parabens such as methyl or propyl paraben, catechol, resorcinol, cyclohexanol, 3-pentanol, and m-cresol.

The therapeutic composition described herein may have a varying concentration of the anti-PD-1 antibody, antigen-binding fragment thereof, or fusion protein. For example, the compositions may comprise an anti-PD-1 antibody, antigen-binding fragment thereof or fusion protein at 10 mg/ml to 200 mg/ml, 25 mg/ml to 130 mg/ml, 50 mg/ml to 125 mg/ml, 75 mg/ml to 110 mg/ml, or 80 mg/ml to 100 mg/ml. The compositions also may comprise an anti-PD-1 antibody, antigen-binding fragment thereof or fusion protein at about 10 mg/ml, 20 mg/ml, 30 mg/ml, 40 mg/ml, 50 mg/ml, 60 mg/ml, 70 mg/ml, 80 mg/ml, 90 mg/ml, 100 mg/ml, 110 mg/ml, 120 mg/ml, 130 mg/ml, 140 mg/ml, or 150 mg/ml. In some embodiments, the therapeutic composition may be lyophilized and provided in a composition for reconstitution prior to administration.

Diagnostic Uses

The anti-PD-1 antibodies, antigen-binding fragments thereof or the fusion proteins of the present disclosure may be used to detect and/or measure PD-1 in a sample, e.g., for diagnostic purposes. The anti-PD-1 antibodies, antigen-binding fragments thereof or the fusion proteins disclosed herein may be used in an assay to detect a disease or disorder such as cancer, autoimmune disease, or chronic viral infection. Exemplary diagnostic assays for PD-1 may comprise, e.g., contacting a sample, obtained from a patient, with an anti-PD-1 antibody, antigen-binding fragment thereof, or a fusion protein of the disclosure, wherein the anti-PD-1 antibody, antigen-binding fragment thereof, or the fusion protein is labeled with a detectable label or reporter molecule or used as a capture ligand to selectively isolate PD-1 from patient samples or alternatively used in combination with a secondary antibody which is itself detectably labeled. The detectable label or reporter molecule can be a radioisotope, such as 3H, C, 32P, 35S, or 25 1; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure PD-1 in a sample include enzyme linked immunosorbent assay (ELISA), radioimmunoassay (RIA), and fluorescence-activated cell sorting (FACS).

Kits of the present disclosure can include any combination of agents, compositions, components, reagents, administration devices, or mechanisms, or other entities provided herein. For instance, a kit of the present disclosure may include one or more anti-PD-1 antibodies or antigen-binding fragments thereof or fusion proteins disclosed herein and one or more of a carrier composition, an administration device, and a combination therapy agent. Kits may further include a device to facilitate delivery such as syringe for injection or a tool that facilitates the delivery of therapeutic compositions to the subject in need thereof. Any of the kits provided herein can be included in a container, pack, or dispenser together with instructions for administration.

All other referenced patents and applications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

It is to be understood that this disclosure is not limited to the particular molecules, compositions, methodologies, or protocols described, as these may vary. Any methods and materials similar or equivalent to those described herein can be used in the practice or testing of embodiments of the present disclosure. It is further to be understood that the current disclosure in this specification includes all possible combinations of such particular features. For example, where a particular feature is disclosed in the context of a particular aspect or embodiment of the disclosure herein, or a particular claim, that feature can also be used, to the extent possible, in combination with and/or in the context of other particular aspects and embodiments of the disclosure, and in the disclosure generally.

Where reference is made herein to a method comprising two or more defined steps, the defined steps can be carried out in the order as listed, or in any order or simultaneously (except where the context excludes that possibility), and the method can include one or more other steps which are carried out before any of the defined steps, between two of the defined steps, or after all the defined steps (except where the context excludes those possibilities).

To facilitate a better understanding of the present disclosure, the following examples of specific embodiments are given. The following examples should not be read to limit or define the entire scope of the disclosure.

EXAMPLES

Example 1: Identification of Anti-PD-1 Antibodies from a Distributed Bio SuperHuman 2.0 Inc. Library hPD-1-Fc (human IgV domain fused to the N-terminal of human IgG1Fc; present as dimer in solution) or hPD-1-his (human IgV domain of PD-1 connected to the N-terminal of a six histidine peptide; present as monomer in solution) was immobilized on immuno-tubes, which were coated with an anti-his antibody or an anti-hFc antibody. Biotin-labeled hPD-1-his was captured by strepavidin-conjugated magnetic beads. The phage library was blocked with 3% PBS milk, added to the antigen-coated tubes or mixed with antigen-coated beads, and incubated at room temperature for 0.5-1 h to allow the phages to bind to the immobilized antigens. Unbound phages were washed out, while bound phages were eluted with triethlamine (pH>11). The neutralized phages were used to infect log phase E. coli, which were grown at 30° C. overnight. The harvested bacteria were used to amplify the phage for the next round panning.

The heavy and light chain variable domains of selected scFv antibodies isolated from the phage library were amplified by PCR and inserted into a mammalian expression vector containing modified human IgG 1 constant domains, from which the effector functions have been removed. The full length IgG antibodies were expressed in HEK293 cells and purified by Protein A. Purified antibodies 19B6, 19B10, 23A8, 23H9, 24H9, and 23A11 (see SEQ ID NOs: 1-48, Table 25) were characterized by binding (soluble and cell expressed PD-1) and blocking assays, Biacore kinetics analysis and cytokine secretion in SEB stimulated human PBMC.

71

Figures 2A, 2B:
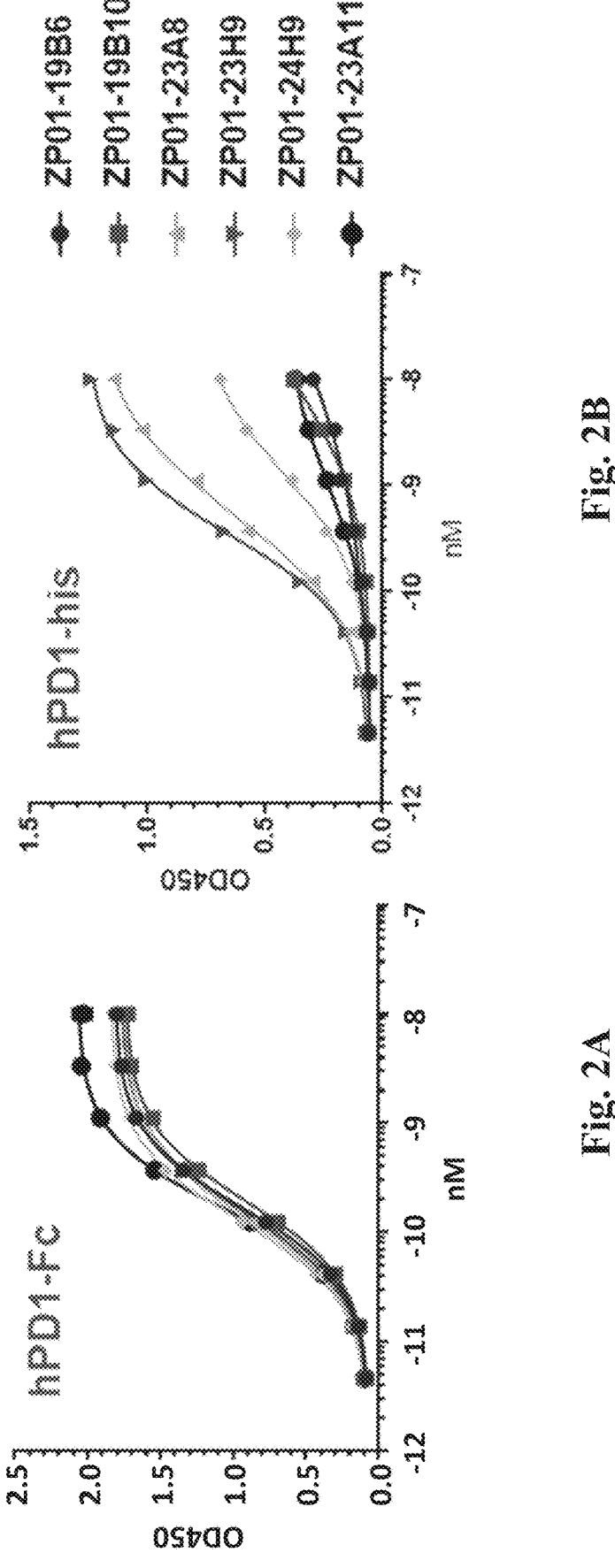
FIG. 2A and FIG. 2B illustrate the binding of antibodies 19B6, 19B10, 23A8, 23H9, 24H9, and 23A11 to hPD-1-Fc (FIG. 2A, labels as in FIG. 2B) as determined by ELISA, and to hPD-1-his (FIG. 2B).

To identify higher affinity antibodies, two light chain-shuffling libraries were constructed by combining the heavy chain of lead antibody 23H9 or 24H9, respectively, with the light chain mixture from RI panning. Higher-affinity and/or more stable variants were identified by panning in conditions that were more restricted. These matured antibodies were converted to IgG, expressed, purified, and characterized again. The higher affinity clones were expressed in CHO cells, purified by protein A and SE-HPLC to obtain higher quality to run further studies. Antibodies 31B1, 33C4, 33G8, 34C1 (see SEQ ID NOs: 49-65, Table 25) were obtained by light chain shuffling using the heavy chain of 23H9. Antibodies 32A11, 32D11, 32D2, 32G6, 38A10, 38A11, 38A4, 38A6, 38A8, 38B1, 38B10, 38B2, 38C11,

72 neutralizing with 1N $H_2SO_4$. $OD_{450}$ was read using a TECAN plate reader (Table 1). The means±S.D. of the $OD_{450}$ reading was plotted against the log antibody concentration using GraphPad Prism8. The $EC_{50}$ value was calculated by plotting log (agonist) vs. response (three parameters) or log (agonist) vs. response-variable slope (four parameters) (FIG. 2). The data points in FIG. 2 represent the mean±S.D. of duplicate determinations. All six antibodies exhibited similar $EC_{50}$ and $OD_{450}$ (10 nM) values when bound to human PD-1-Fc, but exhibited different $EC_{50}$ and $OD_{450}$ (10 nM) values when bound to PD-1-his (Table 1). Antibodies 23A8, 23H9, and 24H9 showed superior binding to hPD-1-his compared to the other antibodies (FIG. 2). Three lead antibodies-23A8, 23H9 and 24H9-were selected based on their binding to PD-1-his (Table 1 and FIG. 2).

TABLE 1

EC50 and OD at 10 nM values for binding of antibodies 19B6, 19B10, 23A8, 23H9, 24H9, and 23A11 to PD-1-Fc or PD-1-his.

| | | 19B6 | 19B10 | 23A8 | 23H9 | 24H9 | 23A11 |
|---|---|---|---|---|---|---|---|
| PD-1-Fc | EC50 [nM] | 0.168 | 0.188 | 0.135 | 0.151 | 0.128 | 0.167 |
| | OD at 10 nM | 1.81 ± 0.00 | 1.73 ± 0.03 | 1.74 ± 0.00 | 1.75 ± 0.08 | 1.84 ± 0.01 | 2.04 ± 0.08 |
| PD-1-his | EC50 [nM] | >100 | 5.34 | 0.523 | 0.350 | 1.31 | 1.00 |
| | OD at 10 nM | 0.30 ± 0.03 | 0.38 ± 0.01 | 1.15 ± 0.04 | 1.25 ± 0.02 | 0.69 ± 0.00 | 0.27 ± 0.02 |

38C6, 38G11, 38G9, 38H3, 39A3, 39B11, 39B3, 39B6, 39F11, 39G5, 39G8, 39H11, 39H2, and 39H7 (see SEQ ID NOs: 66-138, Table 25) were obtained by light chain shuffling using the heavy chain of 24H9.

FIG. 1 represents the sequence alignments of exemplary antibodies generated herein. Table 25 sets forth the amino acid sequence identifiers of the heavy and light chain variable regions and CDRs of selected anti-PD-1 antibodies according to the Kabat CDR definition. The biological properties of the exemplary antibodies generated in accordance with the methods of this Example are described in detail in the Examples set forth below.

Example 2: Antibodies Isolated from Phage Display Library Bind to hPD-1

Figure 3:
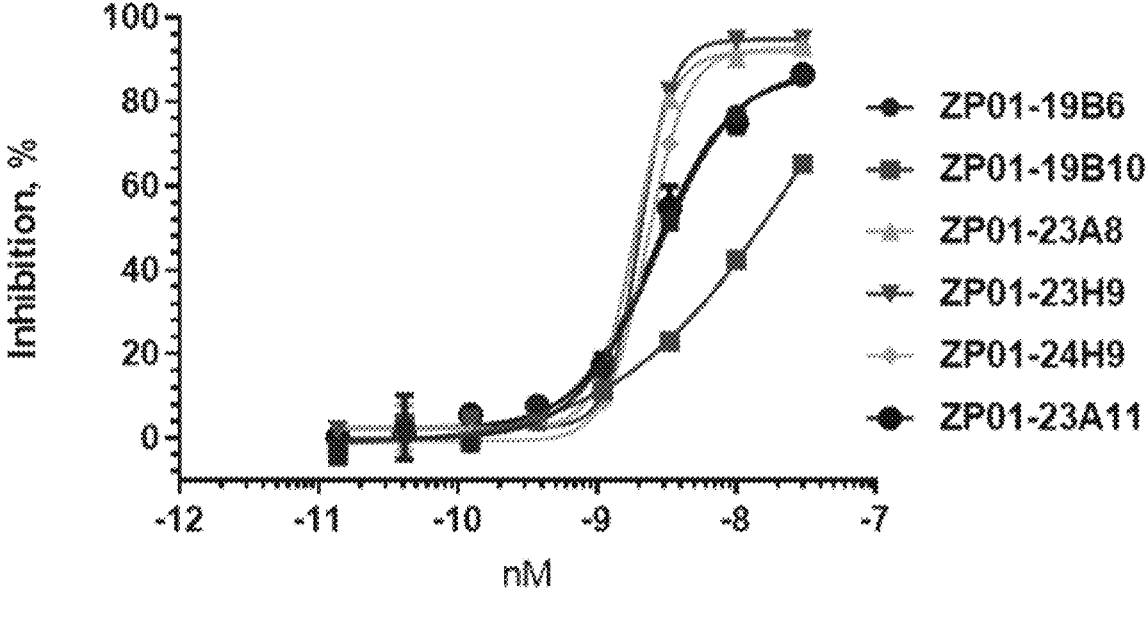
FIG. 3 depicts the ability of antibodies 19B6, 19B10, 23A8, 23H9, 24H9, and 23A11 to block interaction between hPD-1 to hPD-L1.

The ability of anti-hPD1 antibodies 19B6, 19B10, 23A8, 23H9, 24H9, 23A11 (isolated from HEK293 cells) to bind to hPD1 was evaluated using a dose response binding ELISA using the indicated antibodies as primary antibodies. For this, high-binding (Immulon 2HB) plates were directly coated with human PD-1-Fc (R&D, cat #1086-PD-050). Biotin labeled hPD-1-his (Sino Biologicals, cat #10377-H08H) were captured by strepavidin (Jackson 016-000-114) or anti-his antibody (R&D, cat #MAB050-100) which were coated on the plate one day before. Serial dilutions of antibodies 19B6, 19B10, 23A8, 23H9, 24H9, and 23A11 were added to antigen-coated plates and incubated at room temperature for 1-2 hs. After washing the plates with PBST (0.05%) for three times, 1/5000-1/10,000 diluted anti-hFab-HRP antibody (Jackson 109-036-097) was added to the plates, which were incubated at room temperature for about 1 h. Color was developed by adding 1:1 dilution of substrate A and B from TMB (Fisher, cat #5120-0050) followed by Example 3: Antibodies Isolated from Phage Display Library Block hPD-1/hPD-L1 Interactions To examine the ability of anti-hPD1 antibodies 19B6, 19B10, 23A8, 23H9, 24H9, 23A11 (isolated from HEK293 cells) to block hPD-1/hPD-L1 interactions, high-binding (Immulon 2HB) plates were coated with human PD-L1-Fc (R&D, cat #156-B7-100) or PD-L2-Fc (R&D, cat #1224_PL), respectively, and blocked with 3% PBS milk. Serial dilutions of antibodies 19B6, 19B10, 23A8, 23H9, 24H9, and 23A11 were mixed with 0.5 µg/ml (final concentration) of biotin labeled hPD-1-Fc and incubated at room temperature for 1 h. The mixture was transferred to the PD-L1-Fc or PD-L2-Fc coated plate and incubated at RT for additional 1-2 h. After washing plate with PBST (0.05%) three times, 1/5000-1/10,000 diluted Strepavidin-HRP (Thermofisher, cat #21140) was added to the plates, which were incubated at room temperature for about 1 h. Color was developed by adding 1:1 dilution of substrate A and B from TMB, followed by neutralizing with 1N $H_2SO_4$. $OD_{450}$ was read using a TECAN plate reader (Table 2). The means±S.D. of OD reading was plotted against the log antibody concentration using GraphPad Prism8. The EC50 value was calculated by analyzing log (agonist) vs. response (three parameters) or log (agonist) vs. –response variable slope (four parameters). The data points are the means±S.D. of duplicate determinations (FIG. 3). All six antibodies were found to block hPD-1-Fc binding to human PD-L1 with different IC50 values (Table 2 and FIG. 3). All six antibodies have very similar affinity to hPD-Fc. However, antibodies 23A8, 23H9 and 24H9 showed superior blocking activity to hPD-1-his compared to the other antibodies (Table 2 and FIG. 3). The three lead clones 23A8, 23H9, and 24H9 showed >93% inhibition and ≥70% inhibition in the presence of 30 and 3.3 nM antibody, respectively (Table 2 and FIG. 3).

TABLE 2

| Blocking of hPD-1 to hPD-L1 by antibodies 19B6, 19B10, 23A8, 23H9, 24H9, and 23A11. | | | | | | |
| --- | --- | --- | --- | --- | --- | --- |
| Blocking ELISA | 19B6 | 19B10 | 23A8 | 23H9 | 24H9 | 23A11 |
| IC50 [nM] | 2.69 | 28.1 | 1.85 | 2.04 | 2.28 | 2.61 |
| Inhibition % (30 nM) | 85.9 ± 0.8 | 65.2 ± 0.6 | 93.1 ± 0.2 | 94.7 ± 0.14 | 92.9 ± 0.1 | 86.6 ± 3.0 |
| Inhibition % (3.3 nM) | 51.9 ± 2.1 | 22.9 ± 2.4 | 80.5 ± 1.0 | 82.5 ± 0.4 | 70.0 ± 1.1 | 54.9 ± 7.1 |

Example 4: Antibodies Isolated from Phage Display Library Bind to Cells Expressing Human PD-1

Figure 4A:
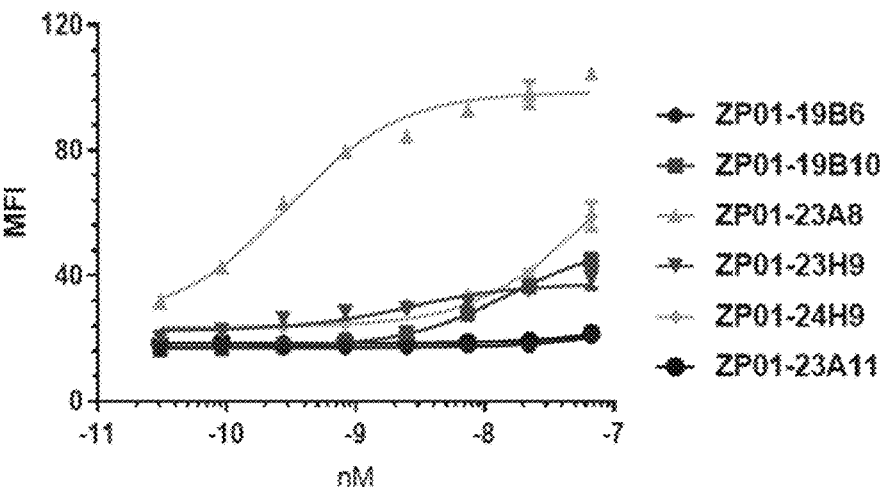
FIG. 4A, FIG. 4B, and FIG. 4C illustrate the binding of antibodies 19B6, 19B10, 23A8, 23H9, 24H9, and 23A11 to hPD-1-293 cells (FIG. 4A), to SEB-activated PBMC from donor "EA" (low PD-1 expression) (FIG. 4B), and to SEB-activated PBMC from donor "AF" (high PD-1 expression) (FIG. 4C), respectively.
Figure 4B:
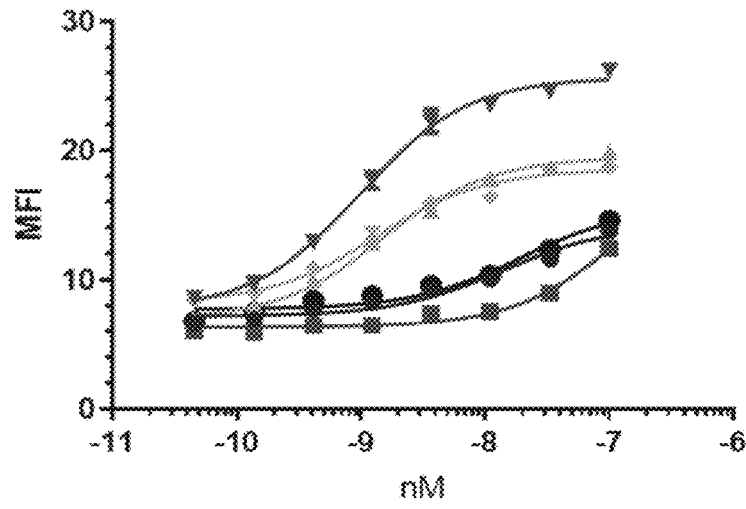
Figure 4C:
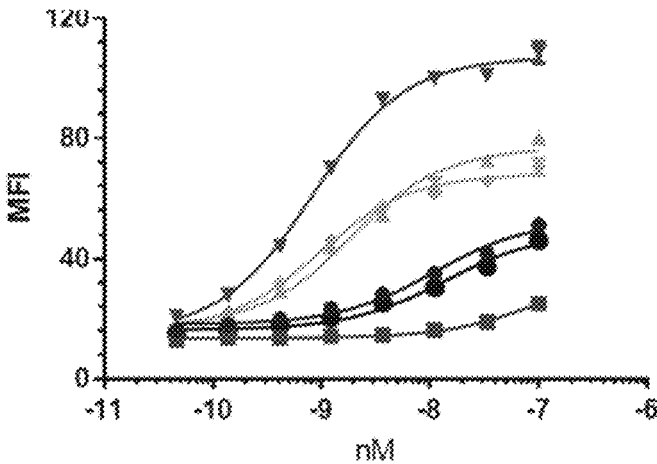

Binding of anti-PD-1 antibodies to HEK293 and Jurkat cells over-expressing human PD-1: Cells were cultured in IMDM medium with glutamine, supplemented with 10% heat-inactive fetal bovine serum (FBS). Cells were first incubated with the indicated anti-PD-1 antibodies, followed HT Sampling Flow Cytometer (EMD Millipore). Data points were generated by calculating the means±S.D. of duplicate determinations (Table 3 and FIG. 4). Antibodies 19B6, 23A8, 23H9, and 24H9 exhibited the highest MFI and lowest EC50 for binding to PBMCs among the antibodies tested and were selected for further characterization (Table 3 and FIG. 4).

TABLE 3

| Binding of indicated anti-PD-1 antibodies to (1) hPD-1-293 cells, (2) SEB-activated PBMCs from donor "EA" (low PD-1 expression), and (3) SEB-activated PBMCs from donor "AF" (high PD-1 expression). | | | | | | | |
| --- | --- | --- | --- | --- | --- | --- | --- |
| Binding to cell-expressed PD1 | | 19B6 | 19B10 | 23A8 | 23H9 | 24H9 | 23A11 |
| hPD1-293 | EC50 [nM] | Very low | 16.0 | 0.299 | 2.53 | 58.7 | Very low |
| | MFI at 68 nM | 20.84 ± 0.48 | 45.07 ± 0.0 | 104.85 ± 1.68 | 38.84 ± 4.03 | 59.04 ± 6.30 | 21.77 ± 0.16 |
| SEB activated PBMC, donor EA | EC50 [nM] | 13.6 | 117 | 1.51 | 0.993 | 1.37 | 19.0 |
| | MFI at 100 nM | 13.74 ± 0.05 | 12.41 | 19.88 ± 0.28 | 26.19 ± 0.18 | 18.71 ± 0.24 | 14.58 ± 0.01 |
| SEB activated PBMC, donor AF | EC50 [nM] | 10.7 | 104 | 1.89 | 0.829 | 0.913 | 13.4 |
| | MFI at 100 nM | 51.23 ± 1.73 | 25.19 ± 0.15 | 80.29 ± 1.33 | 108.59 ± 5.01 | 70.52 ± 3.74 | 46.19 ± 1.18 | by incubation with an PE-anti human IgG1-Fc (R-phyco-erythrin-conjugated goat anti-human IgG: Jackson Immu-noResearch cat #109-116-098). Antibody binding to hPD-1 was determined using a flow cytometry Guava EasyCyte™ HT Sampling Flow Cytometer (EMD Millipore). The data points in FIG. 4 were represent the mean±S.D. of duplicate determinations. Antibodies 23A8, 23H9, and 19B10 showed strongest binding to HEK 293 cells and antibodies 23A8, 24H9, and 19B10 showed highest mean fluorescence intensity (MFI) (Table 4 and FIG. 4).

Binding of anti-PD-1 antibodies to SEB-activated human PBMCs: PBMCs were isolated from LeukoPak (an enriched leukapheresis containing highly concentrated blood cells including monocytes, lymphocytes, platelets, plasma, as well as red cells) using Histopaque-1077 (Sigma) using the manufacturer's instructions. PBMCs were cultured at 2×10⁶/ mL in a 12-well plate containing IMDM (Gibco, Life Technologies) supplemented with 10% FBS (GE Healthcare HyClone) and activated by 1 μg/mL SEB (Staphylococcal enterotoxin B, Sigma) for 3 to 4 days. Activated PBMCs were first incubated with indicated anti-PD-1 antibodies, followed by incubation with a combination of PE-anti human IgG₁-Fc (R-phycoerythrin-conjugated goat anti-human IgG: Jackson ImmunoResearch cat #109-116-098) and either anti human CD4-APC (eBioscience clone RPA-T4 cat #17-0049-42) or anti human CD8-APC (eBioscience clone RPA-T8 cat #17-0088-42). Antibody binding to PD-1 expressed on cells was evaluated using a Guava EasyCyte™

Example 5: Antibodies Isolated from Phage Display Library Disrupt Intercellular PD-1/PD-L1 Interactions To assess the ability of selected anti-PD-1 antibodies to disrupt the binding of PD-1 expressing cells to PD-L1 expressing cells, the Promega PD-1/PD-L1 Blockade Bio-assay was used. This assay consists of two genetically engineered cell lines, PD-1 effector cells and PD-L1 aAPC/ CHO-K1 cells. When co-cultured, the PD-1/PD-L1 interaction inhibits TCR-mediated luminescence. When the PD-1/ PD-L1 interaction is disrupted, TCR activation induces luminescence (via activation of the NFAT pathway) that can be detected by addition of Bio-Glo™ Reagent and quantitation with a luminometer.

Figures 5A, 5B:
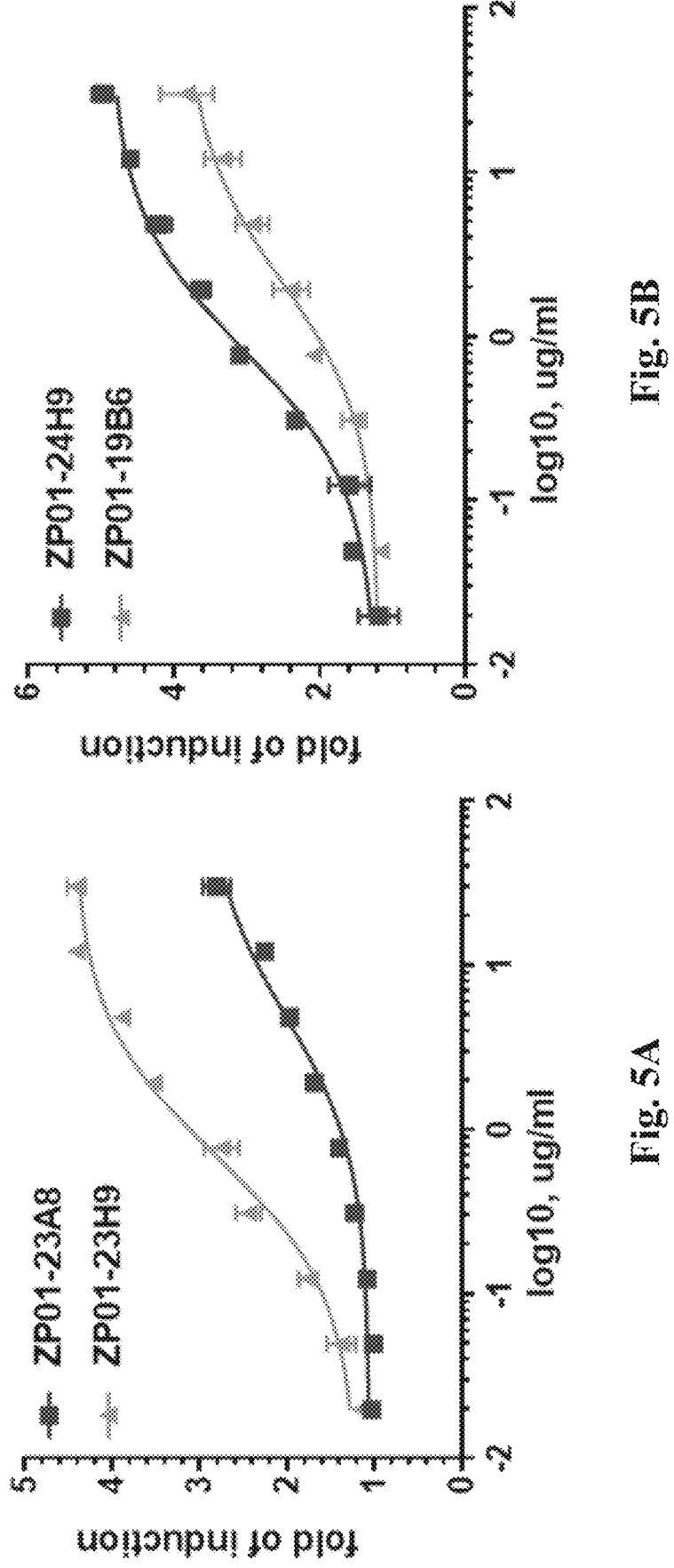
FIG. 5A and FIG. 5B illustrate the ability of antibodies 23A8 and 23H9 (FIG. 5A) as well as 19B6 and 24H9 (FIG. 5B) to block interactions between hPD-1 and hPD-L1.

The experiment was performed according to the manufacturer's instructions. Briefly, PD-L1 aAPC/CHO-K1 cells were plated and incubated for 16-20 h prior to the addition of increasing concentrations of anti-PD-1 antibodies and PD-1 effector cells. After 6 h of incubation at 37° C., Bio-Glo™ Reagent was added and luminescence (recorded as relative light unites, RLU) was measured by using a TECAN plate reader. Fold induction was calculated by RLU (induced-background)/RLU (no antibody control-back-ground). Data points are represented as means±S.D. of duplicate determinations (FIG. 5). Antibodies 19B6, 23A8, 23H9 and 24H9 blocked hPD-1/hPD-L1 interaction with different EC50s and fold induction (Table 4 and FIG. 5).

TABLE 4

| Blocking of hPD-1/hPD-L1 interactions by antibodies 19B6, 23A8, 23H9, and 24H9. | | | | |
|---|---|---|---|---|
| | 23A8 | 23H9 | 24H9 | 19B6 |
| EC 50, μg/mL | 4.73 | 0.688 | 0.823 | 2.127 |
| Fold of induction | 2.81 ± 0.16 | 4.42 ± 0.11 | 3.96 ± 0.12 | 3.04 ± 0.29 |

Antibodies 23H9 and 24H9 were selected for light chain shuffling, wherein the heavy chains of 23H9 or 24H9, respectively, were paired with a library of light chains. Antibodies 31B1, 33C4, 33G8, 34C1 (see SEQ ID NOs: 49-65, Table 25) were obtained by light chain shuffling using the heavy chain of 23H9. Antibodies 32A11, 32D11, 32D2, 32G6, 38A10, 38A11, 38A4, 38A6, 38A8, 38B1, 38B10, 38B2, 38C11, 38C6, 38G11, 38G9, 38H3, 39A3, 39B11, 39B3, 39B6, 39F11, 39G5, 39G8, 39H11, 39H2, and 39H7

(see SEQ ID NOs: 66-138, Table 25 were obtained by light chain shuffling using the heavy chain of 24H9.

Figure 6A:
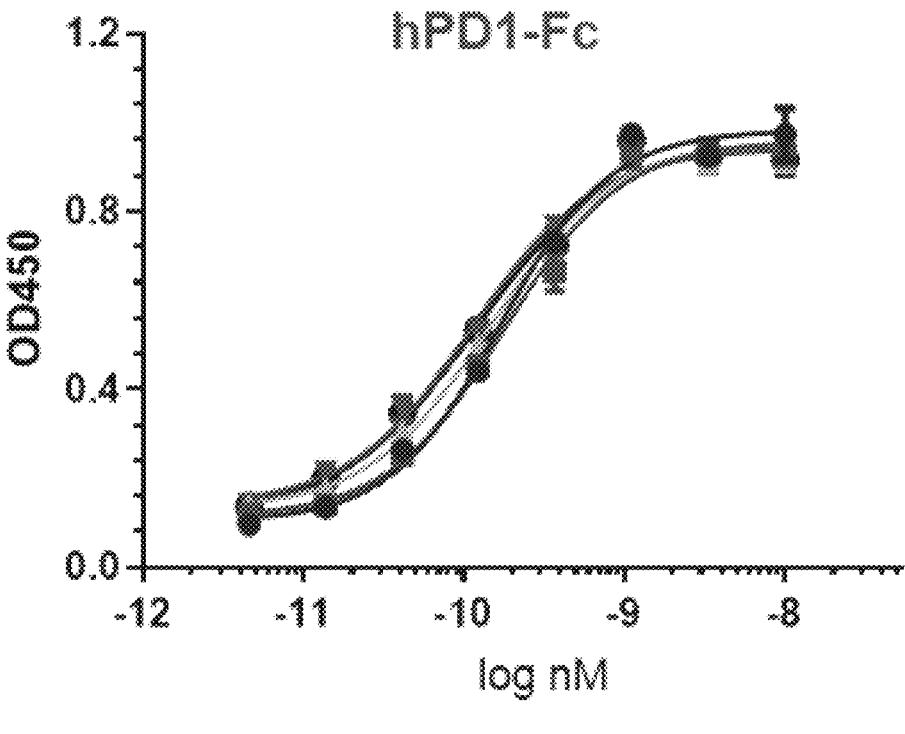
FIG. 6A, FIG. 6B, FIG. 6C, and FIG. 6D depict binding of antibodies 23H9, 31B1, 33C4, 33G8, and 34C1 to hPD-1-Fc (FIG. 6A, same labels as FIG. 6B), binding to strepavidin-captured biotin-hPD-1-his (FIG. 6B), binding to ahis-captured hPD-1-his (FIG. 6C, same labels as FIG. 6D), and blocking of hPD-1-Fc/hPD-L1-Fc interaction (FIG. 6D). No significant difference was observed between the parental antibody 23H9 and its derivatives (FIG. 6A and FIG. 6B). All derivatives had lower EC50 and higher inhibition values than the parental antibody (FIG. 6C and FIG. 6D).
Figure 6B:
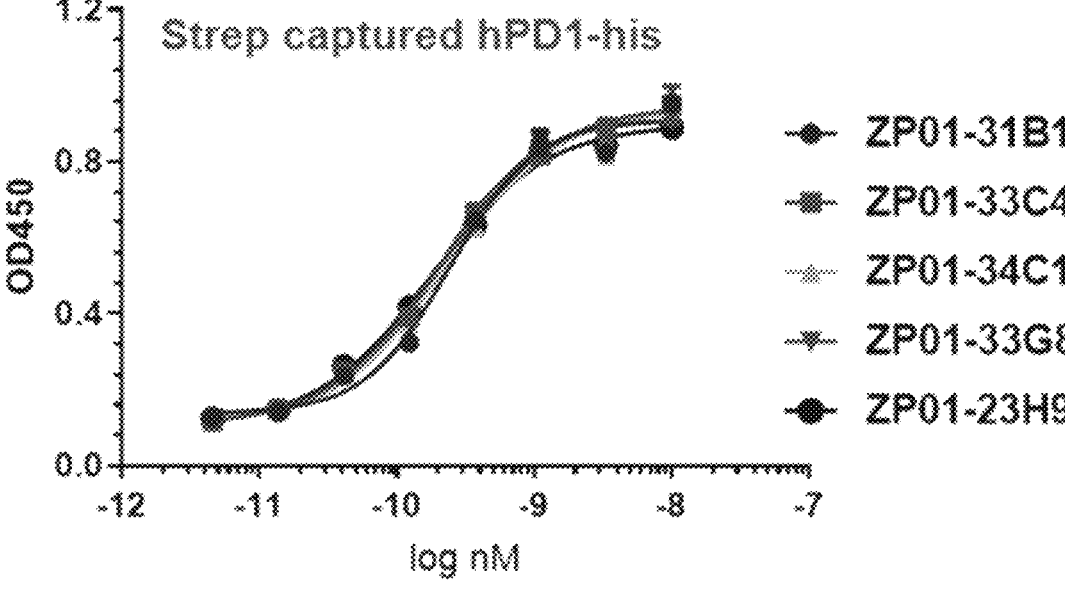
Figure 6C:
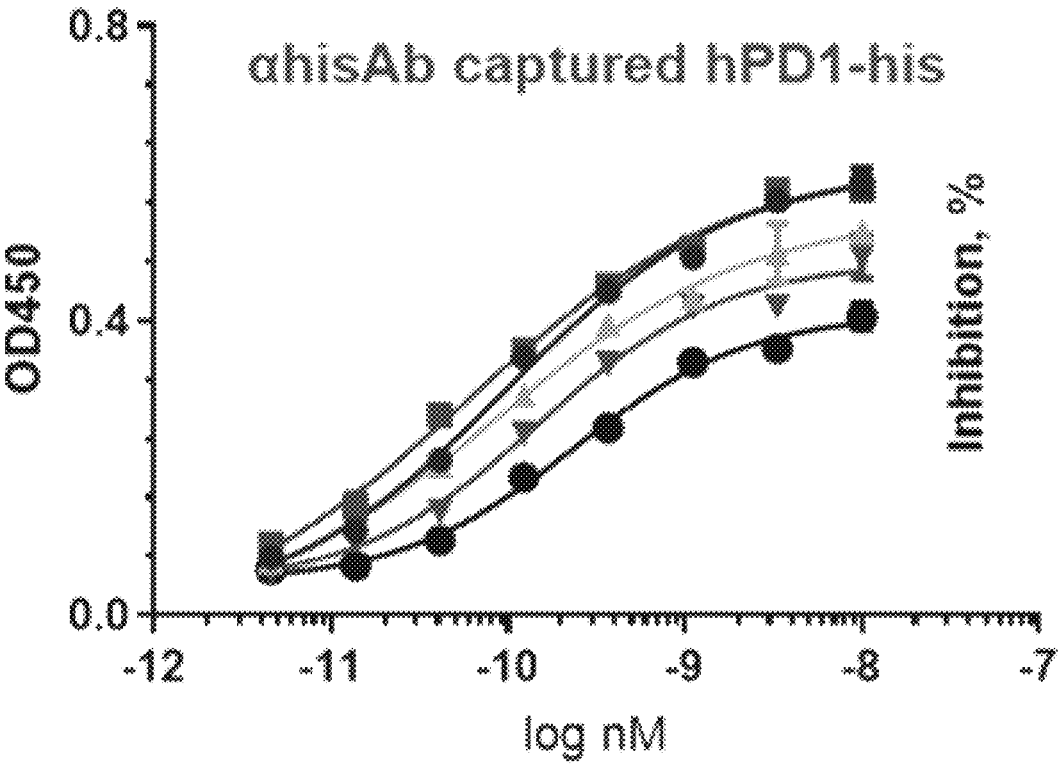
Figure 6D:
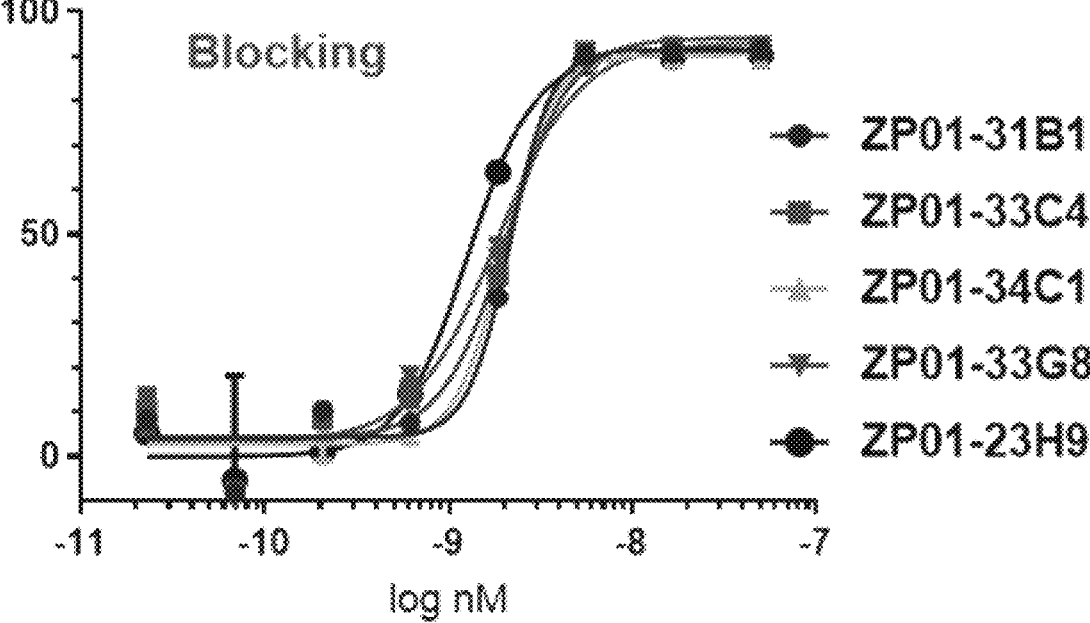

Example 6: Anti-hPD-1 Antibody 23H9 and its Derivatives Bind to hPD-1 and Block hPD-1/hPD-L1 Interactions The ability of anti-hPD1 antibody 23H9 and its derivatives 31B1, 33C4, 33G8, and 34C1 to bind to hPD1 and to block hPD-1/hPD-L1 interactions was determined using the protocols described in Examples 2 and 3, respectively. The parental antibody 23H9 and its derivatives showed no significant difference in binding to hPD-1-Fc and biotin-hPD-1-his captured by strepavidin (Table 5 and FIG. 6A). However, all derivatives were more potent than their parental 23H9 in binding to the anti-his captured hPD-1-his and in blocking interactions of hPD-1-F/hPD-L1-Fc (Table 5 and FIG. 6B). Two clones (31B1 and 33C4) were selected for further characterization (Table 5).

TABLE 5

| Binding of antibodies 23H9, 31B1, 33C4, 33G8, and 34C1 to hPD-1-Fc, binding to strepavidin-captured biotin-hPD-1-his, binding to ahis-captured hPD-1-his, and blocking of hPD-1-Fc/hPD-L1-Fc interaction. | | | | | | | |
|---|---|---|---|---|---|---|---|
| | | Binding/blocking ELISA | 23H9 | 31B1 | 33C4 | –34C1 | 33G8 |
| Binding | hPD1-Fc | EC50, nM | 0.121 | 0.167 | 0.177 | 0.147 | 0.113 |
| | | OD450 at 10 nM | 0.916 ± 0.045 | 0.974 ± 0.082 | 0.925 ± 0.009 | 0.926 ± 0.045 | 0.900 ± 0.006 |
| | Biotin-hPD-1-his captured by Strep | EC50, nM | 0.18 | 0.244 | 0.209 | 0.233 | 0.197 |
| | | OD450 at 10 nM | 0.890 ± 0.004 | 0.953 ± 0.006 | 0.950 ± 0.069 | 0.945 ± 0.014 | 0.909 ± 0.028 |
| | hPD-1-his captured by anti-his | EC50, nM | 0.238 | 0.095 | 0.061 | 0.0866 | 0.149 |
| | | OD450 at 10 nM | 0.406 ± 0.024 | 0.590 ± 0.026 | 0.578 ± 0.015 | 0.521 ± 0.009 | 0.487 ± 0.040 |
| Blocking | PD1/PD-L1 | IC50, nM | 1.27 | 2.15 | 2.06 | 2.01 | 1.81 |
| | | Inhibition % at 50 nM | 90.4 ± 0.3 | 91.4 ± 0.2 | 92.5 ± 0.0 | 89.3 ± 0.1 | 90.5 ± 0.2 |
| | | Inhibition % at 5.6 nM | 88.6 ± 0.5 | 90.2 ± 0.3 | 91.2 ± 0.2 | 89.1 ± 0.1 | 89.9 ± 1.2 |

Figure 7:
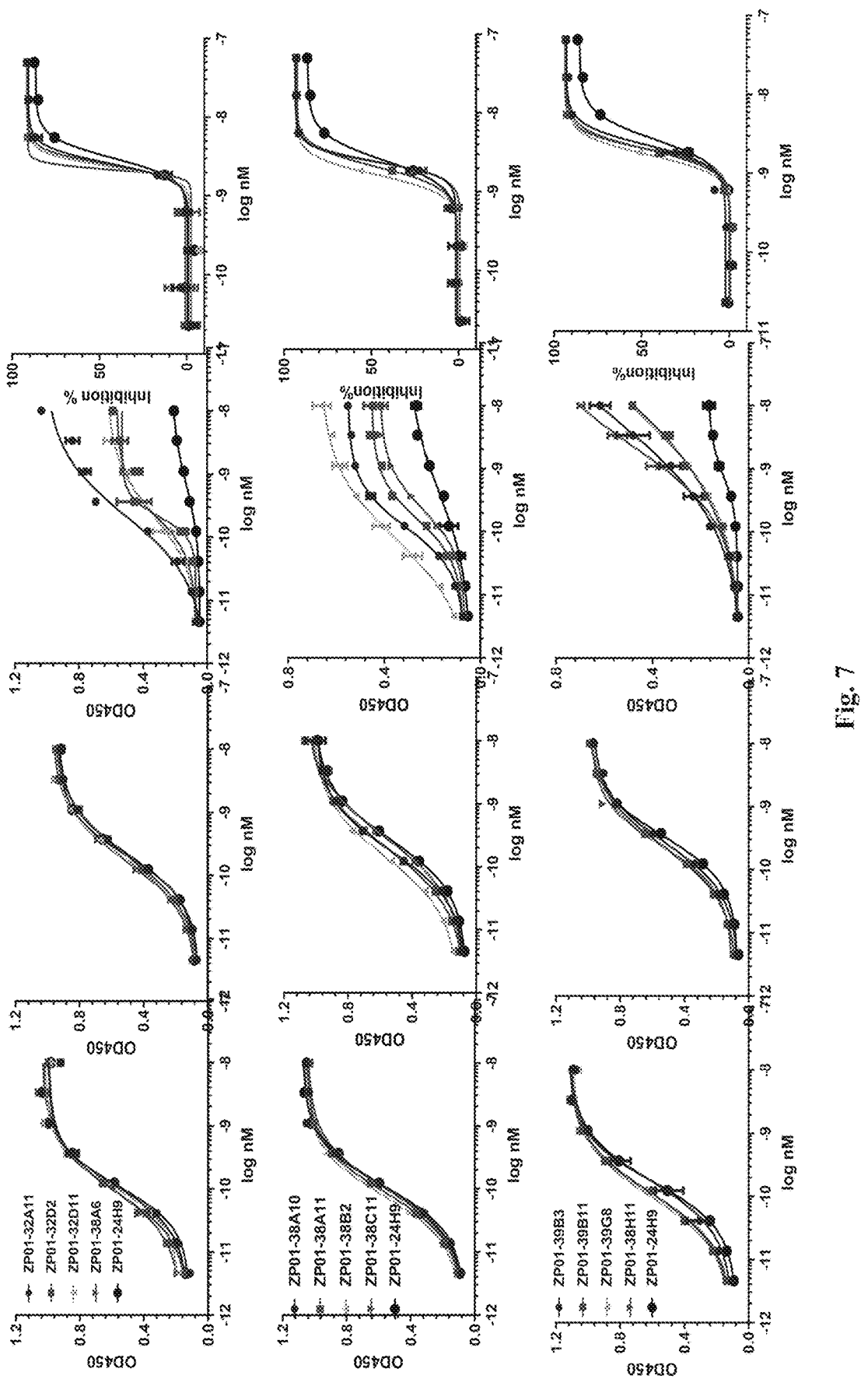
FIG. 7 depicts binding of antibodies 24H9, 32A11, 32D2, 32D11, 38A6, 38A10, 38A11, 38B2, 38C11, 39B3, 39B11, 39G8 and 38H11 to hPD-1-Fc (first, far left column), binding to strepavidin-captured hPD-1-his (second column), binding to ahis captured hPD-1-his (third column), and blocking of hPD-1/hPD-L1 interactions (fourth column).
Figure 8A:
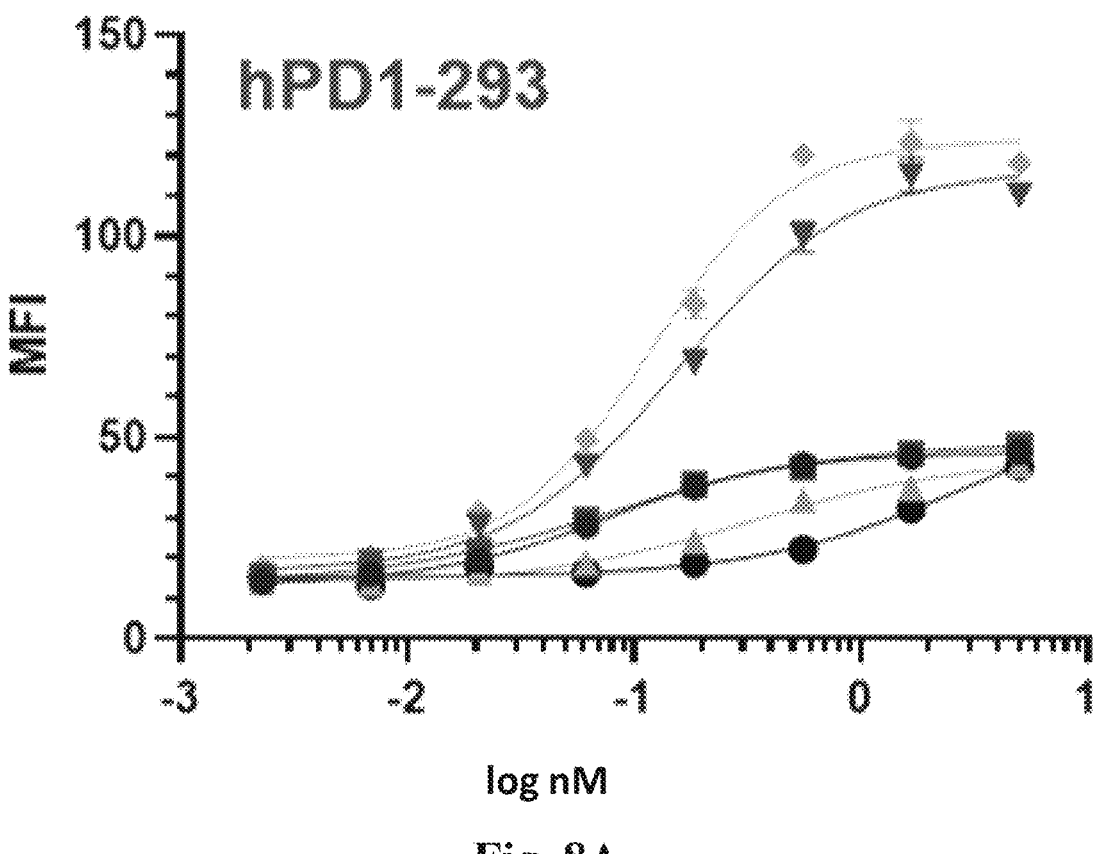
FIG. 8A, FIG. 8B, FIG. 8C, and FIG. 8D depict binding of antibodies 31B1, 33C4, 23H9, 38A6, 24H9, and 38B2 to hPD-1-293 cells (FIG. 8A, same labels as FIG. 8B) and hPD-1 Jurkat cells (FIG. 8B) as well as binding to SEB-activated PBMC from donor FA (FIG. 8C, same labels as FIG. 8D) and donor FB (FIG. 8D).
Figure 8B:
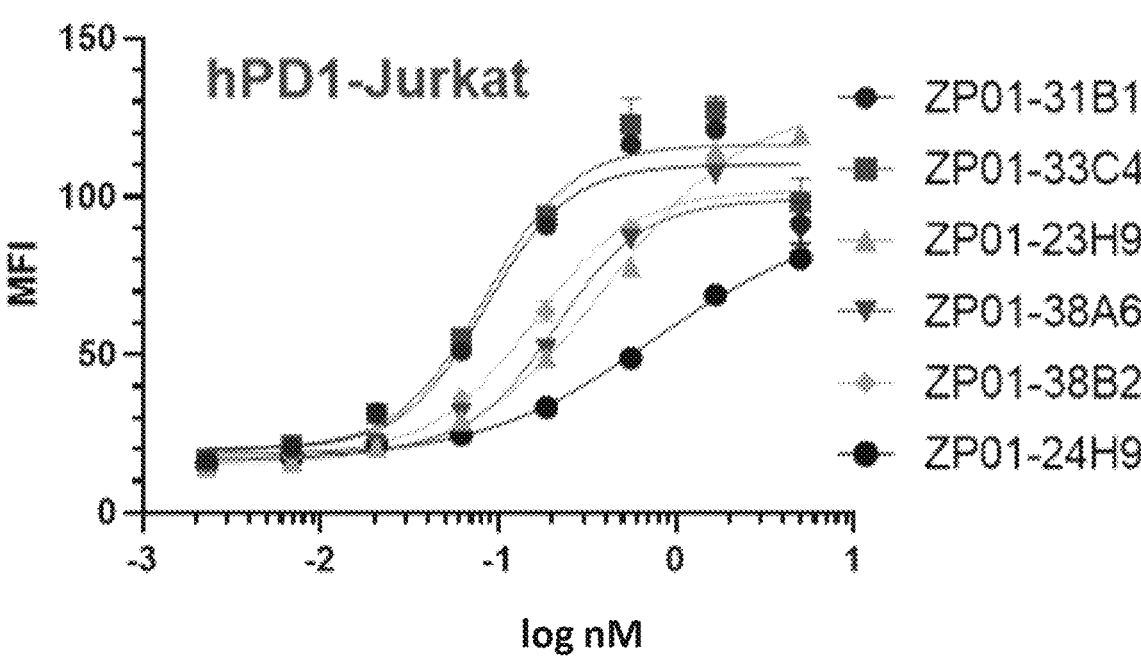
Figure 8C:
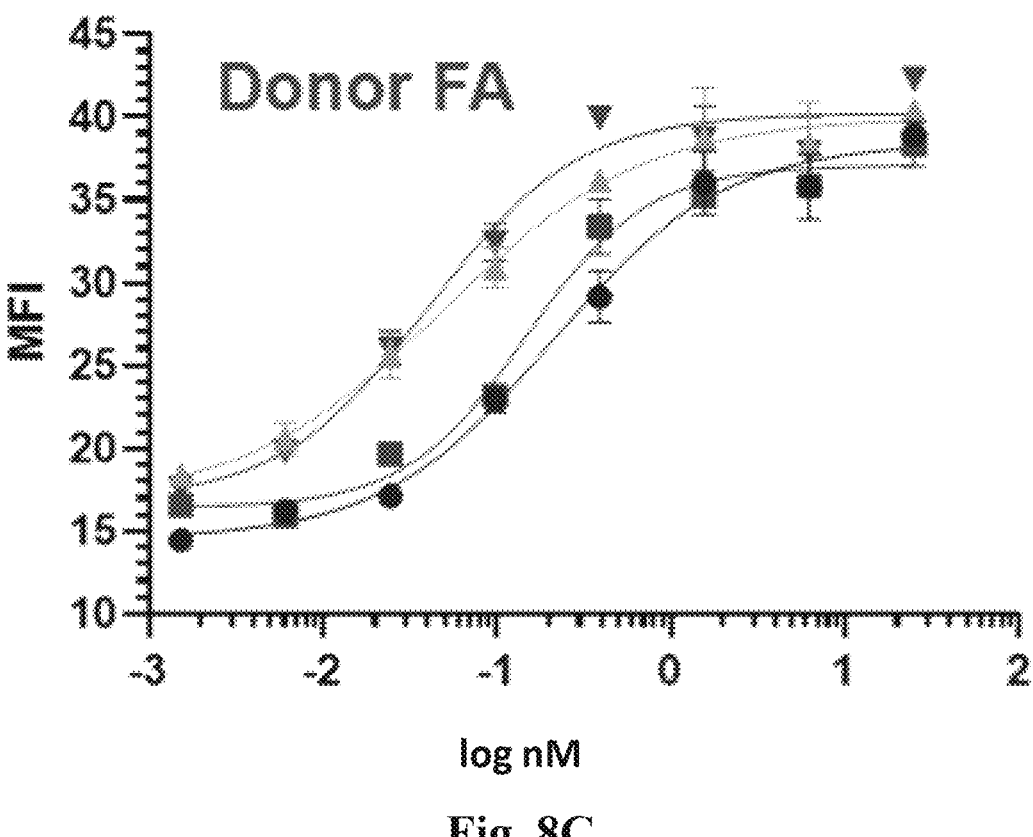
Figure 8D:
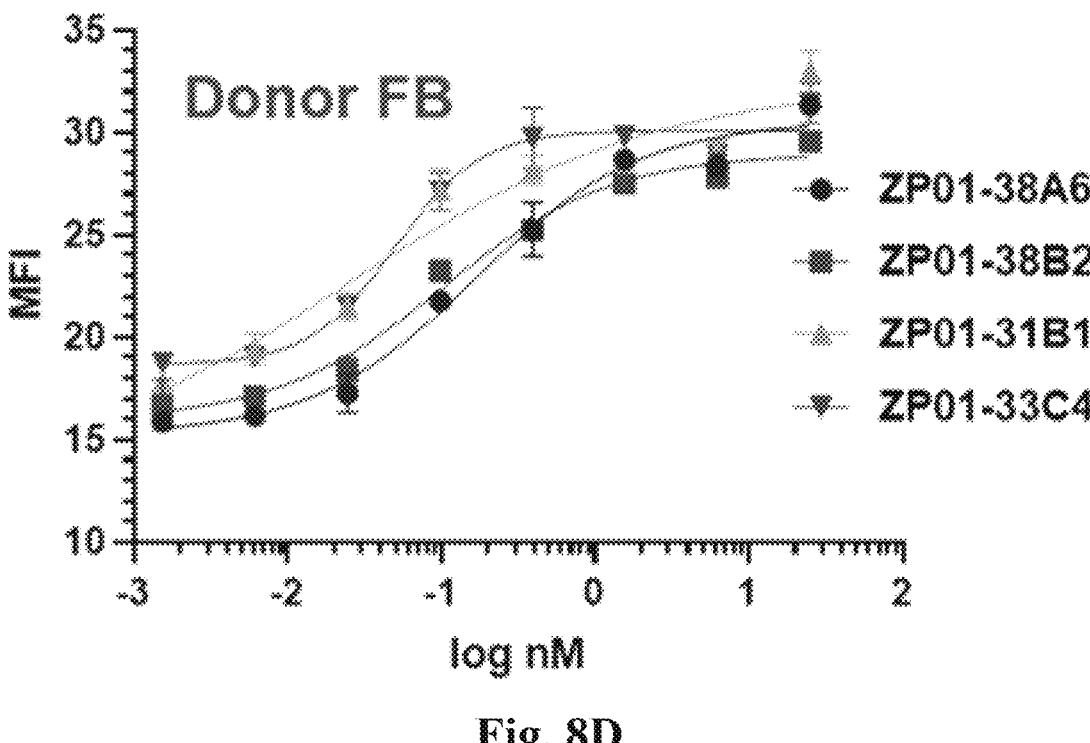

Example 7: Anti-hPD-1 Antibody 24H9 and its Derivatives Bind to hPD-1 and Block hPD-1/hPD-L1 Interactions The ability of anti-hPD1 antibody 24H9 and its derivatives 32A11, 32D2, 32D11, 38A6, 38A10, 38A11, 38B2, 38C11, 39B3, 39B11, 39G8 and 38H11 to bind to hPD1 and to block hPD-1/hPD-L1 interactions was determined using the protocols described in Examples 2 and 3, respectively. The parental antibody 24H9 and its derivatives showed no significant difference in binding to hPD-1-Fc and hPD-1-his captured by strepavidin (FIG. 7). However, all derivatives were found to be more potent than parental 24H9 in binding to the anti-his captured hPD-1-his and blocking interaction of hPD-1-Fc-hPD-L1-Fc (FIG. 7). Two clones (38A6 and 38B2) were picked for further characterization (Table 6).

TABLE 6

| Binding of antibodies 24H9, 32A11, 32D2, 32D11, 38A6, 38A10, 38A11, 38B2, 38C11, 39B3, 39B11, 39G8 and 38H11 to hPD-1-Fc, binding to strepavidin-captured hPD-1-his, binding to αhis captured hPD-1-his, and blocking of hPD-1/hPD-L1 interaction. | | | | | | | | |
|---|---|---|---|---|---|---|---|---|
| | hPD-1-Fc | | Strep captured PD-1-his | | Anti-his captured PD-1-his | | Blocking | |
| Name | EC50 | OD at 10 nM | EC50 | OD at 10 nM | EC50 | OD at 10 nM | IC50 | Inhibition at 50 nM |
| 24H9 | 0.117 | 0.982 ± 0.007 | 0.206 | 0.915 ± 0.019 | 0.738 | 0.207 ± 0.006 | 3.073 | 87.4 ± 0.5 |
| 32A11 | 0.109 | 0.921 ± 0.003 | 0.21 | 0.919 ± 0.005 | 0.221 | 1.035 ± 0.003 | 2.639 | 91.1 ± 0.0 |

TABLE 6-continued

Binding of antibodies
24H9, 32A11, 32D2, 32D11, 38A6, 38A10, 38A11, 38B2, 38C11,
39B3, 39B11, 39G8 and 38H11 to hPD-1-Fc, binding to strepavidin-captured
hPD-1-his, binding to αhis captured hPD-1-his, and blocking of hPD-1/hPD-L1 interaction.

| | hPD-1-Fc | | Strep captured PD-1-his | | Anti-his captured PD-1-his | | Blocking | |
|---|---|---|---|---|---|---|---|---|
| Name | EC50 | OD at 10 nM | EC50 | OD at 10 nM | EC50 | OD at 10 nM | IC50 | Inhibition at 50 nM |
| 32D2 | 0.084 | 0.922 ± 0.027 | 0.203 | 0.932 ± 0.027 | 0.216 | 0.591 ± 0.010 | 2.581 | 91.7 ± 0.1 |
| 32D11 | 0.114 | 0.952 ± 0.039 | 0.177 | 0.935 ± 0.004 | 0.229 | 0.602 ± 0.013 | 2.418 | 91.9 ± 0.1 |
| 38A6 | 0.102 | 0.993 ± 0.004 | 0.175 | 0.948 ± 0.013 | 0.217 | 0.576 ± 0.001 | 2.183 | 91.7 ± 0.2 |
| 24H9 | 0.11 | 1.050 ± 0.018 | 0.272 | 0.994 ± 0.035 | 0.043 | 0.267 ± 0.028 | 2.535 | 86.8 ± 0.4 |
| 38A10 | 0.112 | 1.057 ± 0.025 | 0.19 | 1.003 ± 0.088 | 0.117 | 0.552 ± 0.002 | 2.402 | 92.8 ± 1.1 |
| 38A11 | 0.089 | 1.033 ± 0.014 | 0.204 | 1.069 ± 0.002 | 0.157 | 0.447 ± 0.056 | 2.088 | 93.2 ± 0.1 |
| 38B2 | 0.079 | 1.051 ± 0.004 | 0.145 | 1.044 ± 0.011 | 0.076 | 0.662 ± 0.053 | 1.63 | 93.4 ± 0.0 |
| 38C11 | 0.104 | 1.020 ± 0.024 | 0.293 | 1.049 ± 0.019 | 0.229 | 0.404 ± 0.024 | 2.384 | 92.7 ± 0.0 |
| 24H9 | 0.171 | 1.092 ± 0.010 | 0.336 | 0.971 ± 0.013 | 0.797 | 0.165 ± 0.034 | 2.698 | 86.5 ± 0.3 |
| 39B3 | 0.179 | 1.079 ± 0.009 | 0.264 | 0.963 ± 0.008 | 5.013 | 0.617 ± 0.061 | 2.315 | 92.9 ± 0.1 |
| 39B11 | 0.116 | 1.082 ± 0.011 | 0.234 | 0.990 ± 0.001 | 23.98 | 0.482 ± 0.014 | 2.023 | 93.3 ± 0.0 |
| 39G8 | 0.099 | 1.063 ± 0.019 | 0.224 | 0.981 ± 0.019 | 4.982 | 0.484 ± 0.006 | 1.732 | 93.2 ± 0.0 |
| 38H11 | 0.115 | 1.083 ± 0.018 | 0.235 | 0.956 ± 0.014 | 2.146 | 0.699 ± 0.022 | 2.05 | 93.6 ± 0.1 |

Example 8: The Binding Profile of 23H9 and 24H9 Derivatives Indicate that these Antibodies Bind to Different Binding Epitopes Dose response binding assay using 23H9, 31B1, 33C4, 24H9, 38A6, and 38B2 were performed according to the protocol disclosed in Example 4. The results are shown in FIG. 8. 23H9 derivatives and 24H9 derivatives were found to be more potent in binding to PD-1 expressing cells than their parental antibodies (Table 7). Further, 23H9 derivatives and 24H9 derivatives showed different binding profiles, indicating indicated they bind to different binding epitopes (FIG. 8).

TABLE 7

Binding of indicated antibodies to hPD-1-293 and
hPD-1 Jurkat, and SEB-activated PBMC from donor "FA" and "FB".

| | | 23H9 | 31B1 | 33C4 | 24H9 | 38A6 | 38B2 |
|---|---|---|---|---|---|---|---|
| hPD1-293 | EC50, nM | 0.33 | 0.077 | 0.075 | 2.69 | 0.15 | 0.12 |
| | MFI at 5 nM | 43.01 | 46.4 ± 0.2 | 48.2 ± 1.6 | 42.79 | 110.3 ± 2.5 | 118.3 ± 0.3 |
| hPD1-Jurkat | EC50, nM | 0.42 | 0.084 | 0.084 | 0.77 | 0.21 | 0.16 |
| | MFI at 5 nM | 119.6 | 91.6 ± 6.7 | 98.3 ± 7.5 | 80.6 | 89.5 ± 3.9 | 91.0 ± 0.0 |
| Activated PBMC-(FA) | EC50, nM | NA | 0.049 | 0.041 | NA | 0.21 | 0.15 |
| | MFI at 25 nM | NA | 18.4 ± 0.6 | 17.6 ± 0.2 | NA | 14.5 ± 0.0 | 16.6 ± 0.2 |
| Activated PBMC-(FB) | EC50, nM | NA | 0.025 | 0.050 | NA | 0.17 | 0.10 |
| | MFI at 25 nM | NA | 17.8 ± 0.3 | 18.7 ± 0.4 | NA | 15.9 ± 0.5 | 16.7 ± 1.7 |

Figure 9A:
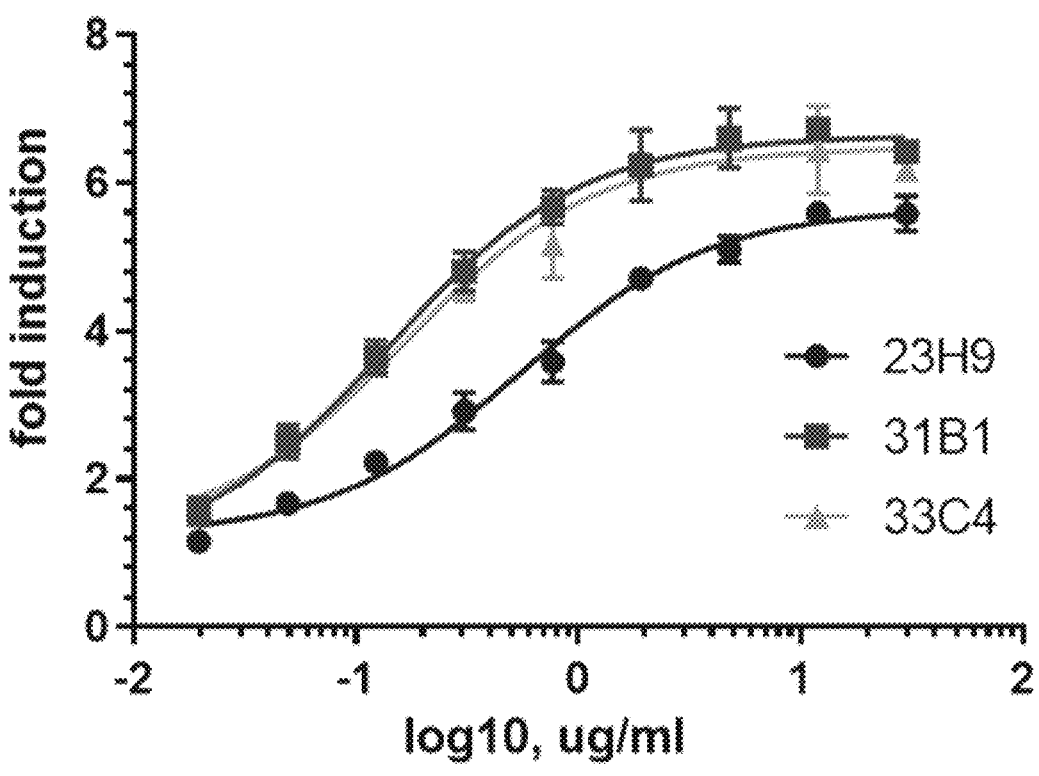
FIG. 9A and FIG. 9B illustrate the ability of antibodies 23H9, 31B1, 33C4, 24H9, 38B2, and 38A6 to block PD-1/PD-L1 interactions using a Promega binding assay.
Figure 9B:
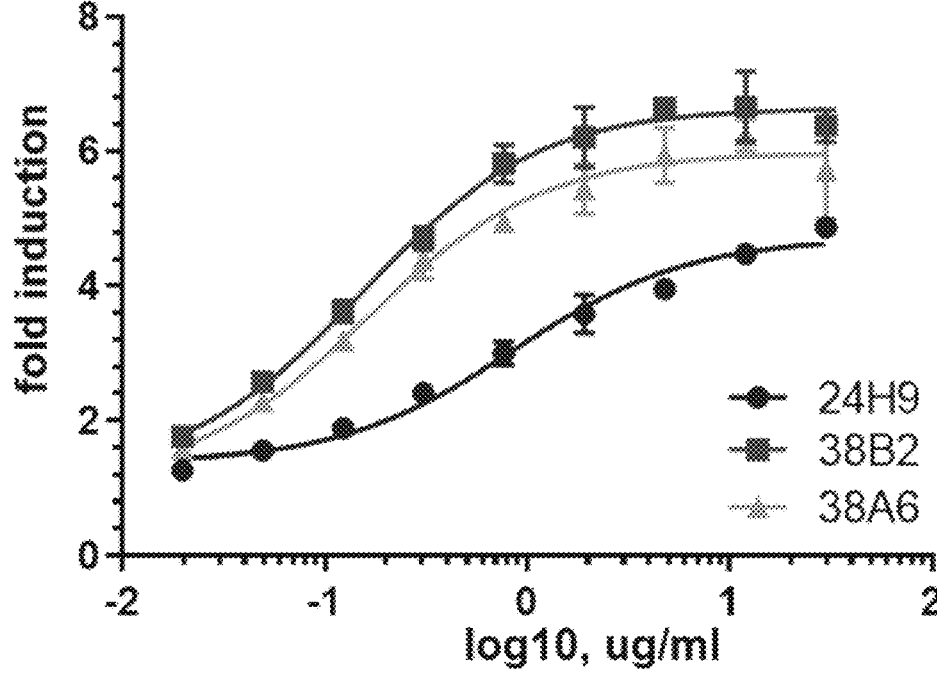

Example 9: Antibodies 23H9, 24H9 and their Derivatives Disrupt Intercellular PD-1/PD-L1 Interactions A PD-1 blockade bioassay was performed using antibodies 23H9, 31B1, 33C4, 24H9, 38A6, and 38B2 according to the protocol outlined in Example 5. All derivatives were found to be more potent than their parental antibody 23H9 and 24H9 in blocking hPD-1-hPD-L1 interactions (FIG. 9). 38B2 and 31B1 were found to show lowest EC50 and maximum fold induction among the six antibodies tested (Table 8 and FIG. 9).

TABLE 8

Blocking of PD-1/PD-L1 interactions by antibodies
23H9, 31B1, 33C4 and 24H9, 38B2, and 38A6 using a Promega binding assay.

| | 23H9 | 31B1 | 33C4 | 24H9 | 38A6 | 38B2 |
|---|---|---|---|---|---|---|
| EC50, μg/ml | 0.551 | 0.139 | 0.165 | 0.855 | 0.164 | 0.154 |
| Fold induction | 5.58 ± 0.28 | 6.48 ± 0.035 | 6.24 ± 0.092 | 4.97 ± 0.049 | 5.66 ± 0.636 | 6.54 ± 0.071 |

Figure 10A:
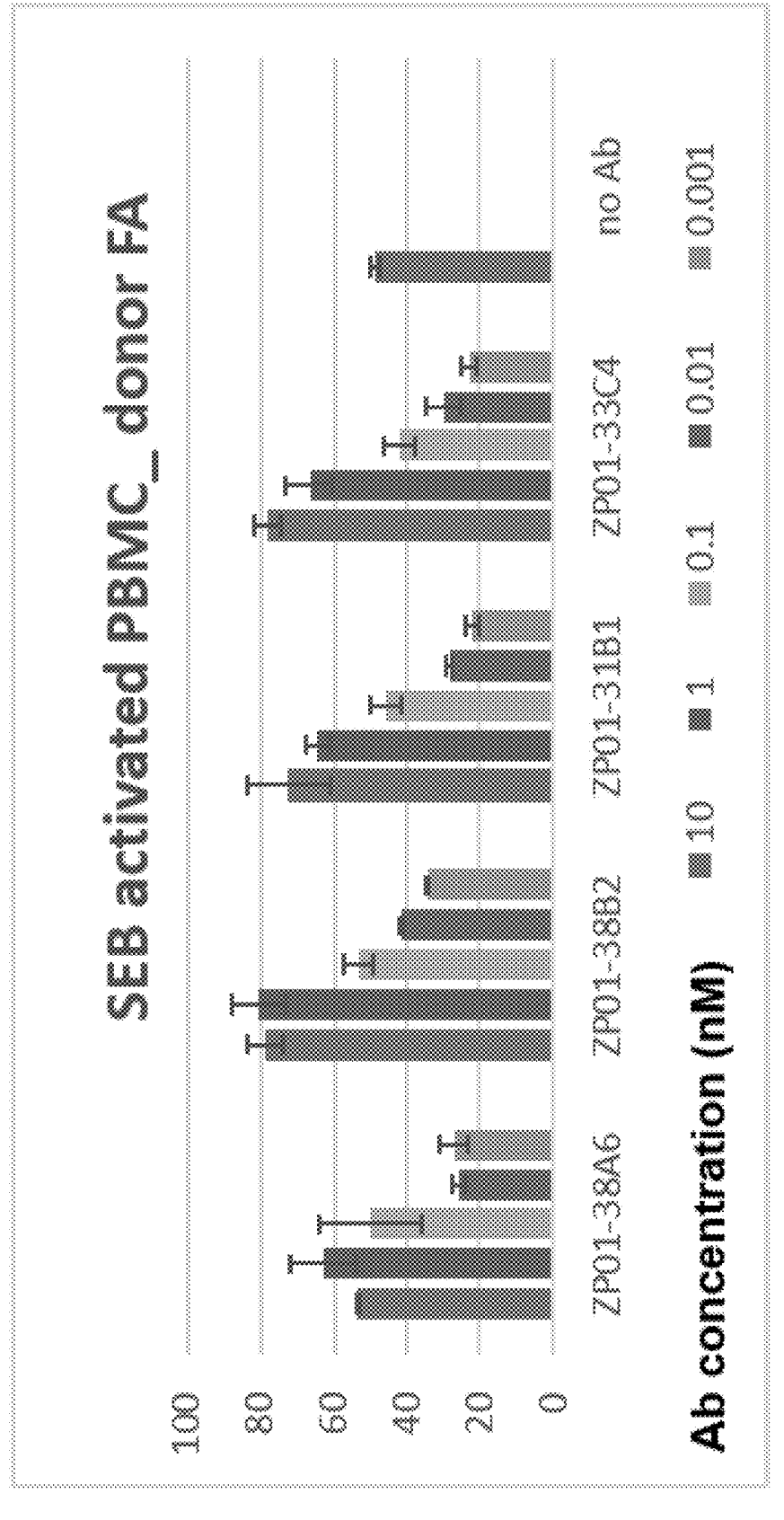
FIG. 10A, FIG. 10B, and FIG. 10C depict IL-2 accumulation for PBMCs from donor FA (FIG. 10A) and IL-2 accumulation for PBMCs from donor EA (FIG. 10B and FIG. 10C), in presence of antibodies 23H9, 31B1, 24H9, and 38B2.

Example 10: The Effect of Anti-PD-1 Antibodies on Cytokine Production in SEB-Activated PBMCs The effect of anti-PD-1 antibodies on cytokine production using 38A6, 38B2, 31B1, and 33C4 in SEB activated PBMC from donor FA was assessed by measuring the amount of cytokines released by PBMCs in the culture medium. PBMCs were isolated from LeukoPak (an enriched leukapheresis containing highly concentrated blood cells including monocytes, lymphocytes, platelets, plasma, as well as red cells) using Histopaque-1077 (Sigma) per manufacture instruction. PBMCs were cultured at $1 \times 10^5$ per well in 96 well plate containing IMDM (Gibco, Life Technologies) supplemented with 10% FBS (GE Healthcare HyClone). The cells were activated by 0.01 μg/mL SEB (Staphylococcal enterotoxin B, Sigma) for 2 days. Supernatants were collected for the measurement of IL-2 using Duoset ELISA Kit (R&D Systems) per the manufacturer's instructions (FIG. 10A).

Figure 10B:
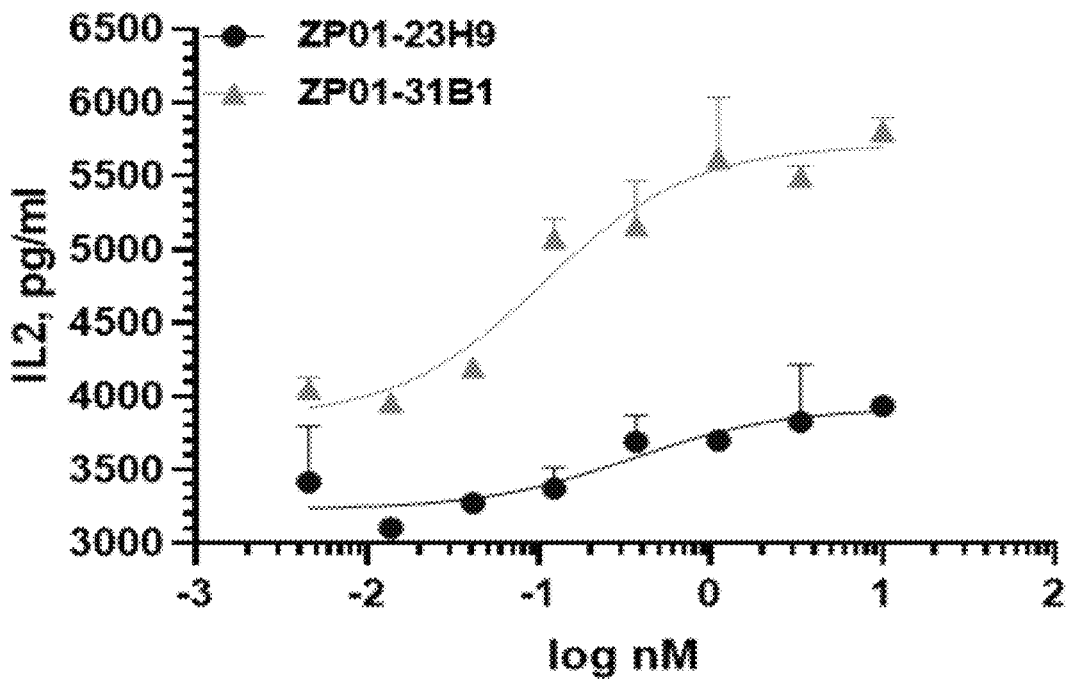
Figure 10C:
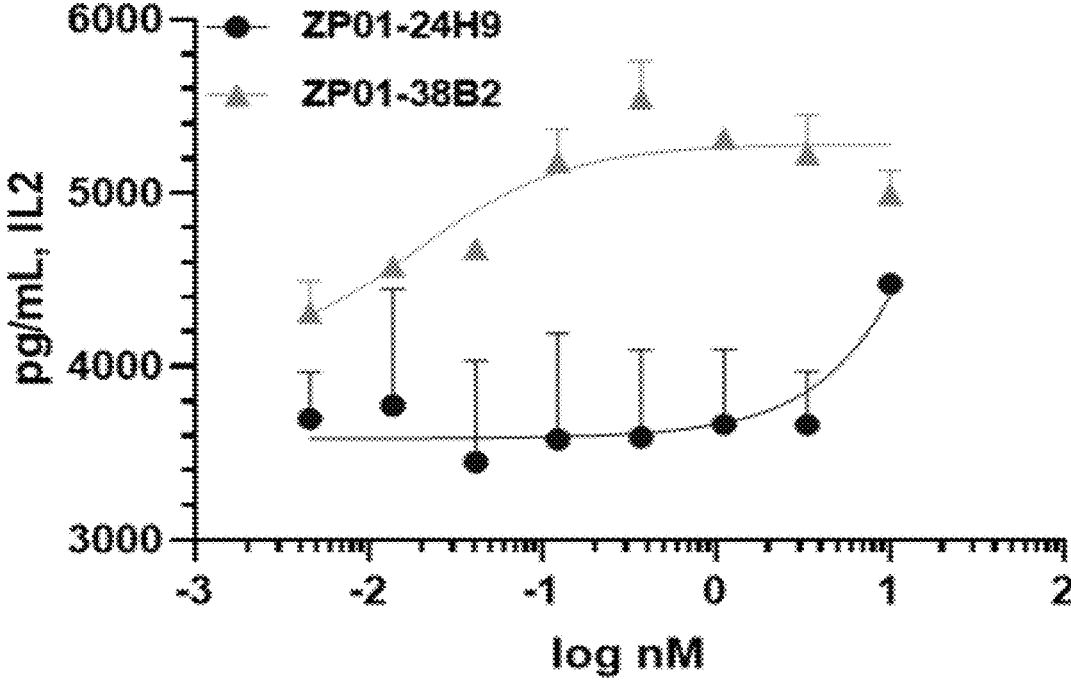
Figure 11:
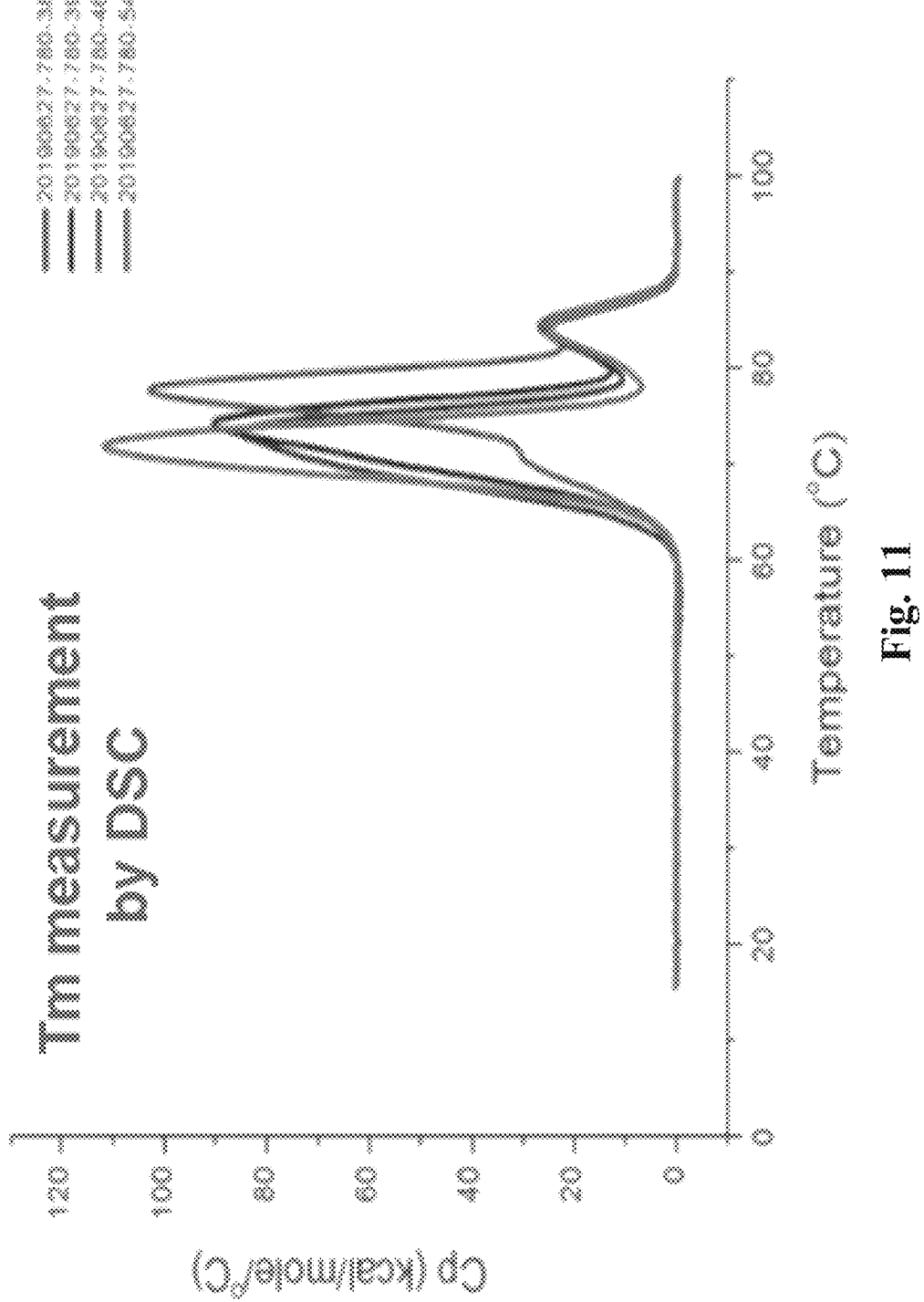
FIG. 11 illustrates the thermo-stability measurement for antibodies 780_38 (31B1), 780_39 (33C4), 780_46 (38A6), and 780_54 (38B2) as determined by differential scanning calorimeter (DSC).

The experiment was repeated to obtain EC50 values for antibodies 23H9, 31B1, 24H9, and 38B2 using PBMCs from donor EA (FIG. 10B).

(SPR) using the Biacore T200. Human PD-1-Fc or PD-1-his protein was immobilized at pH5 onto a Series S CM5 sensor chip using standard amine coupling chemistry. Antibodies 23H9 and 23H9 derivatives 31B1, 33C4 as well as 24H9 and 24H9 derivatives 38A6, 38B2, 32D11, 39G8, 38A10, and 38A11 were injected at 30 μl/min at concentrations ranging from 1.5 to 100 nM over the immobilized surface using 1×HBSEP as the running buffer. The contact time (association phase) was 3 mins. The dissociation time was 6-10 mins. Regeneration was performed after each binding cycle with an injection of 20 mM HCl for 30 sat 30 μl/min flow rate. Sensorgrams were obtained at each concentration and the derived curves were fit to a 1:1 Langmuir binding model using Biaevaluation software. Derivative 31B1 and 33C4 were found to be more potent than the parental 23H9 in their binding to hPD-1-Fc (Table 10). All derivatives of 24H9 were found to be more potent than the parental antibody 24H9 in their binding to hPD-1-his and hPD-1-Fc.

TABLE 10 hPD1 binding characteristics of indicated antibodies as determined by SPR analysis.

| Antibody | hPD1his | | | hPD1Fc | | |
|---|---|---|---|---|---|---|
| | $k_a$ | $k_d$ | $K_D$ | $k_a$ | $k_d$ | $K_D$ |
| 24H9 | 1.64 E+05 | 2.27 E−03 | 1.39 E−08 | 3.97 E+05 | 5.81 E−04 | 1.46 E−09 |
| 38B2 | 1.26 E+05 | 4.01 E−05 | 3.1S E−10 | 9.40 E+05 | 2.34 E−04 | 2.49 E−10 |
| 38A6 | 4.72 E+05 | 5.59 E−04 | 1.18 E−09 | 2.01 E+05 | 9.57 E−05 | 4.77 E−10 |
| 32D11 | 1.67 E+05 | 2.41 E−04 | 1.44 E−09 | 1.54 E+05 | 8.52 E−05 | 5.54 E−10 |
| 39G8 | 1.81 E+05 | 4.67 E−04 | 2.58 E−09 | 2.15 E+05 | 1.71 E−04 | 7.94 E−10 |
| 38A10 | 1.12 E+05 | 5.41 E−04 | 4.82 E−09 | 2.06 E+05 | 1.72 E−04 | 8.34 E−10 |
| 38A11 | 1.07 E+05 | 5.25 E−04 | 4.93 E−09 | 2.20 E+05 | 2.25 E−04 | 1.02 E−09 |

| Antibody | hPD1his $k_a$ | hPD1Fc $k_d$ | hPD1his $K_D$ | hPD1Fc $k_a$ | hPD1his $k_d$ | hPD1Fc $K_D$ |
|---|---|---|---|---|---|---|
| 23H9 | 8.64 E+04 | 4.24 E−04 | 4.91 E−09 | 1.69 E+05 | 1.57 E−04 | 9.28 E−10 |
| 31B1 | 2.78 E+05 | 1.82 E−03 | 6.56 E−09 | 3.44 E+05 | 2.37 E−04 | 6.88 E−10 |
| 33C4 | 9.43 E+04 | 6.35 E−04 | 6.73 E−09 | 2.77 E+05 | 1.60 E−04 | 5.75 E−10 |

IL-2 concentration increased in the presence of all antibodies in a dose-dependent manner (FIGS. 10A, 10B). IL-2 concentrations increased in presence of 23H9 derivative 31B1 and 24H9 derivative 38B2, which were found to be more potent than their parental antibody 23H9 and 24H9, respectively (Table 9 and FIG. 10B).

TABLE 9

IL-2 accumulation for PBMCs from donor EAand respective EC50 and IL-2 accumulation data in presence of antibodies 23H9, 31B1, 24H9, and 38B2.

| | 23H9 | 31B1 | 24H9 | 38B2 |
|---|---|---|---|---|
| EC 50, nM | 0.344 | 0.107 | >10 | 0.019 |
| IL-2, pg/ml in 10 nM | 3931 ± 52 | 5809 ± 90 | 4476 ± 35 | 4995 ± 140 |

Example 11: Biacore Analysis of Selected 23H9 and 24H9 Derivatives

The binding kinetics of the antibodies to either hPD-1-Fc or hPD-1-his was measured by surface plasmon resonance

Example 12: Thermo-Stability Measurement of Selected 23H9 and 24H9 Derivatives by Differential Scanning Calorimeter (DSC)

Selected 23H9 and 24H9 derivatives, 31B1, 33C4, 38A6, and 38B2 were cloned and expressed by WuXi Biologics by using WuXi's mammalian expression vector and CHO knockout cell line. All antibodies were purified using protein A and SEC-HPLC. More than 2.5 mg of purified antibody was obtained from 20 ml culture after Protein A and SEC-HPLC purification. The monomer percentage of all antibodies was over 96% with endotoxin levels lower than 1.0 EU/mg. Differential scanning calorimetry (DSC) was used to determine the stability of the four antibodies. The DSC analysis was performed using a Malven DSC system. The protein sample was first diluted to 1 mg/mL with formulation buffer before analysis. 400 μl respective formulation buffer was added to a 96-well plate as reference and 400 μL protein sample was added. The samples were heated from 10° C. to 100° C. at a heating rate of 90° C./h in the capillary DSC system. The DSC results ($T_m$ onset and $T_m$ values) were analyzed using the vendor's software. The lowest thermal transition midpoint ($T_{m1}$) of 31B1, 33C4, 38A6, and 38B2 were 70.5, 74.0, 71.0, and 71.9° C. respectively (FIG.

11A). The monomer percentage of all antibodies was over 96% with Endotoxin level lower than 1.0 EU/mg (Table 11). 33C4 and 38B2 were found to be most thermostable of all the antibodies tested (Table 11).

TABLE 11

Thermo-stability measurement for antibodies 2
31B1, 33C4, 38A6, and 38B as determined by differential scanning
calorimeter (DSC) and antibody monomer percentage after SEC-HPLC purification.

| | Protein A | | SEC HPLC | | | | | | Endotoxin |
| | Amount | Purity, | Amount | Purity, | | DSC (° C.) | | | (EU/mg, |
| Name | (mg) | % | (mg) | % | $T_{m\,on}$ | $T_{m1}$ | $T_{m2}$ | $T_{m3}$ | LAL) |
|---|---|---|---|---|---|---|---|---|---|
| 780_38 (31B1) | 4.70 | 97.2 | 2.44 | 96.1 | 60.8 | 70.5 | 74.0 | 83.7 | <1.0 |
| 780_39 (33C4) | 4.10 | 95.8 | 2.43 | 96.9 | 62.1 | 74.0 | 83.8 | ND | <1.0 |
| 780_46 (38A6) | 7.95 | 94.6 | 5.22 | 98.7 | 62.8 | 71.0 | 77.6 | 84.9 | <1.0 |
| 780_54 (38B2) | 7.24 | 95.6 | 5.24 | 99.3 | 62.6 | 71.9 | 84.0 | ND | <1.0 |

Figure 12A:
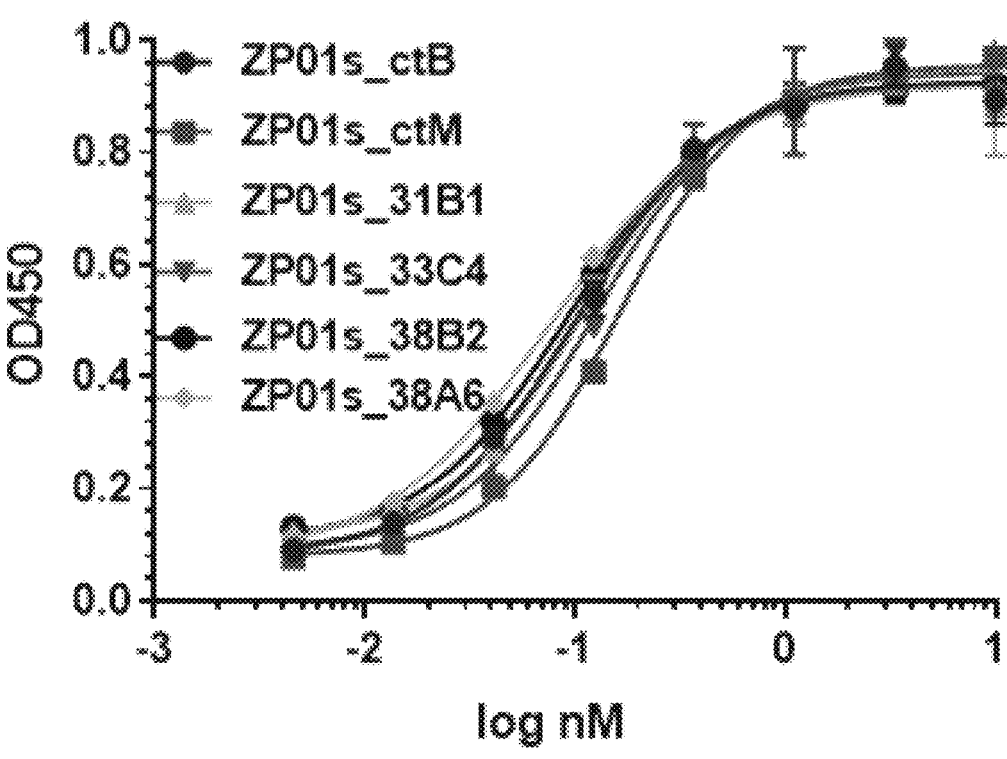
Figure 12B:
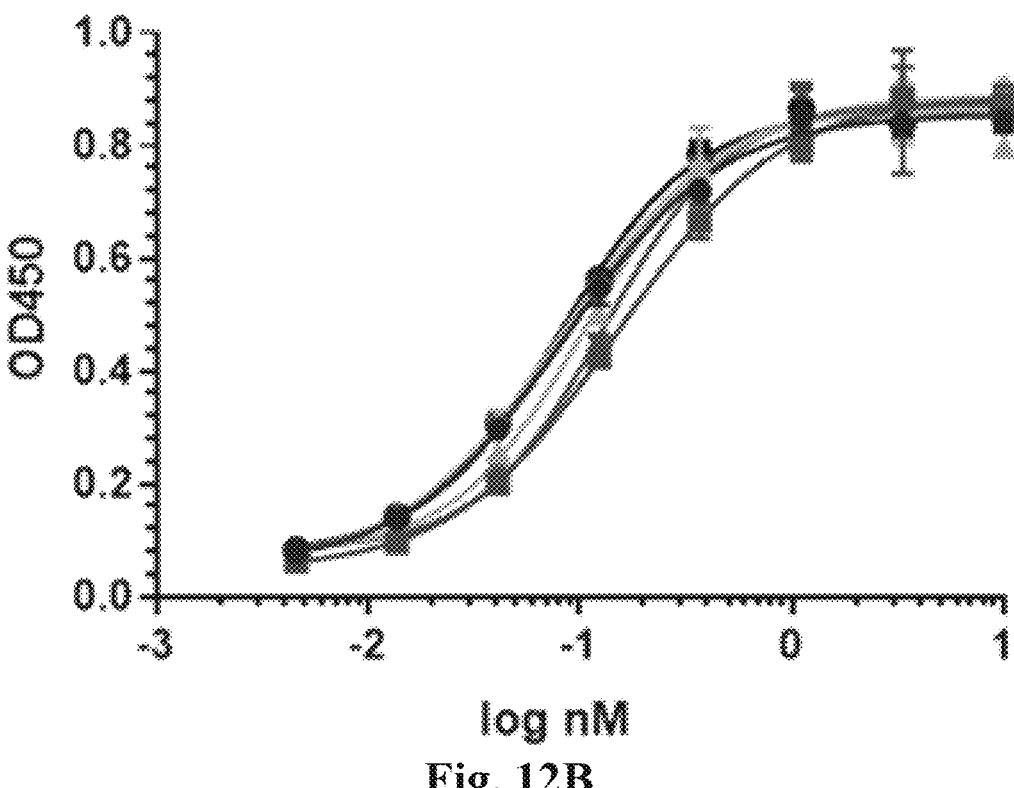
Figure 12C:
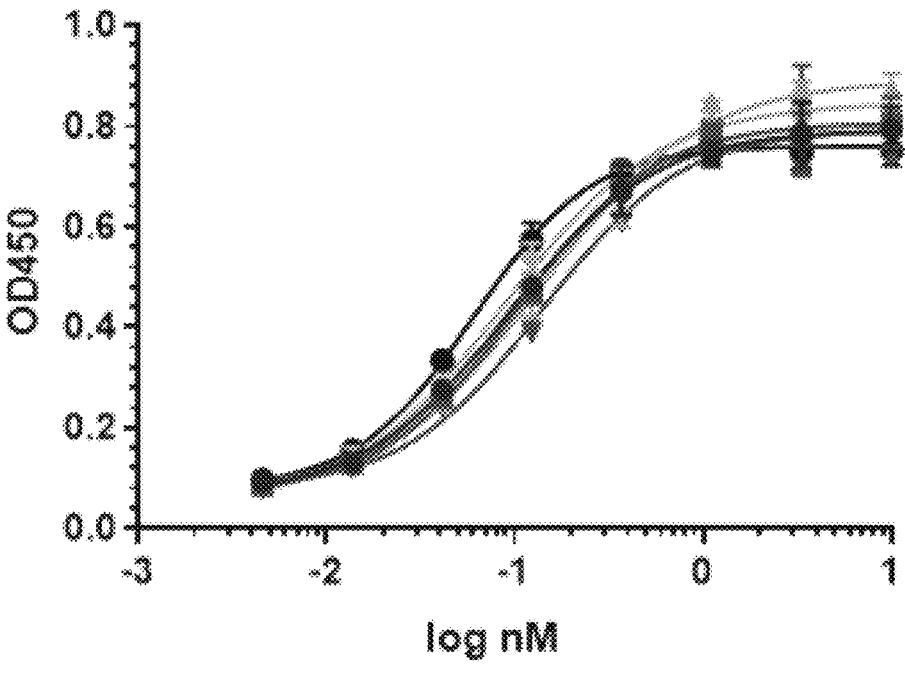

Example 13: Selected 23H9 and 24H9 Derivatives Bind to hPD-1 and Block hPD-1/hPD-L1 as Well as hPD-1/hPD-L2 Interactions Binding and Blocking ELISA were performed using antibodies 31B1, 33C4, 38A6, 38B2 isolated from transient CHOK cells using the protocols outlined in Examples 2 and 3, respectively. Comparison of the antibodies using binding ELISA showed no significant differences among the derivatives in binding to hPD-1-Fc, strepavidin-captured biotin-labeled hPD-1his and anti-his antibody captured hPD-1-his directly bound to the plates (FIG. 12A-C). However, EC50s of 38B2 and 38A6 (both 24H9 derivatives) were lower than 31B2 and 33C4 (both 23H9 derivatives) and were superior to both controls (Table 12 and FIG. 12A-C).

Figure 12D:
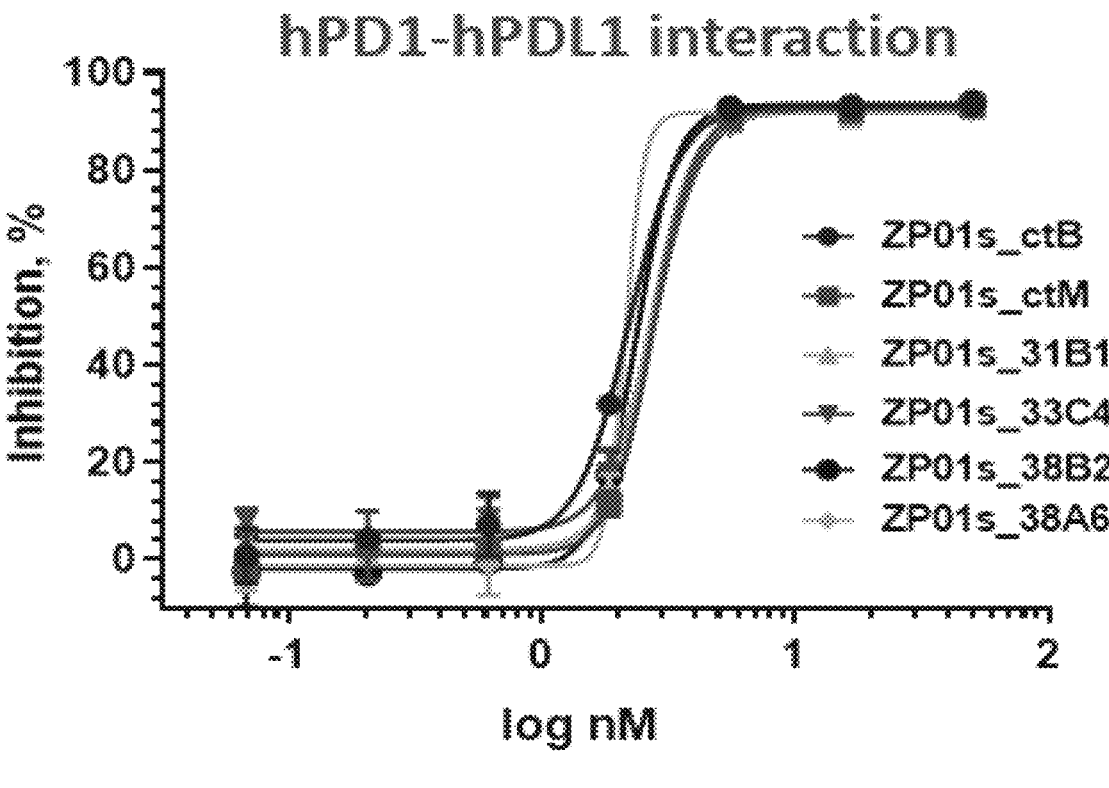
Figure 12E:
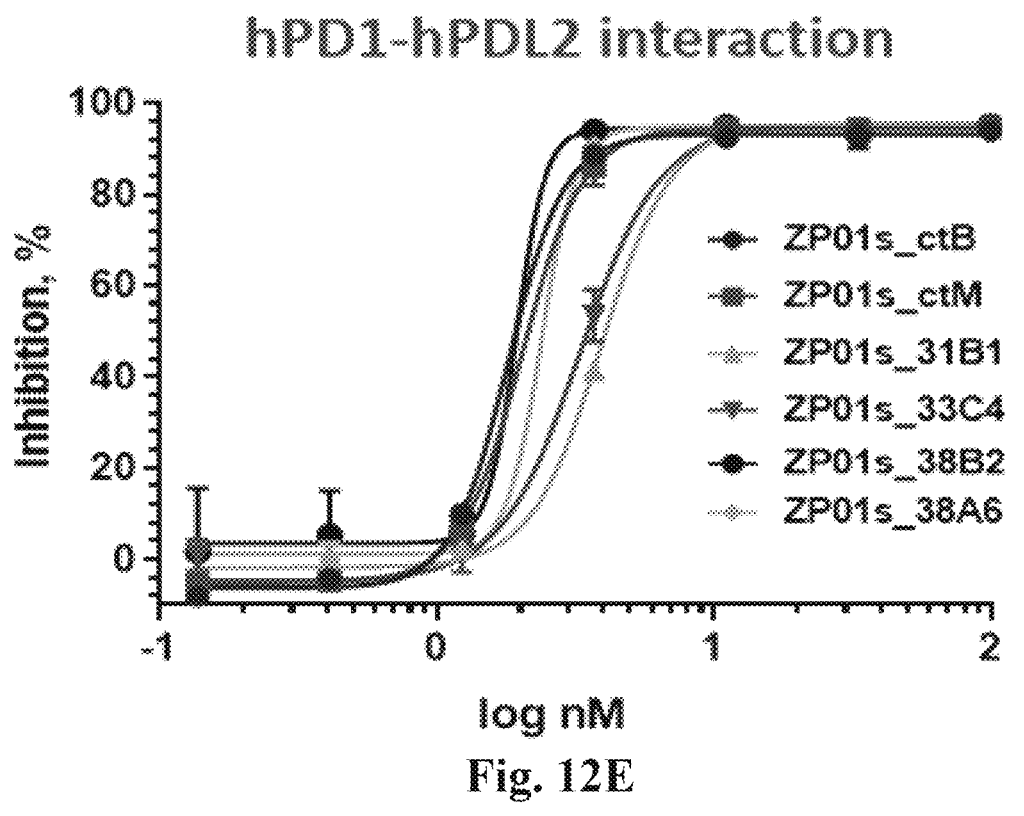
Figure 13A:
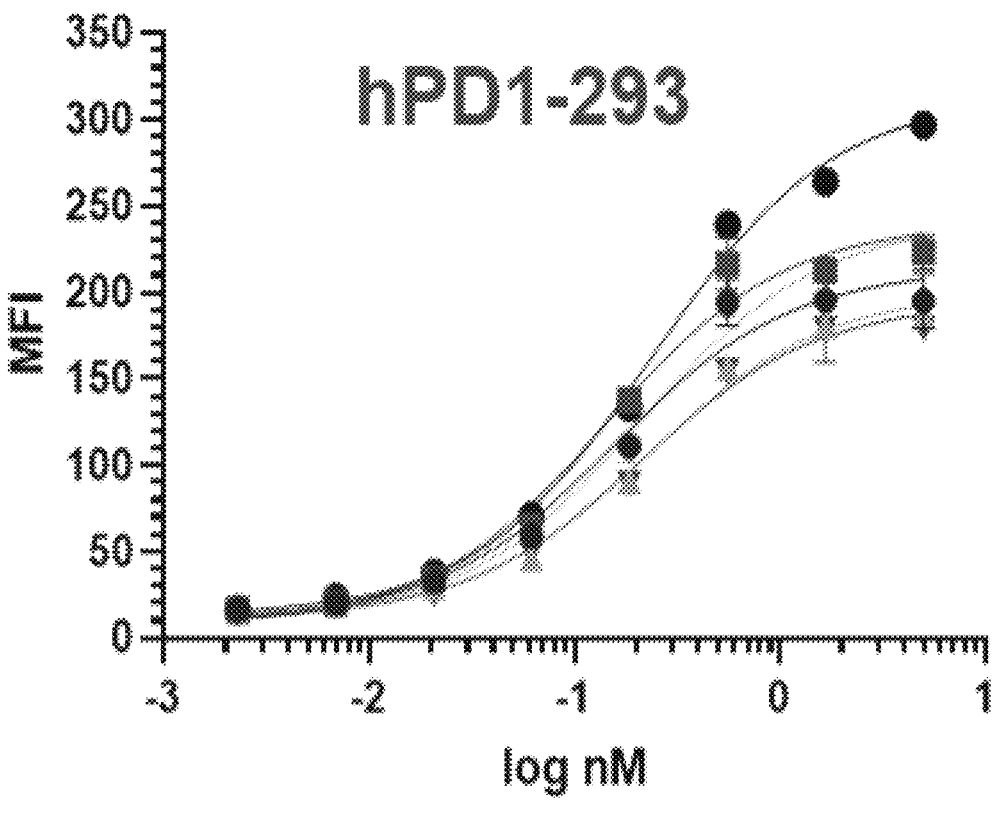
FIG. 13A, FIG. 13B, FIG. 13C, and FIG. 13D depict dose-response binding of antibodies 31B1, 33C4, 38A6, and 38B2 to hPD-1-293 cells (FIG. 13A), hPD-1-Jurkat cells (FIG. 13B), SEB-activated PBMCs from donor FA (FIG. 13C), and SEB-activated PBMCs from donor FB (FIG. 13D).
Figure 13B:
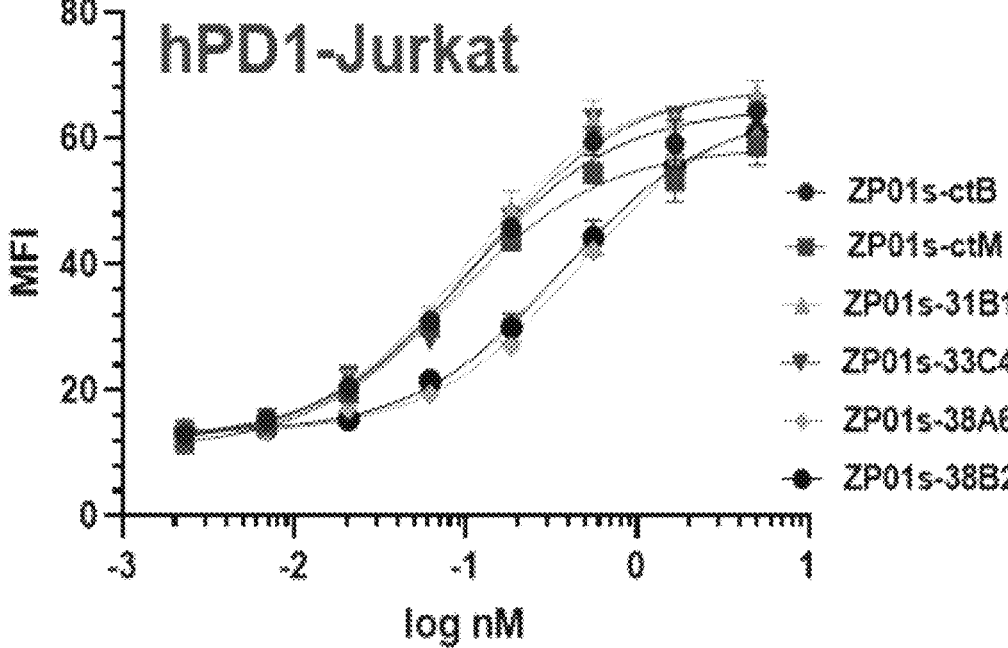
Figure 13C:
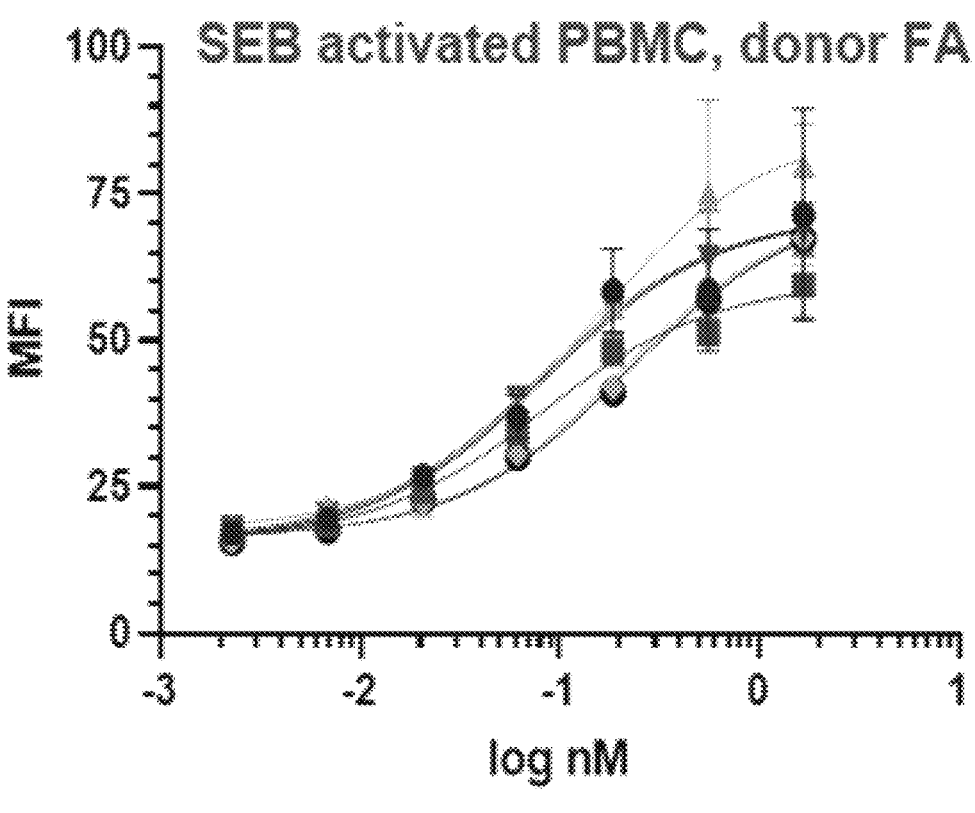
Figure 13D:
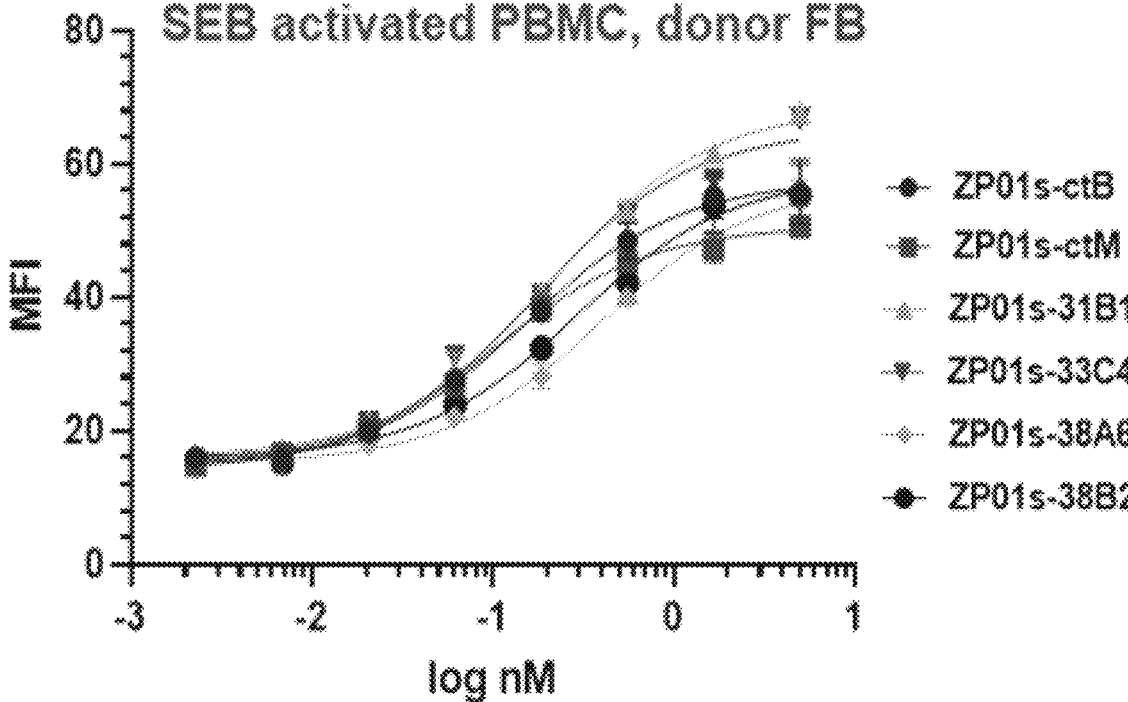

Comparison of the antibodies using blocking ELISAs showed no significant differences among the derivatives in blocking hPD-1/hPD-1 and hPD-1/hPD-L2 interactions (FIG. 12D-E). However, similar to binding ELISA, antibodies 38A6 and 38B2 (both 24H9 derivatives) were found to be more potent than 31B2 and 33C4 (both 23H9 derivatives), especially for the inhibition of hPD-L2 binding to hPD-1 (Table 13 and FIG. 12D-E).

TABLE 12

Binding of antibodies 31B1,
33C4, 38B2, and 38A6 to hPD-1FC, streptavidin-captured
biotin-labeled hPD-1his, and anti-his antibody captured hPD-1his.

| Ec50 nM | ctB | ctM | 31B1 | 33C4 | 38A6 | 38B2 |
|---|---|---|---|---|---|---|
| PD-1-Fc | 0.102 | 0.166 | 0.114 | 0.128 | 0.079 | 0.096 |
| strep/Bio-PD-1-his | 0.084 | 0.15 | 0.104 | 0.131 | 0.084 | 0.081 |
| anti-his/PD-1h-is | 0.094 | 0.105 | 0.139 | 0.142 | 0.089 | 0.060 | ctB = control B (Nivolumab, sold under the brand name Opdivo).
ctM = control M (Pembrolizumab, sold under the brand name Keytruda).

TABLE 13

Ability of indicated antibodies to block
hPD-1-hPD-L1 and hPD-1-hPD-L2 interactions.

| Blocking | | | ctB | ctM | 31b1 | 33C4 | 38A6 | 38B2 |
|---|---|---|---|---|---|---|---|---|
| PD-L1/PD-1 | IC50, nM | | 1.811 | 2.024 | 2.65 | 2.77 | ~2.14 | 2.37 |
| | Inhibition, % | 50 nM | 93.4 ± 0.3 | 93.1 ± 0.5 | 9.28 ± 0.3 | 93.3 ± 0.1 | 92.2 ± 0.0 | 93.9 ± 0.1 |
| | | 5.56 nM | 92.3 ± 0.4 | 90.3 ± 0.22 | 89.7 ± 0.1 | 88.9 ± 0.4 | 92.0 ± 0.8 | 92.7 ± 0.6 |
| PD-L2/PD-1 | IC50, nM | | 2.222 | 2.749 | 3.94 | 3.3 | 2.39 | 1.93 |
| | Inhibition, % | 100 nM | 93.8 ± 0.1 | 94.8 ± 0.1 | 94.5 ± 0.1 | 94.6 ± 0.3 | 94.8 ± 0.1 | 95.1 ± 0.0 |
| | | 3.7 nM | 88.6 ± 0.3 | 85.8 ± 4.0 | 41.4 ± 0.3 | 53.4 ± 5.7 | 90.4 ± 0.8 | 93.9 ± 0.3 | ctB = control B (Nivolumab, sold under the brand name Opdivo).
ctM = control M (Pembrolizumab, sold under the brand name Keytruda).

Example 14: Dose-Response Binding Assay Using 33B1, 33C4, 38A6, and 38B2

Dose response binding assays were performed using antibodies 33B1, 33C4 (both 23H9 derivatives), 38A6 and 38B2 (both 24H9 derivatives) using the protocols outlined in Example 4.

Dose-response binding assays showed no difference between the two derivatives from the same parental antibody in binding of the antibodies to hPD-1 transfected HEK-293 and Jurkat cells, and SEB-activated PBMCs (Table 14 and FIG. 13). However, the derivatives derived from different parental antibodies showed differences of binding to different cell lines, suggesting that 23H9 derivatives and 24H9 derivatives have different binding epitopes (Table 14 and FIG. 13).

TABLE 14

Dose-response binding of antibodies 31B1, 33C4, 38A6, and 38B2 to hPD-1-293 cells, hPD-1-Jurkat cells, SEB-activated PBMCs from donor FA, and SEB-activated PBMCs from donor FB.

| | ctB | | ctM | | 31B1 | |
|---|---|---|---|---|---|---|
| Cell line | EC50 | MFI, 5 nM | EC50 | MFI, 5 nM | EC50 | MFI, 5 nM |
| hPD-1-Jurkat cells | 0.101 | 64.4 ± 1.2 | 0.085 | 58.8 ± 3.1 | 0.100 | 67.0 ± 2.1 |
| hPD-1-293 cells | 0.156 | 195.1 ± 15.7 | 0.141 | 223.4 ± 10.0 | 0.229 | 186 ± 2 |
| SEB activated PBMC, donor FA | 0.084 | 61.6 ± 8.1 | 0.082 | 78.6 ± 5.73 | 0.136 | 98.5 ± 10.1 |
| SEB activated PBMC, donor FB | 0.151 | 55.5 ± 4.9 | 0.102 | 50.6 ± 0.8 | 0.209 | 67.7 ± 0.2 |

| | 33C4 | | 38A6 | | 38B2 | |
|---|---|---|---|---|---|---|
| Cell line | EC50 | MFI, 5 nM | EC50 | MFI, 5 nM | EC50 | MFI, 5 nM |
| hPD-1-Jurkat cells | 0.115 | 65.2 ± 0.8 | 0.451 | 59.9 ± 1.3 | 0.362 | 60.8 ± 3.4 |
| hPD-1-293 cells | 0.213 | 179 ± 7 | 0.211 | 227 ± 6 | 0.239 | 297 ± 2 |
| SEB-activated PBMCs, donor FA | 0.080 | 77.8 ± 2.4 | 0.206 | 65.2 ± 1.0 | 0.224 | 64.2 ± 2.7 |
| SEB-activated PBMCs, donor FB | 0.174 | 66.9 ± 0.1 | 0.387 | 54.7 ± 2.9 | 0.287 | 55.3 ± 5.4 | ctB = control B (Nivolumab, sold under the brand name Opdivo).
ctM = control M (Pembrolizumab, sold under the brand name Keytruda).

Figure 14A:
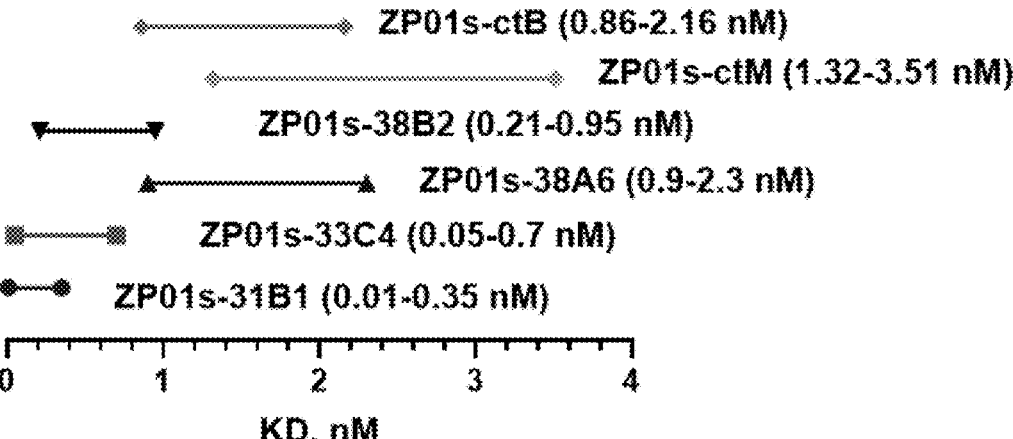
FIG. 14A and FIG. 14B depict KD values obtained for binding of antibodies 38B2, 38A6, 33C4, and 31B1 to hPD-1-his (FIG. 14A) and hPD-1-Fc (FIG. 14B) as determined by SPR.
Figure 14B:
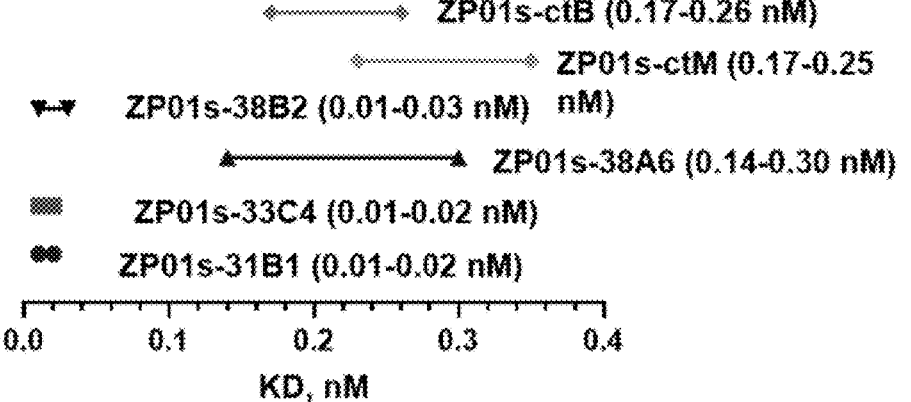

Example 15: Selected 23H9 and 24H9 Derivatives Bind to hPD-1 with High Affinity Binding of selected antibodies to hPD-1 his and hPD-1Fc was determined by SPR. Biacore analysis of 31B1, 33C4, 38A6, and 38B2 was performed using the protocol described in Example 11. All four antibodies were found to have high affinity to both hPD-1-Fc and hPD-1-his (Table 15 and FIG. 14). However, between two derivatives of 23H9, 31B1 was found to be more potent than 33C4 in both binding to PD-1-Fc and PD-1-his (Table 15). Between two derivatives of 24H9, 38B2 was found to be slightly more potent than 38A6 in binding to hPD-1-Fc and showed no significant difference in binding to hPD-1-his. Both 31B1 and 38B2 were found to be superior to the two controls (Table 15).

TABLE 15

Binding of antibodies 38B2, 38A6, 33C4, and 31B1 to hPD-1 his and hPD-1Fc as determined by SPR.

| | KD, nM (Exp. 1) | | KD, nM (Exp. 2) | | KD, nM (Exp. 3) | | KD, nM (Exp. 4) | | Kp range, nM | |
|---|---|---|---|---|---|---|---|---|---|---|
| Name | hpD1-his | hPD1-Fc | hpD1-his | hPD1-Fc | hpD1-his | hPD1-Fc | hpD1-his | hPD1-Fc | hPD1-his | hPD1-Fc |
| ctB | 2.16 | 0.188 | <0.857 | <0.166 | <1.39 | <0.255 | 0.914 | NA | 0.86-2.16 | 0.17-0.26 |
| ctM | 3.51 | 0.225 | <1.39 | <0.345 | <1.39 | <0.322 | 1.32 | NA | 1.32-3.51 | 0.23-0.35 |
| 31B1 | <0.036 | <0.014 | <0.01 | NA | 0.353 | <0.01 | <0.019 | NA | 0.01-0.35 | 0.01-0.02 |
| 33C4 | 0.704 | <0.022 | 0.205 | <0.01 | 0.274 | <0.01 | <0.054 | NA | 0.05-0.70 | 0.01-0.02 |
| 38A6 | 2.3 | <0.188 | <0.586 | <0.136 | <0.574 | <0.301 | <0.090 | NA | 0.09-2.30 | 0.14-0.30 |
| 38B2 | 0.946 | <0.033 | 0.423 | <0.01 | 0.932 | <0.01 | 0.205 | NA | 0.21-0.95 | 0.01-0.03 | ctB = control B (Nivolumab, sold under the brand name Opdivo).
ctM = control M (Pembrolizumab, sold under the brand name Keytruda).

Example 16: Antibodies 31B1 and 38B2 Disrupt Intercellular PD-1/PD-L1 Interactions 31B1 and 38B2

Figures 15A, 15B:
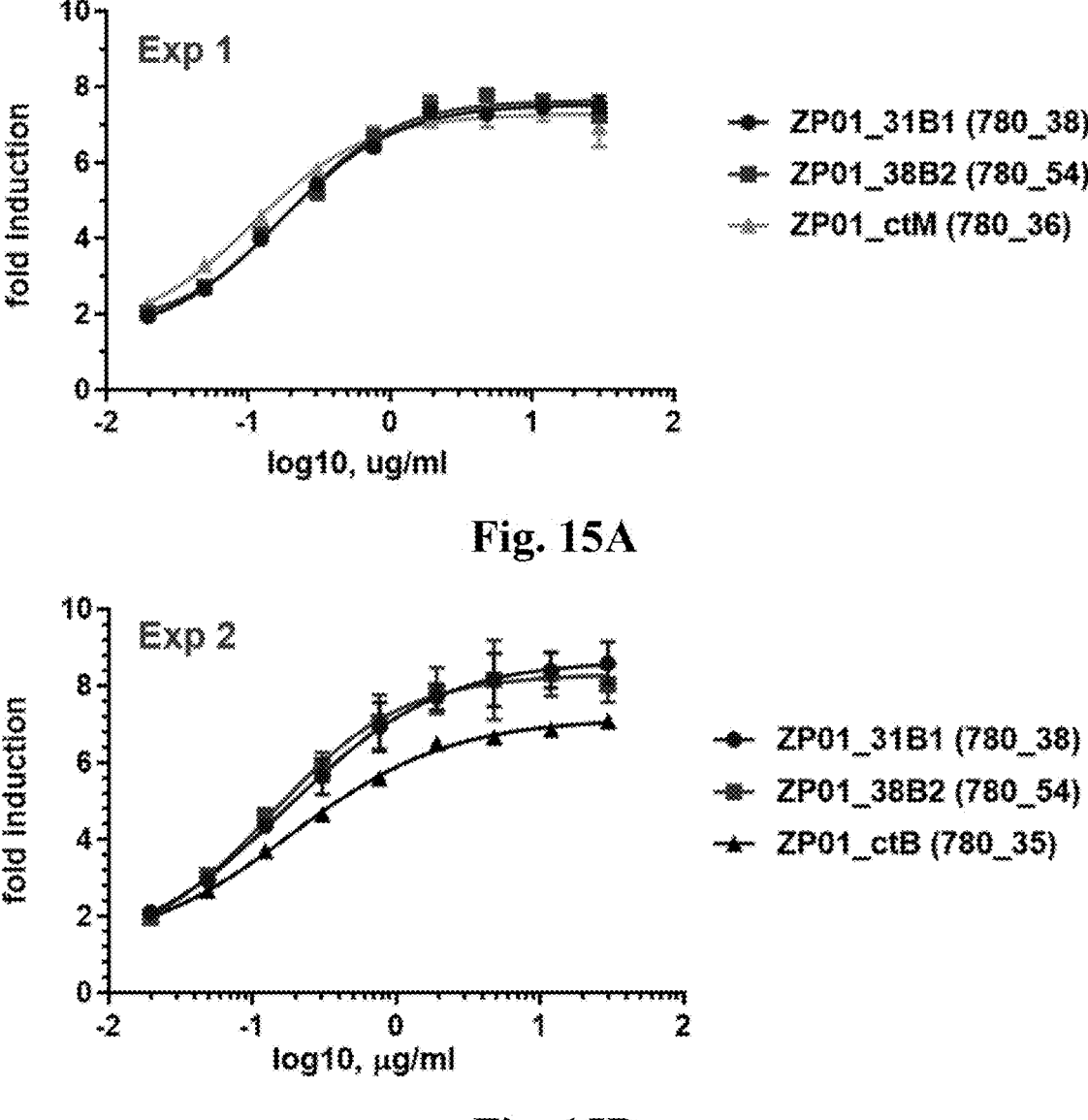
FIG. 15A and FIG. 15B illustrate the ability of antibodies 31B1 and 38B2 to block intercellular hPD-1-hPD-L1 interactions. The EC50 values averaged from two experiments for 31B1 and 38B2 were 0.168 and 0.154 µg/ml, respectively. Fold induction of luminescence was also averaged from two experiments. No significant difference between 31B1 and 38B2 was observed. Both 31B1 and 38B2 were superior to control B (Nivolumab, sold under the brand name Opdivo) and similar to control M (Pembrolizumab, sold under the brand name Keytruda).

To assess the ability of 31B1 and 38B2 to disrupt the binding of PD-1 expressing cells to PD-L1 expressing cells, Promega PD-1/PD-L1 Blockade Bioassays were performed using the protocol described in Example 5. No significant difference was observed in EC50 and fold induction between 31B1 and 38B2 (FIG. 15). Both 31B1 and 38B2 were found to be superior to control B (Nivolumab, sold under the brand name Opdivo) and similar to control M (Pembrolizumab, sold under the brand name Keytruda) (Table 16).

TABLE 16

| Ability of antibodies 31B1 and 38B2 to block intercellular hPD-1-hPD-L1 interactions. | | | | | |
|---|---|---|---|---|---|
| | 31B1 | | 38B2 | | ctM | ctB |
| Reading, 10 mins | Exp. 1 | Exp. 2 | Exp. 1 | Exp. 2 | Exp. 1 | Exp. 2 |
| EC50, μg/ml | 0.168 | 0.172 | 0.189 | 0.135 | 0.109 | 0.187 |
| Fold induction at 12 μg/ml | 7.44 ± 0.18 | 8.40 ± 0.46 | 7.61 ± 0.15 | 8.31 ± 0.58 | 7.40 ± 0.31 | 6.86 ± 0.16 | ctB = control B (Nivolumab, sold under the brand name Opdivo).
ctM = control M (Pembrolizumab, sold under the brand name Keytruda).

Figure 16A:
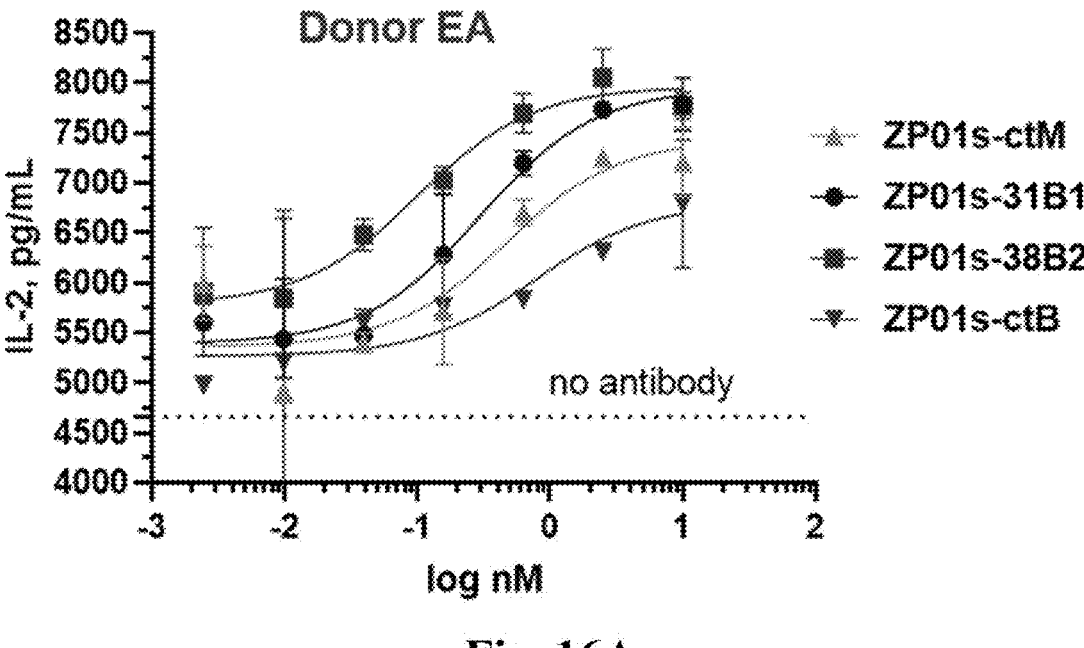
FIG. 16A and FIG. 16B illustrate the effect of anti-PD-1 antibodies 31Bland 38B2 on IL-2 cytokine production in SEB-activated PBMCs from donor EA (FIG. 16A) and donor FA (FIG. 16B). Cytokine IL-2 secretion was examined in SEB-activated human PBMC cells from donor EA and FA. The EC50 values for 38B2, 31B1, ctM and ctB were 0.101, 0.297, 0.210 and 0.548 nM (PBMC from donor EA). The maximum IL-2 secretion by cells treated by 38B2, 31B1, ctM or ctB was 8.05, 7.73, 7.21 and 6.79 ng/ml, respectively. 38B2 was more potent than 31B1 and two control antibodies; 31B1 was more potent than control B and comparable to control M.
Figure 16B:
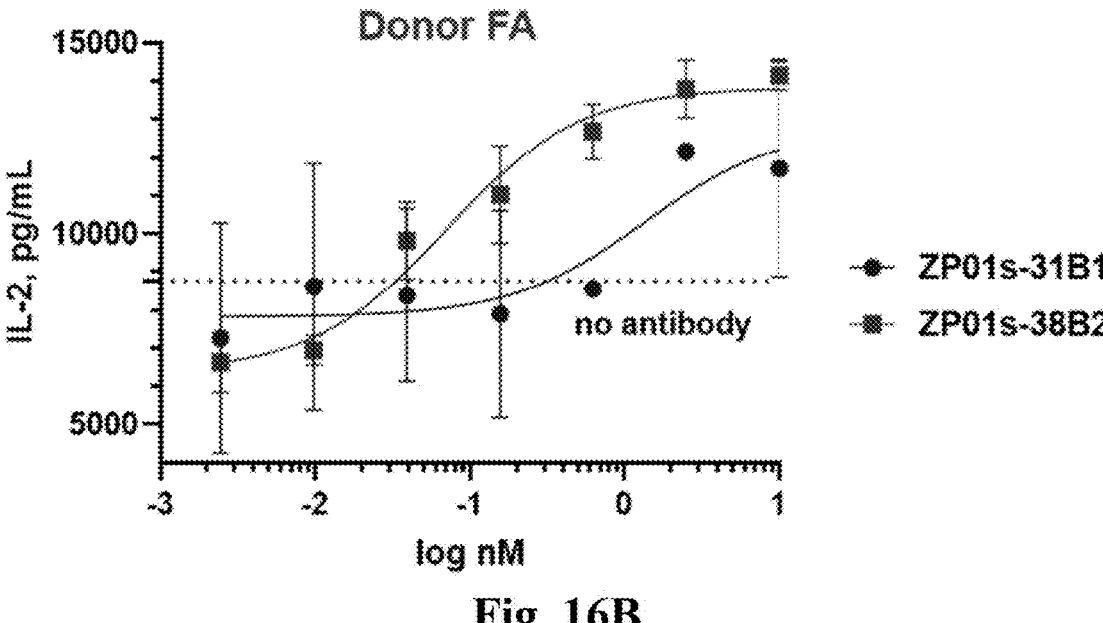
Figure 17A:
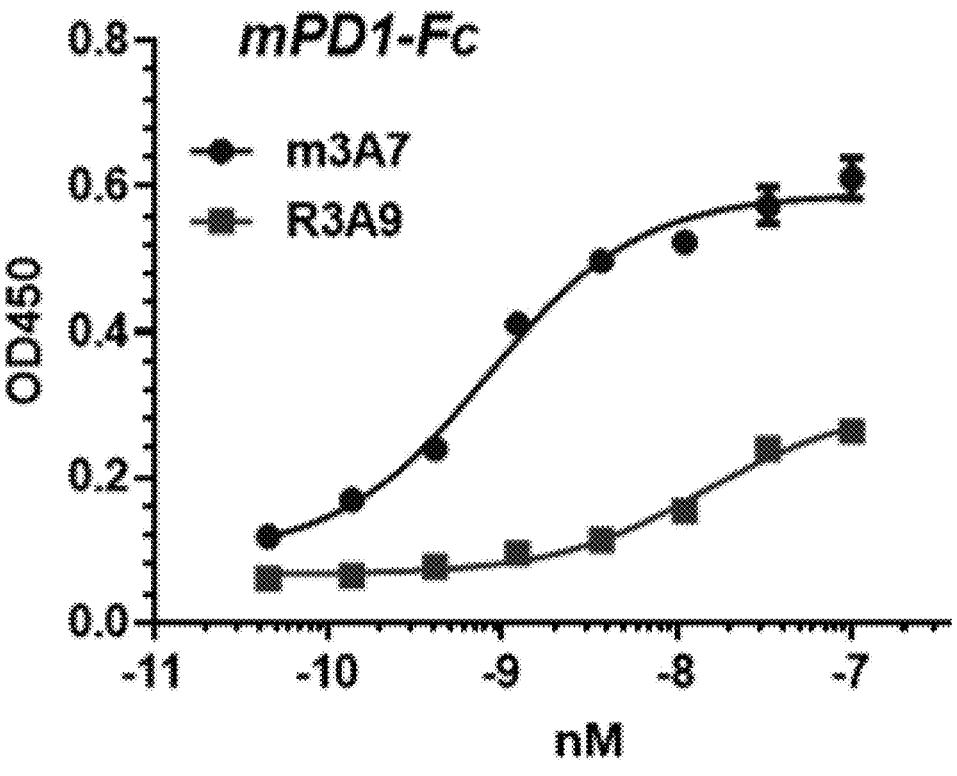
FIG. 17A, FIG. 17B, FIG. 17C, FIG. 17D, FIG. 17E, and FIG. 17F depict the dose dependent binding of antibodies m3A7 and R3A9 to soluble mPD-1-Fc (FIG. 17A), soluble streptavidin-captured mPD-1-Fc (FIG. 17B), soluble streptavidin-captured mPD-1-his (FIG. 17C), cells expressing mPD-1 (FIG. 17C) as well as blocking of mPD-1 to PD-L1 by antibodies m3A7 and R3A9 as determined by ELISA (FIG. 17E) and blockage of intercellular mPD-1/PD-L1 interactions as determined by a Promega assay (FIG. 17F).
Figure 17B:
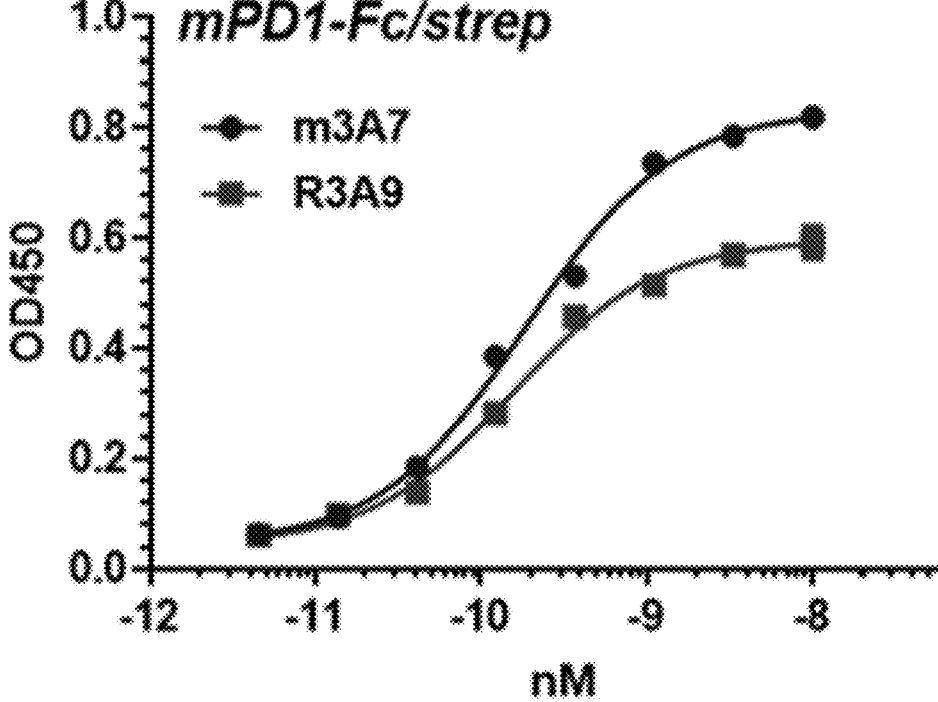
Figure 17C:
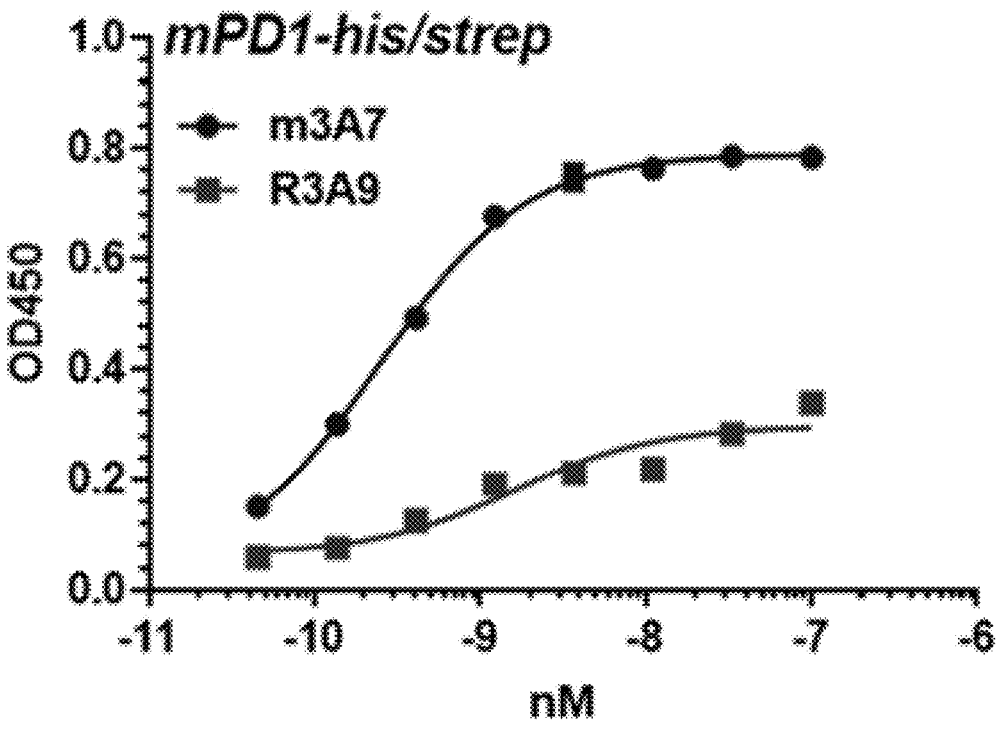
Figure 17D:
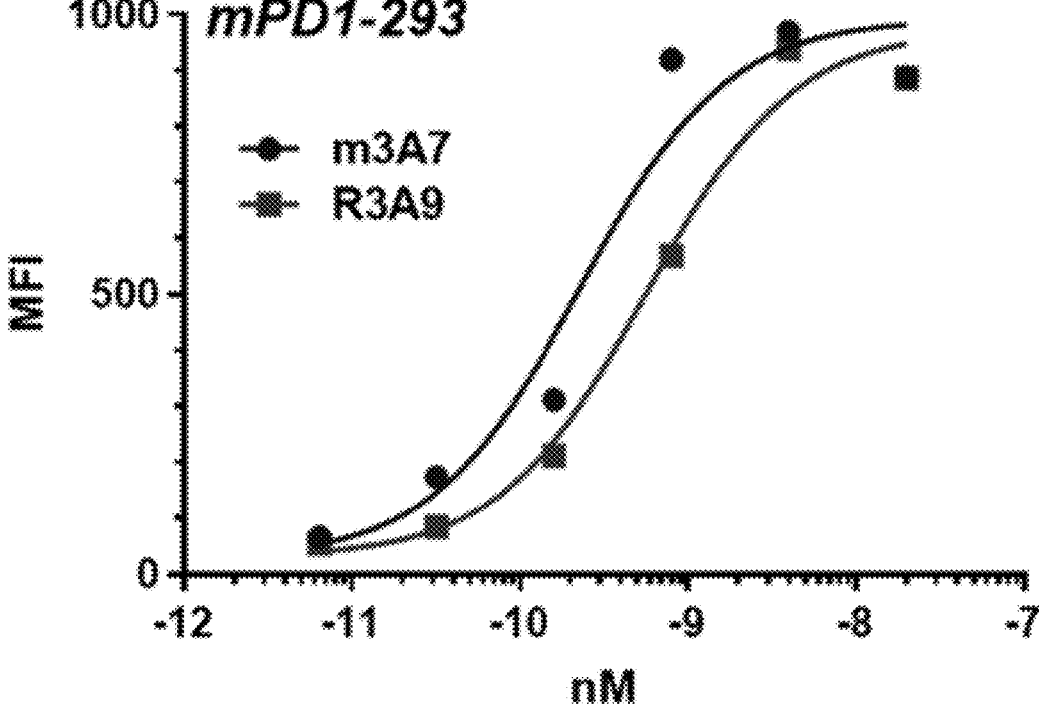
Figure 17E:
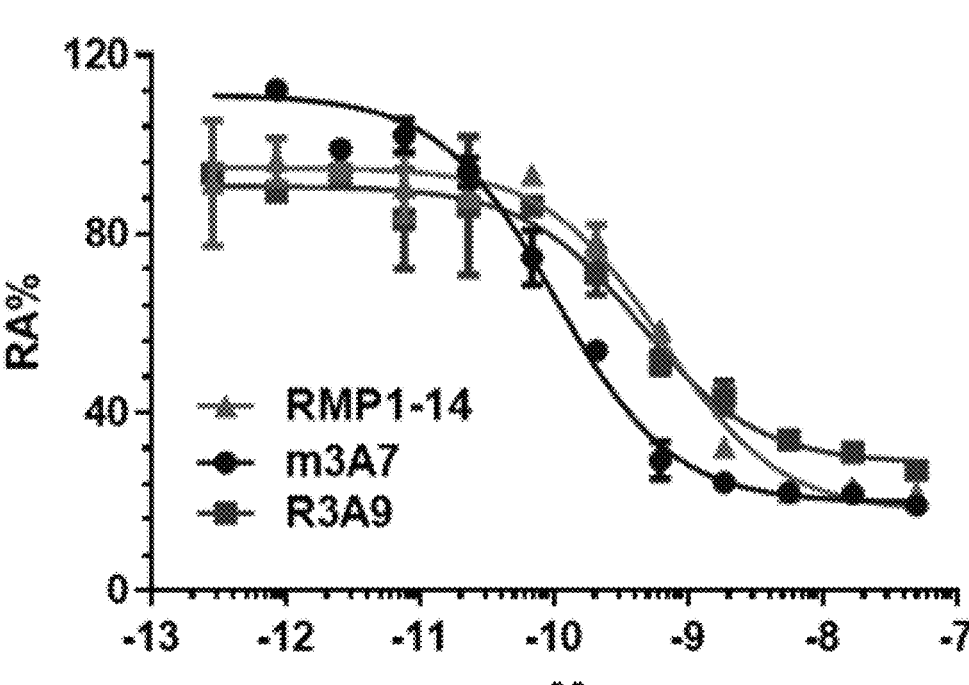
Figure 17F:
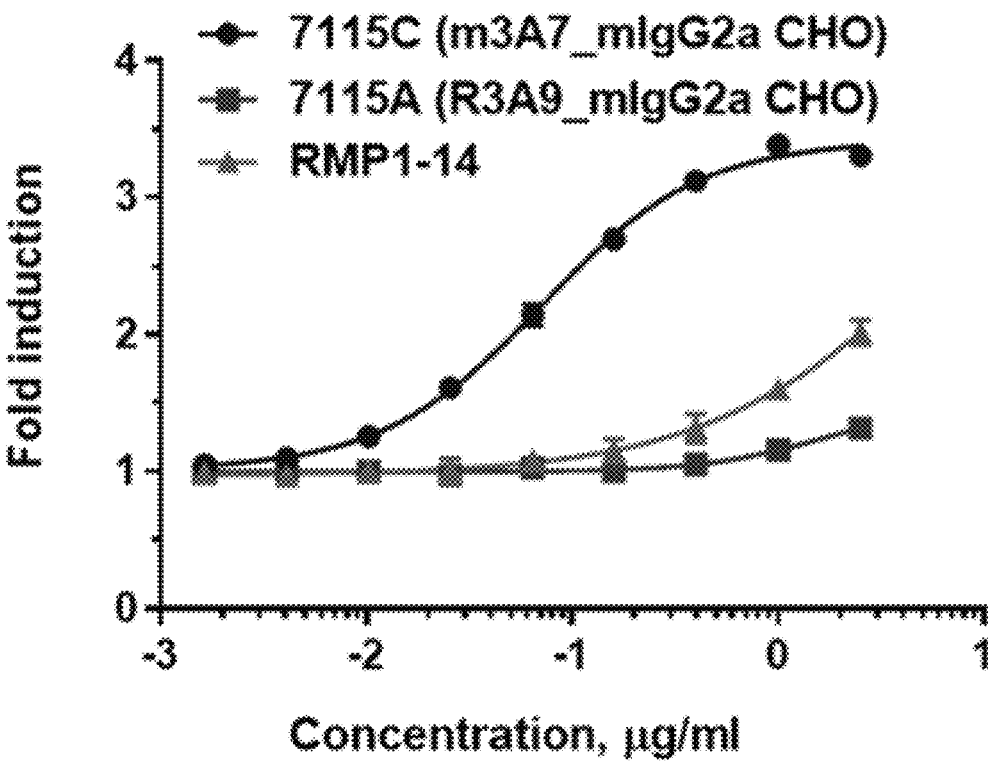

Example 17: The Effect of 31B1 and 38B2 on Cytokine Production in SEB Activated PBMC The effect of 31B1 and 38B2 on cytokine production in SEB-activated PBMCs was determined using the protocol outlined in Example 4. 38B2 was found to be more potent than 31B1 and the two control antibodies tested (Table 17 and FIG. 16).

TABLE 17

| Effect of PD-1 antibodies 31B1 and 38B2 on IL-2 cytokine production in SEB-activated PBMC from donor EA and FA. | | | | | | |
|---|---|---|---|---|---|---|
| | | | 31B1 | | 38B2 | |
| Name | ctM Donor EA | ctB Donor EA | Donor EA | Donor FA | Donor EA | Donor FA |
| EC50, nM | 0.210 | 0.548 | 0.297 | 1.362 | 0.101 | 0.070 |
| IL-2 (ng/mL) at 10 nM | 7.21 ± 0.35 | 6.79 ± 0.64 | 7.79 ± 0.26 | 11.72 ± 2.8 | 7.77 ± 0.13 | 14.14 ± 0.37 |
| IL-2 (ng/ml) at 2.5 nM | 7.25 ± 0.08 | 6.31 ± 0.05 | 7.73 ± 0.03 | 12.16 ± 0.00 | 8.05 ± 0.29 | 13.80 ± 0.75 | ctB = control B (Nivolumab, sold under the brand name Opdivo).
ctM = control M (Pembrolizumab, sold under the brand name Keytruda).

Example 18: Isolation of Antibodies that Cross-React with Human and Mouse from Distributed Bio SuperHuman 2.0 Inc. Library PD-1 antibodies that bind to both murine and human PD-1 were isolated using mPD-1-Fc (mouse IgV domain to fuse to the N-terminus of human IgG1Fc; present as dimer in solution) or mPD-1-his (mouse IgV domain of PD-1 connected to N-terminus of six histidine; present as monomer in solution) using the protocol outlined in Example 1. Derivatives of anti-mPD-1 antibody R3A9 (SEQ ID NOs: 139-146) by light pair shuffling using the VH chain of R3A9. R3A9 and its derivatives (see, e.g., SEQ ID NOs: 147-167) were select to develop further. The antibodies were cloned and expressed by WuXi Biologics using Wuxi's mammalian expression vector and CHO knockout cell line. The antibodies were purified by protein A and SEC-HPLC. More than 2.5 mg purified antibodies are obtained from 20 ml culture after Protein A purification. Antibodies further purified by SEC-HPLC.

The biological properties of selected antibodies generated in accordance with the methods of this Example are described in detail in the Examples set forth below. FIG. 1 and Table 25 provide the amino acid sequences of the heavy and light chain variable regions and CDRs of selected anti-mPD-1 antibodies (Kabat numbering).

Example 19: Anti-mPD-1 Antibody R3A9 and its Derivatives Bind to mPD-1 and Block mPD-1/mPD-L1 Interactions Dose Response Binding and Blocking ELISA were performed using R3A9 and its derivatives using the protocols as outlined in Examples 2 and 3. Binding of antibodies to mPD-1 expressing cells was performed as described in Example 4. Blockage of intercellular PD-1/PD-L1 interactions was examined using the Promega Bioassay described in Example 5. The results are illustrated in FIG. 17.

The R3A9 derivative m3A7 was found to be more potent than the parental R3A9 antibody in both binding to the soluble cell expressed mPD-1 and blocking mPD-1/mPD-L1 interactions (Table 18).

TABLE 18

Dose response binding of antibodies m3A7 and R3A9 to mPD-1-Fc, streptavidin-captured mPD-1FC, streptavidin-captured mPD-1his, and cells expressing mPD-1; blocking of mPD-1 to PD-L1 by ELISA and blockage of intercellular ineractions between mPD-1 to PD-L1 as determined by a Promega assay. RMP1-14 is a control, monoclonal antibody reacts with mouse PD-1.

| EC50/IC50 | Description | M3A7 (7115C) | R3A9 (7115A) | RMP1-14 |
|---|---|---|---|---|
| EC 50, nM | mPD-1-Fc | 0.834 | 14.6 | |
| EC 50, nM | Strep captured mPD-1-Fc | 0.187 | 0.156 | |
| EC 50, nM | Strep captured mPD-1-his | 0.251 | 1.61 | |
| EC 50, nM | mPD-1-293 | 0.228 | 0.566 | |
| IC 50, nM | Blocking of mPD-1/PD-L1 interaction (ELISA) | 0.102 | 0.441 | 0.635 |
| IC 50, µg/ml | Blocking of intercellular mPD-1/PD-L1 interaction | 0.0709 | 1.625 | 5.594 |

Example 20: R3A9 Derivaties m2C1, m2A1, m4D1 and m3A7 Bind to Both Human and Murine PD-1

Figure 18A:
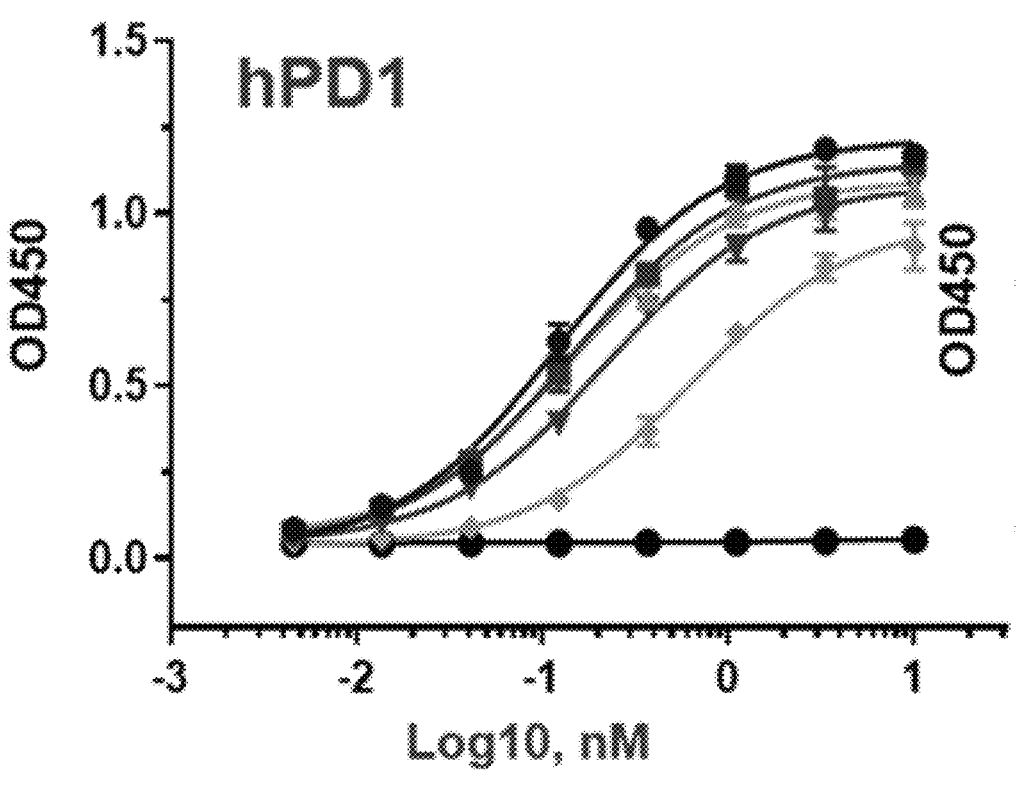
FIG. 18A, FIG. 18B, FIG. 18C, FIG. 18D, and FIG. 18E illustrate binding of antibodies 38B2, m2C1, m2A1, m4D1, m3A7, and R3A9 to hPD-1 (FIG. 18A, labels as in FIG. 18B), mPD-1 (FIG. 18B), and streptavidin-captured biotin mPD-1 (FIG. 18C, labels as in FIG. 18B) as determined by ELISA as well as blocking of mPD-1-mPD-L1 interactions by antibodies 38B2, m2C1, m2A1, m4D1, m3A7, and R3A9 (FIG. 18D, labels as in FIG. 18E), and blocking of hPD-1-hPD-L1 interactions (FIG. 18E) as determined by ELISA).
Figure 18B:
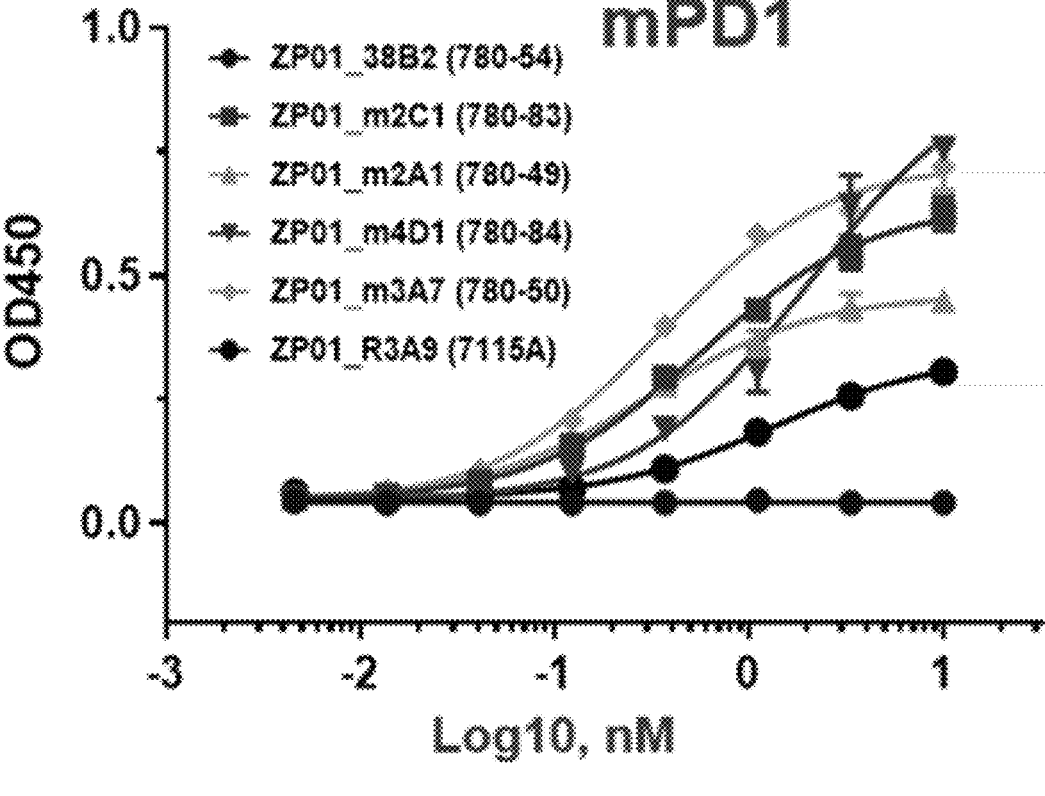
Figure 18C:
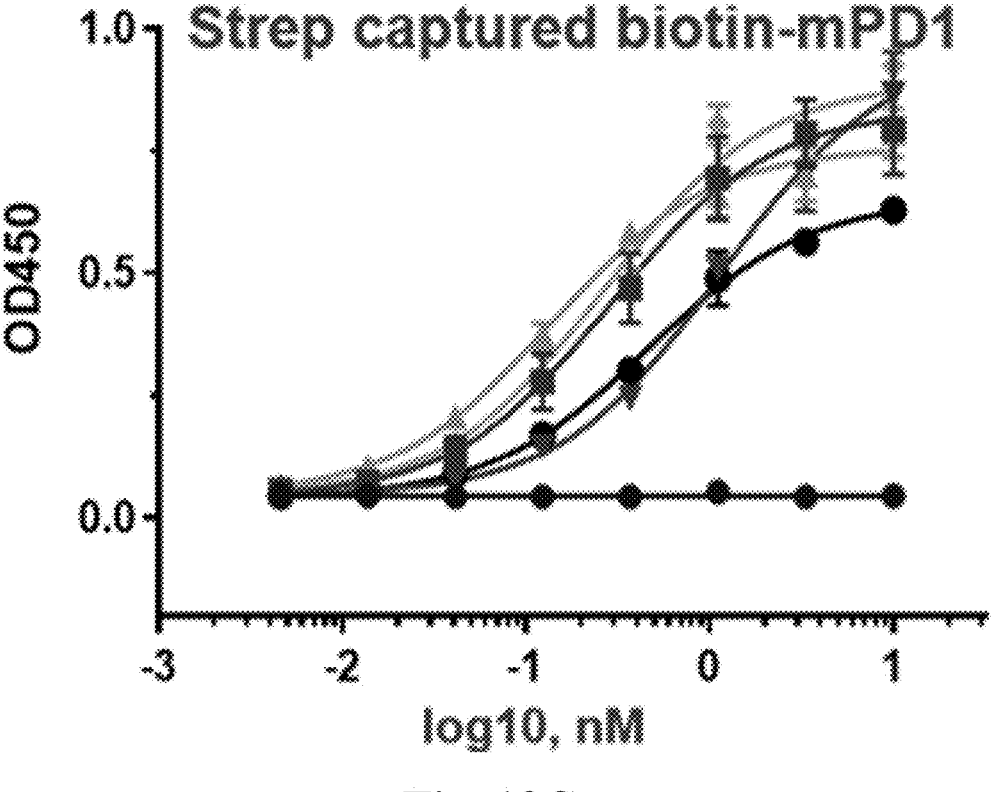
Figure 18D:
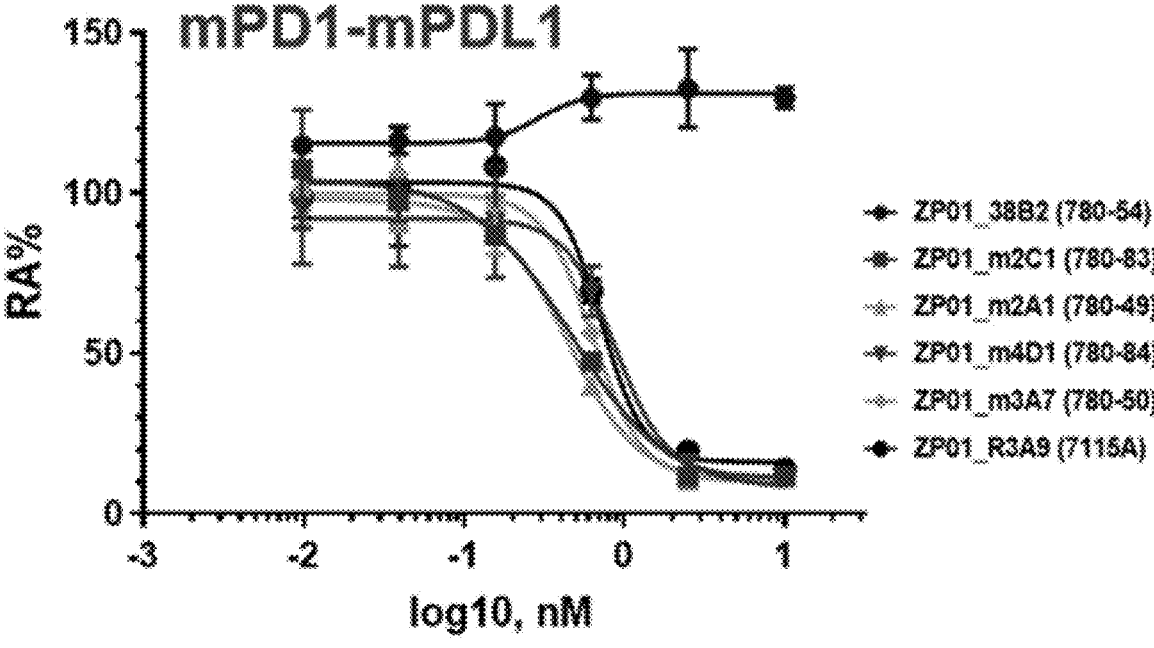
Figure 18E:
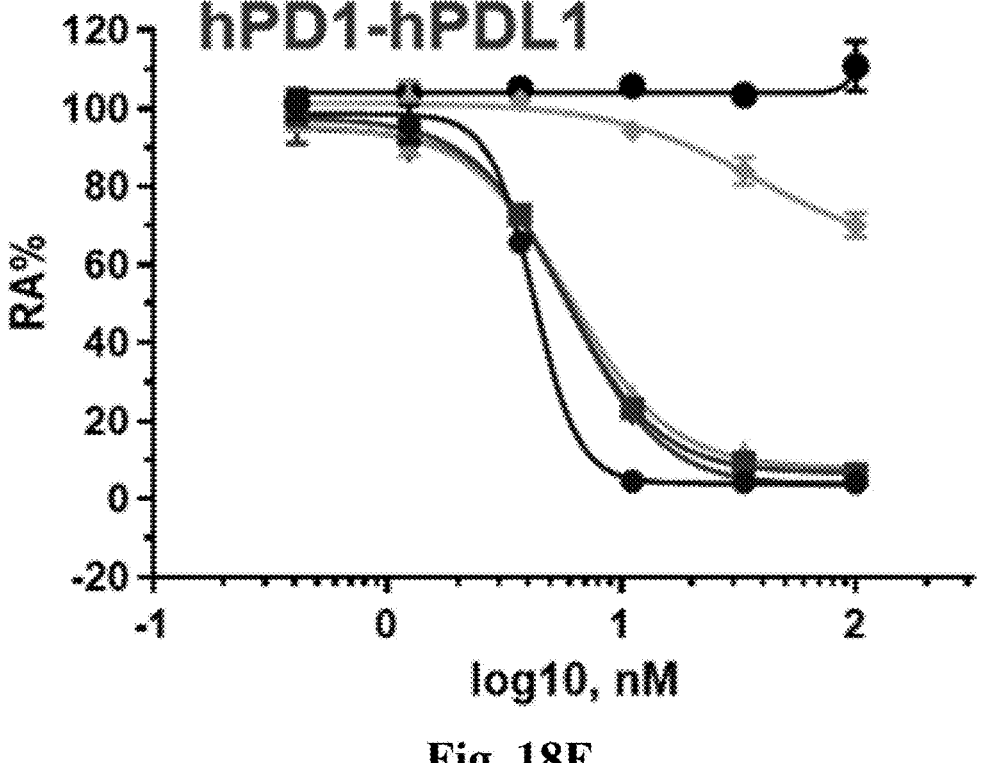
Figure 19A:
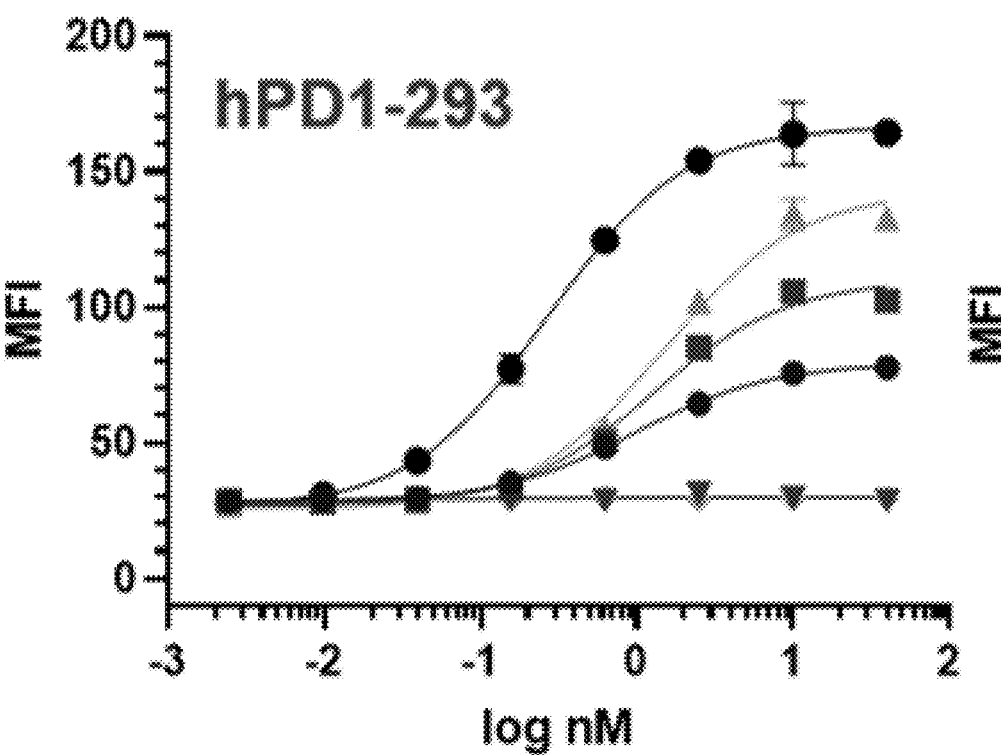
FIG. 19A, FIG. 19B, FIG. 19C, and FIG. 19D depict binding of antibodies m2A1, m2C1, m4D1, R3A9, m3A7 and 38B2 to cells expressing hPD-1 or mPD-1. Cells expressing human PD-1: hPD-293 (FIG. 19A, labels as in FIG. 19D) and hPD-1 Jurkat (FIG. 19B, labels as in FIG. 19D). Cells expressing murine PD-1.
Figure 19B:
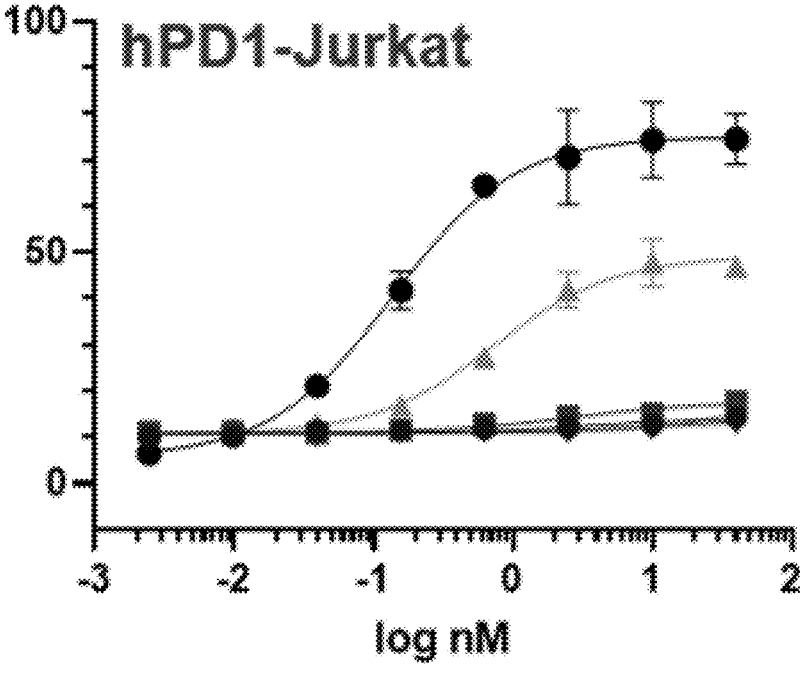
Figure 19C:
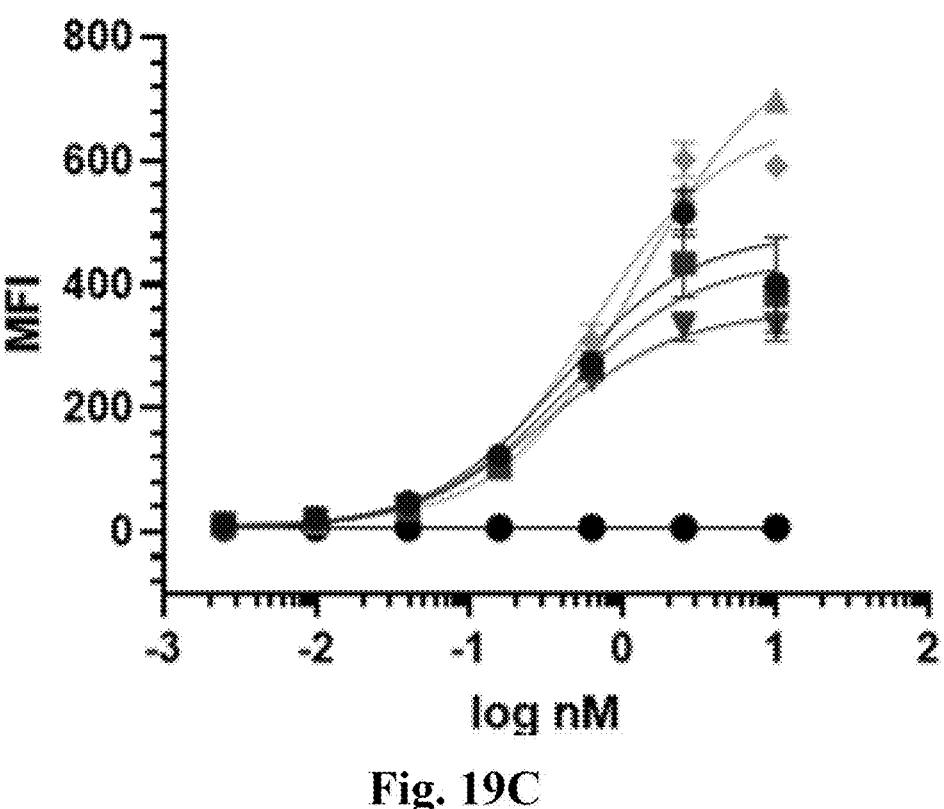
Figure 19D:
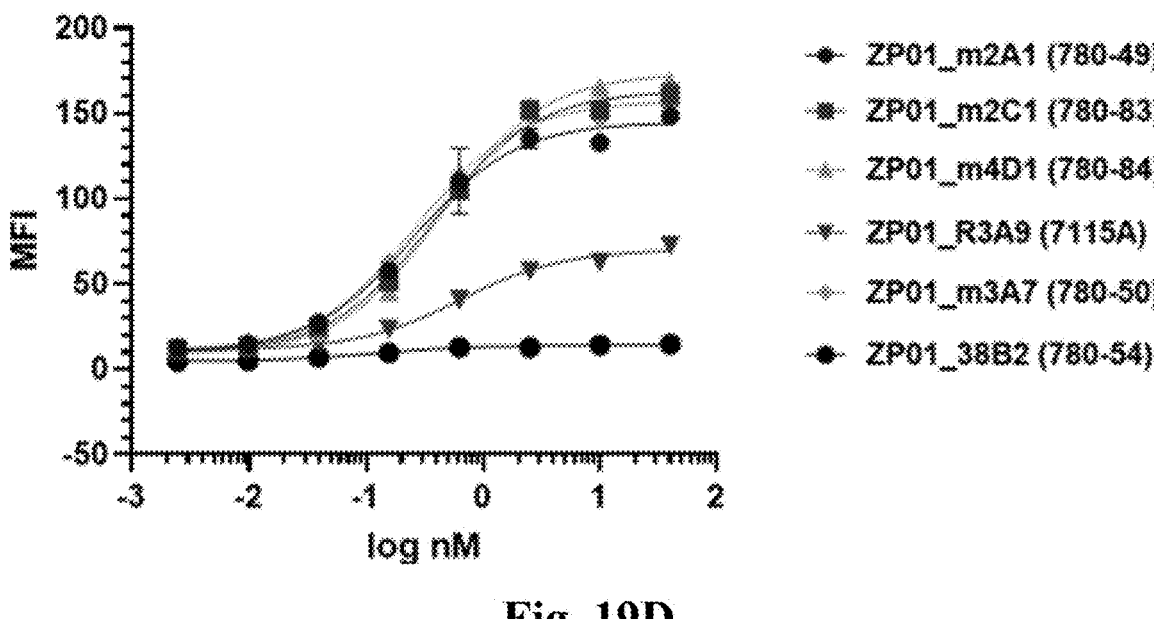

Dose response Binding and Blocking ELISAs for antibodies were performed using the protocols outlined in Examples 2 and 3, respectively. The experiments showed all R3A9 derivaties bound strongly to both hPD-1 and mPD-1 (FIG. 18A-C) and blocked hPD-L1-hPD-1 and mPD-L1/mPD-1 interaction (FIG. 18D-E). Table 19 provides EC50/IC50 data for the antibodies tested.

TABLE 19

Binding of antibodies 38B2, m2C1, m2A1, m4D1, m3A7, and R3A9 to hPD-1, mPD-1, and streptavidin-captured biotin mPD-1, and blocking of mPD-1/mPD-L1 or hPD1/hPDL1 interactions by antibodies 38B2, m2C1, m2A1, m4D1, m3A7, and R3A9.

| EC50/ IC50, nM | Target | hPD1 Ab (38B2) | m2C1 | m2A1 | m4D1 | m3A7 | mPD1 parental (R3A9) |
|---|---|---|---|---|---|---|---|
| EC50, nM | hPD1 | 0.125 | 0.1494 | 0.1465 | 0.2208 | 0.6302 | 3.246 |
| EC50, nM | mPD1 | No binding | 0.5715 | 0.3039 | 2.032 | 0.3495 | 1.356 |
| EC50, nM | strep capt. Biotin-mPD1 | No binding | 0.2912 | 0.1404 | 1.15 | 0.2681 | 0.462 |
| IC50, nM | mPD1/ mPDL1 | No binding | 0.4641 | 0.442 | 0.8818 | 0.5373 | 0.722 |
| IC50, nM | hPD1/ hPDL1 | 4.25 | 5.707 | 6.01 | 6.02 | 37.77 | No binding |

Example 21: R3A9 Bind to Cells Expressing Human or Mouse PD-1

Binding of R3A9 and its R3A9 derivatives m2A1, m2C1, m4D1, m3A7 to PBMCs cells were tested using the protocol outlined in Example 4. Further, Biacore analysis was performed on all the antibodies disclosed in this Example using the protocol provided in Example 11.

Only three derivatives, m4d1, m2A1, and m3C1, were found to bind to both human and mouse PD-1 expressed on cells (Table 21 and FIG. 19). Based on cell binding (Table 20) and Biacore analysis (Table 20), m4D1 was found to show improved binding properties as compared to the other two antibodies tested (Table 20 and FIG. 19).

TABLE 20

Binding affinity data for indicated antibodies as determined by SPR.

| | Biacore Analysis | | | | | | | | |
| | mPD1-his | | | mPD1-Fc | | | hPD1-Fc | | |
| Name | $k_a$ (1/Ms) | $k_d$ (1/s) | $K_D$ (M) | $k_a$ (1/Ms) | $k_d$ (1/s) | $K_D$ (M) | $k_a$ (1/Ms) | $k_d$ (1/s) | $K_D$ (M) |
|---|---|---|---|---|---|---|---|---|---|
| 38B2 | | no binding | | | no binding | | 2.21E+05 | 3.26E−05 | 1.47E−10 |
| m2A1 | 3.75E+05 | 1.07E−03 | 2.83E−09 | 3.33E+05 | 9.05E−04 | 2.73E−09 | 2.40E+05 | 4.01E−04 | 1.67E−09 |
| m2C1 | 2.15E+05 | 6.93E−04 | 3.22E−09 | 2.00E+05 | 5.83E−04 | 2.91E−09 | 1.26E+05 | 3.55E−04 | 2.81E−09 |
| m4D1 | 7.00E+04 | 2.01E−04 | 2.87E−09 | 6.63E+04 | 1.79E−04 | 2.69E−09 | 5.83E+04 | 6.36E−05 | 1.09E−09 |
| m3A7 | 2.72E+05 | 8.23E−04 | 3.03E−09 | 2.61E+05 | 6.59E−04 | 2.53E−09 | 1.71E+05 | 1.76E−02 | 1.03E−07 |
| m3A7 | 2.41E+05 | 4.79E−04 | 1.98E−09 | 2.19E+05 | 4.06E−04 | 1.86E−09 | 1.32E+05 | 2.63E−03 | 1.99E−08 |
| R3A9 | 4.09E+05 | 6.41E−03 | 1.57E−08 | 1.16E+05 | 1.40E−03 | 1.21E−08 | | no binding | |

TABLE 21

Binding of antibodies m2A1, m2C1, m4D1, R3A9, m3A7 and 38B2 to cells expressing hPD-1 or mPD-1.

| | EC50 of cells expressing h/mPD1, nM | | | |
| Name | hPD1-293 | hPD1-Jurkat | mPD1-293 | mPD1-eff |
|---|---|---|---|---|
| 38B2 | 0.267 | 0.137 | ND | ND |
| m2A1 | 0.987 | ND | 0.433 | 0.253 |
| m2C1 | 1.263 | very weak | 0.411 | 0.373 |
| m4D1 | 1.48 | 0.738 | 1.139 | 0.441 |
| m3A7 | ND | ND | 0.609 | 0.27 |
| m3A7 * | NA | NA | NA | N |
| R3A9 | ND | ND | 0.314 | 0.645 |

Example 22: Promega (h/m) PD-1/(h/m) PD-L1 Blockade Bioassay Comparing m4D1 with 38B2 and m3A7

Figures 20A, 20B:
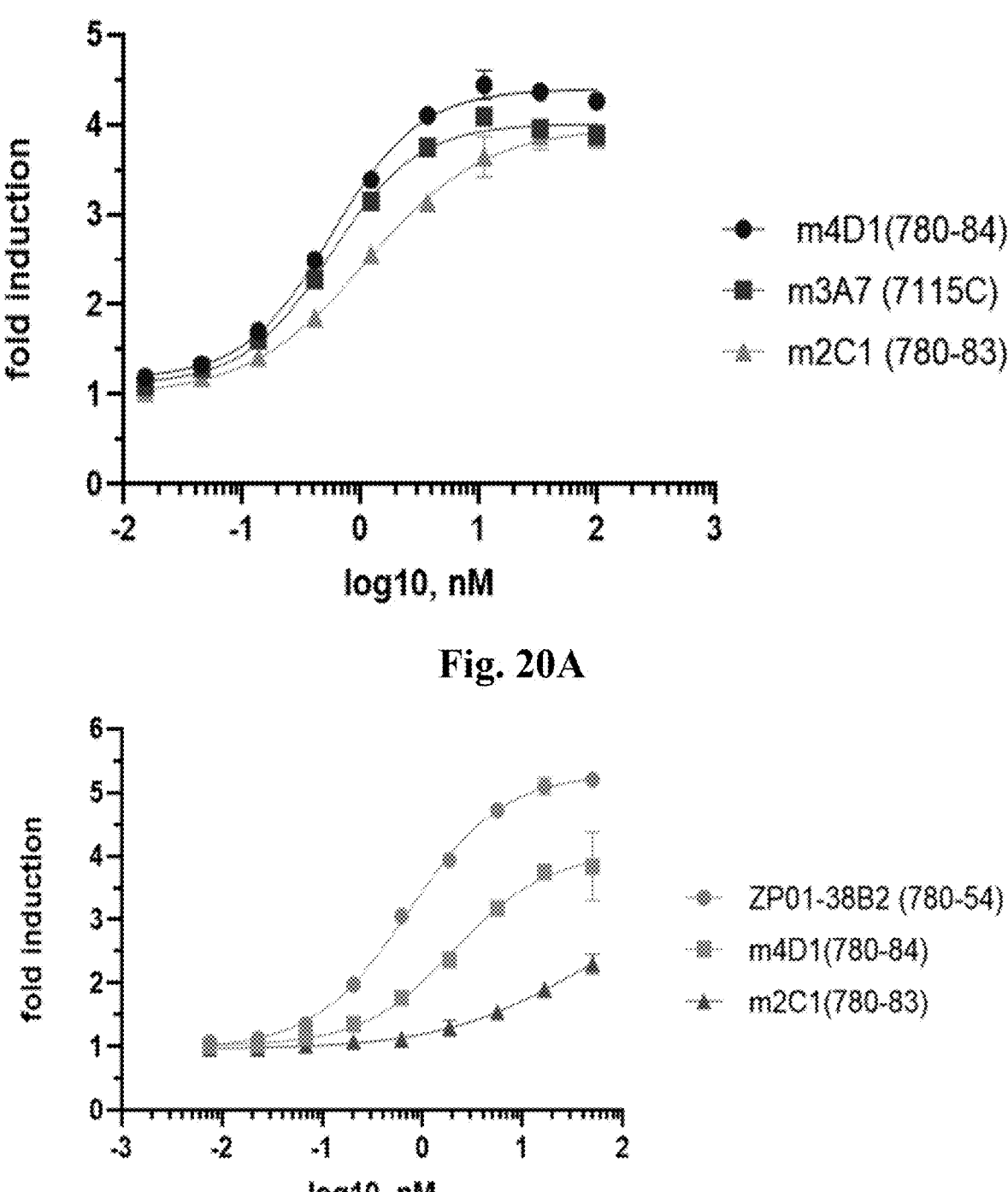
FIG. 20A and FIG. 20B depict blocking of mPD-1/mPD-L1 interactions and blocking of hPD-1-hPD-L1 interactions by antibodies 38B2, m4D1, and m2C1.
Figure 21A:
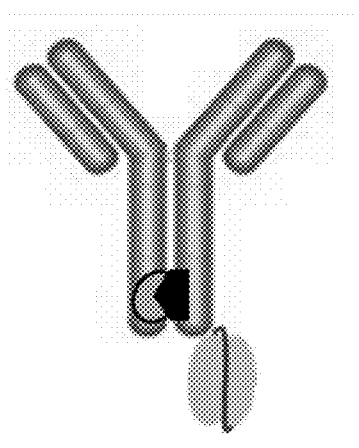
FIG. 21A and FIG. 21B depict schematic diagrams of exemplary PD-1/IL-15 fusion proteins.
Figure 21A:
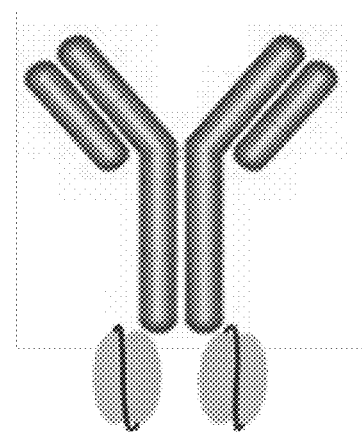
Figure 21A:
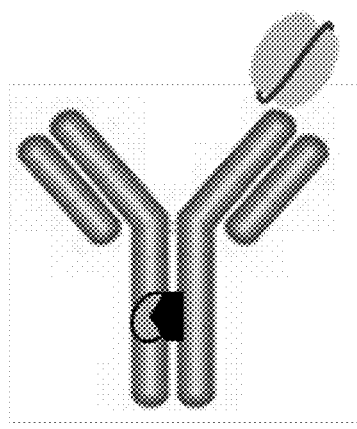
Figure 21A:
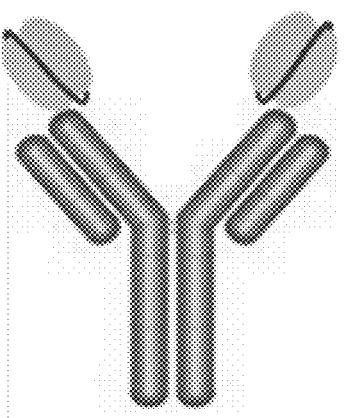
Figure 21B:
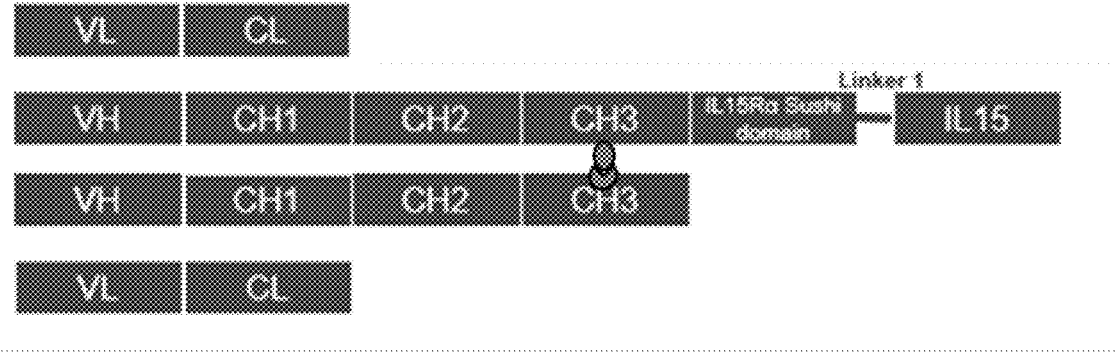
Figure 21B:
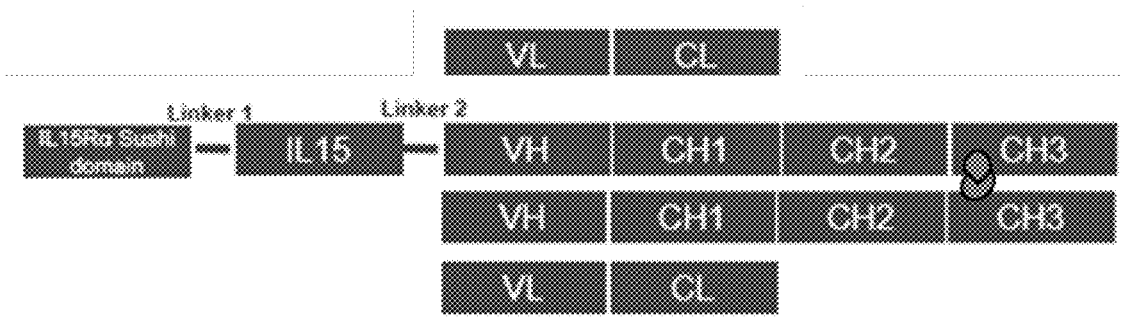
Figure 22A:
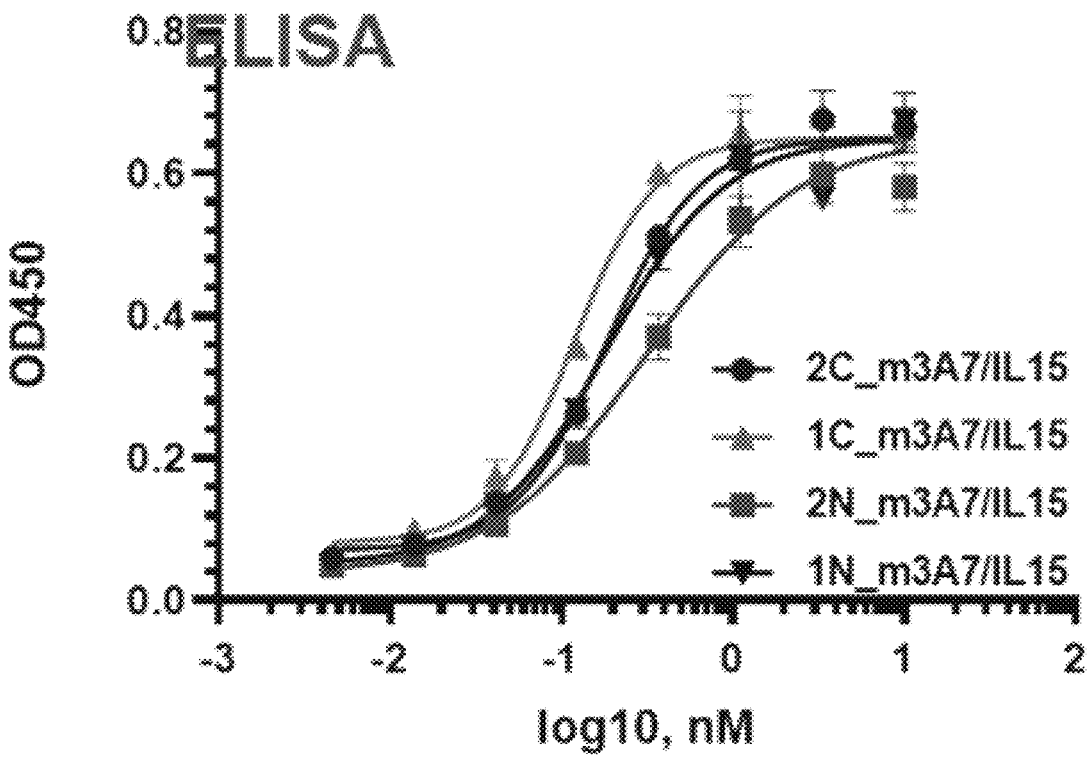
FIG. 22A, FIG. 22B, FIG. 22C, and FIG. 22D depict binding of fusion proteins 1N-m3A7/IL-15, 2N-m3A7/IL-15, 1C-m3A7/IL-15, and 2C-m3A7/IL-15 to mPD-1 (FIG. 22A) and to cells expressing mPD-1 (FIG. 22B) as well as blocking of mPD-L1 to mPD-1 using a competition ELISA (FIG. 22C) or a Promega blocking assay (FIG. 22D).
Figure 22B:
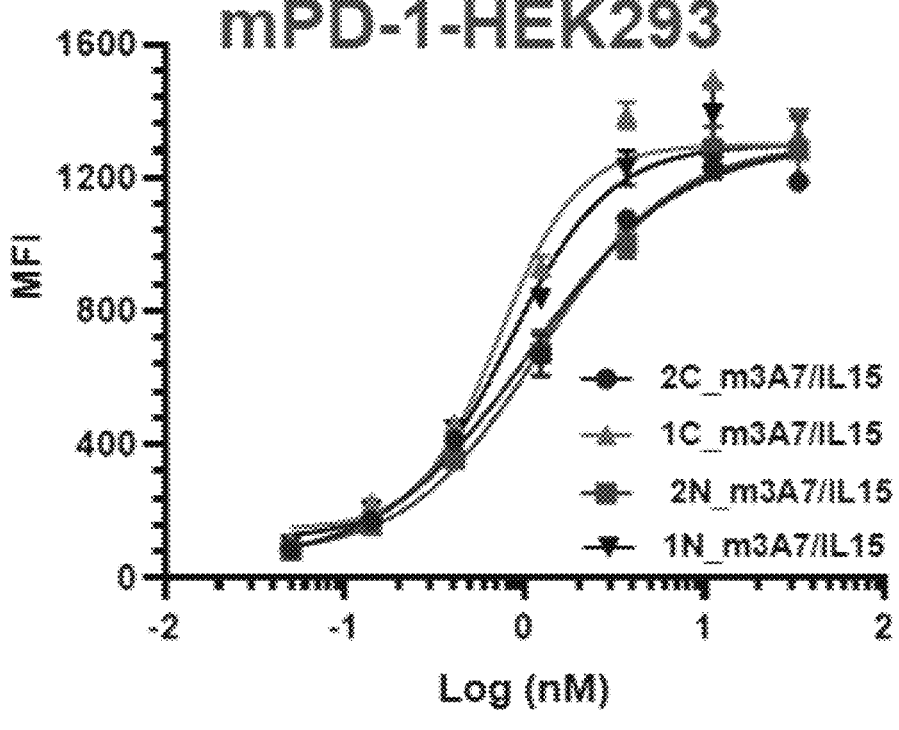
Figure 22C:
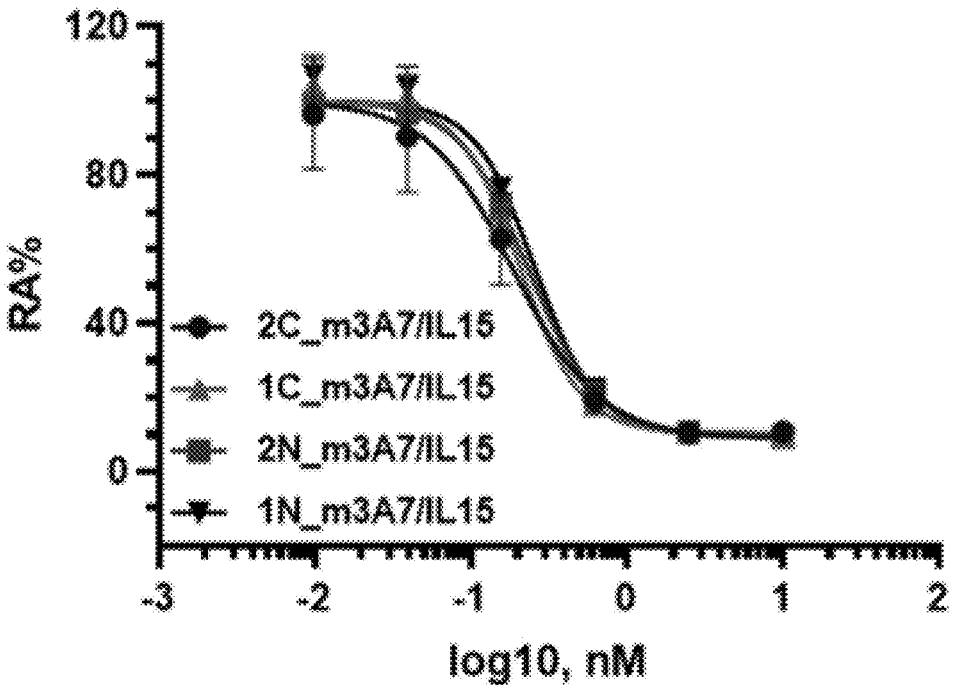
Figure 22D:
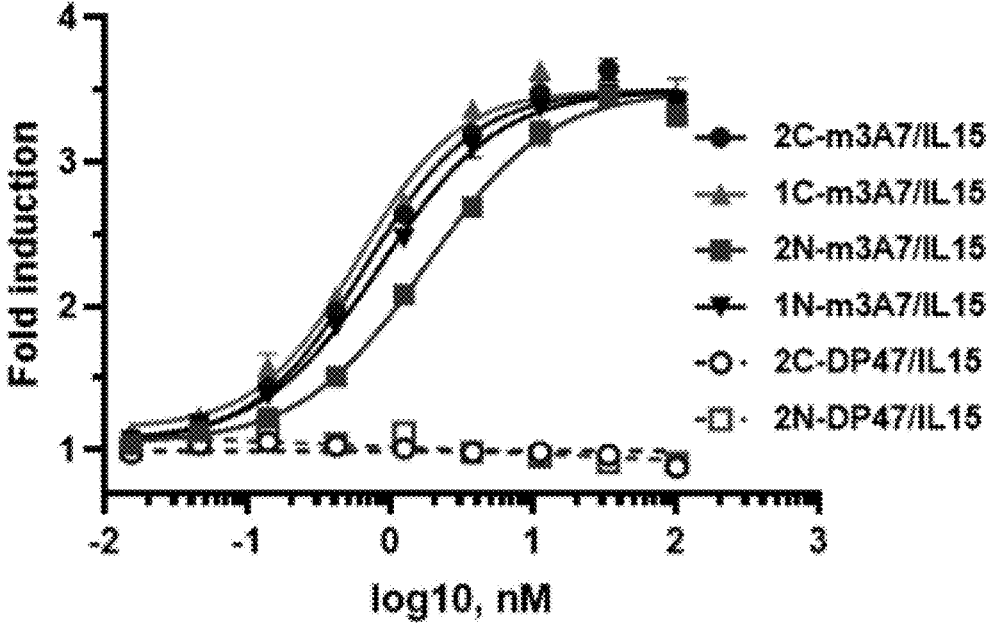

Promega blockade bioassays were performed to compare the potency of m4D1, m3A7 and 38B2 to disrupt intercellular PD-1/PD-L1 interactions using the protocol outlined in Example 4. The results are depicted in FIG. 20.

m4D1 was found to block both hPD-1/PD-L1 and mPD-1/mPD-L1 interactions. Further, m4D1 was found to be as potent as m3A7 in mPD-1/mPD-L1 blockade assay and 3 folds less potent than 38B2 (FIG. 20).

Example 23: Fusion Proteins Comprising Anti-mPD1- or Anti-hPD-1 Antibodies, IL-15 and, IL-15Rα Sushi Domain Anti-mPD-1 fusion antibodies comprising antibody m3A7 (referred to as m3A7/IL-15) were engineered by appending the sushi-domain of IL-15Rα and an IL-15 polypeptide to either the C-terminus or N-terminus of the antibody. The fusion of the IL-15Rα sushi domain along with a portion of the hinge region, linker 1, and IL-15 is called "SD15." See, for an example of an SD15 domain, SEQ ID NO:174 in Table 25, SD15 domain highlighted in bold.

In the first version of the fusion protein, the SD15 domain was fused to the C-terminus of only one of the IgG$_1$ CH1-CH2-CH3 domain (designated "1C-m3A7/IL-15").

In a second version, the SD15 domain was fused to the C-termini of both IgG$_1$ CH1-CH2-CH3 domains (designated "2C-m3A7/IL-15").

In a third version of the fusion protein, the SD15 domain was linked to the N-terminus of only one of the VH domains via a second linker (designated "1N-m3A7/IL-15").

In a fourth version of the fusion protein, the SD15 domain was linked to the N-terminus of both of the VH domains via a second linker (designated "2N-m3A7/IL-15).

In the four constructs above, the light chains were that of a conventional antibody. Amino acid substitutions, L234A, L235A, P329G (LALA-PG) were introduced in both the CH2 domains for eliminating complement binding and fixation as well as Fc-γ dependent antibody-dependent cell-mediated cytotoxity (ADCC).

Further, for heterodimeric fusions, mutations were introduced into constant regions of the heavy chains, wherein the amino acid substitutions were selected from one of the following groups: (1) CH3-1: T366Y ("knob"); CH3-2: Y407T ("hole"), (2) CH3-1: S354C, T366W ("knob"); CH3-2: Y349C, T366S, L368A, Y407V ("hole") and (3) CH3-1: T350V, L351Y, F405A, Y407V ("knob"); CH3-2: T350V, T366L, K392L, T394W ("hole").

The fusion antibodies were expressed transiently in CHOk1 cells. At least 95% purity of the monomer was obtained after purification with Protein A and SEC-HPLC. Four corresponding versions of anti hPD-1/IL-15 fusion antibodies comprising antibody 38B2 (described herein as 38B2-hSD15 or 38B2/IL-15)—1C-38B2-hSD15, 2C-38B2-hSD15, 1N-38B2-hSD15, 2N_-38B2-hSD15—were created following the same procedure. Three corresponding versions of 1N_38B2-SD15 bearing an amino acid substitution in position 65 of the IL-15 sequence, 65A_1N_38B2-hSD15, 65D_1N_38B2-hSd15, and 65S_1N_38B2-hSD15 were created using the same procedure.

Four corresponding versions of control fusion antibodies (DP47/IL-15) 1C-DP47/IL-15, 2C-DP47/IL-15, 1N-DP47/IL-15, 2N-DP47/IL-15 were created following the same procedure. DP47 was used as a non-targeting control antibody. Schematic diagram showing the antibody orientations are shown in FIG. 21.

Example 24: MPD-1/IL-15 Fusion Molecules Bind to Murine PD-1 and Block Interactions Between mPD-1 and mPD-L1

The ability of fusion proteins 1N-m3A7/IL-15, 1C-m3A7/IL-15, 2N-m3A7/IL-15, and 2C-m3A7/IL-15 to bind to mPD-1 and to block interactions between mPD-1 and mPD-L1 was assessed by ELISA, following the protocols described in Example 2 and 3, respectively.

No significant differences in binding and blocking capacity were observed among the four different molecules (Table 22 and FIG. 22).

TABLE 22

Binding to mPD-1 and blocking of mPD-L1 to mPD-1 by fusion proteins 1N_m3A7/IL-15, 2N_m3A7/IIL5, 1C_m3A7/IIL5, and 2C_m3A7/IL-15.

| Name | Ka | Kd | KD |
|---|---|---|---|
| | Binding to mPD-1-his | | |
| 2C-m3A7/IL15 | 2.00E+05 | 4.94E−05 | 2.47E−10 |
| 2N-m3A7/IL15 | 9.21E+04 | 2.61E−05 | 2.83E−10 |
| 1C-m3A7/IL15 | 2.32E+05 | 6.87E−05 | 2.96E−10 |
| 1N-m3A7/IL15 | 1.52E+05 | 6.95E−05 | 4.57E−10 |
| | Binding to mPD-1-Fc* | | |
| 2N-m3A7/IL15 | 1.15E+05 | 1.05E−06 | 9.09E−12 |
| 2C-m3A7/IL15 | 1.81E+05 | 1.08E−05 | 5.93E−11 |
| 1N-m3A7/IL15 | 1.46E+05 | 1.28E−05 | 8.78E−11 |
| 1C-m3A7/IL15 | 2.00E+05 | 1.86E−05 | 9.27E−11 |

*The off rate was too slow and outside the machine limit.

Example 25: Effect of mPD-1/IL-15 Fusion Molecules on IL-2-Dependent Cell Growth Stimulation of Mouse Lymphocytes CTLL2 and C57BL6 Spleen Cells CTLL2 Culture and Proliferation Assay: The murine T lymphocyte cell line CTLL2 was cultured in IMDM medium supplemented with 10% heat-inactivated FBS and 10% IL-2 supplement (T cell culture supplement with ConA, Corning). The following fusion proteins were tested in this example: 1N-m3A7/IL-15, 2N-m3A7/IL-15, 1C-m3A7/IL-15 and 2C-m3A7/IL-15. 1N-DP47/IL-15, 2N-DP47/IL-15, 1C-DP47/IL-15, 2C-DP47/IL-15 and m3A7 were used as controls.

Serial dilutions of antibodies or fusion proteins were added in a 96-well plate, and then cells were seeded at $2.5\times10^4$ per well in IMDM medium supplemented with 10% heat-inactivated FBS. The cells were incubated at 37° C. for 3-5 days and cell proliferation was detected using CellTiter-Glo® luminescent cell viability assay kit (Promega).

Mouse Spleen Cell Isolation and Proliferation Assay: C57BL/6 mouse spleens were homogenized in IMDM medium through the 70 μm cell strainer. 1×RBC lysis buffer (eBioscience) was added to spleen cells and left for 3 min with occasional shaking, and then diluted with 5-fold volume of PBS buffer. After washing with PBS buffer, the splenocyte cell suspension was prepared in complete IMDM medium supplemented with 10% heat-inactivated FBS for proliferation assay immediately. The following fusion proteins were tested in this example: 1N-m3A7/IL-15, 2N-m3A7/IL-15, 1C-m3A7/IL-15 and 2C-m3A7/IL-15. 1N-DP47/IL-15, 2N-DP47/IL-15, 1C-DP47/IL-15, and 2C-DP47/IL-15 were used as controls.

Serial dilutions of the fusion proteins and controls were added in a 96-well plate and then cells were seeded at $1\times10^5$ per well. The cells were cultured for 5-7 days at 37° C. and collected for flow-cytometry analysis. The cells were washed and stained with fixable viability dye Fluor780 (eBioscience) for 30 min at 4° C. The cells were fixed after washing and were permeabilized with Foxp3 transcription factor staining buffer set (eBioscience), followed by staining with CD3 (145-2C11)-PE, CD4 (RM4-5)-APC, CD8α-(53-6.7)-PECy7 and Ki67 (SolA15)-FITC from eBioscience. Proliferative CD4 ($CD4^+Ki67^+$) or CD8 ($CD8^+Ki67^+$) T cell population were analyzed and defined using Guava Flow Cytometry EasyCyte system.

Figure 23A:
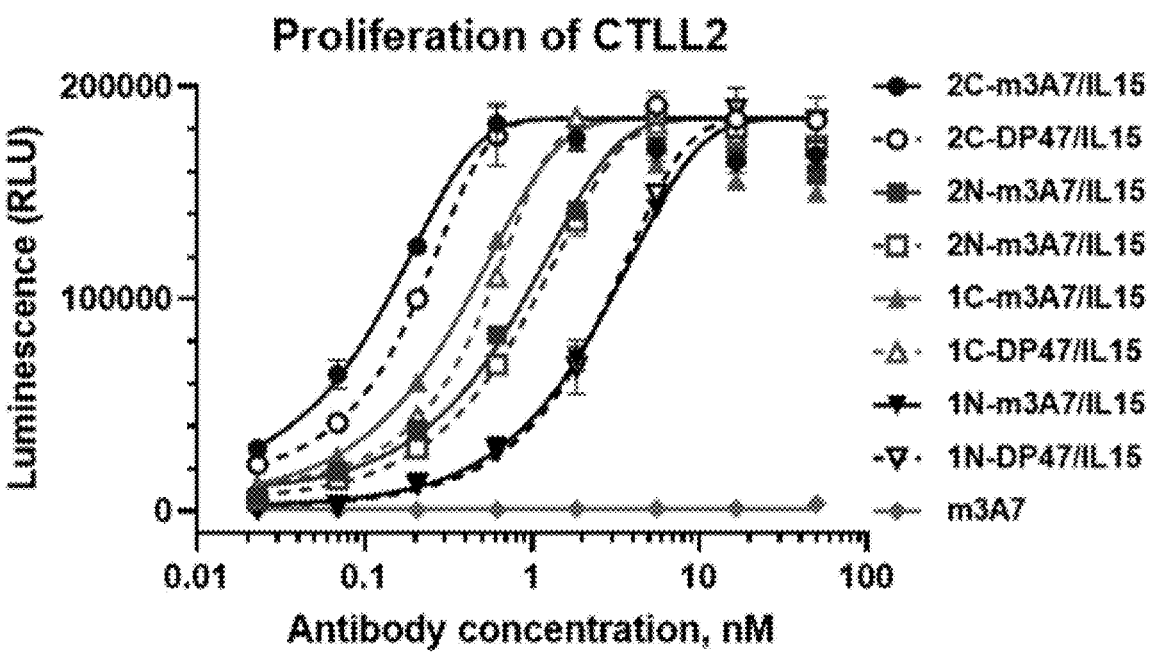
FIG. 23A, FIG. 23B.
Figure 23B:
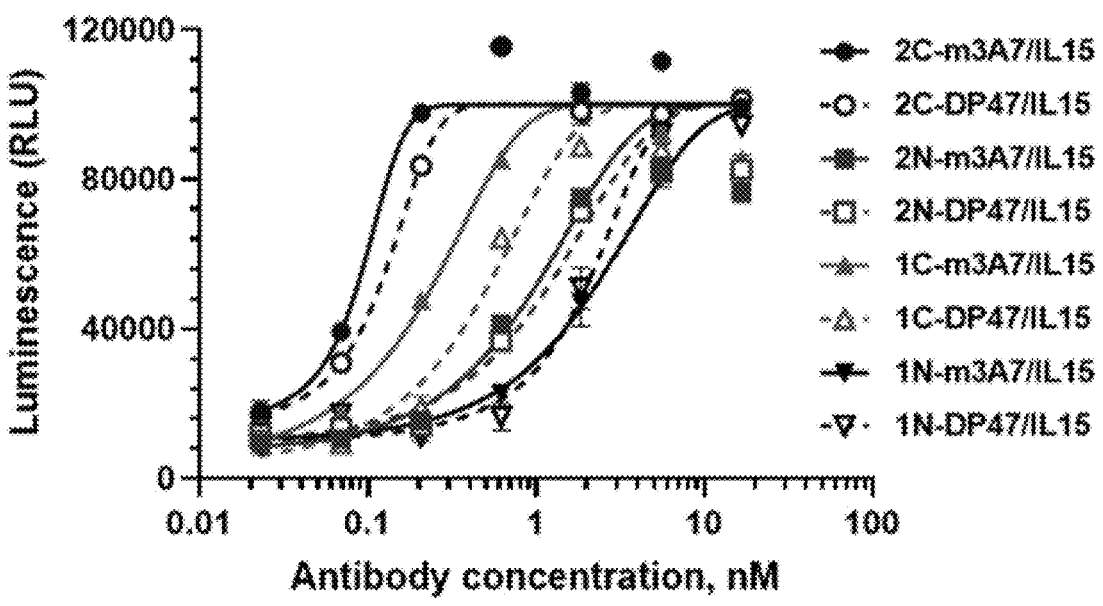
Figure 23C:
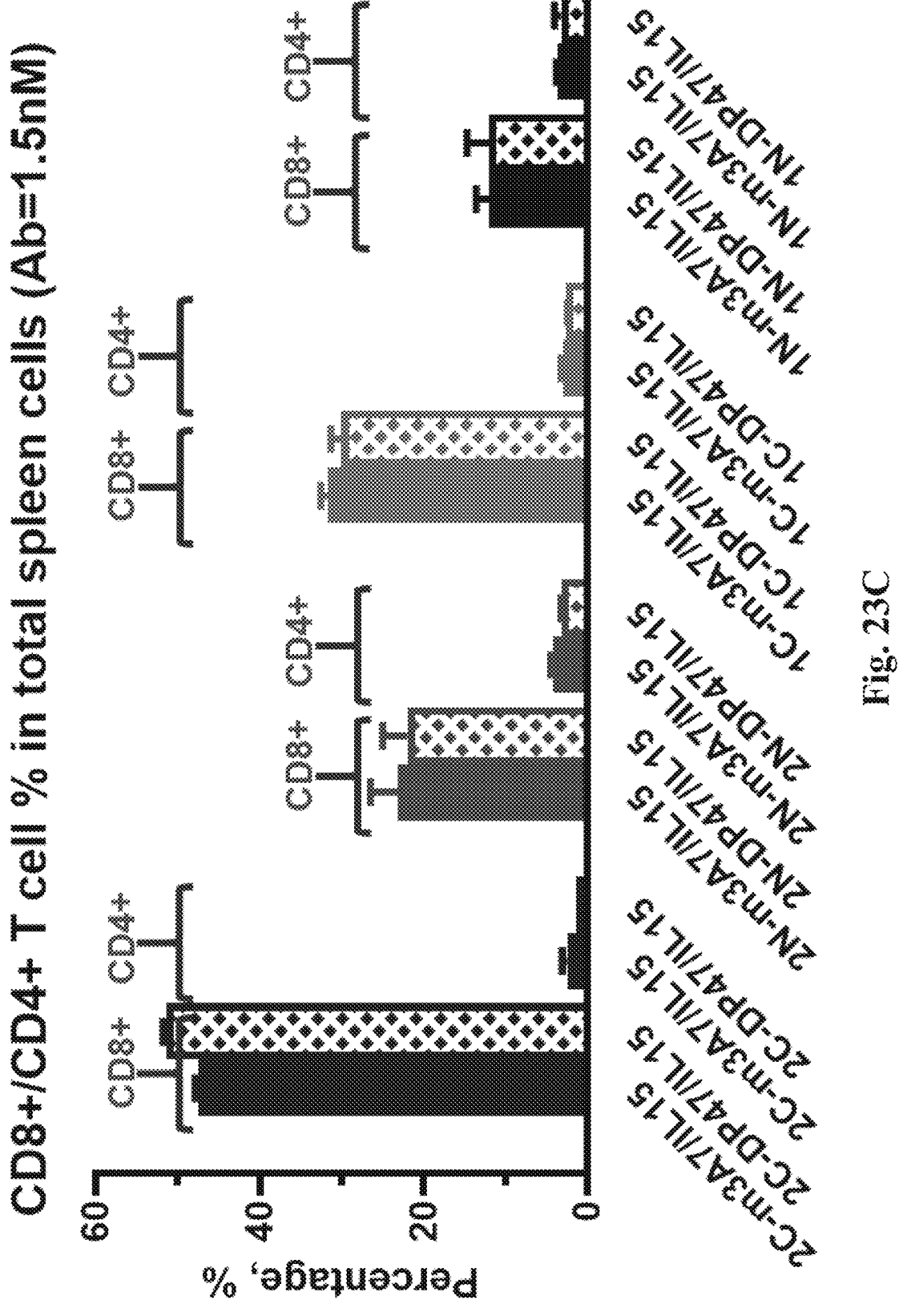
FIG. 23C depict the effect of fusion proteins 1N-m3A7/IL-15, 2N-m3A7/IL-15, 1C-m3A7/IL-15, and 2C-3A7/IL-15 on proliferation of CTLL2 (FIG. 23A) and C57BL6 (FIG. 23B).

All mPD-1/IL-15 fusion constructs stimulated both IL-2 dependent mouse lymphocyte CTLL2 (FIG. 23A) and C57BL6 spleen cell growth (FIG. 23B). Analysis of T cell populations showed that only the percentage of CD8 T cell population increased while the population percentage of CD4 T cells remained unaffected (FIG. 23C). Out of the four constructs tested, 1N-m3A7/IL-15 showed the least stimulatory effect on IL-2 dependent mouse lymphocyte and spleen cell growth and T cell proliferation, while 2C-m3A7/IL-15 showed the most stimulatory effect on the cell growth and T cell proliferation.

Example 26: Efficacy Study of mPD-1/IL-15 Fusion Molecules in PD-1/PD-L1 Lewis Lung Cancer Model To determine if the orientation or the number of IL-15/IL-15Rα sushi domains in a fusion protein have any effect on the ability of the fusion molecules to reduce tumor growth, an in vivo efficacy study in an LL/2 Murine Lung Cancer Syngeneic Model was conducted by Crown Bioscience (Taicang) using the m3A7/IL-15/IL-15Rα sushi fusion proteins Inc. Constructs 1N-m3A7/IL-15 and 1C-m3A7/IL-15 were tested in this Example, while 1N-DP47/IL-15 and 1C-DP47/IL-15 were used as controls.

C57BL/6 strain mice, age from 8 to 10 weeks and weight from 16.5 to 20.7 g, were purchased from Shanghai Lingchang Biotechnology Co., Ltd (Shanghai, China). The LL/2 tumor cells were maintained in vitro with DMEM medium supplemented with 10% fetal bovine serum at 37° C. in presence of 5% $CO_2$. The cells were harvested in exponential growth phase and counted before tumor inoculation. The fusion proteins used in this example were produced by WuXi Biologics and exhibited at least 95% purities and contained more than 95% monomer.

Each mouse was inoculated subcutaneously at the right rear-flank region with LL/2 tumor cells ($3\times10^5$) in 0.1 ml of PBS for tumor development. The date of randomization and the first dosing day was denoted as day 0. When the mean tumor size reached approximately 100 mm$^3$ the randomization process was started. Mice were randomly allocated to different study groups. Randomization was performed based on a "matched distribution" method using the multi-task method (StudyDirector™ software, version 3.1.399.19) randomized block design.

The fusion proteins were diluted according to the indicated dose and 10 μl/kg of fusion proteins was injected intravenously to the mice once every week for three weeks. The mice were weighed twice per week after randomization. Tumor volumes were measured twice per week in two dimensions using a caliper, and the volume was expressed in mm³ using the formula: "V=(L×W×W)/2, where V denoted tumor volume, L denoted tumor length (the longest tumor dimension) and W denoted tumor width (the longest tumor dimension perpendicular to L). Dosing as well as tumor and body weight measurements were conducted in a Laminar Flow Cabinet. The body weights and tumor volumes were measured by using StudyDirector™ software (version 3.1.399.19).

To determine antitumor activity of the fusion proteins, tumor growth inhibition (TGI) percentages were measured and recorded daily using the following formula TGI (%)=100×(1−T/C), where T and C denoted mean tumor volume (or weight) of the treated and control groups respectively for each of the fusion proteins and controls.

Figure 24:
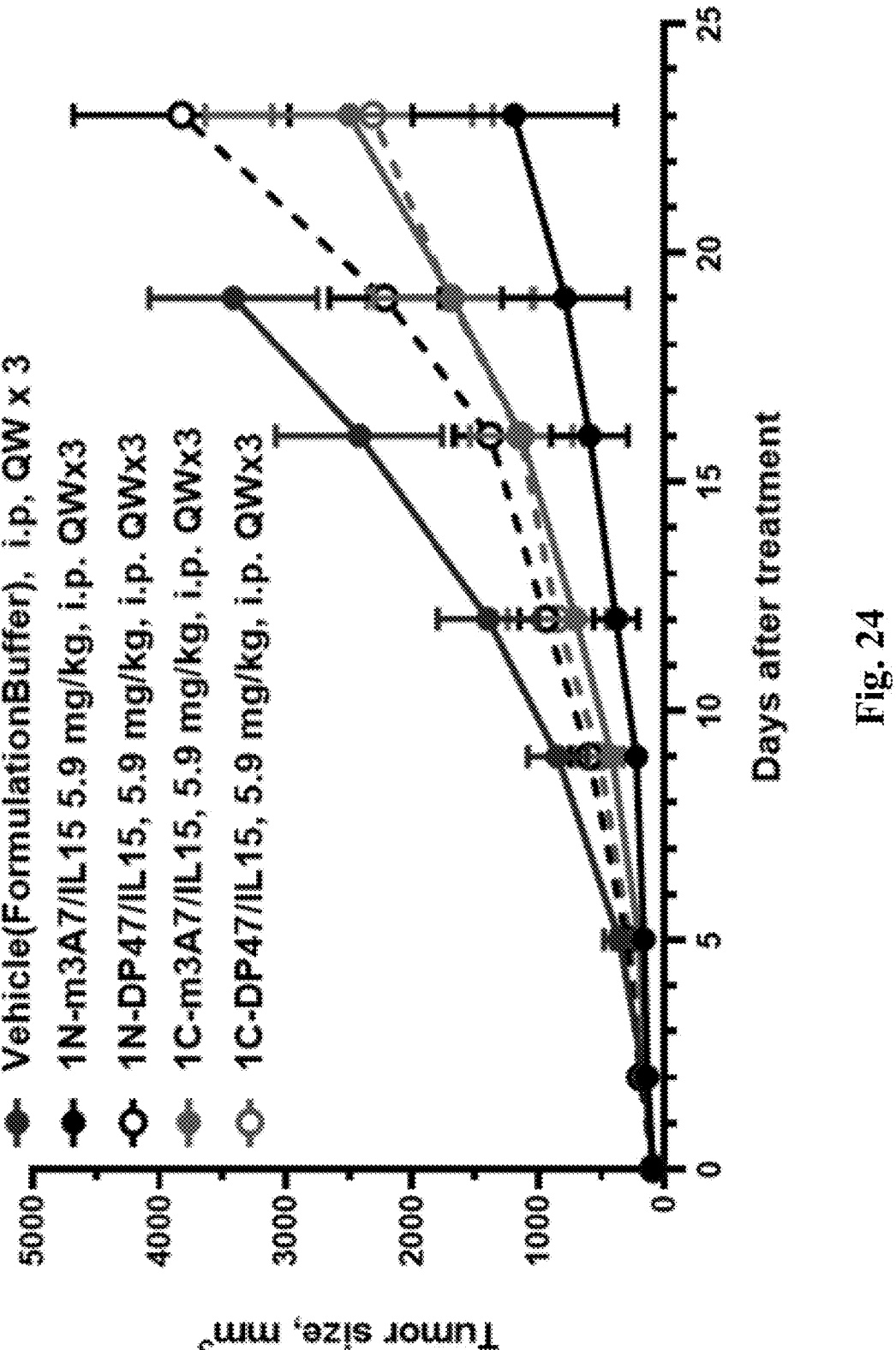
FIG. 24 depicts the ability of anti-PD-L1/SD15 fusion proteins to reduce tumor growth of mice bearing PD-1 expressing tumors in a PD-1/PD-L1 resistant Lewis Lung Model (LL2).

Of the fusion proteins tested, 1N-m3A7/IL-15 showed the most inhibitory effect on tumor growth (Table 23 and FIG. 24).

Taken together, the data obtained from Examples 25 and 26 suggests that compared to the C-terminal fusion antibodies, the N-terminal fusion antibodies reduce the toxicity further because of the lower stimulation for the peripheral T cells. The data further shows that the N-terminal fusion molecules are particularly effective in stimulating tumor infiltrating lymphocytes (TIL) as compared on peripheral T cells due to the cis-presentation; the reduction of IL-2Rβγ binding in N-terminal fusion molecules allows the PD-1/IL-15 to selectively bind to TIL, therefore reducing its toxicity. Finally, the data shows that 1N-fusion molecules are superior to the 2N-fusion molecules.

Serial dilutions of antibodies or fusion proteins were added to a 96-well plate, and then cells were seeded at 2.5×10⁴ per well in IMDM medium supplemented with 10% heat-inactivated FBS. The cells were incubated at 37° C. for 3-5 days and cell proliferation was detected using CellTiter-Glo® luminescent cell viability assay kit (Promega).

Figure 27A:
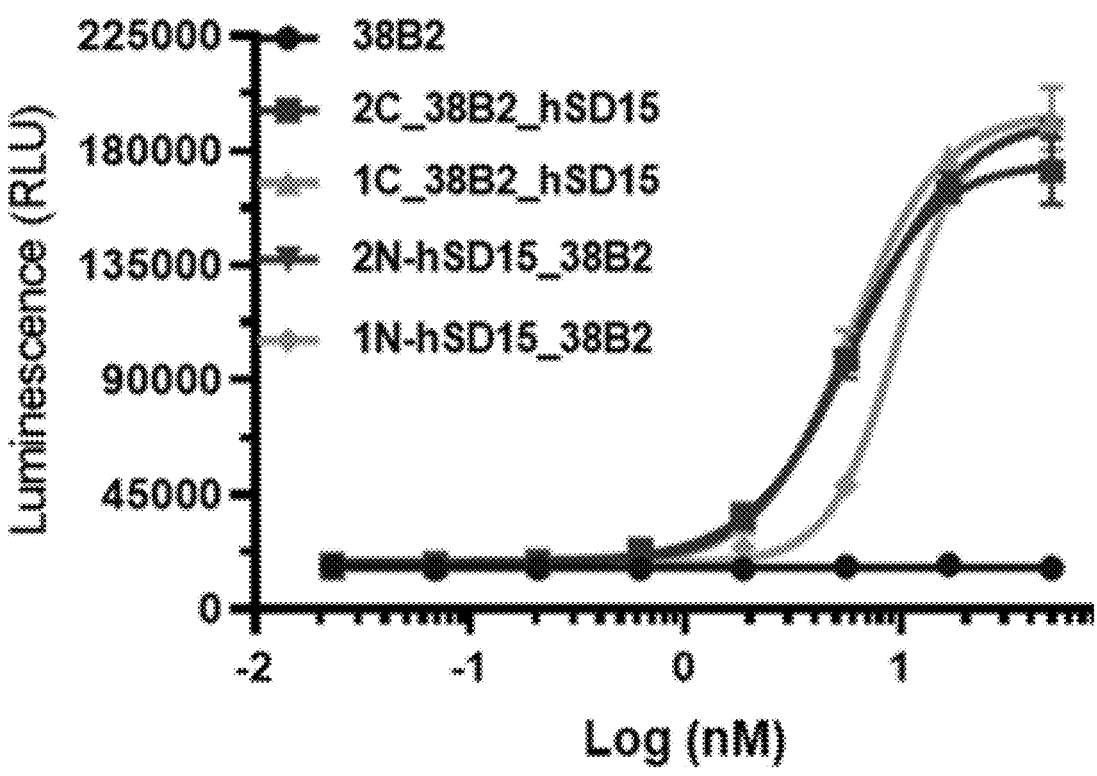
FIG. 27A, FIG. 27B and FIG. 27C illustrate stimulation of the proliferation of M07e cells by the indicated anti-PD-L1-SD15 fusion proteins.
Figure 27B:
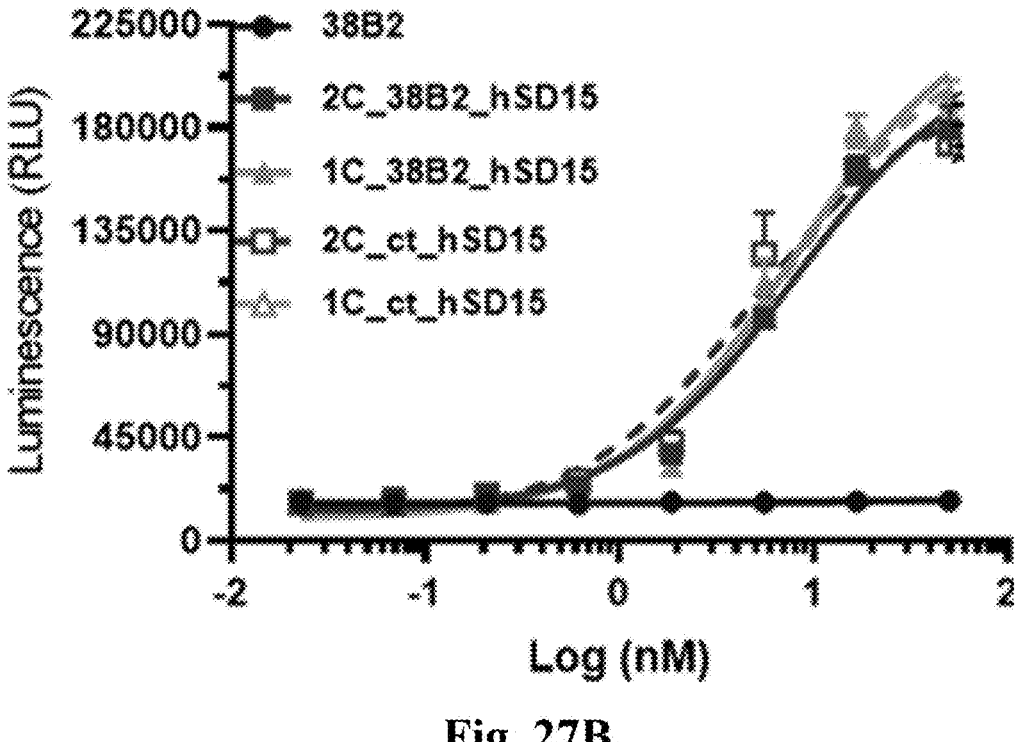
Figure 27C:
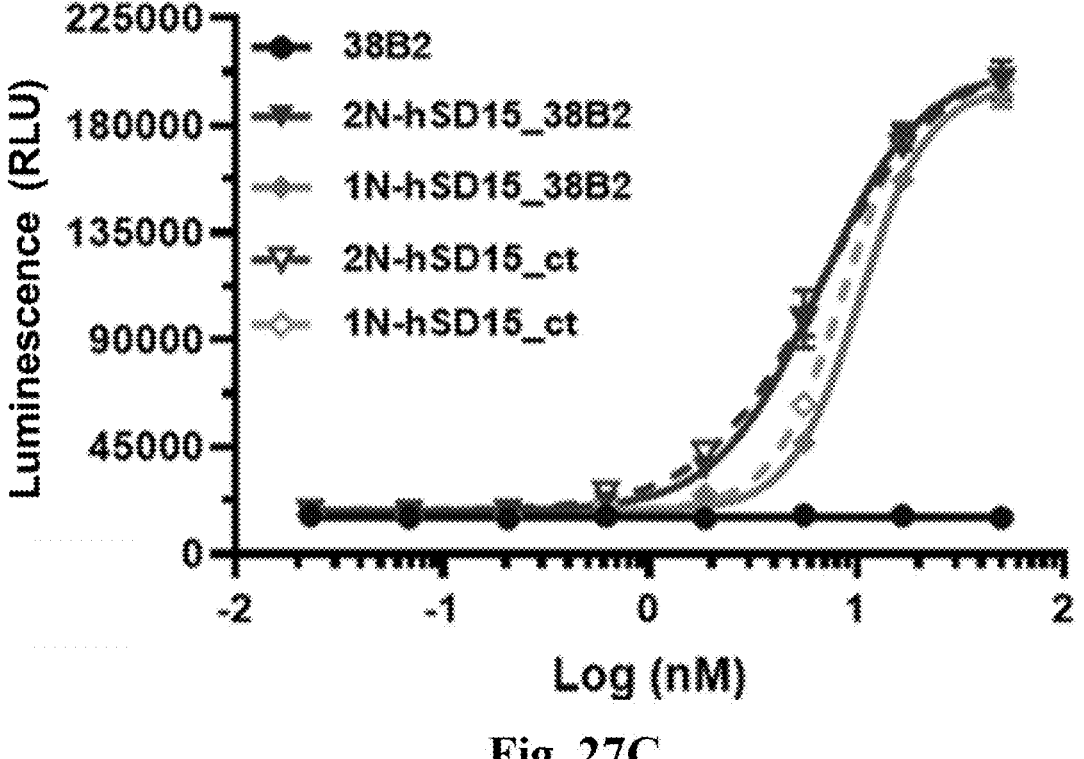

While all tested fusion protein constructs stimulated IL-15 activity, 1N fusions showed a decreased ability to stimulate as compared to 1C, 2C, or 2N constructs (FIG. 27).

Example 29: Efficacy Study of hPD-L1/SD15 Fusion Molecules in CT26 Syngenic Models To determine if the orientation or the number of IL-15/IL-15Rα sushi domains have any effect on the ability of the fusion molecules to inhibit tumor growth, an in vivo efficacy study was performed in a CT26 syngenic model using 1N-SD15-D7A8, 2N-SD15-D7A8, 1C-SD15-D7A8, and 2C-SD15-D7A8. CT26 syngenic model mice were treated with the fusion proteins and observed for tumor development/reduction. CT26 is a murine colon carcinoma line.

Tumor volumes were measured twice per week in two dimensions using a caliper, and the volume was expressed in mm³ using the formula: "V=(L×W×W)/2, where V denoted tumor volume, L denoted tumor length (the longest tumor dimension) and W denoted tumor width (the longest tumor dimension perpendicular to L). Dosing as well as tumor and body weight measurements were conducted in a Laminar

TABLE 23

Ability of anti-PD-L1-SD15
fusion proteins to prolong survival of mice bearing PD-1
expressing tumors in PD-1/PD-L1 resistant Lewis Lung Model.
RMP1-14 is a control, monoclonal antibody reacts with mouse PD-1.

| | Name | | | | | |
|---|---|---|---|---|---|---|
| | Antibody | | 2 × IL15 fusions | | 1 × IL15 fusioons | |
| | RMP1-14 | m3A7 | 2C | 2N | 1C | 1N |
| Dose mg/kg | 10 | 10 | 3.3 | 3.3 | 5.9 | 5.9 |
| nmol/kg | 66.7 | 66.7 | 17.5 | 17.5 | 35.0 | 35.0 |
| Frequency, route | BIW, IP | | QW, IP | | QW, IP | |
| Tumor growth inhibition, % | −4.9 ± 36.6 | 9.6 ± 34.9 | 56.4 ± 25.2 | 49.7 ± 21.4 | 53.1 ± 16.7 | 75.4 ± 12.5 |

Figure 26A:
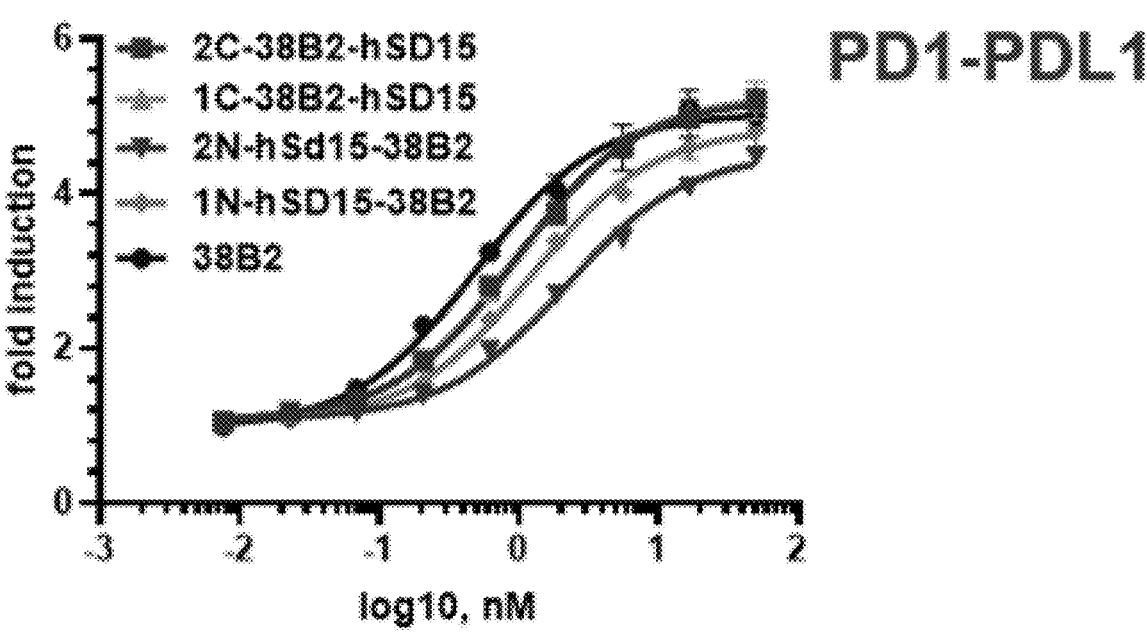
FIG. 26A, FIG. 26B, and FIG. 26C illustrate blocking of PD-1/PD-L1 interactions (FIG. 26A and FIG. 26C) and PD-1/PD-L2 interactions (FIG. 26B) for hPD-1fusion proteins (FIG. 26A and FIG. 26B) and mutated hPD-1 fusion proteins (comprising (38B2)/N65D/S/A-mutated IL-15) (FIG. 26C).
Figure 26B:
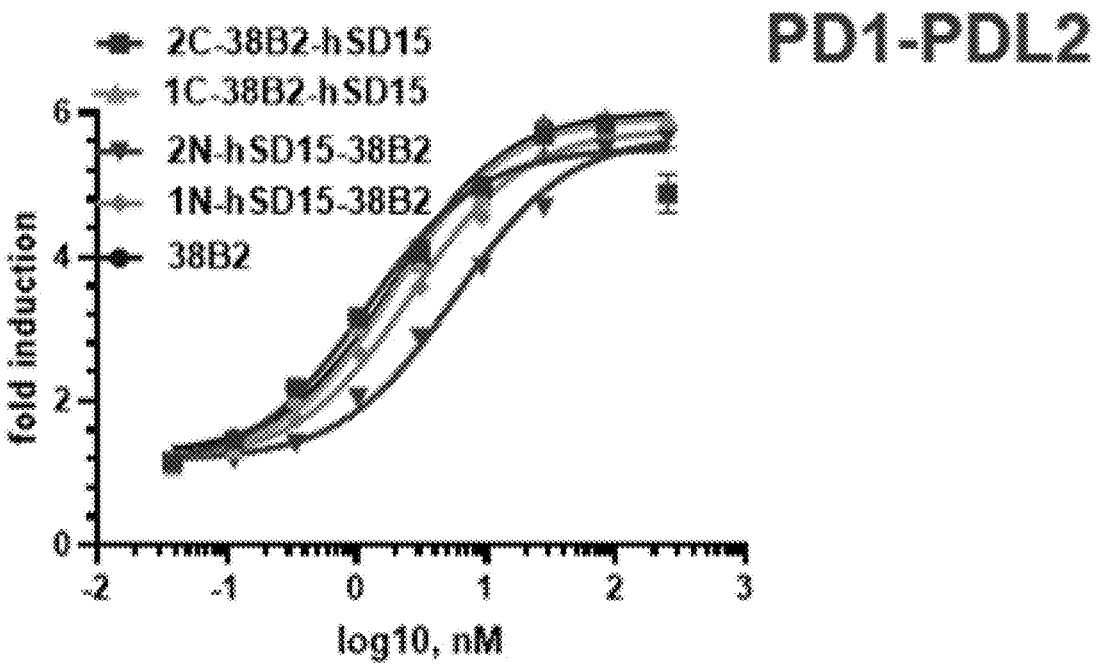
Figure 26C:
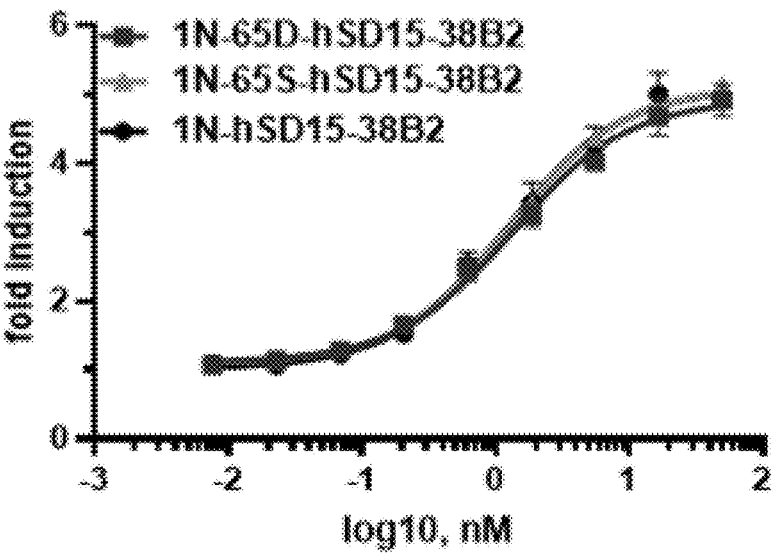

Example 27: HPD-1/IL-15 Fusion Proteins Retained their PD-1/PD-L1 Inhibitory Function Promega Blockade Bioassay was performed as described in Example 5 using fusion proteins 1C-38B2-hSD15, 2C-38B2-hSD15, 1N-38B2-hSD15, 2N-38B2-hSD15, 1N-65D-hSD15-38B2, and 1N-65S-hSD15-38B2. All fusion molecules retained PD-1/PD-L1 inhibitory functions as compared to 38B2 (FIG. 26). 1N-fusions provided the most PD-1/PD-L1 inhibitory functions.

Example 28: HPD-1/IL-15 Fusion Proteins Stimulate IL-15 Activity

ExaM07e Culture and Proliferation Assay: To determine the ability of the fusion proteins to stimulate IL-15 in vitro, the human acute megakaryoblastic leukemia M07e cell line was cultured in IMDM medium supplemented with 15% heat-inactivated FBS and 20% conditioned medium of cell line 5637.

Flow Cabinet. The body weights and tumor volumes were measured by using StudyDirector™ software (version 3.1.399.19).

Figure 28:
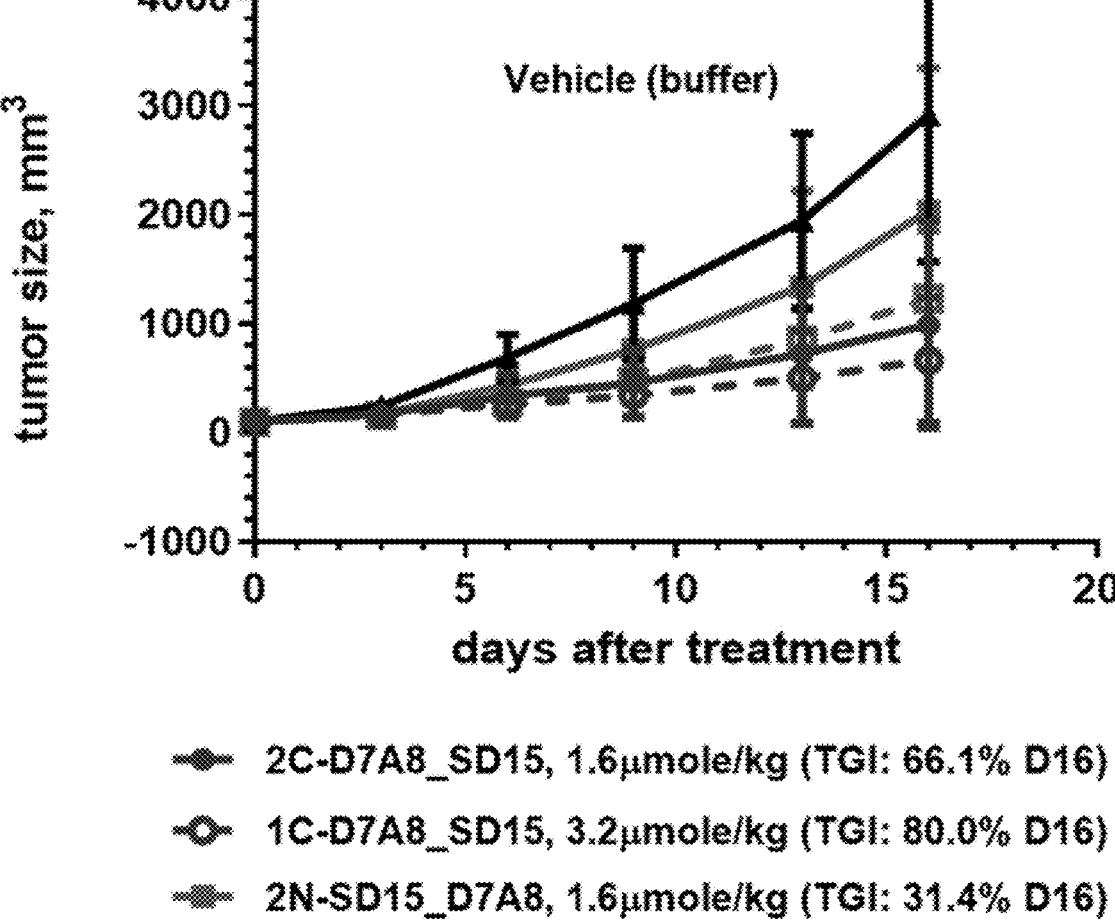
FIG. 28 illustrates the impact of different of anti-PD-L1/IL-15/linker/IL-15Rα sushi domain fusion proteins on tumor size. A CT26 syngeneic model was used. Single dose, IV. Anti-PD-L1 antibody: D7A8.

Results of the efficacy study with PD-L1/IL-15 molecules are shown in FIG. 28.

Example 30: The Presence of IL-15 Amino Acid Substitutions in the 1N-Fusion Proteins Did not Affect the Fusion Protein's PD-1/PD-L1 Inhibitory Function Promega Blockade Bioassays (FIG. 26C, FIG. 29E, and FIG. 29F) and ELISA competition assays (FIGS. 29B and 29C) showed that N65S or N65D amino acid substitutions in 1N-fusion proteins comprising IL-15 did not affect the ability of the fusion proteins to effectively disrupt PD-1/PD-L1 or PD-1/PD-L2 interactions.

Figure 29A:
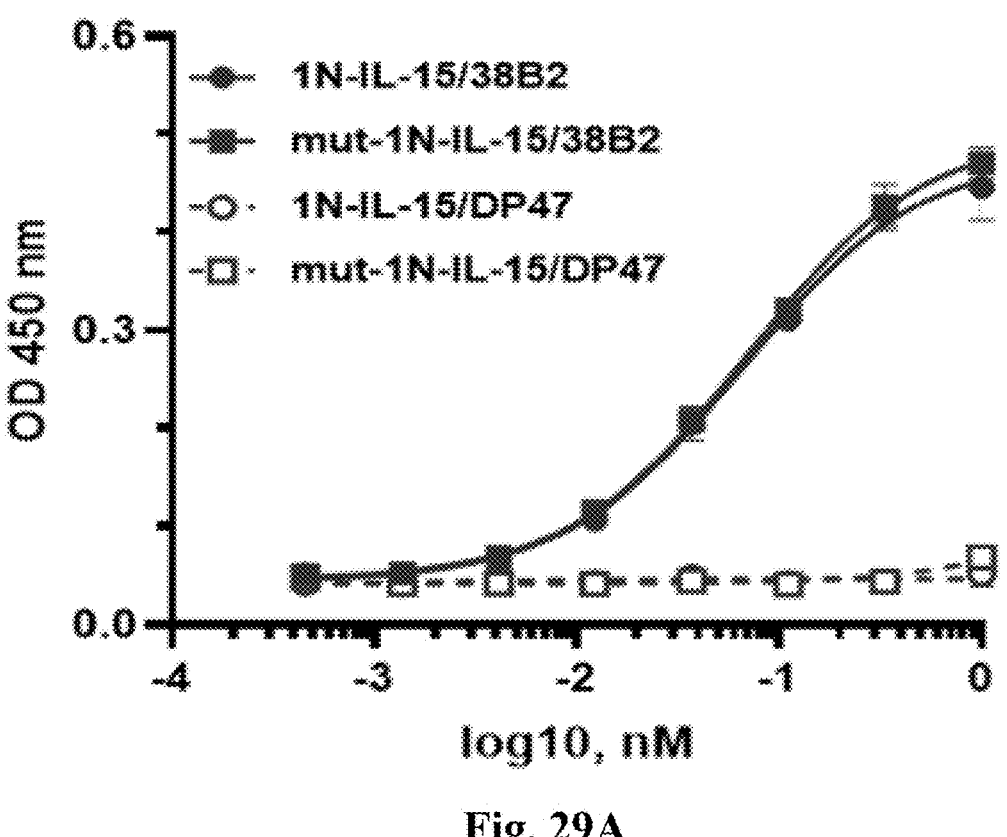
FIG. 29A, FIG. 29B, FIG. 29C, FIG. 29D, FIGS. 29E, and 29F illustrate that the presence of an N65S mutation in IL-15 in a 1N-fusion protein does not affect the ability of the fusion to bind PD-1 and to disrupt PD-1 interactions.
Figure 29B:
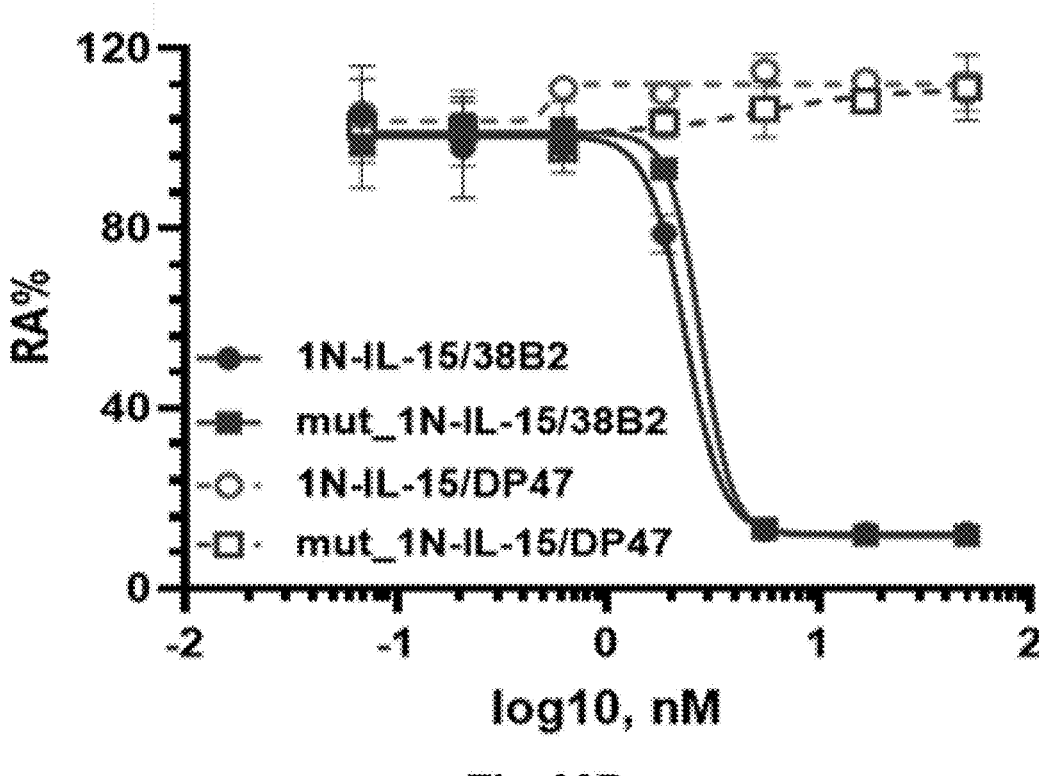
Figure 29C:
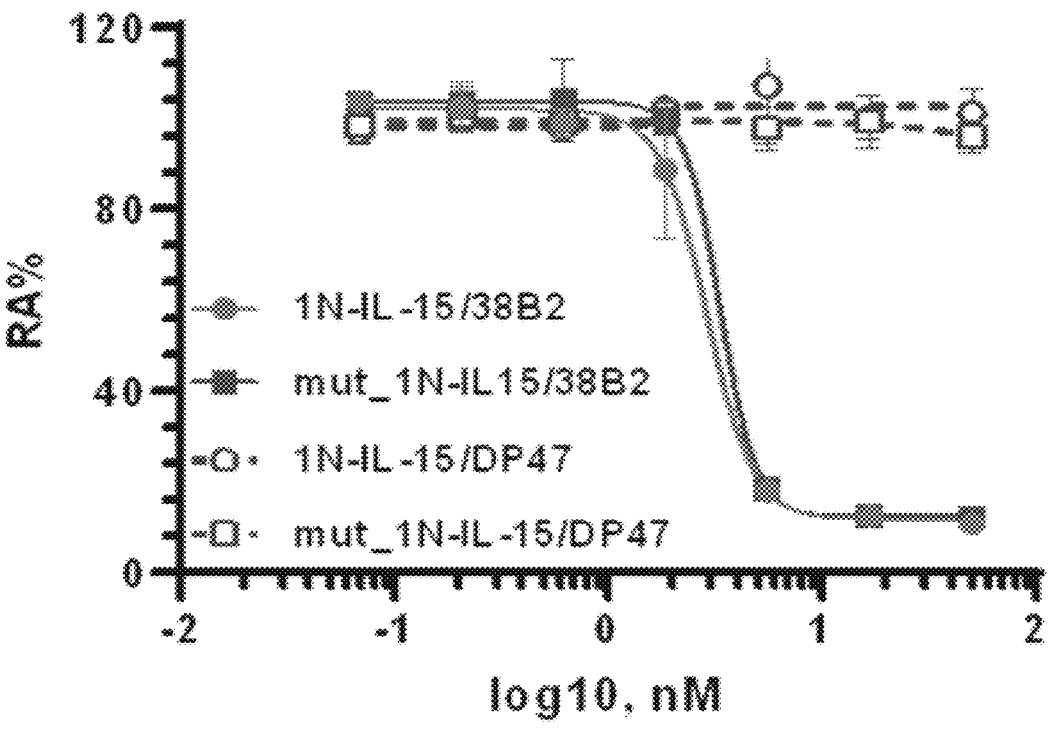
Figure 29D:
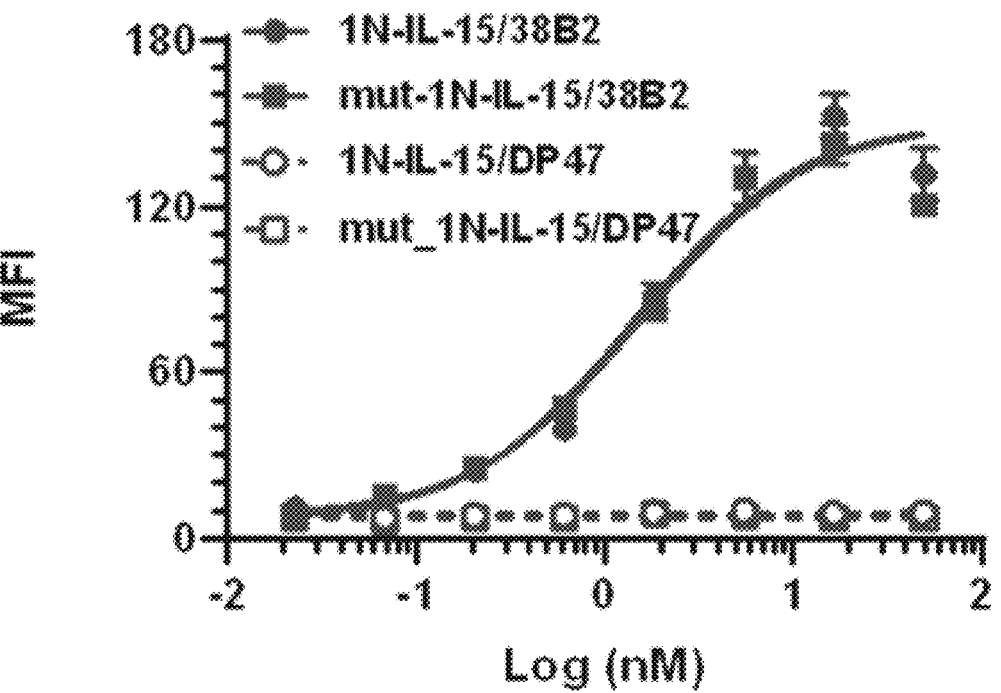
Figure 29E:
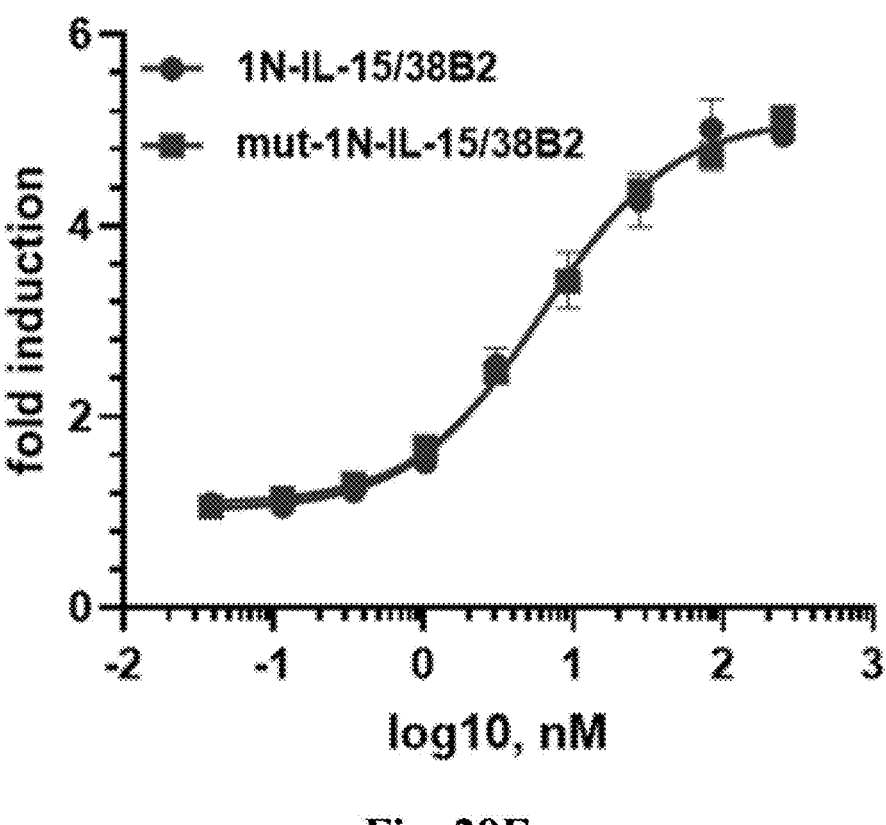
Figure 29F:
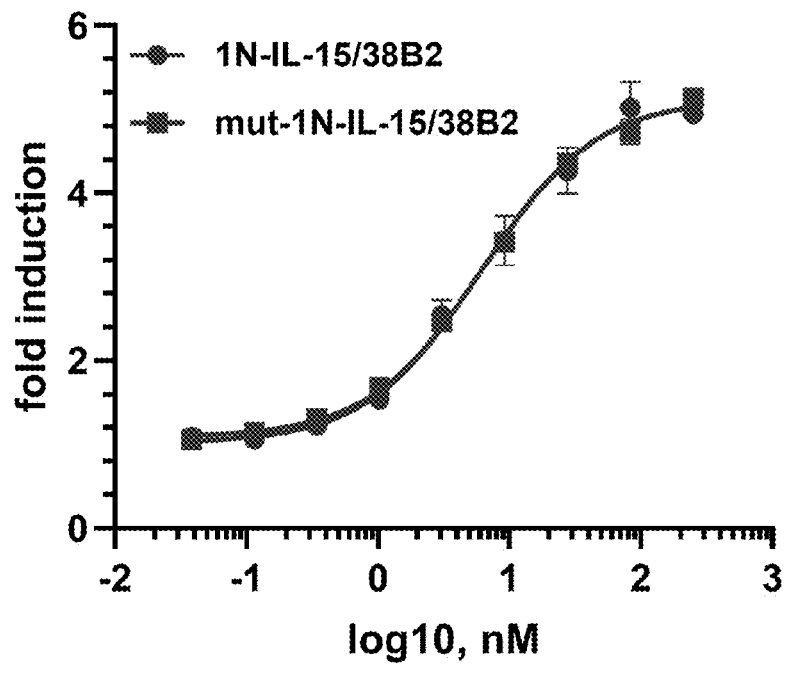

Similarly, no significant differences were observed in the strong binding of 1N-fusion proteins comprising wild-type IL-15 or IL-15 N65S, respectively, to soluble PD-1 or cells expressing PD-1 (FIGS. 29A and 29D).

Figure 30A:
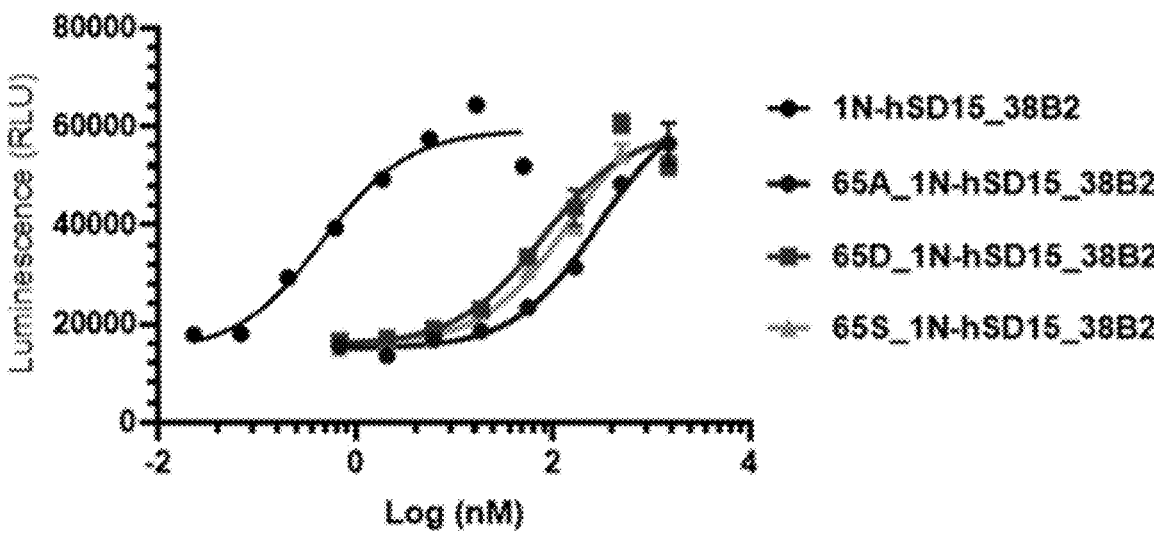
FIG. 30A, FIG. 30B, FIG. 30C, FIG. 30D, and FIG. 30E illustrate that the presence of an N65S mutation in IL-15 in a 1N-fusion protein leads to significant potency decreases of the fusion protein in proliferating human cells.
Figure 30B:
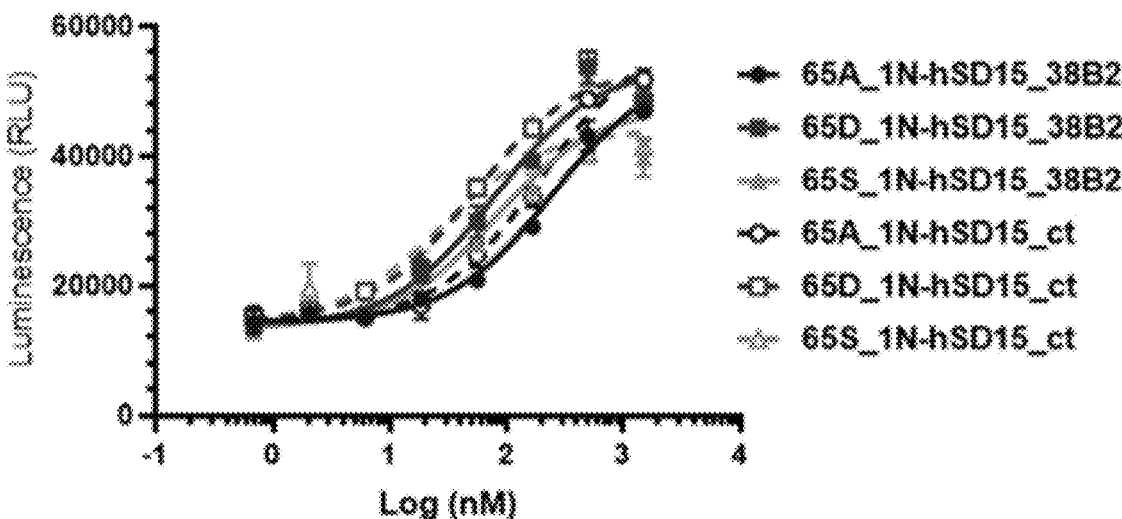
Figure 30C:
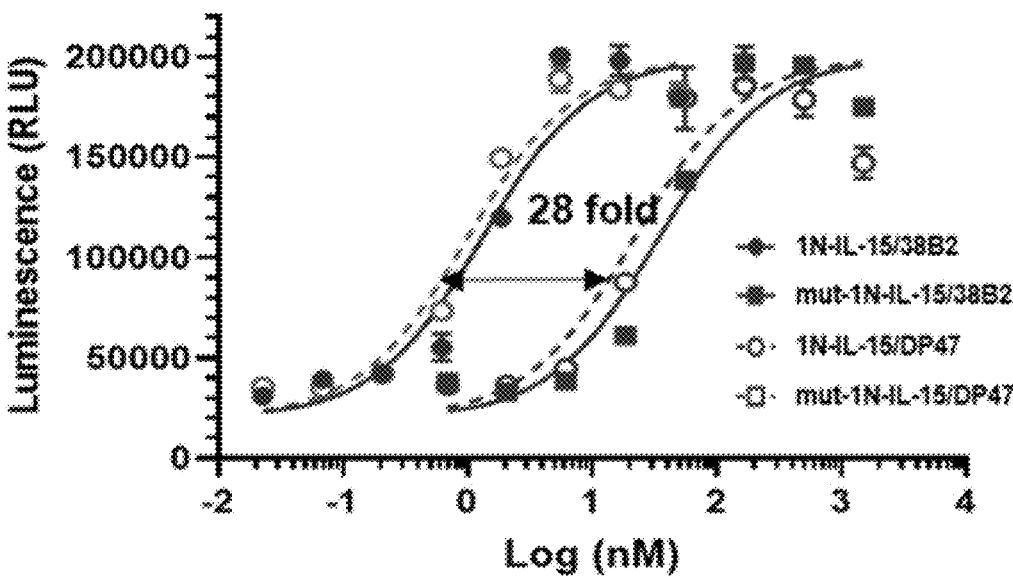
Figure 30D:
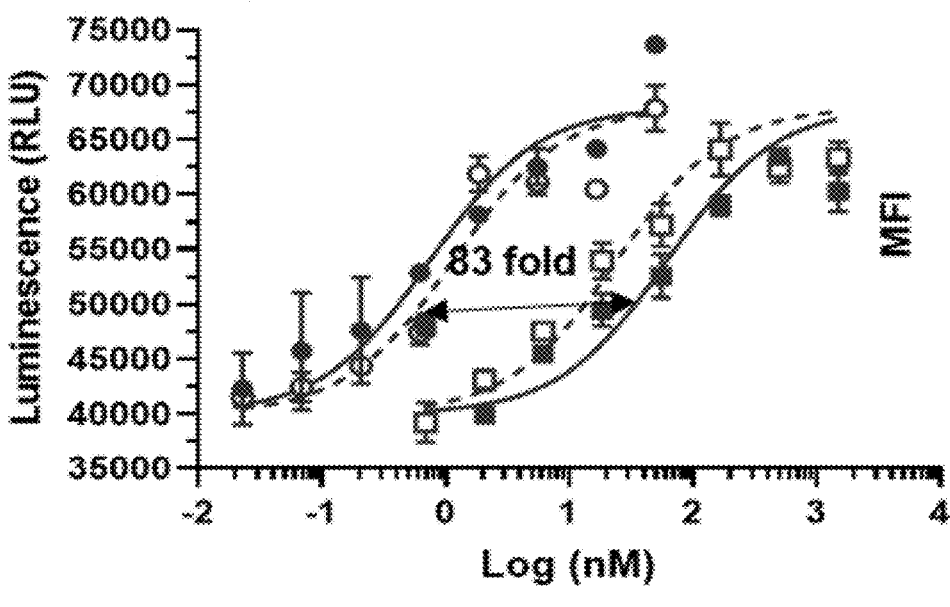
Figure 30E:
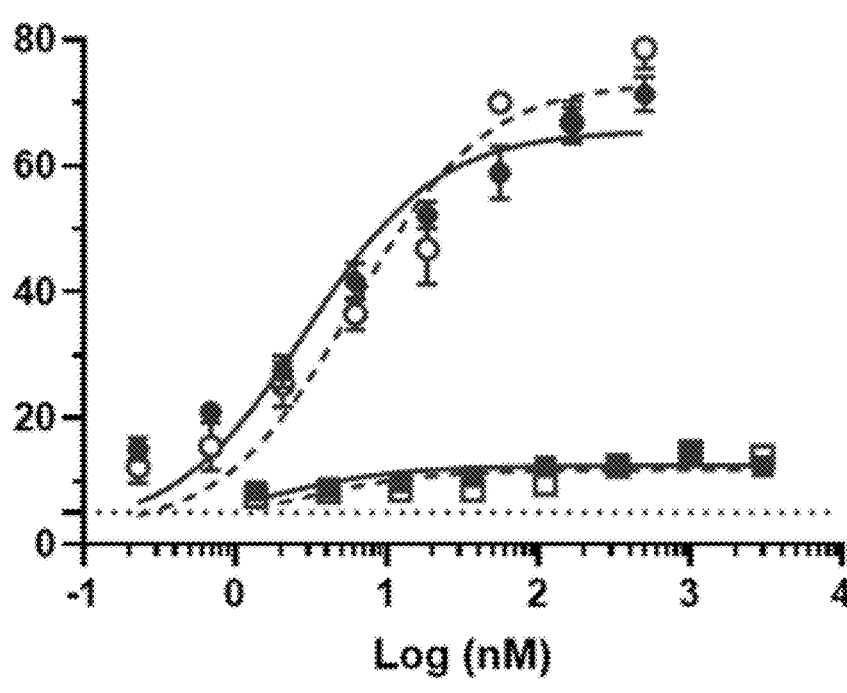
Figure 31A:
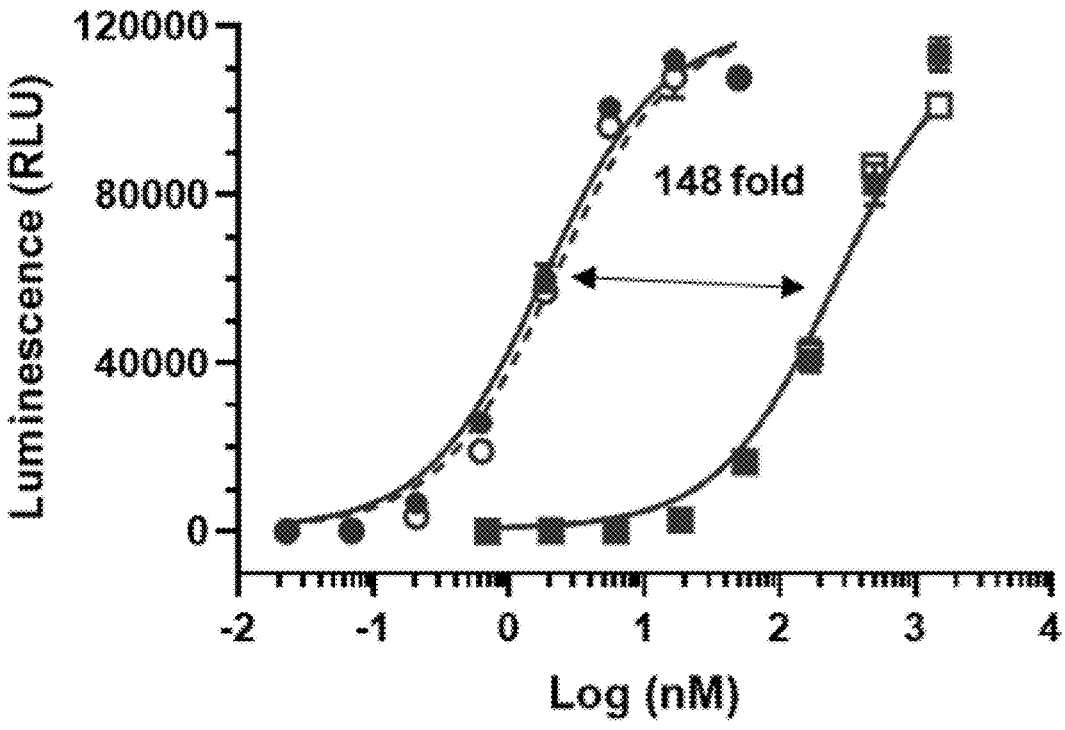
FIG. 31A, FIG. 31B, FIG. 31C, and FIG. 31D illustrate that the presence of an N65S mutation in IL-15 in a 1N-fusion protein leads to significant potency decreases of the fusion protein in proliferating murine cells and an increase in dose response in proliferating CD8+ T cells than CD4+ T cells.
Figure 31B:
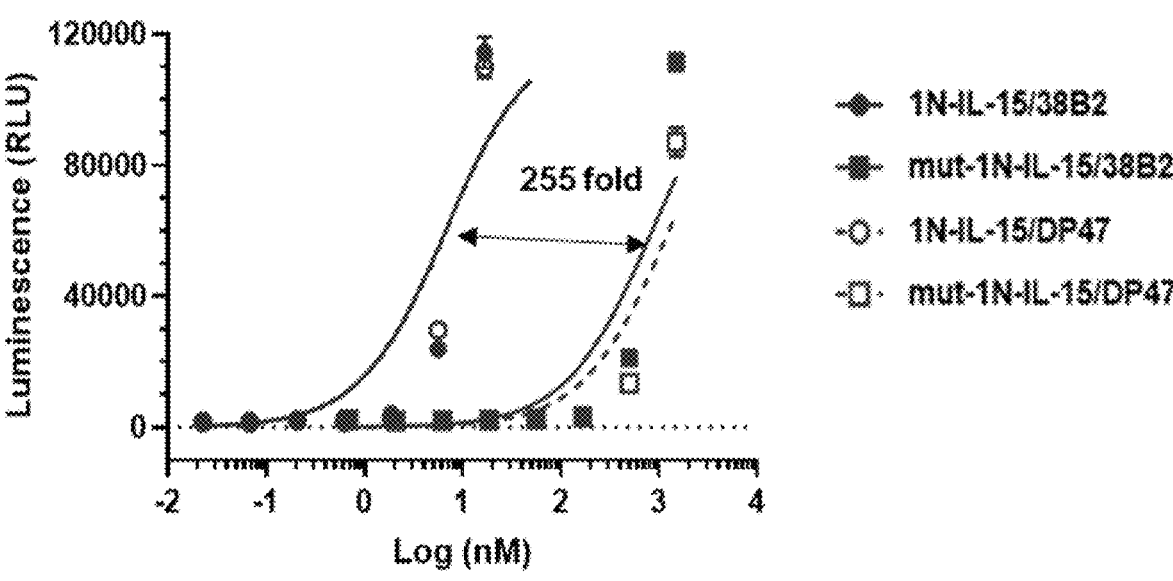

Example 31: 1N-Fusion Proteins Comprising an IL-15 Amino Acid Substitution Showed Weaker IL-15 Simulation In Vitro The ability of 1N-fusion proteins to stimulate IL-15 activity in human and in mouse cells was examined. In the presence of N65S-1N-IL-15/38B2, human acute mega-karyoblastic leukemia cells (M07e, FIGS. 30A, 30B, and 30C), hPBMCs (FIG. 30D), IL-2/IL-15-dependent murine lymphocyte cell lines (CTLL2, FIG. 31A), murine spleen cells (FIG. 31B) grew slower than in the presence of wild type 1N-IL-15/38B2. Binding of N65S-1N-/38B2 to hIL-2Rβ transfected HEK293 diminished (FIG. 30E).

Figure 31C:
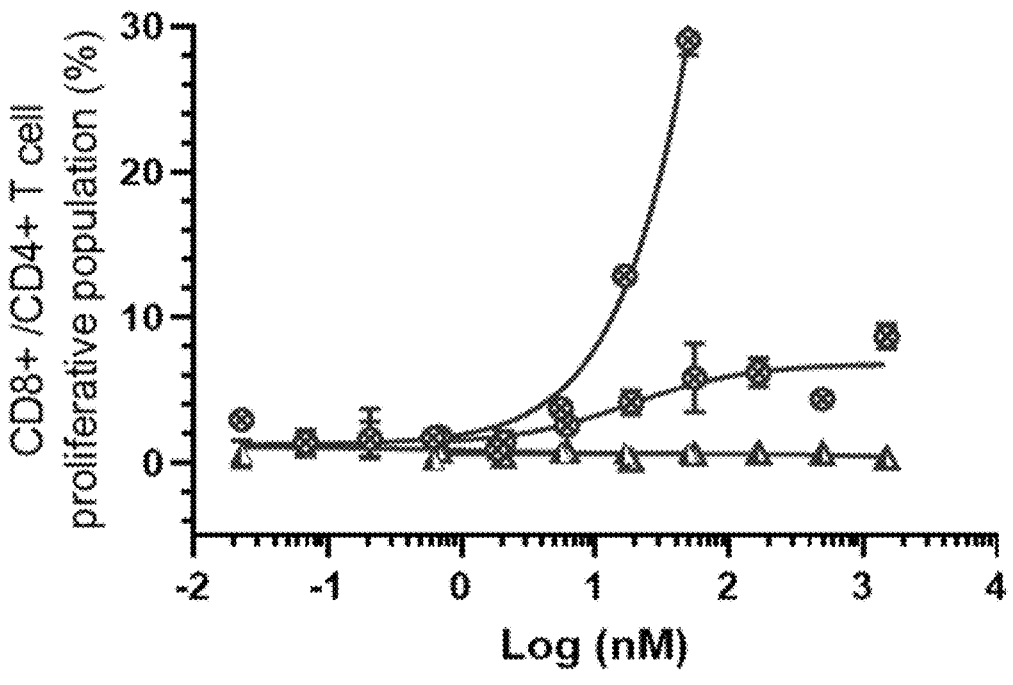
Figure 31D:
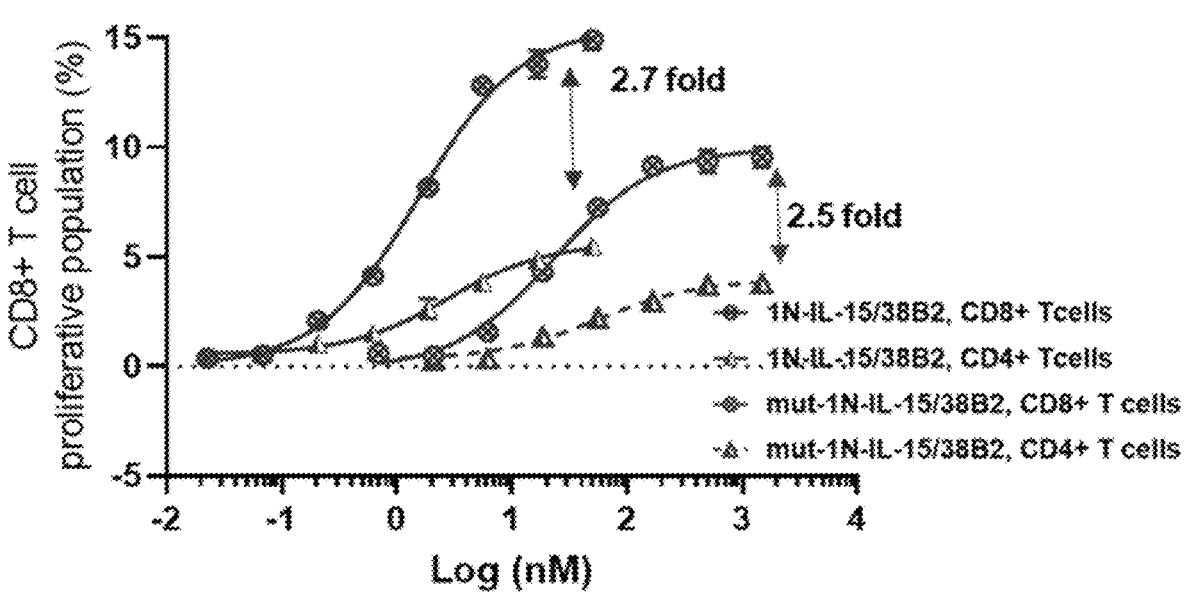

Further, both 1N-IL-15/38B2 and mut-1N-IL-15/38B2 induced a better dose response in proliferating CD8 T cells than CD4 T cells in both mouse spleen (FIG. 31C) and hPBMCs (FIG. 31D).

Example 32: 1N-Fusion Proteins Comprising an IL-15 Amino Acid Substitution Exhibited Strong Anti-Tumor Activity In Vivo in an Anti-PD-1 Antibody-Resistant Mouse Model In vivo efficacy of 1N-fusion proteins comprising wild-type IL-15, IL-15 N65S, or IL-15 N65D, respectively, was evaluated in hPD-1/hPD-L1 transgenic BALB/c mice bearing Keytruda (an anti-PD-1 antibody) resistant hPD-L1-CT26 tumors. The fusion antibodies (once per week) and controls (twice per week) were injected (intraperitoneal) when the tumor size reached approximately 100 mm³.

Figure 32A:
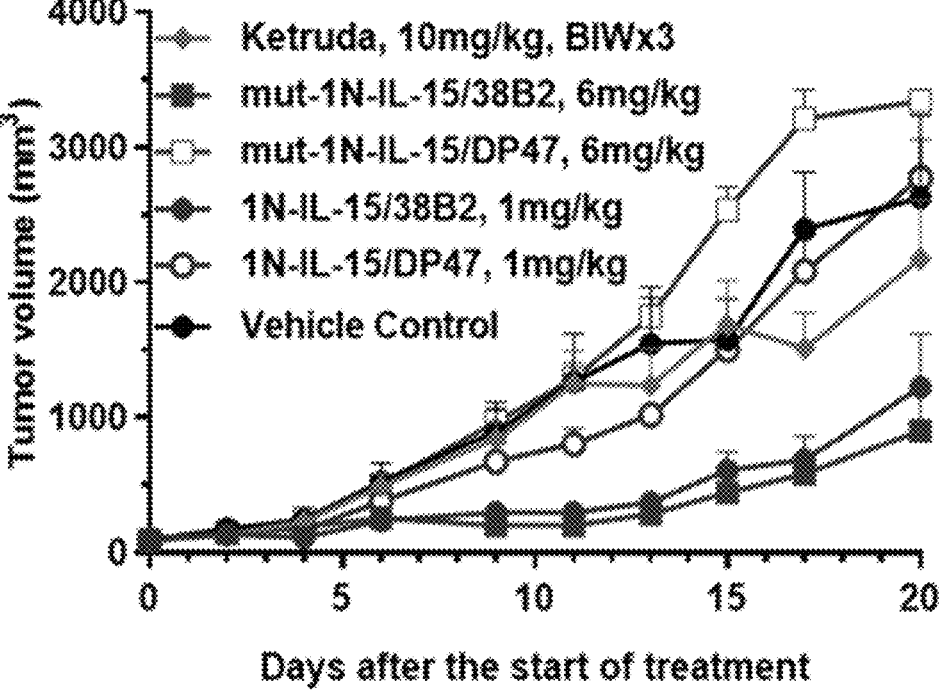
FIG. 32A, FIG. 32B, FIG. 32C, FIG. 32D, FIG. 32E, FIG. 32F, FIG. 32G, FIG. 32H, FIG. 32I, FIG. 32J, and FIG. 32K illustrate that 1N-fusion proteins comprising an IL-15 mutation exhibited strong anti-tumor activity in vivo in an anti-PD-1 antibody-resistant mouse model.
Figure 32B:
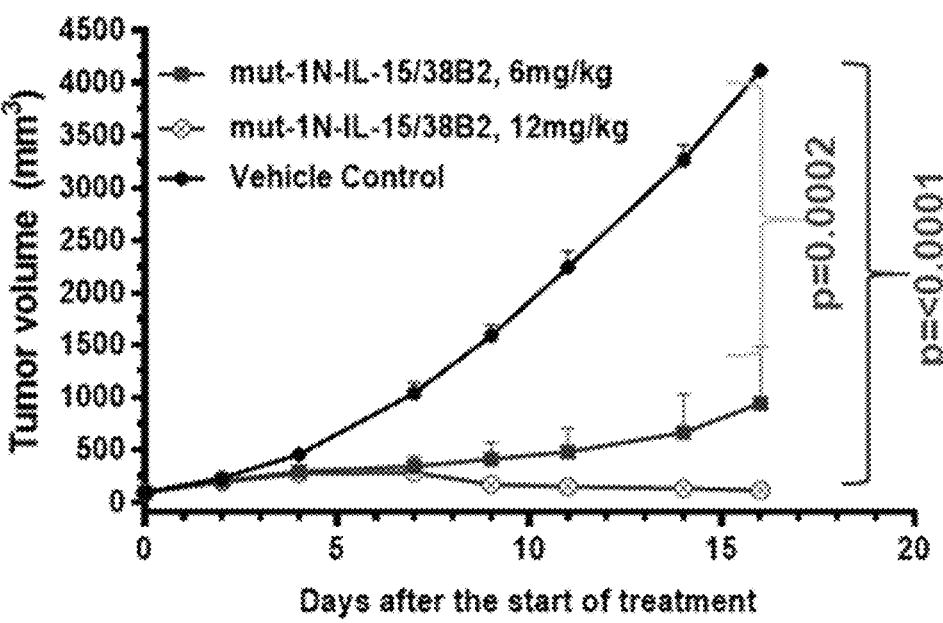
Figure 32C:
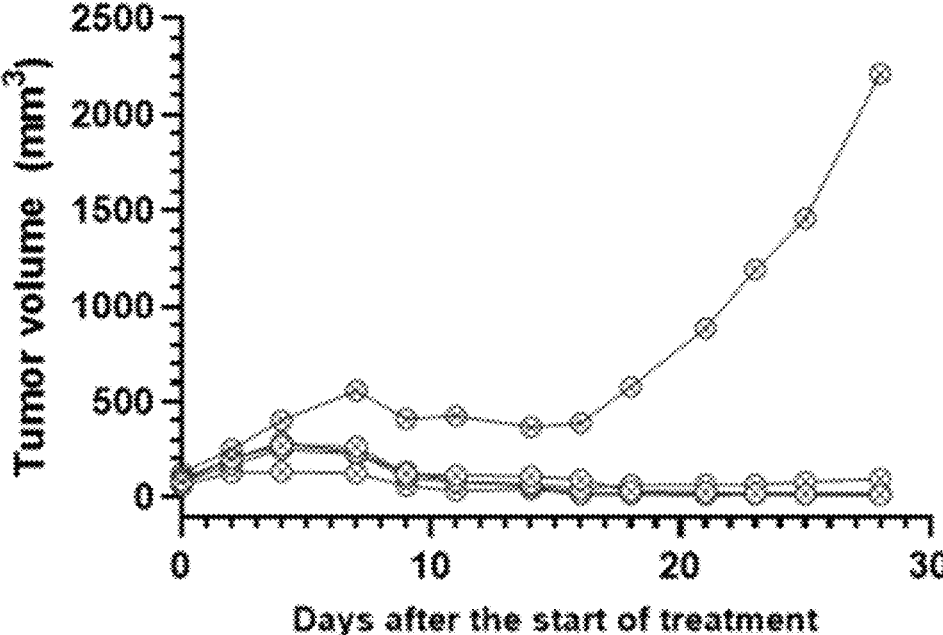
Figure 32D:
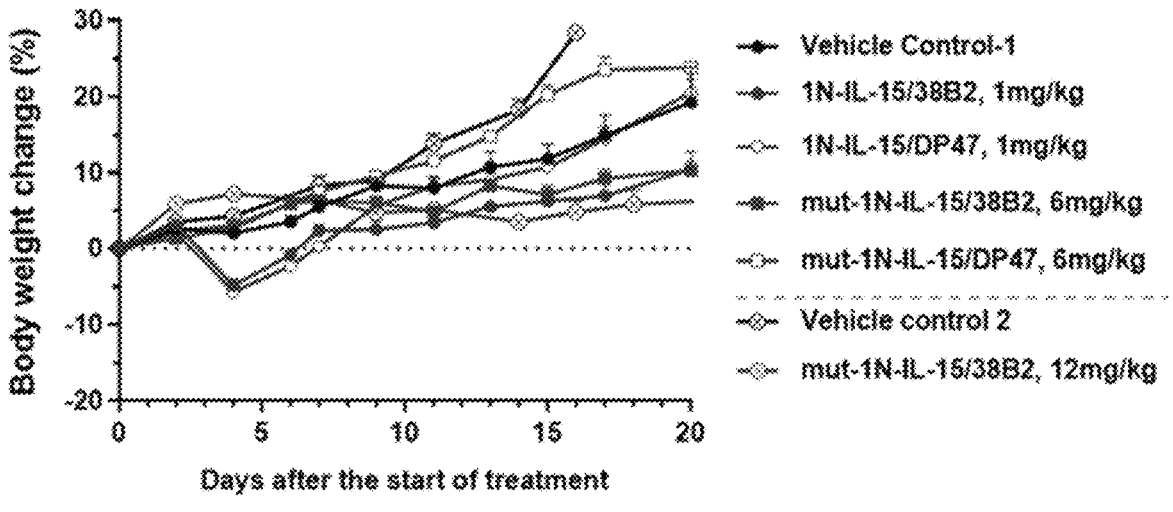
Figure 32E:
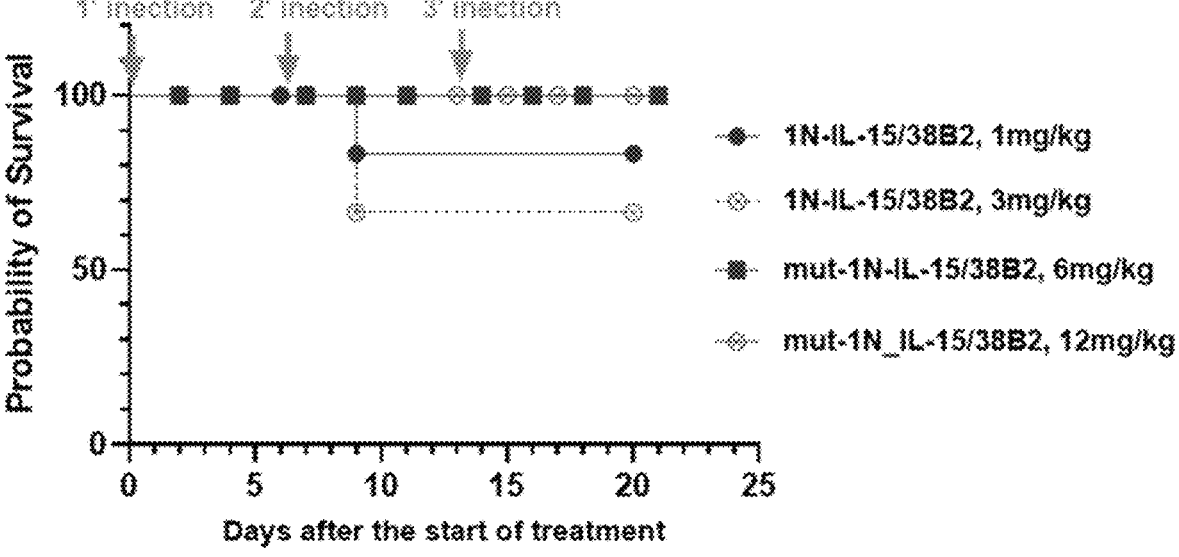
Figure 32F:
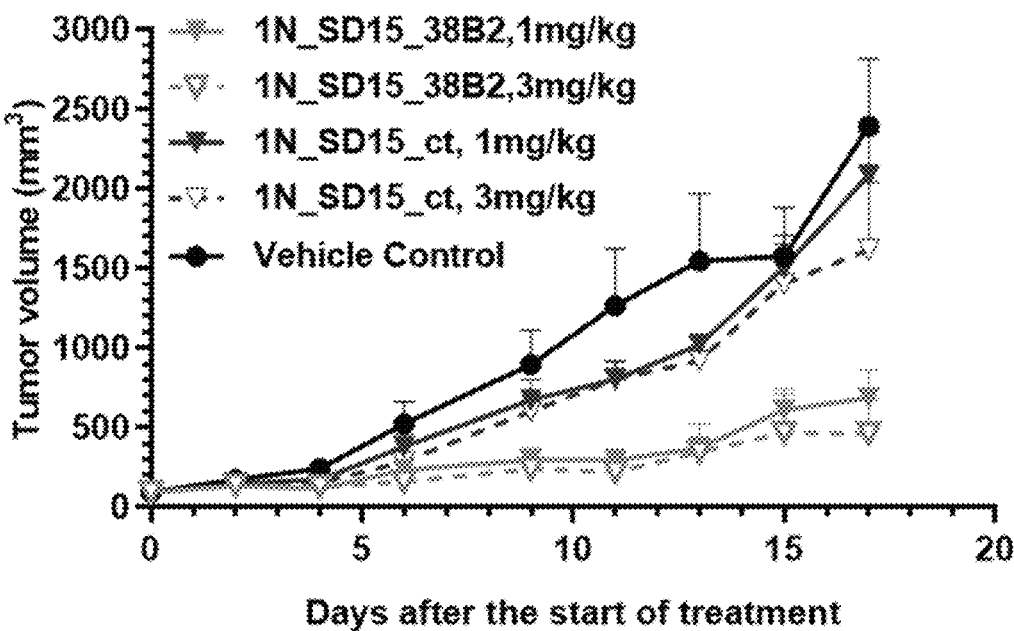
Figure 32G:
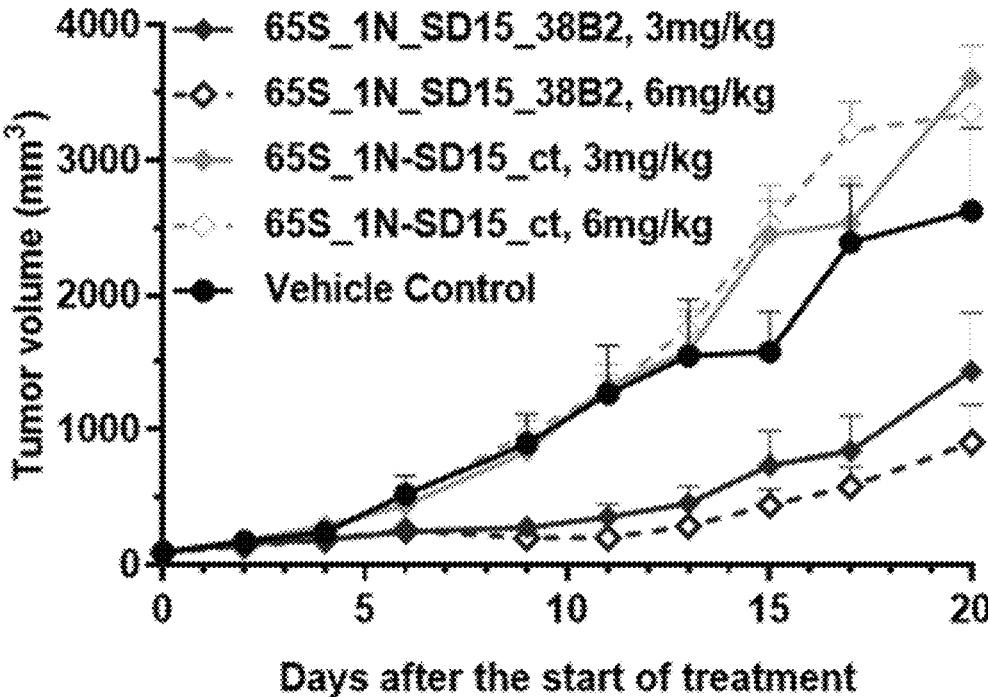
Figure 32H:
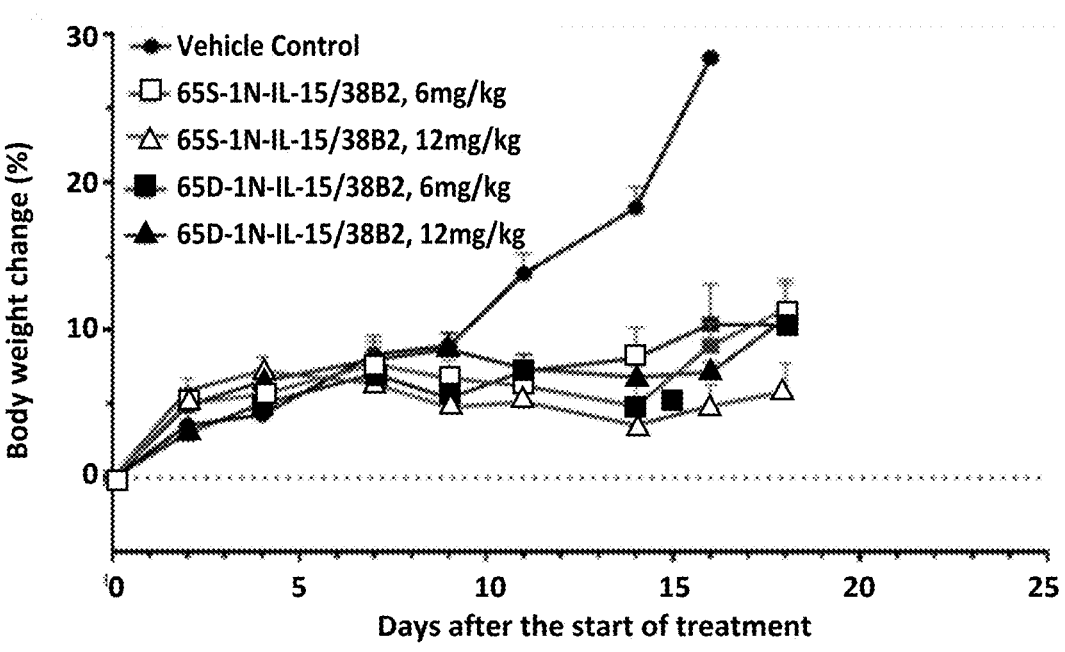

Both 1N-38B2/IL-15 and N65S-1N-38B2/IL-15 exhibited strong antitumor activity (FIG. 32A). Anti-tumor effi-cacy of N65S-1N-38B2/IL-15 was dose dependent (FIG. 32B). 12 mg/kg, QW×3 weeks of N65S-1N-38B2/IL-15 demonstrated tumor regression (FIGS. 32B and 32C). No weight loss or mortality was observed with N65S-1N-38B2/IL-15 when dosed at 12 mg/kg, but significant weight loss and mortality were observed with 1N-38B2/IL-15 when dosed at ≥1 mg/kg (FIG. 32E and FIG. 32E). A non-targeting 1N-IL-15 fusion did not show any anti-tumor efficacy. Significant weight loss (FIG. 32D) and mortality were observed when dosed ≥1 mg/kg for the non-targeting 1N-IL-15 fusion (data not shown).

Figure 32I:
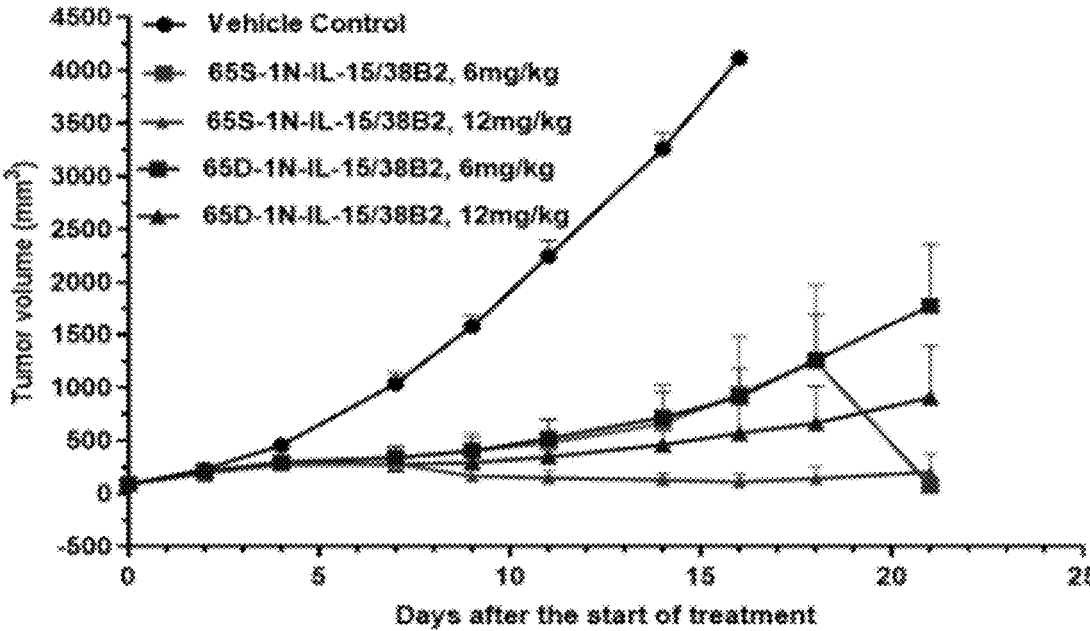
Figure 32J:
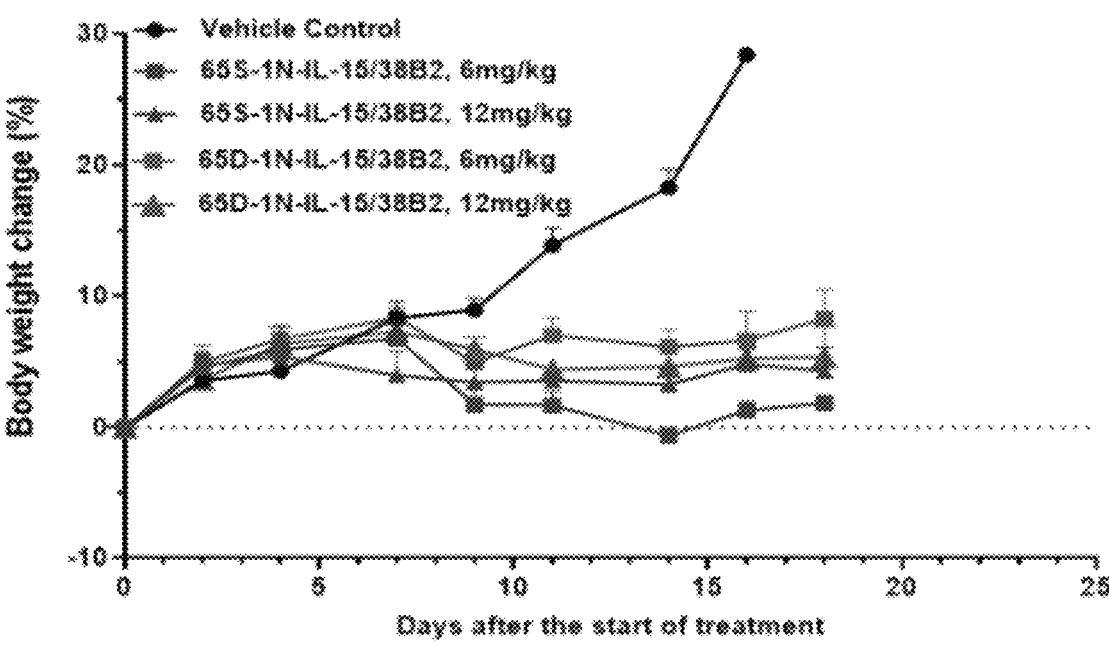
Figure 32K:
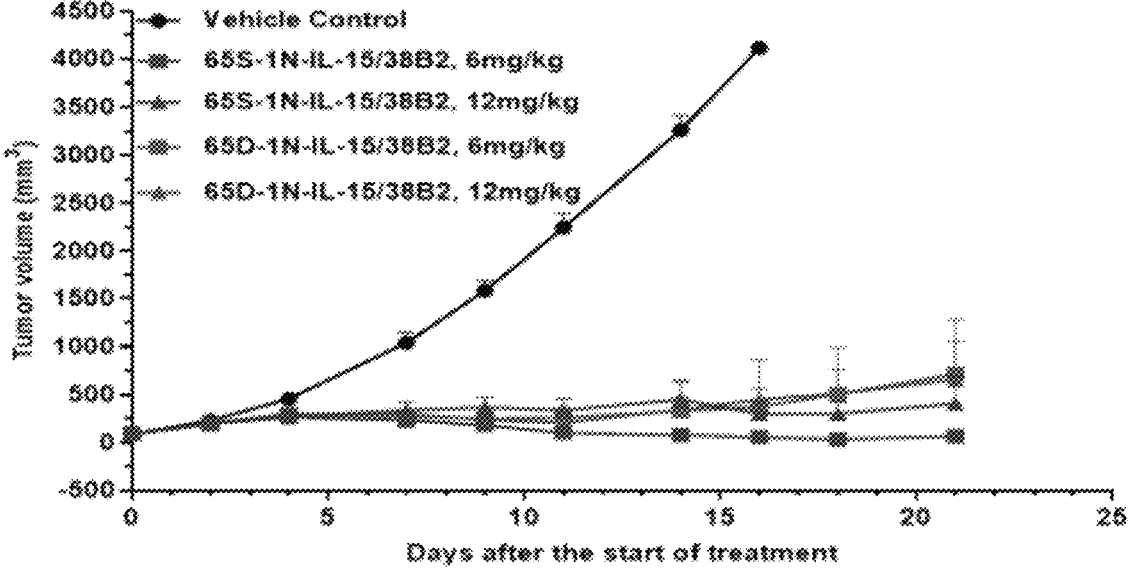

1N-fusion proteins comprising IL-15 N65S showed improved efficacy as compared to 1N-fusion proteins comprising IL-15 N65D (FIGS. 32I and 32K).

In sum, fusion proteins comprising mutated IL-15 lowered IL-15-associated potency and stimulation, resulting in lower toxicity and an increased therapeutic treatment window.

Example 33: 1N-Fusion Proteins Comprising an IL-15 Amino Acid Substitution Exhibited Strong Anti-Tumor Activity In Vivo in Mice that were Rechangelled with Tumor Cells In vivo efficacy of 1N-fusion proteins comprising IL-15 N65S or IL-15 N65D, respectively, was evaluated in hPD-1/hPD-L1 transgenic mice.

0.5×10⁶ of hPDL 1/CT26 was subcutaneously inoculated to the right lower flank of the mice. When the tumor size reached to about 100 mm³, the mice were intraperitoneally injected with 12 mg/kg of N65S-1N-38B2/IL-15 or N65D-1N-38B2/IL-15 once every week and twice every week for three weeks respectively. The tumors in 5 mice (of 6) completely disappeared in about 25 days for N65S-1N-38B2/IL-15 treatment and 40 days for N65D-1N-38B2/IL-15 treatment.

Figure 33:
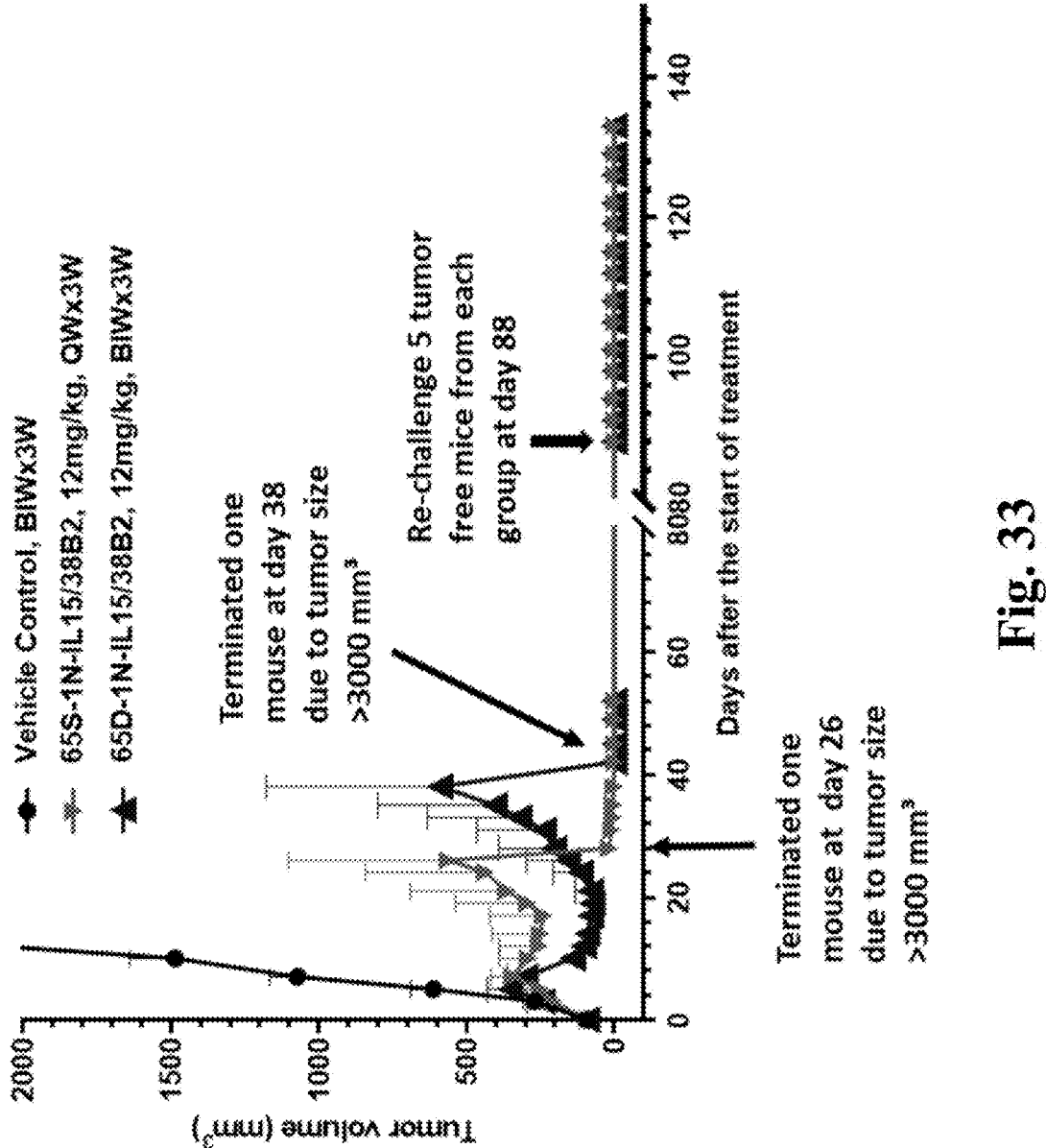
FIG. 33 shows that N65S-1N-38B2/IL-15 and N65D-1N-38B2/IL-15 fusion proteins prevent a re-challenge in mice bearing a hPDL1-CT26 tumor.

At day 88, 0.5×10⁶ of hPDL 1/CT26 cells and 0.1×10⁶ of CT26 cells were subcutaneously inoculated to the left lower flank and left upper flank respectively. No tumor growth was observed for both cell lines up to day 135 days, showing that the fusion protein protect mice against rechallenges with tumor cells (FIG. 33).

Example 34: 1N-Fusion Proteins Comprising an IL-15 Amino Acid Substitution Exhibited Improved Anti-Tumor Activity in hPD1/PDL1 Mice Bearing hPDL1-CT26 Tumor as Compared to Combinations of Non-Targeted Fusion Protein and an Anti-PD-1 Antibody 0.5×10⁶ of hPDL1/CT26 cells were subcutaneously inoculated to the right lower flank of the mice. When the tumor size reached to about 100 mm³, the mice were intraperitoneally injected with 10 mg/kg of 38B2, 12 mg/kg of N65S-1N-38B2/IL-15, and combination of 10 mg/kg of 38B2 with 12 mg/kg of N65S-1N-DP47/IL-15 once every week for three weeks respectively. For the combination treatment, two test articles were injected sequentially with one hour.

The ability to suppress tumor growth was compared for the following constructs: (1) N65S-1N-38B2/IL-15 fusion protein; (2) a non-targeted fusion N65S-1N-DP47/IL-15; (3) a combination of anti-PD-1 antibody 38B2 and the non-targeted fusion (i.e., N65S-1N-DP47/IL-15); and (4) anti-PD-1 antibody 38B2 only.

Figure 34A:
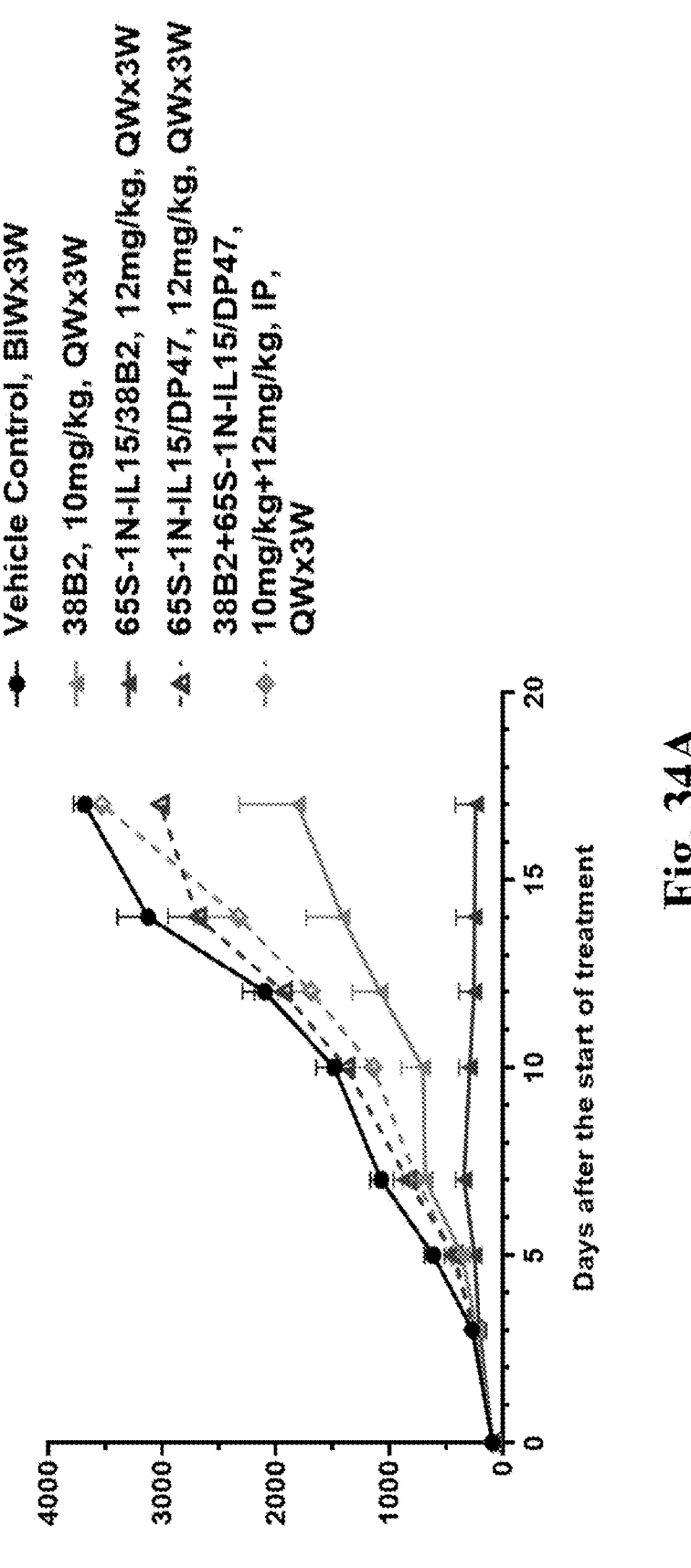
FIG. 34A.
Figure 34B:
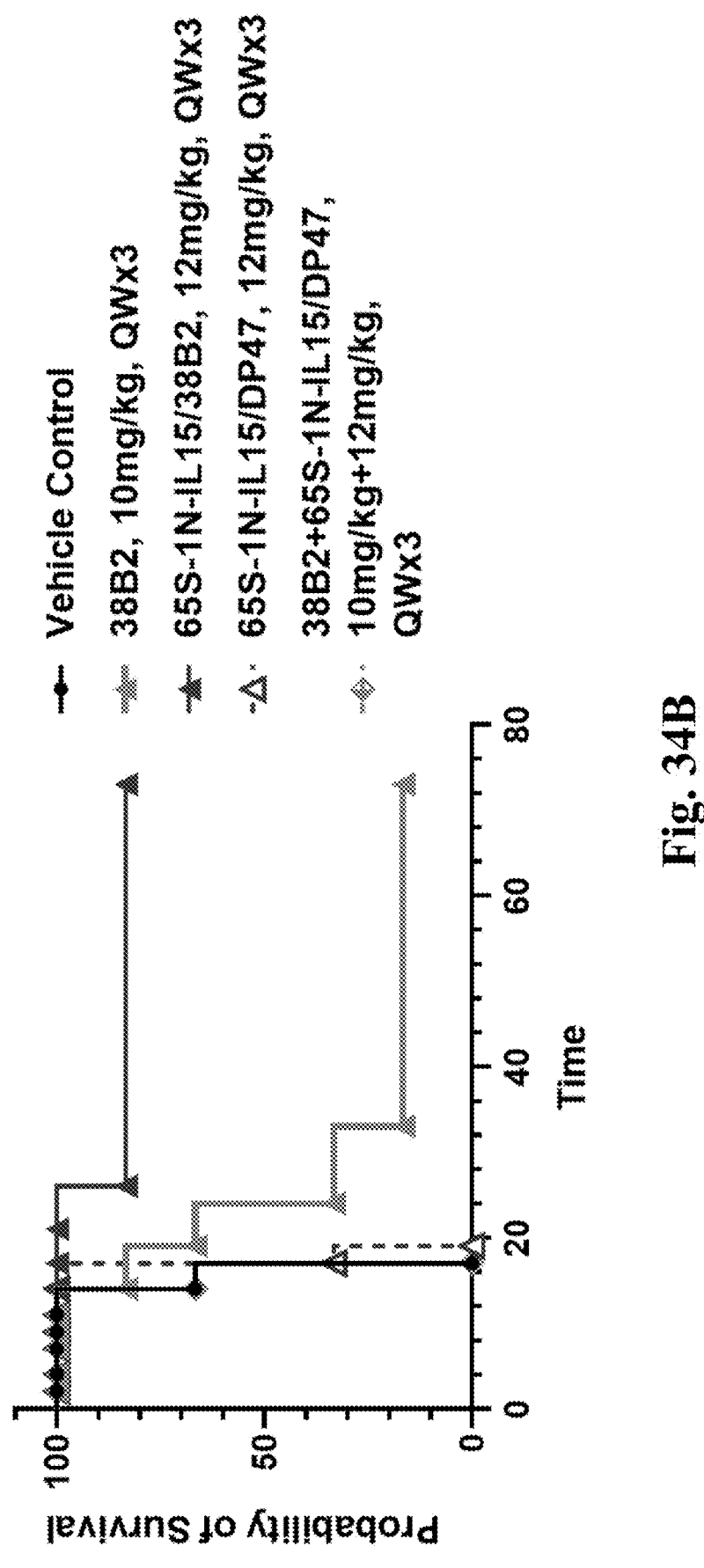
FIG. 34B, and FIG. 34C show that 1N-fusion proteins comprising an IL-15 mutation exhibited improved anti-tumor activity in hPD1/PDL1 mice bearing hPDL1-CT26 tumor as compared to combinations of non-targeted fusion protein and an anti-PD-1 antibody.
Figure 34C:
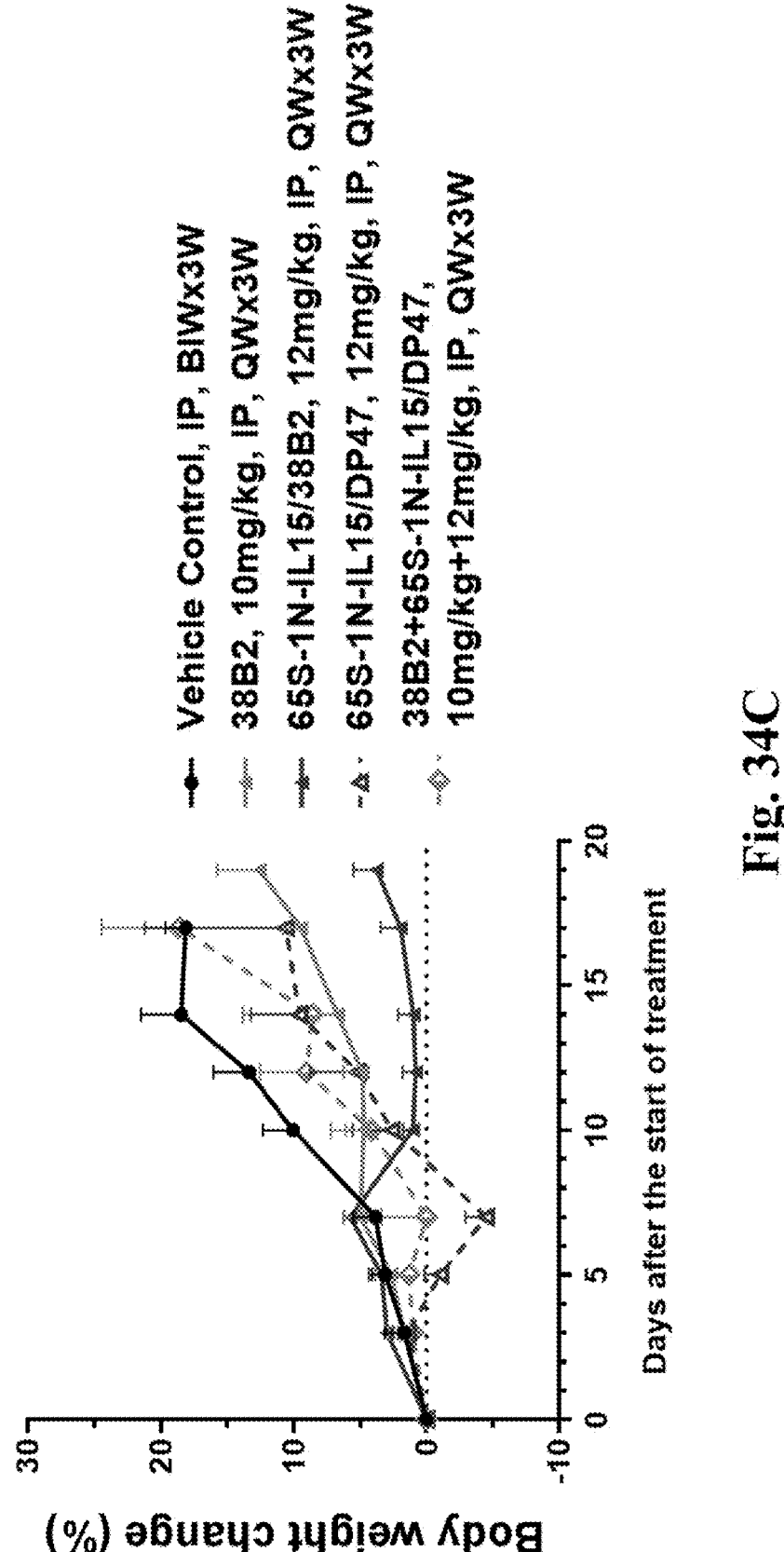

Tumors grew significantly slower in the N65S-1N-38B2/IL-15 group as compared to the combination group (FIG. 34A). 83% (5/6) of the mice were tumor-free in the N65S-1N-38B2/IL-15 fusion group, while no tumor-free mice were observed in the combination group and one tumor-free mouse was observed in the anti-PD-1 antibody 38B2 only group. (FIG. 34B). No body weight loss was observed for 65S-1N-IL15/38B2 fusion group, about −5% bodyweight loss for non-targeted fusion 65S-1N-IL15/DP47 group (FIG. 34C).

This data illustrates the robust anti-tumor activity of N65S-1N-38B2/IL-15 fusion proteins and highlights its bi-functionality and its ability to bind to both PD1 and IL2Rβγ, which are co-expressed on TILs.

Example 35: Additional Administration of an Anti-PD-1 Antibody does not Lead to a Further Increase in Anti-Tumor Activity of 1N-Fusion Proteins 0.5×10⁶ of hPDL 1/CT26 cells were subcutaneously inoculated to the right lower flank of the mice. When the tumor size reached to about 100 mm³, the mice were intraperitoneally injected with 10 mg/kg of 38B2, 12 mg/kg of N65S-1N-38B2/IL-15, and combination of 10 mg/kg of 38B2 with 12 mg/kg of N65S-1N-38B2/IL-15 once every week for three weeks respectively. For the combination treatment, two test articles were mixed first, then injected to the mice.

The ability to suppress tumor growth was compared for the following constructs: (1) N65S-1N-38B2/IL-15 fusion protein; (2) a combination of anti-PD-1 antibody 38B2 and N65S-1N-38B2/IL-15 fusion protein; and (3) anti-PD-1 antibody 38B2 only.

Figure 35A:
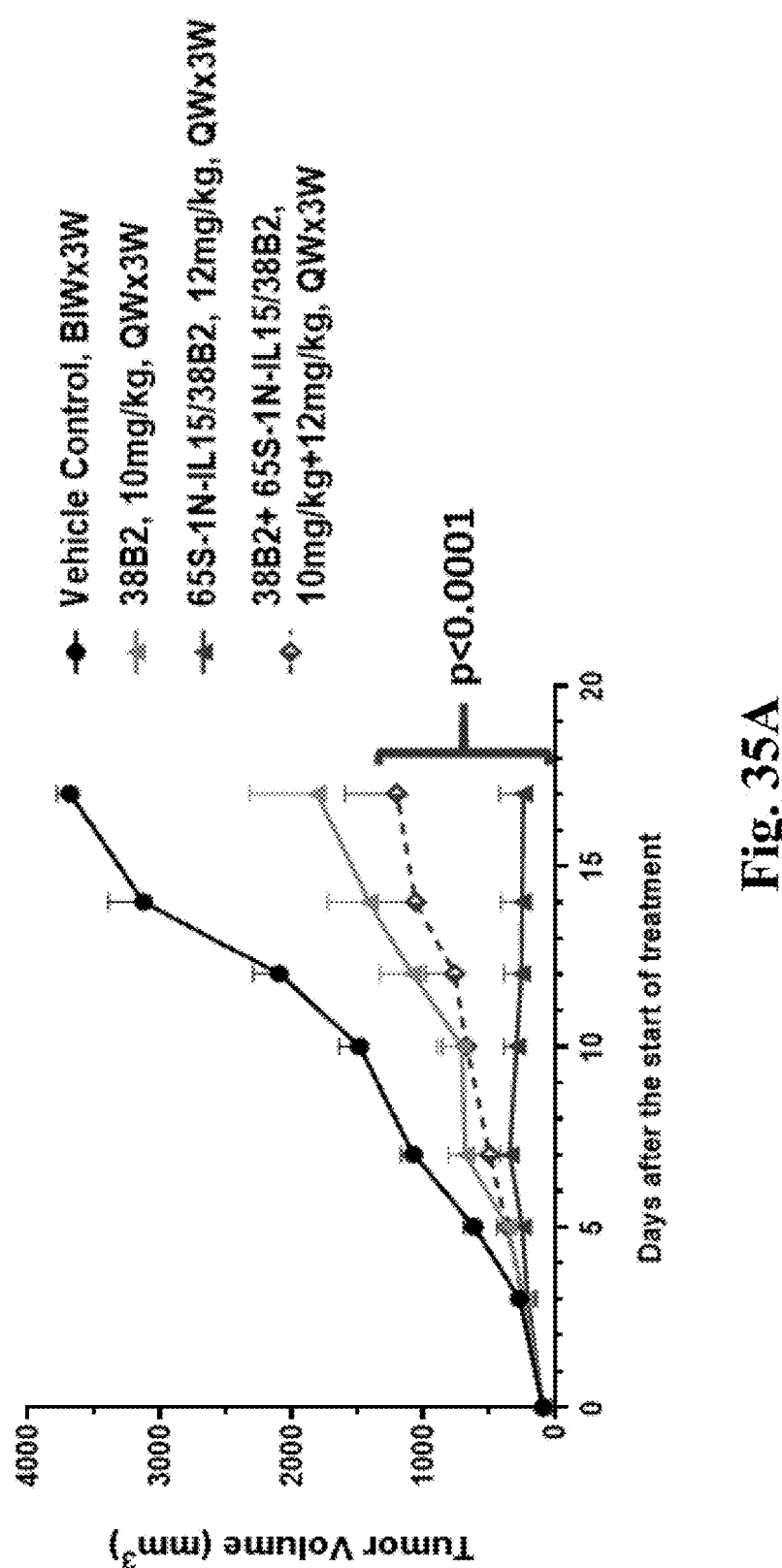
FIG. 35A.
Figure 35B:
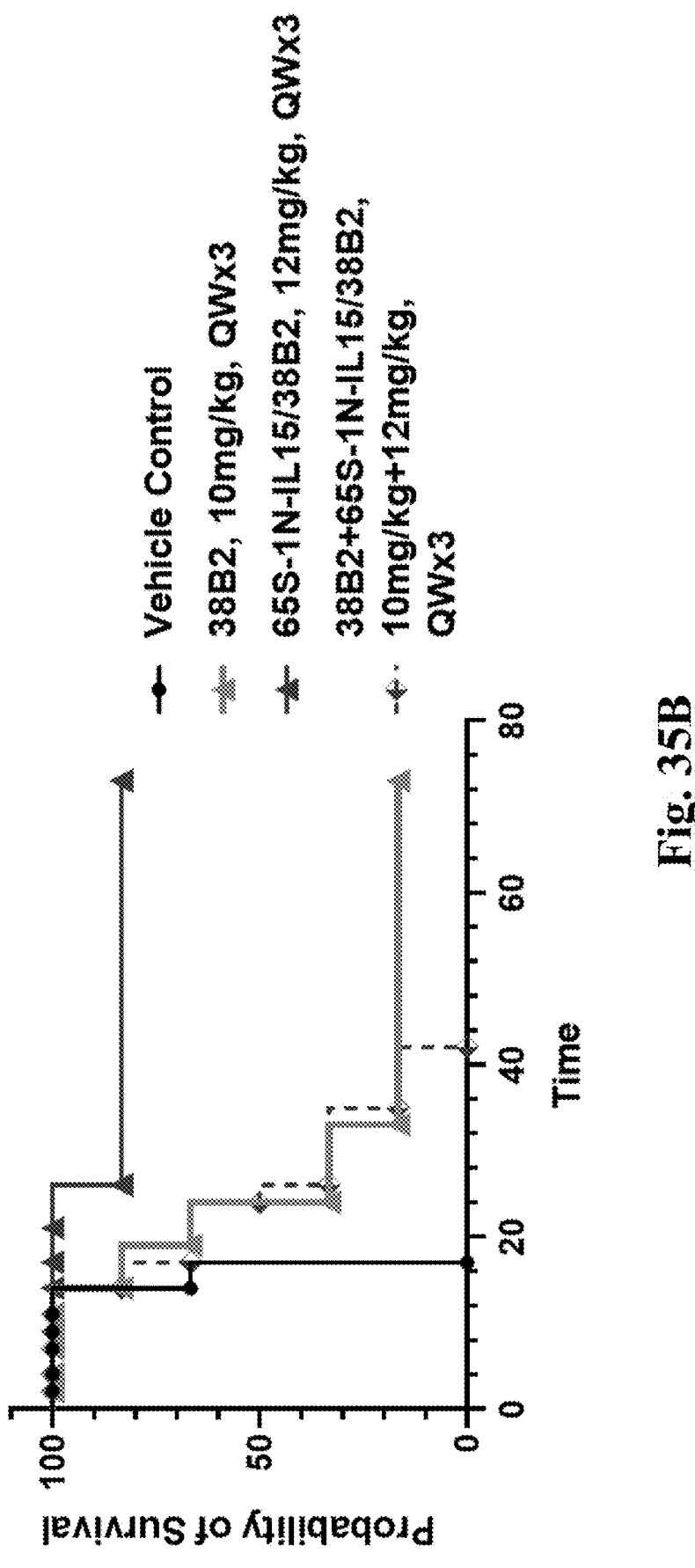
FIG. 35B, and FIG. 35C show that the additional administration of an anti-PD-1 antibody does not lead to a further increase in anti-tumor activity of 1N-fusion proteins.
Figure 35C:
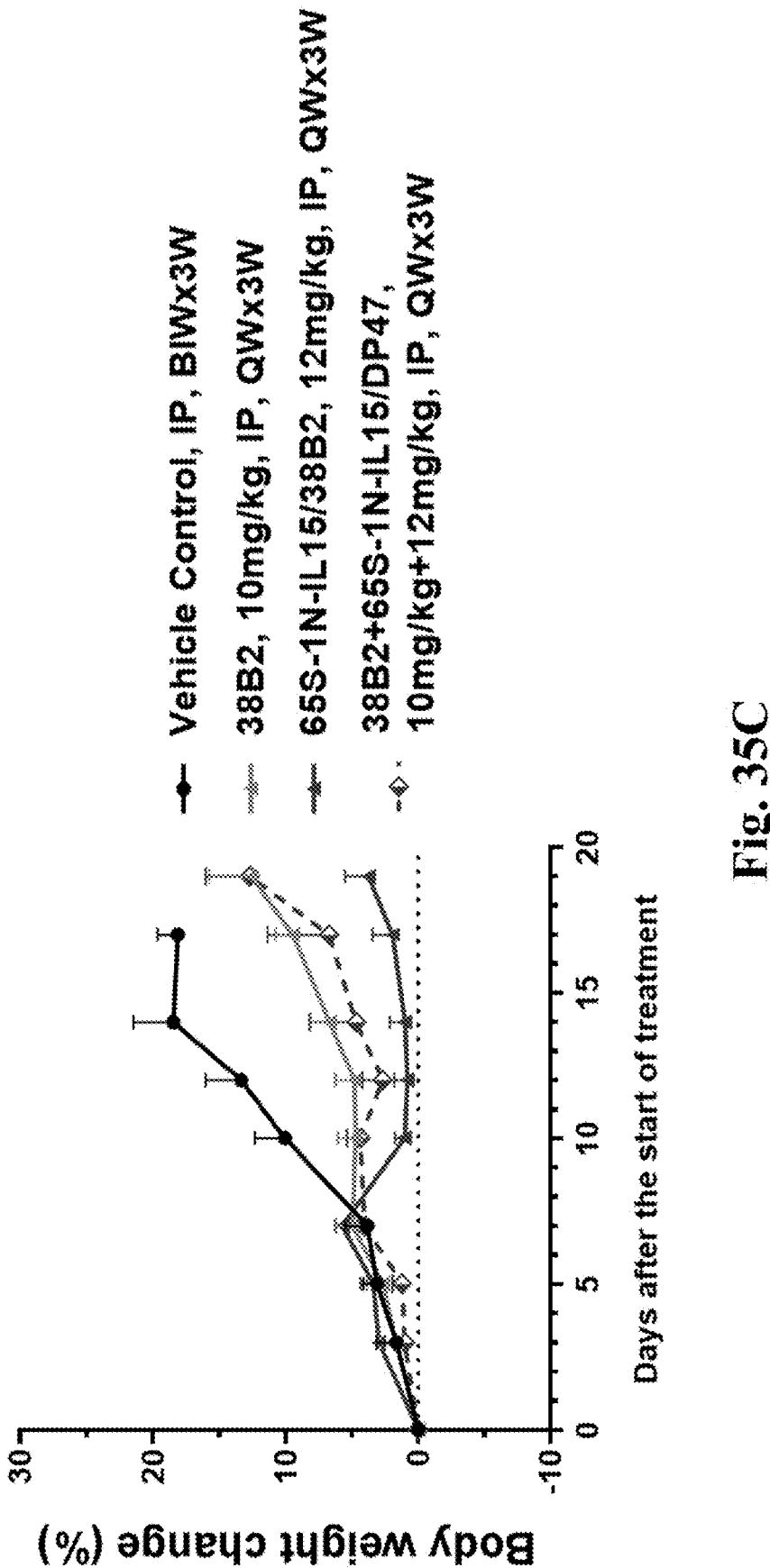

Tumor grew significantly more slowly in the N65S-1N-38B2/IL-15 group as compared to the combination group (FIG. 35A). 83% (5/6) mice were tumor-free in the N65S-1N-38B2/IL-15 group, no tumor-free mice were observed in the combination group and one tumor-free mouse was observed in the antibody only (FIG. 35B). The bodyweight is shown in FIG. 35C.

This data shows that 1N-fusion proteins are more effective in reducing tumor growth than combinations of 1N-fusion proteins and anti-PD-1 antibodies.

Example 36: N65S-1N-38B2/IL-15 Fusion Protein Showed a Long Serum Half-Life in hPD1/PDL1 Transgenic Mice Bearing hPDL1-CT 26 Tumors hPD1/PDL1 transgenic Balb/c mice were inoculated subcutaneously at the right lower flank with hPDL1/CT26 tumor cells ($0.5 \times 10^6$) in 0.1 mL of PBS. The animals were randomized and treatments were started when the average tumor volume reaches approximately 83 mm$^3$. The 5.1 mg/kg (0.35 μmol/kg) of 38B2, or 1 or 6 mg/kg (0.06 or 35 μmol/kg) of N65S-1N-38B2/IL-15 were administrated to the mice either intraperitoneally (IP) or intravenously (IV). After dosing, blood was collected at 0.2 h, 5 h, 2 h, 4 h, 12 h, 24 h, 48 h, 72 h, 120 h and 168 h post injection and the purified serum were used to measure the antibody concentration by the traditional ELISA, in which human PD1 was used as the captured protein and biotin-IL15 and anti-human Fab was used separately to detect the KD050 and 38B2 binding.

Figure 36A:
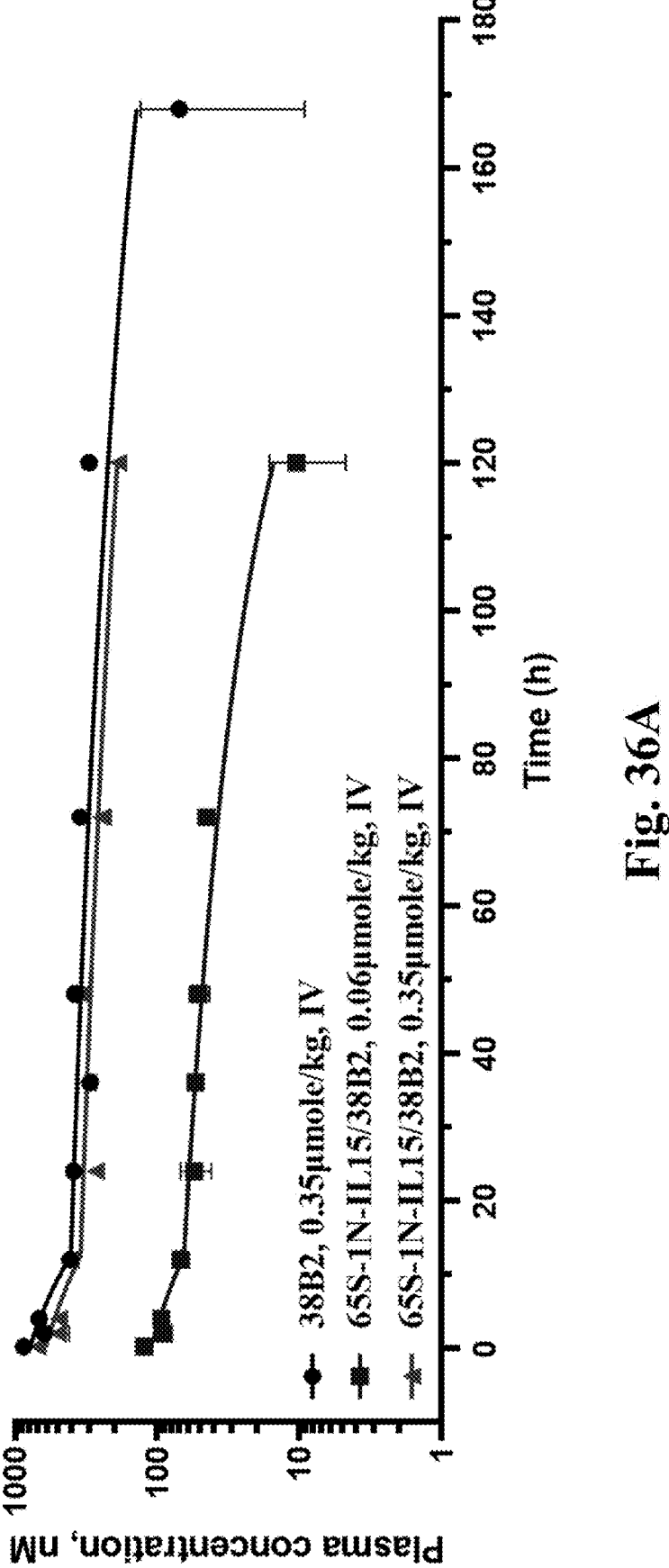
FIG. 36A and FIG. 36B illustrate that N65S-1N-38B2/IL-15 exhibited a similar serum half-life profile as antibody 38B2 in both IV (FIG. 36A) and IP (FIG. 36B) injection with dose response up to 120 h after treatment.
Figure 36B:
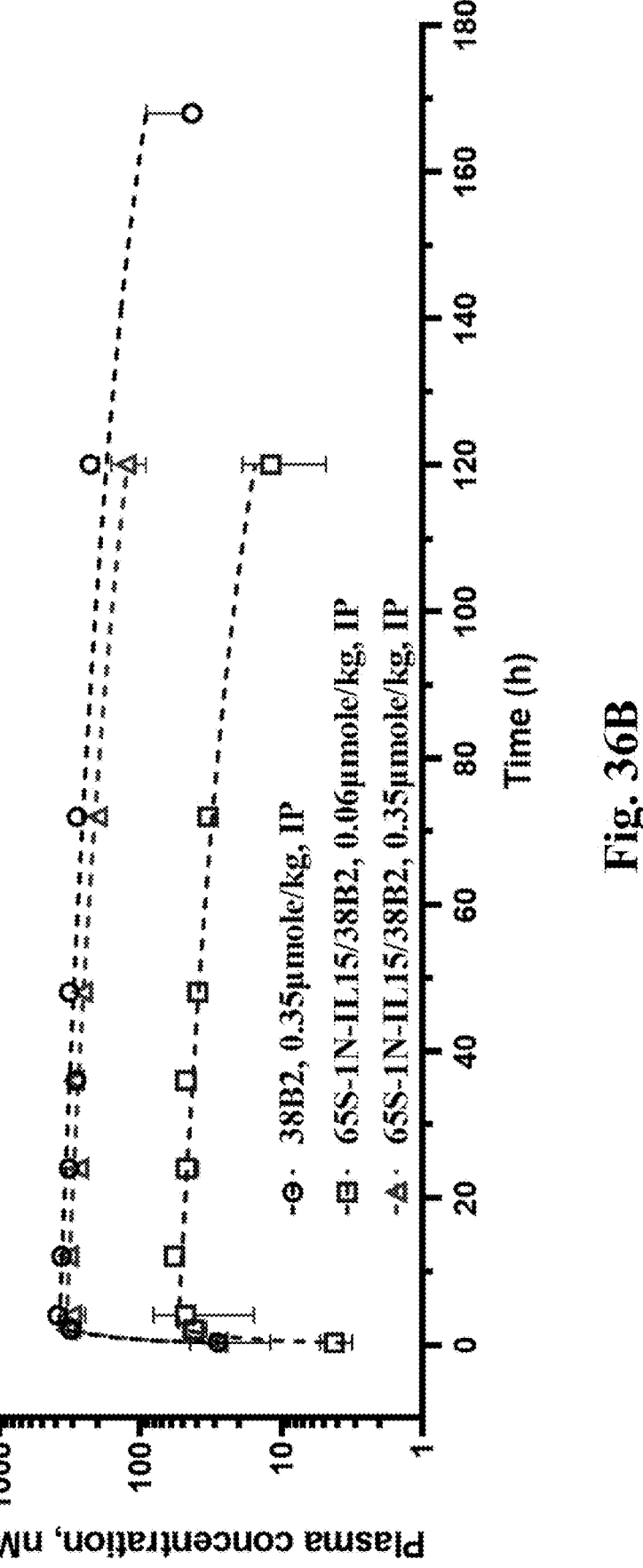

N65S-1N-38B2/IL-15 exhibited a similar serum half-life profile as antibody 38B2 in both IV (FIG. 36A) and IP (FIG. 36B) injection with dose response up to 120 h after treatment.

Figure 37A:
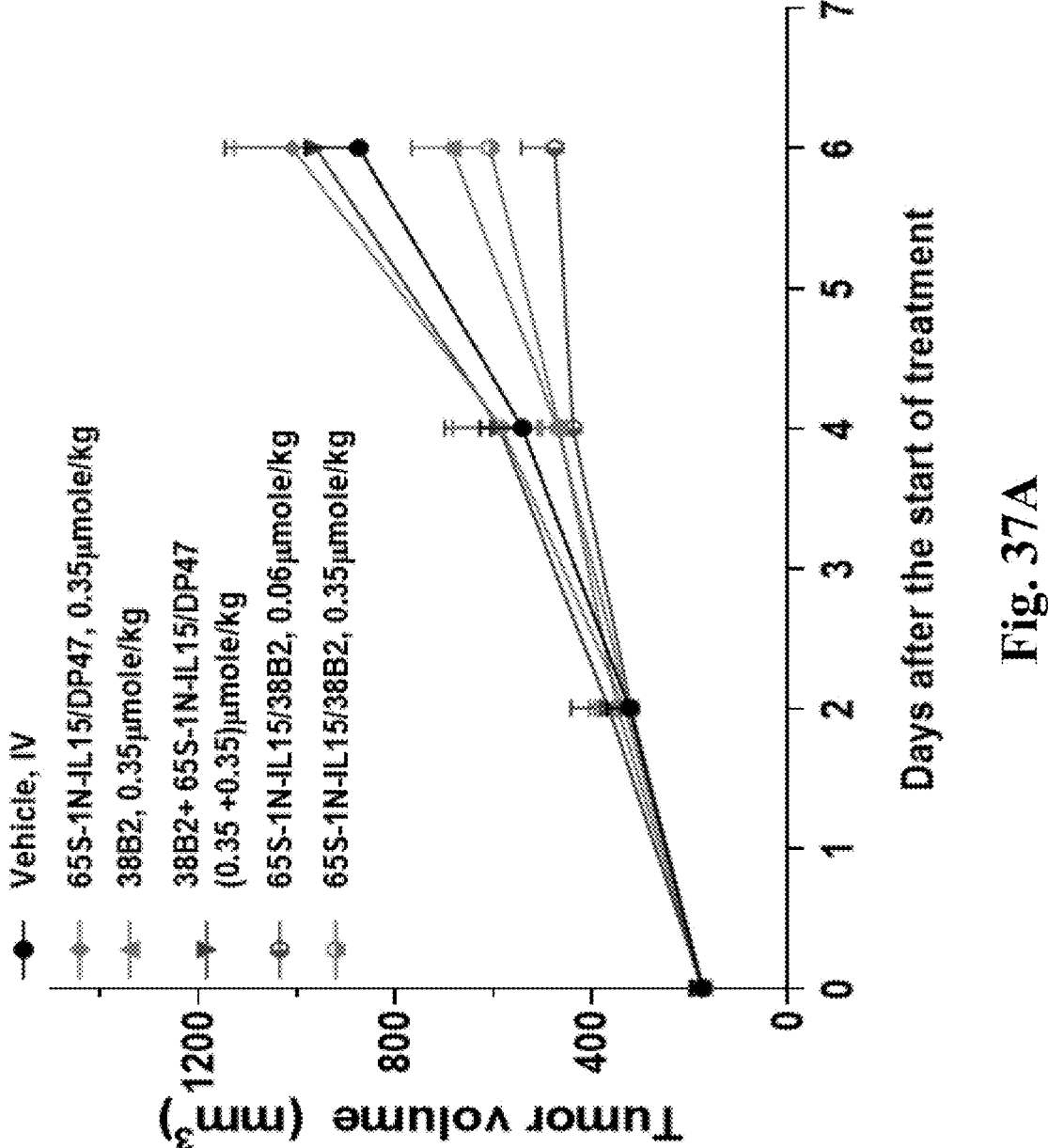
Figure 37B:
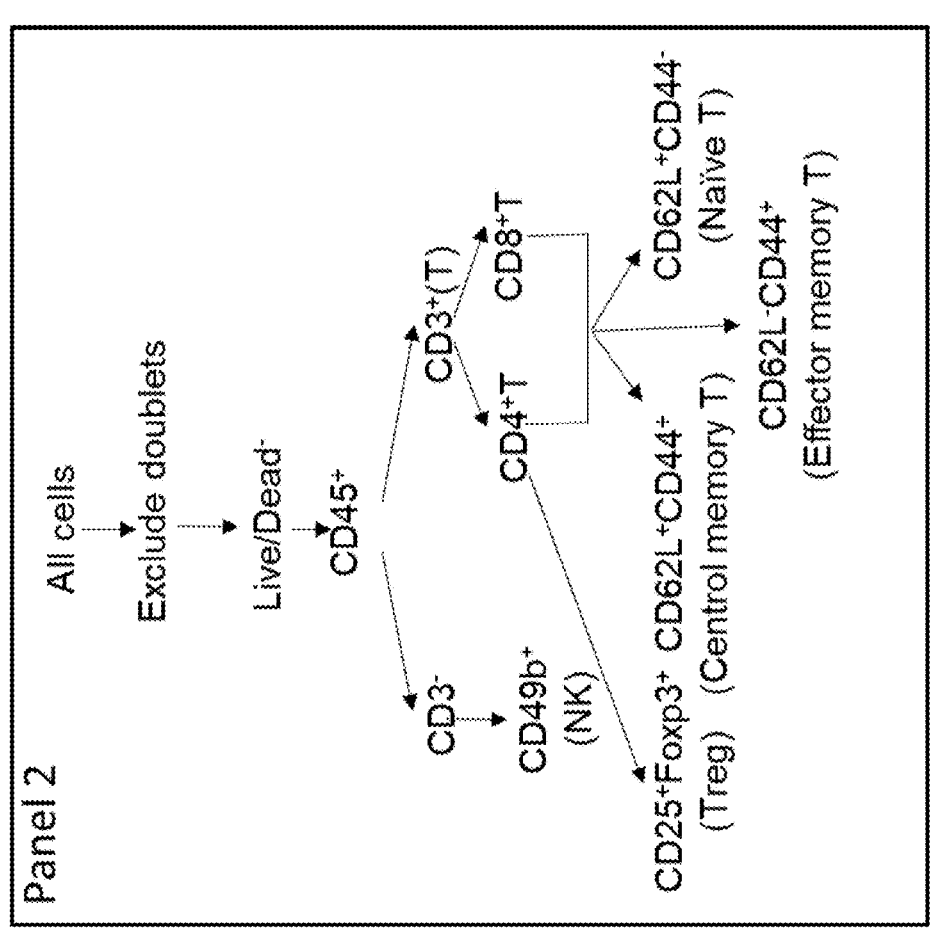
Figure 37B:
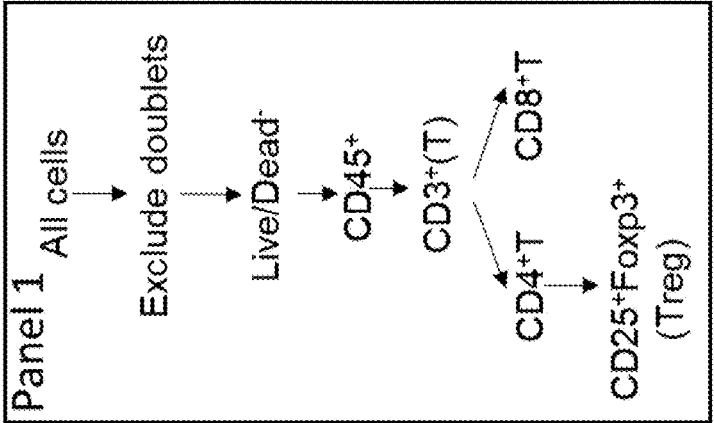

Example 37: Mechanism of Action Study in hPDL1/PD1 Transgenic BALB/c Mice Bearing hPDL1-CT26 Tumors $0.5 \times 10^6$ of hPDL 1/CT26 cells were subcutaneously inoculated to the right lower flank of the hPD1/PDL1 transgenic BALB/c mice. When the tumor size reached to about 175 mm$^3$, the mice were intravenously injected with 0.06 or 0.35 μmol/kg each of (1) N65S-1N-38B2/IL-1, (2) N65S-1N-DP47/IL-15 (non-targeted control), (3) antibody 38B2 and (4) the combination of antibody 38B2 and N65S-1N-38B2/IL-15. The tumor size was measured twice per week and mice were terminated at day 7 after dosing (FIG. 37A). Blood and draining lymph node (DLN) from all groups were collected to perform flow cytometry. Tumors were collected to perform TILs analysis (FIG. 37B). One-way ANOVA was used for statistical analysis. When a significant F-statistics (a ratio of treatment variance to the error variance) was obtained, comparisons between different groups were carried out with Games-Howell (equal variances not assumed) or Tukey (equal variances assumed) test. Comparisons between vehicle and other groups, * p<0.05;  p<0.01; * p<0.001. Error bars represented Standard Error of Mean (SEM).

Figure 37C:
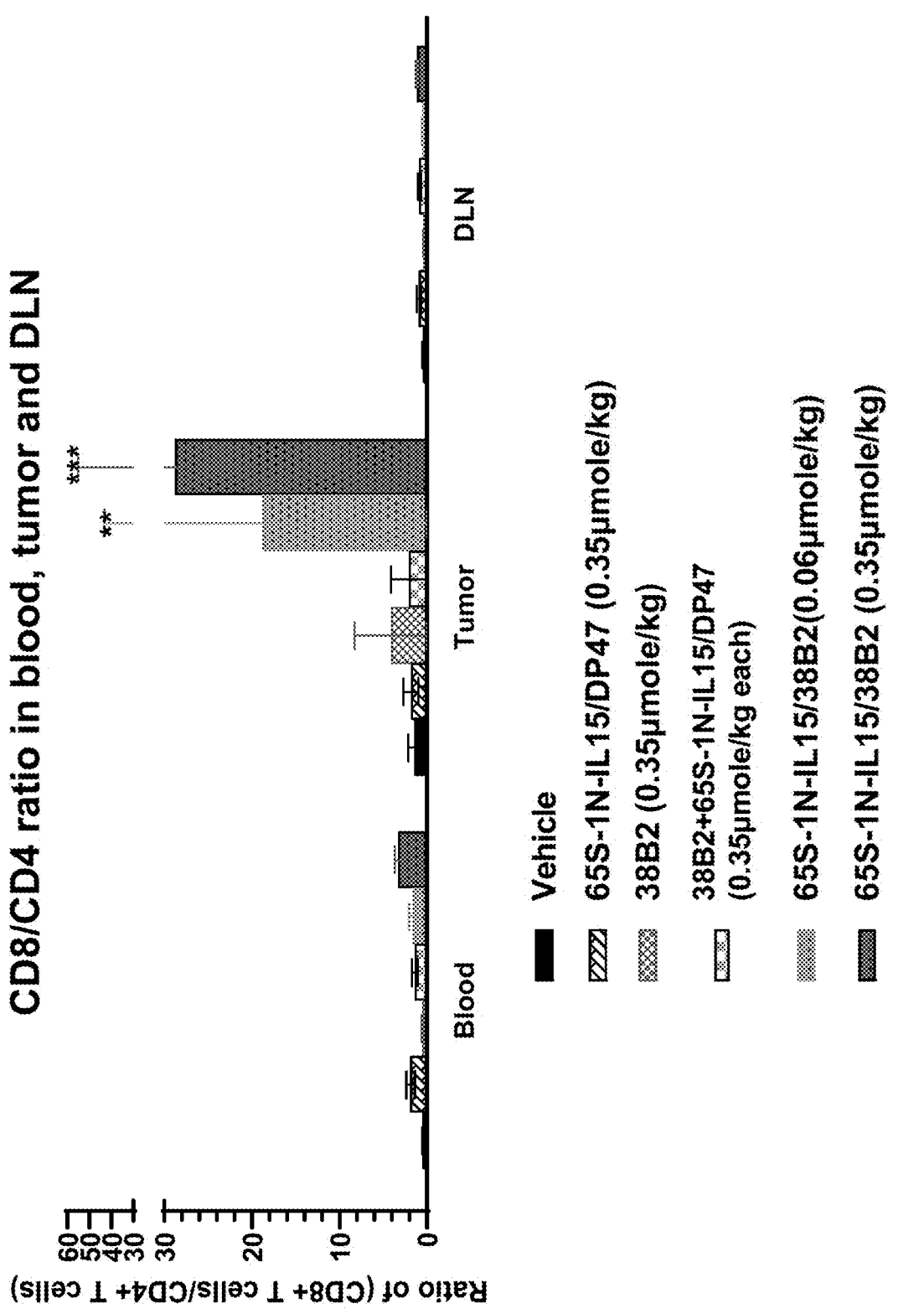

It was shown that N65S-1N-38B2/IL-15 bound to PD1 and IL2Rβγ expressing TIL and differently proliferated CD8+ T cells. Specifically, when analyzing the CD8/CD4 ratio in tumors, the blood, and draining lymph nodes (treated with antibody (1) 38B2, (2) PD1 targeted fusion protein N65S-1N-38B2/IL-15, (3) non-targeted fusion protein N65S-1N-DP47/IL-15, or (4) a combination of 38B2 and N65S-1N-38B2/IL-15), it was found that N65S-1N-38B2/IL-15 promoted CD8+ T cells growth in tumor, but not in the blood and draining lymph nodes. The CD8/CD4 ratio did not change as result of the other treatments ( )1) 38B2, (2) non-targeted fusion protein N65S-1N-DP47/IL-15, or (3) a combination of 38B2 and N65S-1N-38B2/IL-15)) (FIG. 37C).

Next, CD8 and CD4 subtypes in tumors (treated with antibody (1) 38B2, (2) PD1 targeted fusion protein N65S-1N-38B2/IL-15, (3) non-targeted fusion protein N65S-1N-DP47/IL-15, or (4) a combination of 38B2 and N65S-1N-38B2/IL-15) were analyzed. It was found that effector memory CD8 T cells were significantly increased in the tumor for N65S-1N-38B2/IL-15 reated samples and slightly increased for the 38B2 treated samples (FIG. 37D). No difference was observed among the other T cell subtypes in different treatment groups.

Example 38: N65S-1N-m3A7/IL-15 (Surrogate) Efficacy Studies in Multiple Mouse Syngeneic Tumor Models The indicated amount of tumor cells (Table 24) in 0.1 mL of PBS was subcutaneously inoculated to the right flank of the mice. The animals were randomized and treatments were started when the average tumor volume reaches approximately 100 mm$^3$ (between 75-125 mm$^3$). Tumor volumes were measured 2 times per week in two dimensions using a caliper, and the volume was expressed in mm$^3$ using the formula: V=(L×W×W)/2, where V is tumor volume, L is tumor length (the longest tumor dimension) and W is tumor width (the longest tumor dimension perpendicular to L).

Figure 38:
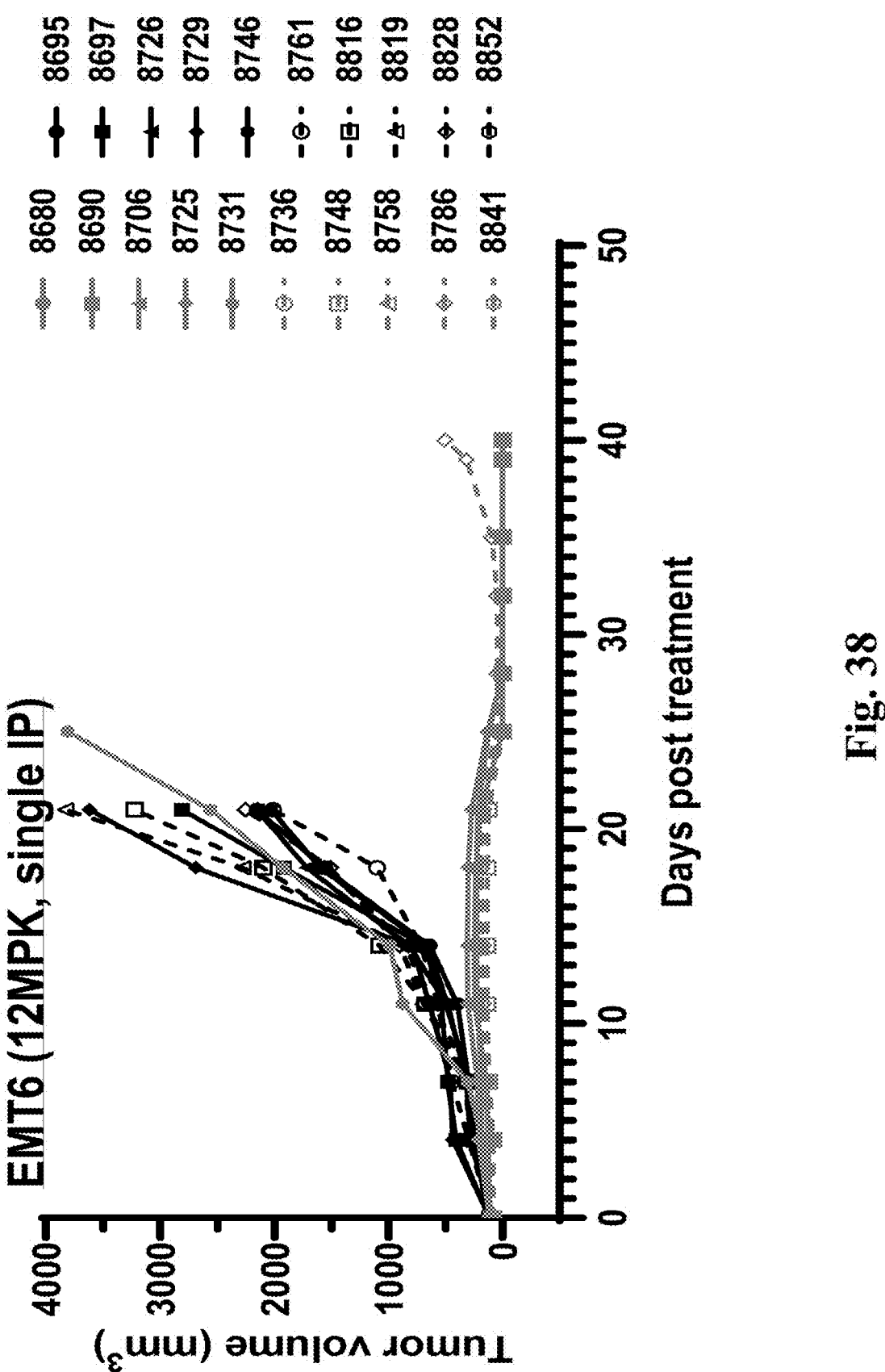
FIG. 38 illustrates that a N65S-1N-m3A7/IL-15 (surrogate) fusion protein showed significant anti-tumor efficacy in numerous mouse syngeneic tumor models. Data for EMT6 as shown as an illustrative example.

Significant anti-tumor efficacies were observed in all 12 models (TGI>50%) in single dose treatment (Table 24). Completed response (tumor free) were found for CT26, EMT6, MC38, H22, A20 and Pan02 (Table 24). Data for EMT6 as shown as an illustrative example (FIG. 38).

TABLE 24

Results of N65S-IN-m3A7/IL-15 (surrogate)
efficacy studies in multiple mouse syngeneic tumor models.

| Model | Number of cells | Cancer type | Mouse strain (sex) | Dose, route | TGI (%) (day) | CR (%) | p |
|---|---|---|---|---|---|---|---|
| CT26 | $5 \times 10^5$ | colorectal | BALB/C (F)* | 12 mg/kg, IP | 93.0 (d17) | 75.0 | <0.0001 |
| EMT6 | $5 \times 10^5$ | breast | BALB/C (F) | 12 mg/kg, IP | 79.7 (d21) | 71.4 | <0.0001 |
| Renca | $1 \times 10^6$ | kidney | BALB/C (F) | 6 mg/kg, IP | 52.4 (d18) | — | <0.0001 |
| MC38 | $1 \times 10^6$ | colorectal | C57BL/6 (F) | 6 mg/kg, IP | 73.7 (d18) | 12.5 | <0.0001 |
| Hepa1-6 | $5 \times 10^6$ | liver | C57BL/6 (F) | 6 mg/kg, IV | 76.4 (d23) | — | <0.0001 |
| H22 | $1 \times 10^6$ | | BALB/C (F) | 6 mg/kg, IV | 89.8 (d18) | 30.0 | <0.0001 |
| LL2 | $3 \times 10^5$ | lung | C57BL/6 (F) | 6 mg/kg, IP | 68.3 (d15) | — | <0.0001 |
| A20 | $5 \times 10^5$ | lymphoma | BALB/C (F) | 6 mg/kg, IP | 76.5 (d15) | 40.0 | <0.0001 |

TABLE 24-continued

Results of N65S-IN-m3A7/IL-15 (surrogate)
efficacy studies in multiple mouse syngeneic tumor models.

| Model | Number of cells | Cancer type | Mouse strain (sex) | Dose, route | TGI (%) (day) | CR (%) | p |
|---|---|---|---|---|---|---|---|
| B16-BL6 | $2 \times 10^5$ | melanoma | C57BL/6 (F) | 6 mg/kg, IV | 46.7 (d13) | — | 0.0033 |
| B16-F10 | $2 \times 10^5$ | | C57BL/6 (F) | 6 mg/kg, IV | 60.2 (d9) | — | 0.0003 |
| Pan02 | $3 \times 10^6$ | pancreatic | C57BL/6 (F) | 6 mg/kg, IV | 76.3 (d30) | 30.0 | 0.0380 |
| RM-1 | $1 \times 10^6$ | prostate | C57BL/6 (M) | 6 mg/kg, IV | 73.0 (d10) | — | <0.0001 |

F = female.
M = male.
TGI = tumor growth inhibition.
CR = completed response.

TABLE 25

Sequences of the disclosure

| Identifier | Sequence | SEQ ID NO |
|---|---|---|
| | Antibodies isolated from phage display library | |
| 19B6 HCDR1 | GYTFTGYYMH | 1 |
| 19B6 HCDR2 | IINPSGGSTSYAQKFQG | 2 |
| 19B6 HCDR3 | TAGYDWLPSGLGMDV | 3 |
| 19B6 VH | QVQLVQSGAEVKKPGASVKVSCKASGYTFTGYYMHWVRQ APGQGLEWMGIINPSGGSTSYAQKFQGRVTMTRDTSTSTVY MELSSLRSEDTAVYYCAKTAGYDWLPSGLGMDVWGQGTT VTVSS | 4 |
| 19B10 HCDR1 | GFTFSSYAMH | 5 |
| 19B10 HCDR2 | GISNSGGNTYYADSVKG | 6 |
| 19B10 HCDR3 | DNYYYYMDV | 7 |
| 19B10 VH | EVQLLESGGGLVQPGGSLRLSCAASGFTFSSYAMHWVRQA PGKGLEWVSGISNSGGNTYYADSVKGRFTISRDNSKNTLYL QMNSLRAEDTAVYYCARDNYYYYMDVWGKGTTVTVSS | 8 |
| 23A8 HCDR1 | GFTFSSSAMH | 9 |
| 23A8 HCDR2 | GISGSGSSTYYADSVKG | 10 |
| 23A8 HCDR3 | DNNYYYYMDV | 11 |
| 23 A8 VH | EVQLLESGGGLVQPGGSLRLSCAASGFTFSSSAMHWVRQAP GKGLEWVSGISGSGSSTYYADSVKGRFTISRDNSKNTLYLQ MNSLRAEDTAVYYCARDNNYYYYMDVWGKGTTVTVSS | 12 |
| 23A11 HCDR1 | GYTFTDYSLH | 13 |
| 23A11 HCDR2 | EVIPMEDTAYYAQTFQG | 14 |
| 23A11 HCDR3 | EPFTMVRGGRYYYYGMDV | 15 |
| 23A11 VH | QVQLVQSGAEVKKPGSSVKVSCKASGYTFTDYSLHWVRQA PGQGLEWMGEVIPMFDTAYYAQTFQGRVTITADESTSTAY MELSSLRSEDTAVYYCAREPFTMVRGGRYYYYGMDVWGQ GTTVTVSS | 16 |
| 23H9 HCDR1 | GGTFSSSVIS | 17 |
| 23H9 HCDR2 | GIIPIFGTANYAQKFQG | 18 |
| 23H9 HCDR3 | EGLGCSGGSCYSGYYYGMDV | 19 |
| 23H9 VH | QVQLVQSGAEVKKPGSSVKVSCKASGGTFSSSVISWVRQAP GQGLEWMGGIIPIFGTANYAQKFQGRVTITADESTSTAYME | 20 |

TABLE 25-continued

Sequences of the disclosure

| Identifier | Sequence | SEQ ID NO |
|---|---|---|
|  | LSSLRSEDTAVYYCAREGLGCSGGSCYSGYYYGMDVWGQ GTTVTVSS |  |
| 24H9 HCDR1 | GFTFSSYWMS | 21 |
| 24H9 HCDR2 | AISGSGGSTYYADSVKG | 22 |
| 24H9 HCDR3 | SPLQWVDV | 23 |
| 24H9 VH | EVQLLESGGGLVQPGGSLRLSCAASGFTFSSYWMSWVRQA PGKGLEWVSAISGSGGSTYYADSVKGRFTISRDNSKNTLYL QMNSLRAEDTAVYYCASSPLQWVDVWGQGTTVTVSS | 24 |
| 19B6 LCDR1 | RASQSINSWLA | 25 |
| 19B6 LCDR2 | YASSLQS | 26 |
| 19B6 LCDR3 | QQGYSVPLS | 27 |
| 19B6 VL | DIQMTQSPSSLSASVGDRVTITCRASQSINSWLAWYQQKPG KAPKLLIYYASSLQSGVPSRFSGSGSGTDFTLTISSLQPEDFA TYYCQQGYSVPLSFGQGTKLEIK | 28 |
| 19B10 LCDR1 | RASQSVSTWLA | 29 |
| 19B10 LCDR2 | AASNLET | 30 |
| 19B10 LCDR3 | QQTYSTPYT | 31 |
| 19B10 VL | DIQMTQSPSSLSASVGDRVTITCRASQSVSTWLAWYQQKPG KAPKLLIYAASNLETGVPSRFSGSGSGTDFTLTISSLQPEDFA TYYCQQTYSTPYTFGQGTKLEIK | 32 |
| 23A8 LCDR1 | RASQSIGTWLA | 33 |
| 23A8 LCDR2 | AASTLRS | 34 |
| 23A8 LCDR3 | QQSYSTPYT | 35 |
| 23A8 VL | DIQMTQSPSSLSASVGDRVTITCRASQSIGTWLAWYQQKPG KAPKLLIYAASTLRSGVPSRFSGSGSGTDFTLTISSLQPEDFA TYYCQQSYSTPYTFGQGTKLEIK | 36 |
| 23A11 LCDR1 | RASQNINKNLN | 37 |
| 23A11 LCDR2 | DASNLQS | 38 |
| 23A11 LCDR3 | QHSET | 39 |
| 23A11 VL | DIQMTQSPSSLSASVGDRVTITCRASQNINKNLNWYQQKPG KAPKLLIYDASNLQSGVPSRFSGSGSGTDFTLTISSLQPEDFA TYYCQHSETFGQGTKVEIK | 40 |
| 23H9 LCDR1 | RSSQSLLHSNGYNYLD | 41 |
| 23H9 LCDR2 | LSSHRAS | 42 |
| 23H9 LCDR3 | MQGAHWPYT | 43 |
| 23H9 VL | DIVMTQSPLSLPVTPGEPASISCRSSQSLLHSNGYNYLDWYL QKPGQSPQLLIYLSSHRASGVPDRFSGSGSGTDFTLKISRVEA EDVGVYYCMQGAHWPYTFGQGTKVEIK | 44 |
| 24H9 LCDR1 | RASQGISSWLA | 45 |
| 24H9 LCDR2 | SASSLQS | 46 |
| 24H9 LCDR3 | QQANSFPFT | 47 |
| 24H9 VL | DIQMTQSPSSLSASVGDRVTITCRASQGISSWLAWYQQKPG KAPKLLIYSASSLQSGVPSRFSGSGSGTDFTLTISSLQPEDFAT YYCQQANSFPFTFGPGTKVDIK | 48 |

TABLE 25-continued

Sequences of the disclosure

| Identifier | Sequence | SEQ ID NO |
|---|---|---|
| 23H9 derivatives obtained by light pair shuffling using the VH chain of 23H9 | | |
| 31B1 LCDR1 | RSSQSLLHSNGYNYLD | 41 |
| 31B1 LCDR2 | EASSLHS | 49 |
| 31B1 LCDR3 | MQGTHWPYT | 50 |
| 31B1 VL | DIVMTQSPLSLPVTPGEPASISCRSSQSLLHSNGYNYLDWYL QKPGQSPQLLIYEASSLHSGVPDRFSGSGSGTDFTLKISRVEA EDVGVYYCMQGTHWPYTFGQGTKVEIK | 51 |
| 33C4 LCDR1 | RSSQSLLHSNGYNYLD | 41 |
| 33C4 LCDR2 | EASSLHT | 52 |
| 33C4 LCDR3 | MQGSHWPYT | 53 |
| 33C4 VL | DIVMTQSPLSLPVTPGEPASISCRSSQSLLHSNGYNYLDWYL QKPGQSPQLLIYEASSLHTGVPDRFSGSGSGTDFTLKISRVEA EDVGVYYCMQGSHWPYTFGQGTKLEIK | 54 |
| 33G8 LCDR1 | RSSQSLLHSNGYNYLD | 41 |
| 33G8 LCDR2 | QASTLGS | 55 |
| 33G8 LCDR3 | MQGTHWPYT | 56 |
| 33G8 VL | DIVMTQSPLSLPVTPGEPASISCRSSQSLLHSNGYNYLDWYL QKPGQSPQLLIYQASTLGSGVPDRFSGSGSGTDFTLKISRVE AEDVGVYYCMQGTHWPYTFGQGTKLEIK | 57 |
| 34C1 LCDR1 | RSSESLLYSNGNTYLD | 58 |
| 34C1 LCDR2 | EVSNRAS | 59 |
| 34C1 LCDR3 | MQGTRWPYT | 60 |
| 34C1 VL | DIVMTQSPLSLPVTPGEPASISCRSSESLLYSNGNTYLDWYL QKPGQSPQLLIYEVSNRASGVPDRFSGSGSGTDFTLKISRVE AEDVGVYYCMQGTRWPYTFGQGTKVEIK | 61 |
| 23H9 derivatives motif LCDR1 | RSSX$_1$SLLX$_2$SNGX$_3$X$_4$YLD wherein X$_1$ is Q or E; wherein X$_2$ is H or Y; wherein X$_3$ is Y or N; and wherein X$_4$ is T or N | 62 |
| 23H9 derivatives motif LCDR2 | X$_5$X$_6$SX$_7$X$_8$X$_9$X$_{10}$ wherein X$_5$ is L, Q or E; wherein X$_6$ is S, A, or V; wherein X$_7$ is H, N, T, or S; wherein X$_8$ is R or L; wherein X$_9$ is G, A, or H; and wherein X$_{10}$ is S or T | 63 |
| 23H9 derivatives motif LCDR3 | MQGX$_{11}$X$_{12}$WPYT wherein X$_{11}$ is A, T, or S; and wherein X$_{12}$ is H or R | 64 |
| 23H9 derivatives motif VL | DIVMTQSPLSLPVTPGEPASISC RSSX$_1$SLLX$_2$SNGX$_3$X$_4$YLD WYLQKPGQSPQLLIY X$_5$X$_6$SX$_7$X$_8$X$_9$X$_{10}$GVPDRFSGSGSGTDFTLKISRVEAEDVGVY YC MQGX$_{11}$X$_{12}$WPYTFGQGTKVEIK | 65 |
| 24H9 derivatives obtained by light pair shuffling using the VH chain of 24H9 | | |
| 32A11 LCDR1 | RASESISIWLA | 66 |
| 32A11 LCDR2 | DASNLET | 67 |
| 32A11 LCDR3 | QQADSFPFT | 68 |

TABLE 25-continued

Sequences of the disclosure

| Identifier | Sequence | SEQ ID NO |
|---|---|---|
| 32A11 VL | DIQMTQSPSSLSASVGDRVTITCRASESISIWLAWYQQKPGK APKLLIYDASNLETGVPSRFSGSGSGTNFTLTISSLQPEDFAT YYCQQADSFPFTFGPGTKVDIK | 69 |
| 32D11 LCDR1 | RASQSINIWLA | 70 |
| 32D11 LCDR2 | DASNLET | 67 |
| 32D11 LCDR3 | QQGYSFPFT | 71 |
| 32D11 VL | DIQMTQSPSSLSASVGDRVTITCRASQSINIWLAWYQQKPGK APKLLIYDASNLETGVPSRFSGSGSGTDFTLTISSLQPEDFAT YYCQQGYSFPFTFGPGTKVDIK | 72 |
| 32D2 LCDR1 | RASQGISRWLA | 73 |
| 32D2 LCDR2 | EASTLQS | 74 |
| 32D2 LCDR3 | QQAYSFPFT | 75 |
| 32D2 VL | DIQMTQSPSSLSASVGDRVTITCRASQGISRWLAWYQQKPG KAPKLLIYEASTLQSGVPSRFSGSGSGTDFTLTISSLQPEDFA TYYCQQAYSFPFTFGQGTKVDIK | 76 |
| 32G6 LCDR1 | RASQSISSWLA | 77 |
| 32G6 LCDR2 | DASTLQS | 78 |
| 32G6 LCDR3 | QQANSFPFT | 47 |
| 32G6 VL | DIQMTQSPSSLSASVGDRVTITCRASQSISSWLAWYQQKPG KAPKLLIYDASTLQSGVPSRFSGSGSGTDFTLTISSLQPEDFA TYYCQQANSFPFTFGPGTKVDIK | 79 |
| 38A10 LCDR1 | RASQSISTWLA | 80 |
| 38A10 LCDR2 | DASRLQN | 81 |
| 38A10 LCDR3 | QQGDSFPFT | 82 |
| 38A10 VL | DIQMTQSPSSLSASVGDRVTITCRASQSISTWLAWYQQKPG KAPKLLIYDASRLQNGVPSRFSGSGSGTDFTLTISSLQPEDFA TYYCQQGDSFPFTFGPGTKVDIK | 83 |
| 38A11 LCDR1 | RASQSISSWLA | 77 |
| 38A11 LCDR2 | DASTLQS | 78 |
| 38A11 LCDR3 | QQGNSFPFT | 84 |
| 38A11 VL | DIQMTQSPSSLSASVGDRVTITCRASQSISSWLAWYQQKPG KAPKLLIYDASTLQSGVPSRFSGSGSGTDFTLTISSLQPEDFA TYYCQQGNSFPFTFGPGTKVDIK | 85 |
| 38A4 LCDR1 | RASQSISSWLA | 77 |
| 38A4 LCDR2 | DASNLQT | 86 |
| 38A4 LCDR3 | QQANSFPFT | 47 |
| 38A4 VL | DIQMTQSPSSLSASVGDRVTITCRASQSISSWLAWYQQKPG KAPKLLIYDASNLQTGVPSRFSGSGSGTDFTLTISSLQPEDFA TYYCQQANSFPFTFGQGTRLEIK | 87 |
| 38A6 LCDR1 | RASQDISRWLG | 88 |
| 38A6 LCDR2 | AASTLQS | 89 |
| 38A6 LCDR3 | QQANSFPFT | 47 |
| 38A6 VL | DIQMTQSPSSLSASVGDRVTITCRASQDISRWLGWYQQKPG KAPKLLIYAASTLQSGVPSRFSGSGSGTDFTLTISSLQPEDFA TYYCQQANSFPFTFGPGTKLEIK | 90 |

TABLE 25-continued

Sequences of the disclosure

| Identifier | Sequence | SEQ ID NO |
|---|---|---|
| 38A8 LCDR1 | RASESISIWLA | 66 |
| 38A8 LCDR2 | DASNLET | 67 |
| 38A8 LCDR3 | QQANSFPFT | 47 |
| 38A8 VL | DIQMTQSPSSLSASVGDRVTITCRASESISIWLAWYQQKPGK APKLLIYDASNLETGVPSRFSGSGSGTDFTLTISSLQPEDFAT YYCQQANSFPFTFGPGTKVDIK | 91 |
| 38B1 LCDR1 | RASQSISTWLA | 80 |
| 38B1 LCDR2 | EASKLER | 92 |
| 38B1 LCDR3 | QQAYSFPFT | 75 |
| 38B1 VL | DIQMTQSPSSLSASVGDRVTITCRASQSISTWLAWYQQKPG KAPKLLIYEASKLERGVPSRFSGSGSGTDFTLTISSLQPEDFA TYYCQQAYSFPFTFGPGTKVDIK | 93 |
| 38B10 LCDR1 | RASQSISTWLA | 80 |
| 38B10 LCDR2 | DASTLQT | 94 |
| 38B10 LCDR3 | QQGYSFPFT | 71 |
| 38B10 VL | DIQMTQSPSSLSASVGDRVTITCRASQSISTWLAWYQQKPG KAPKLLISDASTLQTGVPSRFSGSGSGTDFTLTISSLQPEDFA TYYCQQGYSFPFTFGPGTKVDIK | 95 |
| 38B2 LCDR1 | RASESISSWLA | 96 |
| 38B2 LCDR2 | DASSLES | 97 |
| 38B2 LCDR3 | QQGDSFPFT | 82 |
| 38B2 VL | DIQMTQSPSSLSASVGDRVTITCRASESISSWLAWYQQKPGK APKLLIYDASSLESGVPSRFSGSGSGTDFTLTISSLQPEDFAT YYCQQGDSFPFTFGQGTKLEIK | 98 |
| 38C11 LCDR1 | RASQSISRWLA | 99 |
| 38C11 LCDR2 | DASTVQS | 100 |
| 38C11 LCDR3 | QQANSFPFT | 47 |
| 38C11 VL | DIQMTQSPSSLSASVGDRVTITCRASQSISRWLAWYQQKPG KAPKLLISDASTVQSGVPSRFSGSGSGTDFTLTISSLQPEDFA TYYCQQANSFPFTFGPGTKVDIK | 101 |
| 38C6 LCDR1 | RAGRDINKWVA | 102 |
| 38C6 LCDR2 | DASSLQS | 103 |
| 38C6 LCDR3 | QQANSFPFA | 104 |
| 38C6 VL | DIQMTQSPSSLSASVGDRVTITCRAGRDINKWVAWYQQKPG KAPKLLIYDASSLQSGVPSRFSGSGSGTDFTLTISSLQPEDFA TYYCQQANSFPFAFGQGTKVEIK | 105 |
| 38G11 LCDR1 | RASENISRWLA | 106 |
| 38G11 LCDR2 | DASSLQS | 103 |
| 38G11 LCDR3 | QQANSFPFT | 47 |
| 38G11 VL | DIQMTQSPSSLSASVGDRVTITCRASENISRWLAWYQQKPG KAPKLLIYDASSLQSGVPSRFSGSGSGTDFTLTISSLQPEDFA TYYCQQANSFPFTFGPGTKVDIK | 107 |
| 38G9 LCDR1 | RVSQSISNWLA | 108 |
| 38G9 LCDR2 | DASSLQS | 103 |

TABLE 25-continued

Sequences of the disclosure

| Identifier | Sequence | SEQ ID NO |
|---|---|---|
| 38G9 LCDR3 | QQANSFPFT | 47 |
| 38G9 VL | DIQMTQSPSSLSASVGDRVTITCRVSQSISNWLAWYQQPG KAPKLLIYDASSLQSGVPSRFSGSGSGTDFTLTISSLQPEDFA TYYCQQANSFPFT | 109 |
| 38H3 LCDR1 | RASQGISTWLA | 110 |
| 38H3 LCDR2 | EASRLQS | 111 |
| 38H3 LCDR3 | QQAYSFPFT | 75 |
| 38H3 VL | DIQMTQSPSSLSASVGDRVTITCRASQGISTWLAWYQQPG KAPKLLIYEASRLQSGVPSRFSGSGSGTDFTLTISSLQPEDFA TYYCQQAYSFPFTFGPGTKVDIK | 112 |
| 39A3 LCDR1 | RASQSISSWLA | 77 |
| 39A3 LCDR2 | DASSLQS | 103 |
| 39A3 LCDR3 | QQGDSFPLT | 113 |
| 39A3 VL | DIQMTQSPSSLSASVGDRVTITCRASQSISSWLAWYQQPG KAPKLLIYDASSLQSGVPSRFSGSGSGTDFTLTISSLQPEDFA TYYCQQGDSFPLTFGQGTKVEIK | 114 |
| 39B11 LCDR1 | RASQSISSWLA | 77 |
| 39B11 LCDR2 | EASRLQS | 111 |
| 39B11 LCDR3 | QQANSFPFT | 47 |
| 39B11 VL | DIQMTQSPSSLSASVGDRVTITCRASQSISSWLAWYQQPG KAPKLLIYEASRLQSGVPSRFSGSGSGTDFTLTISSLQPEDFA TYYCQQANSFPFTFGPGTKVDIK | 115 |
| 39B3 LCDR1 | RASQSIGPWLA | 116 |
| 39B3 LCDR2 | DASNLET | 67 |
| 39B3 LCDR3 | QQANSFPFT | 47 |
| 39B3 VL | DIQMTQSPSSLSASVGDRVTITCRASQSIGPWLAWYQQPG KAPKLLIYDASNLETGVPSRFSGSGSGTDFTLTISSLQPEDFA TYYCQQANSFPFTFGPGTKVDIK | 117 |
| 39B6 LCDR1 | RASEDISHWLA | 118 |
| 39B6 LCDR2 | DAKDLHP | 119 |
| 39B6 LCDR3 | QQANSFPFT | 47 |
| 39B6 VL | DIQMTQSPSSLSASVGDRVTITCRASEDISHWLAWYQQPG KAPKLLIYDAKDLHPGVPSRFSGSGSGTDFTLTISSLQPEDFA TYYCQQANSFPFTFGQGTRLEIK | 120 |
| 39F11 LCDR1 | RASQSISTWLA | 80 |
| 39F11 LCDR2 | DASTLQS | 78 |
| 39F11 LCDR3 | QQANSFPFT | 47 |
| 39F11 VL | DIQMTQSPSSLSASVGDRVTITCRASQSISTWLAWYQQPG KAPKLLIYDASTLQSGVPSRFSGSGSGTDFTLTISSLQPEDFA TYYCQQANSFPFTFGPGTKVDIK | 121 |
| 39G5 LCDR1 | RASQNINVWLA | 122 |
| 39G5 LCDR2 | DASSLQS | 103 |
| 39G5 LCDR3 | QQANSFPFT | 47 |

TABLE 25-continued

Sequences of the disclosure

| Identifier | Sequence | SEQ ID NO |
|---|---|---|
| 39G5 VL | DIQMTQSPSSLSASVGDRVTITCRASQNINVWLAWYQQKPG<br>KAPKLLIYDASSLQSGVPSRFSGSGSGTDFTLTISSLQPEDFA<br>TYYCQQANSFPFTFGPGTKVDIK | 123 |
| 39G8 LCDR1 | RASQGISPWLA | 124 |
| 39G8 LCDR2 | DASKLET | 125 |
| 39G8 LCDR3 | QQAYSFPFT | 75 |
| 39G8 VL | DIQMTQSPSSLSASVGDRVTITCRASQGISPWLAWYQQKPG<br>KAPKLLIYDASKLETGVPSRFSGSGSGTDFTLTISSLQPEDFA<br>TYYCQQAYSFPFTFGGGTKVEIK | 126 |
| 39H11 LCDR1 | RASQSIGIWVA | 127 |
| 39H11 LCDR2 | DASNLQS | 38 |
| 39H11 LCDR3 | QQADSFPFT | 68 |
| 39H11 VL | DIQMTQSPSSLSASVGDRVTITCRASQSIGIWVAWYQQKPG<br>KAPKLLIYDASNLQSGVPSRFSGSGSGTDFTLTISSLQPEDFA<br>TYYCQQADSFPFTFGQGTKVEIK | 128 |
| 39H2 LCDR1 | RASQNIGPWLA | 129 |
| 39H2 LCDR2 | DASTLHS | 130 |
| 39H2 LCDR3 | QQANSFPFT | 47 |
| 39H2 VL | DIQMTQSPSSLSASVGDRVTITCRASQNIGPWLAWYQQKPG<br>KAPKLLIYDASTLHSGVPSRFSGSGSGTDFTLTISSLQPEDFA<br>TYYCQQANSFPFTFGQGTRLEIK | 131 |
| 39H7 LCDR1 | RASQSISNWLA | 132 |
| 39H7 LCDR2 | DASNLQA | 133 |
| 39H7 LCDR3 | QQAYSFPFT | 75 |
| 39H7 VL | DIQMTQSPSSLSASVGDRVTITCRASQSISNWLAWYQQKPG<br>KAPKLLIYDASNLQAGVPSRFSGSGSGTDFTLTISSLQPEDFA<br>TYYCQQAYSFPFTFGPGTKVDIK | 134 |
| 24H9<br>derivatives<br>motif LCR1 | $RX_{13}X_{14}X_{15}X_{16}IX_{17}X_{18}WX_{19}X_{20}$<br>wherein $X_{13}$ is A or V;<br>wherein $X_{14}$ is S or G;<br>wherein $X_{15}$ is Q, E, or R;<br>wherein $X_{16}$ is G, S, D or N;<br>wherein $X_{17}$ is G, S, or N;<br>wherein $X_{18}$ is S, I, R, T, K, P, N, H, or V;<br>wherein $X_{19}$ is L or V; and<br>wherein $X_{20}$ is G or A | 135 |
| 24H9<br>derivatives<br>motif LCR2 | $X_{21}AX_{22}X_{23}X_{24}X_{25}X_{26}$<br>wherein $X_{21}$ is S, D, E, or A;<br>wherein $X_{22}$ is S, or K;<br>wherein $X_{23}$ is S, N, T, R, or D;<br>wherein $X_{24}$ is L or V;<br>wherein $X_{25}$ is Q, E, or H; and<br>wherein $X_{26}$ is S, N, A, R, P, or T | 136 |
| 24H9<br>derivatives<br>motif LCR3 | $QQX_{27}X_{28}SFPX_{29}X_{30}$<br>wherein $X_{27}$ is A, or G;<br>wherein $X_{28}$ is N, D, or Y;<br>wherein $X_{29}$ is F or L; and<br>wherein $X_{30}$ is A, or T | 137 |

TABLE 25-continued

| Identifier | Sequence | SEQ ID NO |
|---|---|---|
| | Sequences of the disclosure | |
| 24H9 derivatives motif VK (see SEQ ID NOS: 135-137 for X$_n$) | DIQMTQSPSSLSASVGDRVTITCRX$_{13}$X$_{14}$X$_{15}$X$_{16}$IX$_{17}$X$_{18}$WX$_{19}$X$_{20}$ WYQQKPGKAPKLLIYX$_{21}$AX$_{22}$X$_{23}$X$_{24}$X$_{25}$X$_{26}$GVPSRFSGSGSG TDFTLTISSLQPEDFATYYCQQX$_{27}$X$_{28}$SFPX$_{29}$X$_{30}$FGPGTKVDI K | 138 |
| | Mouse/human PD-1 crossreactive antibodiy isolated from phage display | |
| R3A9 HCDR1 | GHTFTSYYIH | 139 |
| R3A9 HCDR2 | GIINPSGGSTSYAQKFQG | 140 |
| R3A9 HCDR3 | DRAYGGAGDY | 141 |
| R3A9 VH | QVQLVQSGAEVKKPGASVKVSCKASGHTFTSYYIHWVRQA PGQGLEWMGIINPSGGSTSYAQKFQGRVTMTRDTSTSTVYM ELSSLRSEDTAVYYCARDRAYGGAGDYWGQGTLVTVSS | 142 |
| R3A9 LCDR1 | RASQSVGTWLA | 143 |
| R3A9 LCDR2 | SASTLQS | 144 |
| R3A9 LCDR3 | QQSYSAPLT | 145 |
| R3A9 VL | DIQMTQSPSSLSASVGDRVTITCRASQSVGTWLAWYQQKPG KAPKLLIYSASTLQSGVPSRFSGSGSGTDFTLTISSLQPEDFA TYYCQQSYSAPLTFGGGTKVEIK | 146 |
| | R3A9 derivatives obtained by light pair shuffling using the VH chain of R3A9 | |
| m3A7 LCDR1 | RASRSISNWLA | 147 |
| m3A7 LCDR2 | AASSLQS | 148 |
| m3A7 LCDR3 | QQSYSAPVT | 149 |
| m3A7 VL | DIQMTQSPSSLSASVGDRVTITCRASRSISNWLAWYQQKPG KAPKLLIYAASSLQSGVPSRFSGSGSGTDFTLTISSLQPEDFA TYYCQQSYSAPVTFGQGTKVEIK | 150 |
| m2C1 LCDR1 | RASRSISSWLA | 151 |
| m2C1 LCDR2 | AASSLQS | 148 |
| m2C1 LCDR3 | QQSYSIPAT | 152 |
| m2C1 VL | DIQMTQSPSSLSASVGDRVTITCRASRSISSWLAWYQQKPGK APKLLIYAASSLQSGVPSRFSGSGSGTDFTLTISSLQPEDFAT YYCQQSYSIPATFGQGTKVEIK | 153 |
| m2A1 LCDR1 | RASRGISSWLA | 154 |
| m2A1 LCDR2 | AASSLQS | 148 |
| m2A1 LCDR3 | QQSYSPPWT | 155 |
| m2A1 VL | DIQMTQSPSSLSASVGDRVTITCRASRGISSWLAWYQQKPG KAPKLLIYAASSLQSGVPSRFSGSGSGTDFTLTISSLQPEDFA TYYCQQSYSPPWTFGQGTKVEIK | 156 |
| m4A5 LCDR1 | RASQSIDTWLA | 157 |
| m4A5 LCDR2 | AASTLES | 158 |
| m4A5 LCDR3 | QQSYRAPLT | 159 |
| m4A5 VL | DIQMTQSPSSLSASVGDRVTITCRASQSIDTWLAWYQQKPG KAPKLLIYAASTLESGVPSRFSGSGSGTDFTLTISSLQPEDFA TYYCQQSYRAPLTFGQGTKVEIK | 160 |
| m4D1 LCDR1 | RASQSISAWLA | 161 |
| m4D1 LCDR2 | KASSLES | 162 |

TABLE 25-continued

Sequences of the disclosure

| Identifier | Sequence | SEQ ID NO |
|---|---|---|
| m4D1 LCDR3 | QQSYSPPAT | 163 |
| m4D1 VL | DIQMTQSPSSLSASVGDRVTITCRASQSISAWLAWYQQKPG KAPKLLIYKASSLESGVPSRFSGSGSGTDFTLTISSLQPEDFA TYYCQQSYSPPATFGGGTKVEIK | 164 |
| m3C6 LCDR1 | RASQSIDTWLA | 157 |
| m3C6 LCDR2 | EASSLQG | 165 |
| m3C6 LCDR3 | QQSYSTWT | 166 |
| m3C6 VL | DIQMTQSPSSLSASVGDRVTITCRASQSIDTWLAWYQQKPG KAPKLLIYEASSLQGGVPSRFSGSGSGTDFTLTISSLQPEDFA TYYCQQSYSTWTFGQGTKVEIK | 167 |

Heavy and light chains of 38B2 and m3A7

| Identifier | Sequence | SEQ ID NO |
|---|---|---|
| 38B2 full length HC (comprises 24H9 VH (SEQ ID NO: 24)) | EVQLLESGGGLVQPGGSLRLSCAASGFTFSSYWMSWVRQA PGKGLEWVSAISGSGGSTYYADSVKGRFTISRDNSKNTLYL QMNSLRAEDTAVYYCASSPLQWVDVWGQGTTVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPELLGGPSVFLFPP KPKDTLMISRTPEVTCVVVDVSHEDPEVKFNWYVDGVEVH NAKTKPREEQYNSTYRVVSVLTVLHQDWLNGKEYKCKVS NKALPAPIEKTISKAKGQPREPQVYTLPPSREEMTKNQVSLT CLVKGFYPSDIAVEWESNGQPENNYKTTPPVLDSDGSFFLY SKLTVDKSRWQQGNVFSCSVMHEALHNHYTQKSLSLSPG(K) | 168 |
| 38B2 HC (T350V/ T366L/ K392L/ T394W) LALAPG (comprises 24H9 VH (SEQ ID NO: 24)) | EVQLLESGGGLVQPGGSLRLSCAASGFTFSSYWMSWVRQA PGKGLEWVSAISGSGGSTYYADSVKGRFTISRDNSKNTLYL QMNSLRAEDTAVYYCASSPLQWVDVWGQGTTVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPEAAGGPSVFLFPP KPKDTLMISRTPEVTCVVVDVSHEDPEVKFNWYVDGVEVH NAKTKPREEQYNSTYRVVSVLTVLHQDWLNGKEYKCKVS NKALGAPIEKTISKAKGQPREPQVYVLPPSREEMTKNQVSLL CLVKGFYPSDIAVEWESNGQPENNYLTWPPVLDSDGSFFLY SKLTVDKSRWQQGNVFSCSVMHEALHNHYTQKSLSLSPG(K) | 169 |
| 38B2 full length LC (comprises 38B2 VL (SEQ ID NO: 98)) | DIQMTQSPSSLSASVGDRVTITCRASESISSWLAWYQQKPGK APKLLIYDASSLESGVPSRFSGSGSGTDFTLTISSLQPEDFAT YYCQQGDSFPFTFGQGTKLEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKS FNRGEC | 170 |
| m3A7 full length mHC LALAPG (comprises R3A9 VH (SEQ ID NO: 142)) | QVQLVQSGAEVKKPGASVKVSCKASGHTFTSYYIHWVRQA PGQGLEWMGIINPSGGSTSYAQKFQGRVTMTRDTSTSTVYM ELSSLRSEDTAVYYCARDRAYGGAGDYWGQGTLVTVSSAK TTAPSVYPLAPVCGDTTGSSVTLGCLVKGYFPEPVTLTWNS GSLSSGVHTFPAVLQSDLYTLSSSVTVTSSTWPSQSITCNVA HPASSTKVDKKIEPRGPTIKPCPPCKCPAPNAAGGPSVFIFPP KIKDVLMISLSPIVTCVVVDVSEDDPDVQISWFVNNVEVHT AQTQTHREDYNSTLRVVSALPIQHQDWMSGKEFKCKVNNK DLGAPIERTISKPKGSVRAPQVYVLPPPEEEMTKKQVTLTCM VTDFMPEDIYVEWTNNGKTELNYKNTEPVLDSDGSYFMYS KLRVEKKNWVERNSYSCSVVHEGLHNHHTTKSFSRTPG(K) | 171 |
| m3A7 mHC (L351Y/ F405A/ Y407V) LALAPG (comprises R3A9 VH (SEQ ID NO: 142)) | QVQLVQSGAEVKKPGASVKVSCKASGHTFTSYYIHWVRQA PGQGLEWMGIINPSGGSTSYAQKFQGRVTMTRDTSTSTVYM ELSSLRSEDTAVYYCARDRAYGGAGDYWGQGTLVTVSSAK TTAPSVYPLAPVCGDTTGSSVTLGCLVKGYFPEPVTLTWNS GSLSSGVHTFPAVLQSDLYTLSSSVTVTSSTWPSQSITCNVA HPASSTKVDKKIEPRGPTIKPCPPCKCPAPNAAGGPSVFIFPP KIKDVLMISLSPIVTCVVVDVSEDDPDVQISWFVNNVEVHT AQTQTHREDYNSTLRVVSALPIQHQDWMSGKEFKCKVNNK DLGAPIERTISKPKGSVRAPQVYVYPPPEEEMTKKQVTLTCM VTDFMPEDIYVEWTNNGKTELNYKNTEPVLDSDGSYAMVS KLRVEKKNWVERNSYSCSVVHEGLHNHHTTKSFSRTPG(K) | 172 |

TABLE 25-continued

Sequences of the disclosure

| Identifier | Sequence | SEQ ID NO |
|---|---|---|
| m3A7 full length mLC (comprises m3A7 VL (SEQ ID NO: 150)) | DIQMTQSPSSLSASVGDRVTITCRASRSISNWLAWYQQKPG KAPKLLIYAASSLQSGVPSRFSGSGSGTDFTLTISSLQPEDFA TYYCQQSYSAPVTFGQGTKVEIKRADAAPTVSIFPPSSEQLT SGGASVVCFLNNFYPKDINVKWKIDGSERQNGVLNSWTDQ DSKDSTYSMSSTLTLTKDEYERHNSYTCEATHKTSTSPIVKS FNRNEC | 173 |

Fusions of 38B2 heavy chains with SD15

| | | |
|---|---|---|
| hSD15 + 38B2 HC LALAPG (comprises 24H9 VH (SEQ ID NO: 24), linker 1 (SEQ ID NO: 215), and linker 2 (SEQ ID NO: 216)) | ITCPPPMSVEHADIWVKSYSLYSRERYICNSGFKRKAGTS SLTECVLNKATNVAHWTTPSLKCIRDPALVHQRPAPPSG GSGGGGSGGGSGGGGSLQNWVNVISDLKKIEDLIQSMHI DATLYTESDVHPSCKVTAMKCFLLELQVISLESGDASIHD TVENLIILANNSLSSNGNVTESGCKECEELEEKNIKEFLQS FVHIVQMFINTSGGGGSGGGGSGGGGSGGGGSGGGGSGG GGSEVQLLESGGGLVQPGGSLRLSCAASGFTFSSYWMSWV RQAPGKGLEWVSAISGSGGSTYYADSVKGRFTISRDNSKNT LYLQMNSLRAEDTAVYYCASSPLQWVDVWGQGTTVTVSS ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPE*A*AGGPSVF LFPPKPKDTLMISRTPEVTCVVVDVSHEDPEVKF*N*WYVDGV EVHNAKTKPREEQYNSTYRVVSVLTVLHQDWLNGKEYC KVSNKALGAPIEKTISKAKGQPREPQVYTLPPSREEMTKNQ VSLTCLVKGFYPSDIAVEWESNGQPENNYKTTPPVLDSDGS FFLYSKLTVDKSRWQQGNVFSCSVMHEALHNHYTQKSLSL SPG(K) | 174 |
| hSD15 + 38B2HC (T350V/ L351Y/ F405A/ Y407V) LALAPG (comprises 24H9 VH (SEQ ID NO: 24), linker 1 (SEQ ID NO: 215), and linker 2 (SEQ ID NO: 216)) | ITCPPPMSVEHADIWVKSYSLYSRERYICNSGFKRKAGTS SLTECVLNKATNVAHWTTPSLKCIRDPALVHQRPAPPSG GSGGGGSGGGSGGGGSLQNWVNVISDLKKIEDLIQSMHI DATLYTESDVHPSCKVTAMKCFLLELQVISLESGDASIHD TVENLIILANNSLSSNGNVTESGCKECEELEEKNIKEFLQS FVHIVQMFINTSGGGGSGGGGSGGGGSGGGGSGGGGSGG GGSEVQLLESGGGLVQPGGSLRLSCAASGFTFSSYWMSWV RQAPGKGLEWVSAISGSGGSTYYADSVKGRFTISRDNSKNT LYLQMNSLRAEDTAVYYCASSPLQWVDVWGQGTTVTVSS ASTKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPE*A*AGGPSVF LFPPKPKDTLMISRTPEVTCVVVDVSHEDPEVKF*N*WYVDGV EVHNAKTKPREEQYNSTYRVVSVLTVLHQDWLNGKEYC KVSNKALGAPIEKTISKAKGQPREPQVY*VY*PPSREEMTKNQ VSLTCLVKGFYPSDIAVEWESNGQPENNYKTTPPVLDSDGS F*ALV*SKLTVDKSRWQQGNVFSCSVMHEALHNHYTQKSLSL SPG(K) | 175 |
| 38B2HC LALAPG + hSD15 (comprises 24H9 VH (SEQ ID NO: 24) and linker 1 (SEQ ID NO: 215)) | EVQLLESGGGLVQPGGSLRLSCAASGFTFSSYWMSWVRQA PGKGLEWVSAISGSGGSTYYADSVKGRFTISRDNSKNTLYL QMNSLRAEDTAVYYCASSPLQWVDVWGQGTTVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPE*A*AGGPSVFLFPP KPKDTLMISRTPEVTCVVVDVSHEDPEVKF*N*WYVDGVEVH NAKTKPREEQYNSTYRVVSVLTVLHQDWLNGKEYCKVS NKALGAPIEKTISKAKGQPREPQVYTLPPSREEMTKNQVSLT CLVKGFYPSDIAVEWESNGQPENNYKTTPPVLDSDGSFFLY SKLTVDKSRWQQGNVFSCSVMHEALHNHYTQKSLSLSPGS CPPPMSVEHADIWVKSYSLYSRERYICNSGFKRKAGTSSL TECVLNKATNVAHWTTPSLKCIRDPALVHQRPAPPSGGS GGGGSGGGSGGGGSLQNWVNVISDLKKIEDLIQSMHIDA TLYTESDVHPSCKVTAMKCFLLELQVISLESGDASIHDTV ENLIILANNSLSSNGNVTESGCKECEELEEKNIKEFLQSFV HIVQMFINTS | 176 |

TABLE 25-continued

Sequences of the disclosure

| Identifier | Sequence | SEQ ID NO |
|---|---|---|
| 38B2 HC (T350V/ L351Y/ F405A/ Y407V) LALAPG + hSD15 (comprises 24H9 VH (SEQ ID NO: 24) and linker 1 (SEQ ID NO: 215)) | EVQLLESGGGLVQPGGSLRLSCAASGFTFSSYWMSWVRQA PGKGLEWVSAISGSGGSTYYADSVKGRFTISRDNSKNTLYL QMNSLRAEDTAVYYCASSPLQWVDVWGQGTTVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPEAAGGPSVFLFPP KPKDTLMISRTPEVTCVVVDVSHEDPEVKFNWYVDGVEVH NAKTKPREEQYNSTYRVVSVLTVLHQDWLNGKEYKCKVS NKALGAPIEKTISKAKGQPREPQVYVYPPSREEMTKNQVSLT CLVKGFYPSDIAVEWESNGQPENNYKTTPPVLDSDGSFALV SKLTVDKSRWQQGNVFSCSVMHEALHNHYTQKSLSLSPGS CPPPMSVEHADIWVKSYSLYSRERYICNSGFKRKAGTSSL TECVLNKATNVAHWTTPSLKCIRDPALVHQRPAPPSGGS GGGGSGGGGSGGGGSLQNWVNVISDLKKIEDLIQSMHIDA TLYTESDVHPSCKVTAMKCFLLELQVISLESGDASIHDTV ENLIILANNSLSSNGNVTESGCKECEELEEKNIKEFLQSFV HIVQMFINTS | 177 |
| N65A_hSD15 + 38B2 HC (T350V/ L351Y/ F405A/ Y407V) LALAPG (comprises 24H9 VH (SEQ ID NO: 24) and linker 1 (SEQ ID NO: 215), linker 1 (SEQ ID NO: 215), and linker 2 (SEQ ID NO: 216)) | ITCPPPMSVEHADIWVKSYSLYSRERYICNSGFKRKAGTS SLTECVLNKATNVAHWTTPSLKCIRDPALVHQRPAPPSG GSGGGGSGGGGSGGGGSLQNWVNVISDLKKIEDLIQSMHI DATLYTESDVHPSCKVTAMKCFLLELQVISLESGDASIHD TVEALIILANNSLSSNGNVTESGCKECEELEEKNIKEFLQS FVHIVQMFINTSGGGGSGGGGSGGGGSGGGGSGGGGSGG GGS*EVQLLESGGGLVQPGGSLRLSCAASGFTFSSYWMSWV RQAPGKGLEWVSAISGSGGSTYYADSVKGRFTISRDNSKNT LYLQMNSLRAEDTAVYYCASSPLQWVDVWGQGTTVTVSS A*STKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPEAAGGPSVF LFPPKPKDTLMISRTPEVTCVVVDVSHEDPEVKFNWYVDGV EVHNAKTKPREEQYNSTYRVVSVLTVLHQDWLNGKEYKC KVSNKALGAPIEKTISKAKGQPREPQVYVYPPSREEMTKNQ VSLTCLVKGFYPSDIAVEWESNGQPENNYKTTPPVLDSDGS FALVSKLTVDKSRWQQGNVFSCSVMHEALHNHYTQKSLSL SPG(K) | 178 |
| N65D_hSD15 + 38B2 HC (T350V/ L351Y/ F405A/ Y407V) LALAPG (comprises 24H9 VH (SEQ ID NO: 24), linker 1 (SEQ ID NO: 215), and linker 2 (SEQ ID N: 216)) | ITCPPPMSVEHADIWVKSYSLYSRERYICNSGFKRKAGTS SLTECVLNKATNVAHWTTPSLKCIRDPALVHQRPAPPSG GSGGGGSGGGGSGGGGSLQNWVNVISDLKKIEDLIQSMHI DATLYTESDVHPSCKVTAMKCFLLELQVISLESGDASIHD TVEDLIILANNSLSSNGNVTESGCKECEELEEKNIKEFLQS FVHIVQMFINTSGGGGSGGGGSGGGGSGGGGSGGGGSGG GGS*EVQLLESGGGLVQPGGSLRLSCAASGFTFSSYWMSWV RQAPGKGLEWVSAISGSGGSTYYADSVKGRFTISRDNSKNT LYLQMNSLRAEDTAVYYCASSPLQWVDVWGQGTTVTVSS A*STKGPSVFPLAPSSKSTSGGTAALGCLVKDYFPEPVTVSW NSGALTSGVHTFPAVLQSSGLYSLSSVVTVPSSSLGTQTYIC NVNHKPSNTKVDKRVEPKSCDKTHTCPPCPAPEAAGGPSVF LFPPKPKDTLMISRTPEVTCVVVDVSHEDPEVKFNWYVDGV EVHNAKTKPREEQYNSTYRVVSVLTVLHQDWLNGKEYKC KVSNKALGAPIEKTISKAKGQPREPQVYVYPPSREEMTKNQ VSLTCLVKGFYPSDIAVEWESNGQPENNYKTTPPVLDSDGS FALVSKLTVDKSRWQQGNVFSCSVMHEALHNHYTQKSLSL SPG(K) | 179 |
| N65S_hSD15 + 38B2 HC (T350V/ L351Y/ F405A/ Y407V) LALAPG (comprises 24H9 VH (SEQ ID NO: 24), linker 1 (SEQ ID NO: 215), and linker 2 (SEQ ID N: 216)) | ITCPPPMSVEHADIWVKSYSLYSRERYICNSGFKRKAGTS SLTECVLNKATNVAHWTTPSLKCIRDPALVHQRPAPPSG GSGGGGSGGGGSGGGGSLQNWVNVISDLKKIEDLIQSMHI DATLYTESDVHPSCKVTAMKCFLLELQVISLESGDASIHD TVESLIILANNSLSSNGNVTESGCKECEELEEKNIKEFLQS FVHIVQMFINTSGGGGSGGGGSGGGGSGGGGSGGGGSGG GGS*EVQLLESGGGLVQPGGSLRLSCAASGFTFSSYWMSWVRQA PGKGLEWVSAISGSGGSTYYADSVKGRFTISRDNSKNTLYLQMN SLRAEDTAVYYCASSPLQWVDVWGQGTTVTVSS*ASTKGPSVFP LAPSSKSTSGGTAALGCLVKDYFPEPVTVSWNSGALTSGVH TFPAVLQSSGLYSLSSVVTVPSSSLGTQTYICNVNHKPSNTK VDKRVEPKSCDKTHTCPPCPAPEAAGGPSVFLFPPKPKDTL MISRTPEVTCVVVDVSHEDPEVKFNWYVDGVEVHNAKTKP REEQYNSTYRVVSVLTVLHQDWLNGKEYKCKVSNKALGA PIEKTISKAKGQPREPQVYVYPPSREEMTKNQVSLTCLVKGF YPSDIAVEWESNGQPENNYKTTPPVLDSDGSFALVSKLTVD KSRWQQGNVFSCSVMHEALHNHYTQKSLSLSPG(K) | 180 |

TABLE 25-continued

Sequences of the disclosure

| Identifier | Sequence | SEQ ID NO |
|---|---|---|
| | Fusions of m3A7 heavy chains with SD15 | |
| mSD15 + m3A7 mHc LALAPG (comprises R3A9 VH (SEQ ID NO: 142), linker 1 (SEQ ID NO: 215), and linker 2 (SEQ ID N: 216)) | ITCPPPVSIEHADIRVKNYSVNSRERYVCNSGFKRKAGTST LIECVINKNTNVAHWTTPSLKCIRDPALVHQRPAPPSGGS GGGGSGGGSGGGGSLQNWIDVRYDLEKIESLIQSIHIDTT LYTDSDFHPSCKVTAMNCFLLELQVILHEYSNMTLNETV RNVLYLANSTLSSNKNVAESGCKECEELEEKTFTEFLQSF IRIVQMFINTSGGGGSGGGGSGGGGSGGGGSGGGGSGGGG SQVQLVQSGAEVKKPGASVKVSCKASGHTFTSYYIHWVRQ APGQGLEWMGIINPSGGSTSYAQKFQGRVTMTRDTSTSTVY MELSSLRSEDTAVYYCARDRAYGGAGDYWGQGTLVTVSSA KTTAPSVYPLAPVCGDTTGSSVTLGCLVKGYFPEPVTLTWNS GSLSSGVHTFPAVLQSDLYTLSSSVTVTSSTWPSQSITCNVAH PASSTKVDKKIEPRGPTIKPCPPCKCPAPNAAGGPSVFIFPPKI KDVLMISLSPIVTCVVVDVSEDDPDVQISWFVNNVEVHTAQ TQTHREDYNSTLRVVSALPIQHQDWMSGKEFKCKVNNKDL GAPIERTISKPKGSVRAPQVYVLPPPEEEMTKKQVTLTCMVT DFMPEDIYVEWTNNGKTELNYKNTEPVLDSDGSYFMYSKL RVEKKNWVERNSYSCSVVHEGLHNHHTTKSFSRTPG(K) | 181 |
| mSD15 + m3A7 mHc (T366L/ K392L/ T394W) LALAPG (comprises R3A9 VH (SEQ ID NO: 142), linker 1 (SEQ ID NO: 215), and linker 2 (SEQ ID N: 216)) | ITCPPPVSIEHADIRVKNYSVNSRERYVCNSGFKRKAGTST LIECVINKNTNVAHWTTPSLKCIRDPALVHQRPAPPSGGS GGGGSGGGSGGGGSLQNWIDVRYDLEKIESLIQSIHIDTT LYTDSDFHPSCKVTAMNCFLLELQVILHEYSNMTLNETV RNVLYLANSTLSSNKNVAESGCKECEELEEKTFTEFLQSF IRIVQMFINTSGGGGSGGGGSGGGGSGGGGSGGGGSGGGG SQVQLVQSGAEVKKPGASVKVSCKASGHTFTSYYIHWVRQ APGQGLEWMGIINPSGGSTSYAQKFQGRVTMTRDTSTSTVY MELSSLRSEDTAVYYCARDRAYGGAGDYWGQGTLVTVSS AKTTAPSVYPLAPVCGDTTGSSVTLGCLVKGYFPEPVTLTW NSGSLSSGVHTFPAVLQSDLYTLSSSVTVTSSTWPSQSITCN VAHPASSTKVDKKIEPRGPTIKPCPPCKCPAPNAAGGPSVFIF PPKIKDVLMISLSPIVTCVVVDVSEDDPDVQISWFVNNVEVH TAQTQTHREDYNSTLRVVSALPIQHQDWMSGKEFKCKVNN KDLGAPIERTISKPKGSVRAPQVYVLPPPEEEMTKKQVTLLC MVTDFMPEDIYVEWTNNGKTELNYLNWEPVLDSDGSYFM YSKLRVEKKNWVERNSYSCSVVHEGLHNHHTTKSFSRTPG (K) | 182 |
| m3A7 mHc LALPG + mSD15 (comprises R3A9 VH (SEQ ID NO: 142) and linker 1 (SEQ ID NO: 215)) | QVQLVQSGAEVKKPGASVKVSCKASGHTFTSYYIHWVRQA PGQGLEWMGIINPSGGSTSYAQKFQGRVTMTRDTSTSTVYM ELSSLRSEDTAVYYCARDRAYGGAGDYWGQGTLVTVSSAK TTAPSVYPLAPVCGDTTGSSVTLGCLVKGYFPEPVTLTWNS GSLSSGVHTFPAVLQSDLYTLSSSVTVTSSTWPSQSITCNVA HPASSTKVDKKIEPRGPTIKPCPPCKCPAPNAAGGPSVFIFPP KIKDVLMISLSPIVTCVVVDVSEDDPDVQISWFVNNVEVHT AQTQTHREDYNSTLRVVSALPIQHQDWMSGKEFKCKVNNK DLGAPIERTISKPKGSVRAPQVYVLPPPEEEMTKKQVTLTCM VTDFMPEDIYVEWTNNGKTELNYKNTEPVLDSDGSYFMYS KLRVEKKNWVERNSYSCSVVHEGLHNHHTTKSFSRTPGSC PPPVSIEHADIRVKNYSVNSRERYVCNSGFKRKAGTSTLI ECVINKNTNVAHWTTPSLKCIRDPALVHQRPAPPSGGSG GGGSGGGSGGGGSLQNWIDVRYDLEKIESLIQSIHIDTTL YTDSDFHPSCKVTAMNCFLLELQVILHEYSNMTLNETVR NVLYLANSTLSSNKNVAESGCKECEELEEKTFTEFLQSFI RIVQMFINTS | 183 |

TABLE 25-continued

Sequences of the disclosure

| Identifier | Sequence | SEQ ID NO |
|---|---|---|
| m3A7 mHC (T366L/ K392L/ T394W) + mSD15 LALAPG (comprises R3A9 VH (SEQ ID NO: 142) and linker 1 (SEQ ID NO: 215)) | QVQLVQSGAEVKKPGASVKVSCKASGHTFTSYYIHWVRQA PGQGLEWMGIINPSGGSTSYAQKFQGRVTMTRDTSTSTVYM ELSSLRSEDTAVYYCARDRAYGGAGDYWGQGTLVTVSSAK TTAPSVYPLAPVCGDTTGSSVTLGCLVKGYFPEPVTLTWNS GSLSSGVHTFPAVLQSDLYTLSSSVTVTSSTWPSQSITCNVA HPASSTKVDKKIEPRGPTIKPCPPCKCPAPNAAGGPSVFIFPP KIKDVLMISLSPIVTCVVVDVSEDDPDVQISWFVNNVEVHT AQTQTHREDYNSTLRVVSALPIQHQDWMSGKEFKCKVNNK DLGAPIERTISKPKGSVRAPQVYVLPPPEEEMTKKQVTLLCM VTDFMPEDIYVEWTNNGKTELNYLNWEPVLDSDGSYFMYS KLRVEKKNWVERNSYSCSVVHEGLHNHHTTKSFSRTPGSC PPPVSIEHADIRVKNYSVNSRERYVCNSGFKRKAGTSTLI ECVINKNTNVAHWTTPSLKCIRDPALVHQRPAPPSGGSG GGGSGGGSGGGGSLQNWIDVRYDLEKIESLIQSIHIDTTL YTDSDFHPSCKVTAMNCFLLELQVILHEYSNMTLNETVR NVLYLANSTLSSNKNVAESGCKECEELEEKTFTEFLQSFI RIVQMFINTS | 184 |

Heavy and light chains of control antibody DP47 and fusions of DP47 heavy chains with SD15

| Identifier | Sequence | SEQ ID NO |
|---|---|---|
| DP47 mHC (L351Y/ F405A/ Y407V) LALAPG Residues 1-115: DP47 VH | EVQLLESGGGLVQPGGSLRLSCAASGFTFSSYAMSWVRQAP GKGLEWVSAISGSGGSTYYADSVKGRFTISRDNSKNTLYLQ MNSLRAEDTAVYYCAKGSGFDYWGQGTLVTVSSAKTTAPS VYPLAPVCGDTTGSSVTLGCLVKGYFPEPVTLTWNSGSLSS GVHTFPAVLQSDLYTLSSSVTVTSSTWPSQSITCNVAHPASS TKVDKKIEPRGPTIKPCPPCKCPAPNAAGGPSVFIFPPKIKDV LMISLSPIVTCVVVDVSEDDPDVQISWFVNNVEVHTAQTQT HREDYNSTLRVVSALPIQHQDWMSGKEFKCKVNNKDLGAP IERTISKPKGSVRAPQVYVYPPPEEEMTKKQVTLLCMVTDF MPEDIYVEWTNNGKTELNYKNTEPVLDSDGSYAMVSKLRV EKKNWVERNSYSCSVVHEGLHNHHTTKSFSRTPG(K) | 185 |
| DP47 mLC Residues 1-108: DP47 VL | EIVLTQSPGTLSLSPGERATLSCRASQSVSSSYLAWYQQKPG QAPRLLIYGASSRATGIPDRFSGSGSGTDFTLTISRLEPEDFA VYYCQQYGSSPLTFGQGTKVEIKRADAAPTVSIFPPSSEQLT SGGASVVCFLNNFYPKDINVKWKIDGSERQNGVLNSWTDQ DSKDSTYSMSSTLTLTKDEYERHNSYTCEATHKTSTSPIVKS FNRNEC | 186 |
| mSD15 + DP47 mHC LALAPG (comprises DP47 VH (see SEQ ID NO: 185), linker 1 (SEQ ID NO: 215), and linker 2 (SEQ ID N: 216)) | ITCPPPVSIEHADIRVKNYSVNSRERYVCNSGFKRKAGTS TLIECVINKNTNVAHWTTPSLKCIRDPALVHQRPAPPSG GSGGGGSGGGSGGGGSLQNWIDVRYDLEKIESLIQSIHID TTLYTDSDFHPSCKVTAMNCFLLELQVILHEYSNMTLNE TVRNVLYLANSTLSSNKNVAESGCKECEELEEKTFTEFL QSFIRIVQMFINTSGGGGSGGGGSGGGGSGGGGSGGGGSG GGGSEVQLLESGGGLVQPGGSLRLSCAASGFTFSSYAMSWV RQAPGKGLEWVSAISGSGGSTYYADSVKGRFTISRDNSKNT LYLQMNSLRAEDTAVYYCAKGSGFDYWGQGTLVTVSSAK TTAPSVYPLAPVCGDTTGSSVTLGCLVKGYFPEPVTLTWNS GSLSSGVHTFPAVLQSDLYTLSSSVTVTSSTWPSQSITCNVA HPASSTKVDKKIEPRGPTIKPCPPCKCPAPNAAGGPSVFIFPP KIKDVLMISLSPIVTCVVVDVSEDDPDVQISWFVNNVEVHT AQTQTHREDYNSTLRVVSALPIQHQDWMSGKEFKCKVNNK DLGAPIERTISKPKGSVRAPQVYVLPPPEEEMTKKQVTLTCM VTDFMPEDIYVEWTNNGKTELNYKNTEPVLDSDGSYFMYS KLRVEKKNWVERNSYSCSVVHEGLHNHHTTKSFSRTPG(K) | 187 |
| mSD15 + DP47 mHC (T366L/ K392L/ T394W) LALAPG (comprises DP47 VH (see SEQ ID NO: 185), linker 1 (SEQ ID NO: 215), and linker 2 (SEQ ID N: 216)) | ITCPPPVSIEHADIRVKNYSVNSRERYVCNSGFKRKAGTST LIECVINKNTNVAHWTTPSLKCIRDPALVHQRPAPPSGGS GGGGSGGGSGGGGSLQNWIDVRYDLEKIESLIQSIHIDTT LYTDSDFHPSCKVTAMNCFLLELQVILHEYSNMTLNETV RNVLYLANSTLSSNKNVAESGCKECEELEEKTFTEFLQSF IRIVQMFINTSGGGGSGGGGSGGGGSGGGGSGGGGSGGGG SEVQLLESGGGLVQPGGSLRLSCAASGFTFSSYAMSWVRQA PGKGLEWVSAISGSGGSTYYADSVKGRFTISRDNSKNTLYL QMNSLRAEDTAVYYCAKGSGFDYWGQGTLVTVSSAKTTA PSVYPLAPVCGDTTGSSVTLGCLVKGYFPEPVTLTWNSGSL SSGVHTFPAVLQSDLYTLSSSVTVTSSTWPSQSITCNVAHPA SSTKVDKKIEPRGPTIKPCPPCKCPAPNAAGGPSVFIFPPKIKD VLMISLSPIVTCVVVDVSEDDPDVQISWFVNNVEVHTAQTQ THREDYNSTLRVVSALPIQHQDWMSGKEFKCKVNNKDLGA PIERTISKPKGSVRAPQVYVLPPPEEEMTKKQVTLLCMVTDF | 188 |

TABLE 25-continued

Sequences of the disclosure

| Identifier | Sequence | SEQ ID NO |
|---|---|---|
| | MPEDIYVEWTNNGKTELNY*LNW*EPVLDSDGSYFMYSKLRV EKKNWVERNSYSCSVVHEG*LHN*HHTTKSFSRTPG(K) | |
| DP47 mHc LALAPG + mSD15 (comprises DP47 VH (see SEQ ID NO: 185) and linker 1 (SEQ ID NO: 215)) | EVQLLESGGGLVQPGGSLRLSCAASGFTFSSYAMSWVRQAP GKGLEWVSAISGSGGSTYYADSVKGRFTISRDNSKNTLYLQ MNSLRAEDTAVYYCAKGSGFDYWGQGTLVTVSSAKTTAPS VYPLAPVCGDTTGSSVTLGCLVKGYFPEPVTLTWNSGSLSS GVHTFPAVLQSDLYTLSSSVTVTSSTWPSQSITCNVAHPASS TKVDKKIEPRGPTIKPCPPCKCPAPN*AA*GGPSVFIFPPKIKDV LMISLSPIVTCVVVDVSEDDPDVQIS*WF*VNNVEVHTAQTQT HREDYNSTLRVVSALPIQHQDWMSGKEFKCKVNNKDLGAP IERTISKPKGSVRAPQVYVLPPPEEEMTKKQVTLTCM*V*TDF MPEDIYVEWTNNGKTELNYKNTEPVLDSDGSYFMYSKLRV EKKNWVERNSYSCSVVHEGLHNHHTTKSFSRTPGSCPPPVS IEHADIRVKNYSVNSRERYVCNSGFKRKAGTSTLIECVIN KNTNVAHWTTPSLKCIRDPALVHQRPAPPSGGSGGGGS GGGSGGGGSLQNWIDVRYDLEKIESLIQSIHIDTTLYTDS DFHPSCKVTAMNCFLLELQVILHEYSNMTLNETVRNVLY LANSTLSSNKNVAESGCKECEELEEKTFTEFLQSFIRIVQ MFINTS | 189 |
| DP47 mHC (T366L/ K392L/ T394W) LALAPG + mSD15 (comprises DP47 VH (see SEQ ID NO: 185) and linker 1 (SEQ ID NO: 215)) | EVQLLESGGGLVQPGGSLRLSCAASGFTFSSYAMSWVRQAP GKGLEWVSAISGSGGSTYYADSVKGRFTISRDNSKNTLYLQ MNSLRAEDTAVYYCAKGSGFDYWGQGTLVTVSSAKTTAPS VYPLAPVCGDTTGSSVTLGCLVKGYFPEPVTLTWNSGSLSS GVHTFPAVLQSDLYTLSSSVTVTSSTWPSQSITCNVAHPASS TKVDKKIEPRGPTIKPCPPCKCPAPN*AA*GGPSVFIFPPKIKDV LMISLSPIVTCVVVDVSEDDPDVQIS*WF*VNNVEVHTAQTQT HREDYNSTLRVVSALPIQHQDWMSGKEFKCKVNNKDLGAP IERTISKPKGSVRAPQVYVLPPPEEEMTKKQVTL*L*CM*V*TDF MPEDIYVEWTNNGKTELNY*LNW*EPVLDSDGSYFM*Y*SKLRV EKKNWVERNSYSCSVVHEG*LHN*HHTTKSFSRTPGSCPPPVS IEHADIRVKNYSVNSRERYVCNSGFKRKAGTSTLIECVIN KNTNVAHWTTPSLKCIRDPALVHQRPAPPSGGSGGGGSG GGSGGGGSLQNWIDVRYDLEKIESLIQSIHIDTTLYTDSDF HPSCKVTAMNCFLLELQVILHEYSNMTLNETVRNVLYLA NSTLSSNKNVAESGCKECEELEEKTFTEFLQSFIRIVQMFI NTS | 190 |
| DP47 HC (T350V/ T366L/ K392L/ T394W) LALAPG (comprises DP47 VH (see SEQ ID NO: 185)) | EVQLLESGGGLVQPGGSLRLSCAASGFTFSSYAMSWVRQAP GKGLEWVSAISGSGGSTYYADSVKGRFTISRDNSKNTLYLQ MNSLRAEDTAVYYCAKGSGFDYWGQGTLVTVSSASTKGPS VFPLAPSSKSTSGGTAALGCLVKDYFPEPVTVSWNSGALTS GVHTFPAVLQSSGLYSLSSVVTVPSSSLGTQTYICNVNHKPS NTKVDKRVEPKSCDKTHTCPPCPAPE*AA*GGPSVFLFPPKPK DTLMISRTPEVTCVVVDVSHEDPEVK*FN*WYVDGVEVHNAK TKPREEQYNSTYRVVSVLTVLHQDWLNGKEYKCKVSNKAL GAPIEKTISKAKGQPREPQVY*VL*PPSREEMTKNQVSL*L*CLVK GFYPSDIAVEWESNGQPENNY*LTW*PPVLDSDGSFFLYSKLT VDKSRWQQGNVFSCSVMHEAL*HN*HYTQKSLSLSPG(K) | 191 |
| DP47 LC Residues 1-108: DP47 VL | EIVLTQSPGTLSLSPGERATLSCRASQSVSSSYLAWYQQKPG QAPRLLIYGASSRATGIPDRFSGSGSGTDFTLTISRLEPEDFA VYYCQQYGSSPLTFGQGTKVEIKRTVAAPSVFIFPPSDEQLK SGTASVVCLLNNFYPREAKVQWKVDNALQSGNSQESVTEQ DSKDSTYSLSSTLTLSKADYEKHKVYACEVTHQGLSSPVTK SFNRGEC | 192 |
| hSD15 + DP47 HC LALPG (comprises DP47 VH (see SEQ ID NO: 185), linker 1 (SEQ ID NO: 215), and linker 2 (SEQ ID N: 216)) | ITCPPPMSVEHADIWVKSYSLYSRERYICNSGFKRKAGTS SLTECVLNKATNVAHWTTPSLKCIRDPALVHQRPAPPSG GSGGGGSGGGGSGGGGSLQNWVNVISDLKKIEDLIQSMHI DATLYTESDVHPSCKVTAMKCFLLELQVISLESGDASIHD TVENLIILANNSLSSNGNVTESGCKECEELEEKNIKEFLQS FVHIVQMFINTSGGGGSGGGGSGGGGSGGGGSGGGGSGG GGSEVQLLESGGGLVQPGGSLRLSCAASGFTFSSYAMSWVR QAPGKGLEWVSAISGSGGSTYYADSVKGRFTISRDNSKNTL YLQMNSLRAEDTAVYYCAKGSGFDYWGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNV NHKPSNTKVDKRVEPKSCDKTHTCPPCPAPE*AA*GGPSVFLFPP KPKDTLMISRTPEVTCVVVDVSHEDPEVKF*N*WYVDGVEVH NAKTKPREEQYNSTYRVVSVLTVLHQDWL*N*GKEYKCKVS | 193 |

TABLE 25-continued

Sequences of the disclosure

| Identifier | Sequence | SEQ ID NO |
|---|---|---|
| | NKALGAPIEKTISKAKGQPREPQVYTLPPSREEMTKNQVSLT<br>CLVKGFYPSDIAVEWESNGQPENNYKTTPPVLDSDGSFFLY<br>SKLTVDKSRWQQGNVFSCSVMHEALHNHYTQKSLSLSPG(K) | |
| hSD15 +<br>DP47 HC<br>(T350V/<br>L351Y/<br>F405A/<br>Y407V)<br>LALAPG<br>(comprises<br>DP47 VH (see<br>SEQ ID NO:<br>185), linker<br>1 (SEQ ID<br>NO: 215), and<br>linker 2 (SEQ<br>ID N: 216)) | ITCPPPMSVEHADIWVKSYSLYSRERYICNSGFKRKAGTS<br>SLTECVLNKATNVAHWTTPSLKCIRDPALVHQRPAPPSG<br>GSGGGGSGGGSGGGGSLQNWVNVISDLKKIEDLIQSMHI<br>DATLYTESDVHPSCKVTAMKCFLLELQVISLESGDASIHD<br>TVENLIILANNSLSSNGNVTESGCKECEELEEKNIKEFLQS<br>FVHIVQMFINTSGGGGSGGGGSGGGGSGGGGSGGGGSGG<br>GGSEVQLLESGGGLVQPGGSLRLSCAASGFTFSSYAMSWVR<br>QAPGKGLEWVSAISGSGGSTYYADSVKGRFTISRDNSKNTL<br>YLQMNSLRAEDTAVYYCAKGSGFDYWGQGTLVTVSSAST<br>KGPSVFPLAPSSKSTSGGTAALGCLVKDYFPEPVTVSWNSG<br>ALTSGVHTFPAVLQSSGLYSLSSVVTVPSSSLGTQTYICNVN<br>HKPSNTKVDKRVEPKSCDKTHTCPPCPAPEAAGGPSVFLFPP<br>KPKDTLMISRTPEVTCVVVDVSHEDPEVKFNWYVDGVEVH<br>NAKTKPREEQYNSTYRVVSVLTVLHQDWLNGKEYKCKVS<br>NKALGAPIEKTISKAKGQPREPQVYVYPPSREEMTKNQVSLT<br>CLVKGFYPSDIAVEWESNGQPENNYKTTPPVLDSDGSFALV<br>SKLTVDKSRWQQGNVFSCSVMHEALHNHYTQKSLSLSPG(K) | 194 |
| DP47 HC +<br>LALAPG<br>hSD15<br>(comprises<br>DP47 VH (see<br>SEQ ID<br>NO: 185) and<br>linker 1 (SEQ<br>ID NO: 215)) | EVQLLESGGGLVQPGGSLRLSCAASGFTFSSYAMSWVRQAP<br>GKGLEWVSAISGSGGSTYYADSVKGRFTISRDNSKNTLYLQ<br>MNSLRAEDTAVYYCAKGSGFDYWGQGTLVTVSSASTKGPS<br>VFPLAPSSKSTSGGTAALGCLVKDYFPEPVTVSWNSGALTS<br>GVHTFPAVLQSSGLYSLSSVVTVPSSSLGTQTYICNVNHKPS<br>NTKVDKRVEPKSCDKTHTCPPCPAPEAAGGPSVFLFPPKPK<br>DTLMISRTPEVTCVVVDVSHEDPEVKFNWYVDGVEVHNAK<br>TKPREEQYNSTYRVVSVLTVLHQDWLNGKEYKCKVSNKAL<br>GAPIEKTISKAKGQPREPQVYTLPPSREEMTKNQVSLTCLVK<br>GFYPSDIAVEWESNGQPENNYKTTPPVLDSDGSFFLYSKLTV<br>DKSRWQQGNVFSCSVMHEALHNHYTQKSLSLSPGSCPPPM<br>SVEHADIWVKSYSLYSRERYICNSGFKRKAGTSSLTECVL<br>NKATNVAHWTTPSLKCIRDPALVHQRPAPPSGGSGGGG<br>SGGGSGGGGSLQNWVNVISDLKKIEDLIQSMHIDATLYT<br>ESDVHPSCKVTAMKCFLLELQVISLESGDASIHDTVENLII<br>LANNSLSSNGNVTESGCKECEELEEKNIKEFLQSFVHIVQ<br>MFINTS | 195 |
| DP47 HC<br>(T350V/<br>L351Y/<br>F405A/<br>Y407V)<br>LALAPG +<br>hSD15<br>(comprises<br>DP47 VH (see<br>SEQ ID<br>NO: 185) and<br>linker 1 (SEQ<br>ID NO: 215) | EVQLLESGGGLVQPGGSLRLSCAASGFTFSSYAMSWVRQAP<br>GKGLEWVSAISGSGGSTYYADSVKGRFTISRDNSKNTLYLQ<br>MNSLRAEDTAVYYCAKGSGFDYWGQGTLVTVSSASTKGPS<br>VFPLAPSSKSTSGGTAALGCLVKDYFPEPVTVSWNSGALTS<br>GVHTFPAVLQSSGLYSLSSVVTVPSSSLGTQTYICNVNHKPS<br>NTKVDKRVEPKSCDKTHTCPPCPAPEAAGGPSVFLFPPKPK<br>DTLMISRTPEVTCVVVDVSHEDPEVKFNWYVDGVEVHNAK<br>TKPREEQYNSTYRVVSVLTVLHQDWLNGKEYKCKVSNKAL<br>GAPIEKTISKAKGQPREPQVYVYPPSREEMTKNQVSLTCLVK<br>GFYPSDIAVEWESNGQPENNYKTTPPVLDSDGSFALVSKLT<br>VDKSRWQQGNVFSCSVMHEALHNHYTQKSLSLSPGSCPPP<br>MSVEHADIWVKSYSLYSRERYICNSGFKRKAGTSSLTEC<br>VLNKATNVAHWTTPSLKCIRDPALVHQRPAPPSGGSGG<br>GGSGGGSGGGGSLQNWVNVISDLKKIEDLIQSMHIDATL<br>YTESDVHPSCKVTAMKCFLLELQVISLESGDASIHDTVEN<br>LIILANNSLSSNGNVTESGCKECEELEEKNIKEFLQSFVHI<br>VQMFINTS | 196 |

TABLE 25-continued

Sequences of the disclosure

| Identifier | Sequence | SEQ ID NO |
|---|---|---|
| N65A-hSD15 + DP47 HC (T350V/ L351Y/ F405A/ Y407V) LALAPG (comprises DP47 VH (see SEQ ID NO: 185), linker 1 (SEQ ID NO: 215), and linker 2 (SEQ ID N: 216)) | ITCPPPMSVEHADIWVKSYSLYSRERYICNSGFKRKAGTS SLTECVLNKATNVAHWTTPSLKCIRDPALVHQRPAPPSG GSGGGGSGGGSGGGGSLQNWVNVISDLKKIEDLIQSMHI DATLYTESDVHPSCKVTAMKCFLLELQVISLESGDASIHD TVEALIILANNSLSSNGNVTESGCKECEELEEKNIKEFLQS FVHIVQMFINTSGGGGSGGGGSGGGGSGGGGSGGGGSGG GGSEVQLLESGGGLVQPGGSLRLSCAASGFTFSSYAMSWVRQA PGKGLEWVSAISGSGGSTYYADSVKGRFTISRDNSKNTLYLQMN SLRAEDTAVYYCAKGSGFDYWGQGTLVTVSSASTKGPSVFPLA PSSKSTSGGTAALGCLVKDYFPEPVTVSWNSGALTSGVHTF PAVLQSSGLYSLSSVVTVPSSSLGTQTYICNVNHKPSNTKVD KRVEPKSCDKTHTCPPCPAPEAAGGPSVFLFPPKPKDTLMIS RTPEVTCVVVDVSHEDPEVKFNWYVDGVEVHNAKTKPREE QYNSTYRVVSVLTVLHQDWLNGKEYKCKVSNKALGAPIEK TISKAKGQPREPQVYVYPPSREEMTKNQVSLTCLVKGFYPS DIAVEWESNGQPENNYKTTPPVLDSDGSFALVSKLTVDKSR WQQGNVFSCSVMHEALHNHYTQKSLSLSPG(K) | 197 |
| N65D-hSD15 + DP47 HC (T350V/ L351Y/ F405A/Y407V) LALAPG (comprises DP47 VH (see SEQ ID NO: 185), linker 1 (SEQ ID NO: 215), and linker 2 (SEQ ID N: 216)) | ITCPPPMSVEHADIWVKSYSLYSRERYICNSGFKRKAGTS SLTECVLNKATNVAHWTTPSLKCIRDPALVHQRPAPPSG GSGGGGSGGGSGGGGSLQNWVNVISDLKKIEDLIQSMHI DATLYTESDVHPSCKVTAMKCFLLELQVISLESGDASIHD TVEDLIILANNSLSSNGNVTESGCKECEELEEKNIKEFLQS FVHIVQMFINTSGGGGSGGGGSGGGGSGGGGSGGGGSGGGGSGG GGSEVQLLESGGGLVQPGGSLRLSCAASGFTFSSYAMSWVR QAPGKGLEWVSAISGSGGSTYYADSVKGRFTISRDNSKNTL YLQMNSLRAEDTAVYYCAKGSGFDYWGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPEAAGGPSVFLFPP KPKDTLMISRTPEVTCVVVDVSHEDPEVKFNWYVDGVEVH NAKTKPREEQYNSTYRVVSVLTVLHQDWLNGKEYKCKVS NKALGAPIEKTISKAKGQPREPQVYVYPPSREEMTKNQVSLT CLVKGFYPSDIAVEWESNGQPENNYKTTPPVLDSDGSFALV SKLTVDKSRWQQGNVFSCSVMHEALHNHYTQKSLSLSPG(K) | 198 |
| N65S-hSD15 + DP47 HC (T350V/ L351Y/ F405A/ Y407V) LALAPG (comprises DP47 VH (see SEQ ID NO: 185), linker 1 (SEQ ID NO: 215) and linker 2 (SEQ ID N: 216)) | ITCPPPMSVEHADIWVKSYSLYSRERYICNSGFKRKAGTS SLTECVLNKATNVAHWTTPSLKCIRDPALVHQRPAPPSG GSGGGGSGGGSGGGGSLQNWVNVISDLKKIEDLIQSMHI DATLYTESDVHPSCKVTAMKCFLLELQVISLESGDASIHD TVESLIILANNSLSSNGNVTESGCKECEELEEKNIKEFLQS FVHIVQMFINTSGGGGSGGGGSGGGGSGGGGSGGGGSGGGGSGG GGSEVQLLESGGGLVQPGGSLRLSCAASGFTFSSYAMSWVR QAPGKGLEWVSAISGSGGSTYYADSVKGRFTISRDNSKNTL YLQMNSLRAEDTAVYYCAKGSGFDYWGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPEAAGGPSVFLFPP KPKDTLMISRTPEVTCVVVDVSHEDPEVKFNWYVDGVEVH NAKTKPREEQYNSTYRVVSVLTVLHQDWLNGKEYKCKVS NKALGAPIEKTISKAKGQPREPQVYVYPPSREEMTKNQVSLT CLVKGFYPSDIAVEWESNGQPENNYKTTPPVLDSDGSFALV SKLTVDKSRWQQGNVFSCSVMHEALHNHYTQKSLSLSPG(K) | 199 |

Heavy and light chains of anti-PD-L1 antibody D7A8 and fusions of D7A8 heavy chains with SD15

| Identifier | Sequence | SEQ ID NO |
|---|---|---|
| D7A8 VH | EVQLLESGGGLVQPGGSLRLSCAASGFTFSAYRMFWVRQA PGKGLEWVSSIYPSGGITFYADSVKGRFTISRDNSKNTLYLQ MNSLRAEDTAIYYCARIKLGTVTTVDYWGQGTLVTVSS | 200 |
| D7A8 full length HC (comprises D7A8 VH (SEQ ID NO: 200)) | EVQLLESGGGLVQPGGSLRLSCAASGFTFSAYRMFWVRQA PGKGLEWVSSIYPSGGITFYADSVKGRFTISRDNSKNTLYLQ MNSLRAEDTAIYYCARIKLGTVTTVDYWGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPELLGGPSVFLFPP KPKDTLMISRTPEVTCVVVDVSHEDPEVKFNWYVDGVEVH NAKTKPREEQYNSTYRVVSVLTVLHQDWLNGKEYKCKVS NKALPAPIEKTISKAKGQPREPQVYTLPPSREEMTKNQVSLT CLVKGFYPSDIAVEWESNGQPENNYKTTPPVLDSDGSFFLY SKLTVDKSRWQQGNVFSCSVMHEALHNHYTQKSLSLSPG(K) | 201 |

TABLE 25-continued

Sequences of the disclosure

| Identifier | Sequence | SEQ ID NO |
|---|---|---|
| D7A8 HC (S354C/ T366W) LALA (comprises D7A8 VH (SEQ ID NO: 200)) | EVQLLESGGGLVQPGGSLRLSCAASGFTFSAYRMFWVRQA PGKGLEWVSSIYPSGGITFYADSVKGRFTISRDNSKNTLYLQ MNSLRAEDTAIYYCARIKLGTVTTVDYWGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPEA*AGGPSVFLFPP KPKDTLMISRTPEVTCVVVDVSHEDPEVKF*N*YVDGVEVH NAKTKPREEQYNSTYRVVSVLTVLHQDWLNGKEYKCKVS NKALPAPIEKTISKAKGQPREPQVYTLPP*C*REEMTKNQVSL *W*CLVKGFYPSDIAVEWESNGQPENNYKTTPPVLDSDGSFFL *Y*SKLTVDKSRWQQGNVFSCSVMHEALHNHYTQKSLSLSPG (K) | 202 |
| D7A8 HC (T350V/ T366L/ K392L/ T394W) LALA (comprises D7A8 VH SEQ ID NO: 200)) | EVQLLESGGGLVQPGGSLRLSCAASGFTFSAYRMFWVRQA PGKGLEWVSSIYPSGGITFYADSVKGRFTISRDNSKNTLYLQ MNSLRAEDTAIYYCARIKLGTVTTVDYWGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPEA*AGGPSVFLFPP KPKDTLMISRTPEVTCVVVDVSHEDPEVKF*N*YVDGVEVH NAKTKPREEQYNSTYRVVSVLTVLHQDWLNGKEYKCKVS NKALPAPIEKTISKAKGQPREPQVY*V*LPPSREEMTKNQVSL*L* CLVKGFYPSDIAVEWESNGQPENNY*LTW*PVLDSDGSFFL*Y* SKLTVDKSRWQQGNVFSCSVMHEAL*HN*HYTQKSLSLSPG(K) | 203 |
| D7A8 VL | QSALTQPASVSGSPGQSITISCTGTSSDVGAYNYVSWYQQHP GKAPKLMIYDVSNRPSGVSNRFSGSKSGNTASLTISGLQAED EADYYCSSYTSSSTRVFGTGTKVTVLGQP | 204 |
| D7A8 full length LC (comprises D7A8 VL (SEQ ID NO: 204)) | QSALTQPASVSGSPGQSITISCTGTSSDVGAYNYVSWYQQHP GKAPKLMIYDVSNRPSGVSNRFSGSKSGNTASLTISGLQAED EADYYCSSYTSSSTRVFGTGTKVTVLGQPKANPTVTLFPPSS EELQANKATLVCLISDFYPGAVTVAWKADGSPVKAGVETT KPSKQSNNKYAASSYLSLTPEQWKSHRSYSCQVTHEGSTVE KTVAPTEC(S) | 205 |
| hSD15 + D7A8 HC LALA (comprises D7A8 VH (SEQ ID NO: 200), linker 1 (SEQ ID NO: 215), and the linker of SEQ ID N: 244) | ITCPPPMSVEHADIWVKSYSLYSRERYICNSGFKRKAGTS SLTECVLNKATNVAHWTTPSLKCIRDPALVHQRPAPPSG GSGGGGSGGGSGGGGSLQNWVNVISDLKKIEDLIQSMHI DATLYTESDVHPSCKVTAMKCFLLELQVISLESGDASIHD TVENLIILANNSLSSNGNVTESGCKECEELEEKNIKEFLQS FVHIVQMFINTSGGGGSGGGGSGGGGSGGGGSEVQLLESG GGLVQPGGSLRLSCAASGFTFSAYRMFWVRQAPGKGLEWV SSIYPSGGITFYADSVKGRFTISRDNSKNTLYLQMNSLRAED TAIYYCARIKLGTVTTVDYWGQGTLVTVSSASTKGPSVFPL APSSKSTSGGTAALGCLVKDYFPEPVTVSWNSGALTSGVHT FPAVLQSSGLYSLSSVVTVPSSSLGTQTYICNVNHKPSNTKV DKRVEPKSCDKTHTCPPCPAPEA*AGGPSVFLFPPKPKDTLMI SRTPEVTCVVVDVSHEDPEVKF*N*WYVDGVEVHNAKTKPRE EQYNSTYRVVSVLTVLHQDWLNGKEYKCKVSNKALPAPIE KTISKAKGQPREPQVYTLPPSREEMTKNQVSLTCLVKGFYPS DIAVEWESNGQPENNYKTTPPVLDSDGSFFLYSKLTVDKSR WQQGNVFSCSVMHEALHNHYTQKSLSLSPG(K) | 206 |
| hSD15 + D7A8HC (Y349C/ T366S/ L368A/ Y407V) LALA (comprises D7A8 VH (SEQ ID NO: 200), linker 1 (SEQ ID NO: 215), and the linker of SEQ ID N: 244)) | ITCPPPMSVEHADIWVKSYSLYSRERYICNSGFKRKAGTS SLTECVLNKATNVAHWTTPSLKCIRDPALVHQRPAPPSG GSGGGGSGGGSGGGGSLQNWVNVISDLKKIEDLIQSMHI DATLYTESDVHPSCKVTAMKCFLLELQVISLESGDASIHD TVENLIILANNSLSSNGNVTESGCKECEELEEKNIKEFLQS FVHIVQMFINTSGGGGSGGGGSGGGGSGGGGSEVQLLESG GGLVQPGGSLRLSCAASGFTFSAYRMFWVRQAPGKGLEWV SSIYPSGGITFYADSVKGRFTISRDNSKNTLYLQMNSLRAED TAIYYCARIKLGTVTTVDYWGQGTLVTVSSASTKGPSVFPL APSSKSTSGGTAALGCLVKDYFPEPVTVSWNSGALTSGVHT FPAVLQSSGLYSLSSVVTVPSSSLGTQTYICNVNHKPSNTKV DKRVEPKSCDKTHTCPPCPAPEA*AGGPSVFLFPPKPKDTLMI SRTPEVTCVVVDVSHEDPEVKF*N*WYVDGVEVHNAKTKPRE EQYNSTYRVVSVLTVLHQDWLNGKEYKCKVSNKALPAPIE KTISKAKGQPREPQV*C*TLPPSREEMTKNQVSL*SCA*VKGFYPS DIAVEWESNGQPENNY*KTTPPVLDSDGSFFL*V*SKLTVDKSR WQQGNVFSCSVMHEALHNHYTQKSLSLSPG(*K*) | 207 |

TABLE 25-continued

Sequences of the disclosure

| Identifier | Sequence | SEQ ID NO |
|---|---|---|
| hSD15 + D7A8HC (T350V/ L351Y/ F405A/ Y407V) LALA (comprises D7A8 VH (SEQ ID NO: 200), linker 1 (SEQ ID NO: 215), and the linker of SEQ ID N: 244)) | ITCPPPMSVEHADIWVKSYSLYSRERYICNSGFKRKAGTS SLTECVLNKATNVAHWTTPSLKCIRDPALVHQRPAPPSG GSGGGGSGGGSGGGGSLQNWVNVISDLKKIEDLIQSMHI DATLYTESDVHPSCKVTAMKCFLLELQVISLESGDASIHD TVENLIILANNSLSSNGNVTESGCKECEELEEKNIKEFLQS FVHIVQMFINTSGGGGSGGGGSGGGGGSGGGGSEVQLLESG GGLVQPGGSLRLSCAASGFTFSAYRMFWVRQAPGKGLEWV SSIYPSGGITFYADSVKGRFTISRDNSKNTLYLQMNSLRAED TAIYYCARIKLGTVTTVDYWGQGTLVTVSSASTKGPSVFPL APSSKSTSGGTAALGCLVKDYFPEPVTVSWNSGALTSGVHT FPAVLQSSGLYSLSSVVTVPSSSLGTQTYICNVNHKPSNTKV DKRVEPKSCDKTHTCPPCPAPEAAGGPSVFLFPPKPKDTLMI SRTPEVTCVVVDVSHEDPEVKFNWYVDGVEVHNAKTKPRE EQYNSTYRVVSVLTVLHQDWLNGKEYKCKVSNKALPAPIE KTISKAKGQPREPQVYVYPPSREEMTKNQVSLTCLVKGFYP SDIAVEWESNGQPENNYKTTPPVLDSDGSFALVSKLTVDKS RWQQGNVFSCSVMHEALHNHYTQKSLSLSPG(K) | 208 |
| D7A8 HC LALA + hSD15 (comprises D7A8 VH (SEQ ID NO: 200) and linker 1 (SEQ ID NO: 215)) | EVQLLESGGGLVQPGGSLRLSCAASGFTFSAYRMFWVRQA PGKGLEWVSSIYPSGGITFYADSVKGRFTISRDNSKNTLYLQ MNSLRAEDTAIYYCARIKLGTVTTVDYWGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPEAAGGPSVFLFPP KPKDTLMISRTPEVTCVVVDVSHEDPEVKFNWYVDGVEVH NAKTKPREEQYNSTYRVVSVLTVLHQDWLNGKEYKCKVS NKALPAPIEKTISKAKGQPREPQVYTLPPSREEMTKNQVSLT CLVKGFYPSDIAVEWESNGQPENNYKTTPPVLDSDGSFFLY SKLTVDKSRWQQGNVFSCSVMHEALHNHYTQKSLSLSPGS CPPPMSVEHADIWVKSYSLYSRERYICNSGFKRKAGTSSL TECVLNKATNVAHWTTPSLKCIRDPALVHQRPAPPSGGS GGGGSGGGSGGGGSLQNWVNVISDLKKIEDLIQSMHIDA TLYTESDVHPSCKVTAMKCFLLELQVISLESGDASIHDTV ENLIILANNSLSSNGNVTESGCKECEELEEKNIKEFLQSFV HIVQMFINTS | 209 |
| D7A8 HC (Y349C/ T366S/ L368A/ Y407V) LALA + hSD15 (comprises D7A8 VH (SEQ ID NO: 200) and linker 1 (SEQ ID NO: 215)) | EVQLLESGGGLVQPGGSLRLSCAASGFTFSAYRMFWVRQA PGKGLEWVSSIYPSGGITFYADSVKGRFTISRDNSKNTLYLQ MNSLRAEDTAIYYCARIKLGTVTTVDYWGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPEAAGGPSVFLFPP KPKDTLMISRTPEVTCVVVDVSHEDPEVKFNWYVDGVEVH NAKTKPREEQYNSTYRVVSVLTVLHQDWLNGKEYKCKVS NKALPAPIEKTISKAKGQPREPQVCTLPPSREEMTKNQVSLS CAVKGFYPSDIAVEWESNGQPENNYKTTPPVLDSDGSFFLV SKLTVDKSRWQQGNVFSCSVMHEALHNHYTQKSLSLSPGC PPPMSVEHADIWVKSYSLYSRERYICNSGFKRKAGTSSLT ECVLNKATNVAHWTTPSLKCIRDPALVHQRPAPPSGGSG GGGSGGGSGGGGSLQNWVNVISDLKKIEDLIQSMHIDAT LYTESDVHPSCKVTAMKCFLLELQVISLESGDASIHDTVE NLIILANNSLSSNGNVTESGCKECEELEEKNIKEFLQSFV HIVQMFINTS | 210 |
| D7A8 HC (T350V/ L351Y/ F405A/ Y407V) LALA + hSD15 (comprises D7A8 VH (SEQ ID NO: 200) and linker 1 (SEQ ID NO: 215)) | EVQLLESGGGLVQPGGSLRLSCAASGFTFSAYRMFWVRQA PGKGLEWVSSIYPSGGITFYADSVKGRFTISRDNSKNTLYLQ MNSLRAEDTAIYYCARIKLGTVTTVDYWGQGTLVTVSSAST KGPSVFPLAPSSKSTSGGTAALGCLVKDYFPEPVTVSWNSG ALTSGVHTFPAVLQSSGLYSLSSVVTVPSSSLGTQTYICNVN HKPSNTKVDKRVEPKSCDKTHTCPPCPAPEAAGGPSVFLFPP KPKDTLMISRTPEVTCVVVDVSHEDPEVKFNWYVDGVEVH NAKTKPREEQYNSTYRVVSVLTVLHQDWLNGKEYKCKVS NKALPAPIEKTISKAKGQPREPQVYVYPPSREEMTKNQVSLT CLVKGFYPSDIAVEWESNGQPENNYKTTPPVLDSDGSFALV SKLTVDKSRWQQGNVFSCSVMHEALHNHYTQKSLSLSPGC PPPMSVEHADIWVKSYSLYSRERYICNSGFKRKAGTSSLT ECVLNKATNVAHWTTPSLKCIRDPALVHQRPAPPSGGSG GGGSGGGSGGGGSLQNWVNVISDLKKIEDLIQSMHIDAT LYTESDVHPSCKVTAMKCFLLELQVISLESGDASIHDTVE NLIILANNSLSSNGNVTESGCKECEELEEKNIKEFLQSFV HIVQMFINTS | 211 |

TABLE 25-continued

| Identifier | Sequence | SEQ ID NO |
|---|---|---|
| IL-15 and IL-15 Rα sequences | | |
| Human IL-15 (mature protein, residue N65 is in bold) | NWVNVISDLKKIEDLIQSMHIDATLYTESDVHPSCKVTAMK CFLLELQVISLESGDASIHDTVENLIILANNSLSSNGNVTESG CKECEELEEKNIKEFLQSFVHIVQMFINTS | 212 |
| Human IL-15 Rα subunit (signal peptide is underlined, residue N60 is in bold) | MAPRRARGCRTLGLPALLLLLLLRPPATRGITCPPPMSVEHA DIWVKSYSLYSRERYICNSGFKRKAGTSSLTECVLNKATNV AHWTTPSLKCIRDPALVHQRPAPPSTVTTAGVTPQPESLSPS GKEPAASSPSSNNTAATTAAIVPGSQLMPSKSPSTGTTEISSH ESSHGTPSQTTAKNWELTASASHQPPGVYPQHSDTTVAISTS TVLLCGLSAVSLLACYLKSRQTPPLASVEMEAMEALPVTW GTSSRDEDLENCSHHL | 213 |
| IL-15Rα sushi domain (residue corresponding to residue N60 in SEQ ID NO: 213 is shown in bold) | CPPPMSVEHADIWVKSYSLYSRERYICNSGFKRKAGTSSLTE CVLNKATNVAHWTTPSLKC | 214 |
| Linker sequences | | |
| Linker 1 | IRDPALVHQRPAPPSGGSGGGGSGGGSGGGGSLQ | 215 |
| Linker 2 | GGGGSGGGGSGGGGSGGGGSGGGGSGGGGS | 216 |
| Exemplary linker | IRDPSGGGGSGGGGSGGGGSGGGGSGGGGSGGGG | 217 |
| Exemplary linker | IRDPGGGGSGGGGSGGGGSGGGGSGGGGSGGGGS | 218 |
| Exemplary linker | GGGGSGGGGSGGGGSGGGGS | 244 |

VH: heavy variable chain
HC: (full length) heavy chain
VL: light variable chain
LC: (full length) light chain
mHC: murine (full length) heavy chain
mLC: murine (full length) light chain
SD15: bold
LALA/LALAPG substitution: underlined (not bold)
Substitution to stabilize heterodimer of two heavy chains: bold, underlight, italics
Linkers: underlined
Amino acid substitutions in IL-15: double underlined
(K): optional lysine reside

TABLE 26

Sequences of the disclosure

| Name | Dimer of HC | Light chain | Fc amino acid substitution type for heterodimer | Heavy chain 1 | Heavy chain 2 (with IL-15) |
|---|---|---|---|---|---|
| 2N_D7A8_hIL-15 | homo | 205 | none | none | 206 |
| 1N_D7A8_hIL-15 | hetero | 205 | Knobs-into-holes (CW-CSAV) | 202 | 207 |
| | | | ZW1 (VYAV-VLLW) | 203 | 208 |
| 2C_D7A8_hIL-15 | homo | 205 | none | none | 209 |
| 1C_D7A8_hIL-15 | hetero | 205 | Knobs-into-holes (CW-CSAV) | 202 | 210 |
| | | | ZW1 (VYAV-VLLW) | 203 | 211 |
| 2N_DP47_mIL-15 | homo | 186 | none | none | 187 |
| 1N_DP47_mIL-15 | hetero | 186 | Modified ZW1 (VYAV-VLLW) | 185 | 188 |
| 2C_DP47_mIL-15 | homo | 186 | none | none | 189 |

TABLE 26-continued

Sequences of the disclosure

| Name | Dimer of HC | Light chain | Fc amino acid substitution type for heterodimer | Heavy chain 1 | Heavy chain 2 (with IL-15) |
|---|---|---|---|---|---|
| 1C_DP47_mIL-15 | hetero | 186 | Modified ZW1 (VYAV-VLLW) | 185 | 190 |
| 2N_m3A7_mIL-15 | homo | 173 | none | none | 181 |
| 1N_m3A7_mIL-15 | hetero | 173 | Modified ZW1 (VYAV-VLLW) | 172 | 182 |
| 2C_m3A7_mIL-15 | homo | 173 | none | none | 183 |
| 1C_m3A7_mIL-15 | hetero | 173 | Modified ZW1 (VYAV-VLLW) | 172 | 184 |
| 2N_38B2_hIL-15 | homo | 170 | none | none | 174 |
| 1N_38B2_hIL-15 | hetero | 170 | ZW1 (VYAV-VLLW) | 169 | 175 |
| 2C_38B2_hIL-15 | homo | 170 | none | none | 176 |
| 1C_38B2_hIL-15 | hetero | 170 | ZW1 (VYAV-VLLW) | 169 | 177 |
| 2N_DP47_hIL-15 | homo | 192 | none | none | 193 |
| 1N_DP47_hIL-15 | hetero | 192 | ZW1 (VYAV-VLLW) | 191 | 194 |
| 2C_DP47_hIL-15 | homo | 192 | none | none | 195 |
| 1C_DP47_hIL-15 | hetero | 192 | ZW1 (VYAV-VLLW) | 191 | 196 |
| N65A_1N_38B2_hIL-15 | hetero | 170 | ZW1 (VYAV-VLLW) | 169 | 178 |
| N65D_1N_38B2_hIL-15 | hetero | 170 | ZW1 (VYAV-VLLW) | 169 | 179 |
| N65S_1N_38B2_hIL-15 | hetero | 170 | ZW1 (VYAV-VLLW) | 169 | 180 |
| N65A_1N_DP47_IL-15 | hetero | 192 | ZW1 (VYAV-VLLW) | 191 | 197 |
| N65D_1N_DP47_hIL-15 | hetero | 192 | ZW1 (VYAV-VLLW) | 191 | 198 |
| N65S_1N_DP47_hIL-15 | hetero | 192 | ZW1 (VYAV-VLLW) | 191 | 199 |

TABLE 27

Exemplary embodiments of fusion proteins comprising antibody 38B2. All fusion proteins in this table comprise the light chain of 38B2. The individual sequences referenced in this table are provided in Table 28. As an example, in 1N-38B2_1, the first heavy chain comprises heterodimerization amino acid substitutions T350V/T366L/K392L/T394W and the second heavy chain comprises heterodimerization amino acid substitutions T350V/L351Y/F405A/Y407V. In 1N-38B2_2, the first heavy chain comprises hetero-dimerization amino acid substitutions T350V/L351Y/F405A/Y407V and the second heavy chain comprises heterodimerization amino acid substitutions T350V/T366L/K392L/T394W.

| | Heavy chain 1 (HC1) | | Heavy chain 2 (HC2) | | | Fc engineering | |
|---|---|---|---|---|---|---|---|
| Fusion protein name | SEQ ID NO | Name | SEQ ID NO: | Name | Linker between IL-15Rα sushi and IL-15 | Effector region | Heterodimer-ization |
| 1N-38B2_1 | 220 | 38B2HC1-1 | 224 | 65N-38B2HC2-1 | SGGSGGGGSGGGSGGGGSLQ | LALAPG | ZW1 |
| 1N-38B2_2 | 221 | 38B2HC1-2 | 225 | 65N-38B2HC2-2 | SGGSGGGGSGGGSGGGGSLQ | | (VYAV-VLLW) |
| 1N-38B2_3 | 222 | 38B2HC1-3 | 226 | 65N-38B2HC2-3 | SGGSGGGGSGGGSGGGGSLQ | | Knobs-into-holes |
| 1N-38B2_4 | 223 | 38B2HC1-4 | 227 | 65N-38B2HC2-4 | SGGSGGGGSGGGSGGGGSLQ | | (CW-CSAV) |
| 65S-38B2_1 | 220 | 38B2HC1-1 | 228 | 65S-38B2HC2-1 | SGGSGGGGSGGGSGGGGSLQ | LALAPG | ZW1 |
| 65S-38B2_2 | 221 | 38B2HC1-2 | 229 | 65S-38B2HC2-2 | SGGSGGGGSGGGSGGGGSLQ | | (VYAV-VLLW) |
| 65S-38B2_3 | 222 | 38B2HC1-3 | 230 | 65S-38B2HC2-3 | SGGSGGGGSGGGSGGGGSLQ | | Knobs-into-holes |
| 65S-38B2_4 | 223 | 38B2HC1-4 | 231 | 65S-38B2HC2-4 | SGGSGGGGSGGGSGGGGSLQ | | (CW-CSAV) |
| 65S-38B2_5 | 220 | 38B2HC1-1 | 236 | 65S-38B2HC2-5 | SGGGGSGGGGSGGGSGGGGS | LALAPG | ZW1 |
| 65S-38B2_6 | 221 | 38B2HC1-2 | 237 | 65S-38B2HC2-6 | SGGGGSGGGGSGGGSGGGGS | | (VYAV-VLLW) |
| 65S-38B2_7 | 222 | 38B2HC1-3 | 238 | 65S-38B2HC2-7 | SGGGGSGGGGSGGGSGGGGS | | Knobs-into-holes |
| 65S-38B2_8 | 223 | 38B2HC1-4 | 239 | 65S-38B2HC2-8 | SGGGGSGGGGSGGGSGGGGS | | (CW-CSAV) |
| 65D-38B2_1 | 220 | 38B2HC1-1 | 232 | 65D-38B2HC2-1 | SGGSGGGGSGGGSGGGGSLQ | LALAPG | ZW1 |
| 65D-38B2_2 | 221 | 38B2HC1-2 | 233 | 65D-38B2HC2-2 | SGGSGGGGSGGGSGGGGSLQ | | (VYAV-VLLW) |
| 65D-38B2_3 | 222 | 38B2HC1-3 | 234 | 65D-38B2HC2-3 | SGGSGGGGSGGGSGGGGSLQ | | Knobs-into-holes |
| 65D-38B2_4 | 223 | 38B2HC1-4 | 235 | 65D-38B2HC2-4 | SGGSGGGGSGGGSGGGGSLQ | | (CW-CSAV) |
| 65S-38B2_9 | 240 | 38B2HC1-3B | 241 | 65S-38B2HC2-3B | SGGSGGGGSGGGSGGGGSLQ | LALA | Knobs-into-holes (CW-CSAV) |
| 65S-38B2_10 | 240 | 38B2HC1-3B | 242 | 65S-38B2HC2-7B | SGGGGSGGGGSGGGSGGGGS | | Knobs-into-holes (CW-CSAV) |
| 65D-38B2_5 | 240 | 38B2HC1-3B | 243 | 65D-38B2HC2-3B | SGGSGGGGSGGGSGGGGSLQ | | Knobs-into-holes (CW-CSAV) |

TABLE 28

Sequences for fusion protein embodiments provided in Table 27.

| SEQ ID NO: | Name | Amino acid sequence |
|---|---|---|
| 219 | 38B2 LC (comprises 38B2 VL (SEQ ID NO: 98)) | DIQMTQSPSSLSASVGDRVTITCRASESISSWLAWYQQKPGKAPKLLIYDASSLESGVPSRFSGS GSGTDFTLTISSLQPEDFATYYCQQGDSFPFTFGQGTKLEIKRTVAAPSVFIFPPSDEQLKSGTAS VVCLLNNFYPREAKVQWKVDNALQSGNSQESVTEQDSKDSTYSLSSTLTLSKADYEKHKVYACEV THQGLSSPVTKSFNRGEC |
| 220 | 38B2 HC1-1 (T350V/ T366L/ K392L/ T394W) LALAPG | EVQLLESGGGLVQPGGSLRLSCAASGFTFSSYWMSWVRQAPGKGLEWVSAISGSGGSTYYAD SVKGRFTISRDNSKNTLYLQMNSLRAEDTAVYYCASSPLQWVDVWGQGTTVTVSSASTKGPSV FPLAPSSKSTSGGTAALGCLVKDYFPEPVTVSWNSGALTSGVHTFPAVLQSSGLYSLSSVVTVPSSSL GTQTYICNVNHKPSNTKVDKKVEPKSCDKTHTCPPCPAPEAAGGPSVFLFPPKPKDTLMISRTPEVTC VVVDVSHEDPEVKFNWYVDGVEVHNAKTKPREEQYNSTYRVVSVLTVLHQDWLNGKEYKCKVS NKAL*G*APIEKTISKAKGQPREPQVYVLPPSRDELTKNQVSLLCLVKGFYPSDIAVEWESNGQPENNY LTWPPVLDSDGSFFLYSKLTVDKSRWQQGNVFSCSVMHEALHNYTQKSLSLSPGK |
| 221 | 38B2 HC1-2 (T350V/ L351Y/ F405A/ Y407V) LALAPG | EVQLLESGGGLVQPGGSLRLSCAASGFTFSSYWMSWVRQAPGKGLEWVSAISGSGGSTYYAD SVKGRFTISRDNSKNTLYLQMNSLRAEDTAVYYCASSPLQWVDVWGQGTTVTVSSASTKGPSV FPLAPSSKSTSGGTAALGCLVKDYFPEPVTVSWNSGALTSGVHTFPAVLQSSGLYSLSSVVTVPSSSL GTQTYICNVNHKPSNTKVDKKVEPKSCDKTHTCPPCPAPEAAGGPSVFLFPPKPKDTLMISRTPEVTC VVVDVSHEDPEVKFNWYVDGVEVHNAKTKPREEQYNSTYRVVSVLTVLHQDWLNGKEYKCKVS NKAL*G*APIEKTISKAKGQPREPQVYVYPPSRDELTKNQVSLTCLVKGFYPSDIAVEWESNGQPENNY KTTPPVLDSDGSFALVSKLTVDKSRWQQGNVFSCSVMHEALHNYTQKSLSLSPGK |
| 222 | 38B2 HC1-3 (CW-CSAV) S354C/ T366W LALAPG | EVQLLESGGGLVQPGGSLRLSCAASGFTFSSYWMSWVRQAPGKGLEWVSAISGSGGSTYYAD SVKGRFTISRDNSKNTLYLQMNSLRAEDTAVYYCASSPLQWVDVWGQGTTVTVSSASTKGPSV FPLAPSSKSTSGGTAALGCLVKDYFPEPVTVSWNSGALTSGVHTFPAVLQSSGLYSLSSVVTVPSSSL GTQTYICNVNHKPSNTKVDKKVEPKSCDKTHTCPPCPAPEAAGGPSVFLFPPKPKDTLMISRTPEVTC VVVDVSHEDPEVKFNWYVDGVEVHNAKTKPREEQYNSTYRVVSVLTVLHQDWLNGKEYKCKVS NKAL*G*APIEKTISKAKGQPREPQVYTLPPCRDELTKNQVSLWCLVKGFYPSDIAVEWESNGQPENN YKTTPPVLDSDGSFFLYSKLTVDKSRWQQGNVFSCSVMHEALHNYTQKSLSLSPGK |
| 223 | 38B2 HC1-4 (CW-CSAV) Y349C/ T366S/ L368A/ Y407V LALAPG | EVQLLESGGGLVQPGGSLRLSCAASGFTFSSYWMSWVRQAPGKGLEWVSAISGSGGSTYYAD SVKGRFTISRDNSKNTLYLQMNSLRAEDTAVYYCASSPLQWVDVWGQGTTVTVSSASTKGPSV FPLAPSSKSTSGGTAALGCLVKDYFPEPVTVSWNSGALTSGVHTFPAVLQSSGLYSLSSVVTVPSSSL GTQTYICNVNHKPSNTKVDKKVEPKSCDKTHTCPPCPAPEAAGGPSVFLFPPKPKDTLMISRTPEVTC VVVDVSHEDPEVKFNWYVDGVEVHNAKTKPREEQYNSTYRVVSVLTVLHQDWLNGKEYKCKVS NKAL*G*APIEKTISKAKGQPREPQVCTLPPSRDELTKNQVSLSCAVKGFYPSDIAVEWESNGQPENNY KTTPPVLDSDGSFFLVSKLTVDKSRWQQGNVFSCSVMHEALHNYTQKSLSLSPGK |
| 224 | 65N-38B2 HC2-1 (T350V/ L351Y/ F405A/ Y407V) LALAPG | *ITCPPPMSVEHADIWVKSYSLYSRERYICNSGFKRKAGTSSLTECVLNKATNVAHWTTPSLKC<u>IRDPALVHQ</u>* *<u>RPAPPSGG</u>SGGGGSGGGGSGGGGSGGGGSLQNWVNVISDLKKIEDLIQSMHIDATLYTESDVHPSCKVTAMKCFLL* *ELQVISLESGDASIHDTVENLIILANNSLSSNGNVTESGCKECEELEEKNIKEFLQSFVHIVQMFINTS<u>GGGG</u>* <u>*S*GGGGSGGGGSGGGGSGGGGSGGGGS</u>EVQLLESGGGLVQPGGSLRLSCAASGFTFSSYWMSWV RQAPGKGLEWVSAISGSGGSTYYADSVKGRFTISRDNSKNTLYLQMNSLRAEDTAVYYCASSP LQWVDVWGQGTTVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSCDKTHTCPPCPAP EAAGGPSVFLFPPKPKDTLMISRTPEVTCVVVDVSHEDPEVKFNWYVDGVEVHNAKTKPREEQYNS TYRVVSVLTVLHQDWLNGKEYKCKVSNKAL*G*APIEKTISKAKGQPREPQVYVYPPSRDELTKNQVS LTCLVKGFYPSDIAVEWESNGQPENNYKTTPPVLDSDGSFALVSKLTVDKSRWQQGNVFSCSVMHE ALHNYTQKSLSLSPGK |
| 225 | 65N-38B2 HC2-2 (T350V/ T366L/ K392L/ T394W) LALAPG | *ITCPPPMSVEHADIWVKSYSLYSRERYICNSGFKRKAGTSSLTECVLNKATNVAHWTTPSLKC<u>IRDPALVHQ</u>* *<u>RPAPPSGG</u>SGGGGSGGGGSGGGGSGGGGSLQNWVNVISDLKKIEDLIQSMHIDATLYTESDVHPSCKVTAMKCFLL* *ELQVISLESGDASIHDTVENLIILANNSLSSNGNVTESGCKECEELEEKNIKEFLQSFVHIVQMFINTS<u>GGGG</u>* <u>SGGGGSGGGGSGGGGSGGGGSGGGGS</u>EVQLLESGGGLVQPGGSLRLSCAASGFTFSSYWMSWV RQAPGKGLEWVSAISGSGGSTYYADSVKGRFTISRDNSKNTLYLQMNSLRAEDTAVYYCASSP LQWVDVWGQGTTVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSCDKTHTCPPCPAP EAAGGPSVFLFPPKPKDTLMISRTPEVTCVVVDVSHEDPEVKFNWYVDGVEVHNAKTKPREEQYNS TYRVVSVLTVLHQDWLNGKEYKCKVSNKAL*G*APIEKTISKAKGQPREPQVYVLPPSRDELTKNQVS LLCLVKGFYPSDIAVEWESNGQPENNYLTWPPVLDSDGSFFLYSKLTVDKSRWQQGNVFSCSVMH EALHNYTQKSLSLSPGK |
| 226 | 65N-38B2 HC2-3 (CW-CSAV) Y349C/ T366S/ L368A/ Y407V LALAPG | *ITCPPPMSVEHADIWVKSYSLYSRERYICNSGFKRKAGTSSLTECVLNKATNVAHWTTPSLKC<u>IRDPALVHQ</u>* *<u>RPAPPSGG</u>SGGGGSGGGGSGGGGSGGGGSLQNWVNVISDLKKIEDLIQSMHIDATLYTESDVHPSCKVTAMKCFLL* *ELQVISLESGDASIHDTVENLIILANNSLSSNGNVTESGCKECEELEEKNIKEFLQSFVHIVQMFINTS<u>GGGG</u>* <u>SGGGGSGGGGSGGGGSGGGGSGGGGS</u>EVQLLESGGGLVQPGGSLRLSCAASGFTFSSYWMSWV RQAPGKGLEWVSAISGSGGSTYYADSVKGRFTISRDNSKNTLYLQMNSLRAEDTAVYYCASSP LQWVDVWGQGTTVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSCDKTHTCPPCPAP EAAGGPSVFLFPPKPKDTLMISRTPEVTCVVVDVSHEDPEVKFNWYVDGVEVHNAKTKPREEQYNS TYRVVSVLTVLHQDWLNGKEYKCKVSNKAL*G*APIEKTISKAKGQPREPQVCTLPPSRDELTKNQVS LSCAVKGFYPSDIAVEWESNGQPENNYKTTPPVLDSDGSFFLVSKLTVDKSRWQQGNVFSCSVMHE ALHNYTQKSLSLSPGK |

TABLE 28-continued

Sequences for fusion protein embodiments provided in Table 27.

| SEQ ID NO: | Name | Amino acid sequence |
|---|---|---|
| 227 | 65N-38B2 HC2-4 S354C/ T366W LALAPG | *ITCPPPMSVEHADIWVKSYSLYSRERYICNSGFKRKAGTSSLTECVLNKATNVAHWTTPSLKCIRDPALVHQ* *RPAPPSGGSGGGGSGGGSGGGGSLQNWVNVISDLKKIEDLIQSMHIDATLYTESDVHPSCKVTAMKCFLL* *ELQVISLESGDASIHDTVENLIILANNSLSSNGNVTESGCKECEELEEKNIKEFLQSFVHIVQMFINTSGGGG* SGGGGSGGGGSGGGGSGGGGSGGGGSEVQLLESGGGLVQPGGSLRLSCAASGFTFSSYWMSWV RQAPGKGLEWVSAISGSGGSTYYADSVKGRFTISRDNSKNTLYLQMNSLRAEDTAVYYCASSP LQWVDVWGQGTTVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSCDKTHTCPPCPAP EAAGGPSVFLFPPKPKDTLMISRTPEVTCVVVDVSHEDPEVKFNWYVDGVEVHNAKTKPREEQYNS TYRVVSVLTVLHQDWLNGKEYKCKVSNKAL*G*APIEKTISKAKGQPREPQVYTLPPCRDELTKNQVS LWCLVKGFYPSDIA VEWESNGQPENNYKTTPPVLDSDGSFFLYSKLTVDKSRWQ*Q*GNVFSCSVMH EALHNHYTQKSLSLSPGK |
| 228 | 65S-38B2 HC2-1 (T350V/ L351Y/ F405A/ Y407V) LALAPG | *ITCPPPMSVEHADIWVKSYSLYSRERYICNSGFKRKAGTSSLTECVLNKATNVAHWTTPSLKCIRDPALVHQ* *RPAPPSGGSGGGGSGGGSGGGGSLQNWVNVISDLKKIEDLIQSMHIDATLYTESDVHPSCKVTAMKCFLL* *ELQVISLESGDASIHDTVESLIILANNSLSSNGNVTESGCKECEELEEKNIKEFLQSFVHIVQMFINTSGGGG* SGGGGSGGGGSGGGGSGGGGSGGGGSEVQLLESGGGLVQPGGSLRLSCAASGFTFSSYWMSWV RQAPGKGLEWVSAISGSGGSTYYADSVKGRFTISRDNSKNTLYLQMNSLRAEDTAVYYCASSP LQWVDVWGQGTTVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSCDKTHTCPPCPAP EAAGGPSVFLFPPKPKDTLMISRTPEVTCVVVDVSHEDPEVKFNWYVDGVEVHNAKTKPREEQYNS TYRVVSVLTVLHQDWLNGKEYKCKVSNKAL*G*APIEKTISKAKGQPREPQVYVYPPSRDELTKNQVS LTCLVKGFYPSDIAVEWESNGQPENNYKTTPPVLDSDGSFALVSKLTVDKSRWQQGNVFSCSVMHE ALHNHYTQKSLSLSPGK |
| 229 | 65S-38B2 HC2-2 (T350V/ T366L/ K392L/ T394W) LALAPG | *ITCPPPMSVEHADIWVKSYSLYSRERYICNSGFKRKAGTSSLTECVLNKATNVAHWTTPSLKCIRDPALVHQ* *RPAPPSGGSGGGGSGGGSGGGGSLQNWVNVISDLKKIEDLIQSMHIDATLYTESDVHPSCKVTAMKCFLL* *ELQVISLESGDASIHDTVESLIILANNSLSSNGNVTESGCKECEELEEKNIKEFLQSFVHIVQMFINTSGGGG* SGGGGSGGGGSGGGGSGGGGSGGGGSEVQLLESGGGLVQPGGSLRLSCAASGFTFSSYWMSWV RQAPGKGLEWVSAISGSGGSTYYADSVKGRFTISRDNSKNTLYLQMNSLRAEDTAVYYCASSP LQWVDVWGQGTTVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSCDKTHTCPPCPAP EAAGGPSVFLFPPKPKDTLMISRTPEVTCVVVDVSHEDPEVKFNWYVDGVEVHNAKTKPREEQYNS TYRVVSVLTVLHQDWLNGKEYKCKVSNKAL*G*APIEKTISKAKGQPREPQVYVLPPSRDELTKNQVS LLCLVKGFYPSDIAVEWESNGQPENNYLTWPPVLDSDGSFFLYSKLTVDKSRWQQGNVFSCSVMH EALHNHYTQKSLSLSPGK |
| 230 | 65S-38B2 HC2-3 (CW-CSAV) Y349C/ T366S/ L368A/ Y407V LALAPG | *ITCPPPMSVEHADIWVKSYSLYSRERYICNSGFKRKAGTSSLTECVLNKATNVAHWTTPSLKCIRDPALVHQ* *RPAPPSGGSGGGGSGGGSGGGGSLQNWVNVISDLKKIEDLIQSMHIDATLYTESDVHPSCKVTAMKCFLL* *ELQVISLESGDASIHDTVESLIILANNSLSSNGNVTESGCKECEELEEKNIKEFLQSFVHIVQMFINTSGGGG* SGGGGSGGGGSGGGGSGGGGSGGGGSEVQLLESGGGLVQPGGSLRLSCAASGFTFSSYWMSWV RQAPGKGLEWVSAISGSGGSTYYADSVKGRFTISRDNSKNTLYLQMNSLRAEDTAVYYCASSP LQWVDVWGQGTTVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSCDKTHTCPPCPAP EAAGGPSVFLFPPKPKDTLMISRTPEVTCVVVDVSHEDPEVKFNWYVDGVEVHNAKTKPREEQYNS TYRVVSVLTVLHQDWLNGKEYKCKVSNKAL*G*APIEKTISKAKGQPREPQVCTLPPSRDELTKNQVS LSCAVKGFYPSDIAVEWESNGQPENNYKTTPPVLDSDGSFFLVSKLTVDKSRWQQGNVFSCSVMHE ALHNHYTQKSLSLSPGK |
| 231 | 65S-38B2 HC2-4 S354C/ T366W LALAPG | *ITCPPPMSVEHADIWVKSYSLYSRERYICNSGFKRKAGTSSLTECVLNKATNVAHWTTPSLKCIRDPALVHQ* *RPAPPSGGSGGGGSGGGSGGGGSLQNWVNVISDLKKIEDLIQSMHIDATLYTESDVHPSCKVTAMKCFLL* *ELQVISLESGDASIHDTVESLIILANNSLSSNGNVTESGCKECEELEEKNIKEFLQSFVHIVQMFINTSGGGG* SGGGGSGGGGSGGGGSGGGGSGGGGSEVQLLESGGGLVQPGGSLRLSCAASGFTFSSYWMSWV RQAPGKGLEWVSAISGSGGSTYYADSVKGRFTISRDNSKNTLYLQMNSLRAEDTAVYYCASSP LQWVDVWGQGTTVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSCDKTHTCPPCPAP EAAGGPSVFLFPPKPKDTLMISRTPEVTCVVVDVSHEDPEVKFNWYVDGVEVHNAKTKPREEQYNS TYRVVSVLTVLHQDWLNGKEYKCKVSNKAL*G*APIEKTISKAKGQPREPQVYTLPPCRDELTKNQVS LWCLVKGFYPSDIAVEWESNGQPENNYKTTPPVLDSDGSFFLYSKLTVDKSRWQQGNVFSCSVMH EALHNHYTQKSLSLSPGK |
| 232 | 65D-38B2 HC2-1 (T350V/ L351Y/ F405A/ Y407V) LALAPG | *ITCPPPMSVEHADIWVKSYSLYSRERYICNSGFKRKAGTSSLTECVLNKATNVAHWTTPSLKCIRDPALVHQ* *RPAPPSGGSGGGGSGGGSGGGGSLQNWVNVISDLKKIEDLIQSMHIDATLYTESDVHPSCKVTAMKCFLL* *ELQVISLESGDASIHDTVEDLIILANNSLSSNGNVTESGCKECEELEEKNIKEFLQSFVHIVQMFINTSGGGG* SGGGGSGGGGSGGGGSGGGGSGGGGSEVQLLESGGGLVQPGGSLRLSCAASGFTFSSYWMSWV RQAPGKGLEWVSAISGSGGSTYYADSVKGRFTISRDNSKNTLYLQMNSLRAEDTAVYYCASSP LQWVDVWGQGTTVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSCDKTHTCPPCPAP EAAGGPSVFLFPPKPKDTLMISRTPEVTCVVVDVSHEDPEVKFNWYVDGVEVHNAKTKPREEQYNS TYRVVSVLTVLHQDWLNGKEYKCKVSNKAL*G*APIEKTISKAKGQPREPQVYVYPPSRDELTKNQVS LTCLVKGFYPSDIAVEWESNGQPENNYKTTPPVLDSDGSFALVSKLTVDKSRWQQGNVFSCSVMHE ALHNHYTQKSLSLSPGK |

TABLE 28-continued

Sequences for fusion protein embodiments provided in Table 27.

| SEQ ID NO: | Name | Amino acid sequence |
|---|---|---|
| 233 | 65D-38B2 HC2-2 (T350V/ T366L/ K392L/ T394W) LALAPG | *ITCPPPMSVEHADIWVKSYSLYSRERYICNSGFKRKAGTSSLTECVLNKATNVAHWTTPSLKCIRDPALVHQ RPAPPSGGSGGGGSGGGGSGGGGSL*QNWVNVISDLKKIEDLIQSMHIDATLYTESDVHPSCKVTAMKCFLL ELQVISLESGDASIHDTVEDLIILANNSLSSNGNVTESGCKECEELEEKNIKEFLQSFVHIVQMFINTSGGGG SGGGGSGGGGSGGGGSGGGGSGGGGSEVQLLESGGGLVQPGGSLRLSCAASGFTFSSYWMSWV RQAPGKGLEWVSAISGSGGSTYYADSVKGRFTISRDNSKNTLYLQMNSLRAEDTAVYYCASSP LQWVDVWGQGTTVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSCDKTHTCPPCPAP EAAGGPSVFLFPPKPKDTLMISRTPEVTCVVVDVSHEDPEVKFNWYVDGVEVHNAKTKPREEQYNS TYRVVSVLTVLHQDWLNGKEYKCKVSNKAL*G*APIEKTISKAKGQPREPQVYVLPPSRDELTKNQVS LLCLVKGFYPSDIAVEWESNGQPENNYLTWPPVLDSDGSFFLYSKLTVDKSRWQQGNVFSCSVMH EALHNHYTQKSLSLSPGK |
| 234 | 65D-38B2 HC2-3 (CW-CSAV) Y349C/ T366S/ L368A/ Y407V LALAPG | *ITCPPPMSVEHADIWVKSYSLYSRERYICNSGFKRKAGTSSLTECVLNKATNVAHWTTPSLKCIRDPALVHQ RPAPPSGGSGGGGSGGGGSGGGGSL*QNWVNVISDLKKIEDLIQSMHIDATLYTESDVHPSCKVTAMKCFLL ELQVISLESGDASIHDTVEDLIILANNSLSSNGNVTESGCKECEELEEKNIKEFLQSFVHIVQMFINTSGGGG SGGGGSGGGGSGGGGSGGGGSGGGGSEVQLLESGGGLVQPGGSLRLSCAASGFTFSSYWMSWV RQAPGKGLEWVSAISGSGGSTYYADSVKGRFTISRDNSKNTLYLQMNSLRAEDTAVYYCASSP LQWVDVWGQGTTVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSCDKTHTCPPCPAP EAAGGPSVFLFPPKPKDTLMISRTPEVTCVVVDVSHEDPEVKFNWYVDGVEVHNAKTKPREEQYNS TYRVVSVLTVLHQDWLNGKEYKCKVSNKAL*G*APIEKTISKAKGQPREPQVCTLPPSRDELTKNQVS LSCAVKGFYPSDIAVEWESNGQPENNYKTTPPVLDSDGSFFLVSKLTVDKSRWQQGNVFSCSVMHE ALHNHYTQKSLSLSPGK |
| 235 | 65D-38B2 HC2-4 S354C/ T366W LALAPG | *ITCPPPMSVEHADIWVKSYSLYSRERYICNSGFKRKAGTSSLTECVLNKATNVAHWTTPSLKCIRDPALVHQ RPAPPSGGSGGGGSGGGGSGGGGSL*QNWVNVISDLKKIEDLIQSMHIDATLYTESDVHPSCKVTAMKCFLL ELQVISLESGDASIHDTVEDLIILANNSLSSNGNVTESGCKECEELEEKNIKEFLQSFVHIVQMFINTSGGGG SGGGGSGGGGSGGGGSGGGGSGGGGSEVQLLESGGGLVQPGGSLRLSCAASGFTFSSYWMSWV RQAPGKGLEWVSAISGSGGSTYYADSVKGRFTISRDNSKNTLYLQMNSLRAEDTAVYYCASSP LQWVDVWGQGTTVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSCDKTHTCPPCPAP EAAGGPSVFLFPPKPKDTLMISRTPEVTCVVVDVSHEDPEVKFNWYVDGVEVHNAKTKPREEQYNS TYRVVSVLTVLHQDWLNGKEYKCKVSNKAL*G*APIEKTISKAKGQPREPQVYTLPPCRDELTKNQVS LWCLVKGFYPSDIAVEWESNGQPENNYKTTPPVLDSDGSFFLYSKLTVDKSRWQQGNVFSCSVMH EALHNHYTQKSLSLSPGK |
| 236 | 65S-38B2 HC2-5 (T350V/ L351Y/ F405A/ Y407V) LALAPG | *ITCPPPMSVEHADIWVKSYSLYSRERYICNSGFKRKAGTSSLTECVLNKATNVAHWTTPSLKCIRDPALVHQ RPAPPSGGGGSGGGGSGGGGSGGGGS*NWVNVISDLKKIEDLIQSMHIDATLYTESDVHPSCKVTAMKCFLL ELQVISLESGDASIHDTVESLIILANNSLSSNGNVTESGCKECEELEEKNIKEFLQSFVHIVQMFINTSGGGG SGGGGSGGGGSGGGGSGGGGSGGGGSEVQLLESGGGLVQPGGSLRLSCAASGFTFSSYWMSWV RQAPGKGLEWVSAISGSGGSTYYADSVKGRFTISRDNSKNTLYLQMNSLRAEDTAVYYCASSP LQWVDVWGQGTTVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSCDKTHTCPPCPAP EAAGGPSVFLFPPKPKDTLMISRTPEVTCVVVDVSHEDPEVKFNWYVDGVEVHNAKTKPREEQYNS TYRVVSVLTVLHQDWLNGKEYKCKVSNKAL*G*APIEKTISKAKGQPREPQVYVYPPSRDELTKNQVS LTCLVKGFYPSDIAVEWESNGQPENNYKTTPPVLDSDGSFALVSKLTVDKSRWQQGNVFSCSVMHE ALHNHYTQKSLSLSPGK |
| 237 | 65S-38B2 HC2-6 (T350V/ T366L/ K392L/ T394W) LALAPG | *ITCPPPMSVEHADIWVKSYSLYSRERYICNSGFKRKAGTSSLTECVLNKATNVAHWTTPSLKCIRDPALVHQ RPAPPSGGGGSGGGGSGGGGSGGGGS*NWVNVISDLKKIEDLIQSMHIDATLYTESDVHPSCKVTAMKCFLL ELQVISLESGDASIHDTVESLIILANNSLSSNGNVTESGCKECEELEEKNIKEFLQSFVHIVQMFINTSGGGG SGGGGSGGGGSGGGGSGGGGSGGGGSEVQLLESGGGLVQPGGSLRLSCAASGFTFSSYWMSWV RQAPGKGLEWVSAISGSGGSTYYADSVKGRFTISRDNSKNTLYLQMNSLRAEDTAVYYCASSP LQWVDVWGQGTTVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSCDKTHTCPPCPAP EAAGGPSVFLFPPKPKDTLMISRTPEVTCVVVDVSHEDPEVKFNWYVDGVEVHNAKTKPREEQYNS TYRVVSVLTVLHQDWLNGKEYKCKVSNKAL*G*APIEKTISKAKGQPREPQVYVLPPSRDELTKNQVS LLCLVKGFYPSDIAVEWESNGQPENNYLTWPPVLDSDGSFFLYSKLTVDKSRWQQGNVFSCSVMH EALHNHYTQKSLSLSPGK |
| 238 | 65S-38B2 HC2-7 (CW-CSAV) Y349C/ T366S/ L368A/ Y407V LALAPG | *ITCPPPMSVEHADIWVKSYSLYSRERYICNSGFKRKAGTSSLTECVLNKATNVAHWTTPSLKCIRDPALVHQ RPAPPSGGGGSGGGGSGGGGSGGGGS*NWVNVISDLKKIEDLIQSMHIDATLYTESDVHPSCKVTAMKCFLL ELQVISLESGDASIHDTVESLIILANNSLSSNGNVTESGCKECEELEEKNIKEFLQSFVHIVQMFINTSGGGG SGGGGSGGGGSGGGGSGGGGSGGGGSEVQLLESGGGLVQPGGSLRLSCAASGFTFSSYWMSWV RQAPGKGLEWVSAISGSGGSTYYADSVKGRFTISRDNSKNTLYLQMNSLRAEDTAVYYCASSP LQWVDVWGQGTTVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSCDKTHTCPPCPAP EAAGGPSVFLFPPKPKDTLMISRTPEVTCVVVDVSHEDPEVKFNWYVDGVEVHNAKTKPREEQYNS TYRVVSVLTVLHQDWLNGKEYKCKVSNKAL*G*APIEKTISKAKGQPREPQVCTLPPSRDELTKNQVS LSCAVKGFYPSDIAVEWESNGQPENNYKTTPPVLDSDGSFFLVSKLTVDKSRWQQGNVFSCSVMHE ALHNHYTQKSLSLSPGK |

TABLE 28-continued

Sequences for fusion protein embodiments provided in Table 27.

| SEQ ID NO: | Name | Amino acid sequence |
|---|---|---|
| 239 | 65S-38B2 HC2-8 S354C/ T366W LALAPG | *ITCPPPMSVEHADIWVKSYSLYSRERYICNSGFKRKAGTSSLTECVLNKATNVAHWTTPSLKCIRDPALVHQ RPAPPSGGGGSGGGGSGGGSGGGGSNWVNVISDLKKIEDLIQSMHIDATLYTESDVHPSCKVTAMKCFLL ELQVISLESGDASIHDTVESLIILANNSLSSNGNVTESGCKECEELEEKNIKEFLQSFVHIVQMFINTS*GGGG GGGGSGGGGSGGGGSGGGGSGGGGSEVQLLESGGGLVQPGGSLRLSCAASGFTFSSYWMSWV RQAPGKGLEWVSAISGSGGSTYYADSVKGRFTISRDNSKNTLYLQMNSLRAEDTAVYYCASSP LQWVDVWGQGTTVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSCDKTHTCPPCPAP *EAA*GGPSVFLFPPKPKDTLMISRTPEVTCVVVDVSHEDPEVKFNWYVDGVEVHNAKTKPREEQYNS TYRVVSVLTVLHQDWLNGKEYKCKVSNKAL*G*APIEKTISKAKGQPREPQVYTLPPCRDELTKNQVS LWCLVKGFYPSDIAVEWESNGQPENNYKTTPPVLDSDGSFFLYSKLTVDKSRWQQGNVFSCSVMH EALHNHYTQKSLSLSPGK |
| 240 | 38B2 HC1-3B (CW-CSAV) S354C/ T366W LALA | EVQLLESGGGLVQPGGSLRLSCAASGFTFSSYWMSWVRQAPGKGLEWVSAISGSGGSTYYAD SVKGRFTISRDNSKNTLYLQMNSLRAEDTAVYYCASSPLQWVDVWGQGTTVTVSSASTKGPSV FPLAPSSKSTSGGTAALGCLVKDYFPEPVTVSWNSGALTSGVHTFPAVLQSSGLYSLSSVVTVPSSSL GTQTYICNVNHKPSNTKVDKKVEPKSCDKTHTCPPCPAPE*AA*GGPSVFLFPPKPKDTLMISRTPEVTC VVVDVSHEDPEVKFNWYVDGVEVHNAKTKPREEQYNSTYRVVSVLTVLHQDWLNGKEYKCKVS NKAL*P*APIEKTISKAKGQPREPQVYTLPPCRDELTKNQVSLWCLVKGFYPSDIAVEWESNGQPENNY KTTPPVLDSDGSFFLYSKLTVDKSRWQQGNVFSCSVMHEALHNHYTQKSLSLSPGK |
| 241 | 65S-38B2 HC2-3B (CW-CSAV) Y349C/ T366S/ L368A/ Y407V LALA | *ITCPPPMSVEHADIWVKSYSLYSRERYICNSGFKRKAGTSSLTECVLNKATNVAHWTTPSLKCIRDPALVHQ RPAPPSGGGGSGGGGSGGGSGGGGSL*QNWVNVISDLKKIEDLIQSMHIDATLYTESDVHPSCKVTAMKCFLL ELQVISLESGDASIHDTVESLIILANNSLSSNGNVTESGCKECEELEEKNIKEFLQSFVHIVQMFINTS*GGGG GGGGSGGGGSGGGGSGGGGSGGGGSEVQLLESGGGLVQPGGSLRLSCAASGFTFSSYWMSWV RQAPGKGLEWVSAISGSGGSTYYADSVKGRFTISRDNSKNTLYLQMNSLRAEDTAVYYCASSP LQWVDVWGQGTTVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSCDKTHTCPPCPAP *EAA*GGPSVFLFPPKPKDTLMISRTPEVTCVVVDVSHEDPEVKFNWYVDGVEVHNAKTKPREEQYNS TYRVVSVLTVLHQDWLNGKEYKCKVSNKAL*P*APIEKTISKAKGQPREPQVCTLPPSRDELTKNQVS LSCAVKGFYPSDIAVEWESNGQPENNYKTTPPVLDSDGSFFLVSKLTVDKSRWQQGNVFSCSVMHE ALHNHYTQKSLSLSPGK |
| 242 | 65S-38B2 HC2-7B (CW-CSAV) Y349C/ T366S/ L368A/ Y407V LALA | *ITCPPPMSVEHADIWVKSYSLYSRERYICNSGFKRKAGTSSLTECVLNKATNVAHWTTPSLKCIRDPALVHQ RPAPPSGGGGSGGGGSGGGSGGGGSNWVNVISDLKKIEDLIQSMHIDATLYTESDVHPSCKVTAMKCFLL ELQVISLESGDASIHDTVESLIILANNSLSSNGNVTESGCKECEELEEKNIKEFLQSFVHIVQMFINTS*GGGG GGGGSGGGGSGGGGSGGGGSGGGGSEVQLLESGGGLVQPGGSLRLSCAASGFTFSSYWMSWV RQAPGKGLEWVSAISGSGGSTYYADSVKGRFTISRDNSKNTLYLQMNSLRAEDTAVYYCASSP LQWVDVWGQGTTVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSCDKTHTCPPCPAP *EAA*GGPSVFLFPPKPKDTLMISRTPEVTCVVVDVSHEDPEVKFNWYVDGVEVHNAKTKPREEQYNS TYRVVSVLTVLHQDWLNGKEYKCKVSNKAL*P*APIEKTISKAKGQPREPQVCTLPPSRDELTKNQVS LSCAVKGFYPSDIAVEWESNGQPENNYKTTPPVLDSDGSFFLVSKLTVDKSRWQQGNVFSCSVMHE ALHNHYTQKSLSLSPGK |
| 243 | 65D-38B2 HC2-3B (CW-CSAV) Y349C/ T366S/ L368A/ Y407V LALA | *ITCPPPMSVEHADIWVKSYSLYSRERYICNSGFKRKAGTSSLTECVLNKATNVAHWTTPSLKCIRDPALVHQ RPAPPSGGSGGGGSGGGSGGGGSL*QNWVNVISDLKKIEDLIQSMHIDATLYTESDVHPSCKVTAMKCFLL ELQVISLESGDASIHDTVEDLIILANNSLSSNGNVTESGCKECEELEEKNIKEFLQSFVHIVQMFINTS*GGGG GGGGSGGGGSGGGGSGGGGSGGGGSEVQLLESGGGLVQPGGSLRLSCAASGFTFSSYWMSWV RQAPGKGLEWVSAISGSGGSTYYADSVKGRFTISRDNSKNTLYLQMNSLRAEDTAVYYCASSP LQWVDVWGQGTTVTVSSASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDKKVEPKSCDKTHTCPPCPAP *EAA*GGPSVFLFPPKPKDTLMISRTPEVTCVVVDVSHEDPEVKFNWYVDGVEVHNAKTKPREEQYNS TYRVVSVLTVLHQDWLNGKEYKCKVSNKAL*P*APIEKTISKAKGQPREPQVCTLPPSRDELTKNQVS LSCAVKGFYPSDIAVEWESNGQPENNYKTTPPVLDSDGSFFLVSKLTVDKSRWQQGNVFSCSVMHE ALHNHYTQKSLSLSPGK |

Variable chains are in bold (not underlined). LALAPG and LALA amino acid substitutions are indicated in bold and italics. Amino acid substitutions relating to heterodimerization are indicated in bold and underlined. The SD15 portion is shown in italics. Linker regions are indicated in italics and underlined. All 38B2 HC comprise 24H9 VH (SEQ ID NO: 24).

We claim:

1. A fusion protein comprising:

(a) an anti-PD-1 antibody, wherein the sequences of CDR1H, CDR2H and CDR3H comprise SEQ ID NOS: 21, 22, and 23, and the sequences of CDR1L, CDR2L and CDR3L comprise SEQ ID NOS: 96, 97 and 82;

(b) an IL-15Rα sushi domain polypeptide comprising the amino acid sequence of SEQ ID NO: 214, or an amino acid sequence that is at least 95% identical to SEQ ID NO: 214;

(c) an IL-15 polypeptide comprising the amino acid sequence of SEQ ID NO: 212, or an amino acid sequence that is at least 90% identical to SEQ ID NO: 212; and (d) a first linker polypeptide joining the IL-15Rα sushi domain polypeptide and the IL-15 polypeptide;

and further wherein:

the IL-15Rα sushi domain polypeptide and the IL-15 polypeptide are fused to the N-terminus of the heavy chain variable region of the anti-PD-1 antibody, optionally by a second linker.

2. The fusion protein of claim 1, wherein for the anti-PD-1 antibody:

(a) the heavy chain variable region comprises SEQ ID NO: 24, or a sequence that is at least 90% identical to SEQ ID NO: 24; and (b) the light chain variable region comprises SEQ ID NO: 98, or a sequence that is at least 90% identical to SEQ ID NO: 98.

3. The fusion protein of claim 1, wherein for the anti-PD-1 antibody:

(a) the heavy chain variable region comprises a sequence that is at least 95% identical to SEQ ID NO: 24; and (b) the light chain variable region comprises a sequence that is at least 95% identical to SEQ ID NO: 98.

4. The fusion protein of claim 1, wherein the IL-15 polypeptide comprises an amino acid sequence that is at least 95% identical to SEQ ID NO: 212.

5. The fusion protein of claim 1, wherein the anti-PD-1 antibody is an IgG class immunoglobulin.

6. The fusion protein of claim 1, wherein the anti-PD-1 antibody comprises a first heavy chain constant region and a second heavy chain constant region, and wherein the anti-PD-1 antibody or antigen-binding fragment thereof comprises at least one modification in the CH3 domain of each of the first heavy chain constant region and the second heavy chain constant region causing heterodimerization.

7. The fusion protein of claim 6, wherein the anti-PD-1 antibody has isotype IgG$_1$, and wherein:

(a) the CH3 domain of the first heavy chain constant region comprises amino acid substitutions S354C and T366W; and the CH3 domain of the second heavy chain constant region comprises amino acid substitutions Y349C, T366S, L368A, and Y407V;

(b) the CH3 domain of the first heavy chain constant region comprises amino acid substitutions T350V, L351Y, F405A, and Y407V; and the CH3 domain of the second heavy chain constant region comprises amino acid substitutions T350V, T366L, K392L, and T394W; or (c) the CH3 domain of the first heavy chain constant region comprises amino acid substitutions L351Y, F405A, and Y407V; and the CH3 domain of the second heavy chain constant region comprises amino acid substitutions T366L, K392L, and T394W;

wherein all substitutions are indicated according to Kabat EU index numbering.

8. The fusion protein of claim 6, wherein the anti-PD-1 antibody has isotype IgG$_1$, and wherein the Fc domain, if present, comprises one or more amino acid substitutions that reduce binding to an Fc receptor or reduce effector function, wherein the one or more amino acid substitutions are selected from L234A, L235A, and P329G, wherein all substitutions are indicated according to Kabat EU index numbering.

9. The fusion protein of claim 1, wherein the IL-15Rα sushi domain polypeptide is fused to the N-terminus of the IL-15 polypeptide.

10. The fusion protein of claim 1, wherein at least one linker (i) is between 5 and 40 amino acids long or (ii) comprises a sequence selected from the group consisting of SEQ ID NOS: 215-218 and 244.

11. The fusion protein of claim 1, wherein the IL-15 polypeptide is a mutant IL-15 polypeptide comprising one or more amino acid substitutions at positions 45, 65, or 108 as numbered according to the mature human IL-15 sequence of SEQ ID NO: 212, wherein the one or more amino acid substitutions in the IL-15 polypeptide are selected from L45A, N65A, N65D, N65S, N65K, and Q108S as numbered according to the mature human IL-15 sequence of SEQ ID NO: 212.

12. A fusion protein comprising (a) an anti-PD-1 antibody or antigen-binding fragment thereof, (b) an IL-15Rα sushi domain polypeptide, and (c) an IL-15 polypeptide, wherein the fusion protein comprises a light chain sequence comprising SEQ ID NO: 219 and a first heavy chain sequence comprising SEQ ID NO: 240 and a second heavy chain sequence comprising SEQ ID NO: 241.

13. The fusion protein of claim 12 comprising two light chains comprising SEQ ID NO: 219, one heavy chain comprising SEQ ID NO: 240 and one heavy chain comprising SEQ ID NO: 241.

14. A cell comprising nucleic acids encoding the fusion protein of claim 12.

15. A vector comprising nucleic acids encoding the light and heavy chains of the fusion protein of claim 12.

16. A pharmaceutical composition comprising the fusion protein of claim 12; and a pharmaceutically acceptable carrier.

17. A method of inhibiting binding of PD-1 to PD-L1 or PD-L2, in a subject in need thereof, the method comprising administering to the subject an effective amount of the fusion protein of claim 12.

18. A method for increasing T cell activation or stimulating the immune system in a subject in need thereof, the method comprising administering to the subject an effective amount of the fusion protein of claim 12.

19. A method of treating cancer or reducing tumor growth or tumor metastasis in a subject in need thereof, the method comprising administering to the subject an effective amount of fusion protein of claim 12.

* * * * *